United States Patent
Beigelman et al.

(10) Patent No.: US 9,073,960 B2
(45) Date of Patent: Jul. 7, 2015

(54) SUBSTITUTED NUCLEOSIDES, NUCLEOTIDES AND ANALOGS THEREOF

(71) Applicant: Alios BioPharma, Inc., South San Francisco, CA (US)

(72) Inventors: Leonid Beigelman, San Mateo, CA (US); Guangyi Wang, Carlsbad, CA (US); David Bernard Smith, San Mateo, CA (US); Jerome Deval, Pacifica, CA (US); Marija Prhavc, Encinitas, CA (US)

(73) Assignee: ALIOS BIOPHARMA, INC., San Francisco, CA (US)

( * ) Notice: Subject to any disclaimer, the term of this patent is extended or adjusted under 35 U.S.C. 154(b) by 150 days.

(21) Appl. No.: 13/721,988

(22) Filed: Dec. 20, 2012

(65) Prior Publication Data

US 2013/0165400 A1  Jun. 27, 2013

Related U.S. Application Data

(60) Provisional application No. 61/579,560, filed on Dec. 22, 2011, provisional application No. 61/613,836, filed on Mar. 21, 2012.

(51) Int. Cl.
| | |
|---|---|
| C07H 19/06 | (2006.01) |
| C07H 19/10 | (2006.01) |
| C07H 19/12 | (2006.01) |
| C07H 19/16 | (2006.01) |
| C07H 19/20 | (2006.01) |
| C07H 19/207 | (2006.01) |

(52) U.S. Cl.
CPC ............ *C07H 19/06* (2013.01); *C07H 19/10* (2013.01); *C07H 19/16* (2013.01); *C07H 19/20* (2013.01); *C07H 19/12* (2013.01); *C07H 19/207* (2013.01)

(58) Field of Classification Search
None
See application file for complete search history.

(56) References Cited

U.S. PATENT DOCUMENTS

| | | |
|---|---|---|
| 3,832,341 A | 8/1974 | Duschinsky |
| 4,211,773 A | 7/1980 | Lopez et al. |
| 4,230,698 A | 10/1980 | Bobek et al. |
| 4,305,932 A | 12/1981 | Menachemoff et al. |
| 4,626,526 A | 12/1986 | Bristol |
| 4,652,554 A | 3/1987 | Chwang et al. |
| 4,713,383 A | 12/1987 | Francis et al. |
| 4,762,823 A | 8/1988 | Watanabe et al. |
| 4,797,495 A | 1/1989 | Bair |
| 4,880,784 A | 11/1989 | Robins et al. |
| 5,138,045 A | 8/1992 | Cook et al. |
| 5,171,849 A | 12/1992 | Soloway et al. |
| 5,264,618 A | 11/1993 | Basava et al. |
| 5,268,376 A | 12/1993 | Gester |
| 5,296,348 A | 3/1994 | Rakowicz-Szulczynska et al. |
| 5,378,693 A | 1/1995 | Matthews et al. |
| 5,378,825 A | 1/1995 | Cook et al. |
| 5,412,082 A | 5/1995 | Wittman et al. |
| 5,432,272 A | 7/1995 | Benner |
| 5,446,031 A | 8/1995 | Sakata et al. |
| 5,446,137 A | 8/1995 | Maag et al. |
| 5,446,139 A | 8/1995 | Seela et al. |
| 5,447,934 A | 9/1995 | Friebe et al. |
| 5,457,191 A | 10/1995 | Cook et al. |
| 5,466,786 A | 11/1995 | Buhr et al. |
| 5,478,813 A | 12/1995 | Funaishi et al. |
| 5,508,407 A | 4/1996 | Kaldor et al. |
| 5,543,507 A | 8/1996 | Bruice et al. |
| 5,602,240 A | 2/1997 | Cook et al. |
| 5,625,056 A | 4/1997 | Genieser et al. |
| 5,641,784 A | 6/1997 | Kufner-Muehl et al. |
| 5,645,985 A | 7/1997 | Froehler et al. |
| 5,658,731 A | 8/1997 | Sproat et al. |
| 5,670,633 A | 9/1997 | Cook et al. |
| 5,700,919 A | 12/1997 | Seliger et al. |
| 5,777,100 A | 7/1998 | Bullough et al. |
| 5,808,139 A | 9/1998 | Pathirana et al. |
| 5,852,188 A | 12/1998 | Cook |
| 5,977,325 A | 11/1999 | Edwards et al. |
| 6,004,939 A | 12/1999 | Chen et al. |
| 6,083,505 A | 7/2000 | Miller et al. |
| 6,127,121 A | 10/2000 | Dempcy et al. |
| 6,239,265 B1 | 5/2001 | Cook et al. |
| 6,262,241 B1 | 7/2001 | Cook et al. |
| 6,403,568 B1 * | 6/2002 | Ohrui et al. ..................... 514/49 |

(Continued)

FOREIGN PATENT DOCUMENTS

| | | |
|---|---|---|
| CA | 2003408 | 5/1990 |
| CA | 2042795 | 11/1991 |

(Continued)

OTHER PUBLICATIONS

Aggarwal S. et al., "Biochemical Characterization of Enzyme Fidelity of Influenza A Virus RNA Polymerase Complex "(2010) PLoS ONE 5(4):1-12.
Bajwa et al., "Thymidine nucleoside 3',5'-cyclic phosphoramidites and phosphites. Configuration at phosphorus in trivalent and pentavalent cyclic nucleotides by phosphorus-31 and carbon 13-NMR" *Tet. Lett.* (1978) 5:421-424.
Baraniak et al., "Ribonucleoside cyclic 3',5'-phosphoramidates: synthesis, stereochemistry, and conversion into ribonucleoside cyclic 3',5'-phosphorothioates and -[$^{18}$O] phosphates" *J. Chem. Soc. Perkin Trans. 1* (1987) 8:1645-1656.
Baraniak et al., "Synthesis of adenosine cyclic 3',5'-phosphorofluoridate (cAMP-F)" *Tet. Lett.* (1995) 36(44):8119-8122.
Baraniak, J., "Deoxyribonucleoside cyclic 3',5'-phosphorofluoridates" *Phosphorus, Sulfur and Silicon* (1996) 111:80.

(Continued)

Primary Examiner — Layla Bland
(74) Attorney, Agent, or Firm — Knobbe Martens Olson & Bear LLP

(57) ABSTRACT

Disclosed herein are nucleosides, nucleotides and analogs thereof, pharmaceutical compositions that include one or more of nucleosides, nucleotides and analogs thereof, and methods of synthesizing the same. Also disclosed herein are methods of ameliorating and/or treating a disease and/or a condition, including an infection from a paramyxovirus and/or an orthomyxovirus, with a nucleoside, a nucleotide and an analog thereof.

40 Claims, 1 Drawing Sheet

(56) References Cited

U.S. PATENT DOCUMENTS

| | | |
|---|---|---|
| 6,784,166 B2 | 8/2004 | Devos et al. |
| 6,787,525 B1 | 9/2004 | Ludwig et al. |
| 7,094,768 B2 | 8/2006 | Roberts et al. |
| 7,125,855 B2 | 10/2006 | Bhat et al. |
| 7,151,089 B2 | 12/2006 | Roberts et al. |
| 7,629,328 B2 | 12/2009 | Roberts et al. |
| 8,445,669 B2 * | 5/2013 | Sato et al. ............. 536/28.2 |
| 8,580,762 B2 | 11/2013 | Olhava et al. |
| 8,765,710 B2 | 7/2014 | Sofia et al. |
| 2002/0035077 A1 | 3/2002 | Tam et al. |
| 2003/0064945 A1 | 4/2003 | McSwiggen |
| 2003/0096980 A1 | 5/2003 | Froehler et al. |
| 2003/0105051 A1 | 6/2003 | McSwiggen |
| 2003/0124513 A1 | 7/2003 | McSwiggen |
| 2004/0002596 A1 | 1/2004 | Zhi et al. |
| 2004/0014959 A1 | 1/2004 | Christensen et al. |
| 2004/0158055 A1 | 8/2004 | Song et al. |
| 2004/0167096 A1 | 8/2004 | Cheng et al. |
| 2004/0181052 A1 | 9/2004 | Sourena et al. |
| 2004/0229839 A1 | 11/2004 | Babu et al. |
| 2004/0229840 A1 | 11/2004 | Bhat et al. |
| 2004/0259934 A1 | 12/2004 | Olsen et al. |
| 2006/0205685 A1 | 9/2006 | Phiasivongsa et al. |
| 2006/0205687 A1 | 9/2006 | Phiasivongsa et al. |
| 2007/0042988 A1 | 2/2007 | Klumpp et al. |
| 2007/0078130 A1 | 4/2007 | Ansorge et al. |
| 2007/0099865 A1 | 5/2007 | Fishman et al. |
| 2007/0270452 A1 | 11/2007 | Blagg et al. |
| 2008/0255038 A1 | 10/2008 | Hopkins et al. |
| 2009/0076062 A1 | 3/2009 | Maibaum et al. |
| 2009/0124796 A1 | 5/2009 | Yamakawa et al. |
| 2009/0176732 A1 | 7/2009 | Blatt et al. |
| 2009/0274686 A1 | 11/2009 | Or et al. |
| 2010/0029494 A1 | 2/2010 | Cherkasov et al. |
| 2010/0093992 A1 | 4/2010 | Cherkasov et al. |
| 2010/0151001 A1 | 6/2010 | Schott et al. |
| 2010/0227834 A1 | 9/2010 | Fahrig et al. |
| 2010/0234584 A1 | 9/2010 | Chang et al. |
| 2010/0240604 A1 | 9/2010 | Beigelman et al. |
| 2010/0331397 A1 | 12/2010 | Beigelman et al. |
| 2011/0054164 A1 | 3/2011 | Sato et al. |
| 2011/0171192 A1 | 7/2011 | Tomiyama et al. |
| 2012/0035115 A1 | 2/2012 | Manoharan et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0157511 A1 | 6/2012 | Manoharan et al. |
| 2012/0165286 A1 | 6/2012 | Beigelman et al. |
| 2013/0164261 A1 | 6/2013 | Wang et al. |
| 2013/0252920 A1 | 9/2013 | Blatt et al. |
| 2013/0253181 A1 | 9/2013 | Serebryany et al. |
| 2013/0281687 A1 | 10/2013 | Serebryany et al. |
| 2013/0315868 A1 | 11/2013 | Mayes et al. |
| 2013/0323836 A1 | 12/2013 | Manoharan et al. |
| 2014/0088117 A1 | 3/2014 | Burch et al. |
| 2014/0179627 A1 | 6/2014 | Beigelman et al. |
| 2014/0179910 A1 | 6/2014 | Beigelman et al. |
| 2014/0303108 A1 | 10/2014 | Beigelman et al. |
| 2014/0303113 A1 | 10/2014 | Krop et al. |
| 2015/0011497 A1 | 1/2015 | Beigelman et al. |

FOREIGN PATENT DOCUMENTS

| | | |
|---|---|---|
| CA | 2600359 | 9/2006 |
| CN | 103102345 | 5/2013 |
| DE | 2941592 | 4/1980 |
| DE | 4217679 | 12/1993 |
| DE | 102004009704 | 9/2005 |
| DE | 102008035299 | 2/2010 |
| EP | 192315 | 8/1986 |
| EP | 306845 | 3/1989 |
| EP | 365849 | 5/1990 |
| EP | 372268 | 6/1990 |
| EP | 0457326 | 11/1991 |
| EP | 461815 | 12/1991 |
| EP | 535231 | 4/1993 |
| EP | 536936 | 4/1993 |
| EP | 547008 | 6/1993 |
| EP | 1980568 | 10/2008 |
| EP | 2177527 A1 | 1/2009 |
| EP | 2264169 | 12/2010 |
| FR | 2688003 | 9/1993 |
| GB | 2188931 | 10/1987 |
| GB | 2234983 | 2/1991 |
| JP | 60228497 | 11/1985 |
| JP | 63215694 | 9/1988 |
| JP | 05051395 | 3/1993 |
| JP | 07242544 | 9/1995 |
| JP | 09328497 | 12/1997 |
| JP | 2002-302498 | 10/2002 |
| JP | 2003012690 | 1/2003 |
| JP | 2003-055392 | 2/2003 |
| JP | 2003-310293 | 11/2003 |
| JP | 2004-313002 | 11/2004 |
| JP | 2006131596 | 5/2006 |
| JP | 2006-248949 | 9/2006 |
| JP | 2008-214305 | 9/2008 |
| PL | 144 471 | 4/1985 |
| SU | 1417408 | 9/1995 |
| WO | WO 88/03147 | 5/1988 |
| WO | WO 88/10264 | 12/1988 |
| WO | WO 90/06320 | 6/1990 |
| WO | WO 90/06373 | 6/1990 |
| WO | WO 90/08156 | 7/1990 |
| WO | WO 91/10671 | 7/1991 |
| WO | WO 91/19713 | 12/1991 |
| WO | WO 92/01695 | 2/1992 |
| WO | WO 92/01696 | 2/1992 |
| WO | WO 92/02213 | 2/1992 |
| WO | WO 92/12718 | 8/1992 |
| WO | WO 92/21343 | 12/1992 |
| WO | WO 92/21352 | 12/1992 |
| WO | WO 93/12128 | 6/1993 |
| WO | WO 93/17717 | 9/1993 |
| WO | WO 93/20825 | 10/1993 |
| WO | WO 93/23414 | 11/1993 |
| WO | WO 94/02501 | 2/1994 |
| WO | WO 94/22890 | 10/1994 |
| WO | WO 95/006474 | 3/1995 |
| WO | WO 95/07920 | 3/1995 |
| WO | WO 95/15332 | 6/1995 |
| WO | WO 96/14329 | 5/1996 |
| WO | WO 96/40705 | 12/1996 |
| WO | WO 97/26883 | 7/1997 |
| WO | WO 98/16184 | 4/1998 |
| WO | WO 98/16186 | 4/1998 |
| WO | WO 99/14226 | 3/1999 |
| WO | WO 99/61583 | 12/1999 |
| WO | WO 99/66063 | 12/1999 |
| WO | WO 00/34298 | 6/2000 |
| WO | WO 00/66604 | 11/2000 |
| WO | WO 00/69876 | 11/2000 |
| WO | WO 00/69877 | 11/2000 |
| WO | WO 01/19360 | 3/2001 |
| WO | WO 01/27114 | 4/2001 |
| WO | WO 01/43731 | 6/2001 |
| WO | WO 01/68663 | 9/2001 |
| WO | WO 02/03997 | 1/2002 |
| WO | WO 02/31176 | 4/2002 |
| WO | WO 02/32920 | 4/2002 |
| WO | WO 02/055085 | 7/2002 |
| WO | WO 02/057425 | 7/2002 |
| WO | WO 02/083152 | 10/2002 |
| WO | WO 02/100415 | 12/2002 |
| WO | WO 03/022859 | 3/2003 |
| WO | WO 03/026589 | 4/2003 |
| WO | WO 03/026675 | 4/2003 |
| WO | WO 03/035012 | 5/2003 |
| WO | WO 03/039523 | 5/2003 |
| WO | WO 03/048315 | 6/2003 |
| WO | WO 03/062256 | 7/2003 |
| WO | WO 03/070193 | 8/2003 |
| WO | WO 03/070912 | 8/2003 |

(56) References Cited

FOREIGN PATENT DOCUMENTS

| | | |
|---|---|---|
| WO | WO 03/072757 | 9/2003 |
| WO | WO 03/073989 | 9/2003 |
| WO | WO 03/088908 | 10/2003 |
| WO | WO 03/095467 | 11/2003 |
| WO | WO 03/099840 | 12/2003 |
| WO | WO 03/104250 | 12/2003 |
| WO | WO 2004/002422 | 1/2004 |
| WO | WO 2004/002999 | 1/2004 |
| WO | WO 2004/003000 | 1/2004 |
| WO | WO 2004/014312 | 2/2004 |
| WO | WO 2004/037159 | 5/2004 |
| WO | WO 2004/052899 | 6/2004 |
| WO | WO 2004/080466 | 9/2004 |
| WO | WO 2004/091499 | 10/2004 |
| WO | WO 2004/106356 | 12/2004 |
| WO | WO 2005/020884 | 3/2005 |
| WO | WO 2005/021568 | 3/2005 |
| WO | WO 2005/034878 | 4/2005 |
| WO | WO 2005/034940 | 4/2005 |
| WO | WO 2005/044836 | 5/2005 |
| WO | WO 2005/063246 | 7/2005 |
| WO | WO 2005/123755 | 12/2005 |
| WO | WO 2006/000922 | 1/2006 |
| WO | WO 2006/011130 | 2/2006 |
| WO | WO 2006/048884 | 5/2006 |
| WO | WO 2006/050501 | 5/2006 |
| WO | WO 2006/063717 | 6/2006 |
| WO | WO 2006/084281 | 8/2006 |
| WO | WO 2006/094347 | 9/2006 |
| WO | WO 2006/097320 | 9/2006 |
| WO | WO 2006/105440 | 10/2006 |
| WO | WO 2006/116512 | 11/2006 |
| WO | WO 2007/006544 | 1/2007 |
| WO | WO 2007/020193 | 2/2007 |
| WO | WO 2007/038859 | 4/2007 |
| WO | WO 2007/038860 | 4/2007 |
| WO | WO 2007/055170 | 5/2007 |
| WO | WO 2007/113538 | 10/2007 |
| WO | WO 2007/149554 | 12/2007 |
| WO | WO 2008/012555 | 1/2008 |
| WO | WO 2008/017515 | 2/2008 |
| WO | WO 2008/019124 | 2/2008 |
| WO | WO 2008/032103 | 3/2008 |
| WO | WO 2008/083465 | 7/2008 |
| WO | WO 2008/086042 | 7/2008 |
| WO | WO 2008/089105 | 7/2008 |
| WO | WO 2008/089439 | 7/2008 |
| WO | WO 2008/095040 | 8/2008 |
| WO | WO 2008/095050 | 8/2008 |
| WO | WO 2008/100447 | 8/2008 |
| WO | WO 2008/117046 | 10/2008 |
| WO | WO 2008/117047 | 10/2008 |
| WO | WO 2008/121634 | 10/2008 |
| WO | WO 2009/001097 | 12/2008 |
| WO | WO 2009/003042 | 12/2008 |
| WO | WO 2009/009951 | 1/2009 |
| WO | WO 2009/010299 | 1/2009 |
| WO | WO 2009/040269 | 4/2009 |
| WO | WO 2009/050707 | 4/2009 |
| WO | WO 2009/067409 | 5/2009 |
| WO | WO 2009/086201 | 7/2009 |
| WO | WO 2009/105712 | 8/2009 |
| WO | WO 2009/125841 | 10/2009 |
| WO | WO 2009/126293 | 10/2009 |
| WO | WO 2009/129120 | 10/2009 |
| WO | WO 2009/152095 | 12/2009 |
| WO | WO 2010/020786 | 2/2010 |
| WO | WO 2010/026153 | 3/2010 |
| WO | WO 2010/027005 | 3/2010 |
| WO | WO 2010/030858 | 3/2010 |
| WO | WO 2010/030858 A1 | 3/2010 |
| WO | WO 2010/036407 | 4/2010 |
| WO | WO 2010/048552 | 4/2010 |
| WO | WO 2010/075554 | 7/2010 |
| WO | WO 2010/084115 | 7/2010 |
| WO | WO 2010/088924 | 8/2010 |
| WO | WO 2010/089128 | 8/2010 |
| WO | WO 2010/091386 | 8/2010 |
| WO | WO 2010/108140 | 9/2010 |
| WO | WO 2010/132513 | 11/2010 |
| WO | WO 2010/145778 | 12/2010 |
| WO | WO 2011/005860 | 1/2011 |
| WO | WO 2011/029537 | 3/2011 |
| WO | WO 2011/057204 | 5/2011 |
| WO | WO 2011/100131 | 8/2011 |
| WO | WO 2011/123518 | 10/2011 |
| WO | WO 2011/133871 | 10/2011 |
| WO | WO 2012/012465 | 1/2012 |
| WO | WO 2012/040124 | 3/2012 |
| WO | WO 2012/041965 | 4/2012 |
| WO | WO 2012/094248 | 7/2012 |
| WO | WO 2013/019874 | 2/2013 |
| WO | WO 2013/096679 | 6/2013 |
| WO | WO 2013/138210 | 9/2013 |
| WO | WO 2013/142124 | 9/2013 |
| WO | WO 2013/142159 | 9/2013 |
| WO | WO 2013/142525 | 9/2013 |
| WO | WO 2013/151975 | 10/2013 |
| WO | WO 2014/008236 | 1/2014 |
| WO | WO 2014/022639 | 2/2014 |
| WO | WO 2014/026198 | 2/2014 |
| WO | WO 2014/038561 | 3/2014 |
| WO | WO 2014/048532 | 4/2014 |
| WO | WO 2014/070771 | 5/2014 |
| WO | WO 2014/079903 | 5/2014 |
| WO | WO 2014/100498 | 6/2014 |
| WO | WO 2014/164533 | 10/2014 |
| WO | WO 2014/209983 | 12/2014 |

OTHER PUBLICATIONS

Boteloho et al., "Inhibition of cAMP-dependent protein kinase by adenosine cyclic 3',5'- phosphorodithioate, a second cAMP antagonist" *J. Bio. Chem.* (Apr. 15, 1988) 263(11):5301-5305.

Carey, Francis, Organic Chemistry, 2nd ed., McGraw Hill, Inc., New York (1992), pp. 328-331.

Cullis, P., "The stereospecific conversion of P-chiral phosphorothioates into[$^{18}$O]*-phosphates" *Tet. Lett.* (1983) 24(50):5677-5680.

De Vroom et al., "Synthesis of ribonucleoside 3',5'-cyclic phosphorothioate using a modified hydroxybenzotriazole phsophotriester approach" *Recueil Trav. Chim. Pays-Bas* (1987) 106(11):577-580.

Etheve-Quelquejeu et al., "Synthesis of 2'-α-C-allenyl-2'-deoxyuridine: An analogue of 2'azido-2'-deoxyuridine, known inhibitor of ribonucleotide diphosphate reductase (RDPR)" Tet. Lett. (1999) 40(26):4807-4810.

Feldwisch et al., "Purification and characterization of a cAMP-binding protein of *Volvox carteri* f. *nagariensis* Iyengar" *Eur. J. Biochem.* (1995) 229(2):480-489.

Greene, et al., Protective Groups in Organic Synthesis, 3. Ed., John Wiley & Sons, (1999) Cover & Contents pages.

Gopalakrishnan et al. "A virtual screen approach for thymidine monophosphate kinase inhibitors as antitubercular agents based on docking and pharmacophore models" *J. Chem. Inf. Model.* (2005) 45(4):1101-1008.

Gwack et al., "DNA Helicase Activity of the Hepatitis C Virus Nonstructural Protein 3" Eur. J. Biochem. (1997) 250(1):47-54.

Hayakawa et al., "A strategy for the stereoselective preparation of thymidine phosphorothioates with the ® or the (S) configuration of the stereogenic phosphorus atom and their application to the synthesis of oligodeoxyribonucleotides with stereochemically pure phosphate/phosphorothioate chimeric backbone" *Eur. J. Org. Chem.* (2006)17:3834-3844.

Herbert et al., "Structural features of the noncatalytic cGMP binding sites of frog photoreceptor phosphodiesterase using cGMP analogs" *J. Bio. Chem.* (1998) 273(10):5557-5565.

Hrebabecky, et al., "1-(3,5-O-Alkylidene-2-deoxy-4-C-hydroxymethyl-α-L-threo-pentofuranosyl)uracils," Collection of Czechoslovak Chemical Communications (1997), 62(6), 957-970.

Hrebabecky, et al., "Synthesis of deoxy, dideoxy and didehydrodideoxy analogs of 9-(4-C-hydroxymethyl-α-L-

(56) References Cited

OTHER PUBLICATIONS pentofuranosyl)adenine," Collection of Czechoslovak Chemical Communications (1994), 59(7), 1654-64.

Hung et al., "A new nonhydrolysis reactive cGMP analogue, (Rp)-guanosine-3',5'-cyclic-S-(4-bromo-2,3-dioxobuyl)monophorothoate, which targets the cGMP binding site of human platelet PDE3A" Bioorg. Chem. (2008) 36(3):141-147.

Hung et al., "A new nonhydrolyzable reactive cAMP analog, (Sp)-Adenosine-3',5'-cyclic-S-(4-bromo-2,3-dioxobuyl)monophosphorothioate irreversibly inactivates human platelets cGMP-inhibited cAMP phosphodiesterase" Bioorg. Chem. (2002) 30(1):16-31.

Hung et al., "A nonhydrolyzable reactive cAMP analogue, (Sp)-8-[(4-bromo-2,3-dioxobutyl)thio]adenosine 3',5'—cyclic S-(methyl)monophosphorothioate, irreversibly inactivates human platelet cGMP-inhibited cAMP phosphodiesterase at micromolar concentrations" Biochemistry (2002) 41(9):2962-2969.

Hung et al., "New insights from the structure-function analysis of the catalytic region of human platelet phosphodiesterase 3A: a role for the unique 44 amino acid insert" J. Bio. Chem. (Sep. 29, 2006) 281(39):29236-29244.

"IUPAC-IUB Commission on Biochemical Nomenclature Abbreviated Nomenclature of Synthetic Polypeptides (Polymerized Amino Acids)* Revised Recommendations (1971)" Biochemistry. (1972) 11(5):942-944.

Kodama et al., "4'-ethynyl nucleoside analogs: potent inhibitors of multidrug-resistant human immunodeficiency virus variants in vitro", Antimicrobial Agents and Chemotherapy (2001), 45(5), 1539-1546.

Kohgo et al., "Development of nucleosides highly potent against multidrug resistant HIV" Tennen Yuki Kagobutsu Toronkai Koen Yoshishu (2000), $42^{nd}$, 835-840.

Kohgo et al., "Synthesis of 4'-substituted nucleosides and their biological evaluation" Nucleic Acid Symposium Series (1999), 42(Twenty-sixth Symposium on Nucleic Acids Chemistry, 1999), 127-128.

Kohgo et al., "Synthesis of 4'-C-ethynyl-α-D-arabino- and 4'-C-ethynyl-2'-deoxy-β-D-ribopentofuranosyl pyrimidines, and their biological evaluation" Bioscience, Biotechnology, and Biochemistry (1999), 63(6), 1146-1149.

Lesiak et al., "A new approach to syntheses of organic phosphoroselenoates and phosphorodiselenoates. Proof of absolute configuration assignment in diastereomers of cTMPS [thymidine cyclic 3',5'-phosphorothioates]" Polish J. of Chem. (1979) 53(10):2041-2050.

Lesnikowski et al., "A simple procedure for synthesis of diastereoisomers of thymidine cyclic 3',5'-phosphate derivatives" Nucleic Acids Symposium Series No. 18, Seventh Symposium on the Chemistry of Nucleic Acid Components (Aug. 20-Sep. 5, 1987) :273-276.

Lesnikowski et al., "Some aspects of the electron impact induced fragmentation of diastereoisomeric thymidine cyclic 3',5'-phsophoranilidothioates" Organic Mass Spectrometry (1980) 15(9):454-455.

Lin et al., "Novel 3',5'-cyclic nucleotide analog: Adenosine 3',5'-cyclic Boranomonophosphate" Org. Lett. (2001) 3(6):795-797.

McGuigan et al., "The application of the phosphoramidate ProTide approach confers micromolar potency against hepatitis C virus on inactive agent 4'-azidoinosine: kinase bypass on a dual base/sugar modified nucleoside", Bioorg Med Chem Lett. (2009) 19(11):3122-3124.

Mcomie, J. F. W., Protective Groups in Organic Chemistry, Plenum Press, 1973. Cover & Contents pages only.

McMurry, John, Organic Chemistry, 5th ed., Brooks/Cole, Pacific Grove, CA. (2000), Chapter 11.5, pp. 398 and 408.

Misiura et al., "Synthesis, chemical and enzymatic reactivity, and toxicity of dithymidylyI-3',5'- phosphorofluridate and -phosphorothiofluoridate" Bioorg. Med. Chem. (2001) 9(6):1525-1532.

Nomura et al., "Nucleosides and Nucleotides. 185. Synthesis and Biological Activities of 4'α-C-Branched-Chain Sugar Pyrimidine Nucleosides" Journal of Medicinal Chemistry (1999), 42(15), 2901-2908.

Ohrui, H. 4'-C-Ethynyl-2'-Deoxynucleosides, in Modified Nucleosides: in Biochemistry, Biotechnology and Medicine (2008) (ed. P. Herdewijn), Wiley-VCH Verlag GmbH & Co. KGaA, Weinheim, Germany.

Ohrui, "Syntheses of 4'-C-Ethynyl-β-D-arabino- and 4'-C-Ethynyl-2'-deoxy-β-D-ribo-pentofuranosylpyrimidines and -purines and Evaluation of Their Anti-HIV Activity" Journal of Medicinal Chemistry (2000), 43(23), 4516-4525.

Pfundheller, et al., "Oligonucleotides containing 4'-C-aminomethyl-2'-modified thymidines show increased binding affinity towards DNA and RNA," Bioorganic & Medicinal Chemistry Letters (1999), 9(18), 2667-2672.

Pfundheller, et al., "Oligonucleotides containing novel 4'-C- or 3'-C-(aminoalkyl)-branched thymidines" Helvetica Chimica Acta (2000), 83(1), 128-151.

Scott et al., "Mapping ligand interactions with the hyperpolarization activated cyclic nucleotide modulated (HCN) ion channel binding domain using a soluble construct" Biochemistry (2007) 46(33):9417-9431.

Shortnacy-Fowler, et al., "Synthesis and biological activity of 4'-C-hydroxymethyl-2'-fluoro-D-arabinofuranosylpurine Nucleosides," Nucleosides, Nucleotides & Nucleic Acids (2001), 20(4-7), 747-750.

Shortnacy-Fowler,et al., "Synthesis and biological activity of 4'-C-hydroxymethyl-2'-fluoro-D-arabinofuranosylpurine Nucleosides" Nucleosides, Nucleotides & Nucleic Acids (2001),20(8), 1583-1598.

Sidwell et al., "Use of disposable micro tissue culture plates for antiviral and interferon induction studies" Appl. Microbiol. (1971) 22(5):797-801.

Smith, "Design, synthesis, and antiviral properties of 4'-substituted ribonucleosides as inhibitors of hepatitis C virus replication: The discovery of R1479" Bioorganic & Medicinal Chemistry Letters (2007), 17(9), 2570-2576.

Sopchik et al., "Facile preparation of the individual diastereoisomers of thymidine 3',5'-cyclic phosphorothioate (cTMPS)" Tet. Lett. (1981) 22:307-310.

Streitwieser et al., Introduction to Organic Chemistry, 2nd ed., Macmillan Publishing Co. Inc., New York, NY (1981) pp. 169-171.

Sun et al., "Effects of cGMP, cAMP and two other cAMP derivatives on the transcription system of isolated rat liver nuclei" Chinese Biochemical Journal (Oct. 1987) 3(5):455-461.

Tian et al., "Synthesis of 8-chloroadenosine 3',5'-cyclophosphotriesters and phosphoramidates" Progress in Natural Science (Dec. 1994) 4(6):726-731.

Tiwari, et al., "Synthesis and anticancer evaluation of 4'-C-methyl-2'-fluoro arabino nucleosides," Nucleosides, Nucleotides & Nucleic Acids (2009), 28(5-7), 657-677.

Wang et al., "Synthesis and anti-HIV activity of 2'-deoxy-2'-fluoro-4'-C-ethynyl nucleoside analogs" Bioorganic and Biomedical Chemistry Letter (2010), 20(14), 4053-4056.

Wu et al., "Cyclophosphorylation of adenosine" Acta Chemica Sinica (1986) 44(6):635-638.

Yamaguchi et al., "Synthesis of 4'-C-ethynyl-β-D-ribo-pentofuranosyl pyrimidines" Bioscience, Biotechnology, and Biochemistry (1999), 63(4), 736-742.

CAS Registry No. 1034319-11-3, Entry date Jul. 16, 2008, (https://stneasy.cas.org), retrieved on Mar. 21, 2014.

CAS Registry No. 1034318-47-2, Entry date Jul. 16, 2008, (https://stneasy.cas.org), retrieved on Mar. 21, 2014.

CAS Registry No. 959344-43-5, Entry date Dec. 21, 2007, (https://stneasy.cas.org), retrieved on Mar. 21, 2014.

CAS Registry No. 1158729-23-7, Entry date Jun. 17, 2009, (https://stneasy.cas.org), retrieved on Mar. 21, 2014.

CAS Registry No. 130108-92-8, Entry date Oct. 26, 1990, (https://stneasy.cas.org), retrieved on Mar. 21, 2014.

CAS Registry No. 130108-93-9, Entry date Oct. 26, 1990, (https://stneasy.cas.org), retrieved on Mar. 21, 2014.

CAS Registry No. 130108-94-0, Entry date Oct. 26, 1990, (https://stneasy.cas.org), retrieved on Mar. 21, 2014.

(56) References Cited

OTHER PUBLICATIONS

CAS Registry No. 130108-97-3, Entry date Oct. 26, 1990, (https://stneasy.cas.org), retrieved on Mar. 21, 2014.
CAS Registry No. 139418-97-6, Entry date Mar. 6, 1992, (https://stneasy.cas.org), retrieved on Mar. 21, 2014.
CAS Registry No. 139418-99-8, Entry date Mar. 6, 1992, (https://stneasy.cas.org), retrieved on Mar. 21, 2014.
CAS Registry No. 139419-00-4, Entry date Mar. 6, 1992, (https://stneasy.cas.org), retrieved on Mar. 21, 2014.
CAS Registry No. 139442-01-6, Entry date Mar. 6, 1992, (https://stneasy.cas.org), retrieved on Mar. 21, 2014.
CAS Registry No. 690270-29-2, Entry date Jun. 7, 2004, (https://stneasy.cas.org), retrieved on Mar. 21, 2014.
CAS Registry No. 926309-82-2, Entry date Mar. 14, 2007, (https://stneasy.cas.org), retrieved on Mar. 21, 2014.
International Preliminary Report on Patentability dated Dec. 11, 2013 for PCT Application No. PCT/US2012/071063, filed Dec. 20, 2012.
International Search Report and Written Opinion dated Jul. 9, 2013 for PCT Application No. PCT/US2013/033018, filed Mar. 19, 2013.
Smith et al., "The Design, Synthesis, and Antiviral Activity of Monofluoro and Difluoro Analogues of 4'-Azidocytidine against Hepatitis C Virus Replication: The Discovery of 4'-Azido-2'-deoxy-2'-fluorocytidine and 4'-Azido-2'-dideoxy-2',2'-difluorocytidine" *J. of Med. Chem.* (2009) 52:2971-2978.
Second Written Opinion dated Feb. 26, 2014 for PCT Application No. PCT/US2013/033018, filed Mar. 19, 2013.
International Search Report and Witten Opinion issued on May 3, 2013 in PCT Application No. PCT/US2012/071063, filed on Dec. 20, 2012.
CAS Registry No. 1026639-60-0, STN Entry Date Jun. 8, 2008.
CAS Registry No. 1026065-66-6, STN Entry Date Jun. 6, 2008.
Chang, W. et al: "Synthesis and Anti-HCV Activity of 3',4'-Oxetane Nucleosides" *Bioorganic & Medicinal Chemistry Letters*(2010), 20(15): 4539-4543.
Kohgo, S. et al: "Synthesis of 4'-C-Ethynyl-—-D-arabino- and 4'-C-Ethynyl-2'-deoxy-lf-Dcribo-pentofuranosyl Pyrimidines, and Their Biological Evaluation" *Bioscience, Biotechnology, and Biochemistry* (1999), 63(6): 1146-1149.
Kozak, J. et al: "Synthesis of 4'—Trifluoromethyl Nucleoside Analogs" *Nucleosides & Nucleotides* (1998),17(12): 2221-2239.
Waga, T. et al: "Synthesis and Biological Evaluation of 4'-C-Methyl Nucleosides", *Nucleosides & Nucleotides* (1996), 15(1-3): 287-304.
Wang, Q. et al: "Synthesis and Anti-HIV Activity of 2'-Deoxy-2'-Fluoro-4'-C- Ethynyl Nucleoside Analogs" *Bioorganic & Medicinal Chemistry Letters* (2010), 20(14): 4053-4056.
International Preliminary Report on Patentability dated Jul. 2, 2014 for PCT Application No. PCT/US2013/033018, filed Mar. 19, 2013.
Anisuzzaman et al., "Synthesis of a carboranyl nucleoside for potential use in neutron capture therapy of cancer", Polyhedron (1990), 9(6), 891-2.
Avery et al., "Biochemical pharmacology of 2-chlorodeoxyadenosine in malignant human hematopoietic cell lines and therapeutic effects of 2-bromodeoxyadenosine in drug combinations in mice", Cancer Research (1989), 49(18), 4972-8.
Brink et al., "2-C-Nitromethyl and 2-C-aminomethyl derivatives of D-ribose. Preparation of 2'-C- nitromethyluridines", Journal of the Chemical Society, Perkin Transactions 1: Organic and Bio-Organic Chemistry (1972-1999) (1977), (14), 1608-12.
Cass et al., "Mediated transport of nucleosides by human erythrocytes. Specificity toward purine nucleosides as permeants", Biochimica et Biophysica Acta, Biomembranes (1973), 291(3), 734-46.
Chwang et al., "2'-O-Nitro-1-beta-D-arabinofuranosylcytosine. A new derivative of 1-b-D-arabinofuranosylcytosine that resists enzymic deamination and has antileukemic activity", Journal of Medicinal Chemistry (1983), 26(2), 280-3.

Chwang et al., "Synthesis of 2'-O-nitro-9-beta-D-arabinofuranosyladenine and 2'-O-nitro-9-beta-Darabinofuranosylhypoxanthine", Tetrahedron Letters (1983), 24(31), 3183-6.
Chwang et al., 9-beta-D-arabinofuranosylpurines that are cytotoxic to variants of human leukemia lymphoblast cells resistant to both 1-beta-D-arabinofuranosylcytosine and 9-beta-Darabinofuranosyladenine, Biochemical Pharmacology (1983), 32(17), 2643-6.
Gore, et al., "Influence of 2'-Fluoro versus 2'-O-Methyl Substituent on the Sugar Puckering of 4'-C-Aminomethyluridine", Journal of Organic Chemistry (2013), 78(19), 9956-9962.
Hrebabecky et al., "Synthesis of 1-[3-azido-2,3-dideoxy-4-C-(hydroxymethyl)-alpha-L-threo-pentofuranosyl]thymine, 1-[2,3-dideoxy-4-C-(hydroxymethyl)-alpha-L-glycero-pentofuranosyl]thymine, and 1-[2,3-dideoxy-4-C-(hydroxymethyl)-alpha-L-glycero-pent-2-enofuranosyl]thymine", Collection of Czechoslovak Chemical Communications (1993), 58(2), 409-20.
Marquez et al., "Design, synthesis, and antiviral activity of nucleoside and nucleotide analogs", ACS Symposium Series (1989), 401(Nucleotide Analogues Antiviral Agents), 140-55.
Matsuda et al, "Nucleosides and nucleotides. 100. 2'-C-Cyano-2'-deoxy-1-b-D-arabinofuranosylcytosine (CNDAC): design of a potential mechanism-based DNA-strand-breaking antineoplastic nucleoside", Journal of Medicinal Chemistry (1991), 34(9), 2917-19.
Matsuda et al., "Nucleosides and nucleotides. 94. Radical deoxygenation of tert-alcohols in 1-(2-C-alkylpentofuranosyl)pyrimidines: synthesis of (2'S)-2'-deoxy-2'-C-methylcytidine, an antileukemic nucleoside", Journal of Medicinal Chemistry (1991), 34(1), 234-9.
Matsuda et al., "Nucleosides and nucleotides. Part 78. Radical deoxygenation of tert-alcohols in 2'- branched-chain sugar pyrimidine nucleosides: synthesis and antileukemic activity of 2'-deoxy-2'(S)- methylcytidine", Chemical & Pharmaceutical Bulletin (1987), 35(9), 3967-70.
Matsuda et al., Synthesis of a new potent antitumor nucleoside, 2'-C-cyano-2'-deoxy-1-beta-D-arabinofuranosylcytosine, Nucleic Acids Symposium Series (1990), 22(Symp. Nucleic Acids Technol., 1990), 51-2.
Maury et al., "Inhibition and substrate specificity of adenosine deaminase. Interaction with 2',3'- and/or 5'-substituted adenine nucleoside derivatives", Nucleosides & Nucleotides (1991), 10(8), 1677-92.
Murphey-Corb et al., "Response of simian immunodeficiency virus to the novel nucleoside reverse transcriptase inhibitor 4'-ethynyl-2-fluoro-2'-deoxyadenosine in vitro and in vivo", Antimicrobial Agents and Chemotherapy (2012), 56(9), 4707-4712.
Novak et al., "Nucleic acid components and their analogs. CXLIII. Nucleosides derived from 2-deoxy-2(R)-C-methyl-erythro-D-pentose", Collection of Czechoslovak Chemical Communications (1971), 36(11), 3670-7.
Novak et al., "Nucleosides of (2R)-2-C-methyl-2-deoxy-erythro-D-pentose", Tetrahedron Letters (1969), (21), 1627-8.
Office Action dated Oct. 31, 2014 for Eurasian Patent Application 201491493, filed Mar. 19, 2013.
Robins et al., "Nucleic acid related compounds. 73. Fluorination of uridine 2'-thioethers with xenon difluoride or (diethylamino)sulfur trifluoride. Synthesis of stable 2'-[alkyl(or aryl)sulfonyl]-2'-deoxy-2'-fluorouridines", Journal of Organic Chemistry (1992), 57(8), 2357-64.
Roth et. al., "A recombinant, infectious human parainfluenza virus type 3 expressing the enhanced green fluorescent protein for use in high-throughput antiviral assays"Antiviral Res. (2009) 82(1):12-2.
Soloway et al., "The development of carboranyl nucleic acid precursors for use in neutron capture therapy of tumors", Pure and Applied Chemistry (1991), 63(3), 411-13.
Tanaka, M. et al., "Antitumor activity of a novel nucleoside, 2'-C-cyano-2'-deoxy-1-beta-D-arabinofuranosylcytosine (CNDAC) against murine and human tumors", Cancer Letters (Shannon, Ireland) (1992), 64(1), 67-74.

(56) References Cited

OTHER PUBLICATIONS

Ueda et al., Nucleosides and nucleotides. 86. Synthesis and biological activity of branched chain-sugar nucleosides, Nucleosides & Nucleotides (1989), vol. Date 1988, 8(5-6), 743-52.

Velazquez et al. "Synthesis of 2'-C-cyano-2'-deoxy- and 2'-C-cyano-2',3'-dideoxy-beta-D-arabinofuranosyl nucleosides", Tetrahedron (1992), 48(9), 1683-94.

Verhoef et al., "Differential sensitivity of human T and B lymphoblasts to cytotoxic nucleoside analogs", UCLA Symposia on Molecular and Cellular Biology, New Series (1983), 4(Ration. Basis Chemother.), 261-73.

Vial et al., Synthesis of 2'- and 3'-amino-substituted uridine, thymidine and adenosine, and their inhibitions of HIV replication, Antiviral Chemistry & Chemotherapy (1990), 1(3), 183-202.

Xi, Zhen et al., New stereocontrolled synthesis of isomeric C-branched-beta-D-nucleosides by intramolecular free-radical cyclization-opening reactions based on temporary silicon connection, Tetrahedron (1992), 48(2), 349-70.

Yoshimura et al., "Nucleosides and nucleotides. 102. Stereoselective radical deoxygenation of tert- propargyl alcohols in sugar moiety of pyrimidine nucleosides: synthesis of 2'-C-alkynyl-2'-deoxy-1-beta-D-arabinofuranosylpyrimidines", Tetrahedron Letters (1991), 32(42), 6003-6.

* cited by examiner

| Compound | Structure |
|---|---|
| BMS-433771 | 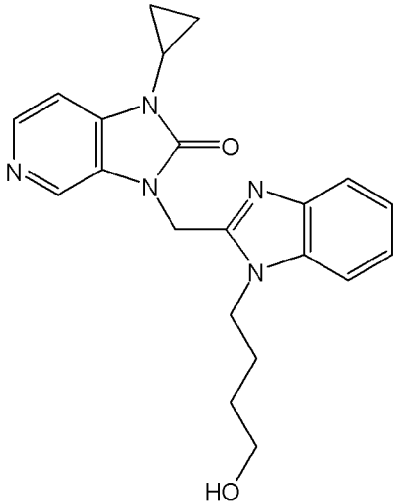 |
| TMC-353121 | 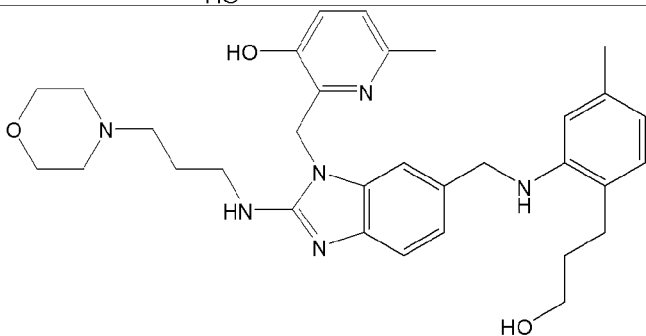 |

SUBSTITUTED NUCLEOSIDES, NUCLEOTIDES AND ANALOGS THEREOF

This application claims the benefit of U.S. Provisional Application Nos. 61/579,560, filed Dec. 22, 2011; and 61/613,836, filed Mar. 21, 2012; which are incorporated herein by reference in their entireties; including any drawings.

BACKGROUND

1. Field

The present application relates to the fields of chemistry, biochemistry and medicine. More particularly, disclosed herein are nucleoside, nucleotides and analogs thereof, pharmaceutical compositions that include one or more nucleosides, nucleotides and analogs thereof, and methods of synthesizing the same. Also disclosed herein are methods of ameliorating and/or treating a paramyxovirus and/or an orthomyxovirus viral infection with one or more nucleosides, nucleotides and analogs thereof.

2. Description

Respiratory viral infections, including upper and lower respiratory tract viral infections, infects and is the leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs.

Nucleoside analogs are a class of compounds that have been shown to exert antiviral activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I), Formula (II) and/or Formula (III), or a pharmaceutically acceptable salt of the foregoing.

Some embodiments disclosed herein relate to methods of ameliorating and/or treating a paramyxovirus viral infection that can include administering to a subject suffering from the paramyxovirus viral infection an effective amount of one or more compounds of Formula (I), Formula (II) and/or Formula (III), or a pharmaceutically acceptable salt of the foregoing, or a pharmaceutical composition that includes one or more compounds of Formula (I), Formula (II) and/or Formula (III), or a pharmaceutically acceptable salt of the foregoing. Other embodiments described herein relate to using one or more compounds of Formula (I), Formula (II) and/or Formula (III), or a pharmaceutically acceptable salt of the foregoing, in the manufacture of a medicament for ameliorating and/or treating a paramyxovirus viral infection. Still other embodiments described herein relate to compounds of Formula (I), Formula (II) and/or Formula (III), or a pharmaceutically acceptable salt of the foregoing, that can be used for ameliorating and/or treating a paramyxovirus viral infection. Yet still other embodiments disclosed herein relate to methods of ameliorating and/or treating a paramyxovirus viral infection that can include contacting a cell infected with the paramyxovirus with an effective amount of one or more compounds of Formula (I), Formula (II) and/or Formula (III), or a pharmaceutically acceptable salt of the foregoing, or a pharmaceutical composition that includes one or more compounds of Formula (I), Formula (II) and/or Formula (III), or a pharmaceutically acceptable salt of the foregoing. Some embodiments disclosed herein relate to methods of inhibiting the replication of a paramyxovirus that can include contacting a cell infection with the paramyxovirus with an effective amount of one or more compounds of Formula (I), Formula (II) and/or Formula (III), or a pharmaceutically acceptable salt of the foregoing, or a pharmaceutical composition that includes one or more compounds of Formula (I), Formula (II) and/or Formula (III), or a pharmaceutically acceptable salt of the foregoing. For example, the paramyxovirus viral infection can be caused by a henipavirus, a morbillivirus, a respirovirus, a rubulavirus, a pneumovirus (including a respiratory syncytial viral infection), a metapneumovirus, hendravirus, nipahvirus, measles, sendai virus, mumps, a human parainfluenza virus (HPIV-1, HPIV-2, HPIV-3 and HPIV-4) and/or a metapneumovirus.

Some embodiments disclosed herein relate to methods of ameliorating and/or treating an orthomyxovirus viral infection that can include administering to a subject suffering from the orthomyxovirus viral infection an effective amount of one or more compounds of Formula (I), Formula (II) and/or Formula (III), or a pharmaceutically acceptable salt of the foregoing, or a pharmaceutical composition that includes one or more compounds of Formula (I), Formula (II) and/or Formula (III), or a pharmaceutically acceptable salt of the foregoing. Other embodiments described herein relate to using one or more compounds of Formula (I), Formula (II) and/or Formula (III), or a pharmaceutically acceptable salt of the foregoing, in the manufacture of a medicament for ameliorating and/or treating an orthomyxovirus viral infection. Still other embodiments described herein relate to compounds of Formula (I), Formula (II) and/or Formula (III), or a pharmaceutically acceptable salt of the foregoing, that can be used for ameliorating and/or treating an orthomyxovirus viral infection. Yet still other embodiments disclosed herein relate to methods of ameliorating and/or treating an orthomyxovirus viral infection that can include contacting a cell infected with the orthomyxovirus with an effective amount of one or more compounds of Formula (I), Formula (II) and/or Formula (III), or a pharmaceutically acceptable salt of the foregoing, or a pharmaceutical composition that includes one or more compounds of Formula (I), Formula (II) and/or Formula (III), or a pharmaceutically acceptable salt of the foregoing. Some embodiments disclosed herein relate to methods of inhibiting the replication of an orthomyxovirus that can include contacting a cell infection with the orthomyxovirus with an effective amount of one or more compounds of Formula (I), Formula (II) and/or Formula (III), or a pharmaceutically acceptable salt of the foregoing, or a pharmaceutical composition that includes one or more compounds of Formula (I), Formula (II) and/or Formula (III), or a pharmaceutically acceptable salt of the foregoing. For example, the orthomyxovirus viral infection can be an influenza viral infection (such as influenza A, B and/or C).

Some embodiments disclosed herein relate to methods of ameliorating and/or treating a paramyxovirus viral infection and/or an orthomyxovirus viral infection that can include administering to a subject suffering from the viral infection an effective amount of a compound described herein or a pharmaceutically acceptable salt thereof (for example, one or more compounds of Formulae (I), (II) and/or (III), or a pharmaceutically acceptable salt of the foregoing), or a pharmaceutical composition that includes one or more compounds described herein, in combination with one or more agents described herein. Some embodiments disclosed herein relate to methods of ameliorating and/or treating a paramyxovirus viral infection and/or an orthomyxovirus viral infection that can include contacting a cell infected with the virus with an effective amount of a compound described herein or a pharmaceutically acceptable salt thereof (for example, one or more compounds of Formulae (I), (II) and/or (III), or a pharmaceutically acceptable salt of the foregoing), or a pharmaceutical composition that includes one or more compounds described herein, in combination with one or more agents described herein.

BRIEF DESCRIPTION OF THE DRAWINGS

FIG. 1 shows example RSV agents.

DETAILED DESCRIPTION

Paramyxoviridae family is a family of single stranded RNA viruses. Several genera of the paramyxoviridae family include henipavirus, morbillivirus, respirovirus, rubulavirus, pneumovirus and metapneumovirus. These viruses can be transmitted person to person via direct or close contact with contaminated respiratory droplets or fomites. Species of henipavirus include hendravirus and nipahvirus. A species of morbillivirus is measles. Species of respirovirus include sendai virus and human parainfluenza viruses 1 and 3; and species of rubulavirus include mumps virus and human parainfluenza viruses 2 and 4. A species of metapneumovirus is human metapneumovirus.

Human Respiratory Syncytial Virus (RSV), a species of pneumovirus, can cause respiratory infections, and can be associated with bronchiolitis and pneumonia. Symptoms of an RSV infection include coughing, sneezing, runny nose, fever, decrease in appetite, and wheezing. RSV is the most common cause of bronchiolitis and pneumonia in children under one year of age in the world, and can be the cause of tracheobronchitis in older children and adults. In the United States, between 75,000 and 125,000 infants are hospitalized each year with RSV. Among adults older than 65 years of age, an estimated 14,000 deaths and 177,000 hospitalizations have been attributed to RSV.

Treatment options for people infected with RSV are currently limited. Antibiotics, usually prescribed to treat bacterial infections, and over-the-counter medication are not effective in treating RSV and may help only to relieve some of the symptoms. In severe cases, a nebulized bronchodilator, such as albuterol, may be prescribed to relieve some of the symptoms, such as wheezing. RespiGram® (RSV-IGIV, MedImmune, approved for high risk children younger than 24 months of age), Synagis® (palivizumab, MedImmune, approved for high risk children younger than 24 months of age), and Virzole® (ribavirin by aerosol, ICN pharmaceuticals) have been approved for treatment of RSV.

Symptoms of the measles include fever, cough, runny nose, red eyes and a generalized rash. Some individuals with measles can develop pneumonia, ear infections and bronchitis. Mumps leads to swelling of the salivary glands. Symptoms of mumps include fever, loss of appetite and fatigue. Individuals are often immunized against measles and mumps via a three-part MMR vaccine (measles, mumps, and rubella). Human parainfluenza virus includes four serotypes types, and can cause upper and lower respiratory tract infections. Human parainfluenza virus 1 (HPIV-1) can be associated with croup; human parainfluenza virus 3 (HPIV-3) can be associated with bronchiolitis and pneumonia. According to the Centers of Disease Control and Prevention (CDC), there are no vaccines against human parainfluenza virus.

Influenza is a single stranded RNA virus and a member of the Orthomyxoviridae family. There are currently three species of influenza; influenza A, influenza B and influenza C. Influenza A has been further classified based on the viral surface proteins into hemagglutinin (H or HA) and neuramidase (N). There are approximately 16H antigens (H1 to H16) and 9 N antigens (N1 to N9). Influenza A includes several subtype, including H1N1, H1N2, H2N2, H3N1, H3N2, H3N8, H5N1, H5N2, H5N3, H5N8, H5N9, H7N1, H7N2, H7N3, H7N4, H7N7, H9N2, H10N7. As with RSV, influenza viruses can be transmitted from person to person via direct contact with infected secretions and/or contaminated surfaces or objections. Complications from an influenza viral infection include pneumonia, bronchitis, dehydration, and sinus and ear infections. Medications currently approved by the FDA against an influenza infection include amantadine, rimantadine, Relenza® (zanamivir, GlaxoSmithKline) and Tamiflu® (oseltamivir, Genentech).

DEFINITIONS

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^{1A}, R^{2A}, R^{3A}, R^{4A}, R^{5A}, R^{6A}, R^{7A}, R^{8A}, R^{9A}, R^{10A}, R^{11A}, R^{12A}, R^{13A}, R^{14A}, R^{15A}, R^{16A}, R^{17A}, R^{18A}, R^{19A}, R^{20A}, R^{21A}, R^{22A}, R^{23A}, R^{24A}, R^{25A}, R^{26A}, R^{27A}, R^{28A}, R^{29A}, R^{30A}, R^{31A}, R^{32A}, R^{33A}, R^{34A}, R^{35A}, R^{36A}, R^{37A}, R^{38A}, R^{1B}, R^{2B}, R^{3B}, R^{4B}, R^{5B}, R^{6B}, R^{7B}, R^{8B}, R^{9B}, R^{10B}, R^{11B}, R^{12B}, R^{13B}, R^{14B}, R^{1C}, R^{2C}, R^{3C}, R^{4C}, R^{5C}, R^{6C}, R^{7C}, R^{8C}, R^{9C}, R^{10C}, R^{11C}, R^{12C}, R^{13C}, R^{14C}, R^{15C}, R^{16C}, R^{17C}, R^{18C}, R^{19C}, R^{20C}, R^{21C}, R^{22C}$ and $R^{23C}$ represent substituents that can be attached to the indicated atom. An R group may be substituted or unsubstituted. If two "R" groups are described as being "taken together" the R groups and the atoms they are attached to can form a cycloalkyl, cycloalkenyl, cycloalkynyl, aryl, heteroaryl or heterocycle. For example, without limitation, if $R^a$ and $R^b$ of an $NR^aR^b$ group are indicated to be "taken together," it means that they are covalently bonded to one another to form a ring:

$$-N\begin{smallmatrix}R^a\\|\\R^b\end{smallmatrix}$$

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl"

groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl, and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, a cycloalkynyl, aryl, heteroaryl, heteroalicyclyl, aralkyl, (heteroaryl)alkyl or (heteroalicyclyl)alkyl is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

As used herein, "arylthio" refers to RS—, in which R is an aryl, such as, but not limited to, phenyl. An arylthio may be substituted or unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl.

The term "amino" as used herein refers to a —$NH_2$ group.
As used herein, the term "hydroxy" refers to a —OH group.
A "cyano" group refers to a "—CN" group.
The term "azido" as used herein refers to a —$N_3$ group.
An "isocyanato" group refers to a "—NCO" group.
A "thiocyanato" group refers to a "—CNS" group.
An "isothiocyanato" group refers to an "—NCS" group.
A "mercapto" group refers to an "—SH" group.
A "carbonyl" group refers to a C=O group.
An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An N-sulfonamido may be substituted or unsubstituted.

An "O-carbamyl" group refers to a "—OC(=O)N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An N-carbamyl may be substituted or unsubstituted.

An "O-thiocarbamyl" group refers to a "—OC(=S)—N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An N-thiocarbamyl may be substituted or unsubstituted.

A "C-amido" group refers to a "—C(=O)N($R_A R_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4,N^4$-ethanocytosin, $N^6,N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)—, and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "phosphorothioate" and "phosphothioate" refer to a compound of the general formula

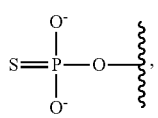

its protonated forms (for example,

and its tautomers (such as

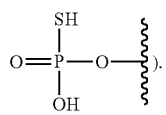

As used herein, the term "phosphate" is used in its ordinary sense as understood by those skilled in the art, and includes its protonated forms (for example,

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, triiso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' preferred, 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

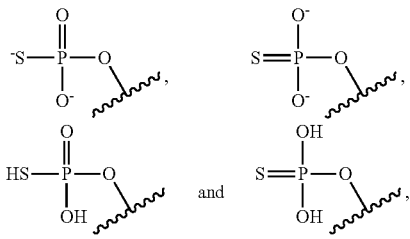

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound selected from Formula (I), Formula (II) and Formula (III), or a pharmaceutically acceptable salt of the foregoing:

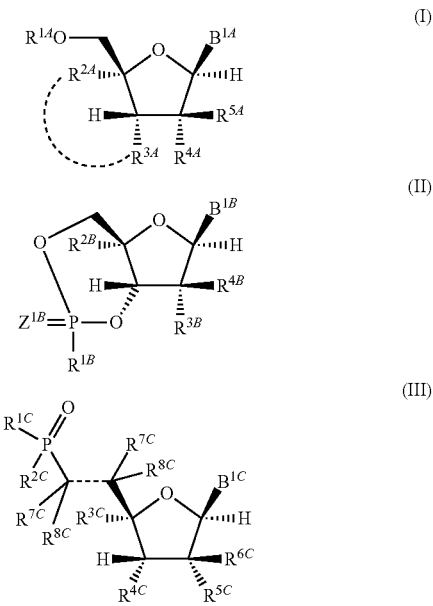

wherein: $B^{1A}$, $B^{1B}$ and $B^{1C}$ can be independently an optionally substituted heterocyclic base or an optionally substituted heterocyclic base with a protected amino group; $R^{1A}$ can be selected from hydrogen, an optionally substituted acyl, an optionally substituted O-linked amino acid,

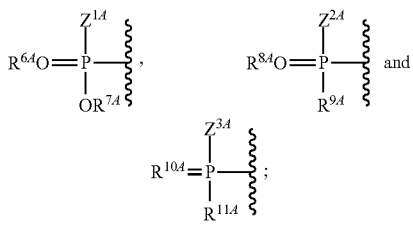

when the dashed line (------) of Formula (I) is a single bond, $R^{2A}$ can be $CH_2$, and $R^{3A}$ can be O (oxygen); when the dashed line (------) of Formula (I) is absent, $R^{2A}$ can be selected from an optionally substituted $C_{1-6}$ alkyl, an optionally substituted $C_{2-6}$ alkenyl, an optionally substituted $C_{2-6}$ alkynyl, an optionally substituted $C_{3-6}$ cycloalkyl, an optionally substituted —O—$C_{1-6}$ alkyl, an optionally substituted O—$C_{3-6}$ alkenyl, an optionally substituted O—$C_{3-6}$ alkenyl and cyano, and $R^{3A}$ can be selected from OH, —OC(=O)R"$^A$ and an optionally substituted O-linked amino acid; $R^{1B}$ can be selected from $O^-$, OH,

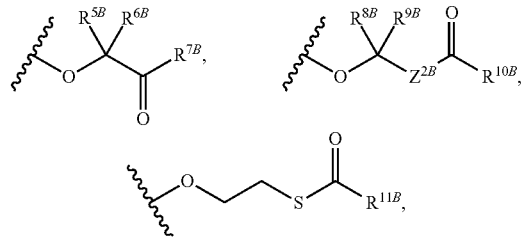

an optionally substituted N-linked amino acid and an optionally substituted N-linked amino acid ester derivative; $R^{1C}$ and $R^{2C}$ can be independently selected from $O^-$, OH, an optionally substituted $C_{1-6}$ alkoxy,

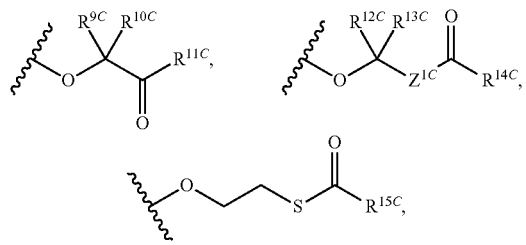

an optionally substituted N-linked amino acid and an optionally substituted N-linked amino acid ester derivative; or $R^{1C}$ can be

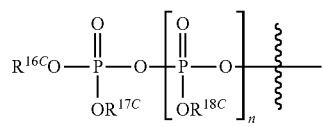

and $R^{2C}$ can be $O^-$ or OH; $R^{2B}$ and $R^{3C}$ can be independently selected from an optionally substituted $C_{1-6}$ alkyl, an optionally substituted $C_{2-6}$ alkenyl, an optionally substituted $C_{2-6}$ alkynyl, an optionally substituted —O—$C_{1-6}$ alkyl, an optionally substituted —O—$C_{3-6}$ alkenyl, an optionally substituted —O—$C_{3-6}$ alkynyl, an optionally substituted $C_{3-6}$ cycloalkyl and cyano; $R^{4C}$ can be selected from OH, —OC(=O)R"'$^C$ and an optionally substituted O-linked amino acid; $R^{4A}$, $R^{3B}$ and $R^{5C}$ can be independently a halogen; $R^{5A}$, $R^{4B}$ and $R^{6C}$ can be independently hydrogen or halogen; $R^{6A}$, $R^{7A}$ and $R^{8A}$ can be independently selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—$(CR^{15A}R^{16A})_p$—O—$C_{1-24}$ alkyl, an optionally substituted *—$(CR^{17A}R^{18A})_q$—O—$C_{1-24}$ alkenyl,

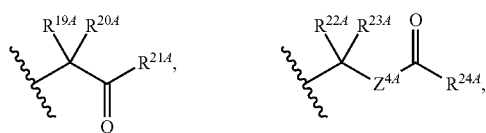

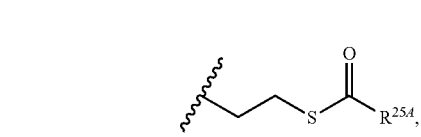

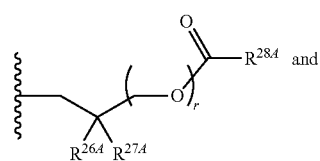

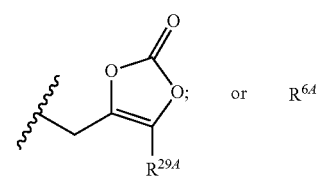

can be

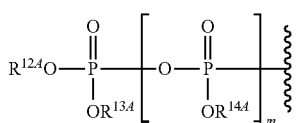

and $R^{7A}$ can be absent or hydrogen; or $R^{6A}$ and $R^{7A}$ can be taken together to form a moiety selected from an optionally substituted

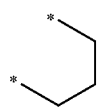

and an optionally substituted

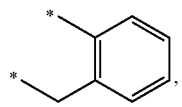

wherein the oxygens connected to $R^{6A}$ and $R^{7A}$, the phosphorus and the moiety form a six-membered to ten-membered ring system; $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative; $R^{10A}$ and $R^{11A}$ can be independently an optionally substituted N-linked amino acid or an optionally substituted N-linked amino acid ester derivative; $R^{12A}$, $R^{13A}$ and $R^{14A}$ can be independently absent or hydrogen; each $R^{15A}$, each $R^{16A}$, each $R^{17A}$ and each $R^{18A}$ can be independently hydrogen, an optionally substituted $C_{1-24}$ alkyl or alkoxy; $R^{19A}$, $R^{20A}$, $R^{22A}$, $R^{23A}$, $R^{5B}$, $R^{6B}$, $R^{8B}$, $R^{9B}$, $R^{9C}$, $R^{10C}$, $R^{12C}$ and $R^{13C}$ can be independently selected from hydrogen, an optionally substituted $C_{1-24}$ alkyl and an optionally substituted aryl; $R^{21A}$, $R^{24A}$, $R^{7B}$, $R^{10B}$, $R^{11C}$ and $R^{14C}$ can be independently selected from hydrogen, an optionally substituted $C_{1-24}$ alkyl, an optionally substituted aryl, an optionally substituted —O—$C_{1-24}$ alkyl and an optionally substituted —O-aryl; $R^{25A}$, $R^{29A}$, $R^{11B}$ and $R^{15C}$ can be independently selected from hydrogen, an optionally substituted $C_{1-24}$ alkyl and an optionally substituted aryl; $R^{16C}$, $R^{17C}$ and $R^{18C}$ can be independently absent or hydrogen; $R^{26A}$ and $R^{27A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30A}$ and $R^{31A}$ can be independently selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; for Formula (III), ------ can be a single bond or a double bond; when ------ is a single bond, each $R^{7C}$ and each $R^{8C}$ can be independently hydrogen or halogen; and when ------ is a double bond, each $R^{7C}$ is absent and each $R^{8C}$ can be independently hydrogen or halogen; $R^{nA}$ and $R^{nC}$ can be independently an optionally substituted $C_{1-24}$-alkyl, m and n can be independently 0 or 1; p and q can be independently selected from 1, 2 and 3; r can be 1 or 2; $Z^{1A}$, $Z^{2A}$, $Z^{3A}$, $Z^{4A}$, $Z^{1B}$, $Z^{2B}$ and $Z^{1C}$ can be independently O or S; and provided that when the dashed line (------) of Formula (I) is absent; $R^{1A}$ is

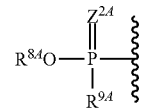

wherein $R^{8A}$ is an unsubstituted $C_{1-4}$ alkyl or phenyl optionally para-substituted with a halogen or methyl and $R^{9A}$ is methyl ester, ethyl ester, isopropyl ester, n-butyl ester, benzyl ester or phenyl ester of an amino acid selected from glycine, alanine, valine, leucine, phenylalanine, tryptophan, methionine and proline; $R^{3A}$ is OH; $R^{4A}$ is fluoro; $R^{5A}$ is fluoro or hydrogen; and $B^{1A}$ is an unsubstituted uracil; then $R^{2A}$ cannot be —$OCH_3$; provided that when the dashed line (------) of Formula (I) is absent; $R^{1A}$ is H; $R^{3A}$ is OH; $R^{4A}$ is fluoro; $R^{5A}$ is fluoro; and $B^{1A}$ is an unsubstituted cytosine; then $R^{2A}$ cannot be allenyl; provided that when the dashed line (------) of Formula (I) is absent; $R^{1A}$ is H; $R^{3A}$ is OH; $R^{4A}$ is fluoro; $R^{5A}$ is hydrogen; and $B^{1A}$ is an unsubstituted thymine; then $R^{2A}$ cannot be $C_1$ alkyl substituted with an optionally substituted N-amido (for example, —NC(=O)$CF_3$); and provided that when the dashed line (------) of Formula (I) is absent; $R^{1A}$ is H; $R^{3A}$ is OH; $R^{4A}$ is fluoro; $R^{5A}$ is fluoro; and $B^{1A}$ is an unsubstituted cytosine; then $R^{2A}$ cannot be ethynyl.

In some embodiments, the compound can be a compound of Formula (I), or a pharmaceutically acceptable salt thereof, wherein: $B^{1A}$ can be an optionally substituted heterocyclic base or an optionally substituted heterocyclic base with a protected amino group; $R^{1A}$ can be selected from hydrogen,

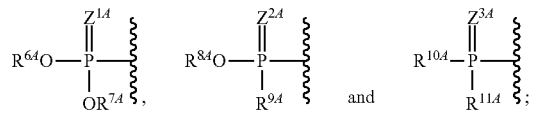

when the dashed line (------) of Formula (I) is a single bond, $R^{2A}$ is $CH_2$, and $R^{3A}$ is O (oxygen); when the dashed line (------) of Formula (I) is absent, $R^{2A}$ can be selected from an optionally substituted $C_{1-6}$ alkyl, an optionally substituted $C_{2-6}$ alkenyl, an optionally substituted $C_{2-6}$ alkynyl, an optionally substituted —O—$C_{1-6}$ alkyl, an optionally substituted —O—$C_{3-6}$ alkenyl, an optionally substituted —O—$C_{3-6}$ alkynyl and cyano, and $R^{3A}$ is OH; $R^{4A}$ can be a halogen; $R^{5A}$ can be hydrogen or halogen; $R^{6A}$, $R^{7A}$ and $R^{8A}$ can be independently selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—$(CR^{15A}R^{16A})_p$—O—$C_{1-24}$ alkyl, an optionally substituted *—$(CR^{17A}R^{18A})_q$—O—$C_{1-24}$ alkenyl,

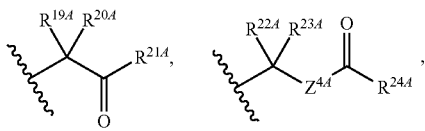

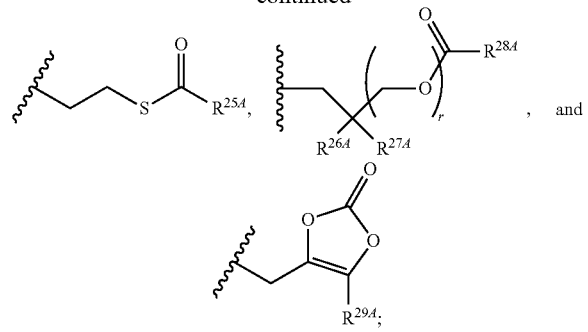

or $R^{6A}$ can be

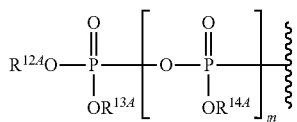

and $R^{7A}$ can be absent or hydrogen; or $R^{6A}$ and $R^{7A}$ can be taken together to form a moiety selected from an optionally substituted

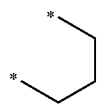

and an optionally substituted

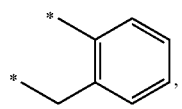

wherein the oxygens connected to $R^{6A}$ and $R^{7A}$, the phosphorus and the moiety form a six-membered to ten-membered ring system. $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative; $R^{10A}$ and $R^{11A}$ can be independently an optionally substituted N-linked amino acid or an optionally substituted N-linked amino acid ester derivative; $R^{12A}$, $R^{13A}$ and $R^{14A}$ can be independently absent or hydrogen; each $R^{15A}$, each $R^{16A}$, each $R^{17A}$ and each $R^{18A}$ can be independently hydrogen, an optionally substituted $C_{1-24}$ alkyl or alkoxy; $R^{19A}$, $R^{20A}$, $R^{22A}$ and $R^{23A}$ can be independently selected from hydrogen, an optionally substituted $C_{1-24}$ alkyl and an optionally substituted aryl; $R^{21A}$ and $R^{24A}$ can be independently selected from hydrogen, an optionally substituted $C_{1-24}$ alkyl, an optionally substituted aryl, an optionally substituted —O—$C_{1-24}$ alkyl and an optionally substituted —O-aryl; $R^{25A}$ and $R^{29A}$ can be independently selected from hydrogen, an optionally substituted $C_{1-24}$ alkyl and an optionally substituted aryl; $R^{26A}$ and $R^{27A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; $R^{30A}$ and $R^{31A}$ can be independently selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; m can be 0 or 1; p and q can be independently selected from 1, 2 and 3; r can be 1 or 2; $Z^{1A}$, $Z^{2A}$, $Z^{3A}$ and $Z^{4A}$ can be independently O or S. In some embodiments, a compound of Formula (I) can have a structure shown herein, provided that when the dashed line (------) of Formula (I) is absent; $R^{1A}$ is

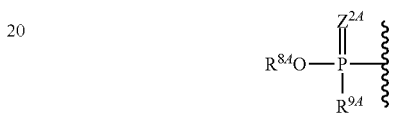

wherein $R^{8A}$ is an unsubstituted $C_{1-4}$ alkyl or phenyl optionally para-substituted with a halogen or methyl and $R^{9A}$ is methyl ester, ethyl ester, isopropyl ester, n-butyl ester, benzyl ester or phenyl ester of an amino acid selected from glycine, alanine, valine, leucine, phenylalanine, tryptophan, methionine and proline; $R^{3A}$ is OH; $R^{4A}$ is fluoro; $R^{5A}$ is fluoro or hydrogen; and $B^{1A}$ is an unsubstituted uracil; then $R^{2A}$ cannot be —OCH$_3$; provided that when the dashed line (------) of Formula (I) is absent; $R^{1A}$ is H; $R^{3A}$ is OH; $R^{4A}$ is fluoro; $R^{5A}$ is fluoro; and $B^{1A}$ is an unsubstituted cytosine; then $R^{2A}$ cannot be allenyl; provided that when the dashed line (------) of Formula (I) is absent; $R^{1A}$ is H; $R^{3A}$ is OH; $R^{4A}$ is fluoro; $R^{5A}$ is hydrogen; and $B^{1A}$ is an unsubstituted thymine; then $R^{2A}$ cannot be $C_1$ alkyl substituted with an N-amido; and provided that when the dashed line (------) of Formula (I) is absent; $R^{1A}$ is H; $R^{3A}$ is OH; $R^{4A}$ is fluoro; $R^{5A}$ is fluoro; and $B^{1A}$ is an unsubstituted cytosine; then $R^{2A}$ cannot be ethynyl.

In some embodiments, $R^{1A}$ can be

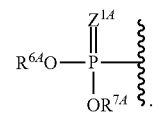

In some embodiments, $R^{6A}$ and $R^{7A}$ can be both hydrogen. In other embodiments, $R^{6A}$ and $R^{7A}$ can be both absent. In still other embodiments, at least one $R^{6A}$ and $R^{7A}$ can be absent. In yet still other embodiments, at least one $R^{6A}$ and $R^{7A}$ can be hydrogen. Those skilled in the art understand that when $R^{6A}$ and/or $R^{7A}$ are absent, the associated oxygen(s) will have a negative charge. For example, when $R^{6A}$ is absent, the oxygen associated with $R^{6A}$ will have a negative charge. In some embodiments, $Z^{1A}$ can be O (oxygen). In other embodiments, $Z^{1A}$ can be S (sulfur). In some embodiments, $R^{1A}$ can be a monophosphate. In other embodiments, $R^{1A}$ can be a monothiophosphate.

In some embodiments, when $R^{1A}$ is

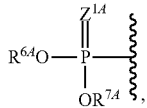

one of $R^{6A}$ and $R^{7A}$ can be hydrogen, and the other of $R^{6A}$ and $R^{7A}$ is selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, one of $R^{6A}$ and $R^{7A}$ can be hydrogen, and the other of $R^{6A}$ and $R^{7A}$ can be an optionally substituted $C_{1-24}$ alkyl. In other embodiments, both $R^{6A}$ and $R^{7A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl). In some embodiments, both $R^{6A}$ and $R^{7A}$ can be an optionally substituted $C_{1-24}$ alkyl. In other embodiments, both $R^{6A}$ and $R^{7A}$ can be an optionally substituted $C_{2-24}$ alkenyl. In some embodiments, $R^{6A}$ and $R^{7A}$ can be independently an optionally substituted version of the following: myristoleyl, myristyl, palmitoleyl, palmityl, sapienyl, oleyl, elaidyl, vaccenyl, linoleyl, α-linolenyl, arachidonyl, eicosapentaenyl, erucyl, docosahexaenyl, caprylyl, capryl, lauryl, stearyl, arachidyl, behenyl, lignoceryl, and cerotyl.

In some embodiments, at least one of $R^{6A}$ and $R^{7A}$ can be $*—(CR^{15A}R^{16A})_p—O—C_{1-24}$ alkyl. In other embodiments, $R^{6A}$ and $R^{7A}$ can be both $*—(CR^{15A}R^{16A})_p—O—C_{1-24}$ alkyl. In some embodiments, each $R^{15A}$ and each $R^{16A}$ are hydrogen. In other embodiments, at least one of $R^{15A}$ and $R^{16A}$ is an optionally substituted $C_{1-24}$ alkyl. In other embodiments, at least one of $R^{15A}$ and $R^{16A}$ is an alkoxy (for example, benzoxy). In some embodiments, p can be 1. In other embodiments, p can be 2. In still other embodiments, p can be 3.

In some embodiments, at least one of $R^{6A}$ and $R^{7A}$ can be $*—(CR^{17A}R^{18A})_q—O—C_{2-24}$ alkenyl. In other embodiments, $R^{6A}$ and $R^{7A}$ can be both $*—(CR^{17A}R^{18A})_q—O—C_{2-24}$ alkenyl. In some embodiments, each $R^{17A}$ and each $R^{18A}$ are hydrogen. In other embodiments, at least one of $R^{17A}$ and $R^{18A}$ is an optionally substituted $C_{1-24}$ alkyl. In some embodiments, q can be 1. In other embodiments, q can be 2. In still other embodiments, q can be 3. When at least one of $R^{6A}$ and $R^{7A}$ is $*—(CR^{15A}R^{16A})_p—O—C_{1-24}$ alkyl or $*—(CR^{17A}R^{18A})_q—O—C_{2-24}$ alkenyl, the $C_{1-24}$ alkyl can be selected from caprylyl, capryl, lauryl, myristyl, palmityl, stearyl, arachidyl, behenyl, lignoceryl, and cerotyl, and the $C_{2-24}$ alkenyl can be selected from myristoleyl, palmitoleyl, sapienyl, oleyl, elaidyl, vaccenyl, linoleyl, α-linolenyl, arachidonyl, eicosapentaenyl, erucyl and docosahexaenyl.

In some embodiments, when $R^{1A}$ is

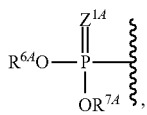

at least one of $R^{6A}$ and $R^{7A}$ can be selected from

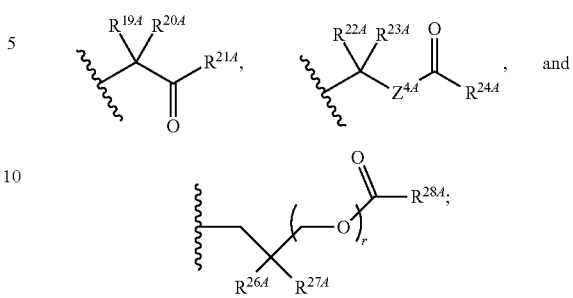

and the other of $R^{6A}$ and $R^{7A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

In some embodiments, at least one of $R^{6A}$ and $R^{7A}$ can be

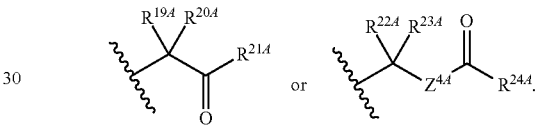

In some embodiments, both $R^{6A}$ and $R^{7A}$ can be

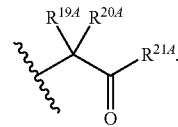

When one or both of $R^{6A}$ and $R^{7A}$ are

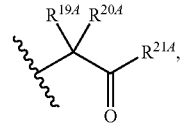

$R^{19A}$ and $R^{20A}$ can be independently selected from hydrogen, an optionally substituted $C_{1-24}$ alkyl and an optionally substituted aryl; and $R^{21A}$ can be selected from hydrogen, an optionally substituted $C_{1-24}$ alkyl, an optionally substituted aryl, an optionally substituted —O—$C_{1-24}$ alkyl and an optionally substituted —O-aryl. In some embodiments, $R^{19A}$ and $R^{20A}$ can be hydrogen. In other embodiments, at least one of $R^{19A}$ and $R^{20A}$ can be an optionally substituted $C_{1-24}$ alkyl or an optionally substituted aryl. In some embodiments, $R^{21A}$ can be an optionally substituted $C_{1-24}$ alkyl. In other embodiments, $R^{21A}$ can be an optionally substituted aryl. In still other embodiments, $R^{21A}$ can be an optionally substituted —O—$C_{1-24}$ alkyl or an optionally substituted —O-aryl.

In some embodiments, both $R^{6A}$ and $R^{7A}$ can be

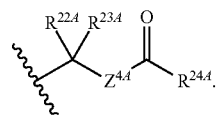

When one or both of $R^{6A}$ and $R^{7A}$ are

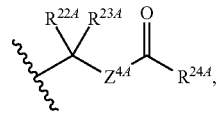

$R^{22A}$ and $R^{23A}$ can be independently selected from hydrogen, an optionally substituted $C_{1-24}$ alkyl and an optionally substituted aryl; $R^{24A}$ can be independently selected from hydrogen, an optionally substituted $C_{1-24}$ alkyl, an optionally substituted aryl, an optionally substituted —O—$C_{1-24}$ alkyl and an optionally substituted —O-aryl; and $Z^{4A}$ can be independently O (oxygen) or S (sulfur). In some embodiments, $R^{22A}$ and $R^{23A}$ can be hydrogen. In other embodiments, at least one of $R^{22A}$ and $R^{23A}$ can be an optionally substituted $C_{1-24}$ alkyl or an optionally substituted aryl. In some embodiments, $R^{24A}$ can be an optionally substituted $C_{1-24}$ alkyl. In other embodiments, $R^{24A}$ can be an optionally substituted aryl. In still other embodiments, $R^{24A}$ can be an optionally substituted —O—$C_{1-24}$ alkyl or an optionally substituted —O-aryl. In some embodiments, $Z^{4A}$ can be O (oxygen). In other embodiments, $Z^{4A}$ can be or S (sulfur). In some embodiments, one or both of $R^{6A}$ and $R^{7A}$ can be isopropylcarbonyloxymethyl. In some embodiments, one or both of $R^{6A}$ and $R^{7A}$ can be pivaloyloxymethyl.

In some embodiments, both $R^{6A}$ and $R^{7A}$ can be

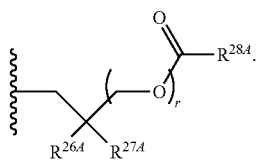

When one or both of $R^{6A}$ and $R^{7A}$ are

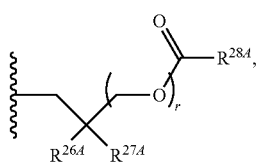

$R^{26A}$ and $R^{27A}$ can be independently —C≡N or an optionally substituted substituent selected from $C_{2-8}$ organylcarbonyl, $C_{2-8}$ alkoxycarbonyl and $C_{2-8}$ organylaminocarbonyl; $R^{28A}$ can be selected from hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and r can be 1 or 2. In some embodiments, $R^{26A}$ can be —C≡N and $R^{27A}$ can be an optionally substituted $C_{2-8}$ alkoxycarbonyl, such as —C(=O)OCH$_3$. In other embodiments, $R^{26A}$ can be —C≡N and $R^{27A}$ can be an optionally substituted $C_{2-8}$ organylaminocarbonyl, for example, —C(=O)NHCH$_2$CH$_3$ and —C(=O)NHCH$_2$CH$_2$phenyl. In some embodiments, both $R^{26A}$ and $R^{27A}$ can be an optionally substituted $C_{2-8}$ organylcarbonyl, such as —C(=O)CH$_3$. In some embodiments, both $R^{26A}$ and $R^{27A}$ can be an optionally substituted $C_{1-8}$ alkoxycarbonyl, for example, —C(=O)OCH$_2$CH$_3$ and —C(=O)OCH$_3$. In some embodiments, including those described in this paragraph, $R^{28A}$ can be an optionally substituted $C_{1-4}$-alkyl. In some embodiment, $R^{28A}$ can be methyl or tert-butyl. In some embodiments, r can be 1. In other embodiments, r can be 2.

Example of

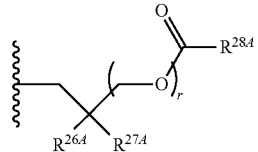

include, but are not limited to the following:

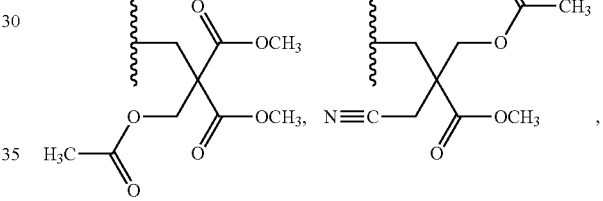

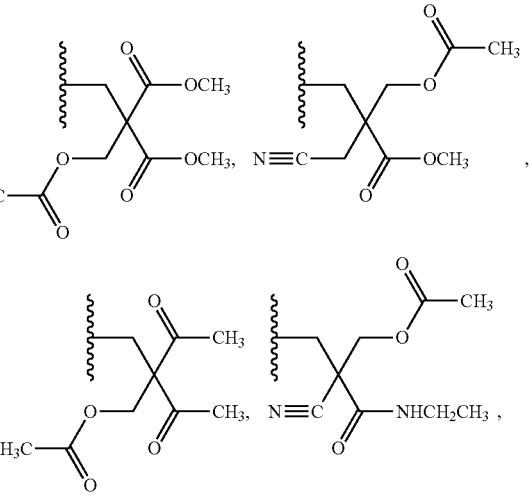

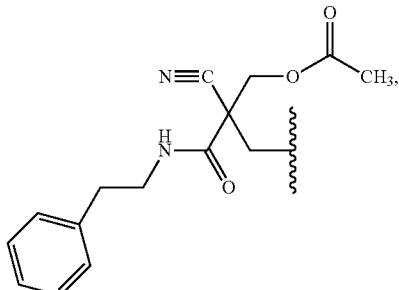

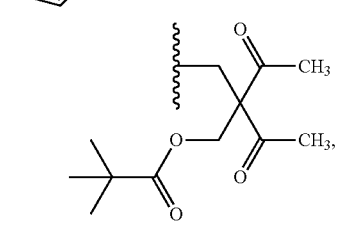

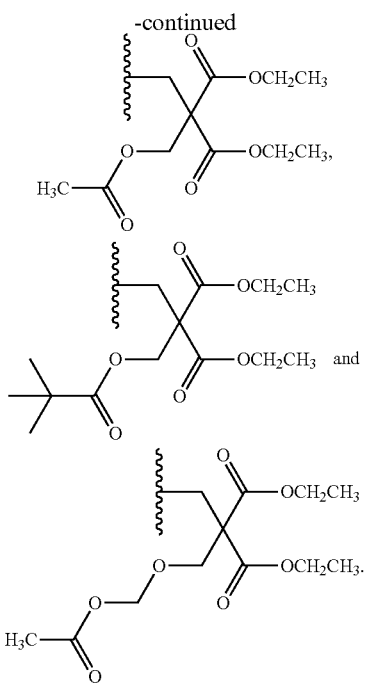

In some embodiments, $R^{6A}$ and $R^{7A}$ can be both an optionally substituted aryl. In some embodiments, at least one of $R^{6A}$ and $R^{7A}$ can be an optionally substituted aryl. For example, both $R^{6A}$ and $R^{7A}$ can be an optionally substituted phenyl or an optionally substituted naphthyl. When substituted, the substituted aryl can be substituted with 1, 2, 3 or more than 3 substituents. When more the two substituents are present, the substituents can be the same or different. In some embodiments, when at least one of $R^{6A}$ and $R^{7A}$ is a substituted phenyl, the substituted phenyl can be a para-, ortho- or meta-substituted phenyl.

In some embodiments, $R^{6A}$ and $R^{7A}$ can be both an optionally substituted aryl($C_{1-6}$ alkyl). In some embodiments, at least one of $R^{6A}$ and $R^{7A}$ can be an optionally substituted aryl($C_{1-6}$ alkyl). For example, both $R^{6A}$ and $R^{7A}$ can be an optionally substituted benzyl. When substituted, the substituted benzyl group can be substituted with 1, 2, 3 or more than 3 substituents. When more the two substituents are present, the substituents can be the same or different. In some embodiments, the aryl group of the aryl($C_{1-6}$ alkyl) can be a para-, ortho- or meta-substituted phenyl.

In some embodiments, $R^{6A}$ and $R^{7A}$ can be both

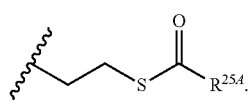

In some embodiments, at least one of $R^{6A}$ and $R^{7A}$ can be

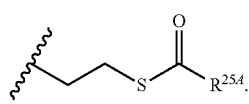

In some embodiments, $R^{25A}$ can be hydrogen. In other embodiments, $R^{25A}$ can be an optionally substituted $C_{1-24}$ alkyl. In still other embodiments, $R^{25A}$ can be an optionally substituted aryl. In some embodiments, $R^{25A}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained).

In some embodiments, $R^{6A}$ and $R^{7A}$ can be both

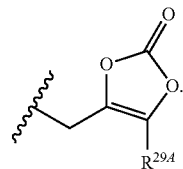

In some embodiments, at least one of $R^{6A}$ and $R^{7A}$ can be

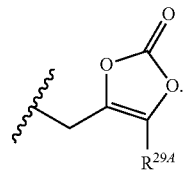

In some embodiments, $R^{29A}$ can be hydrogen. In other embodiments, $R^{29A}$ can be an optionally substituted $C_{1-24}$ alkyl. In some embodiments, $R^{29A}$ can be a $C_{1-4}$ alkyl, such as methyl, ethyl, n-propyl, iso-propyl, n-butyl, iso-butyl and t-butyl. In still other embodiments, $R^{29A}$ can be an optionally substituted aryl, such as an optionally substituted phenyl or an optionally substituted naphthyl.

In some embodiments, $R^{1A}$ can be

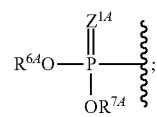

$R^{6A}$ can be

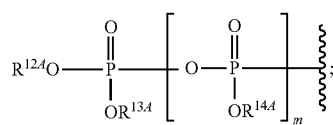

$R^{7A}$ can be absent or hydrogen; $R^{12A}$, $R^{13A}$ and $R^{14A}$ can be independently absent or hydrogen; and m can be 0 or 1. In some embodiments, m can be 0, and $R^{7A}$, $R^{12A}$ and $R^{13A}$ can be independently absent or hydrogen. In other embodiments, m can be 1, and $R^{7A}$, $R^{12A}$, $R^{13A}$ and $R^{14A}$ can be independently absent or hydrogen. Those skilled in the art understand that when m is 0, $R^{6A}$ can be diphosphate, when $Z^{1A}$ is oxygen, or an alpha-thiodiphosphate, when $Z^{1A}$ is sulfur. Likewise, those skilled in the art understand that when m is 1, $R^{6A}$ can be triphosphate, when $Z^{1A}$ is oxygen, or an alpha-thiotriphosphate, when $Z^{1A}$ is sulfur.

In some embodiments, $R^{6A}$ and $R^{7A}$ can be taken together to form an optionally substituted

For example, $R^{1A}$ can be an optionally substituted

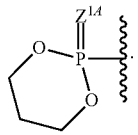

When substituted, the ring can be substituted 1, 2, 3 or 3 or more times. When substituted with multiple substituents, the substituents can be the same or different. In some embodiments, when $R^{1A}$ is

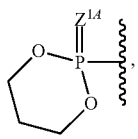

the ring can be substituted with an optionally substituted aryl group and/or an optionally substituted heteroaryl. An example of a suitable heteroaryl is pyridinyl. In some embodiments, $R^{6A}$ and $R^{7A}$ can be taken together to form an optionally substituted

such as

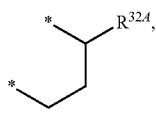

wherein $R^{32A}$ can be an optionally substituted aryl, an optionally substituted heteroaryl or an optionally substituted heterocyclyl.

In some embodiments, $R^{6A}$ and $R^{7A}$ can be taken together to form an optionally substituted

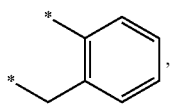

wherein the oxygens connected to $R^{6A}$ and $R^{7A}$, the phosphorus and the moiety form a six-membered to ten-membered ring system. Example of an optionally substituted

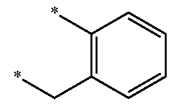

include

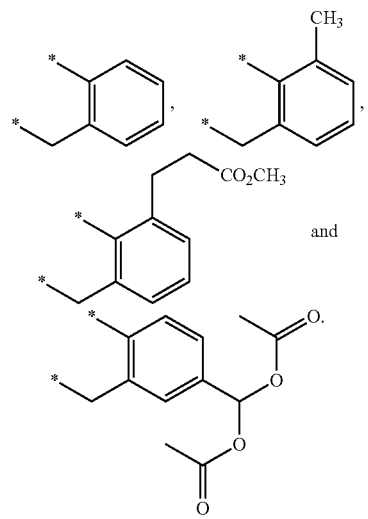

In some embodiments, $R^{6A}$ and $R^{7A}$ can be the same. In some embodiments, $R^{6A}$ and $R^{7A}$ can be the different.

In some embodiments, $Z^{1A}$ can be oxygen. In other embodiments, $Z^{1A}$ can be sulfur.

In some embodiments, $R^{1A}$ can be

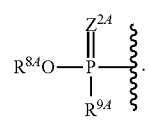

In some embodiments, $R^{8A}$ can be selected from absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9A}$ can be independently selected from an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be hydrogen, and $R^{9A}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained), and hexyl (branched and straight-chained). In other embodiments, $R^{8A}$ can be hydrogen, and $R^{9A}$ can be $NR^{30A}R^{31A}$, wherein $R^{30}$ and $R^{31}$ can be independently selected from hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl.

In some embodiments, $R^{8A}$ can be absent or hydrogen; and $R^{9A}$ can be an optionally substituted N-linked amino acid or an optionally substituted N-linked amino acid ester derivative. In other embodiments, $R^{8A}$ can be an optionally substituted aryl; and $R^{9A}$ can be an optionally substituted N-linked amino acid or an optionally substituted N-linked amino acid ester derivative. In still other embodiments, $R^{8A}$ can be an optionally substituted heteroaryl; and $R^{9A}$ can be an optionally substituted N-linked amino acid or an optionally substituted N-linked amino acid ester derivative. In some embodiments, $R^{9A}$ can be selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. Examples of an optionally substituted N-linked amino acid ester derivatives include optionally substituted versions of the following: alanine isopropyl ester, alanine cyclohexyl ester, alanine neopentyl ester, valine isopropyl ester and leucine isopropyl ester. In some embodiments, $R^{9A}$ can have the structure

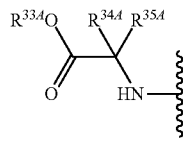

wherein $R^{33A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{34A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{35A}$ can be hydrogen or an optionally substituted $C_{1-4}$-alkyl; or $R^{34A}$ and $R^{35A}$ can be taken together to form an optionally substituted $C_{3-6}$ cycloalkyl.

When $R^{34A}$ is substituted, $R^{34A}$ can be substituted with one or more substituents selected from N-amido, mercapto, alkylthio, an optionally substituted aryl, hydroxy, an optionally substituted heteroaryl, O-carboxy, and amino. In some embodiments, $R^{34A}$ can be an unsubstituted $C_{1-6}$-alkyl, such as those described herein. In some embodiments, $R^{34A}$ can be hydrogen. In other embodiments, $R^{34A}$ can be methyl. In some embodiments, $R^{33A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{33A}$ can be methyl or isopropyl. In some embodiments, $R^{33A}$ can be ethyl or neopentyl. In other embodiments, $R^{33A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{33A}$ can be an optionally substituted cyclohexyl. In still other embodiments, $R^{33A}$ can be an optionally substituted aryl, such as phenyl and naphthyl. In yet still other embodiments, $R^{33A}$ can be an optionally substituted aryl($C_{1-6}$ alkyl). In some embodiments, $R^{33A}$ can be an optionally substituted benzyl. In some embodiments, $R^{33A}$ can be an optionally substituted $C_{1-6}$ haloalkyl, for example, $CF_3$. In some embodiments, $R^{35A}$ can be hydrogen. In other embodiments, $R^{35A}$ can be an optionally substituted $C_{1-4}$-alkyl, such as methyl, ethyl, n-propyl, isopropyl, n-butyl, isobutyl and tert-butyl. In an embodiment, $R^{35A}$ can be methyl. In some embodiments, $R^{34A}$ and $R^{35A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{34A}$ and $R^{35A}$, the carbon to which $R^{34A}$ and $R^{35A}$ are attached may be a chiral center. In some embodiment, the carbon to which $R^{34A}$ and $R^{35A}$ are attached may be a (R)-chiral center. In other embodiments, the carbon to which $R^{34A}$ and $R^{35A}$ are attached may be a (S)-chiral center.

In some embodiments, when $R^{1A}$ is

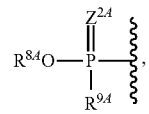

$Z^{2A}$ can be O (oxygen). In other embodiments, when $R^{1A}$ is

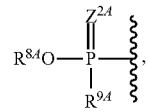

$Z^{2A}$ can be S (sulfur).

In some embodiments, $R^{1A}$ can be

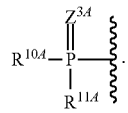

In some embodiments, $R^{10A}$ and $R^{11A}$ can be both an optionally substituted N-linked amino acid or an optionally substituted N-linked amino acid ester derivative. In some embodiments, $R^{10A}$ and $R^{11A}$ can be independently selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{10A}$ and $R^{11A}$ can be an optionally substituted version of the following: alanine isopropyl ester, alanine cyclohexyl ester, alanine neopentyl ester, valine isopropyl ester and leucine isopropyl ester. In some embodiments, $R^{10A}$ and $R^{11A}$ can independently have the structure

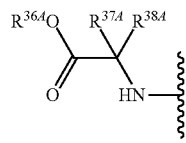

wherein $R^{36A}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{37A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{38A}$ can be hydrogen or an optionally substituted $C_{1-4}$-alkyl; or $R^{37A}$ and $R^{38A}$ can be taken together to form an optionally substituted $C_{3-6}$ cycloalkyl.

When $R^{37A}$ is substituted, $R^{37A}$ can be substituted with one or more substituents selected from N-amido, mercapto, alkylthio, an optionally substituted aryl, hydroxy, an optionally substituted heteroaryl, O-carboxy, and amino. In some embodiments, $R^{37A}$ can be an unsubstituted $C_{1-6}$-alkyl, such as those described herein. In some embodiments, $R^{37A}$ can be hydrogen. In other embodiments, $R^{37A}$ can be methyl. In some embodiments, $R^{36A}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{36A}$ can be methyl or isopropyl. In some embodiments, $R^{36A}$ can be ethyl or neopentyl. In other embodiments, $R^{36A}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{36A}$ can be an optionally substituted cyclohexyl. In still other embodiments, $R^{36A}$ can be an optionally substituted aryl, such as phenyl and naphthyl. In yet still other embodiments, $R^{36A}$ can be an optionally substituted aryl($C_{1-6}$ alkyl). In some embodiments, $R^{36A}$ can be an optionally substituted benzyl. In some embodiments, $R^{36A}$ can be an optionally substituted $C_{1-6}$ haloalkyl, for example, $CF_3$. In some embodiments, $R^{38A}$ can be hydrogen. In other embodiments, $R^{38A}$ can be an optionally substituted $C_{1-4}$-alkyl, such as methyl, ethyl, n-propyl, isopropyl, n-butyl, isobutyl and tert-butyl. In an embodiment, $R^{38A}$ can be methyl. In some embodiments, $R^{37A}$ and $R^{38A}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{37A}$ and $R^{38A}$, the carbon to which $R^{37A}$ and $R^{38A}$ are attached may be a chiral center. In some embodiment, the carbon to which $R^{37A}$ and $R^{38A}$ are attached may be a (R)-chiral center. In other embodiments, the carbon to which $R^{37A}$ and $R^{38A}$ are attached may be a (S)-chiral center.

Examples of suitable

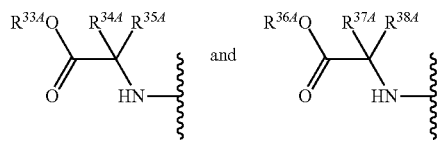

groups include the following:

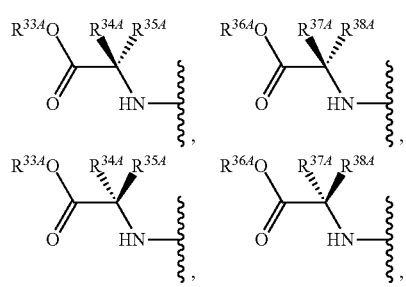

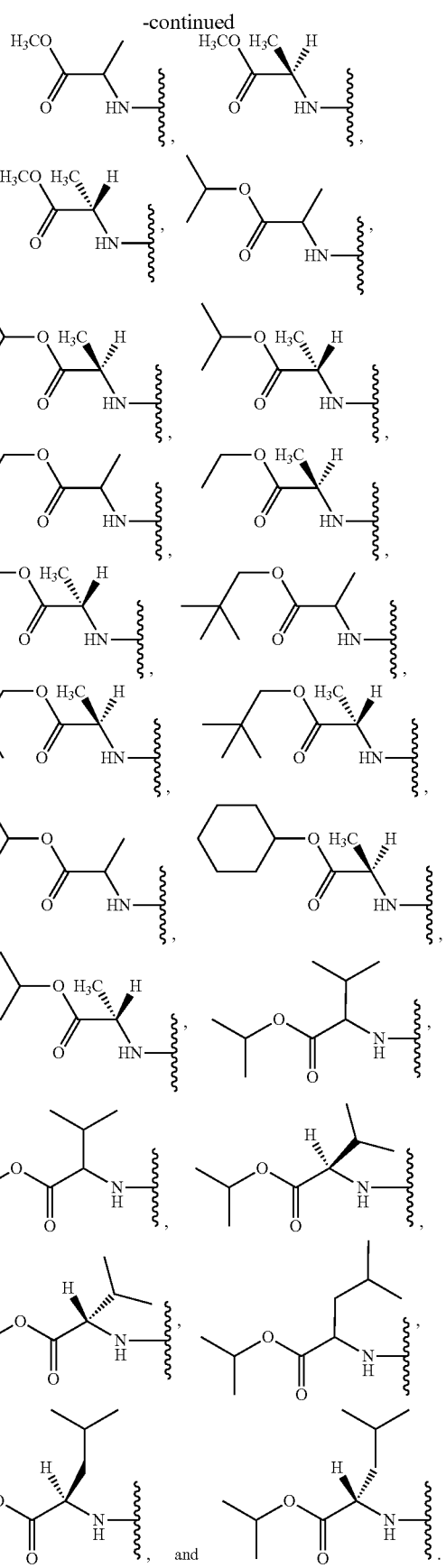

In some embodiments, $R^{10A}$ and $R^{11A}$ can be the same. In some embodiments, $R^{10A}$ and $R^{11A}$ can be the different.

In some embodiments, $Z^{3A}$ can be O (oxygen). In other embodiments, $Z^{3A}$ can be S (sulfur).

In some embodiments, $R^{1A}$ can be hydrogen. In some embodiments, $R^{1A}$ can be an optionally substituted acyl. In other embodiments, $R^{1A}$ can be —C(=O)$R^{39A}$, wherein $R^{39A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R^{39A}$ can be a substituted $C_{1-12}$ alkyl. In other embodiments, $R^{39A}$ can be an unsubstituted $C_{1-12}$ alkyl.

In still other embodiments, $R^{1A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

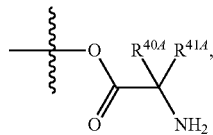

wherein $R^{40A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{41A}$ can be hydrogen or an optionally substituted $C_{1-4}$-alkyl; or $R^{40A}$ and $R^{41A}$ can be taken together to form an optionally substituted $C_{3-6}$ cycloalkyl. Those skilled in the art understand that when $R^{1A}$ is an optionally substituted O-linked amino acid, the oxygen of $R^{1A}$O— of Formula (I) is part of the optionally substituted O-linked amino acid. For example, when $R^{1A}$ is

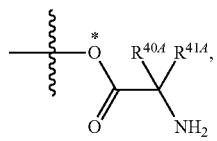

the oxygen indicated with "*" is the oxygen of $R^{1A}$O— of Formula (I).

When $R^{40A}$ is substituted, $R^{40A}$ can be substituted with one or more substituents selected from N-amido, mercapto, alkylthio, an optionally substituted aryl, hydroxy, an optionally substituted heteroaryl, O-carboxy, and amino. In some embodiments, $R^{40A}$ can be an unsubstituted $C_{1-6}$-alkyl, such as those described herein. In some embodiments, $R^{40A}$ can be hydrogen. In other embodiments, $R^{40A}$ can be methyl. In some embodiments, $R^{41A}$ can be hydrogen. In other embodiments, $R^{41A}$ can be an optionally substituted $C_{1-4}$-alkyl, such as methyl, ethyl, n-propyl, isopropyl, n-butyl, isobutyl and tert-butyl. In an embodiment, $R^{41A}$ can be methyl. Depending on the groups that are selected for $R^{40A}$ and $R^{41A}$, the carbon to which $R^{40A}$ and $R^{41A}$ are attached may be a chiral center. In some embodiment, the carbon to which $R^{40A}$ and $R^{41A}$ are attached may be a (R)-chiral center. In other embodiments, the carbon to which $R^{40A}$ and $R^{41A}$ are attached may be a (S)-chiral center.

Examples of suitable

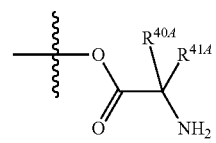

include the following:

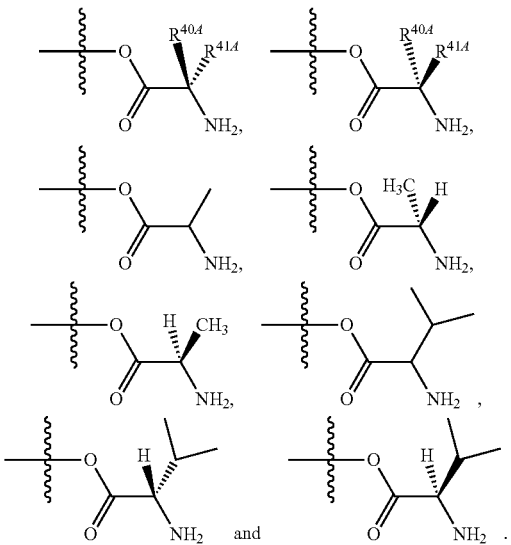

In some embodiments, the dashed line (------) can be a single bond, $R^{2A}$ can be CH$_2$, and $R^{3A}$ can be O (oxygen). When the dashed line (------) is a single bond, $R^{2A}$ is CH$_2$, and $R^{3A}$ is O (oxygen), a 4-membered ring is formed that includes the 4'-carbon and 3'-carbon of the pentose ring. In other embodiments, the dashed line (------) can be absent, $R^{2A}$ can be selected from an optionally substituted $C_{1-6}$ alkyl, an optionally substituted $C_{2-6}$ alkenyl, an optionally substituted $C_{2-6}$ alkynyl, an optionally substituted —O—$C_{1-6}$ alkyl, an optionally substituted —O—$C_{3-6}$ alkenyl, an optionally substituted —O—$C_{3-6}$ alkynyl and cyano, and $R^{3A}$ can be selected from OH, —OC(=O)$R'''^{A}$ and an optionally substituted O-linked amino acid.

Various groups can be attached to the 4'-position of the pentose ring. In some embodiments, $R^{2A}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained), and hexyl (branched and straight-chained). In some embodiments, $R^{2A}$ can be an unsubstituted $C_{1-6}$ alkyl. In other embodiments, $R^{2A}$ can be a substituted $C_{1-6}$ alkyl. For example, $R^{2A}$ can be a halogen substituted $C_{1-6}$ alkyl, a hydroxy substituted $C_{1-6}$ alkyl, an alkoxy substituted $C_{1-6}$ alkyl or a sulfenyl substituted $C_{1-6}$ alkyl (for example, —$C_{1-6}$ alkyl-S—$C_{1-6}$ alkyl). In other embodiments, $R^{2A}$ can be a $C_{1-6}$ haloalkyl. In other embodiments, $R^{2A}$ can be an optionally substituted $C_{2-6}$ alkenyl. In some embodiments, $R^{2A}$ can be a substituted $C_{2-6}$ alkenyl. In other embodiments, $R^{2A}$ can be an unsubstituted $C_{2-6}$ alkenyl. For example, $R^{2A}$ can be ethenyl, propenyl or allenyl. In still other embodiments, $R^{2A}$ can be an optionally substituted $C_{2-6}$ alkynyl. In some embodiments, $R^{2A}$ can be a substituted $C_{2-6}$ alkynyl. In other embodiments, $R^{2A}$ can be an unsubstituted $C_{2-6}$ alkynyl. Suitable $C_{2-6}$ alkynyls include ethynyl and propynyl. In yet still other embodiments, $R^{2A}$ can be an optionally substituted $C_{3-6}$ cycloalkyl. In some embodiments, $R^{2A}$ can be a substituted $C_{3-6}$ cycloalkyl. In other embodiments, $R^{2A}$ can be an unsubstituted $C_{3-6}$ cycloalkyl. A non-limiting list of $C_{3-6}$ cycloalkyls include cyclopropyl, cyclobutyl, cyclopentyl and cyclohexyl. In some embodiments, $R^{2A}$ can be an optionally substituted —O—$C_{1-6}$ alkyl. In some embodiments, $R^{2A}$ can be a substituted —O—$C_{1-6}$ alkyl. In other embodiments, $R^{2A}$ can be an unsubstituted —O—$C_{1-6}$ alkyl. Examples of suitable O—$C_{1-6}$ alkyl groups include methoxy, ethoxy, n-propoxy, iso-propoxy, n-butoxy, isobutoxy, tert-butoxy, pentoxy (branched and straight-chained), and hexoxy (branched and straight-chained). In other embodiments, $R^{2A}$ can be an optionally substituted —O—$C_{3-6}$ alkenyl. In some embodiments, $R^{2A}$ can be a substituted —O—$C_{3-6}$ alkenyl. In other embodiments, $R^{2A}$ can be an unsubstituted —O—$C_{3-6}$ alkenyl. In still other embodiments, $R^{2A}$ can be an optionally substituted —O—$C_{3-6}$ alkynyl. In some embodiments, $R^{2A}$ can be a substituted —O—$C_{3-6}$ alkynyl. In other embodiments, $R^{2A}$ can be an unsubstituted —O—$C_{3-6}$ alkynyl. In yet still other embodiments, $R^{2A}$ can be cyano.

The groups attached to the 3'-position of the pentose ring can vary. In some embodiments, including those of paragraph [0120], $R^{3A}$ can be OH. In other embodiments, including those of paragraph [0120], $R^{3A}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

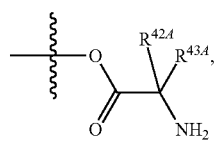

wherein $R^{42A}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{43A}$ can be hydrogen or an optionally substituted $C_{1-4}$-alkyl; or $R^{42A}$ and $R^{43A}$ can be taken together to form an optionally substituted $C_{3-6}$ cycloalkyl.

When $R^{42A}$ is substituted, $R^{42A}$ can be substituted with one or more substituents selected from N-amido, mercapto, alkylthio, an optionally substituted aryl, hydroxy, an optionally substituted heteroaryl, O-carboxy, and amino. In some embodiments, $R^{42A}$ can be an unsubstituted $C_{1-6}$-alkyl, such as those described herein. In some embodiments, $R^{42A}$ can be hydrogen. In other embodiments, $R^{42A}$ can be methyl. In some embodiments, $R^{43A}$ can be hydrogen. In other embodiments, $R^{43A}$ can be an optionally substituted $C_{1-4}$-alkyl, such as methyl, ethyl, n-propyl, isopropyl, n-butyl, isobutyl and tert-butyl. In an embodiment, $R^{43A}$ can be methyl. Depending on the groups that are selected for $R^{42A}$ and $R^{43A}$, the carbon to which $R^{42A}$ and $R^{43A}$ are attached may be a chiral center. In some embodiment, the carbon to which $R^{42A}$ and $R^{43A}$ are attached may be a (R)-chiral center. In other embodiments, the carbon to which $R^{42A}$ and $R^{43A}$ are attached may be a (S)-chiral center.

Examples of suitable

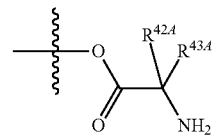

include the following:

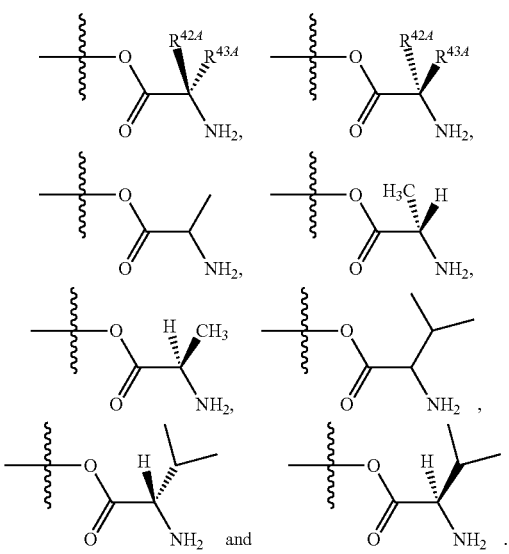

In still other embodiments, including those of paragraph [0120], $R^{3A}$ can be —OC(=O)R'''$^A$, wherein R'''$^A$ can be an optionally substituted $C_{1-24}$ alkyl. In some embodiments, R'''$^A$ can be a substituted $C_{1-8}$ alkyl. In other embodiments, R'''$^A$ can be an unsubstituted $C_{1-8}$ alkyl. In still other embodiments, including those of paragraph [0120], $R^{3A}$ can be an optionally substituted —O-acyl. In yet still other embodiments, including those of paragraph [0120], $R^{3A}$ can be —OC(=O)R$^{44A}$, wherein R$^{44A}$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl(C$_{1-6}$ alkyl) and an optionally substituted heterocyclyl (C$_{1-6}$ alkyl). In some embodiments, R$^{44A}$ can be a substituted C$_{1-12}$ alkyl. In other embodiments, R$^{44A}$ can be an unsubstituted C$_{1-12}$ alkyl.

Various substituents can be present at the 2'-position of the pentose ring. In some embodiments, R$^{5A}$ can be hydrogen. In other embodiments, R$^{5A}$ can be halogen, for example, fluoro. In some embodiments, R$^{4A}$ can be halogen, such as fluoro. In some embodiments, R$^{5A}$ can be hydrogen and R$^{4A}$ can be halogen. In other embodiments, R$^{4A}$ and R$^{5A}$ can both be halogen.

In some embodiments, ---- can be a single bond, R$^{4A}$ can be fluoro, R$^{5A}$ can be hydrogen and R$^{2A}$ can be a C$_{1-6}$ haloalkyl. In some embodiments, ---- can be a single bond, R$^{4A}$ can be fluoro, R$^{5A}$ can be hydrogen, R$^{2A}$ can be a C$_{1-6}$ haloalkyl and B$^{1A}$ can be cytosine.

In some embodiments, R$^{2A}$ cannot be methoxy. In some embodiments, R$^{2A}$ cannot be methoxy when B$^{1A}$ is substituted or unsubstituted uracil. In some embodiments, B$^{1A}$ is substituted or unsubstituted cytosine. In other embodiments, B$^{1A}$ is substituted or unsubstituted thymine. In still other embodiments, B$^{1A}$ cannot be an unsubstituted uracil. In some embodiments, R$^{2A}$ cannot be methoxy when Z$^{1A}$ is

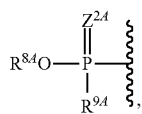

wherein R$^{8A}$ is an unsubstituted C$_{1-6}$ alkyl or a para-substituted phenyl; and R$^{9A}$ is an optionally substituted N-linked amino acid or an optionally substituted N-linked amino acid ester derivative. In some embodiments, R$^{2A}$ cannot be methoxy when Z$^{1A}$ is

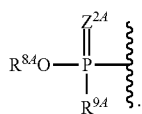

In some embodiments, R$^{2A}$ cannot be an alkoxy (for example, when Z$^{1A}$ is

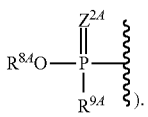

In some embodiments, B$^{1A}$ cannot be cytosine when R$^{2A}$ is an unsubstituted alkenyl or an unsubstituted alkynyl. In some embodiments, B$^{1A}$ cannot be thymine when R$^{2A}$ is an optionally substituted alkyl. In some embodiments, R$^{2A}$ cannot be an unsubstituted alkoxy (such as methoxy), an optionally substituted alkenyl (such as allenyl), an unsubstituted alkynyl (such as ethynyl) or a C$_1$ alkyl substituted with a non-halogen substituent. In some embodiments, R$^{2A}$ cannot be an unsubstituted alkoxy (such as methoxy), an optionally substituted alkenyl (such as allenyl), an optionallys substituted substituted alkynyl (such as ethynyl) or a C$_{1-4}$ alkyl substituted with a non-halogen substituent. In some embodiments R$^{1A}$ cannot be H. In some embodiments R$^{1A}$ cannot be H when B$^{1A}$ is an optionally substituted cytosine or an optionally substituted thymine.

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

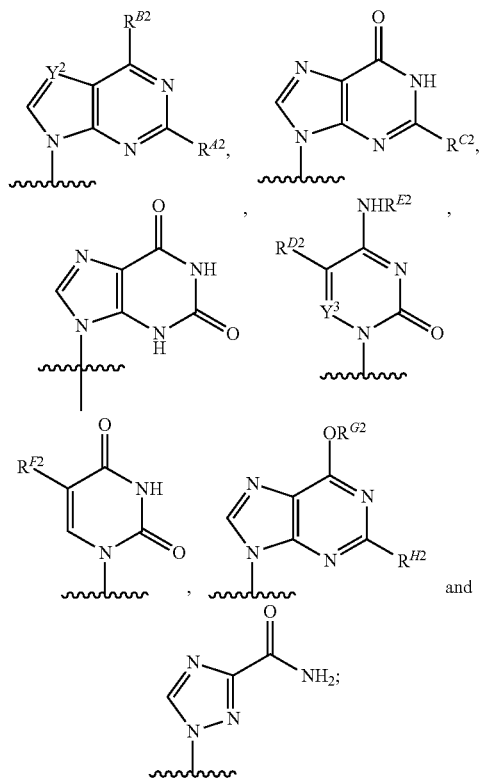

wherein: R$^{A2}$ can be selected from hydrogen, halogen and NHR$^{J2}$, wherein R$^{J2}$ can be selected from hydrogen, —C(═O)R$^{K2}$ and —C(═O)OR$^{L2}$; R$^{B2}$ can be halogen or NHR$^{W2}$, wherein R$^{W2}$ can be selected from hydrogen, an optionally substituted C$_{1-6}$ alkyl, an optionally substituted C$_{2-6}$ alkenyl, an optionally substituted C$_{3-8}$ cycloalkyl, —C(═O)R$^{M2}$ and —C(═O)OR$^{N2}$; R$^{C2}$ can be hydrogen or NHR$^{O2}$, wherein R$^{O2}$ can be selected from hydrogen, —C(═O)R$^{P2}$ and —C(═O)OR$^{Q2}$; R$^{D2}$ can be selected from hydrogen, halogen, an optionally substituted C$_{1-6}$ alkyl, an optionally substituted C$_{2-6}$ alkenyl and an optionally substituted C$_{2-6}$ alkynyl; R$^{E2}$ can be selected from hydrogen, hydroxy, an optionally substituted C$_{1-6}$ alkyl, an optionally substituted C$_{3-8}$ cycloalkyl, —C(═O)R$^{R2}$ and —C(═O)OR$^{S2}$; R$^{F2}$ can be selected from hydrogen, halogen, an optionally substituted C$_{1-6}$ alkyl, an optionally substituted C$_{2-6}$ alkenyl and an optionally substituted C$_{2-6}$ alkynyl; Y$^2$ and Y$^3$ can be independently N (nitrogen) or CR$^{I2}$, wherein R$^{I2}$ can be selected from hydrogen, halogen, an optionally substituted C$_{1-6}$-alkyl, an optionally substituted C$_{2-6}$-alkenyl and an optionally substituted C$_{2-6}$-alkynyl; R$^{G2}$ can be an optionally substituted C$_{1-6}$ alkyl; R$^{H2}$ can be hydrogen or NHR$^{T2}$, wherein R$^{T2}$ can be independently selected from hydrogen, —C(═O)R$^{U2}$ and —C(═O)OR$^{V2}$; and R$^{K2}$, R$^{L2}$, R$^{M2}$, R$^{N2}$, R$^{P2}$, R$^{Q2}$, R$^{R2}$, R$^{S2}$, R$^{U2}$ and R$^{V2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl). In some embodiments, the structures shown above can be modified by replacing one or more hydrogens with substituents selected from the list of substituents provided for the definition of "substituted."

In some embodiments, $B^{1A}$ can be

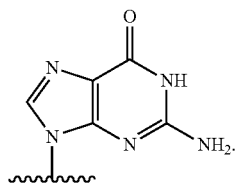 [SMILES: *n1cnc2c(=O)[nH]c(N)nc21]

In other embodiments, $B^{1A}$ can be

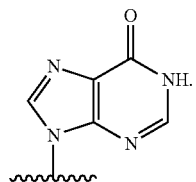 [SMILES: *n1cnc2c(=O)[nH]cnc21]

In still other embodiments, $B^{1A}$ can be

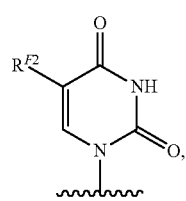

such as

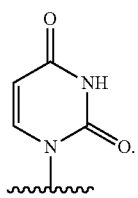 [SMILES: *n1ccc(=O)[nH]c1=O]

In yet still other embodiments, $B^{1A}$ can be

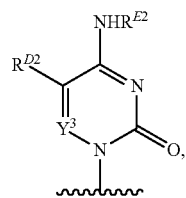

for example,

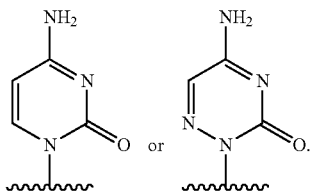 [SMILES: *n1ccc(N)nc1=O ; *n1ncc(N)nc1=O]

In some embodiments, $R^{D2}$ can be hydrogen. In other embodiments, $B^{1A}$ can be

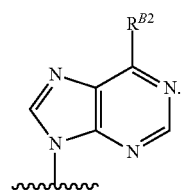

In some embodiments, $R^{B2}$ can be $NH_2$. In other embodiments, $R^{B2}$ can be $NHR^{W2}$, wherein $R^{W2}$ can be —C(=O)$R^{M2}$ or —C(=O)O$R^{N2}$. In still other embodiments, $B^{1A}$ can be

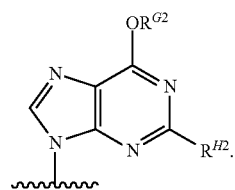

In some embodiments, $B^{1A}$ can be

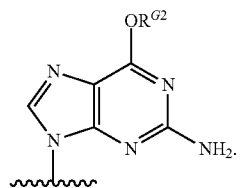

In some embodiments, a compound of Formula (I) can have a structure selected from one of the following:

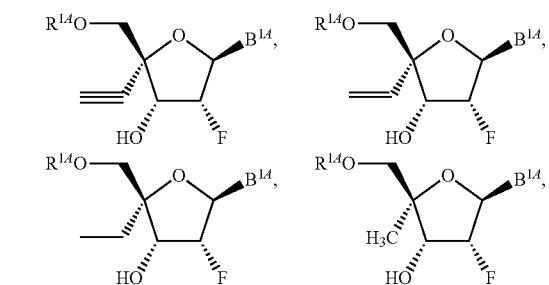

-continued

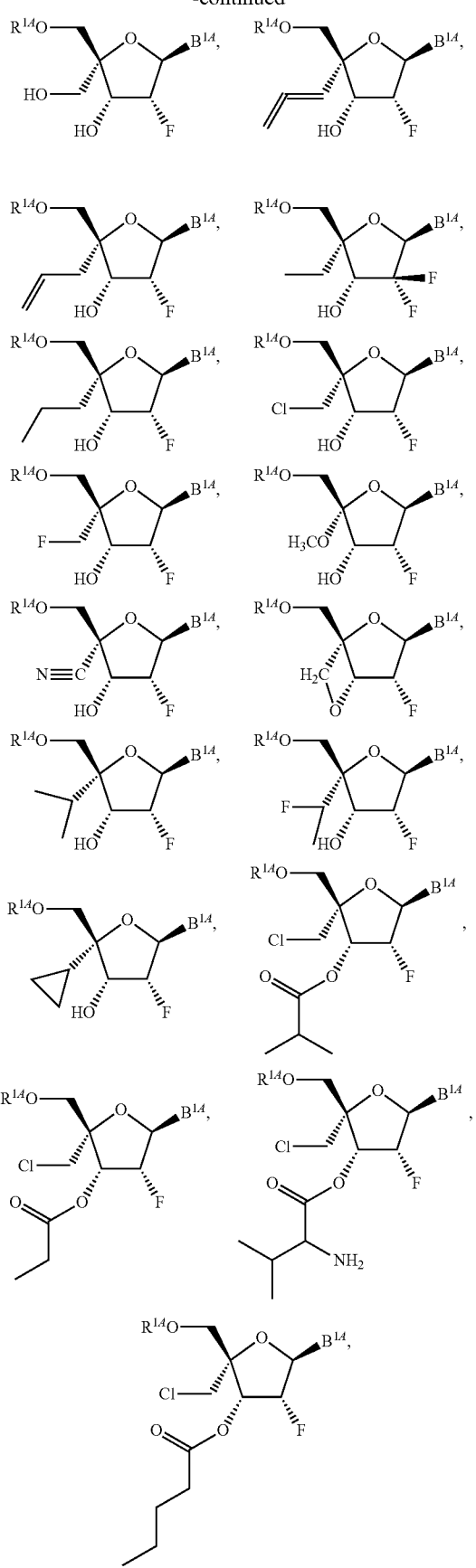

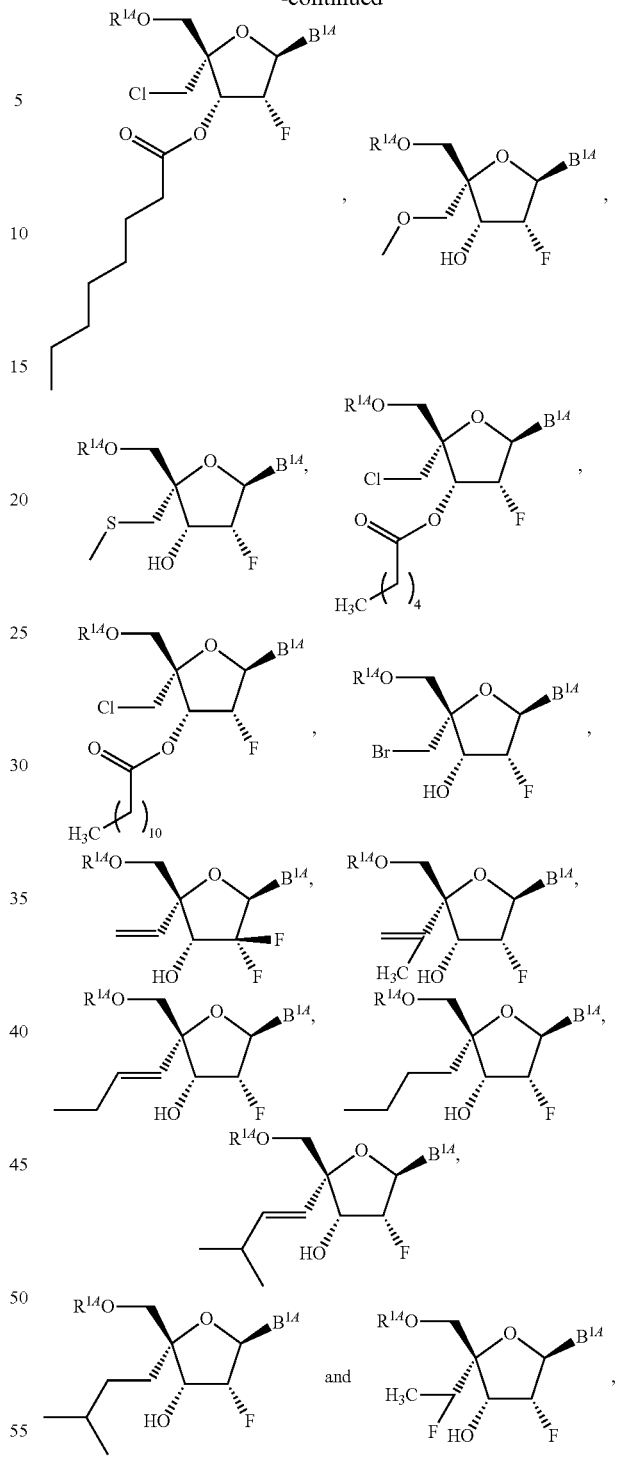

or a pharmaceutically acceptable salt of the foregoing. In some embodiments of this paragraph, $B^{14}$ can be an optionally substituted purine base. In other embodiments of this paragraph, $B^{14}$ can be an optionally substituted pyrimidine base. In some embodiments of this paragraph, $B^{14}$ can be guanine. In other embodiments of this paragraph, $B^{14}$ can be thymine. In still other embodiments of this paragraph, $B^{14}$ can be cytosine. In yet still other embodiments of this paragraph, $B^{14}$ can be uracil. In some embodiments of this paragraph, $B^{14}$ can be adenine. In some embodiments of this paragraph, $R^{1A}$ can be hydrogen. In other embodiments of this paragraph, $R^{1A}$ can be an optionally substituted acyl. In still other embodiments of this paragraph, $R^{1A}$ can be mono-, di- or tri-phosphate. In yet other embodiments of this paragraph, $R^{1A}$ can be phosphoroamidate. In some embodiments of this paragraph, $R^{1A}$ can be an acyloxyalkyl ester phosphate prodrug.

In some embodiments, the compound can be a compound of Formula (II), or a pharmaceutically acceptable salt thereof, wherein: $B^{1B}$ can be an optionally substituted heterocyclic base or an optionally substituted heterocyclic base with a protected amino group; $R^{1B}$ can be selected from O$^-$, OH,

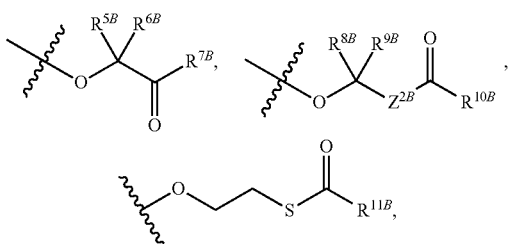

an optionally substituted N-linked amino acid and an optionally substituted N-linked amino acid ester derivative; $R^{2B}$ can be selected from an optionally substituted $C_{1-6}$ alkyl, an optionally substituted $C_{2-6}$ alkenyl, an optionally substituted $C_{2-6}$ alkynyl, an optionally substituted —O—$C_{1-6}$ alkyl, an optionally substituted —O—$C_{3-6}$ alkenyl, an optionally substituted —O—$C_{3-6}$ alkynyl and cyano; $R^{3B}$ can be a halogen; $R^{4B}$ can be hydrogen or halogen; $R^{5B}$, $R^{6B}$, $R^{8B}$ and $R^{9B}$ can be independently selected from hydrogen, an optionally substituted $C_{1-24}$ alkyl and an optionally substituted aryl; $R^{7B}$ and $R^{10B}$ can be independently selected from hydrogen, an optionally substituted $C_{1-24}$ alkyl, an optionally substituted aryl, an optionally substituted —O—$C_{1-24}$ alkyl and an optionally substituted —O-aryl; $R^{11B}$ can be selected from hydrogen, an optionally substituted $C_{1-24}$ alkyl and an optionally substituted aryl; $Z^{1B}$ and $Z^{2B}$ can be independently O or S.

In some embodiments, $R^{1B}$ can be O$^-$. In other embodiments, $R^{1B}$ can be OH.

In some embodiments, $R^{1B}$ can be

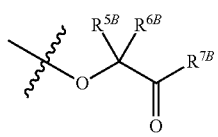

wherein $R^{5B}$ and $R^{6B}$ can be independently selected from hydrogen, an optionally substituted $C_{1-24}$ alkyl and an optionally substituted aryl; and $R^{7B}$ can be selected from hydrogen, an optionally substituted $C_{1-24}$ alkyl, an optionally substituted aryl, an optionally substituted —O—$C_{1-24}$ alkyl and an optionally substituted —O-aryl. In some embodiments, $R^{5B}$ and $R^{6B}$ can be hydrogen. In other embodiments, at least one of $R^{5B}$ and $R^{6B}$ can be an optionally substituted $C_{1-24}$ alkyl or an optionally substituted aryl. In some embodiments, $R^{7B}$ can be an optionally substituted $C_{1-24}$ alkyl. In other embodiments, $R^{7B}$ can be an optionally substituted aryl. In still other embodiments, $R^{7B}$ can be an optionally substituted —O—$C_{1-24}$ alkyl or an optionally substituted —O-aryl.

In some embodiments, $R^{1B}$ can be

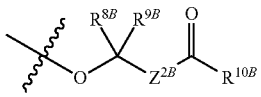

wherein $R^{8B}$ and $R^{9B}$ can be independently selected from hydrogen, an optionally substituted $C_{1-24}$ alkyl and an optionally substituted aryl; $R^{10B}$ can be independently selected from hydrogen, an optionally substituted $C_{1-24}$ alkyl, an optionally substituted aryl, an optionally substituted —O—$C_{1-24}$ alkyl and an optionally substituted —O-aryl; and $Z^{2B}$ can be independently O (oxygen) or S (sulfur). In some embodiments, $R^{8B}$ and $R^{9B}$ can be hydrogen. In other embodiments, at least one of $R^{8B}$ and $R^{9B}$ can be an optionally substituted $C_{1-24}$ alkyl or an optionally substituted aryl. In some embodiments, $R^{10B}$ can be an optionally substituted $C_{1-24}$ alkyl. In other embodiments, $R^{10B}$ can be an optionally substituted aryl. In still other embodiments, $R^{10B}$ can be an optionally substituted —O—$C_{1-24}$ alkyl or an optionally substituted —O-aryl. In some embodiments, $Z^{2B}$ can be O (oxygen). In other embodiments, $Z^{2B}$ can be or S (sulfur). In some embodiments, $R^{1B}$ can be isopropylcarbonyloxymethyloxy. In some embodiments, $R^{1B}$ can be pivaloyloxymethyloxy.

In some embodiments, $R^{1B}$ can be

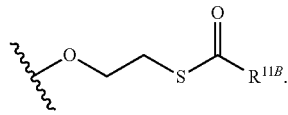

In some embodiments, $R^{11B}$ can be hydrogen. In other embodiments, $R^{11B}$ can be an optionally substituted $C_{1-24}$ alkyl. In still other embodiments, $R^{11B}$ can be an optionally substituted aryl. In some embodiments, $R^{11B}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained).

In some embodiments, $R^{1B}$ can be an optionally substituted N-linked amino acid or an optionally substituted N-linked amino acid ester derivative. For example, $R^{1B}$ can be optionally substituted version of the following: alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{1B}$ can be selected from alanine isopropyl ester, alanine cyclohexyl ester, alanine neopentyl ester, valine isopropyl ester and leucine isopropyl ester. In some embodiments, $R^{1B}$ can have the structure

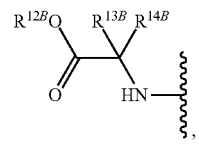

wherein $R^{12B}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{13B}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{14B}$ can be hydrogen or an optionally substituted $C_{1-4}$-alkyl; or $R^{13B}$ and $R^{14B}$ can be taken together to form an optionally substituted $C_{3-6}$ cycloalkyl.

When $R^{13B}$ is substituted, $R^{13B}$ can be substituted with one or more substituents selected from N-amido, mercapto, alkylthio, an optionally substituted aryl, hydroxy, an optionally substituted heteroaryl, O-carboxy, and amino. In some embodiments, $R^{13B}$ can be an unsubstituted $C_{1-6}$-alkyl, such as those described herein. In some embodiments, $R^{13B}$ can be hydrogen. In other embodiments, $R^{13B}$ can be methyl. In some embodiments, $R^{12B}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{12B}$ can be methyl or isopropyl. In some embodiments, $R^{12B}$ can be ethyl or neopentyl. In other embodiments, $R^{12B}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{12B}$ can be an optionally substituted cyclohexyl. In still other embodiments, $R^{12B}$ can be an optionally substituted aryl, such as phenyl and naphthyl. In yet still other embodiments, $R^{12B}$ can be an optionally substituted aryl($C_{1-6}$ alkyl). In some embodiments, $R^{12B}$ can be an optionally substituted benzyl. In some embodiments, $R^{12B}$ can be an optionally substituted $C_{1-6}$ haloalkyl, for example, $CF_3$. In some embodiments, $R^{14B}$ can be hydrogen. In other embodiments, $R^{14B}$ can be an optionally substituted $C_{1-4}$-alkyl, such as methyl, ethyl, n-propyl, isopropyl, n-butyl, isobutyl and tert-butyl. In an embodiment, $R^{14B}$ can be methyl. In some embodiments, $R^{13B}$ and $R^{14B}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{13B}$ and $R^{14B}$, the carbon to which $R^{13B}$ and $R^{14B}$ are attached may be a chiral center. In some embodiment, the carbon to which $R^{13B}$ and $R^{14B}$ are attached may be a (R)-chiral center. In other embodiments, the carbon to which $R^{13B}$ and $R^{14B}$ are attached may be a (S)-chiral center.

Examples of suitable

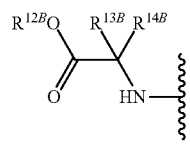

groups include the following:

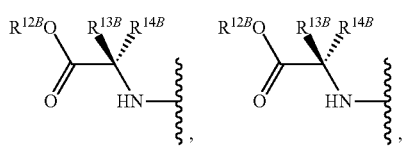

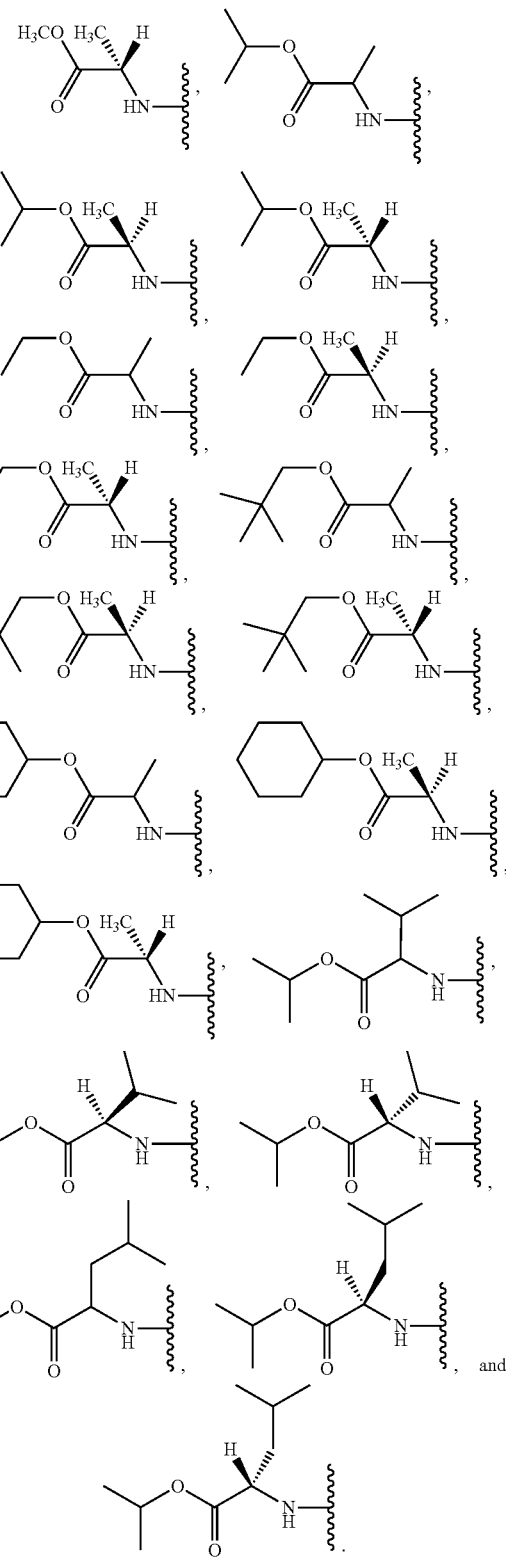

A variety of substituents can be present at the 4'-position of the pentose ring. In some embodiments, $R^{2B}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained), and hexyl (branched and straight-chained). In some embodiments, $R^{2B}$ can be an unsubstituted $C_{1-6}$ alkyl. In other embodiments, $R^{2B}$ can be a substituted $C_{1-6}$ alkyl. For example, $R^{2B}$ can be a halogen substituted $C_{1-6}$ alkyl, a hydroxy substituted $C_{1-6}$ alkyl, an alkoxy substituted $C_{1-6}$ alkyl or a sulfenyl substituted $C_{1-6}$ alkyl (for example, —$C_{1-6}$ alkyl-S—$C_{1-6}$ alkyl). In other embodiments, $R^{2B}$ can be a $C_{1-6}$ haloalkyl. In other embodiments, $R^{2B}$ can be an optionally substituted $C_{2-6}$ alkenyl. In some embodiments, $R^{2B}$ can be a substituted $C_{2-6}$ alkenyl. In other embodiments, $R^{2B}$ can be an unsubstituted $C_{2-6}$ alkenyl. For example, $R^{2B}$ can be ethenyl, propenyl or allenyl. In still other embodiments, $R^{2B}$ can be an optionally substituted $C_{2-6}$ alkynyl. In some embodiments, $R^{2B}$ can be a substituted $C_{2-6}$ alkynyl. In other embodiments, $R^{2B}$ can be an unsubstituted $C_{2-6}$ alkynyl. Suitable $C_{2-6}$ alkynyls include ethynyl and propynyl. In yet still other embodiments, $R^{2B}$ can be an optionally substituted $C_{3-6}$ cycloalkyl. In some embodiments, $R^{2B}$ can be a substituted $C_{3-6}$ cycloalkyl. In other embodiments, $R^{2B}$ can be an unsubstituted $C_{3-6}$ cycloalkyl. A non-limiting list of $C_{3-6}$ cycloalkyls include cyclopropyl, cyclobutyl, cyclopentyl and cyclohexyl. In some embodiments, $R^{2B}$ can be an optionally substituted —O—$C_{1-6}$ alkyl. In some embodiments, $R^{2B}$ can be a substituted —O—$C_{1-6}$ alkyl. In other embodiments, $R^{2B}$ can be an unsubstituted —O—$C_{1-6}$ alkyl. Examples of suitable O—$C_{1-6}$ alkyl groups include methoxy, ethoxy, n-propoxy, iso-propoxy, n-butoxy, isobutoxy, tert-butoxy, pentoxy (branched and straight-chained), and hexoxy (branched and straight-chained). In other embodiments, $R^{2B}$ can be an optionally substituted —O—$C_{3-6}$ alkenyl. In some embodiments, $R^{2B}$ can be a substituted —O—$C_{3-6}$ alkenyl. In other embodiments, $R^{2B}$ can be an unsubstituted —O—$C_{3-6}$ alkenyl. In still other embodiments, $R^{2B}$ can be an optionally substituted —O—$C_{3-6}$ alkynyl. In some embodiments, $R^{2B}$ can be a substituted —O—$C_{3-6}$ alkynyl. In other embodiments, $R^{2B}$ can be an unsubstituted —O—$C_{3-6}$ alkynyl. In yet still other embodiments, $R^{2B}$ can be cyano.

Variety of substituents can be present at the 2'-position of the pentose ring. In some embodiments, $R^{4B}$ can be hydrogen. In other embodiments, $R^{4B}$ can be halogen, such as fluoro. In some embodiments, $R^{3B}$ can be halogen, such as fluoro. In some embodiments, $R^{4B}$ can be hydrogen and $R^{3B}$ can be halogen. In other embodiments, $R^{3B}$ and $R^{4B}$ can be both halogen. For example, $R^{3B}$ and $R^{4B}$ can be both fluoro.

In some embodiments, $Z^{1B}$ can be O (oxygen). In other embodiments, $Z^{1B}$ can be S (sulfur).

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

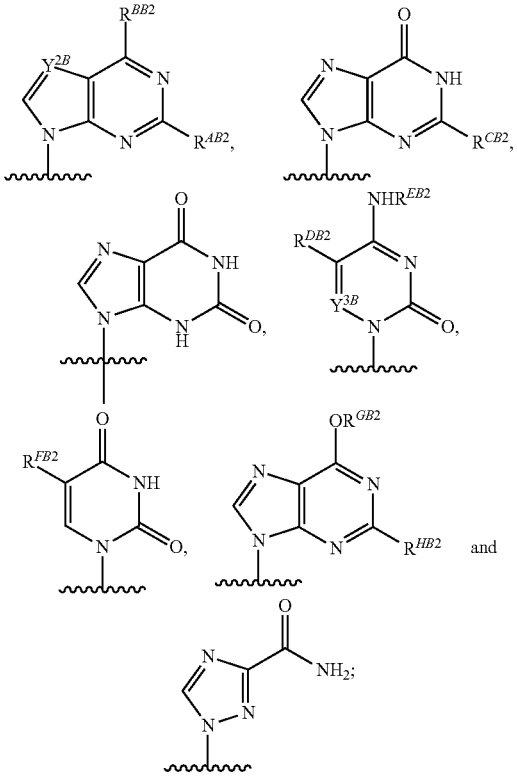

wherein: $R^{AB2}$ can be selected from hydrogen, halogen and NHR$^{JB2}$, wherein $R^{JB2}$ can be selected from hydrogen, —C(=O)$R^{KB2}$ and —C(=O)O$R^{LB2}$; $R^{BB2}$ can be halogen or NHR$^{WB2}$, wherein $R^{WB2}$ can be selected from hydrogen, an optionally substituted $C_{1-6}$ alkyl, an optionally substituted $C_{2-6}$ alkenyl, an optionally substituted $C_{3-8}$ cycloalkyl, —C(=O)$R^{MB2}$ and —C(=O)O$R^{NB2}$; $R^{CB2}$ can be hydrogen or NHR$^{OB2}$, wherein $R^{OB2}$ can be selected from hydrogen, —C(=O)$R^{PB2}$ and —C(=O)O$R^{QB2}$; $R^{DB2}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{EB2}$ can be selected from hydrogen, hydroxy, an optionally substituted $C_{1-6}$ alkyl, an optionally substituted $C_{3-8}$ cycloalkyl, —C(=O)$R^{RB2}$ and —C(=O)O$R^{SB2}$; $R^{FB2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^{2B}$ and $Y^{3B}$ can be independently N (nitrogen) or CR$^{IB2}$, wherein $R^{IB2}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{GB2}$ can be an optionally substituted $C_{1-6}$ alkyl; $R^{HB2}$ can be hydrogen or NHR$^{TB2}$, wherein $R^{TB2}$ can be independently selected from hydrogen, —C(=O)$R^{UB2}$ and —C(=O)O$R^{VB2}$; and $R^{KB2}$, $R^{LB2}$, $R^{MB2}$, $R^{NB2}$, $R^{PB2}$, $R^{QB2}$, $R^{RB2}$, $R^{SB2}$, $R^{UB2}$ and $R^{VB2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl). In some embodiments, the structures shown above can be modified by replacing one or more hydrogens with substituents selected from the list of substituents provided for the definition of "substituted."

In some embodiments, $B^{1B}$ can be

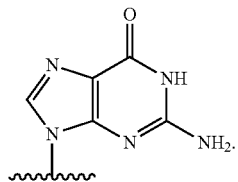 [SMILES: *n1cnc2c(=O)[nH]c(N)nc21]

In other embodiments, $B^{1B}$ can be

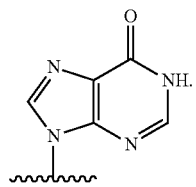 [SMILES: *n1cnc2c(=O)[nH]cnc21]

In still other embodiments, $B^{1B}$ can be

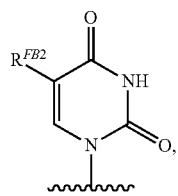

such as

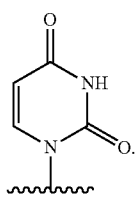 [SMILES: *n1ccc(=O)[nH]c1=O]

In yet still other embodiments, $B^{1B}$ can be

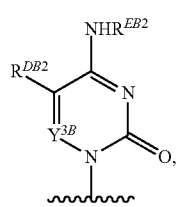

for example,

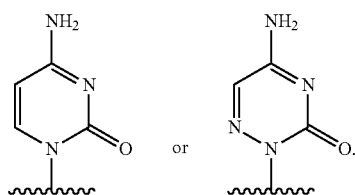 [SMILES: *n1ccc(N)nc1=O ; *n1ncc(N)nc1=O]

In some embodiments, $R^{DB2}$ can be hydrogen. In other embodiments, $B^{1B}$ can be

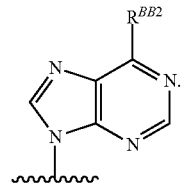

In some embodiments, $R^{BB2}$ can be $NH_2$. In other embodiments, $R^{BB2}$ can be $NHR^{WB2}$, wherein $R^{WB2}$ can be $-C(=O)R^{MB2}$ or $-C(=O)OR^{NB2}$. In still other embodiments, $B^{1B}$ can be

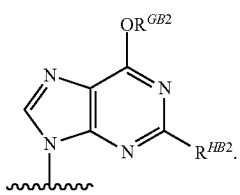

In some embodiments, $B^{1B}$ can be

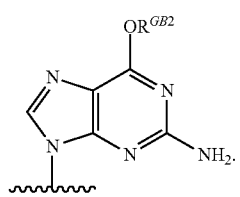

In some embodiments, a compound of Formula (II) can have the following structure:

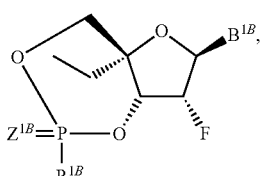

or a pharmaceutically acceptable salt of the foregoing. In some embodiments of this paragraph, $B^{1B}$ can be an optionally substituted purine base. In other embodiments of this paragraph, $B^{1B}$ can be an optionally substituted pyrimidine base. In some embodiments of this paragraph, $B^{1B}$ can be guanine. In other embodiments of this paragraph, $B^{1B}$ can be thymine. In still other embodiments of this paragraph, $B^{1B}$ can be cytosine. In yet still other embodiments of this paragraph, $B^{1B}$ can be uracil. In some embodiments of this paragraph, $B^{1B}$ can be adenine. In some embodiments of this paragraph, $Z^{1B}$ can be oxygen. In some embodiments of this paragraph, $Z^{1B}$ can be sulfur. In still other embodiments of this paragraph, $R^{1B}$ can be alkylcarbonyloxyalkoxy.

In some embodiments, the compound can be a compound of Formula (III), or a pharmaceutically acceptable salt thereof, wherein: $B^{1C}$ can be an optionally substituted heterocyclic base or an optionally substituted heterocyclic base with a protected amino group; $R^{1C}$ and $R^{2C}$ can be independently selected from O⁻, OH, an optionally substituted $C_{1-6}$ alkoxy,

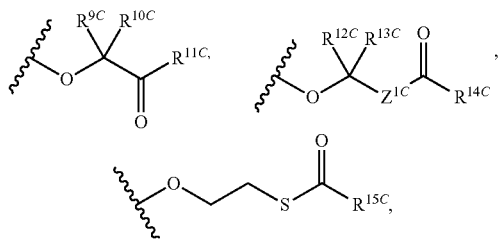

an optionally substituted N-linked amino acid and an optionally substituted N-linked amino acid ester derivative; $R^{3C}$ can be selected from an optionally substituted $C_{1-6}$ alkyl, an optionally substituted $C_{2-6}$ alkenyl, an optionally substituted $C_{2-6}$ alkynyl, an optionally substituted —O—$C_{1-6}$ alkyl, an optionally substituted —O—$C_{3-6}$ alkenyl, an optionally substituted —O—$C_{3-6}$ alkynyl, an optionally substituted $C_{3-6}$ cycloalkyl and cyano; $R^{4C}$ can be selected from OH, —OC(=O)$R''^{C}$ and an optionally substituted O-linked amino acid; $R^{5C}$ can be a halogen; $R^{6C}$ can be hydrogen or halogen; $R^{9C}$, $R^{10C}$, $R^{12C}$ and $R^{13C}$ can be independently selected from hydrogen, an optionally substituted $C_{1-24}$ alkyl and an optionally substituted aryl; $R^{11C}$ and $R^{14C}$ can be independently selected from hydrogen, an optionally substituted $C_{1-24}$ alkyl, an optionally substituted aryl, an optionally substituted —O—$C_{1-24}$ alkyl and an optionally substituted —O-aryl; $R^{15C}$ can be selected from hydrogen, an optionally substituted $C_{1-24}$ alkyl and an optionally substituted aryl; ------- can be a single bond or a double bond; when ------- is a single bond, each $R^{7C}$ and each $R^{8C}$ can be independently hydrogen or halogen; and when ------- is a double bond, each $R^{7C}$ is absent and each $R^{8C}$ can be independently hydrogen or halogen; $Z^{1C}$ can be O (oxygen) or S (sulfur); and $R''^{C}$ can be an optionally substituted $C_{1-24}$-alkyl.

In some embodiments, can be a single bond such that Formula (III) has the structure

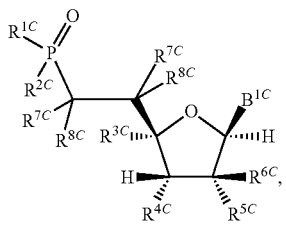

wherein each $R^{7C}$ and each $R^{8C}$ can be independently hydrogen or halogen. In some embodiments, the $R^{7C}$ and the $R^{8C}$ groups can all be hydrogen. In other embodiments, one $R^{7C}$ can be halogen, one $R^{7C}$ can be hydrogen and both $R^{8C}$ groups can all be hydrogen. In still other embodiments, one $R^{7C}$ can be halogen, one $R^{7C}$ can be hydrogen, one $R^{8C}$ can be halogen and one $R^{8C}$ can be hydrogen. In some embodiments, the carbon adjacent to the phosphorus and the 5'-carbon can each be independently a (S)-chiral center. In some embodiments, the carbon adjacent to the phosphorus and the 5'-carbon can each be independently a (R)-chiral center.

In some embodiments, can be a double bond such that Formula (III) has the structure

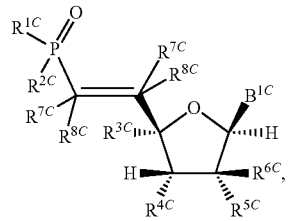

wherein each $R^{7C}$ is absent and each $R^{8C}$ can be independently hydrogen or halogen. In some embodiments, both $R^{8C}$ groups can be hydrogen. In other embodiments, one $R^{8C}$ can be halogen and the other $R^{8C}$ can be hydrogen. In some embodiments, both $R^{8C}$ groups can be halogen. In some embodiments, the double bond has a (4-configuration. In some embodiments, the double bond has a (E)-configuration.

In some embodiments, $R^{1C}$ and/or $R^{2C}$ can be O⁻. In other embodiments, $R^{1C}$ and/or $R^{2C}$ can be OH. In some embodiments, $R^{1C}$ and $R^{2C}$ can be both OH.

In some embodiments, $R^{1C}$ and/or $R^{2C}$ can be

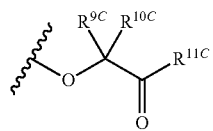

wherein $R^{9C}$ and $R^{10C}$ can be independently selected from hydrogen, an optionally substituted $C_{1-24}$ alkyl and an optionally substituted aryl; and $R^{11C}$ can be selected from hydrogen, an optionally substituted $C_{1-24}$ alkyl, an optionally substituted aryl, an optionally substituted —O—$C_{1-24}$ alkyl and an optionally substituted —O-aryl. In some embodiments, $R^{9C}$ and $R^{10C}$ can be hydrogen. In other embodiments, at least one of $R^{9C}$ and $R^{10C}$ can be an optionally substituted $C_{1-24}$ alkyl or an optionally substituted aryl. In some embodiments, $R^{11C}$ can be an optionally substituted $C_{1-24}$ alkyl. In other embodiments, $R^{11C}$ can be an optionally substituted aryl. In still other embodiments, $R^{11C}$ can be an optionally substituted —O—$C_{1-24}$ alkyl or an optionally substituted —O-aryl. In some embodiments, $R^{1C}$ and $R^{2C}$ can be both

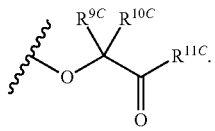

In some embodiments, $R^{1C}$ and/or $R^{2C}$ can be

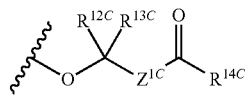

wherein $R^{12C}$ and $R^{13C}$ can be independently selected from hydrogen, an optionally substituted $C_{1-24}$ alkyl and an optionally substituted aryl; $R^{14C}$ can be independently selected from hydrogen, an optionally substituted $C_{1-24}$ alkyl, an optionally substituted aryl, an optionally substituted —O—$C_{1-24}$ alkyl and an optionally substituted —O-aryl; and $Z^{1C}$ can be independently O (oxygen) or S (sulfur). In some embodiments, $R^{12C}$ and $R^{13C}$ can be hydrogen. In other embodiments, at least one of $R^{12C}$ and $R^{13C}$ can be an optionally substituted $C_{1-24}$ alkyl or an optionally substituted aryl. In some embodiments, $R^{14C}$ can be an optionally substituted $C_{1-24}$ alkyl. In other embodiments, $R^{14C}$ can be an optionally substituted aryl. In still other embodiments, $R^{14C}$ can be an optionally substituted —O—$C_{1-24}$ alkyl or an optionally substituted —O-aryl. In some embodiments, $Z^{1C}$ can be O (oxygen). In other embodiments, $Z^{1C}$ can be or S (sulfur). In some embodiments, $R^{1C}$ and/or $R^{2C}$ can be isopropylcarbonyloxymethoxy. In some embodiments, $R^{1C}$ and/or $R^{2C}$ can be pivaloyloxymethoxy. In some embodiments, $R^{1C}$ and $R^{2C}$ can be both

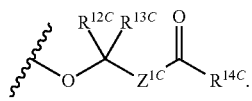

In some embodiments, $R^{1C}$ and $R^{2C}$ can be both isopropylcarbonyloxymethoxy. In other embodiments, $R^{1C}$ and $R^{2C}$ can be both pivaloyloxymethoxy.

In some embodiments, $R^{1C}$ and/or $R^{2C}$ can be

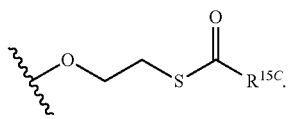

In some embodiments, $R^{15C}$ can be hydrogen. In other embodiments, $R^{15C}$ can be an optionally substituted $C_{1-24}$ alkyl. In still other embodiments, $R^{15C}$ can be an optionally substituted aryl. In some embodiments, $R^{15C}$ can be a $C_{1-6}$ alkyl, for example, methyl, ethyl, n-propyl, isopropyl, n-butyl, isobutyl, tert-butyl, pentyl (branched and straight-chained), and hexyl (branched and straight-chained). In some embodiments, $R^{1C}$ and $R^{2C}$ can be both

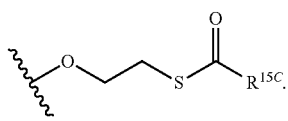

In some embodiments, $R^{1C}$ and/or $R^{2C}$ can be an optionally substituted N-linked amino acid or an optionally substituted N-linked amino acid ester derivative. For example, $R^{1C}$ and/or $R^{2C}$ can be optionally substituted version of the following: alanine, asparagine, aspartate, cysteine, glutamate, glutamine, glycine, proline, serine, tyrosine, arginine, histidine, isoleucine, leucine, lysine, methionine, phenylalanine, threonine, tryptophan, valine and ester derivatives thereof. In some embodiments, $R^{1C}$ and/or $R^{2C}$ can be selected from alanine isopropyl ester, alanine cyclohexyl ester, alanine neopentyl ester, valine isopropyl ester and leucine isopropyl ester. In some embodiments, $R^{1C}$ and/or $R^{2C}$ can have the structure

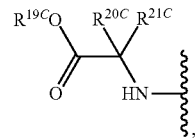

wherein $R^{19C}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{20C}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{21C}$ can be hydrogen or an optionally substituted $C_{1-4}$-alkyl; or $R^{20C}$ and $R^{21C}$ can be taken together to form an optionally substituted $C_{3-6}$ cycloalkyl.

When $R^{20C}$ is substituted, $R^{20C}$ can be substituted with one or more substituents selected from N-amido, mercapto, alkylthio, an optionally substituted aryl, hydroxy, an optionally substituted heteroaryl, O-carboxy, and amino. In some embodiments, $R^{20C}$ can be an unsubstituted $C_{1-6}$-alkyl, such as those described herein. In some embodiments, $R^{20C}$ can be hydrogen. In other embodiments, $R^{20C}$ can be methyl. In some embodiments, $R^{19C}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained). In some embodiments, $R^{19C}$ can be methyl or isopropyl. In some embodiments, $R^{19C}$ can be ethyl or neopentyl. In other embodiments, $R^{19C}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. In an embodiment, $R^{19C}$ can be an optionally substituted cyclohexyl. In still other embodiments, $R^{19C}$ can be an optionally substituted aryl, such as phenyl and naphthyl. In yet still other embodiments, $R^{19C}$ can be an optionally substituted aryl($C_{1-6}$ alkyl). In some embodiments, $R^{19C}$ can be an optionally substituted benzyl. In some embodiments, $R^{19C}$ can be an optionally substituted $C_{1-6}$ haloalkyl, for example, $CF_3$. In some embodiments, $R^{21C}$ can be hydrogen. In other embodiments, $R^{21C}$ can be an optionally substituted $C_{1-4}$-alkyl, such as methyl, ethyl, n-propyl, isopropyl, n-butyl, isobutyl and tert-butyl. In an embodiment, $R^{21C}$ can be methyl. In some embodiments, $R^{20C}$ and $R^{21C}$ can be taken together to form an optionally substituted $C_{3-6}$ cycloalkyl. Examples of optionally substituted $C_{3-6}$ cycloalkyl include optionally substituted variants of the following: cyclopropyl, cyclobutyl, cyclopentyl, and cyclohexyl. Depending on the groups that are selected for $R^{20C}$ and $R^{21C}$, the carbon to which $R^{20C}$ and $R^{21C}$ are attached may be a chiral center. In some embodiment, the carbon to which $R^{20C}$ and $R^{21C}$ are attached may be a (R)-chiral center. In other embodiments, the carbon to which $R^{20C}$ and $R^{21C}$ are attached may be a (S)-chiral center.

Examples of suitable

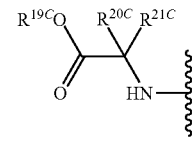

groups include the following:

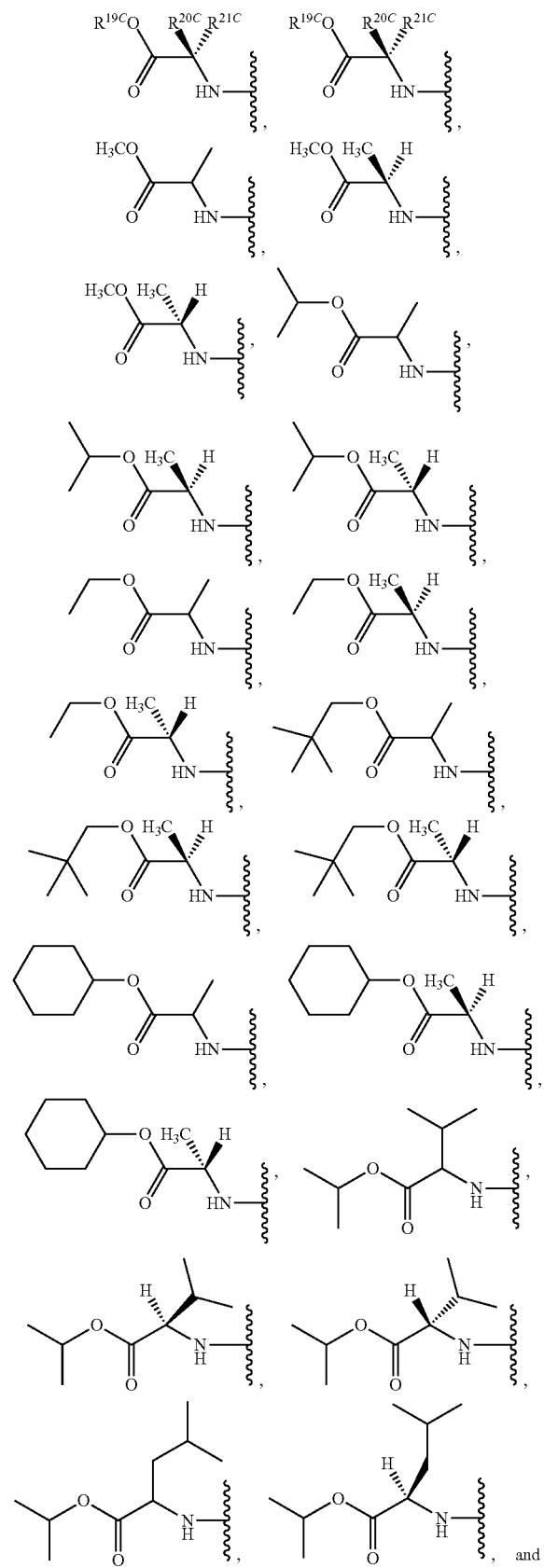

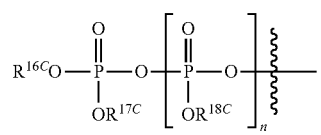

In some embodiments, $R^{1C}$ and $R^{2C}$ can be the same. In other embodiments, $R^{1C}$ and $R^{2C}$ can be different.

In some embodiments, $R^{1C}$ can be can be O⁻ or OH, wherein $R^{16C}$, $R^{17C}$ and $R^{18C}$ can be absent or hydrogen; and n can be 0 or 1. Those skilled in the art understand that when $R^{16C}$, $R^{17C}$ and/or $R^{18C}$ are absent, the associated oxygen will be negatively charge. In some embodiments, when n is 0, the compound of Formula (III) will be a diphosphate. In other embodiments, when n is 1, the compound of Formula (III) will be a triphosphate.

A variety of substituents can be present at the 4'-position of the pentose ring. In some embodiments, $R^{3C}$ can be an optionally substituted $C_{1-6}$ alkyl. Examples of suitable $C_{1-6}$ alkyls include methyl, ethyl, n-propyl, isopropyl, n-butyl, isobutyl, tert-butyl, pentyl (branched and straight-chained), and hexyl (branched and straight-chained). In some embodiments, $R^{3C}$ can be an unsubstituted $C_{1-6}$ alkyl. In other embodiments, $R^{3C}$ can be a substituted $C_{1-6}$ alkyl. For example, $R^{3C}$ can be a halogen substituted $C_{1-6}$ alkyl. In other embodiments, $R^{3C}$ can be an optionally substituted $C_{2-6}$ alkenyl. In some embodiments, $R^3$ can be a substituted $C_{2-6}$ alkenyl. In other embodiments, $R^{3C}$ can be an unsubstituted $C_{2-6}$ alkenyl. For example, $R^{3C}$ can be ethenyl, propenyl or allenyl. In still other embodiments, $R^{3C}$ can be an optionally substituted $C_{2-6}$ alkynyl. In some embodiments, $R^{3C}$ can be a substituted $C_{2-6}$ alkynyl. In other embodiments, $R^{3C}$ can be an unsubstituted $C_{2-6}$ alkynyl. Suitable $C_{2-6}$ alkynyls include ethynyl and propynyl. In yet still other embodiments, $R^{3C}$ can be an optionally substituted $C_{3-6}$ cycloalkyl. In some embodiments, $R^{3C}$ can be a substituted $C_{3-6}$ cycloalkyl. In other embodiments, $R^{3C}$ can be an unsubstituted $C_{3-6}$ cycloalkyl. A non-limiting list of $C_{3-6}$ cycloalkyls include cyclopropyl, cyclobutyl, cyclopentyl and cyclohexyl. In some embodiments, $R^{3C}$ can be an optionally substituted —O—$C_{1-6}$ alkyl. In some embodiments, $R^{3C}$ can be a substituted —O—$C_{1-6}$ alkyl. In other embodiments, $R^{3C}$ can be an unsubstituted —O—$C_{1-6}$ alkyl. Examples of suitable O—$C_{1-6}$ alkyl groups include methoxy, ethoxy, n-propoxy, iso-propoxy, n-butoxy, isobutoxy, tert-butoxy, pentoxy (branched and straight-chained), and hexoxy (branched and straight-chained). In other embodiments, $R^3C$ can be an optionally substituted —O—$C_{3-6}$ alkenyl. In some embodiments, $R^{3C}$ can be a substituted —O—$C_{3-6}$ alkenyl. In other embodiments, $R^{3C}$ can be an unsubstituted —O—$C_{3-6}$ alkenyl. In still other embodiments, $R^{3C}$ can be an optionally substituted —O—$C_{3-6}$ alkynyl. In some embodiments, $R^{3C}$ can be a substituted —O—$C_{3-6}$ alkynyl. In other embodiments, $R^3C$ can be an unsubstituted —O—$C_{3-6}$ alkynyl. In yet still other embodiments, $R^{3C}$ can be cyano. The substituents that can be present on the 3'-position of the pentose ring can vary. In some embodiments, $R^{4C}$ can be OH. In other embodiments, $R^{4C}$ can be an optionally substituted O-linked amino acid. Examples of suitable O-linked amino acids include alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. In some embodiments, the O-linked amino acid can have the structure

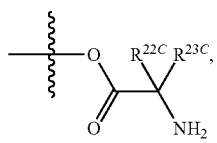

wherein $R^{22C}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{23C}$ can be hydrogen or an optionally substituted $C_{1-4}$-alkyl; or $R^{22C}$ and $R^{23C}$ can be taken together to form an optionally substituted $C_{3-6}$ cycloalkyl.

When $R^{22C}$ is substituted, $R^{22C}$ can be substituted with one or more substituents selected from N-amido, mercapto, alkylthio, an optionally substituted aryl, hydroxy, an optionally substituted heteroaryl, O-carboxy, and amino. In some embodiments, $R^{22C}$ can be an unsubstituted $C_{1-6}$-alkyl, such as those described herein. In some embodiments, $R^{22C}$ can be hydrogen. In other embodiments, $R^{22C}$ can be methyl. In some embodiments, $R^{23C}$ can be hydrogen. In other embodiments, $R^{23C}$ can be an optionally substituted $C_{1-4}$-alkyl, such as methyl, ethyl, n-propyl, isopropyl, n-butyl, isobutyl and tert-butyl. In an embodiment, $R^{23C}$ can be methyl. Depending on the groups that are selected for $R^{22C}$ and $R^{23C}$, the carbon to which $R^{22C}$ and $R^{23C}$ are attached may be a chiral center. In some embodiment, the carbon to which $R^{22C}$ and $R^{23C}$ are attached may be a (R)-chiral center. In other embodiments, the carbon to which $R^{22C}$ and $R^{23C}$ are attached may be a (S)-chiral center.

Examples of suitable

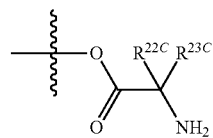

include the following:

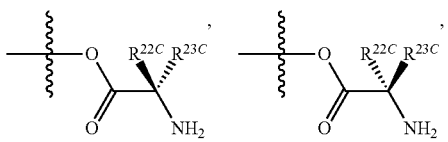

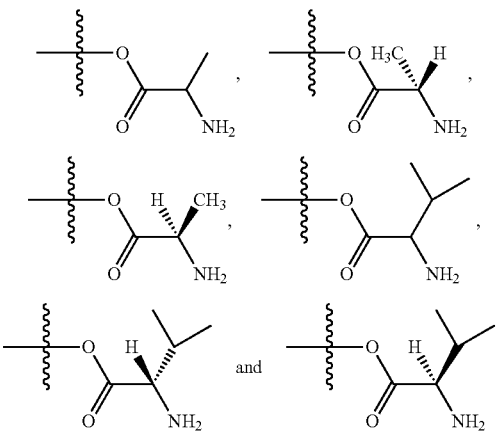

In still other embodiments, $R^{4C}$ can be $-OC(=O)R'''^C$, wherein $R'''^C$ can be an optionally substituted $C_{1-24}$ alkyl. In some embodiments, $R'''^C$ can be a substituted $C_{1-12}$ alkyl. In other embodiments, $R'''^C$ can be an unsubstituted $C_{1-12}$ alkyl. In still other embodiments, $R'''^C$ can be a substituted $C_{1-8}$ alkyl. In yet still other embodiments, $R'''^C$ can be an unsubstituted $C_{1-8}$ alkyl. In some embodiments, $R^{4C}$ can be an optionally substituted acyl. In other embodiments, $R^{4C}$ can be $-OC(=O)R'''^C$, wherein $R'''^C$ can be selected from an optionally substituted $C_{1-12}$ alkyl, an optionally substituted $C_{2-12}$ alkenyl, an optionally substituted $C_{2-12}$ alkynyl, an optionally substituted $C_{3-8}$ cycloalkyl, an optionally substituted $C_{5-8}$ cycloalkenyl, an optionally substituted $C_{6-10}$ aryl, an optionally substituted heteroaryl, an optionally substituted heterocyclyl, an optionally substituted aryl($C_{1-6}$ alkyl), an optionally substituted heteroaryl($C_{1-6}$ alkyl) and an optionally substituted heterocyclyl($C_{1-6}$ alkyl). In some embodiments, $R'''^C$ can be a substituted $C_{1-12}$ alkyl. In other embodiments, $R'''^C$ can be an unsubstituted $C_{1-12}$ alkyl.

A variety of substituents can also be present at the 2'-position of the pentose ring. In some embodiments, $R^{6C}$ can be hydrogen. In other embodiments, $R^{6C}$ can be halogen, such as fluoro. In some embodiments, $R^{5C}$ can be halogen, such as fluoro. In some embodiments, $R^{6C}$ can be hydrogen and $R^{5C}$ can be halogen. In other embodiments, $R^{5C}$ and $R^{6C}$ can be both halogen. For example, $R^{5C}$ and $R^{6C}$ can be both fluoro.

Various optionally substituted heterocyclic bases can be attached to the pentose ring. In some embodiments, one or more of the amine and/or amino groups may be protected with a suitable protecting group. For example, an amino group may be protected by transforming the amine and/or amino group to an amide or a carbamate. In some embodiments, an optionally substituted heterocyclic base or an optionally substituted heterocyclic base with one or more protected amino groups can have one of the following structures:

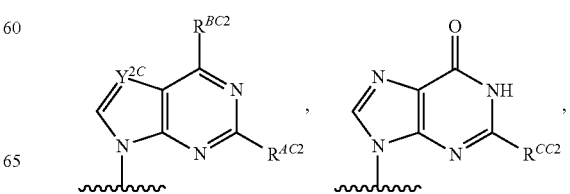

-continued

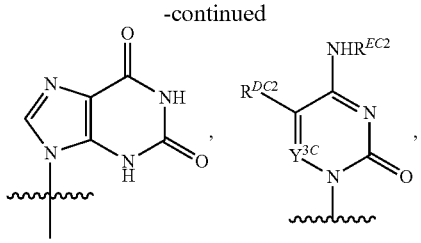

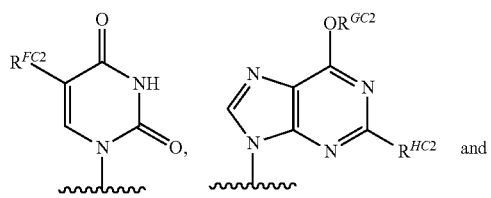

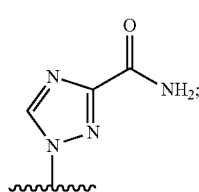

wherein: $R^{AC2}$ can be selected from hydrogen, halogen and $NHR^{JC2}$, wherein $R^{JC2}$ can be selected from hydrogen, can be halogen or $NHR^{WC2}$, wherein $R^{WC2}$ can be selected from hydrogen, an optionally substituted $C_{1-6}$ alkyl, an optionally substituted $C_{2-6}$ alkenyl, an optionally substituted $C_{3-8}$ cycloalkyl, —C(=O)$R^{MC2}$ and —C(=O)O$R^{NC2}$; $R^{CC2}$ can be hydrogen or $NHR^{OC2}$, wherein $R^{OC2}$ can be selected from hydrogen, —C(=O)$R^{PC2}$ and —C(=O)O$R^{QC2}$; $R^{DC2}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{EC2}$ can be selected from hydrogen, hydroxy, an optionally substituted $C_{1-6}$ alkyl, an optionally substituted $C_{3-8}$ cycloalkyl, —C(=O)$R^{RC2}$ and —C(=O)O$R^{SC2}$; $R^{FC2}$ can be selected from hydrogen, halogen, an optionally substituted $C_{1-6}$ alkyl, an optionally substituted $C_{2-6}$ alkenyl and an optionally substituted $C_{2-6}$ alkynyl; $Y^{2C}$ and $Y^{3C}$ can be independently N (nitrogen) or $CR^{IC2}$, wherein $R^{IC2}$ can be selected from hydrogen, halogen, an optionally substituted $C_{1-6}$-alkyl, an optionally substituted $C_{2-6}$-alkenyl and an optionally substituted $C_{2-6}$-alkynyl; $R^{GC2}$ can be an optionally substituted $C_{1-6}$ alkyl; $R^{HC2}$ can be hydrogen or $NHR^{TC2}$, wherein $R^{TC2}$ can be independently selected from hydrogen, —C(=O)$R^{UC2}$ and —C(=O)O$R^{VC2}$; and $R^{KC2}$, $R^{LC2}$, $R^{MC2}$, $R^{NC2}$, $R^{PC2}$, $R^{QC2}$, $R^{RC2}$, $R^{SC2}$, $R^{UC2}$ and $R^{VC2}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl). In some embodiments, the structures shown above can be modified by replacing one or more hydrogens with substituents selected from the list of substituents provided for the definition of "substituted."

In some embodiments, $B^{1C}$ can be

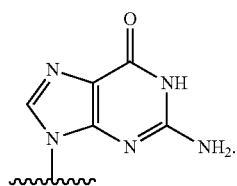 [SMILES: *n1cnc2c(=O)[nH]c(N)nc21]

In other embodiments, $B^{1C}$ can be

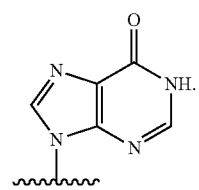 [SMILES: *n1cnc2c(=O)[nH]cnc21]

In still other embodiments, $B^{1C}$ can be

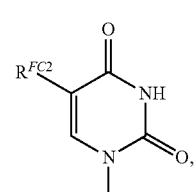

such as

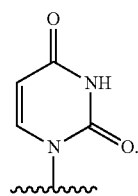 [SMILES: *n1ccc(=O)[nH]c1=O]

In yet still other embodiments, $B^{1C}$ can be

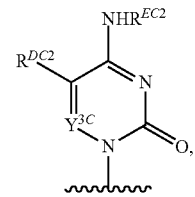

for example,

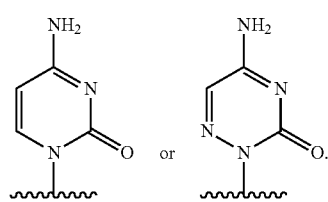 [SMILES: *n1ccc(N)nc1=O ; "or" ; *n1ncc(N)nc1=O]

In some embodiments, $R^{DC2}$ can be hydrogen. In other embodiments, $B^{1C}$ can be

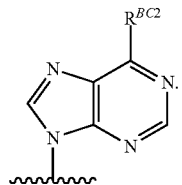

In some embodiments, $R^{BC2}$ can be NH$_2$. In other embodiments, $R^{BC2}$ can be NHR$^{WC2}$, wherein $R^{WC2}$ can be —C(=O)R$^{MC2}$ or —C(=O)OR$^{NC2}$. In still other embodiments, $B^{1C}$ can be

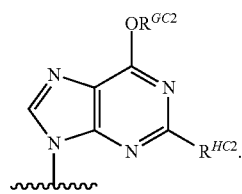

In some embodiments, $B^{1C}$ can be

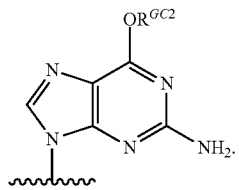

In some embodiments, the compound of Formula (III) can have one of the following structures:

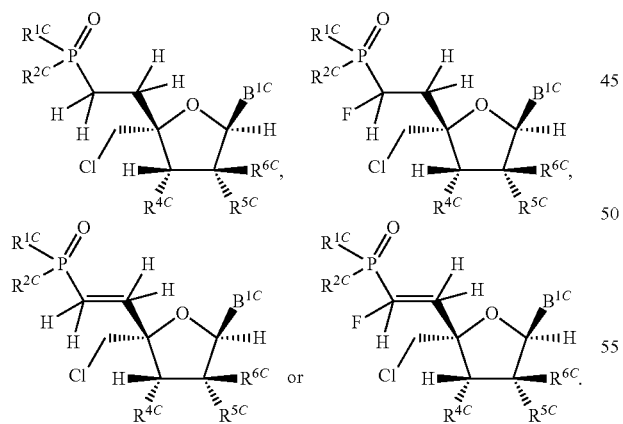

In some embodiments of this paragraph, $B^{1C}$ can be an optionally substituted purine base. In other embodiments of this paragraph, $B^{1C}$ can be an optionally substituted pyrimidine base. In some embodiments of this paragraph, $B^{1C}$ can be guanine. In other embodiments of this paragraph, $B^{1C}$ can be thymine. In still other embodiments of this paragraph, $B^{1C}$ can be cytosine. In yet still other embodiments of this paragraph, $B^{1C}$ can be uracil. In some embodiments of this paragraph, $B^{1C}$ can be adenine. In some embodiments of this paragraph, $R^{1C}$ and $R^{2C}$ can each be an optionally substituted $C_{1-4}$ alkyl. In other embodiments of this paragraph, $R^{1A}$ can be an optionally substituted acyl. In still other embodiments of this paragraph, $R^{1C}$ and $R^{2C}$ can form a mono-, di- or tri-phosphate. In yet other embodiments of this paragraph, $R^{1C}$ and $R^{2C}$ can each be an alkylcarbonyloxyalkoxy. In some embodiments of this paragraph, $R^{4C}$ can be OH. In some embodiments of this paragraph, $R^{5C}$ can be F and $R^{6C}$ can be hydrogen.

Examples of suitable compounds of Formula (I) include, but are not limited to the following:

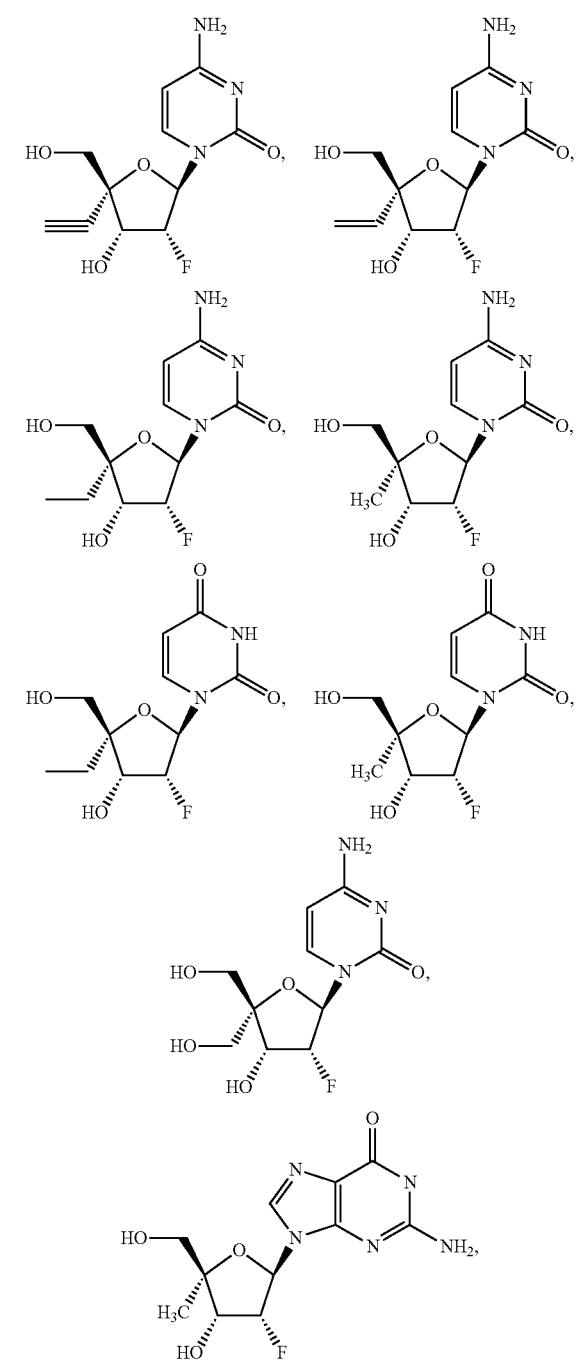

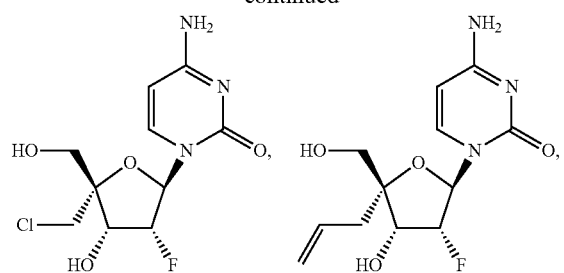
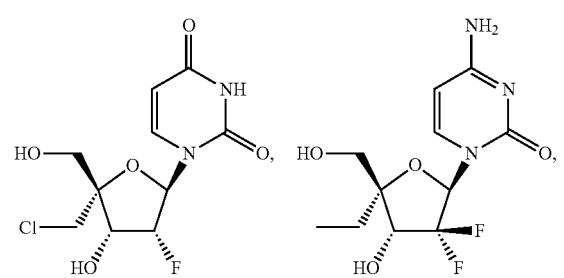
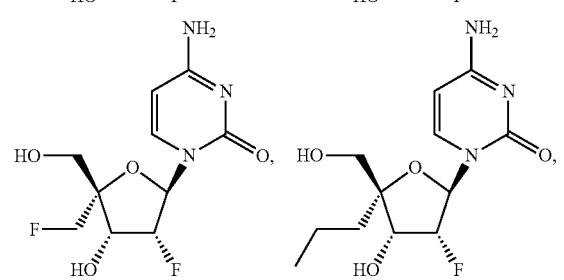
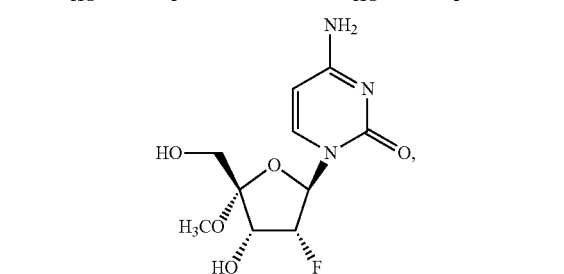
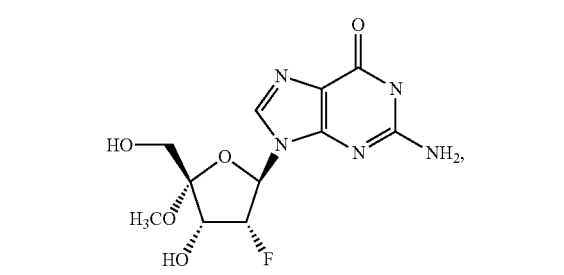
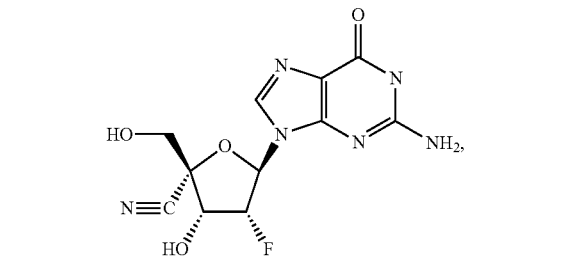
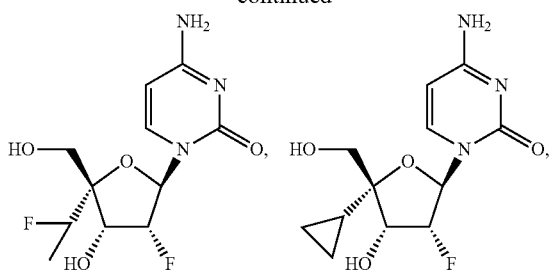
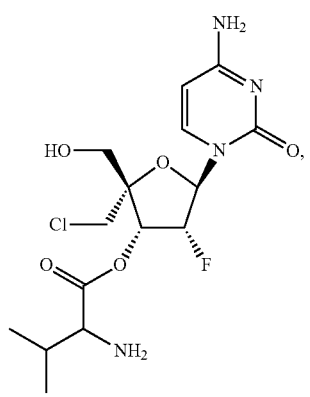
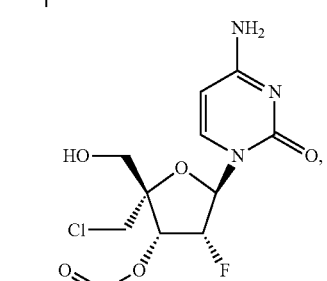
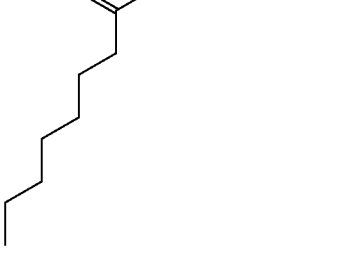
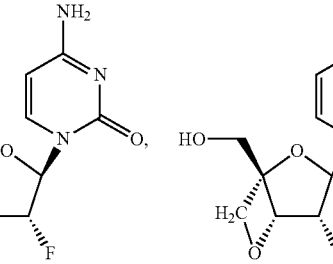
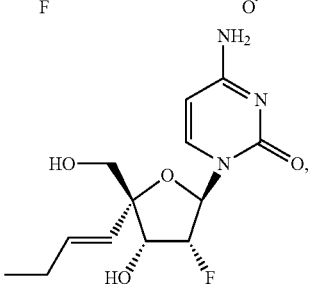

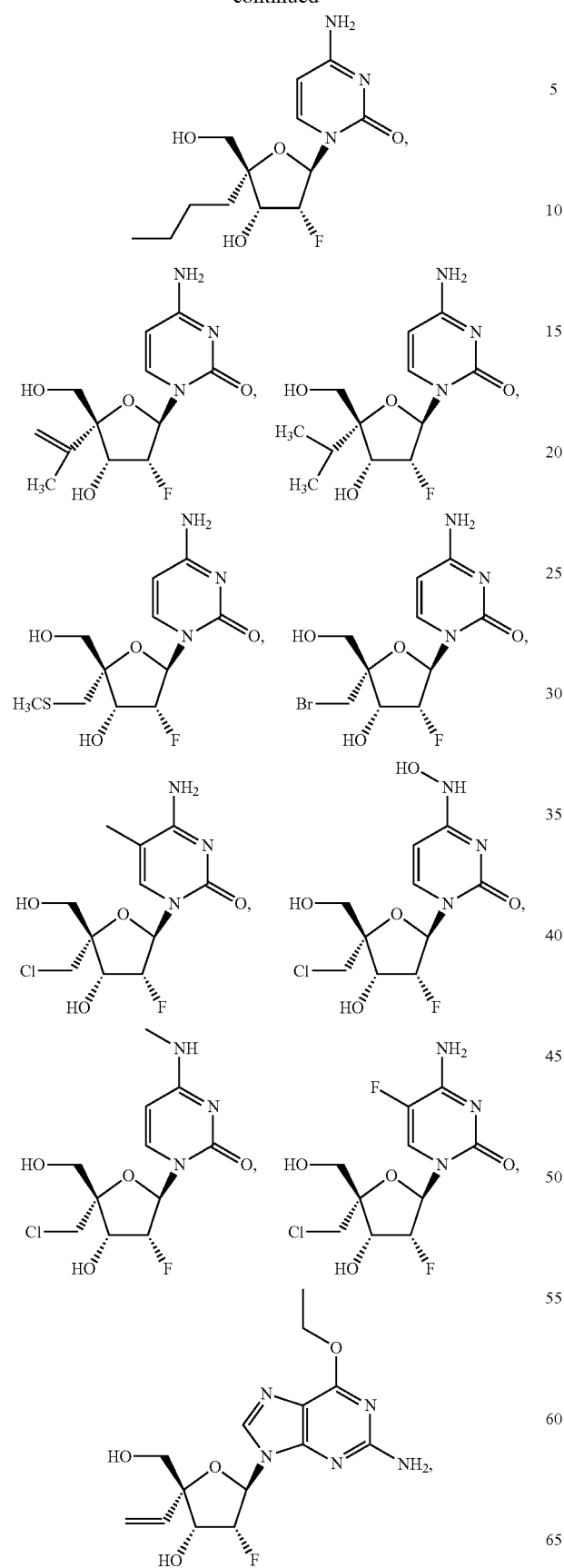
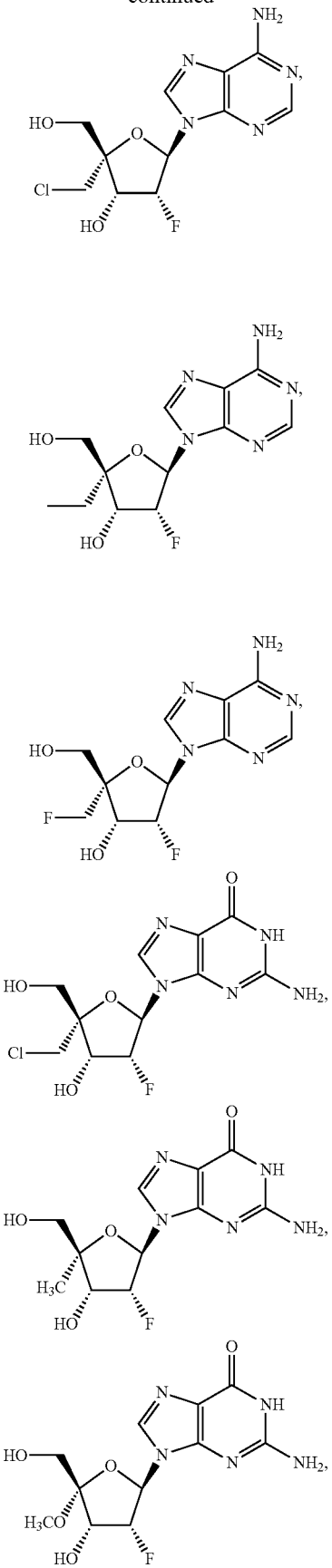

-continued
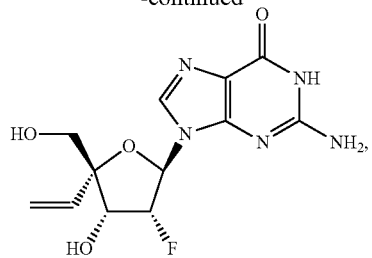
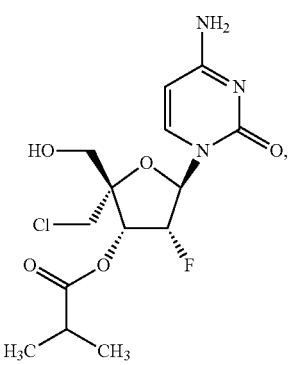
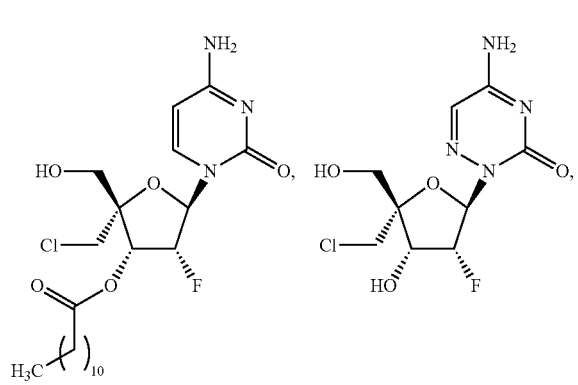
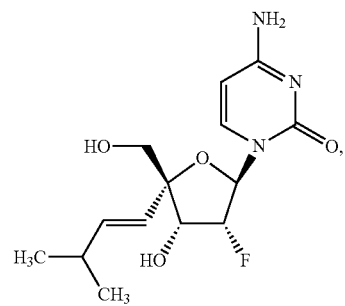
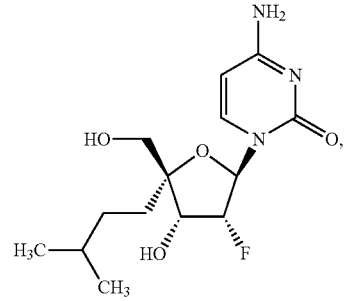
-continued
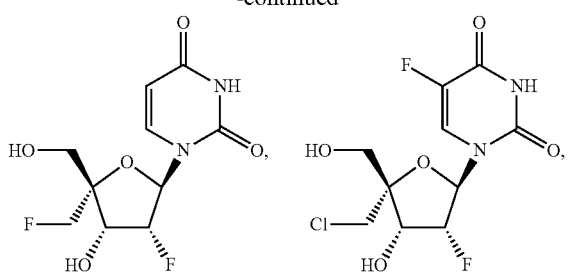
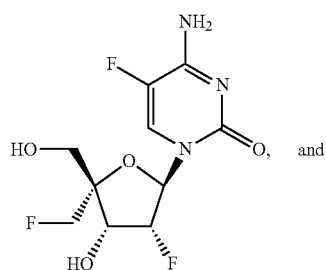
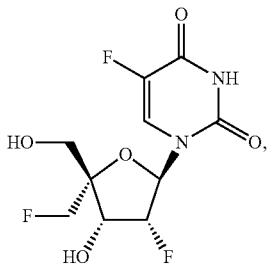
or a pharmaceutically acceptable salt of the foregoing.
Additional examples of a compound of Formula (I) include the following:
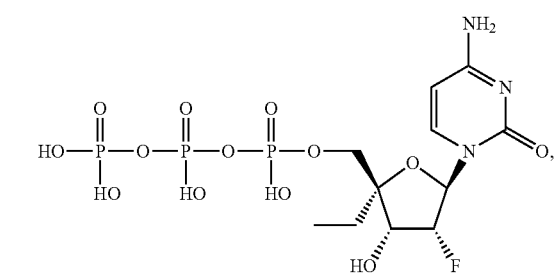
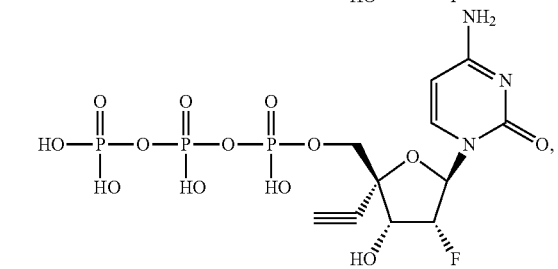

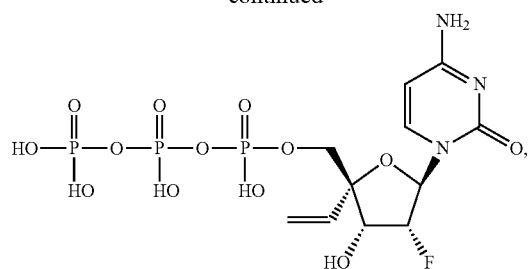
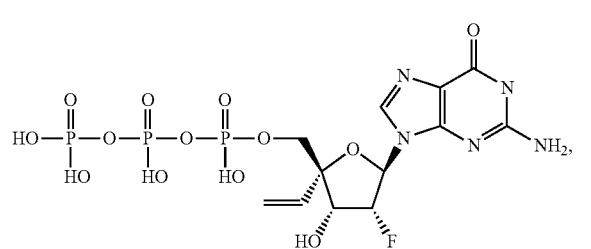
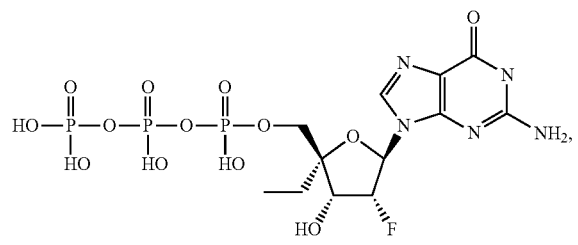
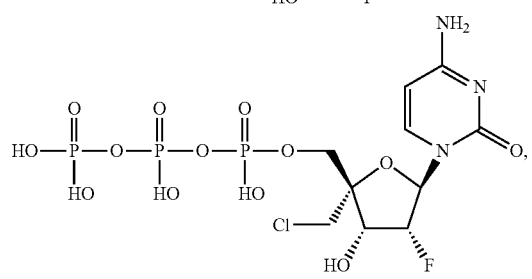
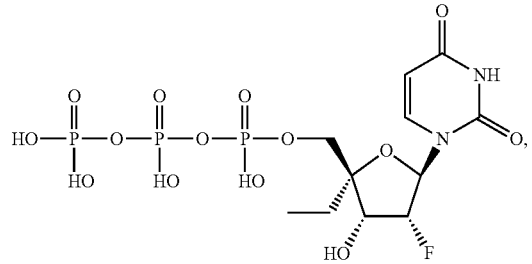
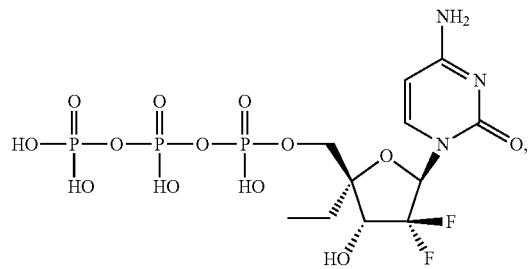
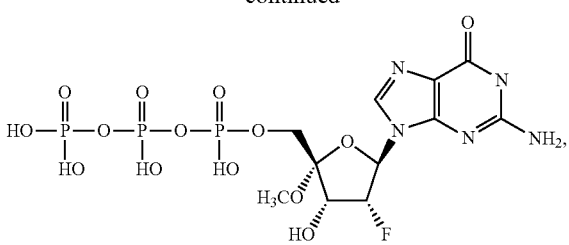
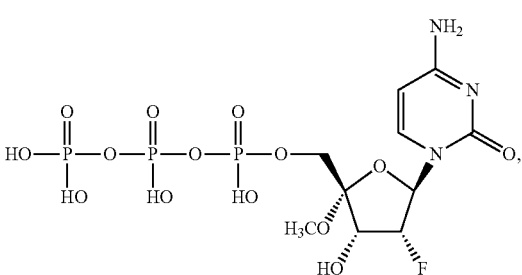
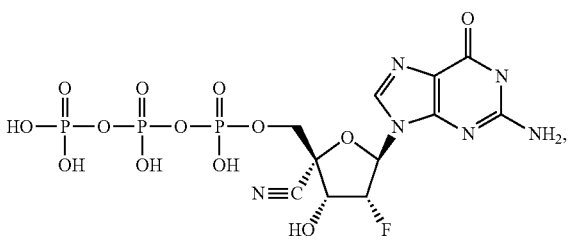
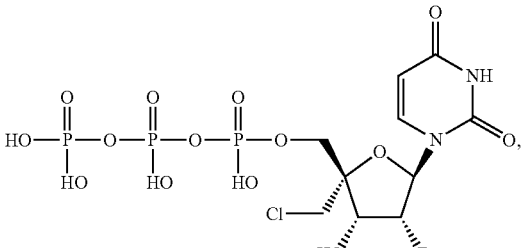
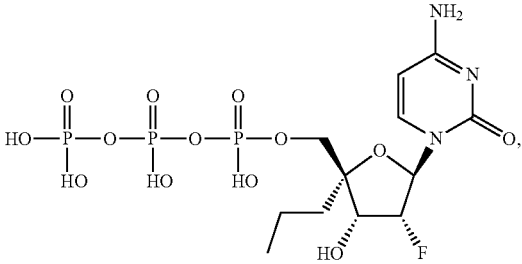
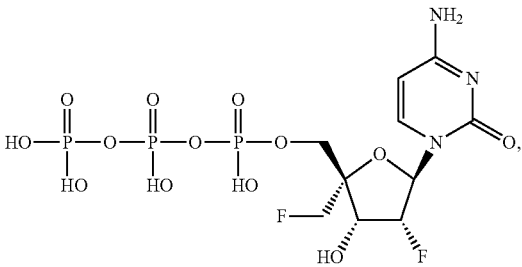

71
-continued
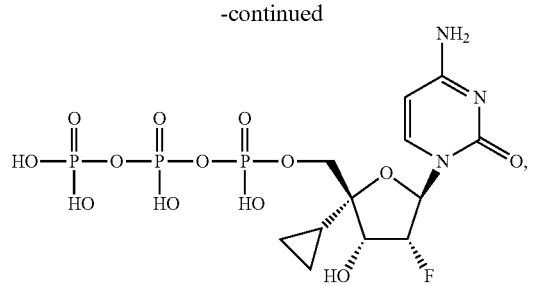
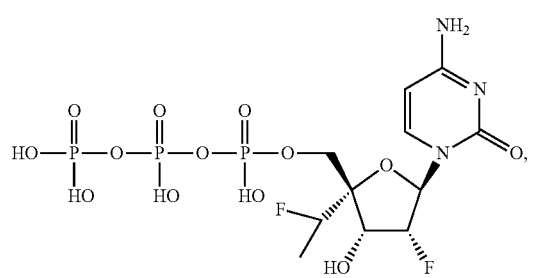
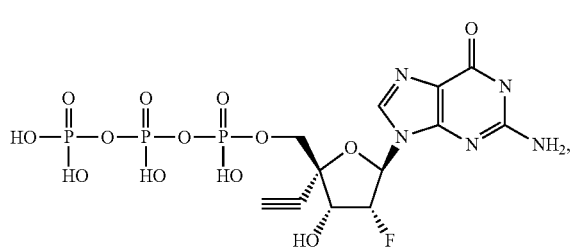
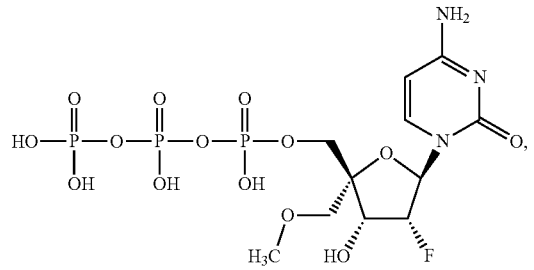
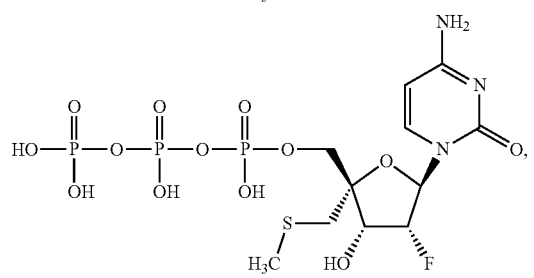
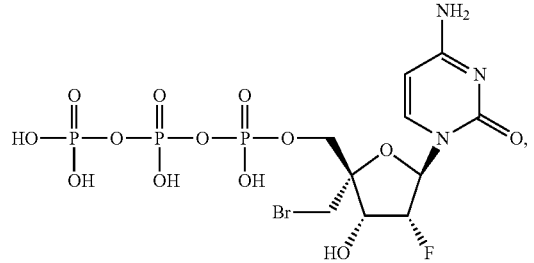
72
-continued
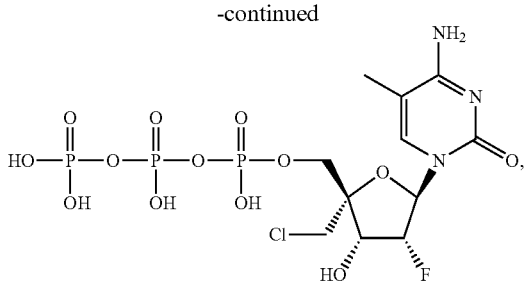
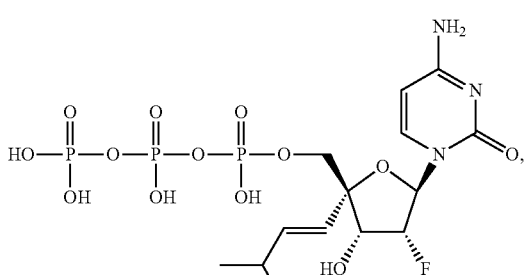
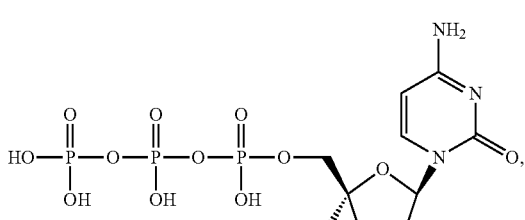
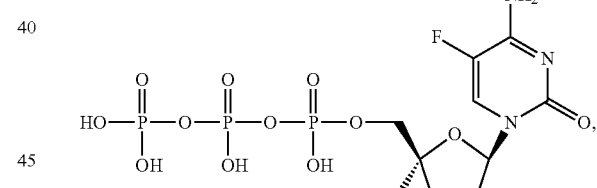
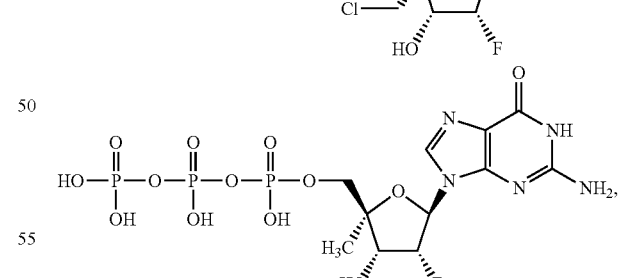
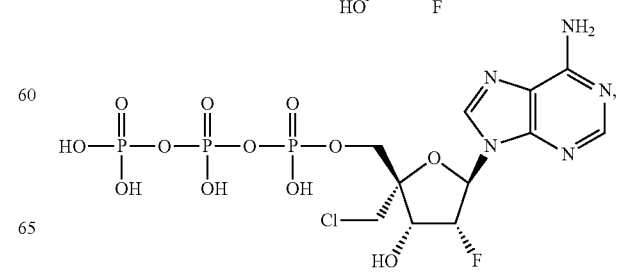

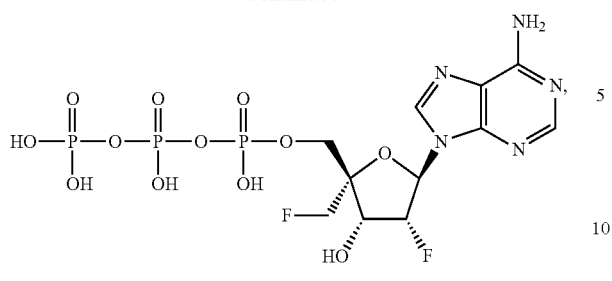
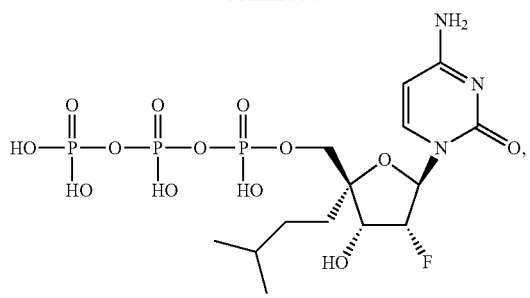
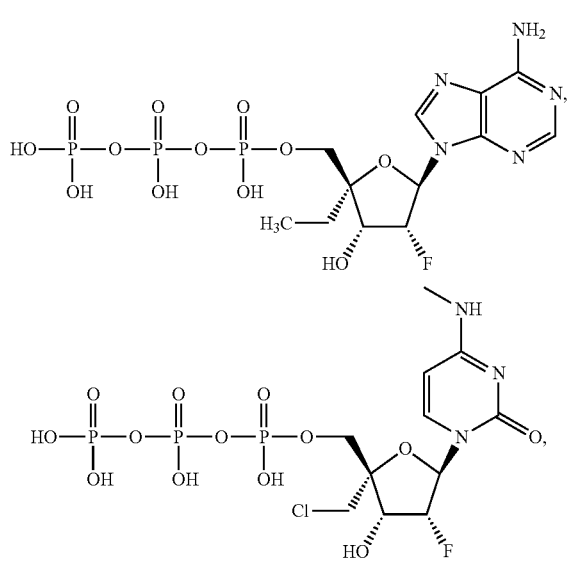
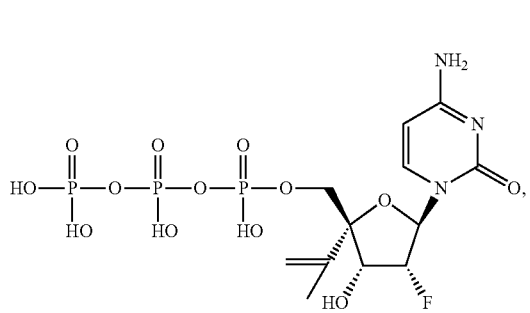
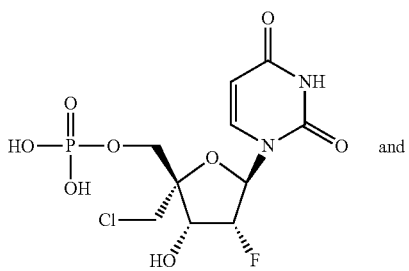
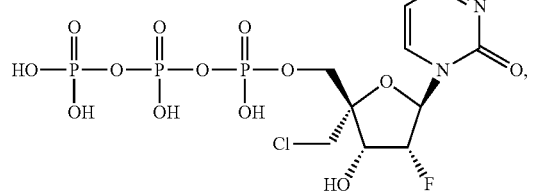
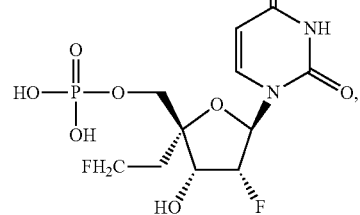
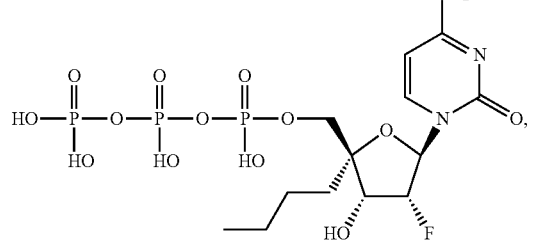
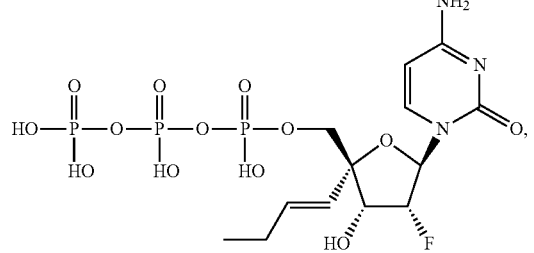
or a pharmaceutically acceptable salt of the foregoing.
Further examples of a compound of Formula (I) include, but are not limited to the following:
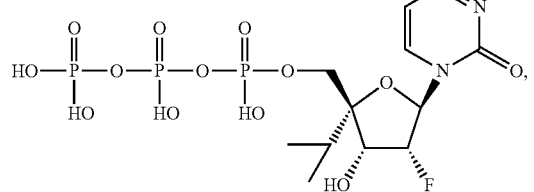
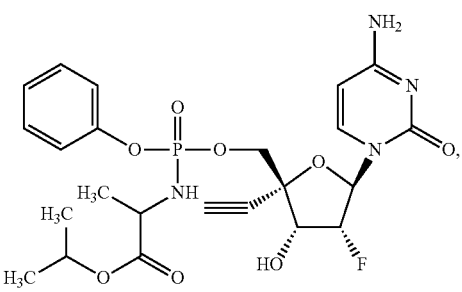

75
-continued
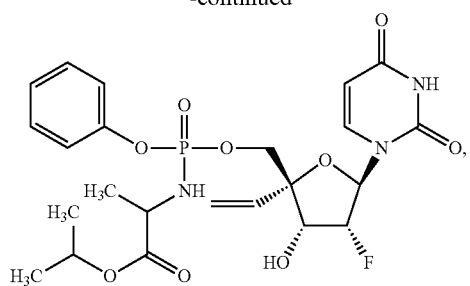
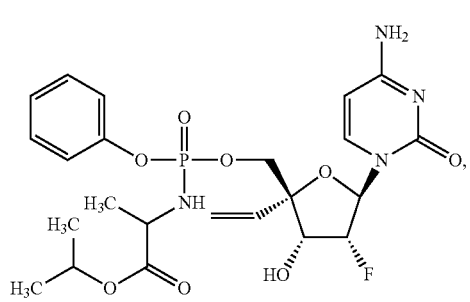
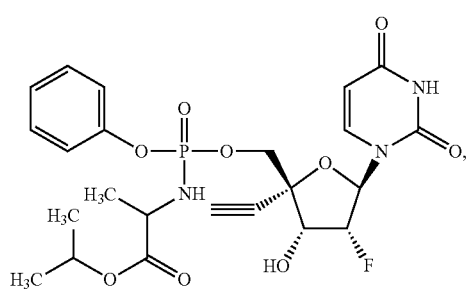
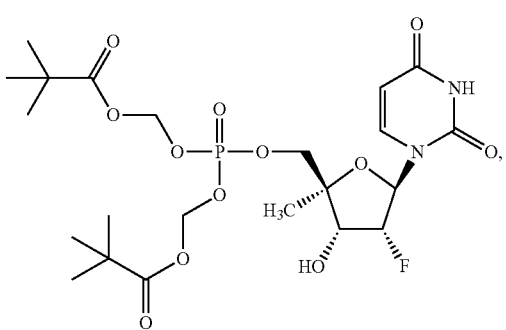
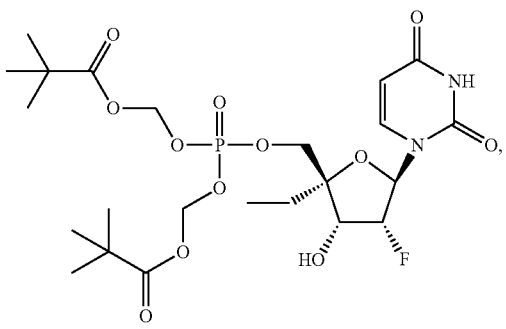
76
-continued
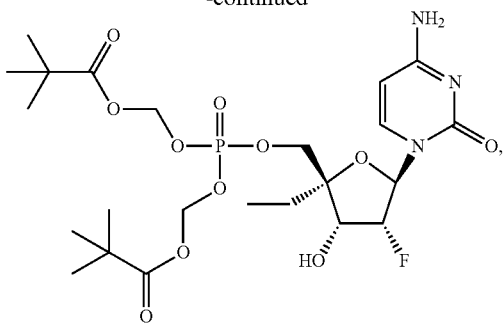
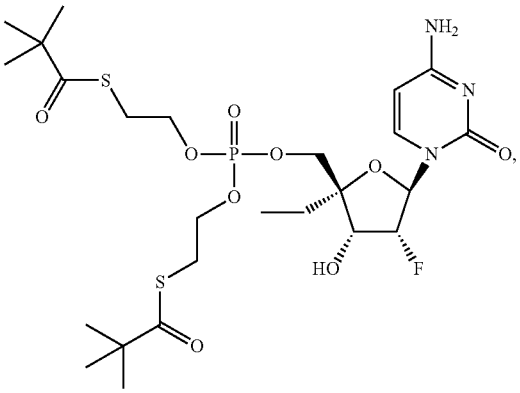
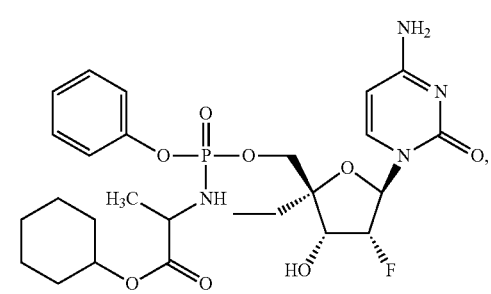
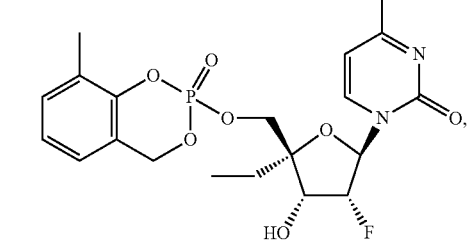
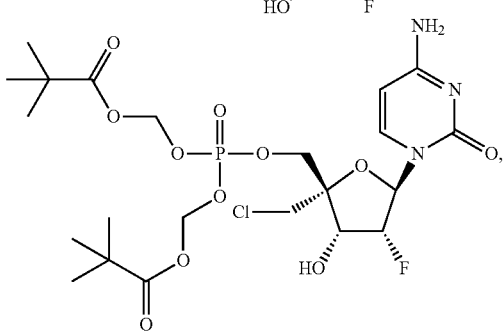

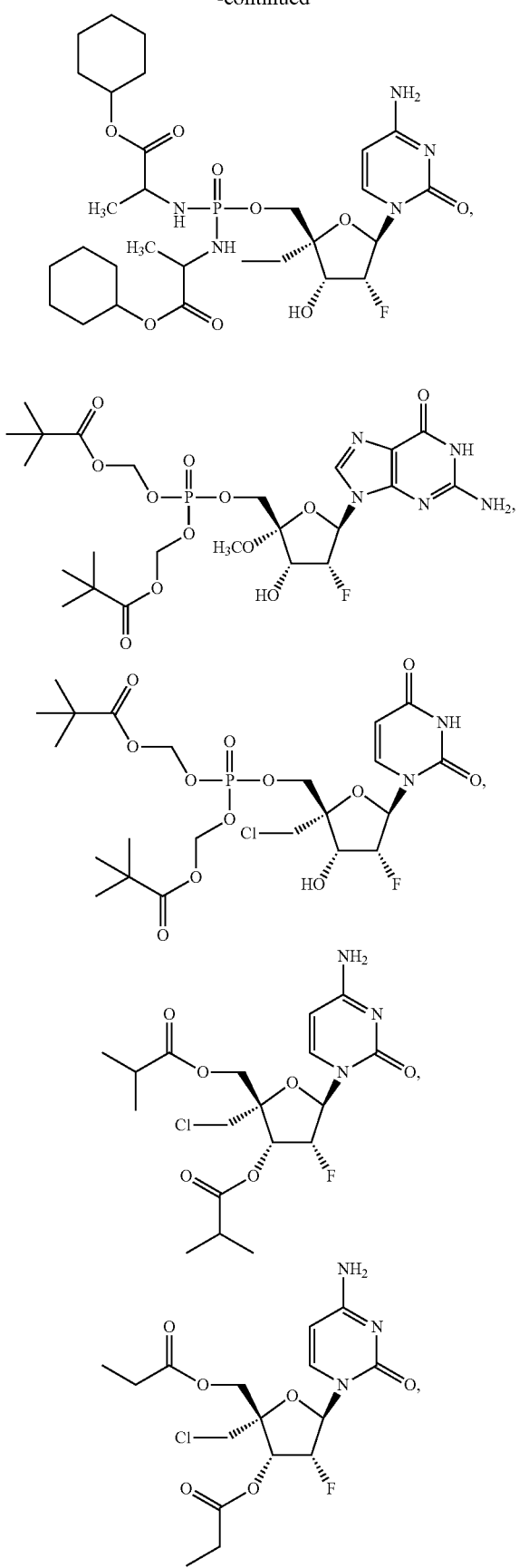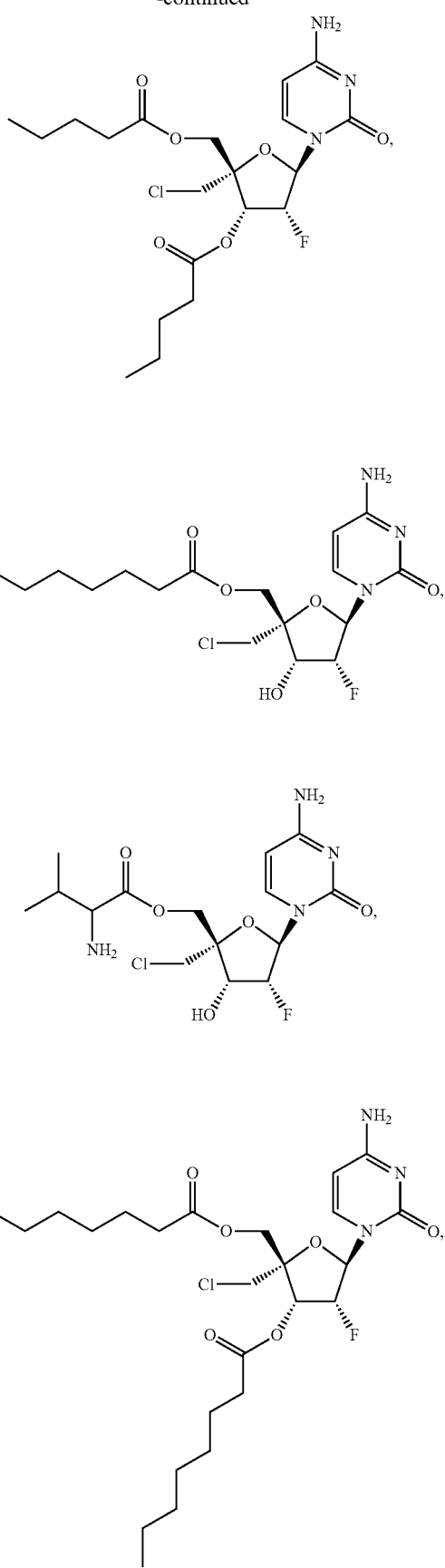

79
-continued
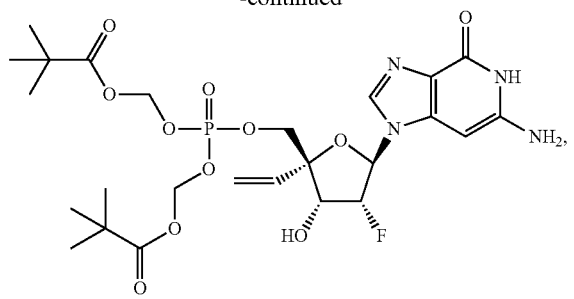
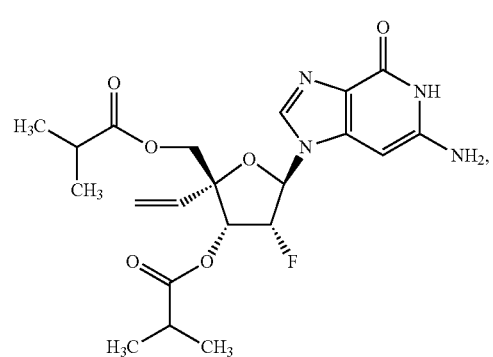
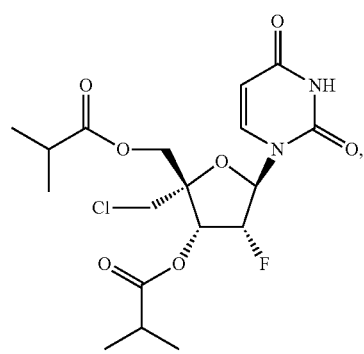
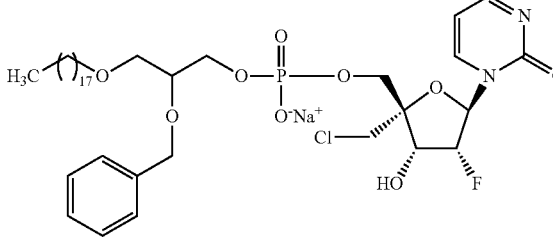
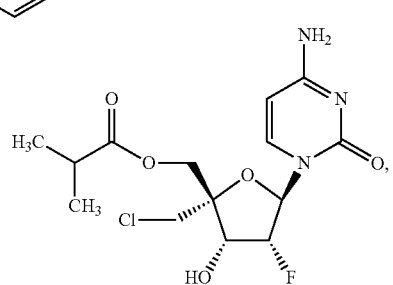
80
-continued
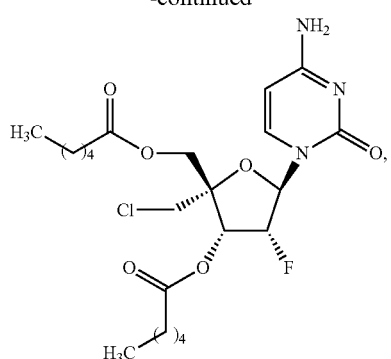
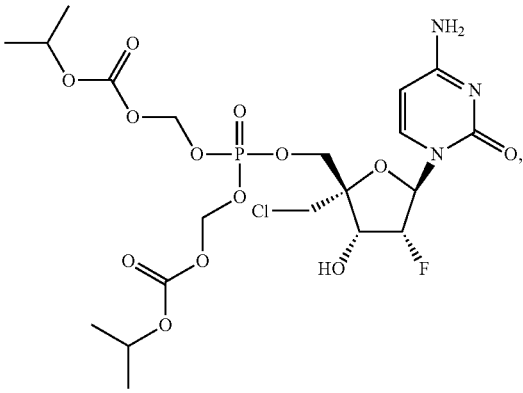
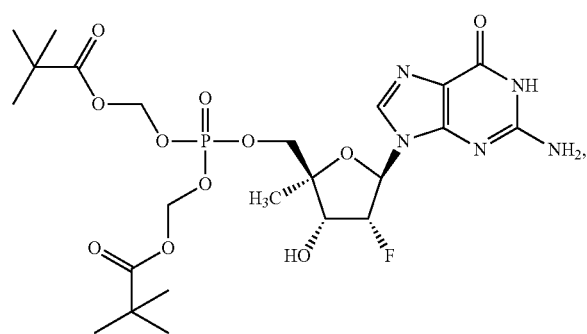
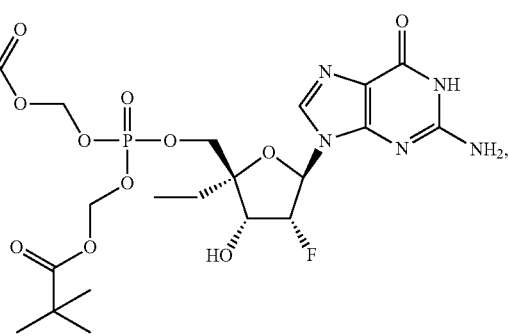

81
-continued
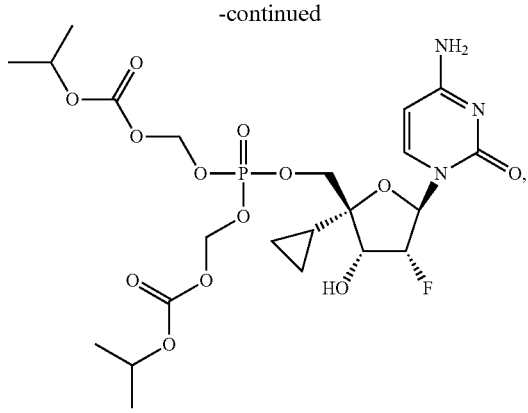
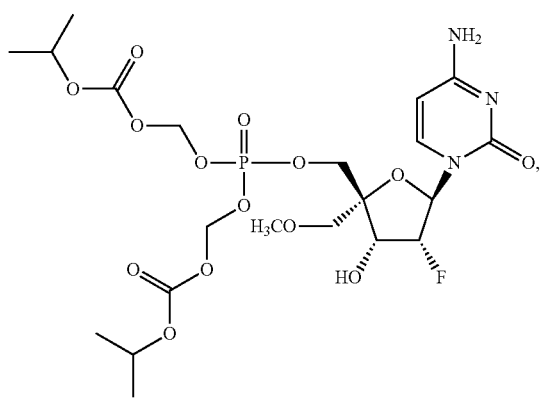
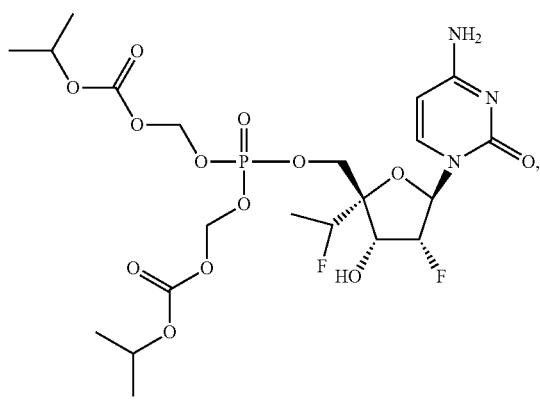
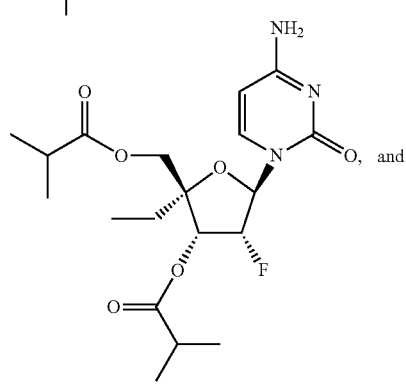
82
-continued
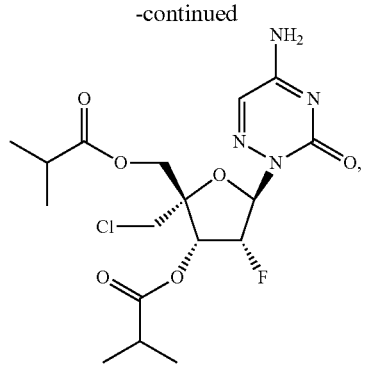
or a pharmaceutically acceptable salt of the foregoing.
Examples of a compound of Formula (II) include, but are not limited to, the following:
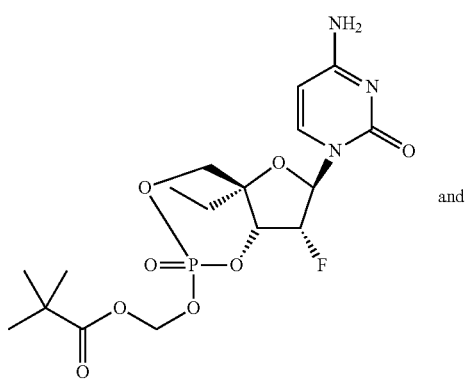
and
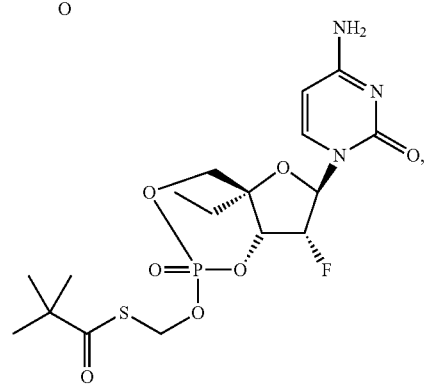
or a pharmaceutically acceptable salt of the foregoing.
Examples of a compound of Formula (III) include, but are not limited to, the following:
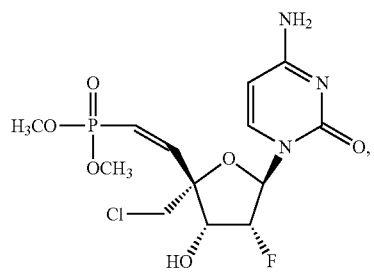

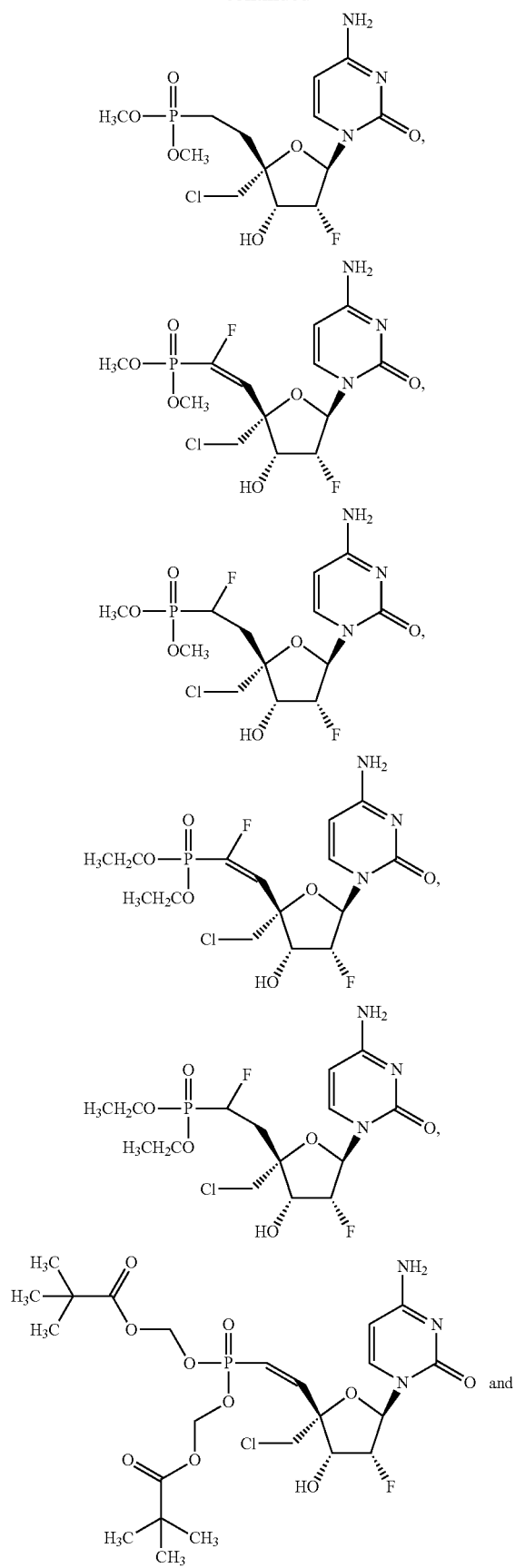
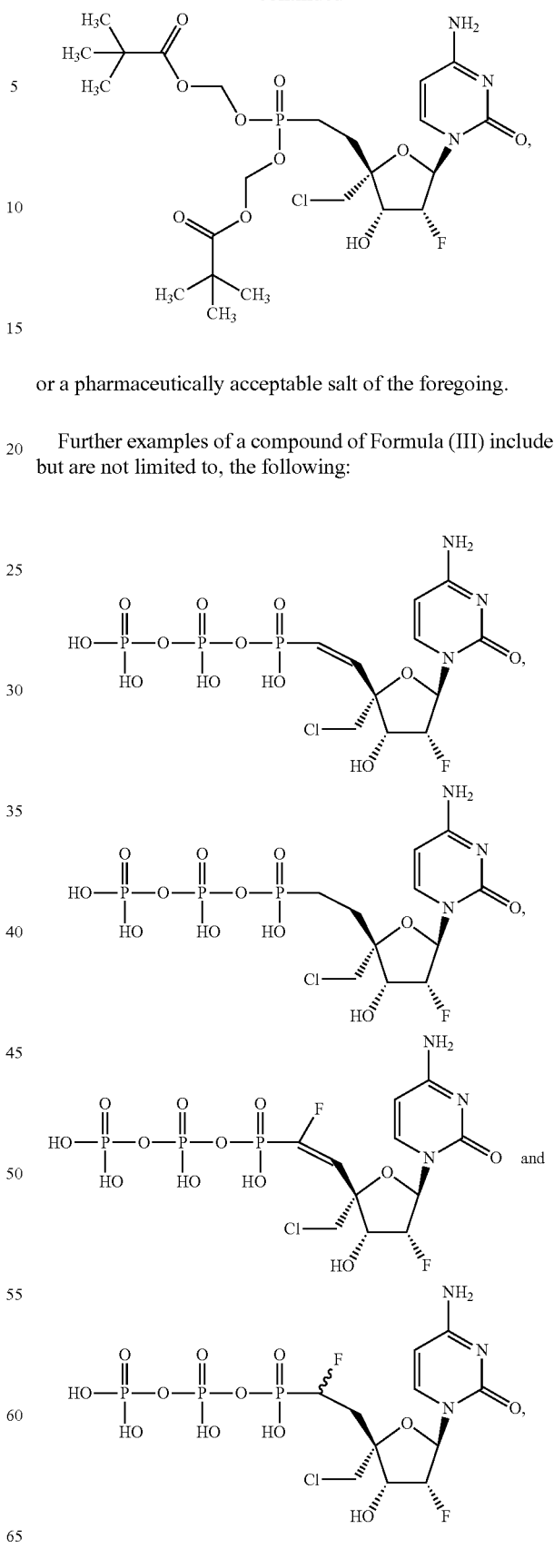
or a pharmaceutically acceptable salt of the foregoing.
Further examples of a compound of Formula (III) include, but are not limited to, the following:
or a pharmaceutically acceptable salt of the foregoing.

Synthesis

Compounds of Formula (I) Formula (II) and Formula (III), and those described herein may be prepared in various ways. Some compounds of Formulae (I), (II) and (III) can be obtained commercially and/or prepared utilizing known synthetic procedures. General synthetic routes to the compounds of Formulae (I), (II) and (III), and some examples of starting materials used to synthesize the compounds of Formulae (I), (II) and (III) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

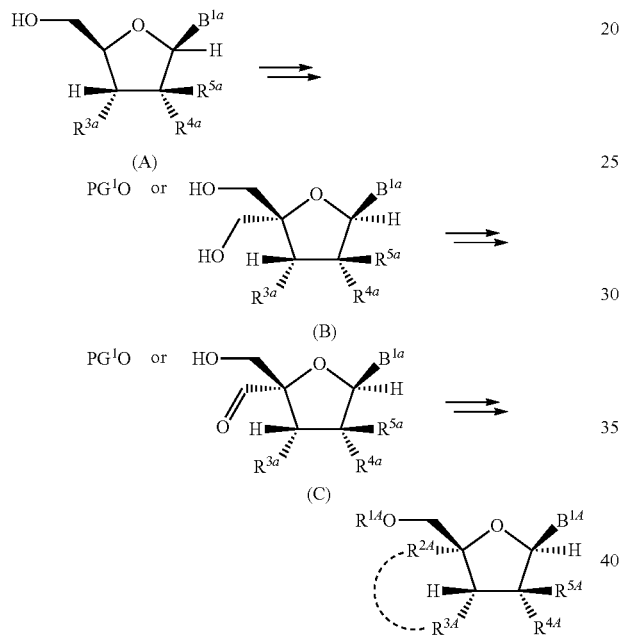

As shown in Scheme 1, compounds of Formula (I) can be prepared from a nucleoside, for example, a nucleoside of Formula (A). In Scheme 1, $R^{3a}$, $R^{4a}$, $R^{5a}$, and $B^{1a}$ can be the same as $R^{3A}$, $R^{4A}$, $R^{5A}$, and $B^{1A}$ as described herein for Formula (I), and $PG^1$ is a suitable protecting group. A hydroxyalkyl group can be formed at the 4'-position of the pentose ring using suitable conditions known to those skilled in the art. Examples of suitable conditions for forming a hydroxyalkyl include the use of 2-iodoxybenzoic acid (IBX) aqueous formaldehyde and sodium borohydride. A compound of Formula (B) can be oxidized to an aldehyde using a suitable oxidizing agent(s) to form a compound of Formula (C). An example of suitable oxidizing agent is Dess-Martin periodinane. An optionally substituted $C_{2-6}$ alkenyl or an optionally substituted $C_{2-6}$ alkynyl can be formed at the 4'-position using methods known to those skilled in the art, for example, Wittig reagent and n-BuLi, Wittig-type reactions, Peterson olefination reaction, and Corey Fuchs reaction. An optionally substituted $C_{1-6}$ alkyl can be obtained by hydrogenating the unsaturated group attached to the 4'-position, for example, using hydrogen over palladium on carbon.

Alternatively, a compound of Formula (B) can be transformed to a haloalkyl using a suitable agent(s), for example, to an iodide using imidazole, triphenylphosphine and iodine; to a fluoro using diethylaminosulfur trifluoride (DAST); or to a chloro using triphenylphosphine and carbontetrachloride in dichloroethylene (DCE). An iodoalkyl can be transformed to an unsubstituted $C_{1-6}$ alkyl group using methods known to those skilled in the art, for example, hydrogen over palladium on carbon. A compound of Formula (C) can be reacted with hydroxylamine to form an oxime. The oxime can be transformed to a cyano group using methods known to those skilled in the art, for example, using methanesulfonyl chloride.

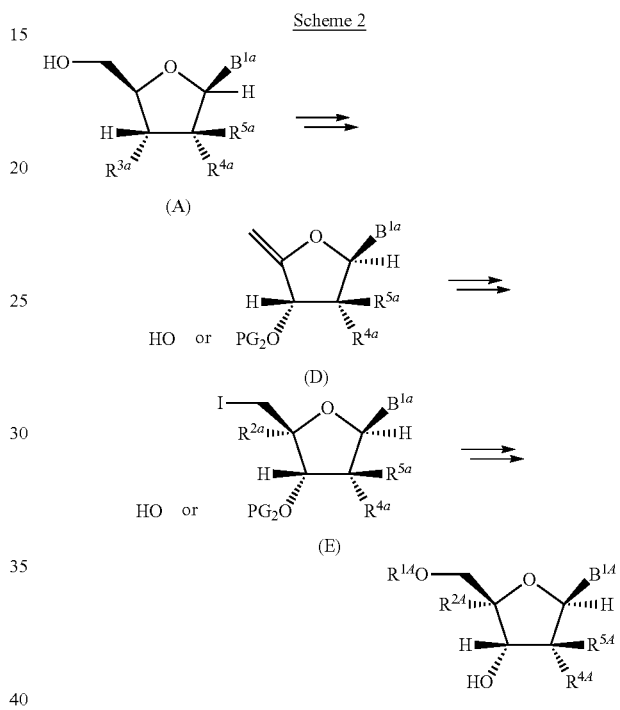

As shown in Scheme 2, compounds of Formula (I), where $R^{2A}$ is an optionally substituted —O—$C_{1-6}$ alkyl, an optionally substituted —O—$C_{3-6}$ alkenyl or an optionally substituted —O—$C_{3-6}$ alkynyl, can be prepared from a nucleoside, for example, a nucleoside of Formula (A). In Scheme 2, $R^{2a}$, $R^{3a}$, $R^{4a}$, $R^{5a}$ and $B^{1a}$ can be the same as $R^{2A}$, $R^{3A}$, $R^{4A}$, $R^{5A}$ and $B^{1A}$ as described herein for Formula (I), and $PG^2$ can be a suitable protecting group. The nucleoside can undergo elimination and form an olefin having the general formula of Formula (D). A compound of Formula (D) can be treated with an iodinating reagent in the presence of lead carbonate and an alkoxy source to form a compound of Formula (E). A compound of Formula (E) can then be transformed to a compound of Formula (I) through displacement of the iodide with an oxygen nucleophile.

Scheme 3

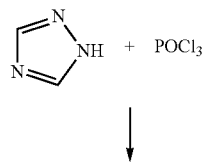

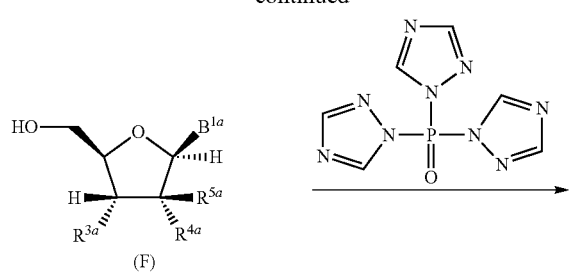

(F)

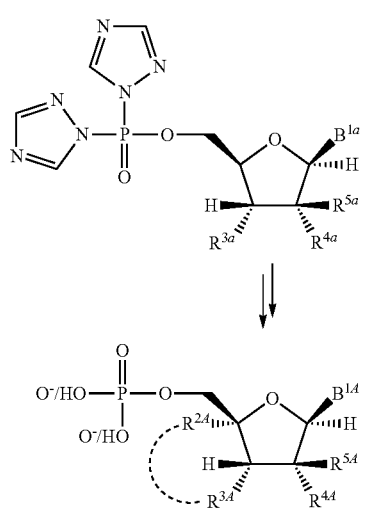

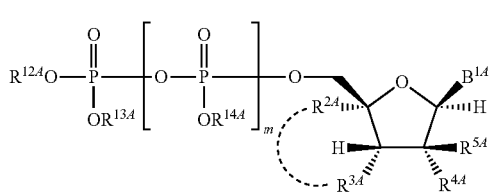

Scheme 4

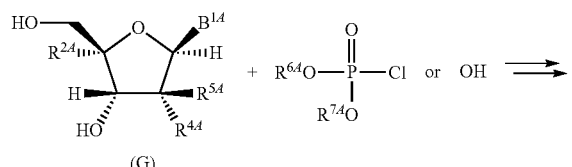

(G)

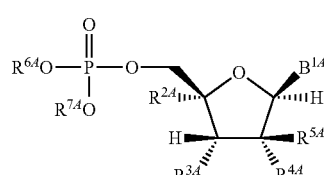

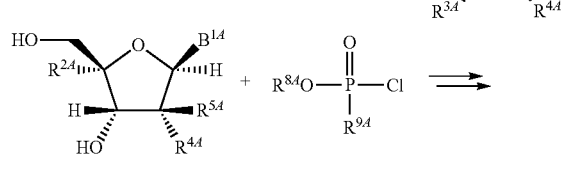

(G)

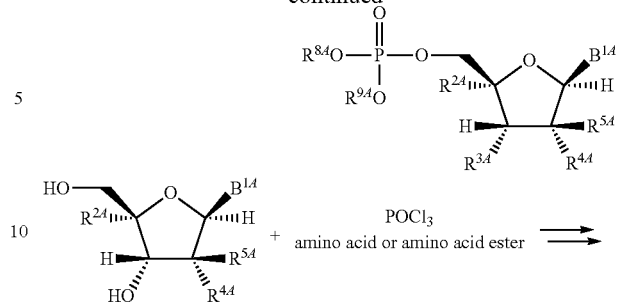

(G)

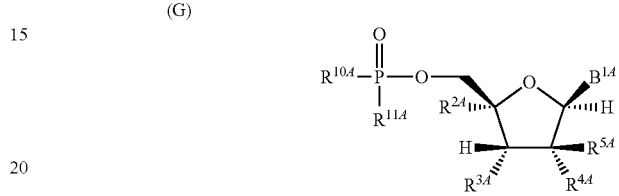

Compounds of Formula (I) having a phosphorus containing group attached to the 5'-position of the pentose ring can be prepared using various methods known to those skilled in the art. Examples of methods are shown in Schemes 3 and 4. A phosphorus containing precursor can be coupled to the nucleoside, for example, a compound of Formula (F) or a compound of Formula (G). As shown in Scheme 3, following the coupling of the phosphorus containing precursor, any leaving groups can be cleaved under suitable conditions, such as hydrolysis. Further phosphorus containing groups can be added using methods known to those skilled in the art, for example using a pyrophosphate.

In some embodiments, an alkoxide can be generated from a compound of Formula (G) using an organometallic reagent, such as a Grignard reagent. The alkoxide can be coupled to the phosphorus containing precursor. Suitable Grignard reagents are known to those skilled in the art and include, but are not limited to, alkylmagnesium chlorides and alkylmagnesium bromides. In some embodiments, an appropriate base can be used. Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)). Alternatively, a phosphorus containing precursor can be added to the nucleoside and form a phosphite. The phosphite can be oxidized to a phosphate using conditions known to those skilled in the art. Suitable conditions include, but are not limited to, meta-chloroperoxybenzoic acid (MCPBA) and iodine as the oxidizing agent and water as the oxygen donor.

When compounds of Formula (I) have $Z^{1A}$, $Z^{2A}$ or $Z^{3A}$ being sulfur, the sulfur can be added in various manners known to those skilled in the art. In some embodiments, the sulfur can be part of the phosphorus containing precursor, for example,

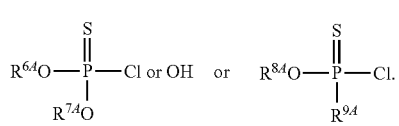

Alternatively, the sulfur can be added using a sulfurization reagent. Suitable sulfurization agents are known to those skilled in the art, and include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

Suitable phosphorus containing precursors can be commercially obtained or prepared by synthetic methods known to those skilled in the art. Examples of general structures of phosphorus containing precursors are shown in Schemes 3 and 4.

Scheme 5:

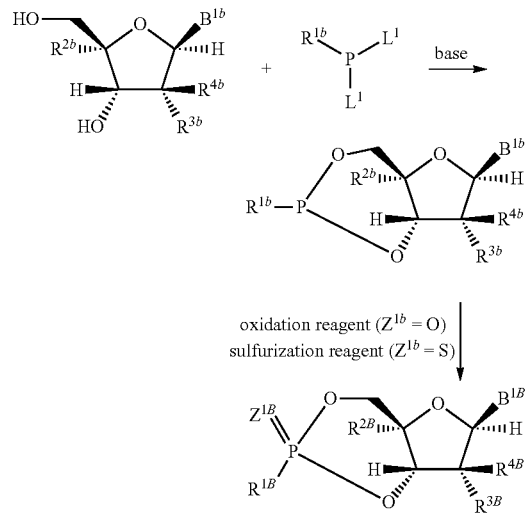

A method for forming a compound of Formula (II) is shown in Scheme 5. In Scheme 5, $R^{1b}$, $R^{2b}$, $R^{3b}$, $R^{4b}$ and $B^{1b}$ can be the same as $R^{1B}$, $R^{2B}$, $R^{3B}$, $R^{4B}$ and $B^{1B}$ as described herein for Formula (II), each $L^1$ can be a halogen, a sulfonate ester or an amine (mono- or di-substituted), and X can be oxygen or sulfur. As shown in Scheme 5, a compound having a hydroxy group attached to the 3'-carbon and a hydroxy group attached to the 5'-carbon can be reacted with a compound having the formula, $(R^{1b})P(L^1)_2$, in the presence of a base, to produce a phosphite compound. Suitable bases are known to those skilled in the art and described herein. The phosphorus can then be oxidized to phosphorus(V) using a suitable oxidizing agent, to produce a compound where X is O (oxygen). Alternatively, the phosphite compound can be reacted with a sulfurization reagent to produce a compound where X is S (sulfur). Suitable oxidizing and sulfurization agents are known to those skilled in the art. For example, the oxidation can be carried out using iodine as the oxidizing agent and water as the oxygen donor. Suitable sulfurization agents are described herein.

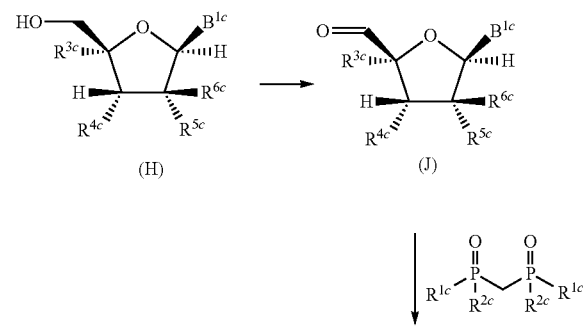

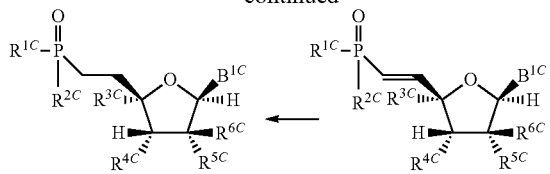

A method for forming a compound of Formula (III) is shown in Scheme 6. In Scheme 6, $R^{1c}$, $R^{2c}$, $R^{3c}$, $R^{4c}$, $R^{5c}$, $R^{6c}$ and $B^{1c}$ can be the same as $R^{1C}$, $R^{2C}$, $R^{3C}$, $R^{4C}$, $R^{5C}$, $R^{6C}$ and $B^{1C}$ as described herein for Formula (III), and $R^{7C}$ and $R^{8C}$ are not shown. The oxygen attached to the 5'-carbon of the compound of Formula (H) can be oxidized to a ketone using methods and reagents known to those skilled in the art. For example, an oxidizing agent, such as Dess-Martin periodinane, can be utilized. A phosphorus-containing reagent can then be added to a compound of Formula (J) in the presence of a strong base (e.g., sodium hydride). The double bond can be hydrogenated, for example using hydrogen gas or Pd/C, to a single bond. Additional phosphates can be added via phosphorylation to form a di- or tri-phosphate using suitable reagents, such as a pyrophosphate (e.g., tetrabutylammonium pyrophosphate).

An acyl group can be added to the 5'-position and/or the 3'-position of a compound of Formula (I) or (III) using methods known to those skilled in the art. One suitable method is using an anhydride in pyridine.

During the synthesis of any of the compounds described herein, if desired, any hydroxy groups attached to the pentose ring, and any —NH and/or $NH_2$ groups present on the $B^{1a}$, $B^{1b}$ and $B^{1c}$ can be protected with one or more suitable protecting groups. Suitable protecting groups are described herein. For example, when $R^{3a}$ and/or $R^{4c}$ is a hydroxy group, $R^{3a}$ and/or $R^{4c}$ can be protected with a triarylmethyl group or a silyl group. Likewise, any —NH and/or $NH_2$ groups present on the $B^{1a}$, $B^{1b}$ and $B^{1c}$ can be protected, such as with a triarylmethyl and a silyl group(s). Examples of triarylmethyl groups include but are not limited to, trityl, monomethoxytrityl (MMTr), 4,4'-dimethoxytrityl (DMTr), 4,4',4"-trimethoxytrityl (TMTr), 4,4',4"-tris-(benzoyloxy) trityl (TBTr), 4,4',4"-tris(4,5-dichlorophthalimido) trityl (CPTr), 4,4',4"-tris(levulinyloxy) trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4"-tris-(tert-butylphenyl)methyl (TTTr) and 4,4'-di-3,5-hexadienoxytrityl. Examples of silyl groups include, but are not limited to, trimethylsilyl (TMS), tert-butyldimethylsilyl (TB-DMS), triisopropylsilyl (TIPS), tert-butyldiphenylsilyl (TB-DPS), tri-iso-propylsilyloxymethyl and [2-(trimethylsilyl)ethoxy]methyl. Alternatively, $R^{3a}$ and $R^{4a}$ and/or $R^{4c}$ and $R^{5c}$ can be protected by a single achiral or chiral protecting group, for example, by forming an orthoester, a cyclic acetal or a cyclic ketal. Suitable orthoesters include methoxymethylene acetal, ethoxymethylene acetal, 2-oxacyclopentylidene orthoester, dimethoxymethylene orthoester, 1-methoxyethylidene orthoester, 1-ethoxyethylidene orthoester, methylidene orthoester, phthalide orthoester 1,2-dimethoxyethylidene orthoester, and alpha-methoxybenzylidene orthoester; suitable cyclic acetals include methylene acetal, ethylidene acetal, t-butylmethylidene acetal, 3-(benzyloxy)propyl acetal, benzylidene acetal, 3,4-dimethoxybenzylidene acetal and p-acetoxybenzylidene acetal; and suitable cyclic ketals include 1-t-butylethylidene ketal, 1-phenylethylidene ketal, isopropylidene ketal, cyclopentylidene ketal, cyclohexylidene ketal, cycloheptylidene ketal and 1-(4-methoxyphenyl)ethylidene ketal. Those skilled in the art will appreciate that groups attached to the pentose ring and any —NH and/or $NH_2$ groups present on the $B^{1a}$, $B^{1b}$ and $B^{1c}$ can be protected with various protecting groups, and any protecting groups present can be exchanged for other protecting groups. The selection and exchange of the protecting groups is within the skill of those of ordinary skill in the art. Any protecting group(s) can be removed by methods known in the art, for example, with an acid (e.g., a mineral or an organic acid), a base or a fluoride source.

Pharmaceutical Compositions

Some embodiments described herein relates to a pharmaceutical composition, that can include an effective amount of one or more compounds described herein (e.g., a compound of Formula (I), a compound of Formula (II) and/or a compound of Formula (III), or a pharmaceutically acceptable salt of the foregoing) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use:

Some embodiments described herein relate to a method of ameliorating, treating and/or preventing a viral infection selected from a paramyxovirus viral infection and an orthomyxovirus viral infection, which can include administering to a subject an effective amount of one or more compounds described herein, or a pharmaceutical composition that includes one or more compounds described herein (e.g., a compound of Formula (I), a compound of Formula (II) and/or a compound of Formula (III), or a pharmaceutically acceptable salt of the foregoing). In some embodiments, the subject is identified as suffering from the viral infection (for example, a paramyxovirus viral infection or an orthomyxovirus viral infection).

Other embodiments described herein relate to a method of inhibiting viral replication of a virus selected from a paramyxovirus and an orthomyxovirus, which can include contacting a cell infected with the virus with an effective amount of a compound of Formula (I), or a pharmaceutically acceptable salt thereof, an effective amount of a compound of Formula (II), or a pharmaceutically acceptable salt thereof, an effective amount of a compound of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing).

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate a respiratory syncytial viral (RSV) infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent a respiratory syncytial viral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of a respiratory syncytial virus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the RSV polymerase complex.

In other embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (II), or a pharmaceutically acceptable salt of the foregoing) can be used to treat and/or ameliorate an influenza viral infection. In other embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to prevent an influenza viral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of an influenza virus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the influenza polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate a hendraviral infection and/or nipahviral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent a hendraviral infection and/or nipahviral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of a hendravirus and/or nipahvirus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the hendravirus polymerase complex and/or nipahvirus polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate measles. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent measles. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of a measles virus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the measles polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate mumps. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent mumps. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of a mumps virus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the mumps polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate a sendai viral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent a sendai viral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of a sendai virus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the sendai virus polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate a HPIV-1 infection and/or HPIV-3 infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent a HPIV-1 infection and/or HPIV-3 infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of HPIV-1 and/or HPIV-3. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the HPIV-1 polymerase complex and/or HPIV-3 polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate a HPIV-2 infection and/or HPIV-4 infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent a HPIV-2 infection and/or HPIV-4 infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of HPIV-2 and/or HPIV-4. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the HPIV-2 polymerase complex and/or HPIV-4 polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to treat and/or ameliorate a human metapneumoviral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used to prevent a human metapneumoviral infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the replication of a human metapneumovirus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to inhibit the human metapneumovirus polymerase complex.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate an upper respiratory viral infection caused by a virus selected from a henipavirus, a morbillivirus, a respirovirus, a rubulavirus, a pneumovirus, a metapneumovirus and influenza virus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate a lower respiratory viral infection caused by a virus selected from a henipavirus, a morbillivirus, a respirovirus, a rubulavirus, a pneumovirus, a metapneumovirus and influenza virus. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used treat and/or ameliorate one or more symptoms of an infection caused by a virus selected from a henipavirus, a morbillivirus, a respirovirus, a rubulavirus, a pneumovirus, a metapneumovirus and influenza virus (such as those described herein).

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate an upper respiratory viral infection caused by RSV infection, measles, mumps, parainfluenza infection, metapneumovirus and/or influenza infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate a lower respiratory viral infection caused by RSV infection, measles, mumps, parainfluenza infection, metapneumovirus and/or influenza infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I) a compound of Formula (II) and/or a compound of Formula (III), or a pharmaceutically acceptable salt of the foregoing) can be used treat and/or ameliorate one or more symptoms of an infection caused by RSV infection, measles, mumps, parainfluenza infection, metapneumovirus and/or influenza infection (such as those described herein).

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate bronchiolitis and/or tracheobronchitis due to a RSV infection, influenza infection and/or human parainfluenza virus 3 (HPIV-3) infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate pneumonia due to a RSV infection, influenza infection and/or human parainfluenza virus 3 (HPIV-3) infection. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate croup due to a RSV infection, influenza infection and/or human parainfluenza virus 1 (HPIV-1) infection.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate a fever, cough, runny nose, red eyes, a generalized rash, pneumonia, an ear infection and/or bronchitis due to measles. In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used treat and/or ameliorate swelling of the salivary glands, fever, loss of appetite and/or fatigue due to mumps.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to prevent an influenza viral infection. In some embodiments, the influenza viral infection can be an influenza A viral infection. In other embodiments, the influenza viral infection can be an influenza B viral infection. In still other embodiments, the influenza viral infection can be an influenza C viral infection. In some embodiments, one or more compounds of Formula (I), or a pharmaceutically acceptable salt thereof, one or more compounds of Formula (II), or a pharmaceutically acceptable salt thereof, and/or one or more compounds of Formula (III), or a pharmaceutically acceptable salt thereof, can be used to treat and/or ameliorate one or more subtypes of influenza. For example, one or more compounds of Formula (I), or a pharmaceutically acceptable salt thereof, one or more compounds of Formula (II), or a pharmaceutically acceptable salt thereof, and/or one or more compounds of Formula (III), or a pharmaceutically acceptable salt thereof, can be used to treat H1N1 and/or H3N2.

In some embodiments, an effective amount of one or more compounds of Formula (I), or a pharmaceutically acceptable salt thereof, one or more compounds of Formula (II), or a pharmaceutically acceptable salt thereof, an effective amount of one or more compounds of Formula (III), or a pharmaceutically acceptable salt thereof, and/or a pharmaceutical composition that includes one or more compounds described herein (e.g., a compound of Formula (I), a compound of Formula (II) and/or a compound of Formula (III), or a pharmaceutically acceptable salt of the foregoing) can be used to prevent a human parainfluenza viral infection. In some embodiments, the human parainfluenza viral infection can be a human parainfluenza virus 1 (HPIV-1). In other embodiments, the human parainfluenza viral infection can be a human parainfluenza virus 2 (HPIV-2). In other embodiments, the human parainfluenza viral infection can be a human parainfluenza virus 3 (HPIV-3). In other embodiments, the human parainfluenza viral infection can be a human parainfluenza virus 4 (HPIV-4). In some embodiments, one or more compounds of Formula (I), or a pharmaceutically acceptable salt thereof, one or more compounds of Formula (II), or a pharmaceutically acceptable salt thereof, and/or one or more compounds of Formula (III), or a pharmaceutically acceptable salt thereof, can be used to treat and/or ameliorate one or more subtypes of human parainfluenza virus. For example, one or more compounds of Formula (I), or a pharmaceutically acceptable salt thereof, one or more compounds of Formula (II), or a pharmaceutically acceptable salt thereof, and/or one or more compounds of Formula (III), or a pharmaceutically acceptable salt thereof, can be used to treat HPIV-1 and/or HPIV-3.

The one or more compounds of Formula (I) or a pharmaceutically acceptable salt thereof, one or more compounds of Formula (II), or a pharmaceutically acceptable salt thereof, and/or one or more compounds of Formula (III), or a pharmaceutically acceptable salt thereof, that can be used to treat, ameliorate and/or prevent a paramyxovirus and/or or an orthomyxovirus viral infection can be a compound of Formula (I), or pharmaceutically acceptable salt thereof, and/or a compound of Formula (II), or a pharmaceutically acceptable salt thereof, and/or a compound of Formula (III), or a pharmaceutically acceptable salt thereof, provided in any of the embodiments described in paragraphs [0085]-[0171].

As used herein, the terms "prevent" and "preventing," mean a subject does not develop an infection because the subject has an immunity against the infection, or if a subject becomes infected, the severity of the disease is less compared to the severity of the disease if the subject has not been administered/received the compound. Examples of forms of prevention include prophylactic administration to a subject who has been or may be exposed to an infectious agent, such as a paramyxovirus (e.g., RSV) and/or an orthomyxovirus (e.g., influenza).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

Various indicators for determining the effectiveness of a method for treating a viral infection, such as a paramyxovirus and/or an orthomyxovirus infection, are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, an effective amount of a compound of Formulae (I), (II) and/or (III), or a pharmaceutically acceptable salt of the foregoing, is an amount that is effective to reduce viral titers to undetectable levels, for example, to about 1000 to about 5000, to about 500 to about 1000, or to about 100 to about 500 genome copies/mL serum. In some embodiments, an effective amount of a compound of Formulae (I), (II) and/or (III), or a pharmaceutically acceptable salt of the foregoing, is an amount that is effective to reduce viral load compared to the viral load before administration of the compound of Formulae (I), (II) and/or (III), or a pharmaceutically acceptable salt of the foregoing. For example, wherein the viral load is measure before administration of the compound of Formulae (I), (II) and/or (III), or a pharmaceutically acceptable salt of the foregoing, and again after completion of the treatment regime with the compound of Formulae (I), (II) and/or (III), or a pharmaceutically acceptable salt of the foregoing (for example, 1 week after completion). In some embodiments, an effective amount of a compound of Formulae (I), (II) and/or (III), or a pharmaceutically acceptable salt of the foregoing, can be an amount that is effective to reduce viral load to lower than about 100 genome copies/mL serum. In some embodiments, an effective amount of a compound of Formulae (I), (II) and/or (III), or a pharmaceutically acceptable salt of the foregoing, is an amount that is effective to achieve a reduction in viral titer in the serum of the subject in the range of about 1.5-log to about a 2.5-log reduction, about a 3-log to about a 4-log reduction, or a greater than about 5-log reduction compared to the viral load before administration of the compound of Formulae (I), (II) and/or (III), or a pharmaceutically acceptable salt of the foregoing. For example, wherein the viral load is measure before administration of the compound of Formulae (I), (II) and/or (III), or a pharmaceutically acceptable salt of the foregoing, and again after completion of the treatment regime with the compound of Formulae (I), (II) and/or (III), or a pharmaceutically acceptable salt of the foregoing (for example, 1 week after completion).

In some embodiments, a compound of Formulae (I), (II) and/or (III), or a pharmaceutically acceptable salt of the foregoing, can result in at least a 1, 2, 3, 4, 5, 10, 15, 20, 25, 50, 75, 100-fold or more reduction in the replication of a paramyxovirus and/or an orthomyxovirus relative to pre-treatment levels in a subject, as determined after completion of the treatment regime (for example, 1 week after completion). In some embodiments, a compound of Formulae (I), (II) and/or (III), or a pharmaceutically acceptable salt of the foregoing, can result in a reduction of the replication of a paramyxovirus and/or an orthomyxovirus relative to pre-treatment levels in the range of about 2 to about 5 fold, about 10 to about 20 fold, about 15 to about 40 fold, or about 50 to about 100 fold. In some embodiments, a compound of Formulae (I), (II) and/or (III), or a pharmaceutically acceptable salt of the foregoing, can result in a reduction of paramyxovirus replication in the range of 1 to 1.5 log, 1.5 log to 2 log, 2 log to 2.5 log, 2.5 to 3 log, 3 log to 3.5 log or 3.5 to 4 log more reduction of paramyxovirus replication compared to the reduction of paramyxovirus reduction achieved by ribavirin (Virazole®), or may achieve the same reduction as that of ribavirin (Virazole®) therapy in a shorter period of time, for example, in one week, two weeks, one month, two months, or three months, as compared to the reduction achieved after six months of ribavirin (Virazole®) therapy. In some embodiments, a compound of Formulae (I), (II) and/or (III), or a pharmaceutically acceptable salt of the foregoing, can result in a reduction of orthomyxovirus replication in the range of 1 to 1.5 log, 1.5 log to 2 log, 2 log to 2.5 log, 2.5 to 3 log, 3 log to 3.5 log or 3.5 to 4 log more reduction of orthomyxovirus replication compared to the reduction of orthomyxovirus reduction achieved by oseltamivir (Tamiflu®), or may achieve the same reduction as that of oseltamivir (Tamiflu®) therapy in a shorter period of time, for example, in one week, two weeks, one month, two months, or three months, as compared to the reduction achieved after six months of oseltamivir (Tamiflu®) therapy.

In some embodiments, an effective amount of a compound of Formula (I), a compound of Formula (II) and/or a compound of Formula (III), or a pharmaceutically acceptable salt of the foregoing, is an amount that is effective to achieve a sustained viral response, for example, non-detectable or substantially non-detectable paramyxovirus and/or orthomyxovirus RNA (e.g., less than about 500, less than about 400, less than about 200, or less than about 100 genome copies per milliliter serum) is found in the subject's serum for a period of at least about one week, two weeks, one month, at least about two months, at least about three months, at least about four months, at least about five months, or at least about six months following cessation of therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), a compound of Formula (II) and/or a compound of Formula (III), or a pharmaceutically acceptable salt of the foregoing, can be administered to a subject infected with RSV that is resistant to one or more different anti-RSV agents (for example, ribavirin). In some embodiments, development of resistant RSV strains can be delayed when subjects are treated with a compound of Formula (I), a compound of Formula (II) and/or a compound of Formula (III), or a pharmaceutically acceptable salt of the foregoing, compared to the development of RSV strains resistant to other RSV drugs. In some embodiments, a compound of Formula (I), a compound of Formula (II) and/or a compound of Formula (III), or a pharmaceutically acceptable salt of the foregoing, can be administered to a subject infected with an influenza virus that is resistant to one or more different anti-influenza agents (for example, amantadine and rimantadine). In some embodiments, development of resistant influenza strains can be delayed when subjects are treated with a compound of Formula (I), a compound of Formula (II) and/or a compound of Formula (III), or a pharmaceutically acceptable salt of the foregoing, compared to the development of influenza strains resistant to other influenza drugs.

In some embodiments, a compound of Formula (I), a compound of Formula (II) and/or a compound of Formula (III), or a pharmaceutically acceptable salt of the foregoing, can decrease the percentage of subjects that experience complications from a RSV viral infection compared to the percentage of subjects that experience complication being treated with ribavirin. In some embodiments, a compound of Formula (I), a compound of Formula (II) and/or a compound of Formula (III), or a pharmaceutically acceptable salt of the foregoing, can decrease the percentage of subjects that experience complications from an influenza viral infection compared to the percentage of subjects that experience complication being treated with oseltamivir. For example, the percentage of subjects being treated with a compound of Formula (I), a compound of Formula (II) and/or a compound of Formula (III), or a pharmaceutically acceptable salt of the foregoing, that experience complications can be 10%, 25%, 40%, 50%, 60%, 70%, 80% and 90% less compared to subjects being treated with ribavirin or oseltamivir.

In some embodiments, a compound of Formula (I), a compound of Formula (II) and/or a compound of Formula (III), or a pharmaceutically acceptable salt of the foregoing, or a pharmaceutical composition that includes a compound described herein, can be used in combination with one or more additional agent(s). In some embodiments, a compound of Formula (I), a compound of Formula (II) and/or a compound of Formula (III), or a pharmaceutically acceptable salt of the foregoing, can be used in combination with one or more agents currently used for treating RSV. For example, the additional agent can be ribavirin, palivizumab and RSV-IGIV. For the treatment of RSV, additional agents include but are not limited to ALN-RSV01 (Alnylam Pharmaceuticals), BMS-433771 (1-cyclopropyl-3-[[1-(4-hydroxybutyl)benzimidazol-2-yl]methyl]imidazo[4,5-c]pyridin-2-one), RFI-641 ((4,4"-bis-{4,6-bis-[3-(bis-carbamoylmethyl-sulfamoyl)-phenylamino]-(1,3,5)triazin-2-ylamino}-biphenyl-2,2"-disulfonic-acid)), RSV604 ((S)-1-(2-fluorophenyl)-3-(2-oxo-5-phenyl-2,3-dihydro-1H-benzo[e][1,4]di-azepin-3-yl)-urea), MDT-637 ((4Z)-2-methylsulfanyl-4-[(E)-3-thiophen-2-ylprop-2-enylidene]-1,3-thiazol-5-one), BTA9881, TMC-353121 (Tibotec), MBX-300, YM-53403 (N-cyclopropyl-6-[4-[(2-phenylbenzoyl)amino]benzoyl]-4,5-dihydrothieno[3,2-d][1]benz azepine-2-carboxamide), motavizumab (Medi-524, MedImmune), Medi-559, Medi-534, Medi-557, RV568 and a RSV-F Particle Vaccine (Novavax). In some embodiments, a compound of Formula (I), a compound of Formula (II) and/or a compound of Formula (III), or a pharmaceutically acceptable salt of the foregoing, can be used in combination with one or more agents currently used for treating influenza. For example, the additional agent can be amantadine, rimantadine, zanamivir and oseltamivir. For the treatment of influenza, additional agents include but are not limited to peramivir ((1S,2S,3S,4R)-3-[(1S)-1-acetamido-2-ethylbutyl]-4-(diaminomethylideneamino)-2-hydroxycyclopentane-1-carboxylic acid), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), favipiravir (T-705, 6-fluoro-3-hydroxy-2-pyrazinecarboxamide), fludase (DAS181, NexBio), ADS-8902 (Adamas Pharmaceuticals), IFN-b (Synairgen), beraprost (4-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid), Neugene® and VGX-3400X (Inovio).

In some embodiments, a compound of Formula (I), a compound of Formula (II) and/or a compound of Formula (III), or a pharmaceutically acceptable salt of the foregoing, can be administered with one or more additional agent(s) together in a single pharmaceutical composition. In some embodiments, a compound of Formula (I), a compound of Formula (II) and/or a compound of Formula (III), or a pharmaceutically acceptable salt of the foregoing, can be administered with one or more additional agent(s) as two or more separate pharmaceutical compositions. For example, a compound of Formula (I), a compound of Formula (II) and/or a compound of Formula (III), or a pharmaceutically acceptable salt of the foregoing, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), a compound of Formula (II) and/or a compound of Formula (III), or a pharmaceutically acceptable salt of the foregoing, and at least one of the other additional agent(s) can be in a second pharmaceutical composition.

The order of administration of a compound of Formula (I), a compound of Formula (II) and/or a compound of Formula (III), or a pharmaceutically acceptable salt of the foregoing, with one or more additional agent(s) can vary. In some embodiments, a compound of Formula (I), a compound of Formula (II) and/or a compound of Formula (III), or a pharmaceutically acceptable salt of the foregoing, can be administered prior to all additional agents. In other embodiments, a compound of Formula (I), a compound of Formula (II) and/or a compound of Formula (III), or a pharmaceutically acceptable salt of the foregoing, can be administered prior to at least one additional agent. In still other embodiments, a compound of Formula (I), a compound of Formula (II) and/or a compound of Formula (III), or a pharmaceutically acceptable salt of the foregoing, can be administered concomitantly with one or more additional agent(s). In yet still other embodiments, a compound of Formula (I), a compound of Formula (II) and/or a compound of Formula (III), or a pharmaceutically acceptable salt of the foregoing, can be administered subsequent to the administration of at least one additional agent. In some embodiments, a compound of Formula (I), a compound of Formula (II) and/or a compound of Formula (III), or a pharmaceutically acceptable salt of the foregoing, can be administered subsequent to the administration of all additional agents.

A potential advantage of utilizing a compound of Formula (I), a compound of Formula (II) and/or a compound of Formula (III), or a pharmaceutically acceptable salt of the foregoing, in combination with one or more additional agent(s) described in paragraph [0222], including pharmaceutically acceptable salts and prodrugs thereof, may be a reduction in the required amount(s) of one or more compounds of paragraph [0222] (including pharmaceutically acceptable salts and prodrugs thereof) that is effective in treating a disease condition disclosed herein (for example, RSV and/or influenza), as compared to the amount required to achieve same therapeutic result when one or more compounds described in paragraph [0222], including pharmaceutically acceptable salts and prodrugs thereof, are administered without a compound of Formula (I), a compound of Formula (II) and/or a compound of Formula (III), or a pharmaceutically acceptable salt the foregoing. For example, the amount of a compound described in paragraph [0222], including a pharmaceutically acceptable salt and prodrug thereof, can be less compared to the amount of the compound described in paragraph [0222], including a pharmaceutically acceptable salt and prodrug thereof, needed to achieve the same viral load reduction when administered as a monotherapy. Another potential advantage of utilizing a compound of Formula (I), a compound of Formula (II) and/or a compound of Formula (III), or a pharmaceutically acceptable salt of the foregoing, in combination with one or more additional agent(s) described in paragraph [0222], including pharmaceutically acceptable salts and prodrugs thereof, is that the use of two or more compounds having different mechanism of actions can create a higher barrier to the development of resistant viral strains compared to the barrier when a compound is administered as monotherapy.

Additional advantages of utilizing a compound of Formula (I), a compound of Formula (II) and/or a compound of Formula (III), or a pharmaceutically acceptable salt the foregoing, in combination with one or more additional agent(s) described in paragraph [0222], including pharmaceutically acceptable salts and prodrugs thereof, may include little to no cross resistance between a compound of Formula (I), a compound of Formula (II) and/or a compound of Formula (III), or a pharmaceutically acceptable salt the foregoing, and one or more additional agent(s) described in paragraph [0222] (including pharmaceutically acceptable salts and prodrugs thereof); different routes for elimination of a compound of Formula (I), a compound of Formula (II) and/or a compound of Formula (III), or a pharmaceutically acceptable salt the foregoing, and one or more additional agent(s) described in paragraph [0222] (including pharmaceutically acceptable salts and prodrugs thereof); little to no overlapping toxicities between a compound of Formula (I), a compound of Formula (II) and/or a compound of Formula (III), or a pharmaceutically acceptable salt the foregoing, and one or more additional agent(s) described in paragraph [0222] (including pharmaceutically acceptable salts and prodrugs thereof); little to no significant effects on cytochrome P450; and/or little to no pharmacokinetic interactions between a compound of Formula (I), or a pharmaceutically acceptable salt thereof, and one or more additional agent(s) described in paragraph [0222] (including pharmaceutically acceptable salts and prodrugs thereof).

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Example 1

Preparation of Compound (1a)

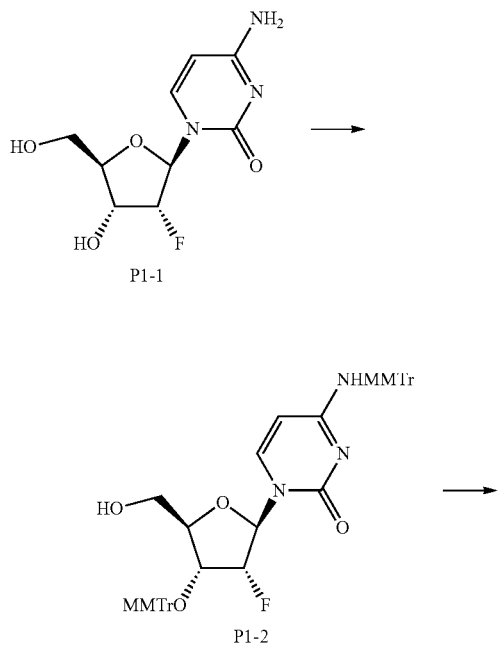

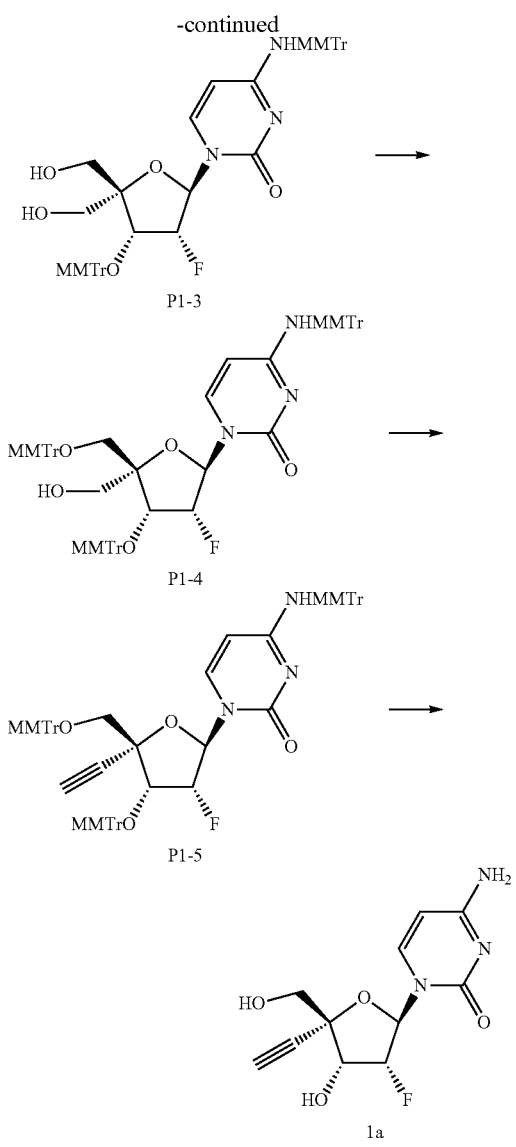

Preparation of (P1-2):

To an ice cooled solution of P1-1 (10.0 g, 40.8 mmol) in dry pyridine (100 mL) was added TBSCl in pyridine (1M, 53 mL) dropwise at room temperature (R.T.). The reaction mixture was stirred at R.T. for 16 hours. The reaction mixture was then quenched with water, concentrated to give a residue. The residue was separated by ethyl acetate (EA) and saturated NaHCO$_3$ aq. solution. The organic phase was dried and concentrated. The residue was purified on a silica gel column (5% MeOH in DCM) to give a crude 5'-O-TBS protected intermediate as a white solid (13.4 g, 91%). The intermediate was dissolved in anhydrous DCM (100 mL) and sym-collidine (17.9 g, 149.2 mmol), AgNO$_3$ (25 g, 149.2 mmol) and MMTrCl (45 g, 149.2 mmol) were added. The mixture was stirred at R.T. for 16 hours. The mixture was quenched with water, and the organic layer was separated and concentrated. The residue purified on a silica gel column (30% PE in EA) to give the crude product. The crude product was dissolved in 1M TBAF (50 mL) in THF. The mixture was stirred at R.T. for 2 hours. The solvent was removed, and the residue was purified on a silica gel column (50% PE in EA) to give P1-2 as a white solid (21.4 g, 66% for three steps).

Preparation of (P1-3):

To a solution of pyridine (521 mg, 6.59 mmol) in anhydrous DMSO (5 mL) was added TFA (636 mg, 5.58 mmol) dropwise at 10° C. under nitrogen. The reaction mixture was stirred until the solution became clear. The solution was then added into a mixture of P1-2 (4.0 g, 5.07 mmol) and DCC (3.86 g, 18.76 mmol) in anhydrous DMSO (18 mL) at R.T. under nitrogen. The reaction mixture was stirred at 30° C. overnight. Water (80 mL) was added into the mixture, diluted with EtOAc (100 mL) and filtered. The filtrate was extracted with DCM (100 mL×6). The organic layer was washed with saturated aq. NaHCO$_3$, dried over Na$_2$SO$_4$ and concentrated in vacuo. The residue was purified on a silica gel column eluted with 1% MeOH in DCM to give the intermediate (3.5 g, 87.7%) as a yellow solid. The intermediate (3.5 g, 4.45 mmol) was dissolved in dioxane (25 mL) and aq. HCHO (668 mg, 22.25 mmol) was added at R.T. 2N NaOH (4.5 mL, 8.9 mmol) was then added. The reaction mixture was stirred at 30° C. overnight. NaBH$_4$ (593 mg, 15.6 mmol) was added in by portions at 5° C., and the mixture was stirred at R.T. for 15 min. The reaction was quenched with water, and the mixture was extracted with EtOAc (100 mL×3). The organic layer was dried over Na$_2$SO$_4$ and concentrated in vacuo. The residue was purified on a silica gel column eluted with 1% MeOH in DCM to give P1-3 as a yellow solid (2.5 g, 67%). $^1$H NMR (CDCl$_3$, 400 MHz) δ 6.82-7.50 (m, 29H), 5.40 (d, J=23.2 Hz, 1H), 4.99 (d, J=7.6 Hz, 1H), 4.46 (dd, J$_1$=6.0 Hz, J$_2$=54.4 Hz, 1H), 3.94 (dd, J$_1$=4.4 Hz, J$_2$=12.4 Hz, 1H), 3.78 (s, 6H), 3.42-3.69 (m, 2H), 2.71-3.05 (m, 2H), 2.45 (m, 1H).

Preparation of (P1-4):

To an ice cooled solution of P1-3 (4.0 g, 4.9 mmol) in dry pyridine (20 mL) was added dropwise TBSCl in pyridine (1M, 5.88 mL). The reaction mixture was stirred at R.T. for 16 hours. The reaction mixture was then quenched with water, concentrated to give a residue. The residue was separated in EA and saturated aq. NaHCO$_3$. The organic layer was separated and dried, and then concentrated. The residue was purified on a silica gel column (1% MeOH in DCM) to give the intermediate as a yellow solid (3.2 g, 70%). $^1$H NMR (CDCl$_3$, 400 MHz) δ 7.53-6.83 (m, 29H), 5.51 (d, J=21.2 Hz, 1H), 4.98 (d, J=7.6 Hz, 1H), 4.67 (dd, J$_1$=5.6 Hz, J$_2$=22.4 Hz, 1H), 4.22 (dd, J$_1$=5.6 Hz, J$_2$=53.2 Hz, 1H), 4.07 (m, 1H), 3.89 (m, 1H), 3.80 (s, 6H), 3.70-3.67 (m, 1H), 3.03-2.98 (m, 1H), 2.26 (m, 1H), 0.93 (s, 9H), 0.10 (s, 6H).

The obtained intermediate was dissolved in anhydrous DCM (20 mL) and collidine (360 mg, 3 mmol), and AgNO$_3$ (500 mg, 3 mmol) and MMTrCl (606 mg, 2 mmol) were added. The mixture was stirred at R.T. for 16 hours. The reaction mixture was quenched with water, and the organic layer was separated and concentrated. The residue was purified on a silica gel column (0.5% MeOH in DCM) to give the fully protected intermediate as a yellow solid (3.3 g, 80%). The intermediate was dissolved in 1M TBAF in THF (5 mL) and was stirred at R.T. for 2 hours. The solution was concentrated, and the residue was purified on a silica gel column (1% MeOH in DCM) to give a mixture of P1-3 and P1-4, which was separated by HPLC separation (MeCN and 0.1% HCOOH in water) to give P1-4 as a white solid (1.5 g, 25%).

Preparation of (P1-5):

P1-4 (1.5 g, 1.22 mmol) was suspended in anhydrous DCM (50 mL), and Dess Martin periodinane (1.2 g, 2.73 mmol) was added at 0° C. The reaction mixture was stirred at R.T. for 3 hours. The reaction mixture was then quenched with saturated aq. Na$_2$S$_2$O$_3$ and Na$_2$CO$_3$. The organic layer was separated and dried, and then concentrated to give the aldehyde intermediate as a white solid.

A solution of ClCH$_2$PPh$_3$Br (2.19 g, 5.6 mmol) in anhydrous THF (40 mL) was cooled to −78° C. n-BuLi (2.5 M, 2.3 mL) was added in dropwise. After the addition, the mixture was stirred at 0° C. for 2 hours. A solution of the aldehyde in anhydrous THF (10 mL) was then added. The mixture was stirred at R.T. for 16 hours. The reaction was quenched with saturated NH$_4$Cl aq. and extracted by EA. The organic layer was separated, dried and concentrated. The residue was purified on a silica gel column (1% MeOH in DCM) to give the intermediate as a yellow solid (1.1 g, 73%). To a solution of the intermediate (1.1 g, 0.98 mmol) in anhydrous THF (40 mL) was added n-BuLi (2.5M, 6 mL)-78° C. dropwise. The mixture was stirred at −78° C. for 5 hours and then quenched with a saturated NH$_4$Cl aq. solution. The mixture was extracted with EA. The organic layer was separated, dried and concentrated. The residue was purified on a silica gel column (2% MeOH in DCM) to give P1-5 as a yellow solid (910 mg, 86%).

Preparation of (1a):

P1-5 (910 mg, 0.84 mmol) was suspended in 80% CH$_3$COOH (50 mL), and the reaction mixture was stirred at 40° C. for 15 hours. The solvents were evaporated, and the residue was co-evaporated with toluene to remove traces of acid and water. The residue was purified by HPLC separation (MeCN and 0.1% HCOOH in water) to give pure compound 1a as a white solid (101 mg, 45%). $^1$H NMR (MeOD, 400 MHz) δ 7.90 (d, J=7.2 Hz, 1H), 6.04 (d, J=19.6 Hz, 1H), 5.87 (d, J=7.6 Hz, 1H), 5.00 (dd, J$_1$=5.2 Hz, J$_2$=53.6 Hz, 1H), 4.47 (dd, J$_1$=5.2 Hz, J$_2$=22.8 Hz, 1H), 3.86 (d, J=12.4 Hz, 1H), 3.73 (d, J=12.4 Hz, 1H), 3.08 (s, 1H); ESI-TOF-MS: m/z 270.09 [M+H]$^+$, 539.17 [2M+H]$^+$.

Example 2

Preparation of Compound (2a)

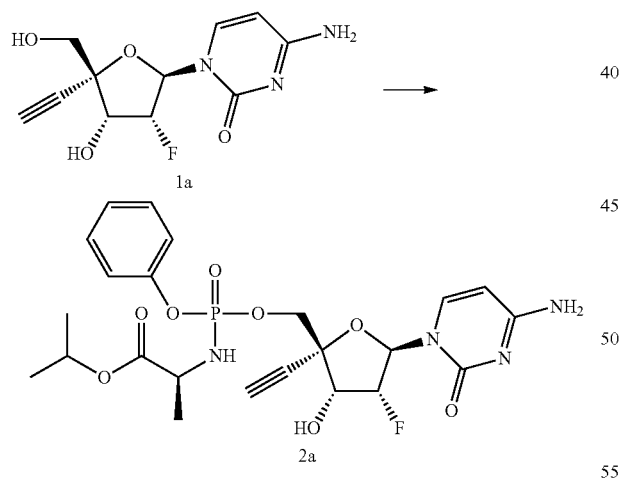

To a stirred solution of compound 1a (50 mg, 0.186 mmol) in anhydrous THF (3 mL) was added dropwise a solution of t-BuMgCl (0.37 mL, 1M in THF) at −78° C. The mixture was then stirred at 0° C. for 30 min and re-cooled to −78° C. A solution of phenyl (isopropoxy-L-alaninyl) phosphorochloridate (104 mg, 0.4 mmol) in THF (0.5 mL) was added dropwise. After addition, the mixture was stirred at 25° C. for 16 hours. The reaction was quenched with HCOOH (80% aq.) at 0° C. The solvent was removed, and the residue was purified on silica gel (DCM:MeOH=50:1 to 10:1) to give compound 2a as a white solid (a mixture of two β isomers, 8.0 mg, 7.9%).

$^1$H NMR (MeOD, 400 MHz) δ 7.71, 7.68 (2d, J=7.6 Hz, 1H), 7.17-7.37 (m, 5H), 6.02, 6.00 (2d, J=20.4 Hz, 1H), 5.90, 5.86 (2d, J=7.6 Hz, 1H), 5.03-5.18 (m, 1H), 4.91-4.99 (m, 1H), 4.45-4.55 (m, 1H), 4.34-4.43 (m, 1H), 4.26-4.33 (m, 1H), 3.87-3.95 (m, 1H), 3.25, 3.22 (2s, 1H), 1.29-1.34 (m, 3H), 1.20-1.22 (m, 6H). $^{31}$P NMR (MeOD, 162 MHz) δ 3.44, 3.27. ESI-LCMS: m/z 539.0 [M+H]$^+$.

Example 3

Preparation of Compound (3a)

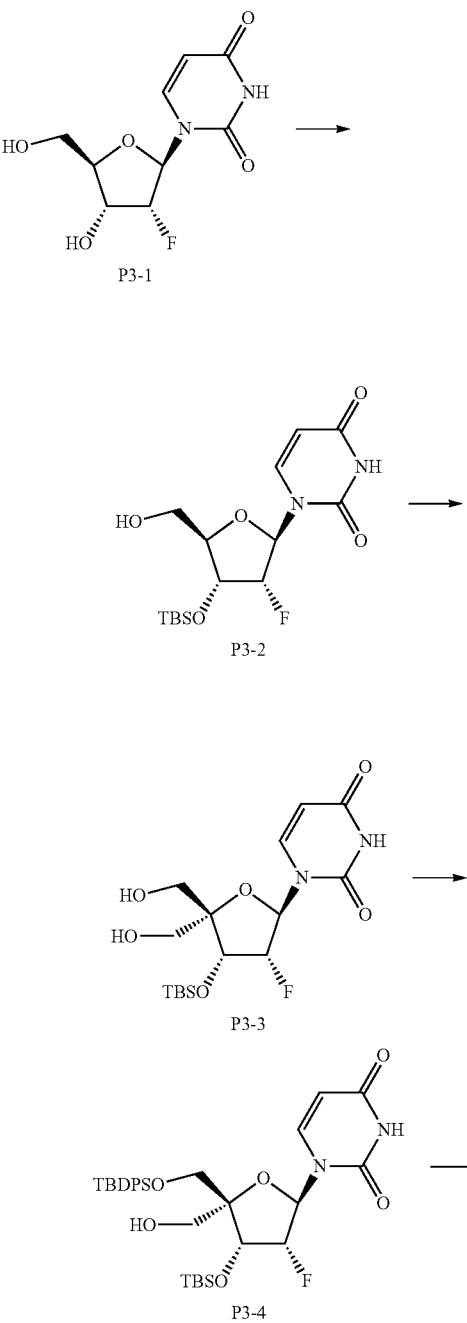

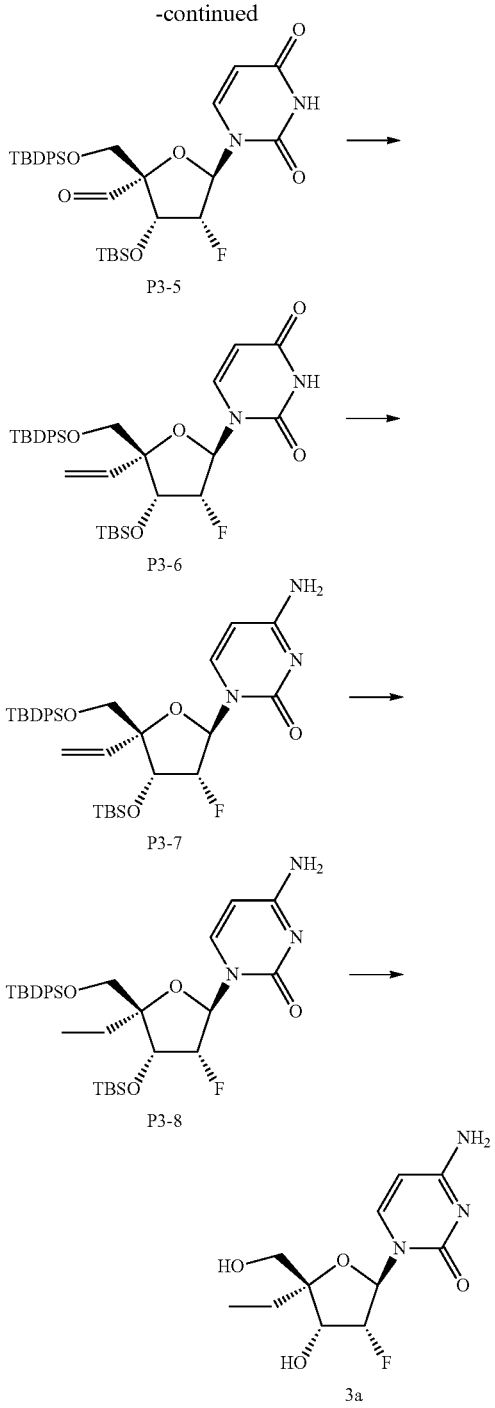

Preparation of (P3-2):

To a solution of P3-1 (100.0 g, 406.5 mmol) in pyridine (750 mL) was added DMTrCl (164.9 g, 487.8 mmol). The solution was stirred at R.T. for 15 hours. MeOH (300 mL) was added, and the mixture was concentrated to dryness under reduced pressure. The residue was dissolved in EtOAc and washed with water. The organic layer was dried over $Na_2SO_4$ and concentrated. The residue was dissolved in DCM (500 mL). Imidazole (44.3 g, 650.4 mmol) and TBSCl (91.9 g, 609.8 mmol) was added. The reaction mixture was stirred at R.T. for 14 hours. The reaction solution was washed with $NaHCO_3$ and brine. The organic layer was dried over $Na_2SO_4$, and concentrated to give the crude as a light yellow solid. The crude (236.4 g, 356.6 mmol) was dissolved in 80% HOAc aq. solution (500 mL). The mixture was stirred at R.T. for 15 hours. The mixture was diluted with EtOAc and washed with a $NaHCO_3$ solution and brine. The organic layer was dried over $Na_2SO_4$ and purified by silica gel column chromatography (1-2% MeOH in DCM) to give P3-2 (131.2 g, 89.6%) as a light yellow solid. $^1$H NMR (DMSO-d6, 400 MHz) δ 11.39 (s, 1H), 7.88 (d, J=7.2 Hz, 1H), 5.89 (dd, $J_1$=18.0 Hz, $J_2$=2.0 Hz, 1H), 5.64 (d, J=8.0 Hz, 1H), 5.21 (dd, $J_1$=$J_2$=7.2 Hz, 1H), 5.18~5.03 (m, 1H), 4.37~4.29 (m, 1H), 3.86 (dd, $J_1$=$J_2$=3.2 Hz, 3H), 3.78~3.73 (m, 1H), 3.51~3.56 (m, 1H), 3.31 (s, 1H), 0.89 (s, 9H), 0.11 (s, 6H); ESI-MS: m/z 802 [M+H]$^+$.

Preparation of (P3-3):

To a solution of P3-2 (131.2 g, 364.0 mmol) in anhydrous $CH_3CN$ (1200 mL) was added IBX (121.2 g, 432.8 mmol) at R.T. The reaction mixture was refluxed for 3 hours and then cooled to 0° C. The precipitate was filtered-off, and the filtrate was concentrated to give the crude aldehyde (121.3 g) as a yellow solid. The aldehyde was dissolved in 1,4-dioxane (1000 mL). 37% $CH_2O$ (81.1 mL, 1.3536 mol) and 2M NaOH aq. solution (253.8 mL, 507.6 mmol) were added. The mixture was stirred at R.T. for 2 hours and then neutralized with AcOH to pH=7. To the solution were added EtOH (400 mL) and $NaBH_4$ (51.2 g, 1.354 mol). The mixture was stirred at R.T. for 30 minutes. The mixture was quenched with saturated aq. $NH_4Cl$ and extracted with EA. The organic layer was dried over $Na_2SO_4$ and concentrated. The residue was purified by silica gel column chromatography (1-3% MeOH in DCM) to give P3-3 (51.4 g, 38.9%) as a white solid.

Preparation of (P3-4):

To a solution of P3-3 (51.4 g, 131.6 mmol) in anhydrous DCM (400 mL) were added pyridine (80 mL) and DMTrCl (49.1 g, 144.7 mmol) at 0° C. The reaction was stirred at R.T. for 14 hours, and then treated with MeOH (30 mL). The solvent was removed, and the residue was purified by silica gel column chromatography (1-3% MeOH in DCM) to give a mono-DMTr protected intermediate as a yellow foam (57.4 g, 62.9%). To the intermediate (57.4 g, 82.8 mmol) in $CH_2Cl_2$ (400 mL) was added imidazole (8.4 g, 124.2 mmol) and TBDPSCl (34.1 g, 124.2 mmol). The mixture was stirred at R.T. for 14 hours. The precipitate was filtered off, and the filtrate was washed with brine and dried over $Na_2SO_4$. The solvent was removed to give the residue (72.45 g) as a white solid. The solid was dissolved in 80% HOAc aq. solution (400 mL). The mixture was stirred at R.T. for 15 hours. The mixture was diluted with EtOAc and washed with $NaHCO_3$ solution and brine. The organic layer was dried over $Na_2SO_4$ and purified by silica gel column chromatography (1-2% MeOH in DCM) to give P3-4 (37.6 g, 84.2%) as a white solid. $^1$H NMR (CD$_3$OD, 400 MHz) δ 7.76 (d, J=4.0 Hz, 1H), 7.70 (dd, $J_1$=1.6 Hz, $J_2$=8.0 Hz, 2H), 7.66~7.64 (m, 2H), 7.48~7.37 (m, 6H), 6.12 (dd, $J_1$=2.8 Hz, $J_2$=16.8 Hz, 1H), 5.22 (d, J=8.0 Hz, 1H). 5.20~5.05 (m, 1H), 4.74 (dd, $J_1$=5.6 Hz, $J_2$=17.6 Hz, 1H), 4.16 (d, J=12.0 Hz, 1H), 3.87~3.80 (m, 2H), 3.56 (d, J=12.0 Hz, 1H), 1.16 (s, 9H), 0.92 (s, 9H), 0.14 (s, 6H).

Preparation of (P3-5):

To a solution of P3-4 (11.8 g, 18.8 mmol) in anhydrous DCM (100 mL) was added Dess-Martin periodinane (16.3 g, 37.6 mmol) at 0° C. under nitrogen. The reaction was stirred R.T. for 2.5 hours. Water (100 mL) was added, and the mixture was then filtered. The filtrate was washed with saturated aq. $NaHCO_3$ and concentrated. The crude residue was purified by silica gel column chromatography (20% EtOAc in hexane) to give P3-5 as a white solid (10.1 g, 86.0%).

Preparation of (P3-6):

To a mixture of methyltriphenylphosphonium bromide (15.7 g, 48.5 mmol) in anhydrous THF (100 mL) was added n-BuLi (19.4 mL, 48.48 mmol) at −78° C. under nitrogen. The reaction was stirred at 0° C. for 30 minutes. A solution of P3-5 (10.1 g, 16.2 mmol) in anhydrous THF (70 mL) was added dropwise at 0° C. under nitrogen. The reaction was stirred at R.T. for 1.5 hours. The reaction was quenched by NH$_4$Cl and extracted with EtOAc. The crude product was purified by silica gel column chromatography (20% EtOAc in hexane) to give P3-6 as a white solid (8.3 g, 82.2%). $^1$H NMR (CDCl$_3$, 400 MHz) δ 8.16 (s, 1H), 8.81 (d, J=8.0 Hz, 1H), 7.58-7.67 (m, 4H), 7.37-7.46 (m, 6H), 6.17 (d, J=16.0 Hz, 1H), 5.91 (dd, J$_1$=10.8 Hz, J$_2$=17.6 Hz, 1H), 5.42 (d, J=17.6 Hz, 1H), 5.22-5.30 (m, 2H), 4.60-4.84 (m, 2H), 3.69 (dd, J$_1$=11.6 Hz, J$_2$=21.2 Hz, 2H), 1.10 (s, 9H), 0.91 (s, 1H), 0.12 (d, J=8.0 Hz, 6H).

Preparation of (P3-7):

To a solution of P3-6 (6.3 g, 10.09 mmol) in anhydrous CH$_3$CN (50 mL) were added TPSCl (6.1 g, 20.2 mmol), DMAP (2.5 g, 20.2 mmol) and NEt$_3$ (3 mL) at R.T. The reaction was stirred at R.T. for 2 hours. NH$_4$OH (25 mL) was added, and the reaction was stirred for 1 hour. The mixture was diluted with DCM (150 mL) and washed with water, 0.1M HCl and saturated aq. NaHCO$_3$. The solvent was removed, and the crude product was purified by silica gel column chromatography (2% MeOH in DCM) to give P3-7 as a yellow solid (5.9 g, 93.6%).

Preparation of (P3-8):

To a solution of P3-7 (5.9 g, 9.5 mmol) in MeOH (10 mL) was added Pd/C (1.5 g) at R.T. The reaction was stirred at R.T. for 2 hours under H$_2$ (balloon). The mixture was filtered, and the filtrate was concentrated in vacuo to give P3-8 as a white solid (5.4 g, 91.3%).

Preparation of (3a):

To a solution of P3-8 (5.4 g, 8.6 mmol) in MeOH (60 mL) was added NH$_4$F (10.0 g), and the reaction mixture was refluxed overnight. After cooling to R.T., the mixture was filtered, and the filtrate was concentrated. The crude product was purified by silica gel column chromatography (10% MeOH in DCM) to give compound 3a as a white solid (1.6 g, 67.8%). $^1$H NMR (CD$_3$OD, 400 MHz) δ 8.08 (d, J=7.6 Hz, 1H), 6.07 (dd, J$_1$=3.2 Hz, J$_2$=15.6 Hz, 1H), 5.88 (d, J=7.2 Hz, 1H), 5.04 (ddd, J$_1$=3.2 Hz, J$_2$=5.2 Hz, J$_3$=54.0 Hz, 1H), 4.45 (dd, J$_1$=5.2 Hz, J$_2$=17.2 Hz, 1H), 3.76 (d, J=12.0 Hz, 1H), 3.57 (d, J=12.0 Hz, 1H), 1.78-1.85 (m, 1H), 1.58-1.67 (m, 1H), 0.95 (t, J=7.6 Hz, 3H); ESI-MS: m/z 274 [M+H]$^+$, 547 [2M+H]$^+$.

Example 4

Preparation of Compound (4a)

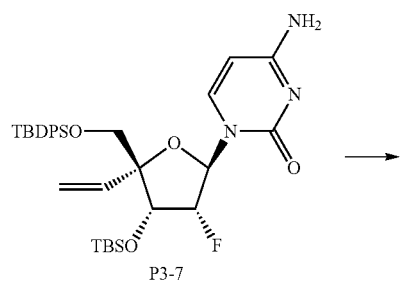

P3-7

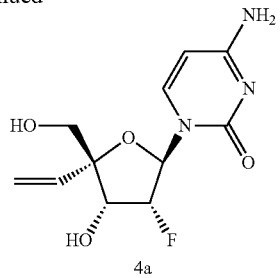

4a

To a solution of P3-7 (280 mg, 0.45 mmol) in MeOH (10 mL) was added NH$_4$F (1.0 g) at R.T. The reaction mixture was refluxed for 5 hours. After cooling to R.T., the mixture was filtered, and the filtrate was concentrated. The crude product was purified by silica gel column chromatography (10% MeOH in DCM) to give compound 4a as a white solid (82 mg, 67.2%1.6 g, 67.8%). $^1$H NMR (CD$_3$OD, 400 MHz) δ 8.11 (d, J=7.6 Hz, 1H), 5.99-6.08 (m, 2H), 5.88 (d, J=7.6 Hz, 1H), 5.47 (dd, J$_1$=1.2 Hz, J$_2$=17.2 Hz, 1H), 5.26 (dd, J$_1$=1.6 Hz, J$_2$=11.2 Hz, 1H), 4.97 (d, J=5.2 Hz, 0.5H), 4.82 (d, J=7.6 Hz, 0.5H), 4.52 (dd, J$_1$=5.2 Hz, J$_2$=23.2 Hz, 1H), 3.65 (d, J=12.4 Hz, 1H), 3.54 (d, J=12.4 Hz, 1H); ESI-MS: m/z 272 [M+H]$^+$, 543 [2M+H]$^+$.

Example 5

Preparation of Compound (5a)

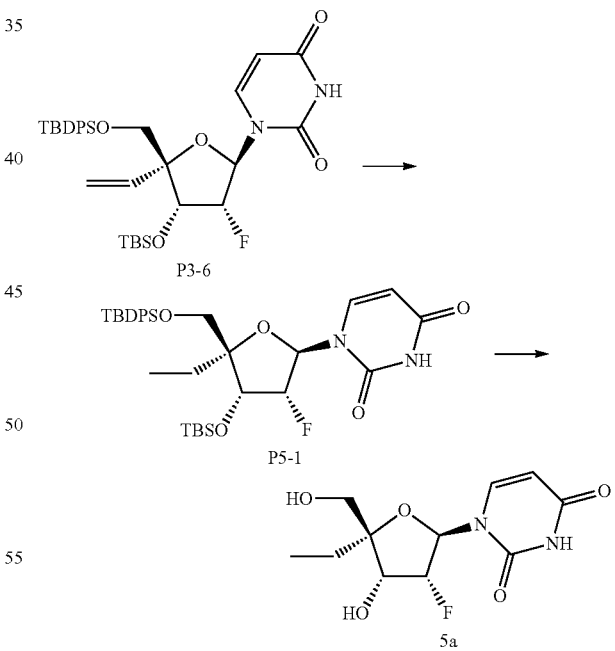

Preparation of (P5-1):

To a solution of P3-6 (600 mg, 0.96 mmol) in MeOH (30 mL) was added 10% Pd/C (320 mg) at R.T. The mixture was stirred under H$_2$ balloon at R.T. for 3 hours. The reaction mixture was filtered, and the filtrate was concentrated to give P5-1 (540 mg, 89.8%) as a colorless solid. The crude product was used directly for the next step without purification.

Preparation of (5a):

To a solution of P5-1 (540 mg, 0.86 mmol) in MeOH (8 mL) was added NH$_4$F (1.2 g, 32.4 mmol) R.T. The mixture was refluxed for 30 hours. The solid was removed by filtration, and the filtrate was concentrated. The residue was purification by silica gel column chromatography (2.5%-9% MeOH in DCM) to give compound 5a (190 mg, 80.6%) as a colorless solid. $^1$H NMR (CD$_3$OD, 400 MHz) δ 8.05 (d, J=8.0 Hz, 1H), 6.09 (dd, J$_1$=4.0 Hz, J$_2$=14.8 Hz, 1H), 5.04-5.20 (m, 1H), 4.42 (dd, J$_1$=5.2 Hz, J$_2$=13.6 Hz, 1H), 3.71 (d, J=11.6 Hz, 1H), 3.57 (d, J=12.0 Hz, 1H), 1.61-1.82 (m, 2H), 0.94 (t, J=7.2 Hz, 3H).

Example 6

Preparation of Compound (6a)

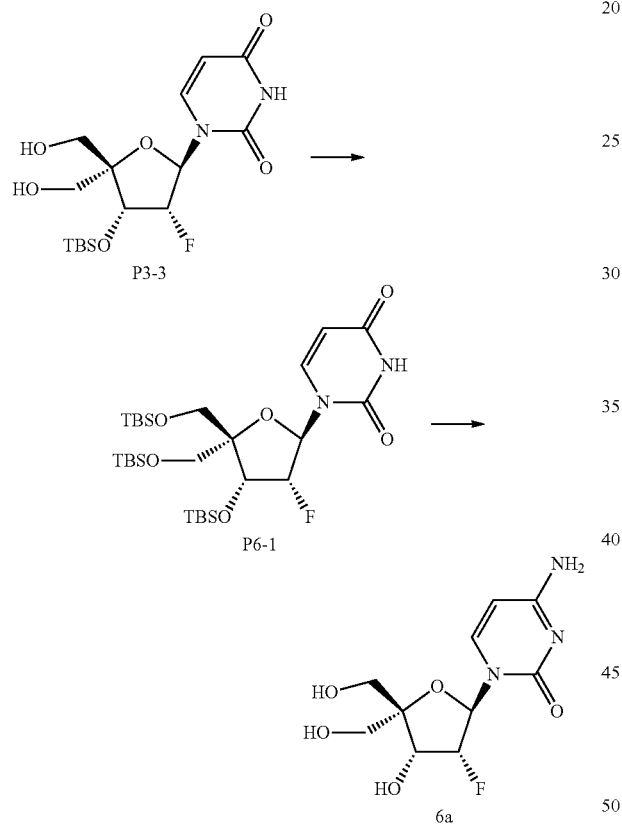

Preparation of (P6-1):

To a solution of P3-3 (800 mg, 2.05 mmol) in anhydrous DCM (15 mL) were added imidazole (558 mg, 8.2 mmol), TBSCl (1.2 g, 8.2 mmol) and AgNO$_3$ (700 mg, 4.1 mmol) at R.T. The reaction mixture was stirred at R.T. overnight. The mixture was filtered, and the filtrate was washed with brine and concentrated in vacuo. The residue was purified by column chromatography on silica gel to give P6-1 as a white solid (950 mg, 79.2%).

Preparation of (6a):

To a solution of P6-1 (600 mg, 0.97 mmol) in anhydrous CH$_3$CN (18 mL) was added DMAP (239 mg, 2.91 mmol), NEt$_3$ (294 mg, 2.91 mmol) and TPSCl (879 mg, 2.91 mmol) at R.T. The reaction was stirred at R.T. for 1 hour. NH$_4$OH (9 mL) was added, and the reaction was stirred for 3 hours. The mixture was diluted with EtOAc (200 mL) and washed with water, 0.1M HCl and saturated aq. NaHCO$_3$. The organic layer was separated, dried and concentrated to give a crude residue. The crude residue was purified by column chromatography on silica gel to give the product as a white solid (500 mg, 83.3%). The solid was treated with NH$_4$F (1.0 g) in MeOH (20 mL) at refluxed temperature for 5 hours. The mixture was filtered, and the filtrate was concentrated in vacuo. The residue was purified by column chromatography on silica gel (15% MeOH in DCM) to give compound 6a as a white solid (132 mg, 59.3%). $^1$H NMR (DMSO-d6, 400 MHz) δ 7.89 (d, J=7.6 Hz, 1H), 7.22 (d, J=18.8 Hz, 2H), 6.09 (dd, J$_1$=4.4 Hz, J$_2$=14.8 Hz, 1H), 5.73 (d, J=5.2 Hz, 1H), 5.52 (d, J=5.6 Hz, 1H), 5.12 (t, J=4.8 Hz, 1H), 4.90-5.06 (m, 1H), 4.50 (t, J=6.0 Hz, 1H), 4.27-4.33 (m, 1H), 3.66 (dd, J$_1$=5.2 Hz, J$_2$=12.0 Hz, 1H), 3.47-3.58 (m, 3H); ESI-MS: m/z 276 [M+H]$^+$, 551 [2M+H]$^+$.

Example 7

Preparation of Compound (7a)

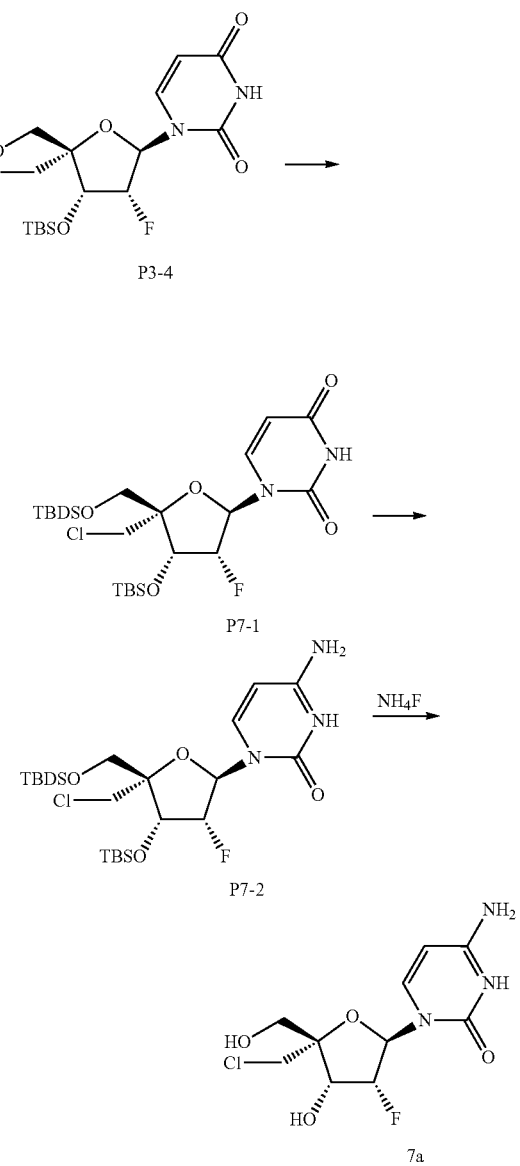

Preparation of (P7-1):

A mixture of P3-4 (1.60 g, 2.5 mmol), PPh₃ (1.3 g, 5.0 mmol) and CCl₄ (0.76 g, 5.0 mmol) in DCE (20 mL) was heated to 130° C. under microwave irradiation under N₂ for 40 mins. After cooled to R.T., the solvent was removed, and the residue was purified on a silica gel column (PE/EA=50/1 to 10/1) to give P7-1 (1.1 g, 68.8%) as a white solid.

Preparation of (P7-2):

P7-1 (0.80 g, 1.3 mmol), DMAP (0.3 g, 2.6 mmol), TPSCl (0.8 g, 2.6 mmol) and Et₃N (0.3 g, 2.6 mmol) were dissolved in MeCN (30 mL). The mixture was stirred at R.T. for 14 hours. NH₃ in THF (saturated at 0° C., 100 mL) was added to the mixture, and the mixture was stirred at R.T. for 2 hours. The solvent was removed, and the residue was purified by column (DCM/MeOH=100:1 to 50:1) to give P7-2 (0.63 g, 78.8%) as a white solid.

Preparation of (7a):

To a solution of P7-2 (0.63 g, 0.98 mmol) in MeOH (10 mL) was added NH₄F (0.3 g), and the reaction was refluxed for 12 hours. The reaction was cooled to R.T., and the precipitate was filtered off. The filtrate was concentrated in vacuo. The residue was purified by silica gel column chromatography (10% MeOH in DCM) to give compound 7a as a white solid (153 mg, 53.5%). ¹H NMR (CD₃OD, 400 MHz) δ 8.05 (d, J=7.2 Hz, 1H), 6.14 (dd, $J_1$=3.6 Hz, $J_2$=15.2 Hz, 1H), 5.92 (d, J=7.2 Hz, 1H), 5.15 (ddd, $J_1$=4.0 Hz, $J_2$=5.2 Hz, $J_3$=53.6 Hz, 1H), 4.57 (dd, $J_1$=4.8 Hz, $J_2$=15.2 Hz, 1H), 3.93 (d, J=11.6 Hz, 1H), 3.75-3.84 (m, 3H); ESI-MS: m/z 294 [M+H]⁺, 587 [2M+H]⁺.

Example 8

Preparation of Compound (8a)

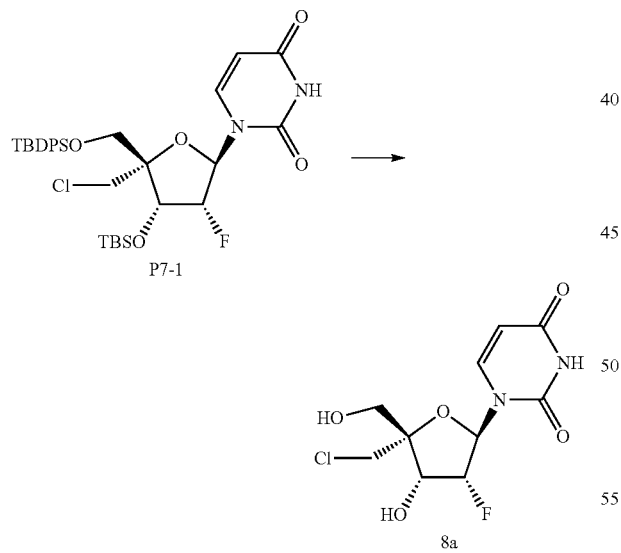

To a solution of P7-1 (630 mg, 0.5 mmol) in MeOH (10 mL) was added NH₄F (0.1 g), and the reaction was refluxed for 12 hours. The mixture was filtered, and the filtrate was concentrated in vacuo. The crude product was purified by silica gel column chromatography (10% MeOH in DCM) to give compound 8a as a white solid (153 mg, 53.5%). ¹H NMR (CD₃OD, 400 MHz) δ 7.99 (d, J=8.0 Hz, 1H), 6.17 (dd, $J_1$=4.4 Hz, $J_2$=14.4 Hz, 1H), 5.70 (d, J=8.0 Hz, 1H), 5.22 (ddd, $J_1$=$J_2$=4.8 Hz, $J_3$=53.2 Hz, 1H), 4.55 (dd, $J_1$=5.2 Hz, $J_2$=12.4 Hz, 1H), 3.88 (d, J=12.0 Hz, 1H), 3.76-3.79 (m, 3H); Negative-ESI-MS: m/z 293 [M–H]⁻.

Example 9

Preparation of Compound (9a)

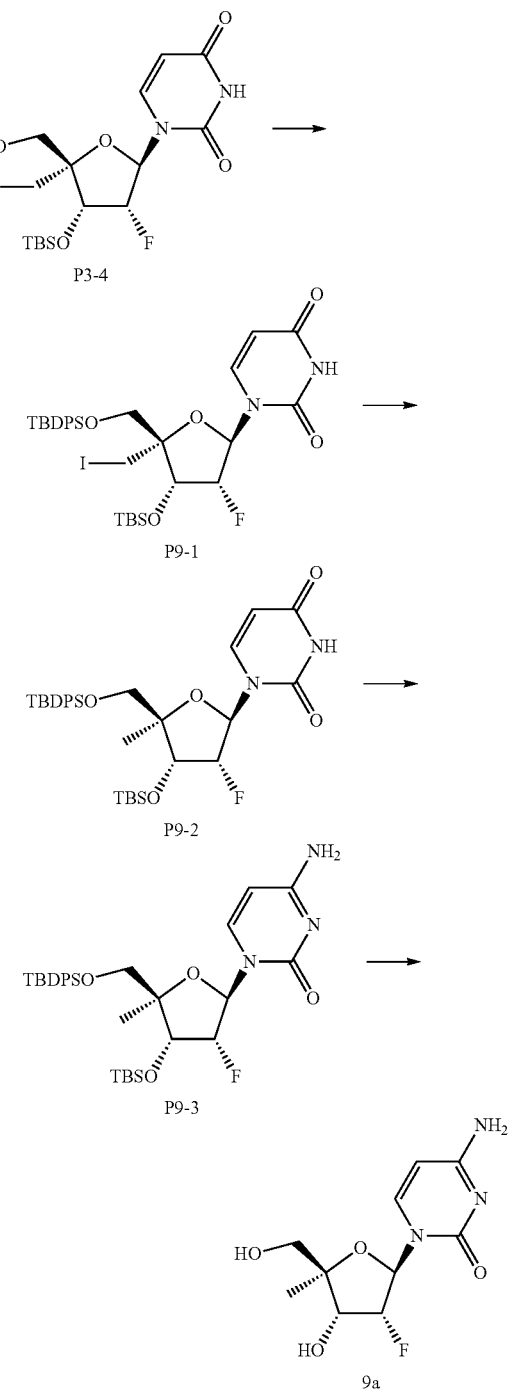

Preparation of (P9-1):

A mixture of P3-4 (3.2 g, 5.0 mmol), Ph₃P (5.2 g, 20 mmol), iodine (2.60 g, 10.2 mmol) and imidazole (1.4 g, 20 mmol) in anhydrous THF (40 mL) was stirred at 80° C. for 14 hours. The reaction was cooled to R.T. and quenched with saturated aq. Na$_2$S$_2$O$_3$. The solution was extracted with EA. The organic layer was dried over Na$_2$SO$_4$ and concentrated. The residue was purified by silica gel column chromatography (20-50% EA in PE) to give P9-1 (1.6 g, 68.2%) as a white solid.

Preparation of (P9-2):

A mixture of P9-1 (1.4 g, 0.2 mmol), Et$_3$N (40 mg, 0.4 mmol) and Pd/C in EtOH (20 mL) was stirred at R.T. under H$_2$ (balloon) overnight. The precipitate was filtered off, and the filtrate was concentrated. The residue was purified on a silica gel column (20%-50% EtOAc in PE) to give P9-2 as a white solid (1.1 g, 78%). $^1$H NMR (CDCl$_3$, 400 MHz) δ 8.11 (br s, 1H), 7.76 (d, J=8.0 Hz, 1H), 7.39-7.67 (m, 10H), 6.18 (dd, J$_1$=3.2 Hz, J$_2$=14.4 Hz, 1H), 5.26-5.30 (m, 1H), 4.86 (m, 1H), 4.42 (dd, J$_1$=5.2 Hz, J$_2$=15.2 Hz, 1H), 3.81 (d, J=11.2 Hz, 1H), 3.58 (d, J=11.2 Hz, 1H), 1.16 (s, 3H), 1.11 (s, 9H), 0.91 (s, 9H), 0.13 (s, 3H), 0.08 (s, 3H).

Preparation of (P9-3):

P9-2 (650 mg, 1.1 mmol), DMAP (270 mg, 2.2 mmol), TPSCl (664 mg, 2.2 mol) and Et$_3$N (222 mg, 2.2 mmol) were dissolved in MeCN (20 mL). The mixture was stirred at R.T. for 14 hours. The reaction was added NH$_3$ in THF (saturated at 0° C.), and the mixture was stirred at R.T. for 2 hours. The solvent was removed, and the residue was purified on a silica gel column (1-10% MeOH in DCM) to give P9-3 (430 mg, crude) as a light yellow syrup.

Preparation of (9a):

A mixture of P9-3 (430 mg, 0.7 mmol) and NH$_4$F (97 mg, 2.1 mmol) in MeOH (10 mL) was refluxed for 14 hours. The solvent was removed, and the residue was purified on a silica gel column (5%-10% MeOH in DCM) to give compound 9a as a white solid (64.8 mg, 35.4%). $^1$H NMR (CD$_3$OD, 400 MHz) δ 8.10 (d, J=7.6 Hz, 1H), 6.03 (dd, J$_1$=2.0 Hz, J$_2$=16.8 Hz, 1H), 5.87 (d, J=7.6 Hz, 1H), 4.98 (m, 1H), 4.37 (dd, J$_1$=5.2 Hz, J$_2$=21.6 Hz, 1H), 3.59 (dd, J$_1$=12.0 Hz, J$_2$=28.4 Hz, 2H), 1.23 (d, J=0.8 Hz, 3H).

Example 10

Preparation of Compound (10a)

To a stirred solution of P9-2 (400 mg, 0.65 mmol) in MeOH (20 mL) was added NH$_4$F (52 mg, 1.5 mmol). The mixture was refluxed overnight. The solvent was removed, and the residue was purified on a silica gel column (5-10% MeOH in DCM) to give compound 10a (140 mg, 82.4%) as a white solid. $^1$H NMR (CD$_3$OD, 400 MHz) δ 8.05 (d, J=8.4 Hz, 1H), 6.06 (dd, J$_1$=2.8 Hz, J$_2$=16.4 Hz, 1H), 5.67 (d, J=8.0 Hz, 1H), 5.08 (m, 1H), 4.37 (d, J$_1$=5.2 Hz, J$_2$=18.8 Hz, 1H), 3.59 (dd, J$_1$=12.0 Hz, J$_2$=26.4 Hz, 2H), 1.23 (s, 3H). ESI-TOF-MS: m/z 283 [M+Na]$^+$.

Example 11

Preparation of Compound (11a)

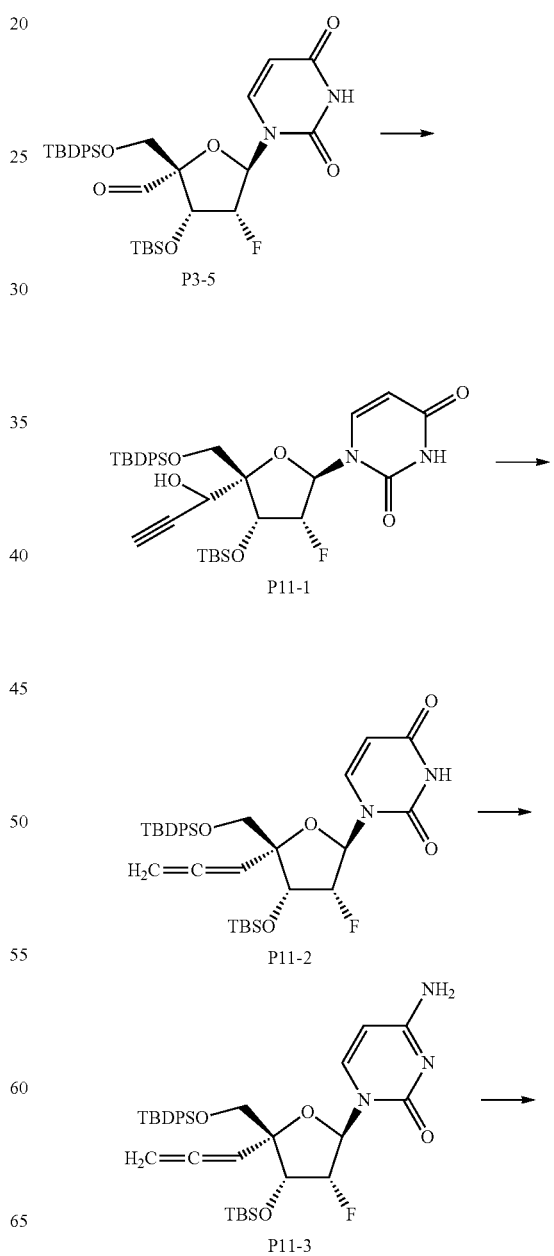

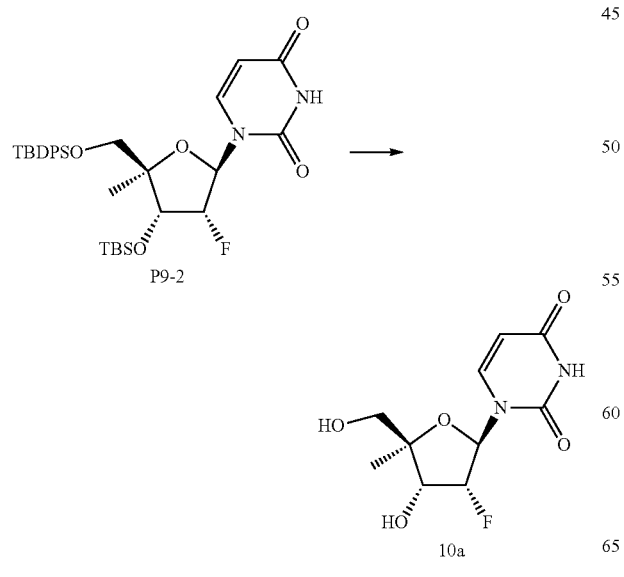

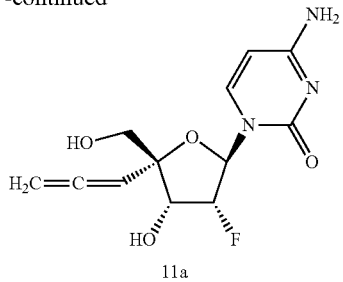

11a

Preparation of (P11-1):

To a solution of P3-5 (2.1 g, 3.5 mmol) in anhydrous THF (25 mL) was added ethynylmagnesium bromide (5.1 mmol) at −78° C. The reaction was stirred at 0° C. for 3 hours. The reaction was quenched with saturated aq. NH$_4$Cl (10 mL). The mixture was diluted with EtOAc (200 mL) and washed with water and brine. The organic layer was dried and concentrated to give a residue. The residue was purified by column chromatography on silica gel (eluting with DCM:MeOH=60:1) to give P11-1 as a white solid (870 mg, 83.3%).

Preparation of (P11-2):

P11-1 (870 mg, 1.34 mmol) was dissolved in anhydrous DCM (12 mL), and methyl chloroformate (2.3 mL) and pyridine (2.5 mL) were added at R.T. The reaction mixture was stirred at R.T. for 1 hour. The mixture was diluted with DCM and washed with saturated aq. NaHCO$_3$. The organic layer was separated, dried and concentrated to give a residue. The residue was purified by column chromatography on silica gel (eluting with PE:EtOAc=8:1) to give a crude product as a white solid (830 mg, 88.4%). To a mixture of Pd$_2$(dba)$_3$ (55 mg, 0.06 mmol) in anhydrous DMF (12 mL) was added P(nBu)$_3$ (35 mg, 0.17 mmol) and HCOONH$_4$ (108 mg, 1.7 mmol) at R.T. under nitrogen. The reaction mixture was stirred at R.T. for 30 min. A solution of the crude product (830 mg, 1.16 mmol) in anhydrous DMF (16 mL) was added, and the reaction mixture was stirred at 70° C. for 3 hours. The reaction was diluted with EtOAc and washed with brine. The organic layer was separated, dried and concentrated to give a residue. The residue was purified by column chromatography on silica gel (eluting with PE:EtOAc=9:1) to give P11-2 as a white solid (510 mg, 67.6%). $^1$H NMR (CD$_3$OD, 400 MHz) δ 7.61-7.75 (m, 5H), 7.36-7.47 (m, 6H), 6.04 (d, J=18.8 Hz, 1H), 5.34 (t, J=6.8 Hz, 1H), 5.21 (dd, J$_1$=1.2 Hz, J$_2$=7.2 Hz, 1H), 5.10 (q, J$_1$=5.2 Hz, J$_2$=53.6 Hz, 1H), 4.80-4.92 (m, 1H), 4.59-4.79 (m, 2H), 3.86 (d, J=12.0 Hz, 1H), 3.75 (d, J=12.0 Hz, 1H), 1.09 (s, 9H), 0.92 (d, J=4.4 Hz, 9H), 0.15 (t, J=4.0 Hz, 6H).

Preparation of (P11-3):

To a solution of P11-2 (490 mg, 0.77 mmol) in anhydrous MeCN (15 mL) was added TPSCl (700 mg, 2.31 mmol), DMAP (282 mg, 2.31 mmol) and TEA (234 mg, 2.31 mmol) at R.T. The reaction mixture was stirred at room temperature for 1 hour. Then NH$_4$OH (8 mL) was added and the reaction mixture was stirred for another 4 hours. The mixture was diluted with EtOAc and washed with water, 1.0 M aq. HCl and saturated aq. NaHCO$_3$. The organic layer was separated and dried, concentrated to give the residue which was purified by HPLC separation (MeCN and 0.1% HCOOH in water) to give P11-3 as a white solid (190 mg, 38.8%). $^1$H NMR (CD$_3$OD, 400 MHz) δ 7.88 (d, J=7.2 Hz, 1H), 7.63-7.70 (m, 4H), 7.37-7.48 (m, 6H), 6.12 (d, J=18.4 Hz, 1H), 5.49 (d, J=7.6 Hz, 1H), 5.34 (t, J=6.8 Hz, 1H), 4.84-5.01 (m, 2H), 4.66-4.78 (m, 2H), 3.89 (d, J=11.6 Hz, 1H), 3.75 (d, J=11.6 Hz, 1H), 1.10 (s, 9H), 0.91 (d, J=3.2 Hz, 9H), 0.13 (t, J=5.2 Hz, 6H).

Preparation of (11a):

To a solution of P11-3 (130 mg, 0.21 mmol) in MeOH (8 mL) was added NH$_4$F (1 g), and the reaction mixture was refluxed for 6 hours. The mixture was filtered, and the filtrate was concentrated in vacuo. The residue was purified by column chromatography on silica gel (eluting with DCM:MeOH=13:1) to give compound 11a as a white solid (47 mg, 79.1%). $^1$H NMR (CD$_3$OD, 400 MHz) δ 8.07 (d, J=7.6 Hz, 1H), 6.05 (dd, J$_1$=1.2 Hz, J$_2$=16.8 Hz, 1H), 5.86 (d, J=7.6 Hz, 1H), 5.40 (dd, J$_1$=J$_2$=6.8 Hz, 1H), 4.87-4.99 (m, 3H), 4.46-4.80 (m, 1H), 3.75 (d, J=12.4 Hz, 1H), 3.68 (d, J=12.4 Hz, 1H); ESI-MS: m/z 284.02 [M+H]$^+$, 567.08 [2M+H]$^+$.

Example 12

Preparation of Compound (12a)

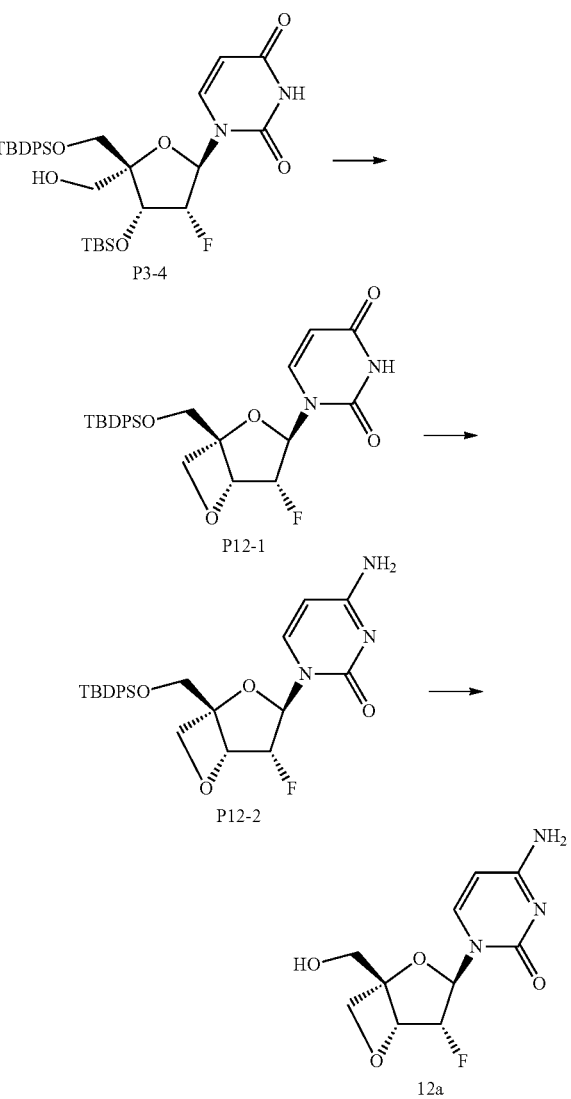

Preparation of (P12-1):

To a solution of P3-4 (500 mg, 0.8 mmol) in anhydrous toluene (12 mL) was added DAST (0.3 mL, 2 mmol) at −65°

C. under nitrogen. The reaction mixture was stirred at R.T. for 2 hours. The reaction was quenched with saturated aq. NaHCO$_3$ and extracted with EtOAc. The organic layer was separated, dried and concentrated to give the residue. The residue was purified by column chromatography on silica gel (eluting with PE:EtOAc=9:1) to give P12-1 as a yellow solid (170 mg, 42.5%). $^1$H NMR (CD$_3$OD, 400 MHz) δ 7.66 (dd, J$_1$=1.6 Hz, J$_2$=18.0 Hz, 4H), 7.54 (d, J=7.6 Hz, 1H), 7.35-7.47 (m, 6H), 6.59 (dd, J$_1$=5.6 Hz, J$_2$=14.0 Hz, 1H), 5.78 (d, J=7.6 Hz, 1H), 5.05-5.24 (m, 2H), 4.93 (d, J=7.6 Hz, 1H), 4.57 (d, J=7.6 Hz, 1H), 3.93-4.00 (m, 2H), 1.07 (d, J=2.4 Hz, 9H).

Preparation of (P12-2):

To a solution of P12-1 (100 mg, 0.2 mmol) in anhydrous MeCN (5 mL) was added TPSCl (182 mg, 0.6 mmol), DMAP (68 mg, 0.6 mmol) and TEA (61 mg, 0.6 mmol) at R.T. under nitrogen. The reaction mixture was stirred at R.T. for 1 hour. NH$_4$OH (3 mL) was added, and the reaction was stirred for 2 hours. The mixture was diluted with EtOAc and washed with water, 1.0 M HCl and saturated aq. NaHCO$_3$. The organic layer was separated, dried and concentrated to give a residue. The residue was purified by column chromatography on silica gel (DCM:MeOH=50:1) to give P12-2 as a yellow solid (96 mg, 96%).

Preparation of (12a):

To a solution of P12-2 (96 mg, 0.2 mmol) in MeOH (5 mL) was added NH$_4$F (500 mg) at R.T. The reaction was refluxed for 3 hours. The mixture was filtered, and the residue was purified by RP HPLC (MeCN and 0.1% HCOOH in water) to give compound 12a as a white solid (25 mg, 48.7%). $^1$H NMR (CD$_3$OD, 400 MHz) δ 7.85 (d, J=7.6 Hz, 1H), 6.59 (dd, J$_1$=5.2 Hz, J$_2$=12.8 Hz, 1H), 6.04 (d, J=7.6 Hz, 1H), 5.10-5.26 (m, 2H), 4.79-4.90 (m, 1H), 4.57 (d, J=7.6 Hz, 1H), 3.82 (d, J=12.4 Hz, 1H), 3.76 (dd, J$_1$=1.6 Hz, J$_2$=12.4 Hz, 1H); ESI-MS: m/z 257.9 [M+H]$^+$, 514.8 [2M+H]$^+$.

Example 13

Preparation of Compound (13a)

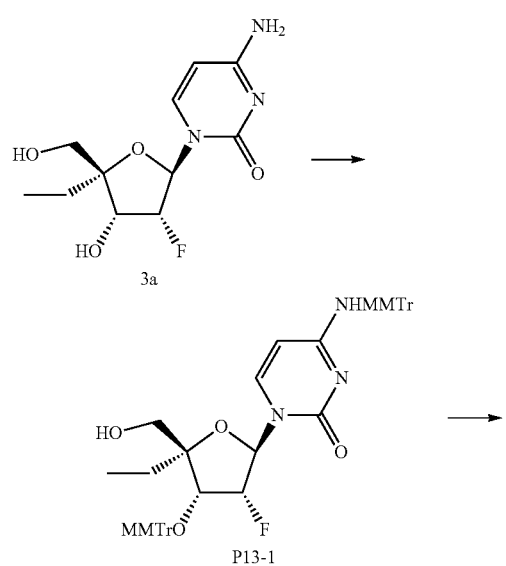

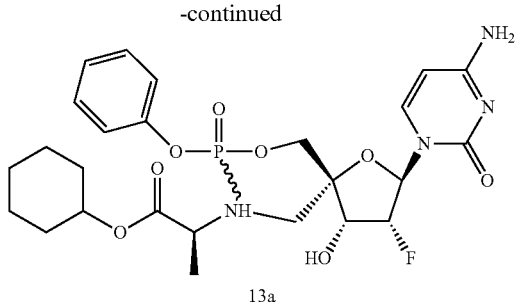

Preparation of (P13-1):

To a solution of compound 3a (700 mg, 2.56 mmol) in anhydrous pyridine (5 mL) were added TBDPSCl (2.8 g, 10.24 mmol), imidazole (522 mg, 7.68 mmol) and AgNO$_3$ (870 mg, 5.12 mmol) at R.T. under N$_2$. The reaction mixture was stirred at R.T. for 3 hours. The mixture was diluted with MeOH and filtered. The mixture was concentrated, and the residue was purified by column chromatography on silica gel (eluting with DCM:MeOH=80:1~40:1) to give the crude intermediate as a yellow solid (1.05 g, 80.8%). $^1$H NMR (DMSO-d6, 400 MHz) δ 7.75 (d, J=7.6 Hz, 1H), 7.61-7.65 (m, 4H), 7.41-7.50 (m, 7H), 6.02 (dd, J$_1$=2.8 Hz, J$_2$=17.2 Hz, 1H), 5.69 (d, J=6.0 Hz, 1H), 5.56 (d, J=7.6 Hz, 1H), 4.96-5.11 (m, 1H), 4.37-4.46 (m, 1H), 3.82 (d, J=10.8 Hz, 1H), 3.62 (d, J=10.8 Hz, 1H), 1.70-1.78 (m, 1H), 1.53-1.59 (m, 1H), 1.02 (s, 9H), 0.79 (t, J=7.6 Hz, 3H). To a solution of the crude intermediate (1.0 g, 1.96 mmol) in anhydrous DCM (15 mL) were added sym-collidine (1.4 g, 11.76 mmol), AgNO$_3$ (1.0 g, 5.88 mmol) and MMTrCl (4.8 g, 15.6 mmol) at R.T. under N$_2$. The reaction mixture was stirred at R.T. overnight. The mixture was filtered and concentrated. The residue was purified by column chromatography on silica gel (eluting with PE:EtOAc=2:1) to give crude full protected intermediates as a white solid (1.1 g, 53.1%). To a solution of the crude intermediate (600 mg, 0.57 mmol) in THF (5 mL) was added TBAF (446 mg, 1.71 mmol)) at R.T. The reaction was stirred at 40-50° C. overnight. The crude product was purified by column chromatography on silica gel eluted with PE:EtOAc=3:2 to give crude P13-1 (350 mg, 75.1%) as a yellow solid.

Preparation of (13a):

To a solution of P13-1 (300 mg, 0.37 mmol) in CH$_3$CN (2.5 mL) were added NMI (2.5 mL) and a solution of phenyl (isopropoxy-L-alaninyl) phosphorochloridate (2.55 g, 7.4 mmol) in CH$_3$CN (2.5 mL) at R.T. under N$_2$. The reaction mixture was stirred at R.T. for 3 hours. The mixture was concentrated in vacuo. The residue was purified by column chromatography on silica gel (PE:EtOAc=1:1) to give crude product as a yellow oil (500 mg, 81%). The crude product was further treated with 80% HCOOH (70 mL) at R.T. overnight. The mixture was concentrated in vacuo, and the crude product was purified by RP HPLC (MeCN and 0.1% HCOOH in water) to give compound 13a as a white solid (a mixture of two β isomers, 86 mg, 40.3% two steps). $^1$H NMR (CD$_3$OD, 400 MHz) δ 7.75, 7.71 (2d, J=7.6 Hz, 1H), 7.33-7.38 (m, 2H), 7.19-7.26 (m, 3H), 6.02-6.10 (m, 1H), 5.87, 5.82 (2d, J=7.6 Hz, 1H), 4.99-5.02 (m, 0.5H), 4.72-4.82 (m, 1.5H), 4.14-4.43

(m, 3H), 3.89-3.94 (m, 1H), 1.68-1.81 (m, 6H), 1.51-1.56 (m, 1H), 1.30-1.43 (m, 8H), 0.96-1.01 (m, 3H); ESI-MS: m/z 582.93 [M+H]$^+$.

Example 14

Preparation of Compound (14a)

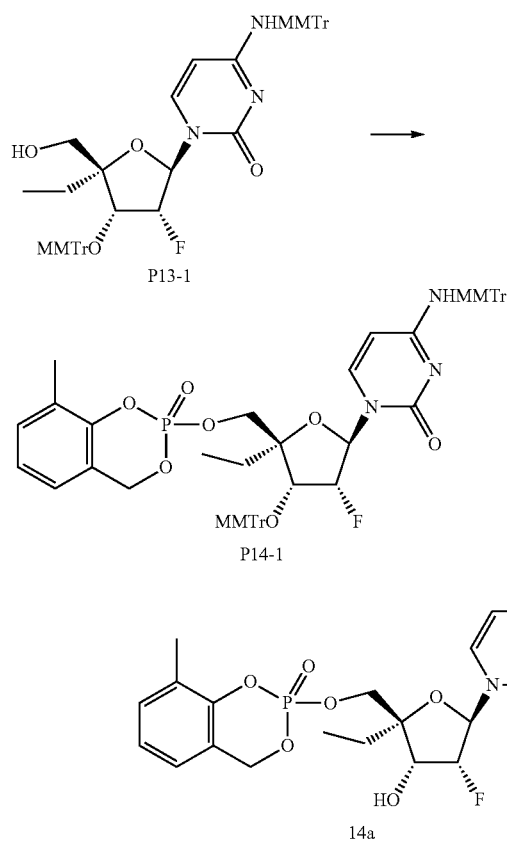

Preparation of (P14-1):

To a stirred solution of P13-1 (451 mg, 0.55 mmol) and NMI (1 mL) in anhydrous acetonitrile (2 mL) was added dropwise a solution of 2-chloro-8-methyl-4H-benzo[d][1,3,2]dioxaphosphinine (855 mg, 4.2 mmol) in acetonitrile (0.2 mL) at 0° C. under N$_2$. The mixture was stirred at R.T. for 2 hours. Solution of I$_2$ (3.2 g, 12.6 mmol), pyridine (9 mL), H$_2$O (3 mL) and DCM (3 mL) was added. The reaction mixture was stirred for 30 mins. The reaction was quenched with NaS$_2$O$_3$ solution and extracted with EA. The organic layer was dried over Na$_2$SO$_4$ and concentrated. The residue was purified by column on silica gel (PE:EA=1:1 to 1:2) to give P14-1 (205 mg, 37%) as a white solid.

Preparation of (14a):

P14-1 (205 mg, 0.21 mmol) was dissolved in 80% HCOOH aq. solution, and the mixture was stirred at R.T. for 16 hours. The solvent was removed, and the residue was purified by RP HPLC(HCOOH system) to give compound 14a as a mixture of 2 P-isomers (24 mg, 18%). $^1$H NMR (CD$_3$OD, 400 MHz) δ 7.60, 7.53 (2d, J=8.0 Hz, 1H), 7.21-7.25 (m, 1H), 7.02-7.12 (m, 2H), 5.95. 5.87 (2dd, J$_1$=2.4 Hz, J$_2$=18.0 Hz, 1H), 5.71, 5.69 (2d, J=8.0 Hz, 1H), 5.38-5.53 (m, 2H), 5.06, 5.04 (2ddd, J$_1$=2.4 Hz, J$_2$=5.6 Hz, J$_3$=54.0 Hz, 1H), 4.32-4.49 (m, 2H), 2.26 (d, J=3.6 Hz, 3H), 1.83-1.92 (m, 1H), 1.64-1.72 (m, 1H), 0.96, 0.93 (2t, J=7.6 Hz, 3H). $^{31}$P NMR (CD$_3$OD, 162 MHz) δ −8.22, −8.50; ESI-LCMS: m/z 456 [M+H]$^+$.

Example 15

Preparation of Compound (15a)

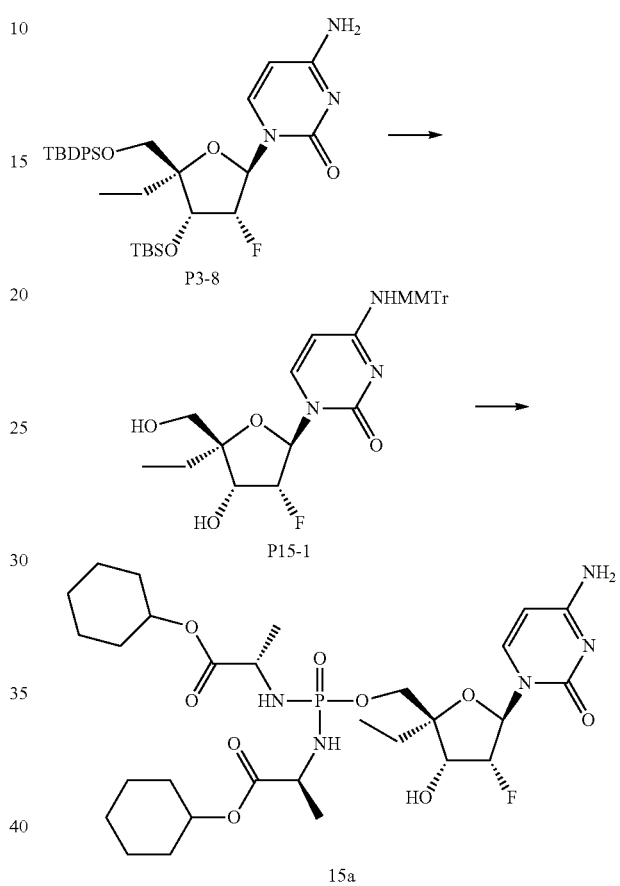

Step 1. Preparation of (P15-1):

To a mixture of P3-8 (2.2 g, 2.5 mmol), AgNO$_3$ (844 mg, 5.0 mmol) and collidine (907 mg, 7.5 mmol) in anhydrous DCM (10 mL) was added MMTrCl (1.54 g, 5.0 mmol) under N$_2$. The reaction mixture was stirred at R.T. overnight. The reaction mixture was filtered through a Buchner Funnel. The filtrate was washed with saturated NaHCO$_3$ solution and brine. The organic layer was separated, dried over anhydrous Na$_2$SO$_4$ and filtered. The filtrate was concentrated to dryness. The residue was purified by column on silica gel (PE: EA=10:1 to 1:2) to give the intermediate (2.3 g, 84%), which was dissolved in a solution of TBAF in THF (1M, 2.6 mL) under N$_2$. The reaction mixture was stirred at R.T. overnight. The residue was dissolved in EA (200 mL) and washed with water and brine. The organic layer was separated, dried over anhydrous Na$_2$SO$_4$ and filtered. The filtrate was concentrated to dryness, and the residue was purified by column on silica gel (DCM/MeOH=100:1 to 30:1) to give P15-1 as a white foam (1.3 g, 94%).

Preparation of (15a):

To a stirred solution of P15-1 (300 mg, 0.55 mmol) and proton sponge (235 mg, 1.1 mmol) in anhydrous MeCN (9 mL) was added with a solution of POCl$_3$ (169 mg, 1.1 mmol)

in MeCN (1 mL) via syringe at 0° C. The mixture was stirred at R.T. for 40 mins. A mixture of (S)-cyclohexyl 2-aminopropanoate hydrochloride (525 mg, 2.55 mmol) and TEA (0.1 mL) was added at 0° C. The mixture was warmed to R.T. and stirred for 3 hours. The reaction mixture was quenched with saturated NaHCO₃, and extracted with EA (100 mL×2). The combined organic layers was dried over Na₂SO₄, concentrated and purified by silica gel column (1~4% MeOH in DCM) to give the crude product (400 mg, 78.15%) as a yellow solid. The crude product was treated with 80% HCOOH (50 mL) at R.T. for 16 hours. The solvent was removed, and the residue was purified by RP HPLC to give compound 15a as a white solid (40 mg, 14%). $^1$H NMR (MeOD, 400 MHz) δ 7.82 (d, J=7.6 Hz, 1H), 6.09 (dd, J$_1$=2.8 Hz, J$_2$=14.0 Hz, 1H), 5.98 (d, J=7.6 Hz, 1H), 5.04 (ddd, J$_1$=3.2 Hz, J$_2$=5.6 Hz, J$_3$=53.6 Hz, 1H), 4.71-4.77 (m, 2H), 4.45 (dd, J$_1$=5.6 Hz, J$_2$=12.4 Hz, 1H), 4.14-4.18 (m, 1H), 3.97-4.01 (m, 1H), 3.84-3.92 (m, 2H), 1.31-1.87 (m, 28H), 0.99 (t, J=7.2 Hz, 3H). $^{31}$P NMR (CD₃OD, 162 MHz) δ 13.94; ESI-LCMS: m/z 660 [M+H]⁺.

Example 16

Preparation of Compound (16a)

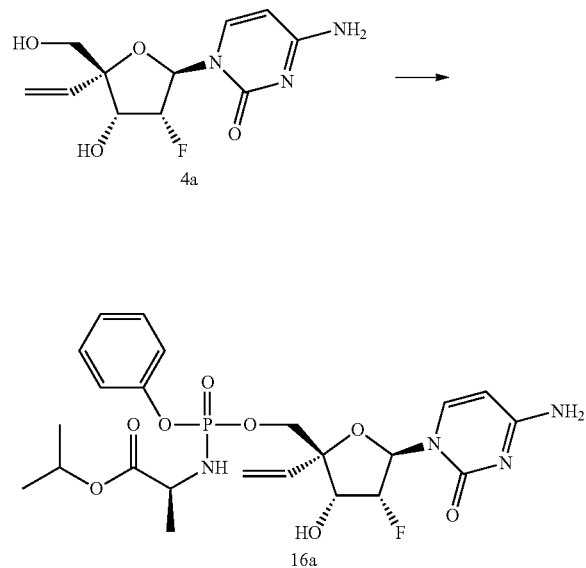

To a stirred solution of compound 4a (150 mg, 0.56 mmol) in anhydrous THF (3 mL) was added dropwise a solution of t-BuMgCl (1.2 mL, 1M in THF) at −78° C. The mixture was stirred at 0° C. for 30 min and re-cooled to −78° C. A solution of phenyl(isopropoxy-L-alaninyl) phosphorochloridate (312 mg, 1.2 mmol) in THF (1.0 mL) was added dropwise. After addition, the mixture was stirred at 25° C. for 16 hours. The reaction was quenched with HCOOH (80% aq.) at 0° C. The solvent was removed, and the residue was purified on silica gel (DCM:MeOH=50:1 to 10:1) to give compound 16a as a white solid (24.0 mg, 15%). $^1$H NMR (MeOD, 400 MHz) δ 7.76 (d, J=7.2 Hz, 1H), 7.17-7.38 (m, 5H), 6.01-6.08 (m, 2H), 5.81 (d, J=7.6 Hz, 1H), 5.54-5.58 (m, 1H), 5.35-5.38 (m, 1H), 4.92-4.97 (m, 2H), 4.45-4.52 (m, 1H), 4.08-4.19 (m, 2H), 3.88-3.92 (m, 1H), 1.28-1.33 (m, 3H), 1.20-1.22 (m, 6H); $^{31}$P NMR (CD₃OD, 162 MHz) δ 7.36; ESI-LCMS: m/z 541.0 [M+H]⁺.

Example 17

Preparation of Compound (17a)

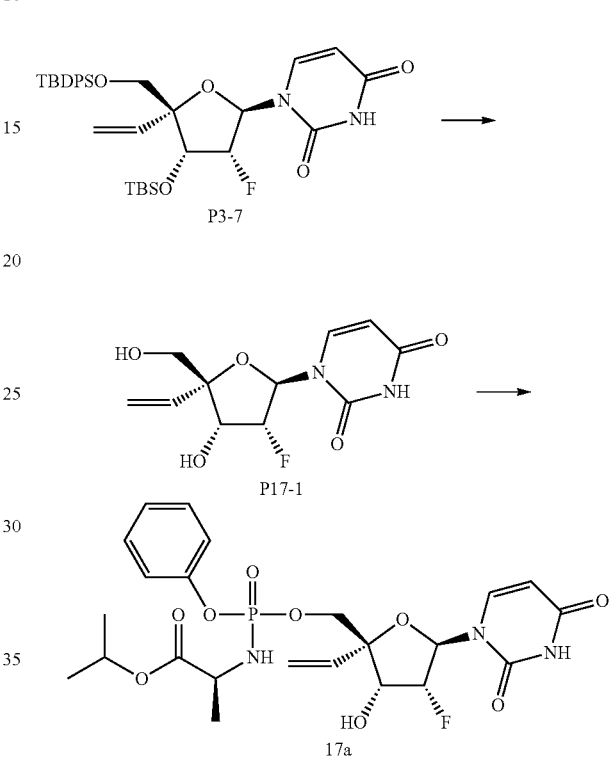

Preparation of (P17-1):

To a solution of P3-7 (1.4 g, 2.3 mmol) in MeOH (50 mL) was added NH₄F (8.0 g) at R.T. The reaction mixture was refluxed overnight. After cooling to R.T., the mixture was filtered, and the filtrate was concentrated. The crude product was purified by silica gel column chromatography (10% MeOH in DCM) to give P17-1 as a white solid (410 mg, 77.8%).

Preparation of (P17):

To a stirred solution of P17-1 (60 mg, 0.19 mmol) in anhydrous THF (3 mL) was added dropwise a solution of t-BuMgCl (0.38 mL, 1M in THF) at −78° C. The mixture was stirred at 0° C. for 30 min and re-cooled to −78° C. A solution of phenyl(isopropoxy-L-alaninyl) phosphorochloridate (104 mg, 0.4 mmol) in THF (0.5 mL) was added dropwise. After addition, the mixture was stirred at 25° C. for 16 hours. The reaction was quenched with HCOOH (80% aq.) at 0° C. The solvent was removed, and the residue was purified on silica gel (DCM:MeOH=50:1 to 10:1) to give compound 17a as a white solid (a mixture of two β isomers, 11.0 mg, 11%). $^1$H NMR (MeOD, 400 MHz) δ 7.71 (2d, J=8.0 Hz, 1H), 7.17-7.37 (m, 5H), 5.98-6.07 (m, 2H), 5.61, 5.68 (2d, J=8.0 Hz, 1H), 5.53-5.58 (m, 1H), 5.35-5.40 (m, 1H), 5.08-5.10 (m, 1H), 4.93-4.99 (m, 1H), 4.52-4.53 (m, 1H), 4.16-4.21 (m, 1H), 4.06-4.11 (m, 1H), 3.86-3.94 (m, 1H), 1.28-1.34 (m, 3H), 1.20-1.22 (m, 6H). $^{31}$P NMR (MeOD, 162 MHz) δ 3.72, 3.45. ESI-LCMS: m/z 542.0 [M+H]$^+$.

Example 18

Preparation of Compound (18a)

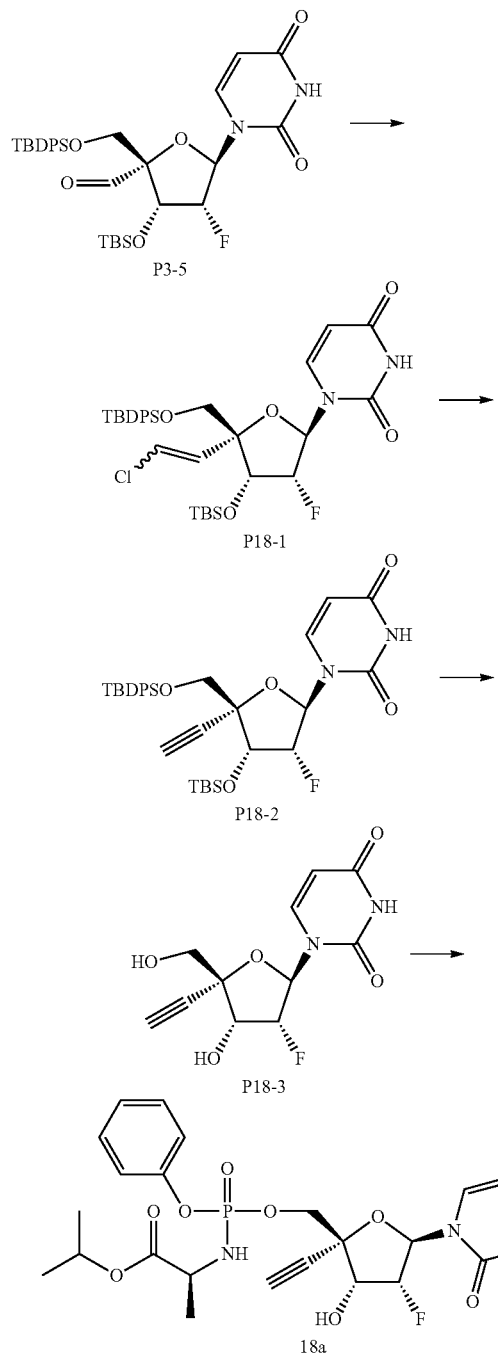

Preparation of (P18-1):

To a solution of (chloromethyl)triphenylphosphonium chloride (2.1 g, 6.0 mmol) in anhydrous THF (10 mL) was added dropwise n-BuLi (4.6 mL, 6.0 mmol) at −70° C. under nitrogen. The reaction was stirred at −70° C. for 50 mins. A solution of compound P3-9 (950 mg, 1.5 mmol) in anhydrous THF (5 mL) was added at −70° C., and the reaction was stirred at 0° C. for 3 hours. The reaction was quenched by saturated aq. NH$_4$Cl and extracted with EtOAc. The organic layer was separated, dried and concentrated to give a residue. The residue was purified by column chromatography on silica gel (eluting with PE:EtOAc=6:1) to give P18-1 as a yellow gum (900 mg, 91.2%).

Preparation of (P18-2):

To a solution of compound P18-1 (600 mg, 0.91 mmol) in anhydrous THF (18 mL) was added dropwise n-BuLi (4.7 mL, 10.9 mmol) at −70° C. under nitrogen. The reaction was stirred at −70° C. for 3 hours. The reaction was quenched by saturated aq. NH$_4$Cl and extracted with EtOAc. The organic layer was separated, dried and concentrated to give a residue. The residue was purified by column chromatography on silica gel (eluting with PE:EtOAc=8:1~5:1) to give P18-2 as a white solid (300 mg, 53.0%).

Preparation of (P18-3):

To a solution of P18-2 (300 mg, 0.44 mmol) in MeOH (10 mL) was added NH$_4$F (1.0 g) at R.T. The reaction was refluxed for 3 hours. After cooling R.T., the mixture was filtered, and the filtrate was concentrated in vacuo. The residue was purified by column chromatography on silica gel (eluting with DCM:MeOH=50:1~30:1) to give P18-3 as a white solid (135 mg, 78.1%). $^1$H NMR (CD$_3$OD, 400 MHz) δ 7.84 (d, J=8.0 Hz, 1H), 6.06 (dd, J$_1$=1.6 Hz, J$_2$=19.6 Hz, 1H), 5.67 (d, J=8.4 Hz, 1H), 5.18-5.03 (m, 1H), 4.50 (dd, J$_1$=5.2 Hz, J$_2$=21.6 Hz, 1H), 3.85 (d, J=12.4 Hz, 1H), 3.72 (d, J=12.4 Hz, 1H), 3.09 (s, 1H).

Preparation of (18a):

To a solution of P18-3 (130 mg, 0.5 mmol) in anhydrous THF (4 mL) was added dropwise t-BuMgCl (1.0 mL, 1.0 mmol) at −70° C. under nitrogen. The reaction was stirred at R.T. for 30 mins. A solution of phenyl(isopropoxy-L-alaninyl) phosphorochloridate in anhydrous THF (1M, 0.8 mL, 0.78 mmol) was added at −70° C., and the reaction mixture was stirred at R.T. for 5 hours. The reaction was quenched by HCOOH, and the mixture was concentrated in vacuo. The residue was purified by column chromatography on silica gel (DCM:MeOH=60:1) to give compound 18a as a white solid (a mixture of two β isomers, 25 mg, 7.7%). $^1$H NMR (CD$_3$OD, 400 MHz) δ 7.64, 7.60 (2d, J=7.6 Hz, 1H), 7.32-7.36 (m, 2H), 7.16-7.25 (m, 3H), 5.95-6.01 (m, 1H), 5.67, 5.62 (2d, J=8.0 Hz, 1H), 5.10-5.25 (m, 1H), 4.93-4.97 (m, 1H), 4.49-4.59 (m, 1H), 4.33-4.42 (m, 1H), 4.24-4.29 (m, 1H), 3.86-3.94 (m, 1H), 3.25, 3.22 (2s, 1H), 1.28-1.34 (m, 3H), 1.20-1.23 (m, 6H); ESI-MS: m/z 540.2 [M+H]$^+$.

Example 19

Preparation of Compound (19a)

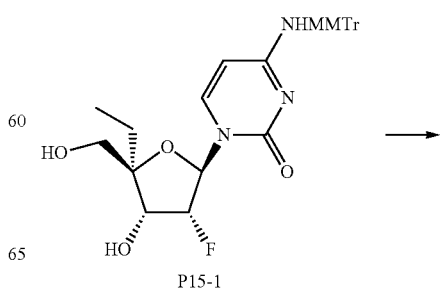

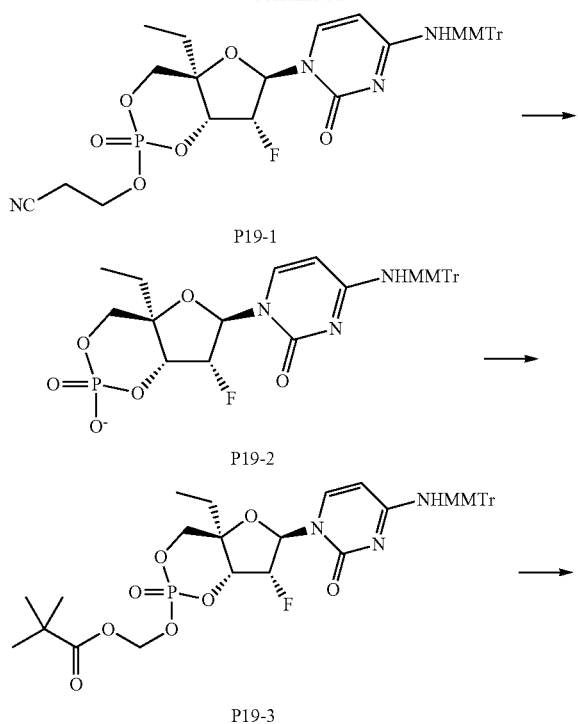

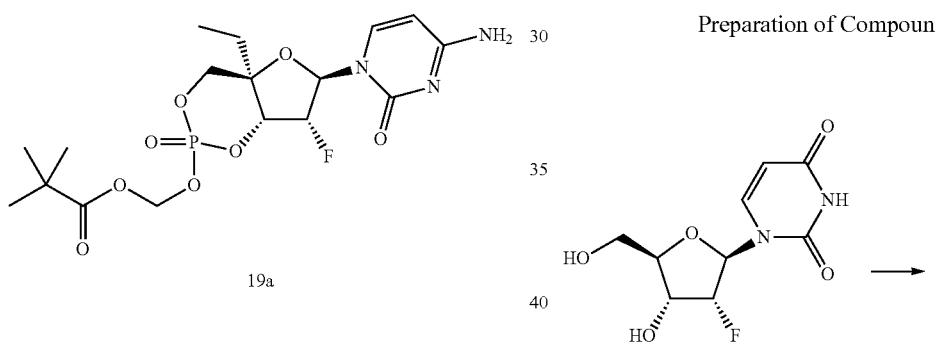

Preparation of (P19-1):

P15-2 (1.2 g, 2.2 mmol) was dissolved in dry acetonitrile (20 mL), and 0.45 M tetrazole (24.0 mL, 11.0 mmol) and 3-(bis(diisopropylamino)phosphinooxy)propanenitrile (1.13 g, 3.74 mmol) was added. The reaction mixture was stirred for 1 hour under $N_2$ at R.T. TBDPH (2.7 mL, 15 mmol) was added, and the mixture was stirred for 1 hour. The reaction was quenched by $Na_2S_2O_3$ solution and extracted with EA. The organic layer was dried over $Na_2SO_4$ and concentrated. The residue was purified by column on silica gel (DCM:MeOH=100:1 to 40:1) to give P19-1 as a white solid (759 mg, 52%).

Preparation of (P19-2):

P19-1 (750 mg, 1.14 mmol) was dissolved in saturated $NH_3$ in MeOH solution. The mixture was stirred for 2 hours at R.T. The solution was concentrated to dryness to give crude P19-2 as a yellow solid (662 mg, 100%). $^1$H NMR (DMSO-d6, 400 MHz) δ 8.60 (s, 1H), 8.28 (s, 1H), 7.48 (d, J=7.6 Hz, 1H), 7.12-7.29 (m, 12H), 6.83 (d, J=8.8 Hz, 2H), 6.29 (d, J=7.6 Hz, 1H), 5.88 (d, J=8.8 Hz, 1H), 5.10 (d, J=4.8 Hz, 1H), 4.42-4.45 (m, 1H), 3.72 (s, 3H), 1.64-1.91 (m, 2H), 1.10-1.13 (m, 2H), 0.83-0.86 (m, 3H). $^{31}$P NMR (CD$_3$OD, 400 MHz) δ −4.48; Negative-ESI-LCMS: m/z 606 [M−H]$^−$.

Preparation of (P19-3):

P19-2 (292 mg, 0.47 mmol) was co-evaporated with pyridine twice and dissolved in anhydrous DMF (0.5 mL). DIPEA (1.2 mL) was added and followed by 2,2-dimethylpropionic acid iodomethyl ester (680 mg, 2.8 mmol). The reaction mixture was stirred at R.T. under $N_2$ for 16 hours. The reaction was quenched by $Na_2S_2O_3$ solution and extracted with EA. The organic layer was dried over $Na_2SO_4$ and concentrated. The residue was purified by column on silica gel (DCM:MeOH=100:1 to 30:1) to give P19-3 as a white solid (95 mg, 30%).

Preparation of (19a):

P19-3 (95 mg, 0.13 mmol) was dissolved in a 80% HCOOH aq. solution, and the mixture was stirred at R.T. for 16 hours. The solvent was removed, and the residue was purified by RP HPLC (MeCN and 0.1% HCOOH in water) to give compound 19a as a white solid (10 mg, 17%). $^1$H NMR (CD$_3$OD, 400 MHz) δ 7.69 (d, J=7.2 Hz, 1H), 5.91 (d, J=7.6 Hz, 1H), 5.84 (d, J=22.0 Hz, 1H), 5.73 (d, J=14.0 Hz, 2H), 5.52 (d, J=5.2 Hz, 1H), 5.13-5.22 (m, 1H), 4.53-4.61 (m, 1H), 4.31 (d, J=9.6 Hz, 1H), 1.92-2.08 (m, 2H), 1.23 (s, 9H), 1.03-1.07 (m, 3H); $^3$H NMR (CD$_3$OD, 162 MHz) δ −7.93; ESI-LCMS: m/z 450 [M+H]$^+$.

Example 20

Preparation of Compound (20a)

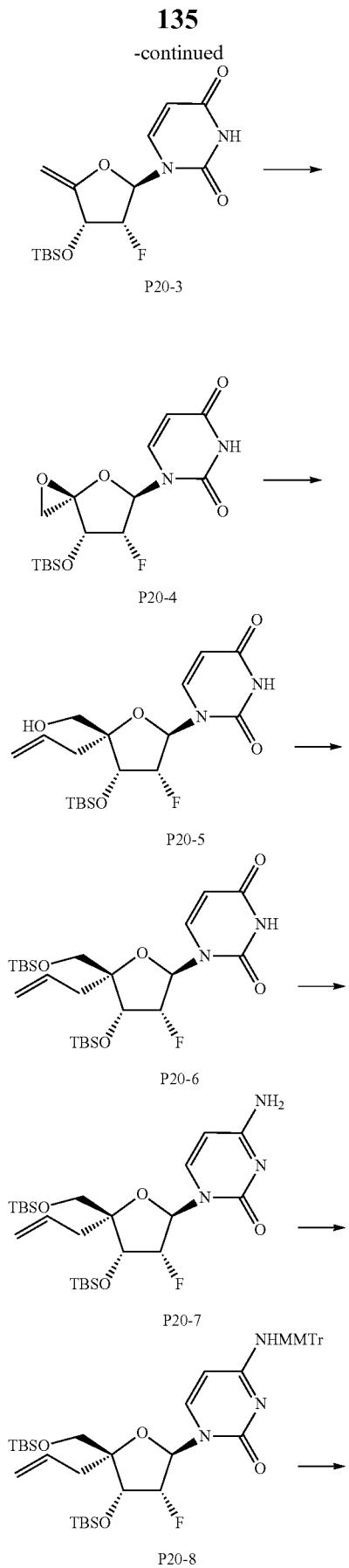

P20-3

P20-4

P20-5

P20-6

P20-7

P20-8

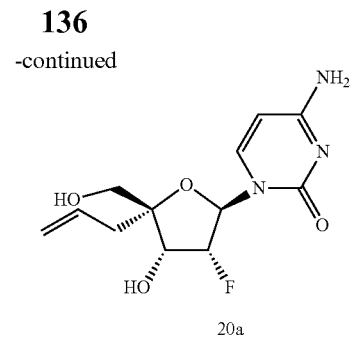

20a

Preparation of (P20-1):

To a stirred suspension of P3-1 (20.0 g, 81.3 mmol), imidazole (15.9 g, 234.0 mmol), PPh$_3$ (53.5 g, 203.3 mmol) and pyridine (90 mL) in anhydrous THF (360 mL) was added dropwise a solution of I$_2$ (41.3 g, 162.6 mmol) in THF (350 mL) at 0° C. After addition, the mixture was warmed to R.T. and stirred for 14 hours. The solution was quenched with aq. Na$_2$S$_2$O$_3$ (150 mL) and extracted with EA. The organic layer was dried over Na$_2$SO$_4$ and concentrated. The residue was purified on a silica gel column (DCM:MeOH=100:1 to 10:1) to afford P20-1 as a white solid (22.1 g, 76.4%). $^1$H NMR (CD$_3$OD, 400 MHz) δ 7.70 (d, J=8.0 Hz, 1H), 5.88 (dd, J$_1$=1.6 Hz, J$_2$=20.8 Hz, 1H), 5.71 (d, J=8.4 Hz, 1H), 5.24 (dd, J$_1$=2.0 Hz, J$_2$=5.2 Hz, 1H), 5.10 (dd, J$_1$=2.0 Hz, J$_2$=5.2 Hz 1H), 3.78-3.83 (m, 1H), 3.61-3.65 (m, 1H), 3.44 (dd, J$_1$=J$_2$=6.0 Hz, 1H).

Preparation of (P20-2):

To a stirred solution of P20-1 (22.1 g, 62.1 mmol) in anhydrous THF (200 mL) was added dropwise DBU (14.2 g, 93.1 mmol) in THF (50 mL) at 0° C. over 10 mins. The mixture was stirred at 60° C. for 6 hours. The reaction was quenched with aq. NaHCO$_3$ (200 mL) and extracted with EA. The organic layer was washed with brine and dried over Na$_2$SO$_4$. The solvent was removed, and the residue was purified on a silica gel column (MeOH:DCM=1/100 to 1/30) to afford P20-2 as a white solid (8.7 g, 61.5%). $^1$H NMR (CD$_3$OD, 400 MHz) δ 7.51 (d, J=8.0 Hz, 1H), 6.05 (dd, J$_1$=1.2 Hz, J$_2$=17.2 Hz, 1H), 5.73 (d, J=8.0 Hz, 1H), 5.26 (dd, J$_1$=1.2 Hz, J$_2$=4.8 Hz, 1H), 5.13 (dd, J$_1$=1.2 Hz, J$_2$=4.8 Hz, 1H), 4.63 (dd, J$_1$=2.0 Hz, J$_2$=3.2 Hz, 1H), 4.41 (dd, J$_1$=J$_2$=2.0 Hz, 1H).

Preparation of (P20-3):

To a stirred solution of P20-2 (3.2 g, 14.0 mmol) in anhydrous pyridine (10 mL) and DCM (100 mL) was added dropwise a solution of TBSCl (4.2 g, 28.0 mmol) at 0° C. Stirring was continued at R.T. for 18 hours. The mixture was diluted with DCM. The organic layer was washed with brine and dried over Na$_2$SO$_4$. The solvent was removed, and the residue was purified on a silica gel column (10% MeOH in DCM) to afford P20-3 as a white solid (3.4 g, 70.8%).

Preparation of (P20-4):

To a stirred solution of NaHCO$_3$ in H$_2$O (250 mL) and acetone (200 mL) was added oxone (30.0×4 g) at 0° C. The mixture was warmed to R.T., and the distillate was collected at −78° C. (120 mL) under slightly reduced pressure to give a solution of DMDO in acetone. To a stirred solution of P20-3 (250.0 mg, 0.7 mmol) in DCM (20 mL) were added a DMDO (120 mL) solution at −40° C. and MgSO$_4$. The mixture was warmed to R.T. and then stirred for 2 hours. The solution was filtrated, and the filtrate was used for the next-step directly.

Preparation of (P20-5):

To a stirred solution of P20-4 (500.0 mg, 1.4 mmol) in anhydrous DCM (50 mL) was added allyl-trimethyl-silane (760.0 mg, 6.7 mmol) and SnCl$_4$ (1.2 g, 4.5 mmol) at −40° C.

The mixture was warmed and stirred at 0° C. for 1 hour. The reaction was quenched with saturated NaHCO$_3$ and extracted with DCM. The organic layer was dried over Na$_2$SO$_4$ and concentrated. The residue was purified on a silica gel column (20-50% EA in PE) to give P20-5 as a white foam (120 mg, 41%). $^1$H NMR (CD$_3$OD, 400 MHz) δ 8.01 (d, J=8.4 Hz, 1H), 6.12 (dd, J$_1$=3.6 Hz, J$_2$=15.2 Hz, 1H), 5.87-5.96 (m, 1H), 5.71 (d, J=8.4 Hz, 1H), 5.06-5.22 (m, 3H), 4.60 (dd, J$_1$=5.6 Hz, J$_2$=14.4 Hz, 1H), 3.72 (d, J=11.6 Hz, 1H), 3.48 (d, J=11.6 Hz, 1H), 2.62-2.67 (m, 1H), 2.23-2.29 (m, 1H); ESI-LCMS: m/z=422 [M+Na]$^+$.

Preparation of (P20-6):

To a stirred solution of P20-5 (270.0 mg, 0.7 mmol) in dry DCM were added imidazole (400.0 mg, 5.9 mmol) and TBSCl (390.0 mg, 2.6 mmol) at R.T. The mixture was stirred at R.T. for 18 hours. The solution was diluted with EA. The solvent was washed with brine and dried over Na$_2$SO$_4$. The solvent was removed, and the residue was purified on a silica gel column (20-40% EA in PE) to afford compound P20-6 as a white foam (280 mg, 80.7%). ESI-LCMS: m/z 537 [M+Na]$^+$.

Preparation of (P20-7):

To a stirred solution of P20-6 (280.0 mg, 0.5 mmol) in dry MeCN were added TPSCl (350.0 mg, 1.2 mmol), NEt$_3$ (400.0 mg, 4.0 mmol) and DMAP (270.0 mg, 2.2 mmol) at R.T. The mixture was stirred at R.T. for 18 hours. The solution was quenched with ammonium. The organic layer was washed with brine and dried over Na$_2$SO$_4$. The solvent was removed, and the residue was purified by TLC (using EA) to afford compound P20-7 as a white foam (240.0 mg, 85.7%). ESI-LCMS: m/z 514 [M+H]$^+$.

Preparation of (P20-8):

To a stirred solution of P20-7 (270.0 mg, 0.5 mmol) in dry DCM were added AgNO$_3$ (1.5 g, 8.8 mmol), MMTrCl (450.0 mg, 1.5 mmol) and collidine (500.0 mg, 4.1 mmol) at R.T. The mixture was stirred at R.T. for 18 hours. The solution was diluted with DCM. The organic layer was washed with brine and dried over Na$_2$SO$_4$. The solvent was removed, and the residue was purified on a silica gel column (20-40% EA in PE) to afford compound P20-8 as a white foam (300 mg, 81.6%). ESI-LCMS: m/z 786 [M+H]$^+$.

Preparation of (20a):

To a stirred solution of P20-8 (170.0 mg, 0.3 mmol) in dry MeOH was added NH$_4$F (300.0 mg, 8.1 mmol), and the mixture was refluxed for 24 hours. The solvent was removed under reduced pressure, and the residue was purified on a silica gel column (2-5% MeOH in DCM) to give the crude product. The crude product was further purified by RP HPLC (water and 0.1% HCOOH in MeCN) to afford compound 20a as a white solid (47.0 mg, 49.8%). $^1$H NMR (CD$_3$OD, 400 MHz) δ 8.13 (d, J=8.4 Hz, 1H), 6.12 (dd, J$_1$=3.2 Hz, J$_2$=12.0 Hz, 1H), 5.87-5.97 (m, 2H), 4.98-5.14 (m, 3H), 4.45 (dd, J$_1$=5.2 Hz, J$_2$=17.6 Hz, 1H), 3.71 (d, J=11.6 Hz, 1H), 3.54 (d, J=11.6 Hz, 1H), 2.54-2.59 (m, 1H), 2.33-2.39 (m, 1H); ESI-LCMS: m/z 286 [M+H]$^+$.

Example 21

Preparation of Compound (21a)

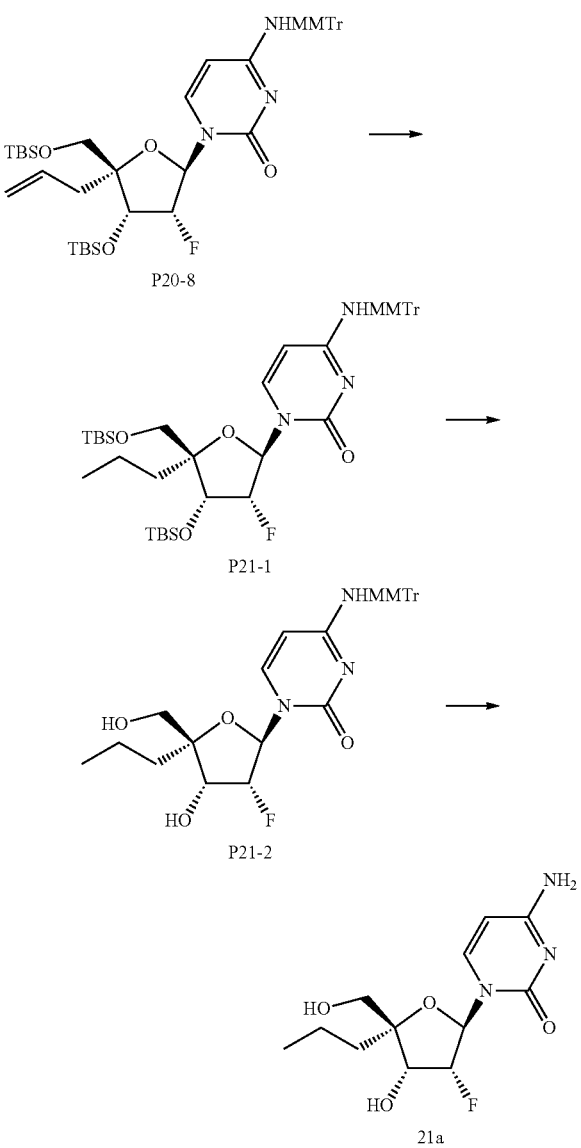

Preparation of (P21-1):

To a stirred solution of P20-8 (250.0 mg, 0.3 mmol) in MeOH was added Pd/C (500.0 mg), and the mixture was stirred under H$_2$ (balloon) for 18 hours at R.T. The reaction was filtered, and the solvent removed under reduced pressure. The residue was purified by prep. TLC (30% EtOAc in PE) to afford P21-1 as a white foam (210.0 mg, 84.0%).

Preparation of (P21-2):

To a stirred solution of P21-1 (210.0 mg, 0.3 mmol) in dry THF was added TBAF (1 mL, μmol), and the mixture was stirred at R.T. for 18 hours. The solvent was removed under reduced pressure, and the residue was purified by prep. TLC (30% EtOAc in PE) to give compound 21a as a white foam (111.2 mg, 74.6%). $^1$H NMR (DMSO-d6, 400 MHz) δ 8.49

(s, 1H), 7.75 (d, J=6.8 Hz, 1H), 6.83-7.32 (m, 14H), 6.25 (d, J=7.6 Hz, 1H), 5.95 (dd, J₁=4.8 Hz, J₂=14.8 Hz, 1H), 5.48 (d, J=5.6 Hz, 1H), 4.86-5.15 (m, 2H), 4.15-4.21 (m, 1H), 3.72 (s, 3H), 3.38-3.49 (m, 2H), 1.24-1.58 (m, 4H), 0.84 (t, J=7.2 Hz, 3H); ESI-MS: m/z 560 [M+H]⁺.

Preparation of (P21):

Compound P21-2 (81 mg) was dissolved in a mixture (5 mL) of formic acid (80%) and water (20%). The resulting solution was stirred at R.T. for 3 hours and then concentrated. The residue was co-evaporated with methanol/toluene three times. Chromatography on silica gel with 5-12% methanol in DCM gave a mixture of two compounds, which was dissolved in methanol with a drop of concentrated aqueous ammonia and concentrated. The residue was purified on silica gel with 5-12% methanol in DCM to give compound 21a (27 mg) as a white solid; ¹H NMR (CD₃OD, 400 MHz) δ 8.05 (d, J=7.6 Hz, 1H), 6.06 (dd, J₁=2.8 Hz, J₂=16 Hz, 1H), 5.87 (d, J=7.6 Hz, 1H), 5.10 (dd, J=3.2, 5.2 Hz, 0.5H), 4.96 (dd, 3.2, 5.2 Hz, 0.5H), 4.42 (dd, J=5.6, 17.2 Hz, 1H), 3.67 (dd, J=11.6, 76 Hz, 2H), 1.70-1.79 (m, 1H), 1.31-1.61 (m, m, 3H), 0.94 (t, J=6.8 Hz, 3H). MS: m/z 417 [M+2-methylheptylamine]⁺.

Example 22

Preparation of Compound (22a)

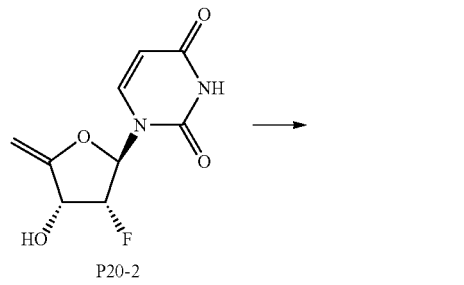

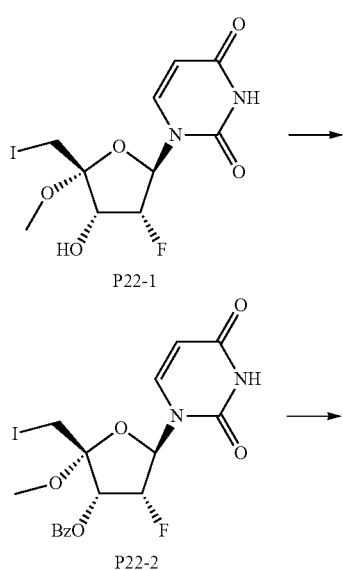

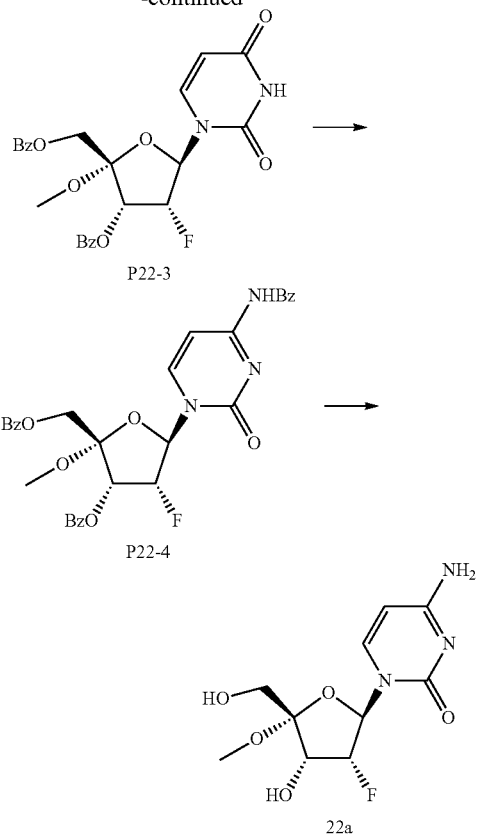

Preparation of (P22-1):

To a solution of P20-2 (5.23 g, 23.1 mmol) in anhydrous MeOH (50 mL) was added PbCO₃ (12.7 g, 46.3 mmol) at R.T. A solution of I₂ (11.7 g, 46.3 mmol) in MeOH (10 mL) was then added dropwise at 0° C. The reaction mixture was stirred at R.T. for overnight. The reaction was quenched with Na₂S₂O₃ and dissolved in EA. The organic layer was dried over Na₂SO₄ and concentrated. The residue was purified by column (DCM/MeOH=100/1 to 20/1) to give P22-1 as a white solid (5.6 g, 71.8%). ¹H NMR (CD₃OD, 400 MHz) δ 7.67 (d, J=8.0 Hz, 1H), 5.88 (dd, J₁=J₂=7.6 Hz, 1H), 5.73 (d, J=8.0 Hz, 1H), 5.24 (dd, J₁=4.4 Hz, J₂=6.4 Hz, 1H), 5.11 (dd, J₁=6.4 Hz, J₂=6.0 Hz, 1H); 4.65 (dd, J₁=20.0 Hz, J₂=20.4 Hz, 1H), 3.67 (d, J=11.6 Hz, 1H), 3.54 (d, J=11.6 Hz, 1H), 3.43 (s, 3H).

Preparation of (P22-2):

To a stirred solution of P22-1 (5.6 g, 14.5 mmol) in anhydrous pyridine (20 mL) was added dropwise BzCl (2.9 g, 20.9 mmol) at 0° C. The mixture was stirred at R.T. for 10 hours. The reaction was quenched with H₂O, and the solution was concentrated. The residue was dissolved in EA and washed with saturated NaHCO₃. The organic layer was dried over Na₂SO₄ and concentrated. The residue was purified on a silica gel column (20~40% EA in PE) to give P22-2 as a white foam (4.9 g, 74.2%).

Preparation of (P22-3):

P22-2 (4.9 g, 10.0 mmol), BzONa (14.4 g, 100 mmol) and 15-crown-5 (22.0 g, 100 mmol) were suspended in DMF (200 mL). The mixture was stirred at 60-70° C. for 3 days. The precipitate was removed by filtration, and the filtrate was diluted with EA. The solvent was washed with brine and dried over Na₂SO₄. The solvent was removed, and the residue was purified on a silica gel column (20-60% EA in PE) to afford P22-3 as a white foam (2.3 g, 47.9%).

Preparation of (P22-4):

P22-3 (2.3 g, 4.8 mmol), DMAP (1.2 g, 9.6 mmol), TPSCl (2.9 g, 9.6 mmol) and Et₃N (0.97 g, 9.6 mmol) were suspended in MeCN (10 mL). The mixture was stirred at R.T. for 14 hours. NH₃ in THF (saturated at 0° C., 100 mL) was added to the mixture, and the mixture stirred at R.T. for 2 hours. The solvent was removed, and the residue was purified by column (DCM/MeOH=100:1 to 50:1) to give the crude product (1.2 g). The crude product was dissolved in pyridine, and BzCl (0.42 g, 3.0 mmol) was added. The mixture was stirred at R.T. for 16 hours and quenched with water. The solvent was removed, and the residue was purified on a silica gel column (PE:EA=2:1 to 1:1) to give P22-4 as a white foam (460 mg, 31%).

Preparation of (22a):

P22-4 (0.46 g, 0.8 mmol) was dissolved in saturated methanolic ammonia (100 mL), and the mixture was stirred at R.T. for 14 hours. The solvent was removed, and the residue was dissolved in H₂O and washed with DCM. The aqueous phase was lyophilized and further purified by prep. HPLC (0.1% formic acid in water/acetonitrile) to give compound 22a as a white solid (145 mg, 78.9%). $^1$H NMR (CD₃OD, 400 MHz) δ 7.88 (d, J=7.6 Hz, 1H), 6.03 (d, J=18.4 Hz, 1H), 5.87 (d, J=7.6 Hz, 1H), 4.86-5.00 (m, 1H), 4.49 (dd, J₁=23.2 Hz, J₂=22.8 Hz, 1H), 3.90 (d, J=12.0 Hz, 1H), 3.66 (d, J=12.0 Hz, 1H), 3.41 (s, 3H); ESI-MS: m/z 276 [M+H]⁺.

Example 23

Preparation of Compound (23a)

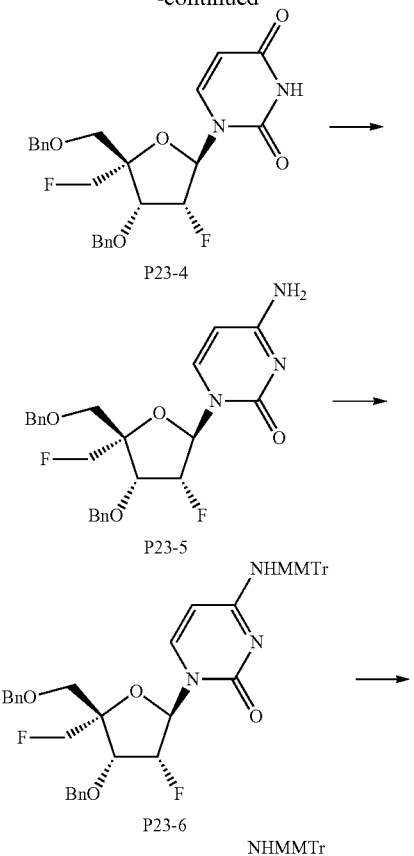

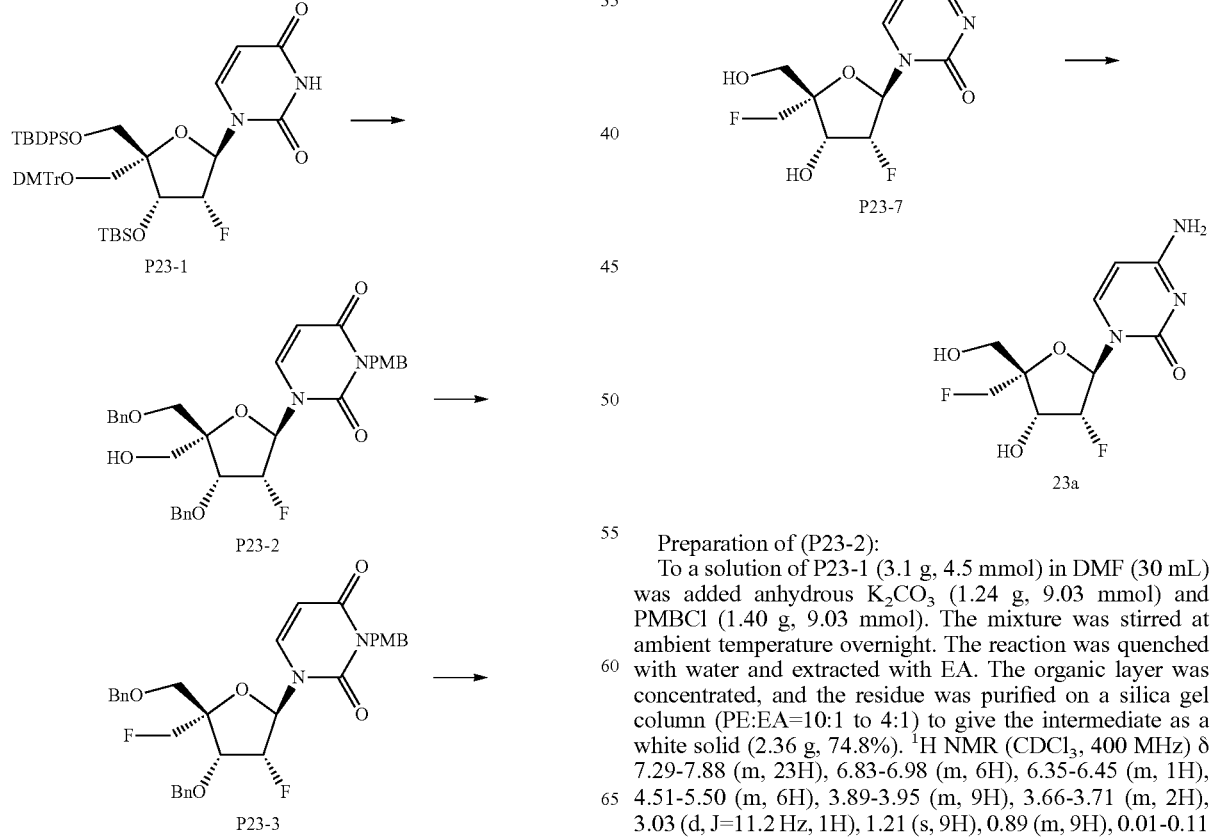

Preparation of (P23-2):

To a solution of P23-1 (3.1 g, 4.5 mmol) in DMF (30 mL) was added anhydrous K₂CO₃ (1.24 g, 9.03 mmol) and PMBCl (1.40 g, 9.03 mmol). The mixture was stirred at ambient temperature overnight. The reaction was quenched with water and extracted with EA. The organic layer was concentrated, and the residue was purified on a silica gel column (PE:EA=10:1 to 4:1) to give the intermediate as a white solid (2.36 g, 74.8%). $^1$H NMR (CDCl₃, 400 MHz) δ 7.29-7.88 (m, 23H), 6.83-6.98 (m, 6H), 6.35-6.45 (m, 1H), 4.51-5.50 (m, 6H), 3.89-3.95 (m, 9H), 3.66-3.71 (m, 2H), 3.03 (d, J=11.2 Hz, 1H), 1.21 (s, 9H), 0.89 (m, 9H), 0.01-0.11 (m, 6H). The intermediate was used in the next step.

To a stirred solution of the intermediate (11.0 g, 10.47 mmol) in anhydrous THF (100 mL) was added TBAF (8.20 g, 31.42 mmol) at R.T., and the mixture was stirred at R.T. for 5 hours. The solution was removed, and the residue was purified on a silica gel column (PE:EA=5:1 to 1:1) to give a second intermediate as a white solid (5.99 g, 82%).

To a stirred solution of the second intermediate (500 mg, 0.716 mmol) in anhydrous DMF (10 mL) was added NaH (51.5 mg, 2.14 mmol) and BnBr (365 mg, 2.14 mmol) dropwise at 0° C. The mixture was stirred at R.T. for overnight. The solution was quenched with water and extracted with EA. The concentrated organic phase was purified on a silica gel column (PE:EA=10:1 to 4:1) to give a third intermediate as a white solid (496 mg, 79%).

The third intermediate (2.5 g, 2.84 mmol) was dissolved in 80% HOAc (25 mL) at R.T., and the mixture was stirred at R.T. for overnight. The reaction was quenched with MeOH, and the solvent was removed. The crude was purified on a silica gel column (PE:EA=5:1 to 1:1) to give P23-2 as a white solid (1.2 g, 73%).

Preparation of (P23-3):

To a stirred solution of DAST (1.39 g, 8.68 mmol) in anhydrous toluene (15 mL) was added dropwise a solution of P23-2 (1.0 g, 1.73 mmol) at −78° C. The mixture was stirred at −78° C. for 30 mins. The solution was heated to 60° C. gradually and then stirred overnight. The mixture was poured into saturated $Na_2CO_3$ solution. The concentrated organic phase was purified on a silica gel column (PE:EA=10:1 to 4:1) to give P23-3 as a white solid (449 mg, 45%). $^1$H NMR ($CD_3OD$, 400 MHz) δ 7.87 (d, J=8.4 Hz, 1H), 7.27-7.37 (m, 12H), 6.82-6.84 (m, 2H), 6.14 (dd, J=16.8, 2.0 Hz, 1H), 5.18-5.50 (m, 4H), 4.96 (s, 2H), 4.45-4.88 (m, 7H), 3.67-3.89 (m, 5H).

Preparation of (P23-4):

A mixture of P23-3 (1.20 g, 2.07 mmol) and CAN (3.41 g, 6.23 mmol) in a solution of MeCN:Water (3:1, 10 mL) was stirred at R.T. overnight. Brine (10 mL) was added, and the mixture was extracted with EA. The combined organic extracts were dried and evaporated under reduced pressure. The residue was purification by chromatography on silica gel (PE:EA=10:1 to 2:1) to give P23-4 as a yellow solid (475 mg, 49.8%).

Preparation of (P23-5):

To a stirred solution of P23-4 (550 mg, 210 mmol) in anhydrous MeCN (10 mL) were added TPSCl (725 mg, 2.40 mmol), DMAP (293 mg, 2.40 mmol) and TEA (242 mg, 2.40 mmol) at R.T., and the mixture was stirred at R.T. overnight. $NH_4OH$ (25 mL) was added, and the mixture was stirred for 2 hours. The solvent was removed, and the residue was purified on a silica gel column (PE:EA=8:1 to 2:1) to give P23-5 as a white solid (700 mg crude). $^1$H NMR ($CD_3OD$, 400 MHz) δ 7.86 (d, J=8.4 Hz, 1H), 7.27-7.36 (m, 10H), 6.13 (dd, $J_1$=17.2 Hz, $J_2$=2.0 Hz, 1H), 5.48-5.53 (m, 1H), 5.11-5.26 (m, 1H), 4.44-4.74 (m, 7H), 3.89 (dd, $J_1$=10.4 Hz, $J_2$=2.0 Hz, 1H), 3.69 (dd, $J_1$=10.8 Hz, $J_2$=1.6 Hz, 1H).

Preparation of (P23-6):

To a stirred solution of P23-5 (1.0 g, 2.18 mmol) in anhydrous DCM (15 mL) was added MMTrCl (2.02 g, 6.56 mmol) and $AgNO_3$ (1.11 g, 6.56 mmol) at R.T., and the mixture was stirred at R.T. overnight. The solid was filtered off and washed with DCM. The filtrate was washed with brine and dried over $Na_2SO_4$. The organic phase was concentrated, and the residue was purified on a silica gel column (PE:EA=8:1 to 2:1) to give P23-6 as a white solid (520 mg, 41%).

Preparation of (P23-7):

To a stirred solution of P23-6 (520 mg, 0.713 mmol) in acetone were added ammonium formate (2.0 g, 31.7 mmol, in portions) and 10% palladium on carbon (1.0 g). The mixture was refluxed for 12 hours. The catalyst was filtered off and washed with solvent. The filtrate was added EA and washed with brine. The concentrated organic phase was purified by column chromatography (DCM:MeOH=100:1 to 15:1) and prep. TLC to give P23-7 as a white solid (270 mg, 69.0%). $^1$H NMR ($CD_3OD$, 400 MHz) δ 8.54 (s, 1H), 7.73 (d, J=7.6 Hz, 1H), 7.13-7.32 (m, 12H), 6.83 (d, J=8.4 Hz, 2H), 6.29 (d, J=7.6 Hz, 1H), 5.99-6.04 (m, 1H), 5.82 (d, J=5.6 Hz, 1H), 5.39 (t, J=5.2 Hz, 1H), 5.09 (t, J=5.2 Hz, 1H), 4.32-4.58 (m, 3H), 3.54-3.72 (m, 5H). ESI-MS: m/z 549.6 $[M+H]^+$.

Preparation of (23a):

P23-7 (130 mg, 0.236 mmol) was dissolved in 80% HCOOH (20 mL) at R.T., and the mixture was stirred at 50° C. for 12 hours. The solvent was removed, and the residue was co-evaporated with toluene twice. The residue was re-dissolved in MeOH (20 mL) at 60° C. and stiffing was continued for 48 hours. The solvent was removed, and the residue was purified by column chromatography (DCM:MeOH=100:1 to 10:1) to give compound 23a as a white solid (45 mg, 69.0%). $^1$H NMR ($CD_3OD$, 400 MHz) δ 8.00 (d, J=7.6 Hz, 1H), 6.13 (dd, $J_1$=16.0 Hz, $J_2$=4.0 Hz, 1H), 5.89 (d, J=7.6 Hz, 1H), 5.18-5.21 (m, 1H), 5.05-5.07 (m, 1H), 4.60 (s, 1H), 4.51-4.57 (m, 2H), 3.84 (dd, $J_1$=12.0 Hz, $J_2$=2.0 Hz, 1H), 3.75 (dd, $J_1$=12.0 Hz, $J_2$=2.0 Hz, 1H). ESI-MS: m/z 277.8 $[M+H]^+$, 554.8 $[2M+H]^+$.

Example 24

Preparation of Compound (24a)

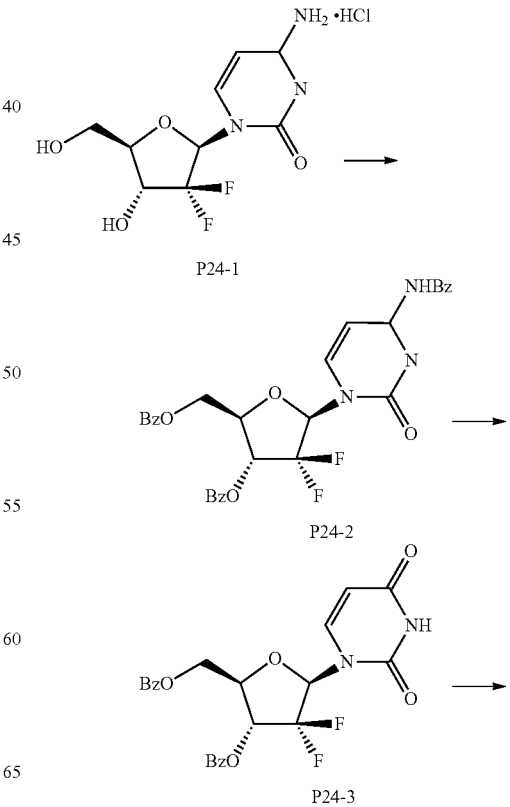

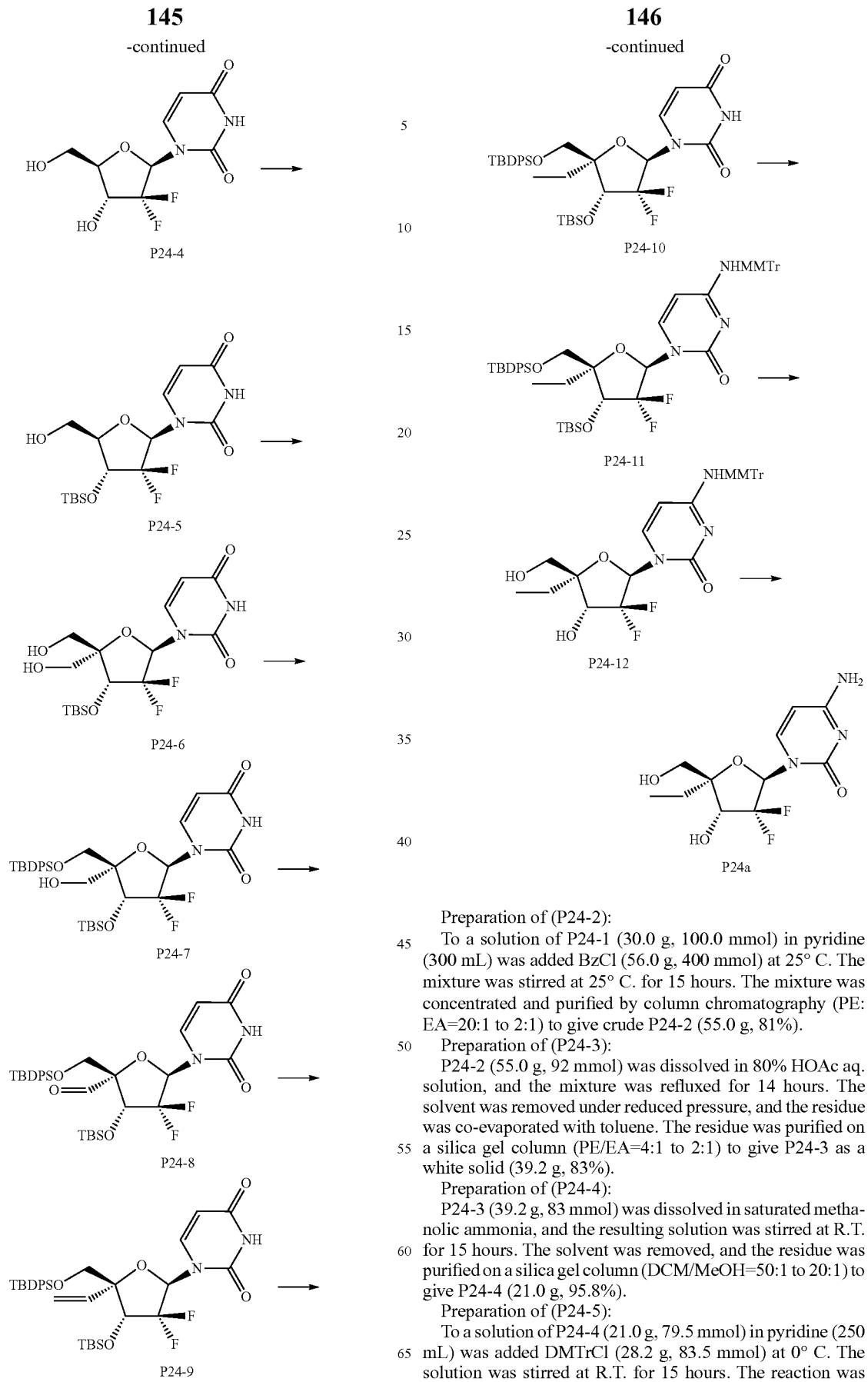

Preparation of (P24-2):

To a solution of P24-1 (30.0 g, 100.0 mmol) in pyridine (300 mL) was added BzCl (56.0 g, 400 mmol) at 25° C. The mixture was stirred at 25° C. for 15 hours. The mixture was concentrated and purified by column chromatography (PE:EA=20:1 to 2:1) to give crude P24-2 (55.0 g, 81%).

Preparation of (P24-3):

P24-2 (55.0 g, 92 mmol) was dissolved in 80% HOAc aq. solution, and the mixture was refluxed for 14 hours. The solvent was removed under reduced pressure, and the residue was co-evaporated with toluene. The residue was purified on a silica gel column (PE/EA=4:1 to 2:1) to give P24-3 as a white solid (39.2 g, 83%).

Preparation of (P24-4):

P24-3 (39.2 g, 83 mmol) was dissolved in saturated methanolic ammonia, and the resulting solution was stirred at R.T. for 15 hours. The solvent was removed, and the residue was purified on a silica gel column (DCM/MeOH=50:1 to 20:1) to give P24-4 (21.0 g, 95.8%).

Preparation of (P24-5):

To a solution of P24-4 (21.0 g, 79.5 mmol) in pyridine (250 mL) was added DMTrCl (28.2 g, 83.5 mmol) at 0° C. The solution was stirred at R.T. for 15 hours. The reaction was quenched with MeOH and concentrated to dryness under reduced pressure. The residue was dissolved in EtOAc and washed with water. The organic layer was dried over $Na_2SO_4$ and concentrated. The residue was dissolved in DCM (300 mL). Imidazole (13.6 g, 200 mmol) and TBSCl (30.0 g, 200 mmol) were added. The reaction mixture was stirred at R.T. for 12 hours. The reaction mixture was washed with $NaHCO_3$ and brine. The organic layer was dried over $Na_2SO_4$ and concentrated. The residue (48.5 g, 79.5 mmol) was dissolved in 80% HOAc aq. solution (400 mL). The mixture was stirred at R.T. for 20 hours. The mixture was diluted with EtOAc and washed with $NaHCO_3$ solution and brine. The organic layer was dried over $Na_2SO_4$ and purified by silica gel column chromatography (1-2% MeOH in DCM) to give P24-5 as a white solid (21.0 g, 70%). $^1H$ NMR (400 MHz, MeOD) 87.83 (d, J=8.0 Hz, 1H), 6.14 (dd, $J_1$=6.0 Hz, $J_2$=10.0 Hz, 1H), 5.73 (d, J=8.4 Hz, 1H), 4.38-4.46 (m, 1H), 3.89-3.91 (m, 1H), 3.88 (dd, $J_1$=2.8 Hz, $J_2$=5.2 Hz, 1H), 3.72 (dd, $J_1$=2.8 Hz, $J_2$=5.2 Hz, 1H), 0.93 (s, 9H), 0.15 (m, 6H). ESI-MS: m/z 379.1 $[M+H]^+$.

Preparation of (P24-6):

To a solution of P24-5 (21.0 g, 55.6 mmol) in anhydrous $CH_3CN$ (200 mL) was added IBX (17.1 g, 61.1 mmol) at R.T. The reaction mixture was refluxed for 1 hour and then cooled to 0° C. The precipitate was filtered off, and the filtrate was concentrated to give the aldehyde as a yellow solid (21.0 g, 55.6 mmol). To a solution of the aldehyde (21.0 g, 55.6 mmol) in dioxane (200 mL) were added 37% $CH_2O$ (22.2 mL, 222.4 mmol) and 2N NaOH aq. solution (55.6 mL, 111.2 mmol). The mixture was stirred at R.T. for 2 hours and then neutralized with AcOH to pH=7. To the reaction were added EtOH (50 mL) and $NaBH_4$ (12.7 g, 333.6 mmol). The mixture was stirred at R.T. for 30 mins. The reaction was quenched with saturated aq. $NH_4Cl$. extracted with EA. The organic layer was dried over $Na_2SO_4$ and concentrated. The residue was purified by silica gel column chromatography (1-3% MeOH in DCM) to give P24-6 as a white solid (13.5 g, 59.5%).

Preparation of (P24-7):

To a solution of P24-6 (13.5 g, 33.1 mmol) in DCM (100 mL) were added pyridine (20 mL) and DMTrCl (11.2 g, 33.1 mmol) at 0° C. The solution was stirred at 25° C. for 3 hours, and then treated with MeOH (30 mL). The solvent was removed, and the residue was purified by silica gel column chromatography (DCM:MeOH=300:1 to 100:1) to give a residue. The residue was dissolved in anhydrous pyridine (150 mL) and TBDPSCl (16.5 g, 60 mmol) and $AgNO_3$ (10.2 g, 60 mmol) were added. The mixture was stirred at 25° C. for 15 hours, and then filtered and concentrated. The mixture was dissolved in EtOAc and washed with brine. The organic layer was dried over $Na_2SO_4$. Purified by silica gel column chromatography (DCM:MeOH=300:1 to 100:1) gave the product as a yellow solid (16.2 g, 85.3%). The solid was dissolved in 80% HOAc aq. solution (400 mL). The mixture was stirred at R.T. for 15 hours. The mixture was diluted with EtOAc and washed with $NaHCO_3$ solution and brine. The organic layer was dried over $Na_2SO_4$ and purified by silica gel column chromatography (DCM:MeOH=200:1 to 50:1) to give P24-7 as a white solid (9.5 g, 86.5%). $^1H$ NMR ($CD_3OD$, 400 MHz) δ 7.39-7.70 (m, 11H), 6.34-6.38 (m, 1H), 5.12 (d, J=8.0 Hz, 1H), 4.79 (dd, $J_1$=10.0 Hz, $J_2$=16.0 Hz, 1H), 4.14 (dd, $J_1$=1.6 Hz, $J_2$=11.6 Hz, 1H), 3.48-3.84 (m, 2H), 3.49 (dd, $J_1$=1.6 Hz, $J_2$=11.6 Hz, 1H), 1.12 (s, 9H), 0.92 (s, 9H), 0.16 (s, 6H).

Preparation of (P24-8):

To a solution of P24-7 (6.0 g, 9.3 mmol) in anhydrous DCM (80 mL) was added Dess-Martin periodinane (7.9 g, 18.6 mmol) at 0° C. under nitrogen. The reaction was stirred at R.T. for 1 hour. The solvent was removed in vacuo, and the residue was triturated with diethyl ether (50 mL). The mixture was filtered through a pad of $MgSO_4$, and the organic solvent was stirred with an equal volume of $Na_2S_2O_3.5H_2O$ in saturated $NaHCO_3$ (50 mL) until the organic layer became clear (approx. 10 min). The organic layer was separated, washed with brine, and dried over $MgSO_4$. After concentration in vacuo, P24-8 was obtained as a red solid (5.8 g, 98%).

Preparation of (P24-9):

To a mixture of methyltriphenylphosphonium bromide (9.6 g, 27.0 mmol) in anhydrous THF (60 mL) was added n-BuLi (10.8 mL, 27.0 mmol) at –70° C. under nitrogen. The reaction was stirred at 0° C. for 30 mins. A solution of P24-8 (5.8 g, 9.0 mmol) in anhydrous THF (20 mL) was added dropwise at 0° C. under nitrogen. The reaction was stirred at R.T. for 12 hours. The reaction was quenched with $NH_4Cl$ and extracted with EtOAc. The organic layer was separated, dried and concentrated, and the residue was purified by silica gel column chromatography (DCM:MeOH=300:1 to 100:1) to give P24-9 as a white solid (3.0 g, 51%).

Preparation of (P24-10):

To a solution of P24-9 (2.9 g, 4.5 mmol) in anhydrous MeOH (20 mL) was added Pd/C (1.4 g) at 25° C. under hydrogen atmosphere. The mixture was stirred at 25° C. for 1 hour. The solution was filtered, evaporated to dryness and purified on a silica gel column (DCM:MeOH=300:1 to 100:1) to give P24-10 as a white solid (2.3 g, 79.3%).

Preparation of (P24-11):

To a solution of P24-10 (1.0 g, 1.55 mmol) in anhydrous $CH_3CN$ (20 mL) were added TPSCl (940 mg, 3.1 mmol), DMAP (380 mg, 3.1 mmol) and $NEt_3$ (470 mg, 4.6 mmol) at R.T. The reaction was stirred at R.T. for 5 hours. $NH_4OH$ (8 mL) was added, and the reaction was stirred for 1 hour. The mixture was diluted with DCM (150 mL) and washed with water, 0.1M HCl and saturated aq. $NaHCO_3$. The solvent was removed, and the residue was purified by silica gel column chromatography (PE:EA=10:1 to 1:1) to give the crude product as a yellow solid (900 mg, 90%). To a solution of the crude product in DCM (10 mL) were added MMTrCl (930 mg, 3.0 mmol), $AgNO_3$ (510 mg, 3.0 mmol) and colliding (720 mg, 6.0 mmol) at R.T. The reaction was stirred for 12 hours at R.T. The reaction was filtered, concentrated and purified by silica gel column chromatography (DCM:MeOH=200:1 to 50:1) to give P24-11 as a yellow solid (1.1 g, 77.6%).

Preparation of (P24-12):

To a solution of P24-11 (1.1 g, 1.2 mmol) in MeOH (40 mL) was added $NH_4F$ (1.0 g, 30 mmol) at 25° C. and stirred at 70° C. for 15 hours. The solution was filtered and evaporated to dryness, and the residue was purified by silica gel column (DCM:MeOH=200:1 to 20:1) to give P24-12 as a white solid (450 mg, 66.6%). $^1H$ NMR (400 MHz, MeOD) 88.58 (s, 1H), 7.62 (d, J=7.6 Hz, 1H), 7.13-7.30 (m, 12H), 6.83-6.85 (m, 2H), 6.29 (d, J=7.6 Hz, 1H), 6.18 (d, J=6.0 Hz, 1H), 5.94 (t, J=8.0 Hz, 1H), 5.22 (t, J=5.2 Hz, 1H), 4.28-4.37 (m, 1H), 3.72 (s, 3H), 3.57-3.62 (m, 1H), 1.39-1.60 (m, 2H), 0.79-0.84 (m, 3H). ESI-LCMS: m/z 563.6 $[M+H]^+$.

Preparation of (24a):

P24-12 (250 mg, 0.44 mmol) was dissolved in 80% HCOOH in $H_2O$ (6.0 g) at 25° C. The mixture was stirred at 35° C. for 15 hours. The solution was evaporated to dryness, dissolved in MeOH (30 mL) and stirred at 60° C. for 12 hours. The solution was evaporated to dryness and purified by silica gel column chromatography (DCM:MeOH=100:1 to 100:1) to give compound 24a as a white solid (125.6 mg, 97%). $^1H$ NMR (400 MHz, MeOD) 87.91 (d, J=7.6 Hz, 1H), 6.19 (t, J=7.6 Hz, 1H), 5.90 (d, J=7.2 Hz, 1H), 4.47 (t, J=13.6 Hz, 1H), 3.67 (d, J=12.0 Hz, 1H), 3.52 (d, J=12.0 Hz, 1H), 1.73-

1.82 (m, 1H), 1.53-1.63 (m, 1H), 095 (t, J=7.6 Hz, 3H).
ESI-LCMS: m/z 291.9 [M+H]+.

Example 25

Preparation of Compound (25a)

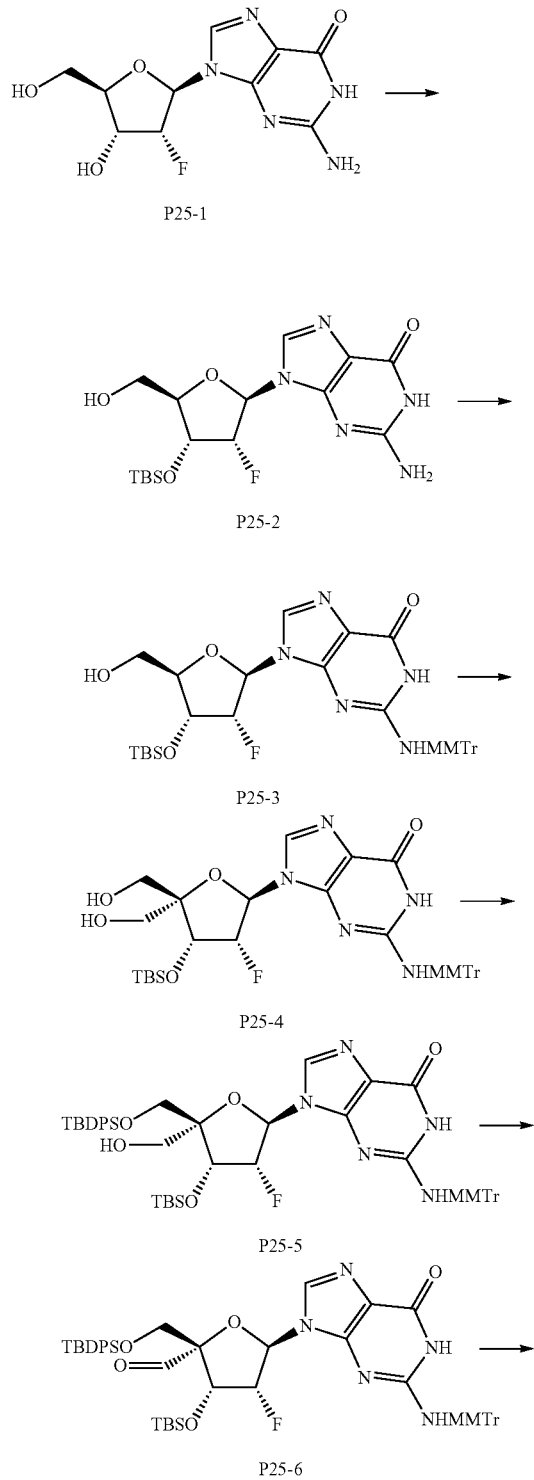

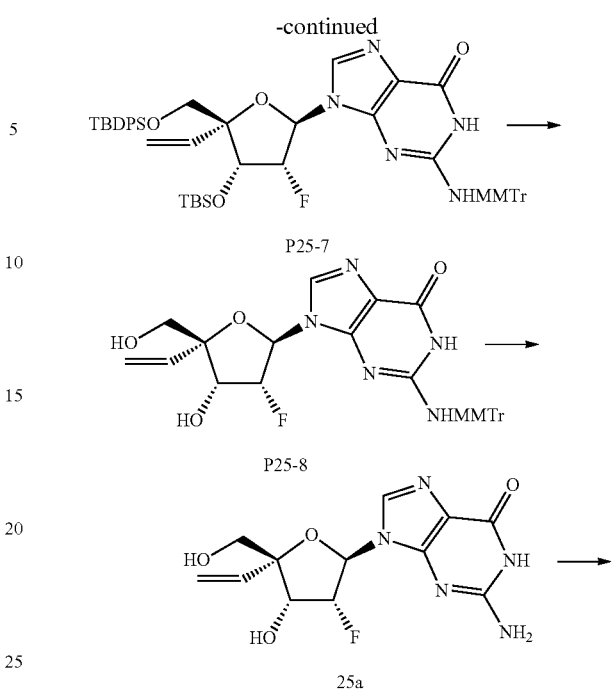

Preparation of (P25-2):

To a solution of P25-1 (20.0 g, 70.16 mmol) in anhydrous pyridine (200 mL) was added imidazole (19.08 g, 280.7 mmol) and TBSCl (42.10 g, 280.7 mmol) at 25° C. The solution was stirred at 25° C. for 15 hours, and then concentrated to dryness under reduced pressure. The residue was washed with EtOAc to give the crude product as a white solid (36.4 g). The crude product was dissolved in THF (150 mL) and H$_2$O (100 mL), and then HOAc (300 mL) was added. The solution was stirred at 80° C. for 13 hours. The reaction was cooled to R.T., and the mixture was concentrated to dryness under reduced pressure. The residue was dissolved washed with EtOAc and dried to give P25-2 as a white solid (31.2 g, 60.9%).

Preparation of (P25-3):

To a stirred solution of P25-2 (31.2 g, 78.2 mmol) in anhydrous pyridine (300 mL) was added Ac$_2$O (11.96 g, 117.3 mmol). The mixture was stirred at 25° C. for 18 hours. MMTrCl (72.3 g, 234.6 mmol) and AgNO$_3$ (39.9 g, 234.6 mmol) were then added. The solution was stirred at 25° C. for 15 hours. And H$_2$O was added to quench the reaction. The solution was concentrated to dryness under reduced pressure. The residue was dissolved in EtOAc and washed with water. The organic layer was dried over Na$_2$SO$_4$ and filtered. The filtrate was concentrated in vacuo to give a residue. The residue was purified by silica gel (DCM:MeOH=200:1 to 50:1) to give the product. The product was dissolved in NH$_3$/MeOH (300 mL), and the mixture was stirred at 25° C. for 20 hours. The solvent was removed, and the residue was purified on a silica gel column (DCM:MeOH=100:1 to 50:1) to give P25-3 as a yellow solid (28.6 g, 86.5%). $^1$H NMR (400 MHz, MeOD) 88.01 (s, 1H), 7.23-7.35 (m, 12H), 6.85-6.87 (m, 2H), 5.60 (dd, J$_1$=11.2 Hz, J$_2$=5.6 Hz, 1H), 4.78-4.94 (m, 1H), 4.44 (dd, J$_1$=8.0 Hz, J$_2$=4.8 Hz, 1H), 3.78 (s, 3H), 3.60-3.63 (m, 1H), 3.50 (dd, J$_1$=32.0 Hz, J$_2$=12.0 Hz, 2H), 3.32 (s, 3H), 0.94 (s, 9H), 0.12-0.14 (m, 6H).

Preparation of (P25-4):

To a solution of P25-3 (7.24 g, 10.79 mmol) in anhydrous CH$_3$CN (100 mL) was added IBX (3.93 g, 14.03 mmol) at 20°

C. The reaction mixture was refluxed at 90° C. for 1 hour. The reaction was filtered, and the filtrate was concentrated to give the aldehyde as a yellow solid (7.1 g). To a solution of the aldehyde (7.1 g, 10.6 mmol) in dioxane (80 mL) was added 37% CH₂O (4.2 mL, 42.4 mmol) and 2N NaOH aq. solution (8.0 mL, 15.9 mmol). The mixture was stirred at 25° C. for 2 hours and then neutralized with AcOH to pH=7. To reaction was added EtOH (30 mL) and NaBH₄ (2.4 g, 63.6 mmol), the reaction was then stirred for 30 mins. The mixture was quenched with saturated aq. NH₄Cl. The mixture was extracted with EA, and the organic layer was dried over Na₂SO₄. The solvent was removed, and the residue was purified by silica gel column chromatography (DCM:MeOH=200:1 to 50:1) to give P25-4 as a yellow solid (4.86 g, 65.4%).

Preparation of (P25-5):

To a solution of P25-4 (3.8 g, 5.4 mmol) in DCM (40 mL) were added pyridine (10 mL) and DMTrCl (1.8 g, 5.4 mmol) at 0° C. The solution was stirred at 25° C. for 1 hour. The reaction mixture was treated with MeOH (15 mL) and concentrated. The residue was purified by silica gel column chromatography (DCM:MeOH=200:1 to 50:1) to give the mono-DMTr protected intermediate as a yellow solid (3.6 g, 66.4%). To a solution of the intermediate in anhydrous pyridine (30 mL) were added TBDPSCl (2.96 g, 10.8 mmol) and AgNO₃ (1.84 g, 10.8 mmol). The mixture was stirred at 25° C. for 15 hours. The mixture was filtered and concentrated, and then dissolved in EtOAc and washed with brine. The organic layer was dried over Na₂SO₄, and then concentrated. The residue was purified by silica gel column chromatography (DCM:MeOH=200:1 to 50:1) to give the pure intermediate as a white solid (3.8 g, 85.1%). To a solution of the intermediate (3.6 g, 2.9 mmol) in anhydrous DCM (50 mL) was added Cl₂CHCOOH (1.8 mL) in anhydrous DCM (18 mL) at −78° C. The mixture was stirred at −10° C. for 30 mins. The mixture was quenched with saturated aq. NaHCO₃ and extracted with DCM. The organic layer was dried over Na₂SO₄, and then purified by silica gel column chromatography (DCM:MeOH=200:1 to 50:1) to give P25-5 as a white solid (2.2 g, 80.7%).

Preparation of (P25-6):

P25-5 (2.2 g, 2.3 mol) was added to a suspension of Dess-Martin periodinane (2.5 g, 5.8 mol) in anhydrous CH₂Cl₂ (30 mL) at 25° C. The mixture was stirred at 25° C. for 4 hours. The solvent was removed in vacuo, and the residue triturated with diethyl ether (30 mL). The mixture was filtered through a pad of MgSO₄. The organic solvent was stirred with an equal volume of Na₂S₂O₃.5H₂O in saturated NaHCO₃ (30 mL) until the organic layer became clear (approx. 10 min). The organic layer was separated, washed with brine, and dried over MgSO₄. The solvent was removed in vacuo to give P25-6 as a yellow solid (2.1 g, 95%).

Preparation of (P25-7):

To a stirred solution of methyl-triphenyl-phosphonium bromide (2.3 g, 6.6 mmol) in anhydrous THF (30 mL) was added dropwise n-BuLi (2.6 mL, 6.6 mmol, 2.5 M in THF) at −78° C. over 1 minute. Stirring was continued at 0° C. for 1 hour. P25-6 (2.1 g, 2.2 mmol) was added to the mixture, and then stirred at 25° C. for 15 hours. The reaction was quenched with saturated NH₄Cl (50 mL). The mixture was extracted with EtOAc. The combined organic phase was dried with Na₂SO₄, filtered and evaporated to dryness to give a light yellow oil. The oil was purified by column chromatography (DCM:MeOH=200:1 to 50:1) to give P25-7 as a white solid (1.6 g, 76%).

Preparation of (P25-8):

To a solution of P25-7 (1.6 g, 1.7 mmol) in MeOH (50 mL) was added NH₄F (1.5 g, 40 mmol), and the mixture was stirred at 70° C. for 15 hours. The solution was filtered and evaporated to dryness. The residue was purified by silica gel column (DCM:MeOH=200:1 to 20:1) to give P25-8 as a white solid (450 mg, 49%). ¹H NMR (400 MHz, MeOD) 87.95 (s, 1H), 7.21-7.33 (m, 12H), 6.82-6.84 (m, 2H), 5.92 (dd, J₁=11.2 Hz, J₂=17.6 Hz, 1H), 5.55-5.59 (m, 1H), 5.18-5.31 (m, 2H), 4.54-4.68 (m, 1H), 4.26-4.33 (m, 1H), 3.76 (s, 3H), 3.43 (dd, J₁=12.4 Hz, J₂=36.4 Hz, 2H). ESI-LCMS: m/z 584.1 [M+H]⁺.

Preparation of (25a):

P25-8 (130 mg, 0.22 mmol) was dissolved in 80% HCOOH and the mixture was stirred at 25° C. for 1 hour. Then the solution was evaporated to dryness. The residue was dissolved in MeOH (30 mL) and stirred at 60° C. for 12 hours. Then the solution was evaporated to dryness, and the residue was washed by EtOAc to give P25 as a white solid (52.3 mg, 76%). ¹H NMR (400 MHz, MeOD) δ 8.03 (s, 1H), 6.17 (dd, J₁=3.2 Hz, J₂=16.8 Hz, 1H), 6.03 (dd, J₁=11.2 Hz, J₂=17.2 Hz, 1H), 5.50 (dd, J₁=1.6 Hz, J₂=17.2 Hz, 1H), 5.23-5.38 (m, 2H), 4.76 (dd, J₁=4.8 Hz, J₂=18.0 Hz, 1H), 3.60 (dd, J₁=12.0 Hz, J₂=44.8 Hz, 2H). ESI-MS: m/z 334.1 [M+Na]⁺.

Example 26

Preparation of Compound (26a)

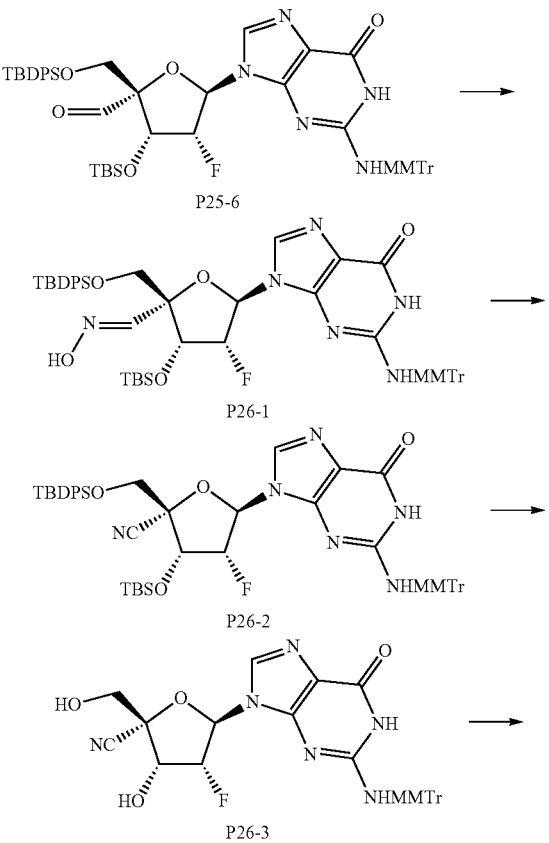

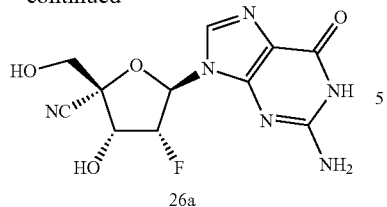

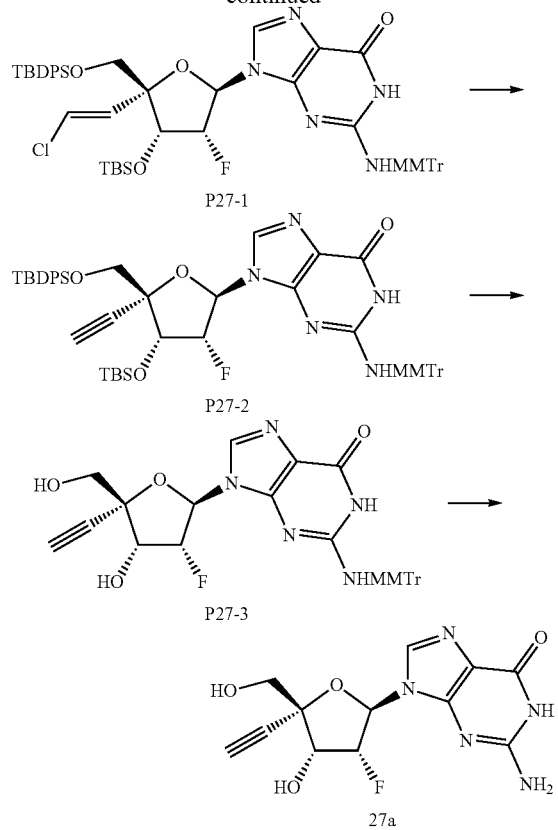

Preparation of (P26-1):

To a stirred solution of P25-6 (2.1 g, 2.2 mmol) in pyridine was added HONH₂HCl (0.61 g, 8.8 mmol) at 25° C. The mixture was stirred at 25° C. for 2 hours. The mixture was concentrated, and the residue was purified by column chromatography (DCM:MeOH=200:1 to 50:1) to give P26-1 as a white solid (1.8 g, 83%).

Preparation of (P26-2):

To a stirred solution of P26-1 (1.4 g, 1.47 mmol) in DCM were added TEA (0.44 g, 4.4 mmol) and methanesulfonyl chloride (0.34 g, 2.9 mmol) at 0° C. The mixture was stirred at 25° C. for 1 hour. The mixture was quenched with saturated aq. NaHCO₃ and extracted with DCM. The organic phase was dried with Na₂SO₄, filtered and evaporated. The residue was purified by column chromatography (DCM:MeOH=200:1 to 50:1) to give P26-2 as a white solid (1.1 g, 79%).

Preparation of (P26-3):

To a solution of P26-2 (1.1 g, 1.18 mmol) in MeOH (50 mL) was added NH₄F (1.5 g, 40 mmol), and the mixture was stirred at 70° C. for 15 hours. The solution was filtered and evaporated to dryness. The residue was purified by silica gel column (DCM:MeOH=200:1 to 20:1) to give P26-3 as a white solid (400 mg, 71%). $^1$H NMR (400 MHz, MeOD) δ 7.80 (s, 1H), 7.20-7.32 (m, 12H), 6.86-6.88 (m, 2H), 5.82 (dd, $J_1$=2.0 Hz, $J_2$=20.0 Hz, 1H), 4.51-4.66 (m, 1H), 3.94 (dd, $J_1$=5.2 Hz, $J_2$=20.8 Hz, 1H), 3.78 (s, 3H), 3.56 (dd, $J_1$=12.4 Hz, $J_2$=42.0 Hz, 2H). ESI-LCMS: m/z 583.1 [M+H]⁺.

Preparation of (26a):

P26-3 (200 mg, 0.34 mmol) was dissolved in 80% HCOOH aq. solution. The mixture was stirred at 25° C. for 1 hour. The solution was evaporated to dryness, dissolved in MeOH (30 mL) and stirred at 60° C. for 12 hours. The solvent was removed, and the residue was washed by EtOAc to give compound 26a as a white solid (100.4 mg, 95%). $^1$H NMR (400 MHz, MeOD) 87.90 (s, 1H), 6.34 (dd, $J_1$=2.0 Hz, $J_2$=19.6 Hz, 1H), 5.49 (ddd, $J_1$=1.6 Hz, $J_2$=4.4 Hz, $J_3$=52.4 Hz, 1H), 5.01 (dd, $J_1$=4.8 Hz, $J_2$=20.8 Hz, 1H), 3.93 (dd, $J_1$=12.4 Hz, $J_2$=44.8 Hz, 2H). ESI-MS: m/z 311.1 [M+H]⁺.

Example 27

Preparation of Compound (27a)

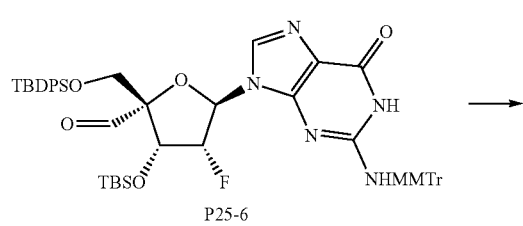

Preparation of (P27-1):

To a stirred solution of chloromethyl-triphenyl-phosphonium chloride (1.9 g, 5.4 mmol) in anhydrous THF (30 mL) was added dropwise n-BuLi (2.16 mL, 5.4 mmol, 2.5 M in THF) at −78° C. over 10 mins. Stirring was continued at −78° C. for 2 hours. P25-6 (1.7 g, 1.8 mmol) was added, and the mixture and stirred at 25° C. for 15 hours. The reaction was quenched with saturated NH₄Cl (50 mL). The mixture was extracted with EtOAc. The combined organic phase was dried with Na₂SO₄, filtered and evaporated to dryness to give a light yellow oil. The oil was purified by column chromatography (DCM:MeOH=200:1 to 50:1) to give P27-1 as a white solid (1.2 g, 70%).

Preparation of (P27-2):

To a stirred solution of P27-1 (1.2 g, 1.3 mmol) in anhydrous THF (20 mL) was added dropwise n-BuLi (8.0 mL, 20 mmol, 2.5 M in THF) at −78° C. over 10 minutes. Stirring was continued at −78° C. for 4 hours. The reaction was quenched with saturated NH₄Cl (50 mL). The mixture was extracted with EtOAc (50×2 mL). The combined organic phase was dried over Na₂SO₄, filtered and evaporated to dryness. The residue was purified by column chromatography (DCM:MeOH=200:1 to 50:1) to give P27-2 as a white solid (1.0 g, 83%).

Preparation of (P27-3):

To a solution of P27-2 (1.0 g, 1.1 mmol) in MeOH (40 mL) was added NH₄F (1.5 g, 40 mmol), and the mixture was stirred at 70° C. for 25 hours. The solution was filtered, and the filtrate was evaporated to dryness. The residue was purified on a silica gel column (DCM:MeOH=200:1 to 20:1) to give P27-3 as a white solid (240 mg, 38%). $^1$H NMR (400 MHz, MeOD) δ 7.85 (s, 1H), 7.21-7.31 (m, 12H), 6.84-6.87 (m, 2H), 5.67 (dd, $J_1$=1.6 Hz, $J_2$=19.2 Hz, 1H), 4.47-4.62 (m, 1H), 3.94 (dd, $J_1$=5.2 Hz, $J_2$=22.4 Hz, 1H), 3.77 (s, 3H), 3.56 (dd, $J_1$=12.4 Hz, $J_2$=47.2 Hz, 2H), 3.04 (s, 1H). ESI-LCMS: m/z 582.1 [M+H]$^+$.

Preparation of (27a):

P27-3 (130 mg, 0.22 mmol) was dissolved in 80% HCOOH aq. solution. The mixture was stirred at 25° C. for 1 hour. The solution was evaporated to dryness. The residue was dissolved in MeOH (30 mL) and stirred at 60° C. for 12 hours. The solvent was removed, and the residue was washed with EtOAc to give compound 27a as a white solid (43.0 mg, 63%). $^1$H NMR (400 MHz, MeOD) δ7.95 (s, 1H), 6.22 (dd, $J_1$=2.4 Hz, $J_2$=18.4 Hz, 1H), 5.49 (ddd, $J_1$=2.0 Hz, $J_2$=4.8 Hz, $J_3$=53.2 Hz, 1H), 4.77 (dd, $J_1$=5.2 Hz, $J_2$=20.0 Hz, 1H), 3.79 (dd, $J_1$=12.4 Hz, $J_2$=46.8 Hz, 2H), 3.12 (s, 3H). ESI-MS: m/z 310.1 [M+H]$^+$.

Example 28

Preparation of Compound (28a)

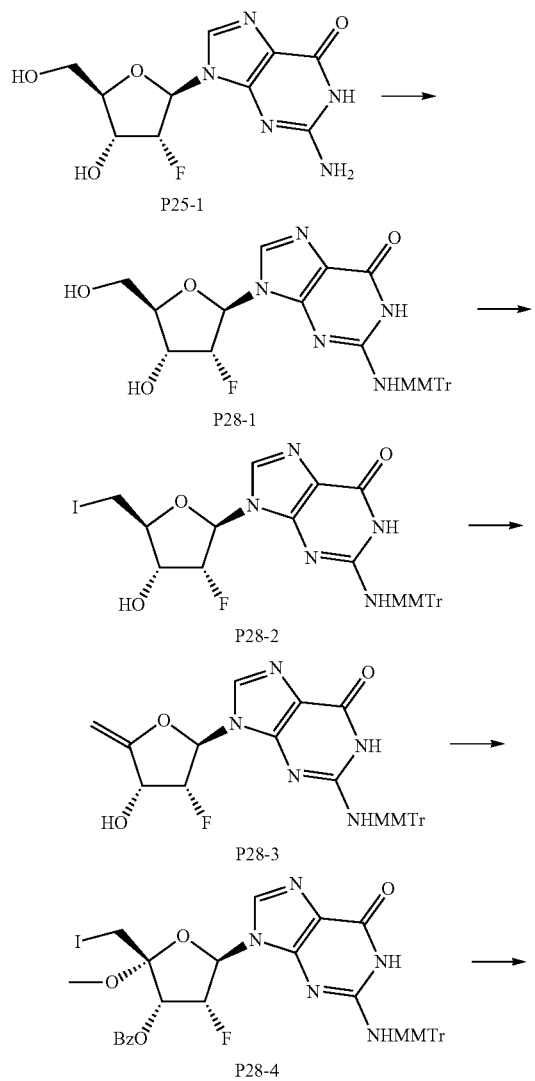

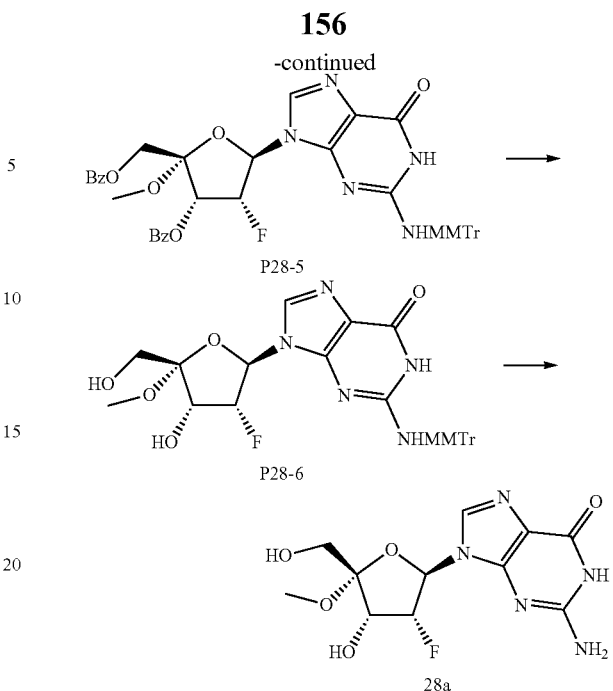

Preparation of (P28-1):

To a stirred solution of P25-1 (5.7 g. 20 mmol) in anhydrous pyridine (20 mL) was added dropwise Ac$_2$O (5.8 mL, 60 mmol) at 0° C. The mixture was stirred at R.T. for 10 hours. AgNO3 (8.5 g, 50 mmol) and MMTrCl (15.5 g, 50 mmol) were added. The mixture was stirred at R.T. for 10 hours. The solution was quenched with saturated NaHCO$_3$ and extracted with EA. The organic layer was dried over Na$_2$SO$_4$ and concentrated. The residue was purified on a silica gel column (DCM/MeOH=100:1 to 50:1) to afford the intermediate as a light yellow solid (12.1 g, 93.4%). The solid was treated with saturated NH$_3$ in MeOH at R.T. for 14 hours. The solvent was removed, and the residue was purified by silica gel column chromatography (DCM/MeOH=80:1 to 30:1) to afford P28-1 as a white solid (9.2 g, 87.5%).

Preparation of (P28-2):

To a stirred solution of P28-1 (9.2 g, 16.5 mmol) in dry THF (300 mL) were added imidazole (9.0 g, 132 mmol) and PPh$_3$ (34.8 g, 132 mmol). A solution of I$_2$ (26.0 g, 103 mmol) in THF (100 mL) was added dropwise under N$_2$ at 0° C. The mixture was stirred at R.T. for 18 hours. The reaction was quenched with Na$_2$S$_2$O$_3$ solution, and the mixture was extracted with EtOAc. The organic layer was dried over Na$_2$SO$_4$ and concentrated. The residue was purified by silica gel column chromatography (DCM/MeOH=80:1 to 30:1) to give P28-2 as a light yellow solid (10.3 g, 93.4%).

Preparation of (P28-3):

To a stirred solution of P28-2 (10.2 g, 15.3 mmol) in dry THF (300 mL) was added DBU (4.7 g, 30.1 mmol). The mixture was stirred at 60° C. for 8 hours. The solution was diluted with NaHCO$_3$ solution and extracted with EtOAc. The organic layer was dried over Na$_2$SO$_4$ and concentrated. The residue was purified by silica gel column chromatography (PE/EtOAc=3:1 to 1:3) to afford P28-3 as a light yellow foam (6.2 g, 75.6%). $^1$H NMR (CD$_3$OD, 400 MHz) δ 7.71 (s, 1H), 7.23-7.76 (m, 14H), 6.74 (d, J=0.8 Hz, 2H), 5.83-5.88 (dd, $J_1$=2.8 Hz, $J_2$=16.0 Hz, 2H), 4.57-4.89 (m, 2H), 4.30-4.35 (m, 1H), 4.79 (s, 3H). ESI-MS: m/z 540 [M+H]$^+$.

Preparation of (P28-4):

To a stirred solution of P28-4 (5.42 g, 10 mmol) in anhydrous CH$_3$OH (100 mL) were added PbCO$_3$ (13.7 g, 53.1 mmol) followed by a solution of I$_2$ (12.3 g, 48.9 mmol) in CH$_3$OH (300 mL) at 0° C. The mixture was stirred at R.T. for 10 hours. The solution was quenched with a Na$_2$S$_2$O$_3$ solution and extracted with DCM. The organic layer was washed with NaHCO$_3$ solution, dried over Na$_2$SO$_4$ and concentrated. The residue was purified by pre-HPLC (MeCN and 0.1% HCOOH in water) to give the pure product as a white foam (2.4 g, 34%). The product was dissolved in dry pyridine (20 mL) and BzCl (723 mg, 5.2 mmol) was added dropwise at 0° C. The mixture was stirred at 0° C. for 1 hour. The solution was quenched with NaHCO$_3$ solution, and extracted with EtOAc. The organic layer was dried over Na$_2$SO$_4$ and concentrated. The residue was purified by silica gel column chromatography (PE/EtOAc=5:1 to :1) to afford P28-4 as a white solid (2.1 g, 77.1%).

Preparation of (P28-5):

P28-4 (2.0 g, 2.5 mmol), BzONa (3.6 g, 25 mmol) and 15-crown-5 (5.5 g, 25 mmol) were suspended in DMF (50 mL). The mixture was stirred at 110-125° C. for 5 days. The precipitate was removed by filtration, and the filtrate was diluted with EA. The solution was washed with brine and dried over Na$_2$SO$_4$. The solvent was removed, and the residue was purified on a silica gel column (PE/EA=10/1 to 2/1) to afford crude P28-5 as a light yellow foam (1.6 g, 80%).

Preparation of (P28-6):

P28-5 (1.6 g, 2.0 mmol) was dissolved in methanolic ammonia (100 mL, saturated), and the mixture was stirred at R.T. for 20 hours. The solvent was removed, and the residue was purified on a silica gel column (DCM/MeOH=100:1 to 20:1) to give P28-6 as a white solid (410 mg, 34.9%). $^1$H NMR (400 MHz, MeOD) δ 7.84 (s, 1H), 7.20-7.33 (m, 12H), 6.83-6.86 (m, 2H), 5.64 (dd, J$_1$=1.6 Hz, J$_2$=18.4 Hz, 1H), 4.46-4.62 (m, 1H), 4.08 (dd, J$_1$=6.0 Hz, J$_2$=22.0 Hz, 1H), 3.76 (s, 3H), 3.58 (dd, J$_1$=12.4 Hz, J$_2$=30.4 Hz, 2H), 3.31 (s, 3H). ESI-LCMS: m/z 588.1 [M+H]$^+$.

Preparation of (28a):

P28-8 (200 mg, 0.34 mmol) was dissolved in 80% HCOOH and the mixture was stirred at 25° C. for 1 hour. The solution was evaporated to dryness, and the residue was dissolved in MeOH (30 mL) and stirred at 60° C. for 12 hours. The solvent was removed, and the residue washed with EtOAc to give compound 28a as a white solid (46.1 mg, 43%). $^1$H NMR (400 MHz, MeOD) 87.92 (s, 1H), 6.22 (dd, J$_1$=1.6 Hz, J$_2$=18.8 Hz, 1H), 5.25 (ddd, J$_1$=1.6 Hz, J$_2$=6.0 Hz, J$_3$=54.0 Hz, 1H), 4.89-4.91 (m, 1H), 3.87 (d, J=11.6 Hz, 1H), 3.67 (d, J=12.0 Hz, 1H), 3.44 (s, 3H). ESI-MS: m/z 316.1 [M+H]$^+$.

Example 29

Preparation of Compound (29a)

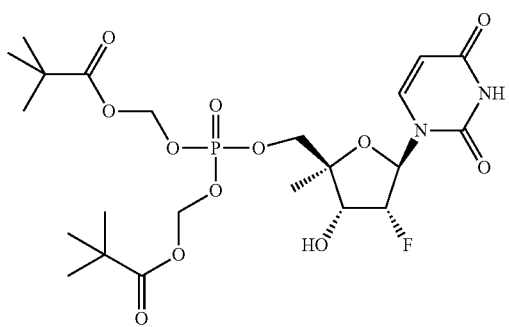 [SMILES: CC(C)(C)C(=O)OCOP(=O)(OCOC(=O)C(C)(C)C)OC[C@@]1(C)O[C@@H](n2ccc(=O)[nH]c2=O)[C@H](F)[C@@H]1O]

DEAD (40% in toluene, 0.15 mL, 0.33 mmol) was added to a stirred solution of triphenylphosphine (78 mg, 0.3 mmol) in anhydrous 1,4-dioxane (0.5 mL) at 0° C. under argon. The mixture was warmed up to R.T. and compound 10a (26 mg, 0.1 mmol) and bis(pivaloyloxymethyl)phosphate (98 mg, 0.3 mmol) were added. The resulting mixture was stirred at 65° C. for 3 days. Diisopropylethylamine (50 μL) was added, and the mixture was stirred at 70° C. for 3 days. Another reaction of the same scale was conducted separately. The two reaction mixtures were combined and concentrated. Chromatography on silica gel with 5-10% methanol in DCM gave the desired product (20 mg) with a minor impurity. A second chromatography on silica gel, followed by RP HPLC with acetonitrile/water, gave the compound (2.8 mg) as a colorless residue; $^1$H NMR (CD$_3$OD, 400 MHz) δ 7.65 (d, J=8.0 Hz, 1H), 5.94 (dd, J$_1$=2.4 Hz, J$_2$=18.8 Hz, 1H), 5.70 (d, J=8.0 Hz, 1H), 5.69 (d, J=0.8 Hz, 1H), 5.68 (s, 1H), 5.654 (d, J=1.2 Hz, 1H), 5.650 (s, 1H), 5.21 (dd, J=2.0, 5.2 Hz, 0.5H), 5.07 (dd, 2.0, 5.2 Hz, 0.5H), 4.42 (dd, J=5.6, 20.8 Hz, 1H), 4.14 (m, 2H), 1.223 (s, 9H), 1.220 (m, 9H); $^{31}$P NMR (CD$_3$OD) 4.92 (s); MS: m/z 698 [M+2-methylheptylamine]$^+$.

Example 30

Preparation of Compound (30a)

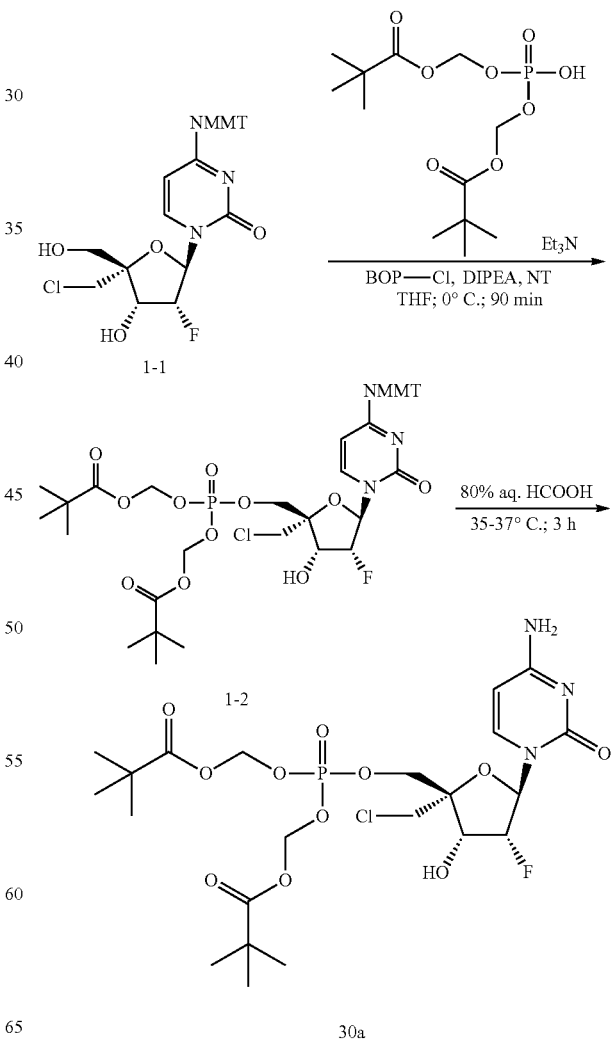

Preparation of (1-2):

To a solution of 1-1 (313 mg; 0.55 mmol) in THF (8 mL) under Ar was added a solution of triethylammonium bis(POM)phosphate in THF (prepared from bis(POM)phosphate (215 mg; 1.2 equiv), THF (2 mL) and Et$_3$N (0.1 mL; 1.3 equiv)). The resulting mixture cooled in an ice-bath. Diisopropylethyl amine (0.38 mL; 4 equiv) was added. BOP-Cl (280 mg; 2 equiv) and 3-nitro-1,2,4-triazole (125 mg; 2 equiv) was then added. The reaction mixture was stirred at 0° C. for 90 mins. The mixture was diluted with CH$_2$Cl$_2$ (60 mL) and washed with saturated aq. NaHCO$_3$ (2×10 mL) and brine. The combined aqueous layers were back extracted with CH$_2$Cl$_2$ (~20 mL). The combined organic extract was dried (Na$_2$SO$_4$) and evaporated. The residue purified on silica (25 g column) with CH$_2$Cl$_2$/i-PrOH solvent system (2-10% gradient). Yield: 140 mg (27%).

Preparation of (30a):

A solution of 1-2 (110 mg; 0.13 mmol) in 80% aq. formic acid was heated at 35-37° C. for 3 hours. The mixture was evaporated to give an oily residue. The residue was co-evaporated 2 times with toluene. Purification on a silica gel column (10 g) with CH$_2$Cl$_2$/MeOH solvent system (4-10% gradient) to afford compound 30a (46 mg, 59% yield). $^{31}$P-NMR (DMSO-d$_6$): δ −4.45. MS: m/z 646 (M+46-1).

Example 31

Preparation of Compound (31a)

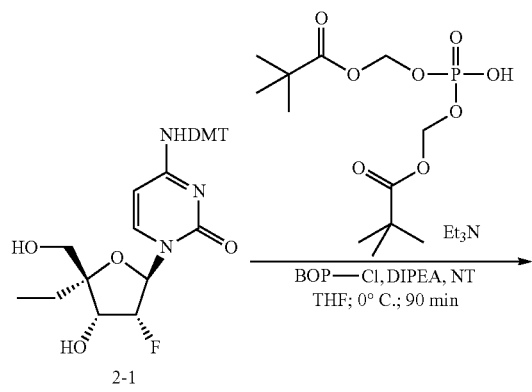

2-1

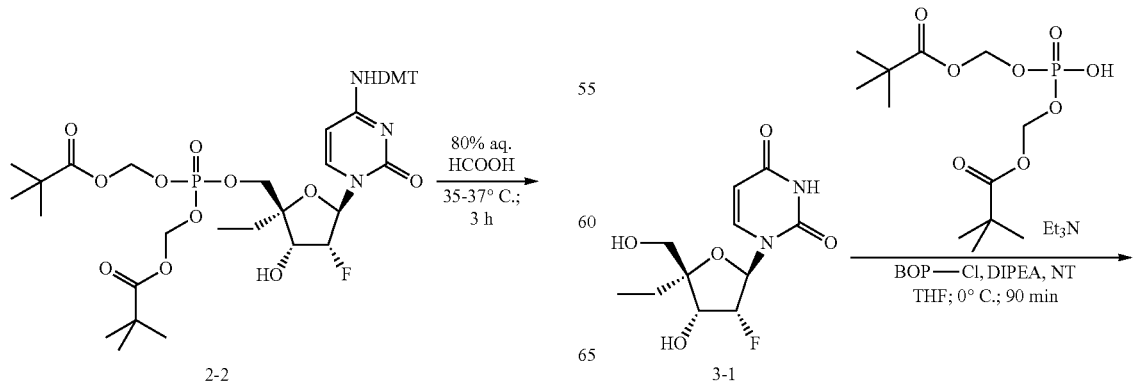

2-2

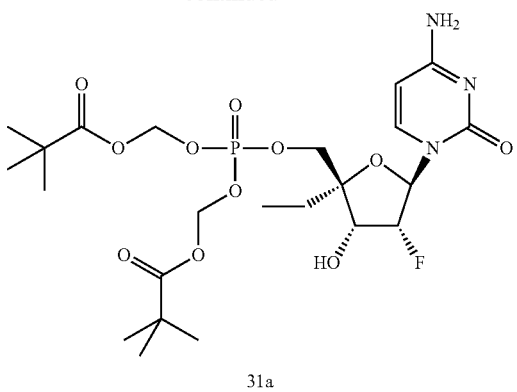

31a

Preparation of (2-2):

To a solution of 2-1 (370 mg; 0.64 mmol) in THF (10 mL) under Ar was added triethylammonium bis(POM)phosphate (330 mg; 1.2 equiv). The mixture cooled in ice-bath, and diisopropylethyl amine (0.42 mL; 4 equiv) was added. BOP-Cl (305 mg; 2 equiv) and 3-nitro-1,2,4-triazole (137 mg; 2 equiv) was then added. The reaction mixture was stirred at 0° C. for 90 mins. The mixture was diluted with CH$_2$Cl$_2$ (50 mL) and washed with saturated aq. NaHCO$_3$ (2×10 mL) and brine. The combined aqueous layers were back extracted with CH$_2$Cl$_2$ (~20 mL). The combined organic extract was dried (Na$_2$SO$_4$), evaporated, and the residue purified on silica (25 g column) with CH$_2$Cl$_2$/i-PrOH solvent system (2-10% gradient). Yield: 154 mg (27%).

Preparation of (31a):

A solution of 2-2 (68 mg; 0.08 mmol) in 80% aq. formic acid was stirred at R.T. for 3 hours. The mixture was evaporated to an oily residue. The residue was co-evaporated 2 times with toluene. Purification on a silica gel column (10 g) with CH$_2$Cl$_2$/MeOH solvent system (4-10% gradient; target compound eluted with 8% MeOH) afforded 31a (35 mg, 78% yield). $^{31}$P-NMR (DMSO-d$_6$): δ −4.19. MS: m/z 580 (M−1), 646 (M+46−1), 550 (M−30−1).

Example 32

Preparation of Compound (32a)

3-1

-continued

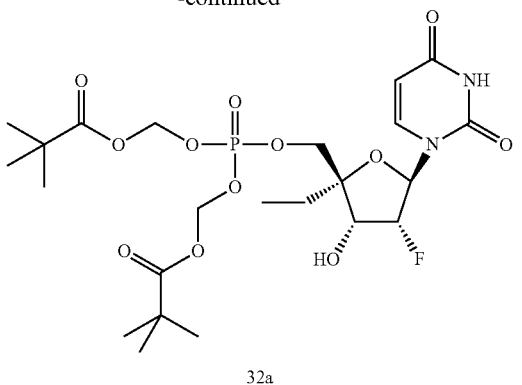

32a

To a solution of 3-1 (71 mg; 0.26 mmol) in THF (4 mL) under Ar was added triethylammonium bis(POM)phosphate (144 mg; 1.2 equiv), and the resulting mixture was cooled in an ice-bath, and diisopropylethyl amine (0.18 mL; 4 equiv) was added. BOP-Cl (132 mg; 2 equiv) and 3-nitro-1,2,4-triazole (59 mg; 2 equiv) was then added. The reaction mixture was stirred at 0° C. for 1 hour. The mixture was diluted with $CH_2Cl_2$ (50 mL) and washed with saturated aq. $NaHCO_3$ (2×10 mL) and brine. The combined aqueous layers were back extracted with $CH_2Cl_2$ (~20 mL). The combined organic extract was dried ($Na_2SO_4$), evaporated, and the residue was purified on silica (10 g column) with $CH_2Cl_2$/MeOH solvent system (4-10% gradient). Compound 32a was repurified by RP-HPLC (35-90% B; A: water, B: MeOH). Yield 75 mg (50%). $^{31}$P-NMR (DMSO-$d_6$): δ −4.14. MS: m/z 627 (M+46−1), 551 (M−30−1).

Example 33

Preparation of Compound (33a)

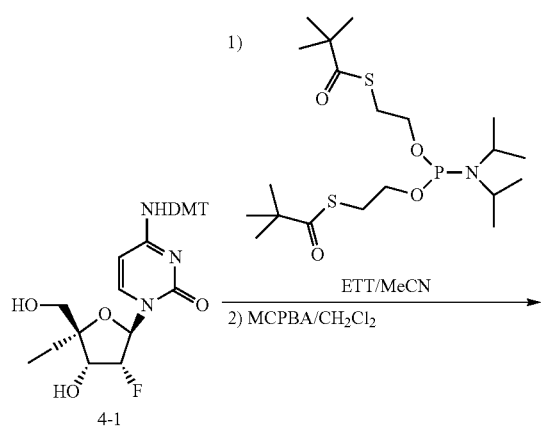

-continued

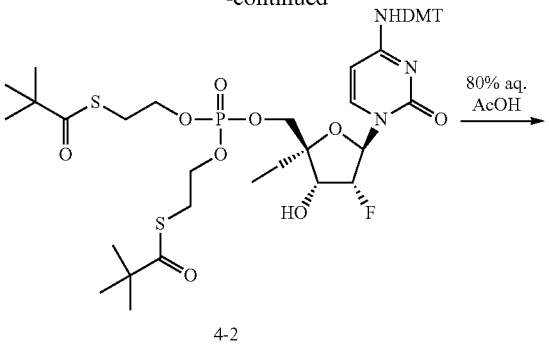

4-2

Preparation of (4-2):

To a solution of 4-1 (0.29 g; 0.5 mmol) in MeCN (8 mL) was added 5-ethylthio-1H-tetrazole in MeCN (0.25 M; 2.4 mL; 1.2 equiv). BisSATE-phosphoramidate (0.24 g; 1.05 equiv.) in MeCN (1.5 mL) was added over 90 mins. The reaction mixture was stirred for 4 hours at R.T., and then cooled to −40° C. MCPBA (0.23 g; 2 equiv.) in $CH_2Cl_2$ (3 mL) was added. The mixture was allowed to warm to R.T. and diluted with EtOAc (50 mL). The mixture was washed with 10% aq. $NaHSO_3$ (2×10 mL), saturated aq. $NaHCO_3$ (2×10 mL) and brine. The mixture was then dried ($Na_2SO_4$). The evaporated residue was purified on silica (10 g column) with $CH_2Cl_2$/MeOH solvent system (4-10% gradient) to afford 4-2 (0.26 g, 55% yield).

Preparation of (33a):

A solution of 4-2 (0.21 g; 0.22 mmol) in 80% aq. AcOH (15 mL) was stirred 4 hours at R.T. The mixture was evaporated and purified on silica (10 g column) with $CH_2Cl_2$/MeOH solvent system (4-10% gradient). Yield: 0.13 g (90%). $^{31}$P-NMR (DMSO-$d_6$): δ −2.00. MS: m/z 686 (M+46−1).

Example 34

Preparation of Compounds (34a)-(34e)

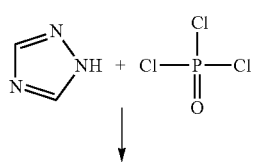

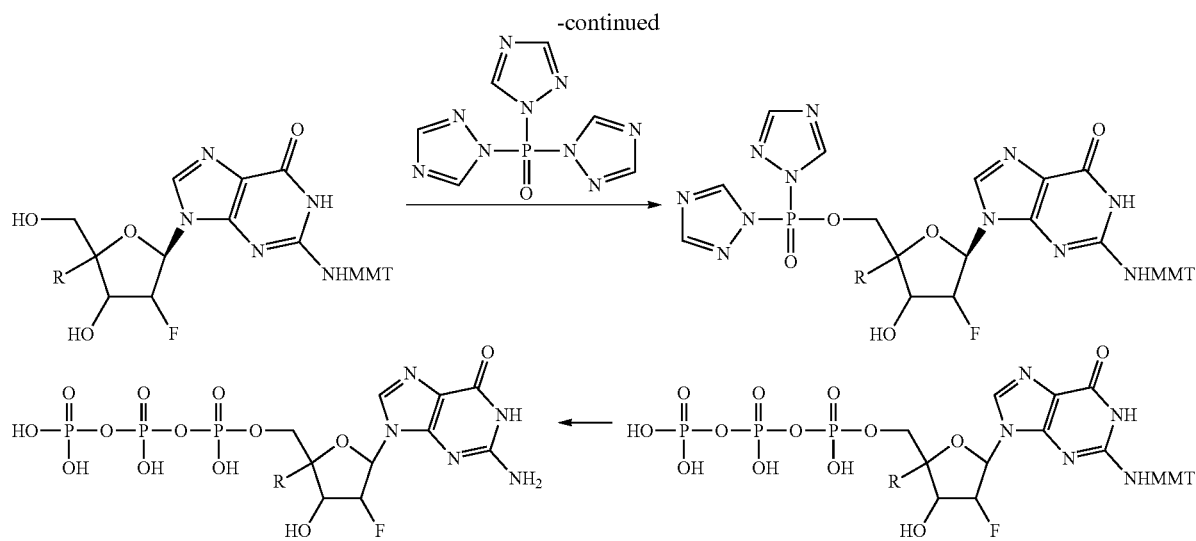

1,2,4-Triazol (42 mg, 0.6 mmol) was suspended of dry CH₃CN (1 mL). Triethylamine was added (0.088 mL, 0.63 mmol), and the mixture was vortexed to obtain a clear solution. After addition of POCl₃ (0.01 mL, 0.1 mmol), the mixture was vortexed and left for 20 min. The mixture was then centrifugated. The supernatant was added to the protected nucleoside (0.05 mmol), and the mixture was kept at ambient temperature for 1 hour. Tris(tetrabutylammonium) hydrogen pyrophosphate (180 mg, 0.2 mmol) was added, and the mixture was kept for 2 hours at R.T. The reaction was quenched with water, evaporated, dissolved in 80% formic acid and left for 2 hours at R.T. Formic acid was evaporated, and the residue dissolved in water (5 mL) and extracted with EA (2×2 mL). The aqueous fraction was loaded onto column HiLoad 16/10 with Q Sepharose High Performance (linear gradient of NaCl from 0 to 1N in 50 mM TRIS-buffer (pH=7.5)). Fractions containing the triphosphate were combined, concentrated and desalted by RP HPLC on Synergy 4 micron Hydro-RP column (Phenominex) using a linear gradient of methanol from 0 to 20% in 50 mM triethylammonium acetate buffer (pH 7.5) for elution. The following compounds shown in Table 1 were synthesized according this procedure:

TABLE 1

| Triphosphates obtained from Example 34 | | | | |
|---|---|---|---|---|
| Compound | $^{31}$P NMR Pα | $^{31}$P NMR Pβ | $^{31}$P NMR Pγ | MS (M⁻) |
| 34a | −11.31 d | −20.82 t | −5.48 d | 550.2 |
| 34b | −9.13 d | −18.18 t | −2.85 d | 548.2 |
| 34c | −10.95 d | −20.62 bs | −5.37 bs | 552.2 |

TABLE 1-continued

Triphosphates obtained from Example 34

| Compound | $^{31}$P NMR Pα | $^{31}$P NMR Pβ | $^{31}$P NMR Pγ | MS (M$^-$) |
|---|---|---|---|---|
| 34d | −11.24 d | −20.82 t | −5.48 d | 554.2 |
| 34e | −12.06 d | −20.97 t | −5.69 d | 549.2 |

Example 35

Preparation of Compound (35a)

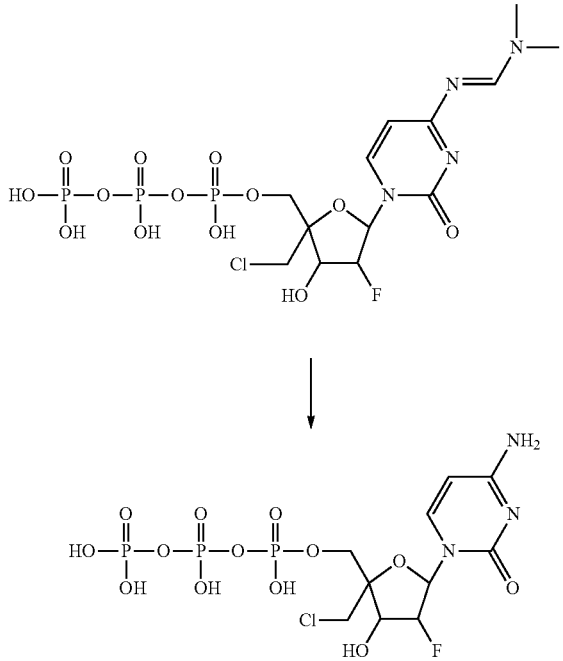

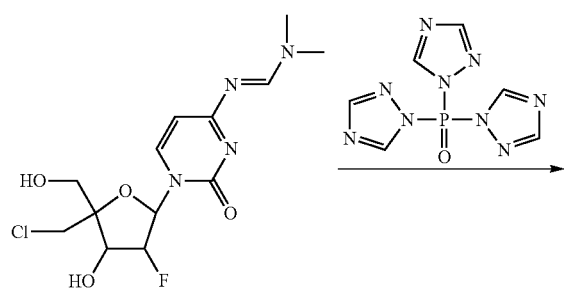

1,2,4-Triazol (42 mg, 0.6 mmol) was suspended in dry CH$_3$CN (1 mL). Triethylamine was added (0.088 mL, 0.63 mmol), and the mixture was vortexed to obtain a clear solution. After addition of POCl$_3$ (0.01 mL, 0.1 mmol), the mixture was vortexed and left for 20 mins. The mixture was centrifugated, and the supernatant was added to the protected nucleoside (0.05 mmol). The mixture was kept at ambient temperature for 1 hour. Tris(tetrabutylammonium) hydrogen pyrophosphate (180 mg, 0.2 mmol) was added, and the mixture was kept for 2 hours at R.T. The reaction was quenched with water, evaporated, dissolved in ammonium hydroxide and left for 2 hours at R.T. The solvent was evaporated, and the residue dissolved in water (10 mL). The mixture was loaded onto a column HiLoad 16/10 with Q Sepharose High Performance. Separation was done in linear gradient of NaCl from 0 to 1N in 50 mM TRIS-buffer (pH7.5). The fractions containing the product were combined, concentrated and desalted by RP HPLC on Synergy 4 micron Hydro-RP column (Phenominex). A linear gradient of methanol from 0 to 20% in 50 mM triethylammonium acetate buffer (pH 7.5) was used for elution. MS (M−1): 532.1. $^{31}$P-NMR (δ ppm): −5.12 (d), −11.31 (d) and −20.43 (t).

Example 36

Preparation of Compounds (36a)-(36d)

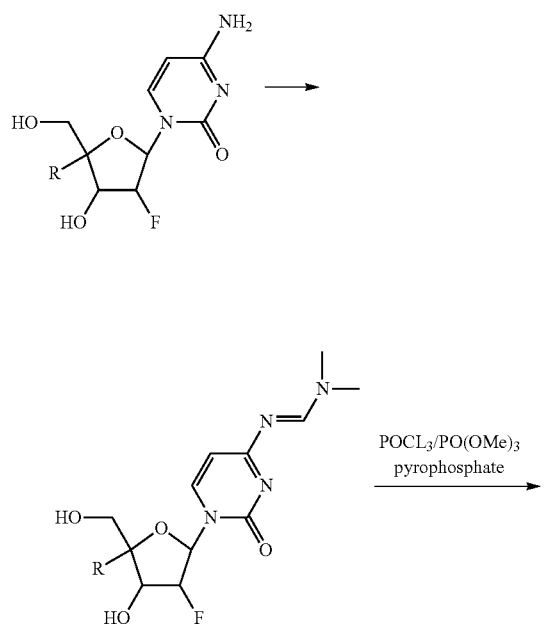

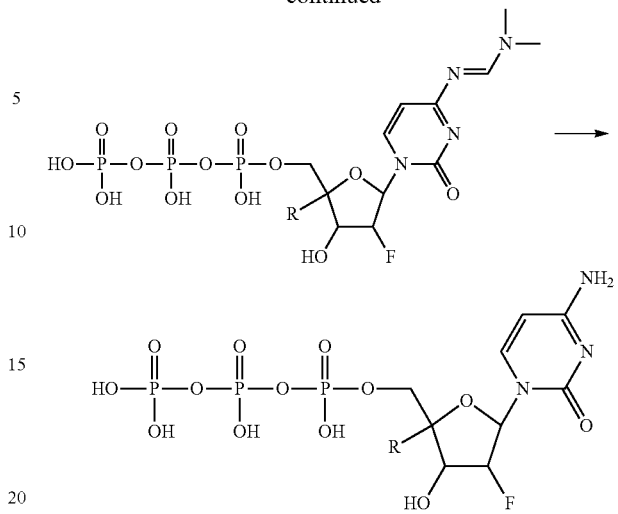

2′-Deoxy-2′-fluoro-4′-alkyl-cytidine (0.09 mmol) was dissolved in the mixture of DMF (5 mL) and N,N′-dimethylacetate in DMF (0.110 mL, 0.9 mmol). The reaction mixture left at R.T. overnight. The solvent was evaporated, and the residue purified by flash chromatography in gradient of methanol in DCM from 3% to 20%. The N-Protected nucleoside was concentrated in vacuum, dried and dissolved in dry trimethylphosphate (0.7 mL). The solution was cooled to 4° C. and POCl$_3$ (0.017 mL, 0.18 mmol) was added. In 1 hour, tributylamine (0.102 mL, 0.3 mmol) was added at R.T. Tributylammonium pyrophosphate (156 mg, 0.34 mmol) was then added. Dry DMF (about 0.100 mL) was added to solubilize pyrophosphate. After 2 hours, the reaction was quenched with TEAB-buffer. The product was isolated by ion-exchange chromatography on AKTA Explorer as described in Example 35. The fractions containing the product were concentrated and treated with NH$_4$OH for 2 hours at R.T. The product was desalted by RP HPLC as described in Example 35.

TABLE 2

Triphosphates obtained from Example 36

| | $^{31}$P NMR Pα | $^{31}$P NMR Pβ | $^{31}$P NMR Pγ | MS (M$^-$) |
|---|---|---|---|---|
| 36a | −11.38 bs | −22.88 bs | −7.62 bs | 512.1 |
| 36b | −11.49 bs | −20.41 bs | −5.34 bs | 510.0 |

TABLE 2-continued
Triphosphates obtained from Example 36
| | ³¹P NMR Pα | ³¹P NMR Pβ | ³¹P NMR Pγ | MS (M⁻) |
|---|---|---|---|---|
| 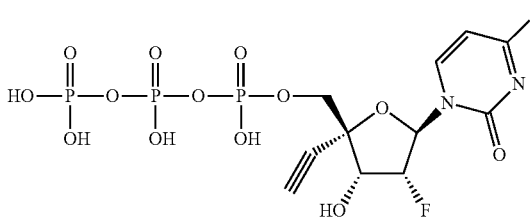 36c | −11.96 bs | −22.07 t | −5.66 d | 508.3 |
| 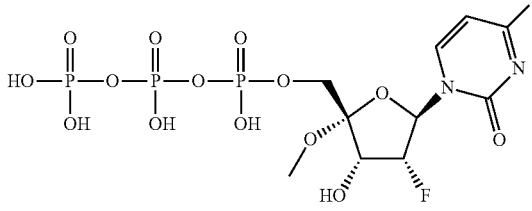 36d | −11.90 d | −23.23 t | −10.66 d | 514.0 |
| 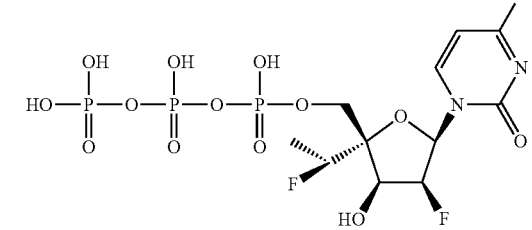 36e | −11.77 d | −23.05 t | −9.70 s | 529.9 |
| 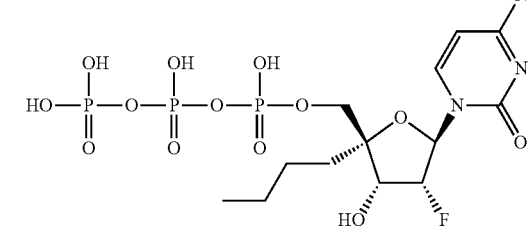 36f | −11.74 d | −23.37 t | −10.85 d | 539.2 |
| 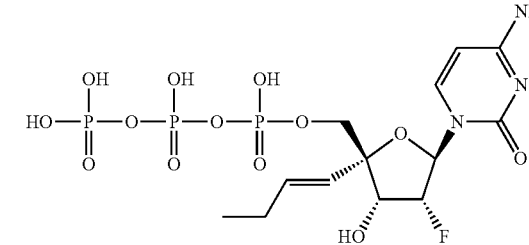 36g | −11.87 d | −23.32 t | −10.83 d | 523.9 |

TABLE 2-continued
Triphosphates obtained from Example 36
| | $^{31}$P NMR Pα | $^{31}$P NMR Pβ | $^{31}$P NMR Pγ | MS (M$^-$) |
|---|---|---|---|---|
| 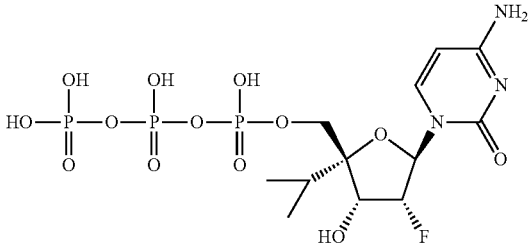 36h | −11.48 d | −23.26 t | −10.63 d | 526.1 |
| 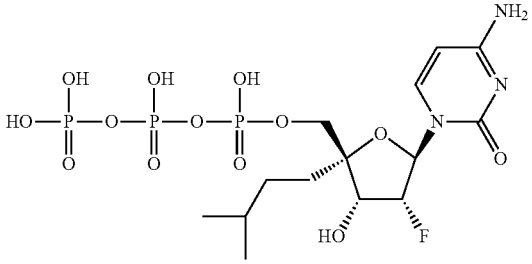 36i | −11.67 d | −23.22 t | −10.77 d | 554.1 |
| 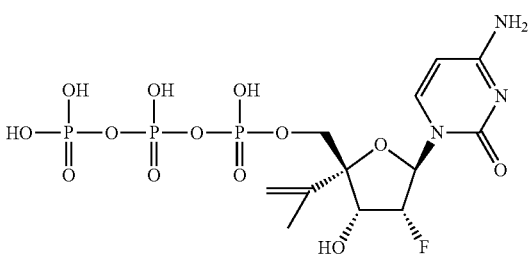 36j | −11.97 d | −23.34 t | −10.92 d | 523.9 |

Example 37

Preparation of Compounds (37a)

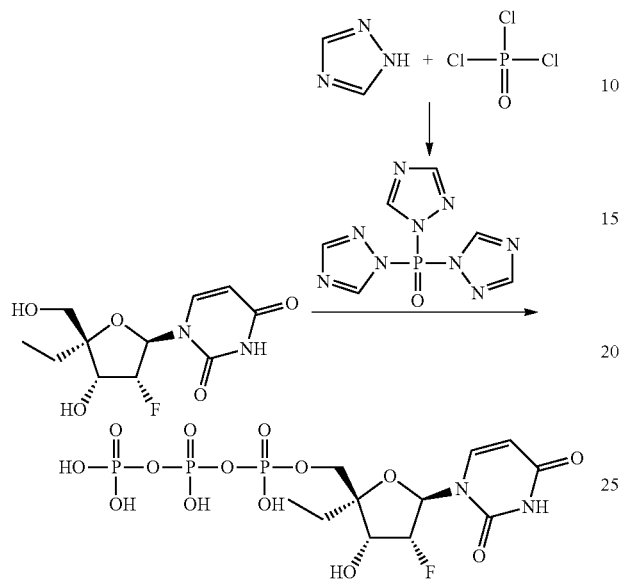

Compound 37a was synthesized by reaction of phosphor (tris-triazolide) with 4'-ethyl-2'-deoxy-2'-fluoro-uridine as described Examples 34 and 35. MS (M−1): 513.1. $^{31}$P-NMR (δ ppm): −9.43 (bs), −11.68 (d) and −23.09 (bs).

Example 38

Preparation of Compounds (38a)

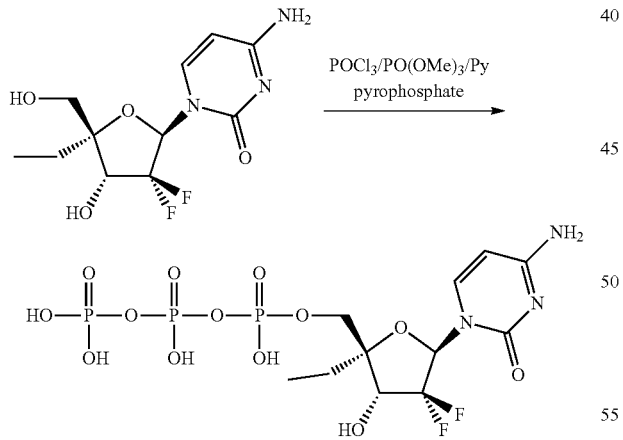

The starting nucleoside (15 mg, 0.05 mmol) was dissolved in dry trimethylphosphate (3 mL). The solution was cooled to 4° C. POCl$_3$ (0.013 mL, 0.125 mmol) was added, followed by pyridine (0.01 mL, 0.125 mmol). In 1 hour, tributylamine (0.035 mL, 0.125 mmol) was added at R.T. followed by tributylammonium pyrophosphate (156 mg, 0.34 mmol). Dry DMF (about 0.100 mL) was added to solubilize pyrophosphate. In 2 hours, the reaction was quenched with TEAB-buffer. The product was isolated by ion-exchange chromatography on AKTA Explorer as described in Example 35. The fractions containing the product were concentrated and treated with NH$_4$OH for 2 hours at R.T. The product was desalted by RP HPLC as described in Example 35. MS (M−1): 529.9. $^{31}$P-NMR (δ ppm): −9.42 (d), −11.59 (d) and −23.03 (t).

Example 39

Preparation of Compound (40a)

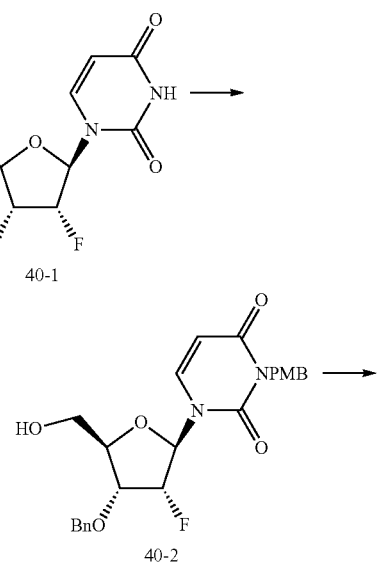

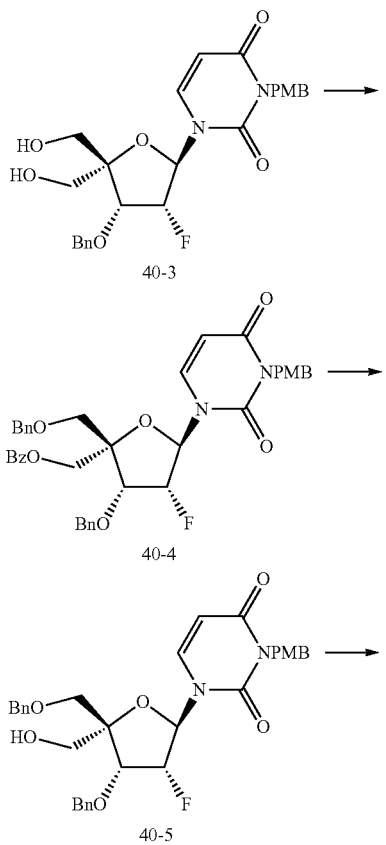

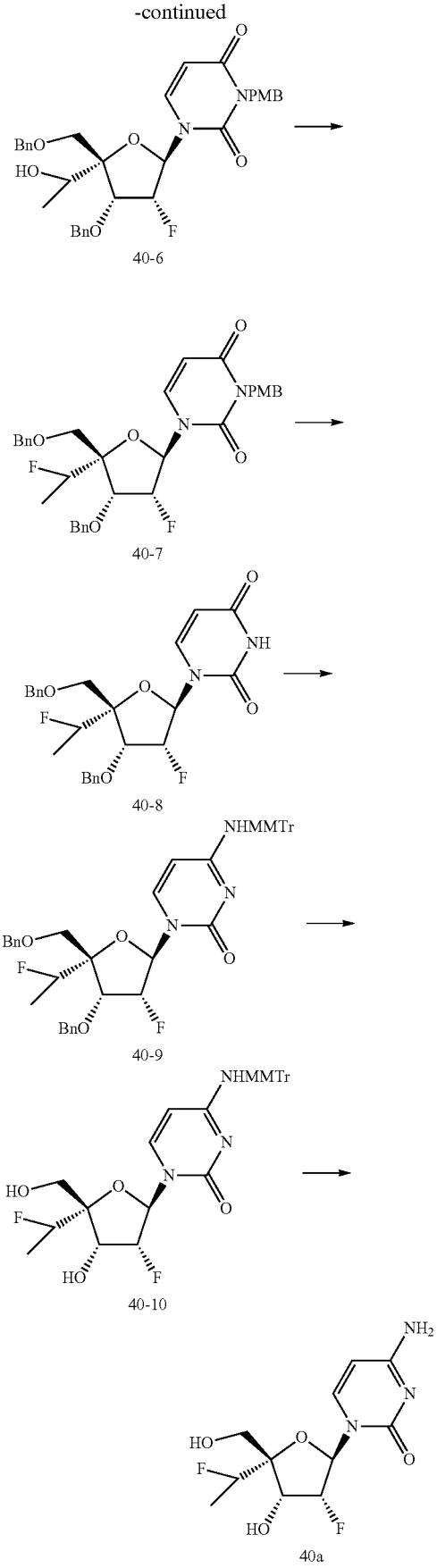

Preparation of (40-2):

To a solution of 40-1 (50.0 g, 205 mmol) in pyridine (250 mL) was added DMTrCl (75.0 g, 225.0 mmol). The solution was stirred at R.T. for 15 hours. MeOH (120 mL) was added, and the mixture was concentrated to dryness under reduced pressure. The residue was dissolved in EA and washed with water. The organic layer was dried over $Na_2SO_4$ and concentrated to give the crude 5'-O-DMTr intermediate (80.52 g) as a light yellow solid. The intermediate was dissolved in anhydrous DMF (300 mL), and $K_2CO_3$ (80.52 g, 583.2 mmol) was added followed by PMBCl (31.7 g, 109.2 mmol). The mixture was stirred at R.T. overnight. The reaction was diluted with EA and washed with brine. The organic phase was dried over $Na_2SO_4$ and concentrated to give crude 5'-O-DMTr-N-3-PMB FdU (98.8 g) as a light yellow solid. The solid was dissolved in DMF (300 mL), and NaH (10.42 g, 260.5 mmol) was added followed by BnBr (73.8 g, 434.2 mmol). The reaction was stirred at R.T. overnight and then was quenched with water. The solution was diluted with EA and washed with brine. The organic phase was dried over $Na_2SO_4$ and concentrated to give the crude fully blocked FdU intermediate, which was purified on a silica gel column (PE:EA=10:1 to 3:1) to the pure fully blocked FdU (101.1 g). The intermediate was treated with 80% HOAc (900 mL) at R.T. overnight, and the solvent was removed. The residue was purified on a silica gel column to give 40-2 as a white foam (42.1 g, 30.2% for 4 steps).

Preparation of (40-3):

To a solution of 40-2 (42.1 g, 92.6 mmol) in anhydrous $CH_3CN$ (300 mL) was added IBX (28.5 g, 121.7 mmol) at R.T. The reaction mixture was refluxed for 1 hour and then cooled to 0° C. The precipitate was filtered-off, and the filtrate was concentrated to give the crude aldehyde (39.22 g) as a yellow solid. To a solution of the aldehyde (39.22 g) in 1,4-dioxane (250 mL) was added 37% $CH_2O$ (28.1 mL, 345.6 mmol) and 2N NaOH aqueous solution (86.4 mL, 172.8 mmol). The mixture was stirred at R.T. for 2 hours and then neutralized with AcOH to pH=7. EtOH (200 mL) and $NaBH_4$ (19.7 g, 518.6 mmol) were added, stirred at R.T. for 30 mins. The mixture was quenched with saturated aqueous $NH_4Cl$, and extracted with EA. The organic layer was dried over $Na_2SO_4$ and concentrated. The residue was purified by silica gel column chromatography (PE:EA=4:1 to 2:1) to give 40-3 (25.5 g, 55.7%) as a white solid.

Preparation of (40-4):

To a stirred solution of 40-3 (25.5 g, 52.5 mmol) in anhydrous pyridine (150 mL) and anhydrous $CH_3CN$ (150 mL) was added BzCl (6.6 g, 52.47 mmol) dropwise at 0° C. The mixture was stirred at R.T. for 14 hours. The reaction was quenched with $H_2O$, and the solution was concentrated. The residue was dissolved in EA and washed with saturated $NaHCO_3$. The organic layer was dried over $Na_2SO_4$ and concentrated. The residue was purified on a silica gel column (PE/EA=5:4) to give the mono-Bz protected intermediate (18.1 g, 60.0%) as a white foam. To a stirred solution of this intermediate (18.1 g, 30.68 mmol) in DMF (100 mL) were added $Cs_2CO_3$ (30.0 g, 92.03 mmol) and BnBr (10.4 g, 61.36 mmol). The mixture was stirred at R.T. overnight. The reaction was quenched with saturated $NH_4Cl$ aq., extracted with EA and washed with brine. The solvent was removed to give crude 40-4 (19.3 g, 95.1%) as a light yellow solid.

Preparation of (40-5):

To a stirred solution of 40-4 (19.3 g, 28.4 mmol) in anhydrous MeOH (230 mL) was added NaOMe (24.9 g, 460 mmol) at R.T. The mixture was stirred for 1 hour. The reaction was quenched with AcOH (10 mL) and concentrated. The residue was purified on a silica gel column (PE/EA=1/2) to afford 40-5 (11.2 g, 54.0%) as a white solid.

Preparation of (40-6):

To a stirred solution of compound 40-5 (200 mg, 0.347 mmol) in anhydrous DCM (5 mL) was added DMP (168 mg, 0.674 mmol) at R.T. The mixture was stirred at R.T. for 2 hours. The solvent was removed, and the residue was purified on a silica gel column (PE:EA=5:1 to 1:1) to give the aldehyde crude as a light yellow solid (200 mg). To a stirred solution of the aldehyde (200 mg) in anhydrous THF (5 mL) was added MeMgBr (1.0 mL, 1.01 mmol) at −78° C. The mixture was stirred at −78° C. for 1 hour. The reaction was quenched with saturated NH$_4$Cl aq. and extracted with EA. The concentrated organic phase was purified by column chromatography (PE:EA=5:1 to 1:1) to give 40-6 (a mixture of stereomers, 135 mg, 65%) as a white solid.

Preparation of (40-7):

To a stirred solution of DAST (1.64 g, 10.17 mmol) in anhydrous toluene (40 mL) was added dropwise a solution of compound 40-6 (1.2 g, 2.03 mmol) at −78° C. The mixture was stirred at −78° C. for 30 mins. The solution was warmed to 60° C. slowly and stiffing was continued overnight. The mixture was poured into a saturated Na$_2$CO$_3$ solution. The concentrated organic phase was concentrated and purified on a silica gel column (PE:EA=10:1 to 3:1) to afford 40-7 as a white solid (1.08 g, 83.88%). $^1$H NMR (CD$_3$OD, 400 MHz) δ 7.87 (d, J=8.4 Hz, 1H), 7.27-7.37 (m, 12H), 6.82-6.84 (m, 2H), 6.14 (d, J=16.8, 2.0 Hz, 1H), 5.18-5.50 (m, 4H), 4.96 (s, 2H), 4.45-4.88 (m, 7H), 3.67-3.89 (m, 5H).

Preparation of (40-8):

A mixture of compound 40-7 (0.91 g, 1.54 mmol) and CAN (2.53 g, 4.61 mmol) in a 3:1 solution of MeCN:water (10 mL) was stirred at R.T. overnight. Brine (10 mL) was added, and the mixture was extracted with EA. The combined organic extracts were dried and evaporated under reduced pressure. Purification by chromatography on silica gel column with PE:EA=10:1 to 2:1 afforded 40-8 as a yellow solid (305 mg, 41.96%).

Preparation of (40-9):

To a stirred solution of 40-8 (350 mg, 0.74 mmol) in anhydrous MeCN (8 mL) were added TPSCl (449 mg, 1.48 mmol), DMAP (180 mg, 1.48 mmol) and TEA (374 mg, 3.70 mmol) at R.T. The mixture was stirred at R.T. overnight. NH$_4$OH (15 mL) was added, and the mixture was stirred for 2 hours. The solvent was removed, and the residue was purified on a silica gel column with PE:EA=8:1 to 1:1 to afford the crude (380 mg crude), which was dissolved in anhydrous DCM (10 mL). A mixture of MMTrCl (695 mg, 2.25 mmol) and AgNO$_3$ (380 mg, 2.25 mmol) was added at R.T., and the mixture was stirred at R.T. overnight. The solid was filtered off and washed with DCM. The filtrate was washed with brine and dried over Na$_2$SO$_4$. The concentrated organic phase was purified on a silica gel column (PE:EA=8:1 to 2:1) to afford 40-9 as a yellow solid (460 mg, 81.33%).

Preparation of (40-10):

To a stirred solution of compound 40-9 (450 mg, 0.61 mmol) in acetone were added ammonium formate (1.29 g, 20.6 mmol, in portions) and 10% palladium on carbon (1.0 g). The mixture was refluxed for 12 h. The catalyst was filtered off and washed with acetone. The filtrate was diluted with EA and washed with brine. The concentrated organic phase was purified by column chromatography (DCM:MeOH=100:1 to 15:1) to afford 40-10 as a white solid (250 mg, 72.8%). $^1$H NMR (DMSO-d6, 400 MHz) δ 8.56 (s, 1H), 7.73 (d, J=7.6 Hz, 1H), 7.14-7.28 (m, 12H), 6.84 (d, J=8.8 Hz, 2H), 6.30 (d, J=7.6 Hz, 1H), 6.03-6.08 (m, 1H), 5.84 (d, J=5.2 Hz, 1H), 5.33-5.35 (m, 1H), 4.97-5.18 (m, 1H), 4.86-4.90 (m, 1H), 4.34 (d, J=4.4 Hz, 1H), 3.72 (s, 3H), 3.54-3.57 (m, 2H), 1.28 (dd, =6.4 Hz, J$_2$=25.6 Hz, 3H). ESI-MS: m/z 563.50 [M+H]$^+$.

Preparation of (40a):

40-10 (101 mg, 0.179 mmol) was dissolved in 80% HOAc (20 mL) at R.T. The mixture was stirred at 50° C. for 5 hours. The solvent was removed, and the residue was co-evaporated with toluene twice. The residue was purified by column chromatography (DCM:MeOH=100:1 to 10:1) to afford 40a as a white solid (36.6 mg, 70.26%). $^1$H NMR (CD$_3$OD, 400 MHz) δ 7.98 (d, J=7.6 Hz, 1H), 6.20-6.24 (m, 1H), 5.92 (d, J=7.2 Hz, 1H), 5.17-5.30 (m, 1H), 4.99-5.14 (m, 1H), 4.51-4.86 (m, 1H), 3.78 (d, J=1.6 Hz, 2H), 1.35-1.43 (m, 3H). ESI-MS: m/z 291.84 [M+H]$^+$, 582.81 [2M+H]$^+$.

Example 40

Preparation of Compound (41a)

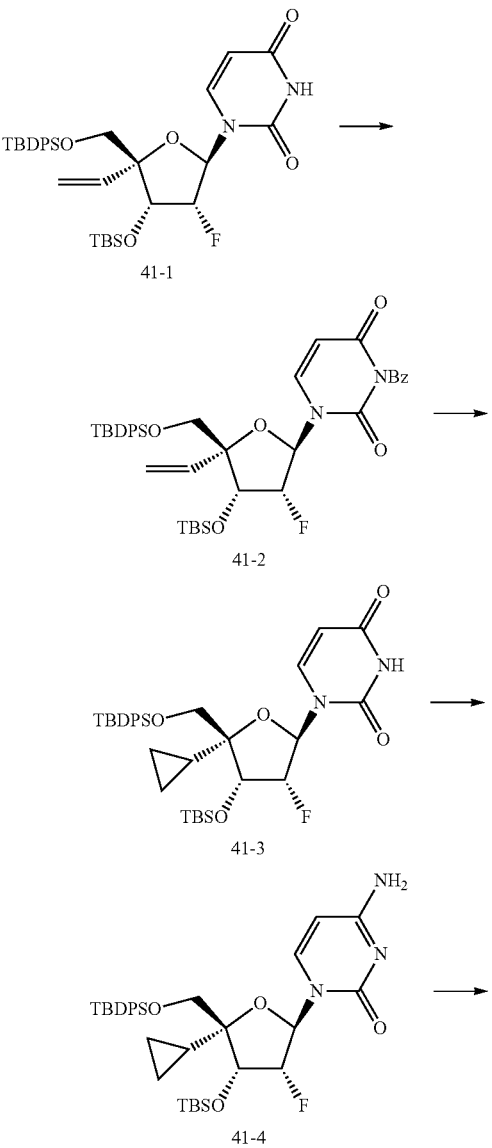

41-1

41-2

41-3

41-4

-continued

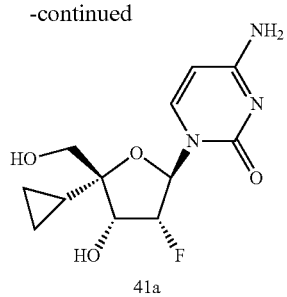
41a

Preparation of (41-2):

To a solution of 41-1 (3 g, 4.8 mmol) in anhydrous DCM (50 mL) were added BzCl (1.3 g, 9.6 mmol), DMAP (1.1 g, 9.6 mmol) and NEt$_3$ (4 mL) at R.T. The reaction was stirred at R.T. for 2 hours. Water was added, and the reaction was stirred for another 1 hour. The mixture was diluted with DCM (150 mL) and washed with water, 0.1M HCl and saturated aqueous NaHCO$_3$. The solvent was removed, and the crude product was purified by silica gel column chromatography (25% EtOAc in PE) to give 41-2 as a yellow solid (2.8 g, 80.0%).

Preparation of (41-3):

A mixture of 41-2 (2.6 g, 3.6 mmol) and Pd(OAc)$_2$ (100 mg) in DCM (50 mL) was suspended in a solution of CH$_2$N$_2$ in Et$_2$O (generated by standard procedure, 350 mL) at −78° C. The reaction was stirred to R.T. overnight. The mixture was quenched with HOAc, and the reaction was stirred for another 1 hour. The mixture was diluted with EtOAc (150 mL) and washed with water and saturated aqueous NaHCO$_3$. The solvent was removed, and the crude was dissolved in NH$_3$.MeOH (sat., 100 mL). The reaction was stirred to R.T. overnight. The crude product was purified by silica gel column chromatography (25% EtOAc in PE) to give 41-3 as a yellow solid (800 mg, 35.2%).

Preparation of (41-4):

To a solution of 41-3 (800 mg, 1.3 mmol) in anhydrous CH$_3$CN (50 mL) were added TPSCl (755 mg, 2.5 mmol), DMAP (305 mg, 2.5 mmol) and NEt$_3$ (400 mg, 4 mmol) at R.T. The reaction was stirred at R.T. for 2 hours. NH$_4$OH (25 mL) was added, and the reaction was stirred for another 1 hour. The mixture was diluted with DCM (150 mL) and washed with water, 0.1M HCl and saturated aqueous NaHCO$_3$. The solvent was removed, and the crude product was purified by silica gel column chromatography (25% EtOAc in PE) to give 41-4 as a yellow solid (340 mg, 42.5%).

Preparation of (41a):

To a solution of 41-4 (200.0 mg) in MeOH (10 mL) was added NH$_4$F (600 mg). The reaction was refluxed for 24 hours. The solvent was removed, and the residue was purified by column chromatography on silica gel (DCM: MeOH=15:1) to give 41a (50.0 mg, 55.9%) as a white solid. $^1$H NMR (CD$_3$OD, 400 MHz) δ 8.13 (d, J=7.6 Hz, 1H), 6.01 (dd, J$_1$=2.4 Hz, J$_2$=15.6 Hz, 1H), 5.85 (d, J=7.6 Hz, 1H), 5.04-4.89 (m, 1H), 4.52 (dd, J$_1$=5.2 Hz, J$_2$=19.6 Hz, 1H), 3.66 (s, 2H), 1.00-0.94 (m, 1H), 0.54-0.30 (m, 4H); ESI-MS: m/z 285.82 [M+H]$^+$, 570.84 [2M+H]$^+$.

Example 41

Preparation of Compound (42a)

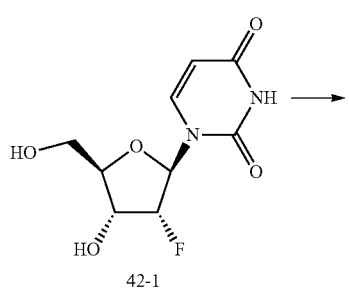
42-1

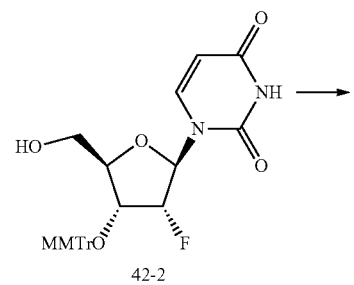
42-2

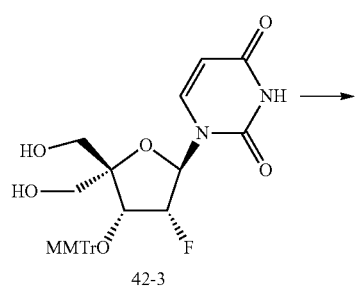
42-3

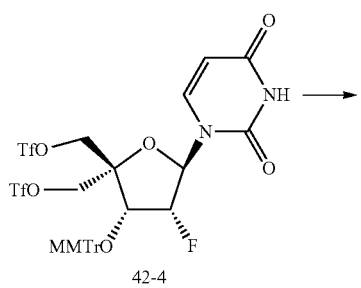
42-4

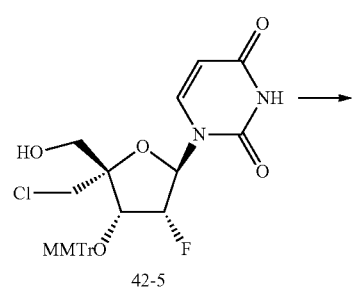
42-5

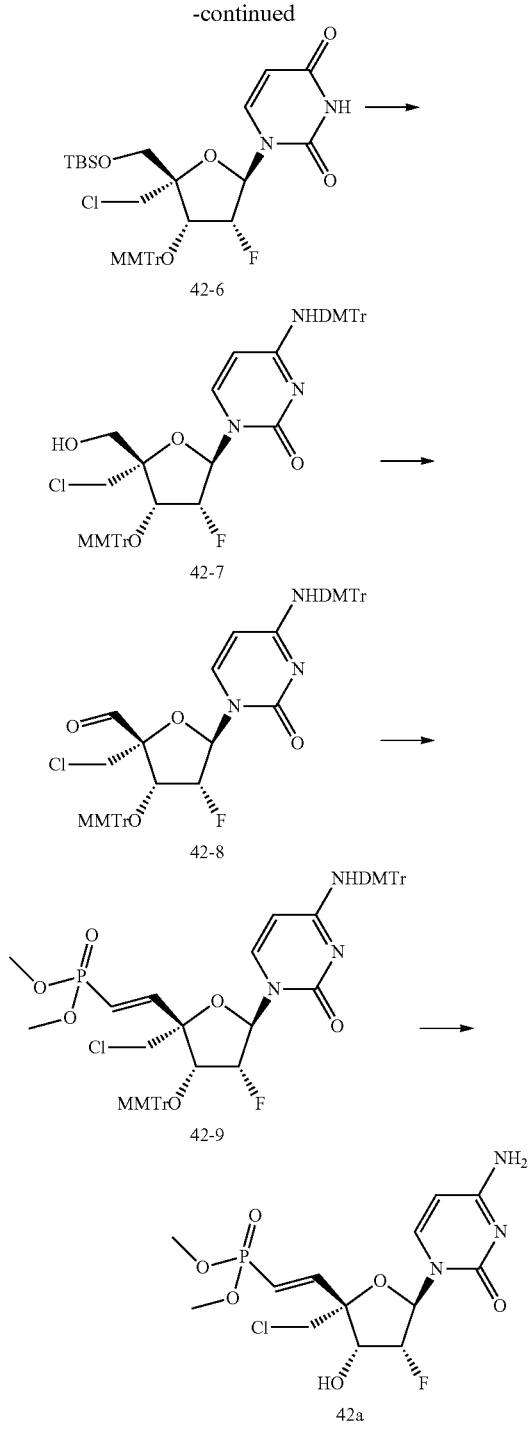

Preparation of (42-2):

To a solution of 42-1 (50 g, 203 mmol) in anhydrous pyridine (200 mL) was added TBDPSCl (83.7 g, 304 mmol, 1.5 eq). The reaction was stirred overnight at R.T. The solution was concentrated under reduced pressure to give a syrup, which was partitioned between ethyl acetate and water. The organic layer was separated, washed with brine, dried over magnesium sulfate and concentrated to give the 5'-OTBDPS ether as a white foam (94 g). The crude ether was dissolved in anhydrous DCM (300 mL), and silver nitrate (66.03 g, 388.4 mmol, 2.0 eq) and collidine (235 mL, 1.94 mol, 10 eq) were added. The mixture was stirred at R.T., and MMTrCl (239.3 g, 776.8 mmol, 4 eq) was added. After being stirred overnight at R.T., the mixture was filtered through Celite and filtrate was diluted with MTBE. The solution was washed successively with 1M citric acid, diluted brine and 5% sodium bicarbonate. The organic solution was dried over sodium sulfate and concentrated under vacuum to give the fully protected intermediate as a yellow foam. The crude intermediate was dissolved in anhydrous THF (250 mL) and treated with TBAF (60 g, 233 mmol, 1.2 eq). The mixture was stirred for 2 hours at R.T., and the solvent was removed under reduced pressure. The residue was taken into ethyl acetate and washed brine. After drying over magnesium sulfate, the solvent was removed in vacuo. The residue was purified by column chromatography (PE:EA=5:1 to 1:1) to give 42-2 as a white foam (91 g, 86.4%).

Preparation of (42-3):

To a solution of 42-2 (13.5 g, 26 mmol) in DCM (100 mL) was added pyridine (6.17 mL, 78 mmol, 3 eq). The solution was cooled to 0° C. and Dess-Martin periodinane (33.8 g, 78 mmol, 3 eq) was added. The mixture was stirred for 4 hours at R.T. and quenched by the addition of a 4% $Na_2S_2O_3$/4% sodium bicarbonate aqueous solution (to pH 6, ~150 mL). The mixture was stirred for another 15 mins. The organic layer was separated, washed with diluted brine and concentrated under reduced pressure. The residue was dissolved in dioxane (100 mL), and the solution was treated with 37% aqueous formaldehyde (21.2 g, 10 eq) and 2N aqueous sodium hydroxide (10 eq). The reaction mixture was stirred at R.T. overnight. The reaction was quenched with saturated $NH_4Cl$ (~150 mL), and the mixture was concentrated under reduced pressure. The residue was partitioned between ethyl acetate and 5% sodium bicarbonate. The organic phase was separated, washed with brine, dried over magnesium sulfate and concentrated. The residue was purified by column chromatography (MeOH:DCM=100:1~50:1) to give 42-3 as a white foam (9.2 g, 83.6%).

Preparation of (42-4):

42-3 (23 g, 42.0 mmol) was co-evaporated with toluene twice. The residue was dissolved in anhydrous DCM (250 mL) and pyridine (20 mL). The solution was cooled to −35° C. Triflic anhydride (24.9 g, 88.1 mmol, 2.1 eq) was added dropwise over 10 mins. At this temperature, the reaction was stirred for 40 mins and then was quenched with water (50 mL) at 0° C. The mixture was stirred 30 mins, and extracted with EA (150 mL×2). The organic phase was dried over $Na_2SO_4$, and filtered through a silica gel pad. The filtrate was concentrated under reduced pressure. The residue was purified by column chromatography (PE:EA=100:1-1:1) to give 42-4 as a brown foam (30.0 g, 88.3%).

Preparation of (42-5):

42-4 (30 g, 36.9 mmol) was co-evaporated twice with toluene and dissolved in anhydrous DMF (150 mL). The solution was cooled to 0° C., and treated with sodium hydride (60% in mineral oil; 1.5 g, 40.6 mmol). The reaction was stirred at R.T. for 1 h. Lithium chloride (4.6 g, 110.7 mmol, 3 eq) was added. Stirring was continued for 2 hours when LCMS indicated complete conversion of the anhydro triflate intermediate to anhydro-chloro compound. The mixture was taken into 100 mL of half saturated ammonium chloride and ethyl acetate. The organic phase was separated, washed with diluted brine and concentrated under reduced pressure. The residue was dissolved in THF (150 mL), and the solution was treated with 1N aqueous sodium hydroxide (~41 mL, 40.1 mmol, 1.1 eq). The mixture was stirred at R.T. for 1 h. The reaction was diluted with half saturated sodium bicarbonate (~60 mL) and extracted with EA. The organic phase was dried (magnesium sulfate) and concentrated under reduced pressure. The residue was purified by column chromatography (DCM:MeOH=300:1~60:1) to give 42-5 as a yellow foam (18.3 g, 87.6%).

Preparation of (42-6):

To a solution of 42-5 (18.3 g, 32.33 mmol) in anhydrous DCM (150 mL) was added TBSCl (17.7 g, 64.6 mmol) and imidazole (6.6 g, 97 mmol). The reaction was stirred overnight at R.T. The reaction was diluted with water and extracted with DCM. The organic layer was separated, washed with brine, dried over Na$_2$SO$_4$ and concentrated. The residue was purified by column chromatography (DCM:MeOH=300:1~80:1) to give 42-6 as a white foam (18.4 g, 83.7%).

Preparation of (42-7):

A solution of 42-6 (18.4 g, 27.1 mmol), DMAP (6.6 g, 54.0 mmol) and TEA (5.4 g, 54.0 mmol) in MeCN (450 mL) was treated with 2,4,6-triispropylbenzenesulfonyl chloride (16.3 g, 54.0 mmol). The mixture was stirred at R.T. for 3 hours. NH$_4$OH (70 mL) was added, and the mixture was stirred for 2 hours. The solution was evaporated under reduced pressure, and the residue was purified on a silica gel column (DCM/MeOH=100:1 to 15:1) to give the crude (18.0 g). The crude was dissolved in anhydrous DCM (150 mL). Collidine (8.1 g, 66.3 mmol, 2.5 eq), silver nitrate (4.5 g, 26.5 mmol, 1.0 eq) and DMTrCl (13.4 g, 39.7 mmol, 1.5 eq) were added. The reaction was stirred overnight at R.T. The mixture was filtered through Celite. The filtrate was washed with brine and extracted with DCM. The organic layer was separated, dried over Na$_2$SO$_4$ and concentrated. The residue was purified by column chromatography (PE:EA=60:1~3:1) as a yellow foam. The foam was dissolved in THF (150 mL) and TBAF (10.4 g, 39.7 mmol, 1.5 eq) was added. The reaction was stirred at R.T. After being concentrated, the mixture was washed with brine and extracted with EA. The organic layer was separated, dried over Na$_2$SO$_4$ and concentrated. The residue was purified by column chromatography (PE:EA=60:1~EA) to give 42-7 as a yellow foam (21.3 g, 92.4%).

Preparation of (42-8):

To a solution of 42-7 (2.0 g, 2.3 mmol) in anhydrous DCM (20 mL) was added Dess-Martin periodinane (1.95 g, 4.6 mmol) at 0° C. under nitrogen. The reaction was stirred at R.T. for 5 hours. The mixture was diluted with EtOAc (100 mL), and washed with a mixture of saturated aqueous Na$_2$S$_2$O$_3$ and saturated aqueous NaHCO$_3$. The crude product was purified by column chromatography on silica gel (PE:EtOAc=2:1) to give 42-8 (1.8 g, 90%) as a yellow solid.

Preparation of (42-9):

To a solution of tetramethyl methylenediphosphonate (390 mg, 1.68 mmol) in anhydrous THF (10 mL) was added NaH (84 mg, 2.1 mmol) at 0° C. under nitrogen. The reaction was stirred at 0° C. for 30 min. A solution of 42-8 (1.2 g, 1.4 mmol) in anhydrous THF (10 mL) was added dropwise at 0° C. The mixture was stirred at R.T. for 1 h. The reaction was quenched with saturated aqueous NH$_4$Cl, and the crude product was purified by column chromatography on silica gel (DCM:MeOH=150:1) to give 42-9 (1.2 g, 88.2%) as a yellow solid. $^1$H NMR (DMSO-d6, 400 MHz) δ 8.51 (s, 1H), 7.46-7.09 (m, 22H), 6.88-6.82 (m, 6H), 6.62 (q, J$_1$=17.2 Hz, J$_2$=22.4 Hz, 1H), 6.12 (d, J=7.2 Hz, 1H), 5.86-5.75 (m, 2H), 5.43 (d, J=25.2 Hz, 1H), 4.63 (dd, J$_1$=4.8 Hz, J$_2$=21.2 Hz, 1H), 4.45 (d, J=12.0 Hz, 1H), 3.94 (d, J=12.0 Hz, 1H), 3.72 (s, 9H), 3.53 (q, J$_1$=11.2 Hz, J$_2$=16.0 Hz, 6H); ESI-MS: m/z 971.59 [M+H]$^+$.

Preparation of (42a):

A solution of 42-9 (300 mg) in 80% HOAc (26 mL) was stirred at 80-90° C. for 2 h. The solvent was removed, and the crude product was purified by column chromatography on silica gel (DCM:MeOH 20:1) to give 42a (70 mg, 57%) as a white solid. $^1$H NMR (DMSO-d6, 400 MHz) δ 7.61 (d, J=7.6 Hz, 1H), 7.35 (d, J=15.2 Hz, 2H), 6.72 (q, J$_1$=17.6 Hz, J$_2$=24.4 Hz, 1H), 6.23 (d, J=6.0 Hz, 1H), 5.99-5.85 (m, 2H), 5.74 (q, J=7.2 Hz, 1H), 5.37-5.21 (m, 1H), 4.69-4.61 (m, 1H), 3.96 (d, J=12.4 Hz, 1H), 3.82 (d, J=12.0 Hz, 1H), 6.72 (q, J$_1$=5.2 Hz, J$_2$=10.8 Hz, 6H); ESI-MS: m/z 397.81 [M+H]$^+$.

Example 42

Preparation of Compound (43a)

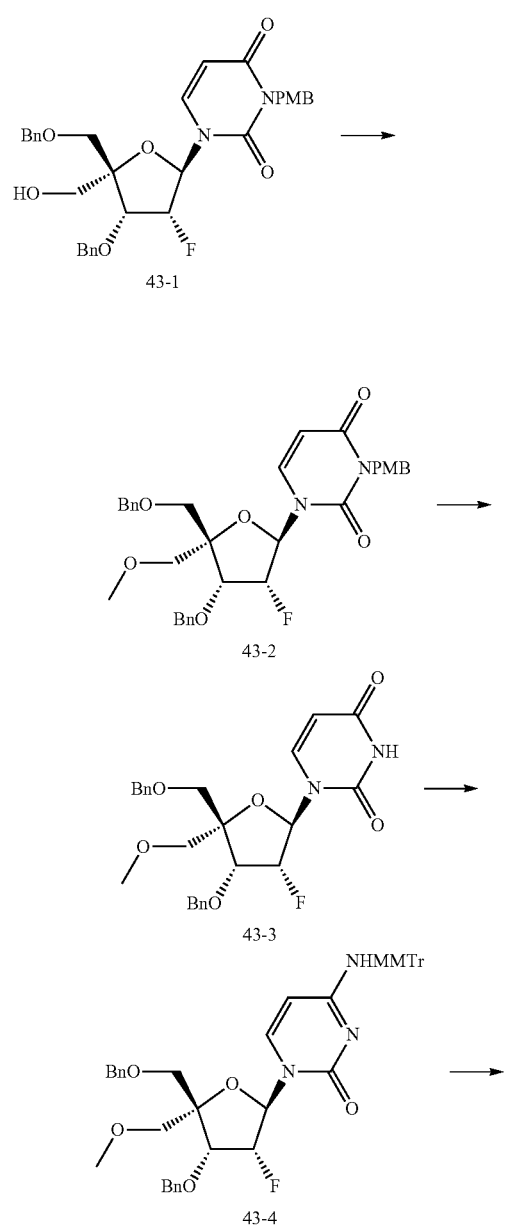

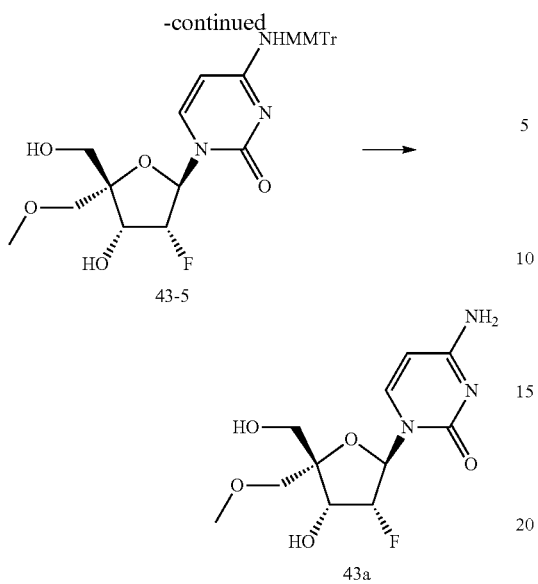

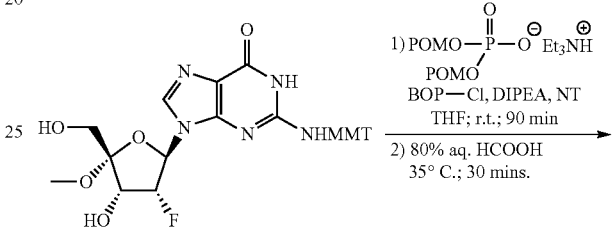

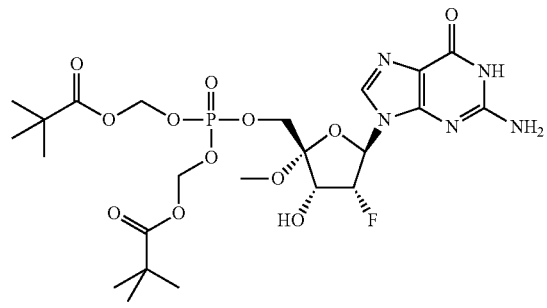

Preparation of (43-2):

To a stirred solution of 43-1 (3.8 g, 6.6 mmol) in anhydrous DMF (100 mL) was added NaH (2.2 g) followed by CH$_3$I (9.3 g, 66 mmol) at 0° C. Stirring was continued at R.T. overnight. The reaction was quenched with saturated NH$_4$Cl aq. The mixture was diluted with EA and washed with brine. The organic layer was dried over Na$_2$SO$_4$ and concentrated. The residue was purified by silica gel column chromatography (PE:EA=2:1) to give 43-2 (3.0 g, 70%) as a white solid.

Preparation of (43-3):

A mixture of 43-2 (3.0 g, 5.1 mmol) and CAN (5.56 g, 10.2 mmol) in a 3:1 solution of MeCN:Water (16 mL) was stirred at R.T. overnight. The solution was diluted with brine (10 mL) and was extracted with EA. The combined organic extracts were dried and evaporated under reduced pressure. Purification by chromatography on silica (PE:EA=1:1) gave 43-3 as a yellow solid (1.71 g, 72%).

Preparation of (43-4):

To a stirred solution of 43-3 (1.7 g, 3.6 mmol) in anhydrous MeCN (50 mL) were added TPSCl (2.2 g, 7.2 mmol), DMAP (880 mg, 7.2 mmol) and TEA (1.1 g, 10.8 mmol) at R.T. The mixture was stirred at R.T. overnight. NH$_4$OH (25 mL) was added, and the mixture was stirred for 2 hours. The solvent was removed, and the residue was purified on a silica gel column (PE:EA=8:1 to 2:1) to give the intermediate (1.4 g). The intermediate was dissolved in anhydrous DCM (30 mL), and MMTrCl (1.6 g, 5.2 mmol), AgNO$_3$ (1.4 g, 7.8 mmol) and collidine (1.57 g, 13 mmol) were added. The mixture was stirred at R.T. overnight. The solid was filtered off and washed with DCM. The filtrate was washed with brine and dried over Na$_2$SO$_4$. The concentrated organic phase was purified on a silica gel column (PE:EA=3:2) to give 43-4 (1.1 g, 57.9%) as a white solid.

Preparation of (43-5):

To a stirred solution of 43-4 (550 mg, 0.74 mmol) in acetone were added ammonium formate (1.0 g, 15.8 mmol, in portions) and 10% palladium on carbon (1.0 g). The mixture was refluxed for 48 hours. The catalyst was filtered off and washed with the acetone. The filtrate was diluted with EA, washed with brine and dried. The concentrated organic phase was purified by column chromatography (DCM:MeOH=50:1) to give 43-5 (330 mg, 72%).

Preparation of (43a):

43-5 (200 mg, 0.36 mmol) was dissolved in 80% CH$_3$COOH (20 mL) at R.T. The mixture was stirred at 60° C. for 12 hours. The solvent was removed. The residue was purified by column chromatography (DCM:MeOH=10:1), and the resulting solid was washed with DCM to give pure 43a as a white solid (44 mg, 42%). $^1$H NMR (CD$_3$OD, 400 MHz) δ 8.02 (d, J=7.2 Hz, 1H), 6.14 (dd, J=3.6 Hz, J$_2$=15.2 Hz, 1H), 5.88 (d, J=7.2 Hz, 1H), 5.10 (ddd, J=4.0 Hz, J$_2$=5.2 Hz, J$_3$=53.6 Hz, 1H), 4.47 (dd, J$_1$=5.2 Hz, J$_2$=14.8 Hz, 1H), 3.84 (d, J=12.0 Hz, 1H), 3.70 (d, J=12.0 Hz, 1H), 3.58-3.64 (m, 2H), 3.36 (s, 3H). ESI-MS: m/z 290 [M+H]$^+$.

Example 43

Preparation of Compound (44a)

To a solution of triethylammonium bis(POM)phosphate (0.3 mmol, prepared from 100 mg of bis(POM)phosphate and 50 μL of Et$_3$N) in THF (3 mL) was added nucleoside 44-1 (150 mg; 0.26 mmol). The mixture was cooled in ice-bath. Diisopropylethyl amine (0.18 mL; 4 equiv) was added then, followed by BOP-Cl (132 mg; 2 equiv) and 3-nitro-1,2,4-triazole (59 mg; 2 equiv). The reaction mixture was stirred at 0° C. for 90 mins., and then diluted with CH$_2$Cl$_2$ (30 mL) and washed with saturated aq. NaHCO$_3$ and brine. The combined aqueous layers were back extracted with CH$_2$Cl$_2$. The combined organic extract was dried (Na$_2$SO$_4$), evaporated, and the residue purified on silica (10 g column) with CH$_2$Cl$_2$/i-PrOH solvent system (3-10% gradient). The obtained mixture of products were treated for 30 mins at 35° C. with 80% aq. HCOOH, and then evaporated and coevaporated with toluene. The evaporated residue was purified on silica (10 g column) with CH$_2$Cl$_2$/MeOH solvent system (5-10% gradient) to obtain 44a (8 mg, 5%). $^{31}$P-NMR (DMSO-d$_6$): δ −5.07. MS: m/z=668 (M+46−1).

Example 44

Preparation of Compound (45a)

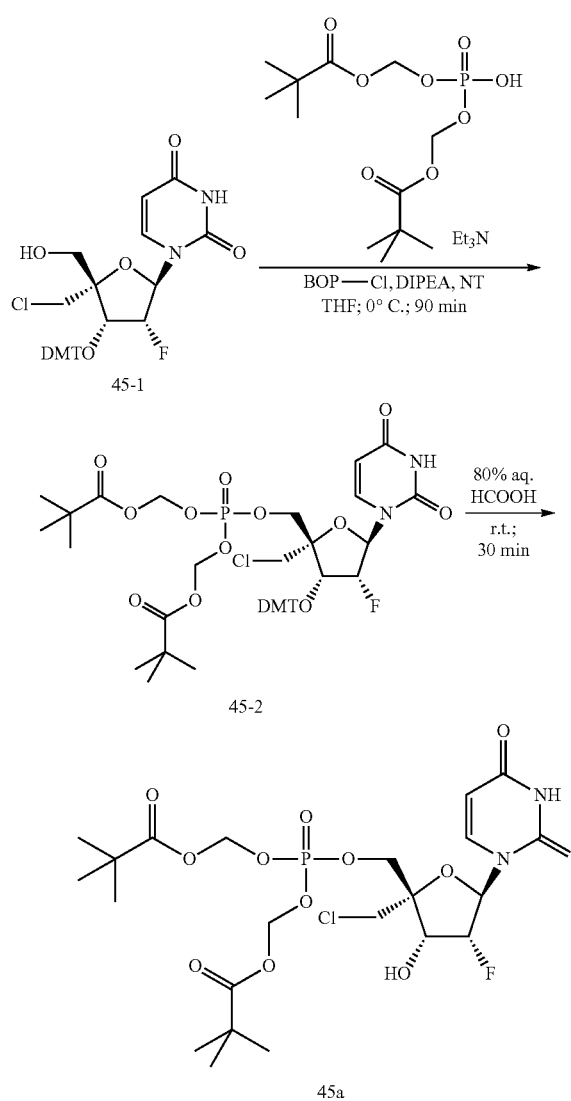

Preparation of (45-2):

To a solution of triethylammonium bis(POM)phosphate (0.7 mmol, prepared from 233 mg of bis(POM)phosphate and 0.1 mL of Et$_3$N) in THF (8 mL) was added nucleoside 45-1 (253 mg; 0.42 mmol), followed by diisopropylethyl amine (0.36 mL; 5 equiv), BOP-Cl (268 mg; 2.5 equiv) and 3-nitro-1,2,4-triazole (120 mg; 2.5 equiv). The reaction mixture was stirred at R.T. for 2 hours. The mixture was diluted with CH$_2$Cl$_2$ (40 mL) and washed with saturated aq. NaHCO$_3$ and brine. The combined aqueous layers were back extracted with CH$_2$Cl$_2$. The combined organic extract was dried (Na$_2$SO$_4$), evaporated, and the residue was purified on silica (10 g column) with hexanes/EtOAc solvent system (40-100% gradient) to yield 45a (180 mg, 47%).

Preparation of (45a):

A solution of compound 45-2 (0.12 g; 0.13 mmol) in 80% aq. HCOOH (8 mL) was stirred 30 mins. at R.T. The mixture was evaporated, coevaporated with toluene and purified on silica (10 g column) with CH$_2$Cl$_2$/MeOH solvent system (4-10% gradient) to yield 45a (55 mg, 70%). $^{31}$P-NMR (DMSO-d$_6$): δ −4.36. MS: m/z=647 (M+46−1).

Example 45

Preparation of Compound (46a)

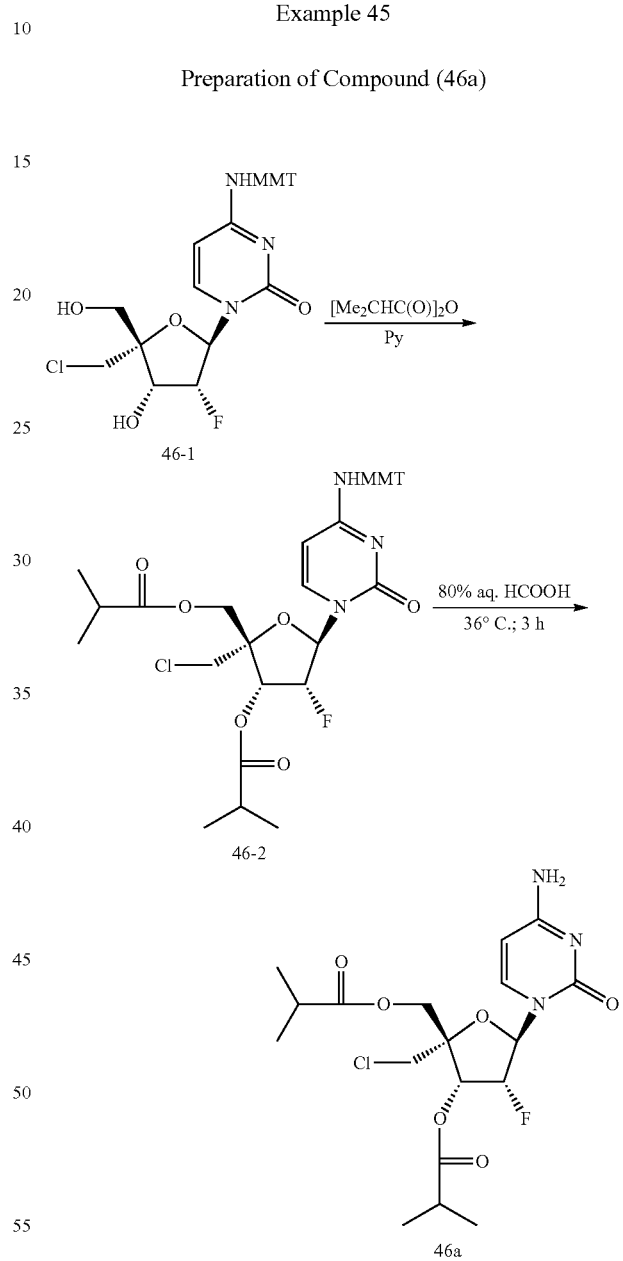

Preparation of (46-2):

A mixture of 46-1 (170 mg; 0.3 mmol) in pyridine (3 mL) and isobutyric anhydride (0.1 mL; 2 equiv) was stirred o/n at R.T. The mixture was concentrated, and the residue was partitioned between EtOAc (30 mL) and saturated aq. NaHCO$_3$. The organic layer was washed with water, brine and dried (Na$_2$SO$_4$). The residue was purified on silica (10 g column) with a hexanes/EtOAc solvent system (30 to 100% gradient) to afford 46-2 (180 mg, 85%).

Preparation of (46a):

A solution of 46-2 (0.18 g; 0.25 mmol) in 80% aq. HCOOH (5 mL) was heated for 3 hours at 36° C. The mixture was then evaporated, coevaporated with toluene and purified on silica (10 g column) with a CH$_2$Cl$_2$/MeOH solvent system (4-10% gradient) to afford 46a (75 mg, 70%). MS: m/z=434 (M+1).

Example 46

Preparation of Compound (47a)

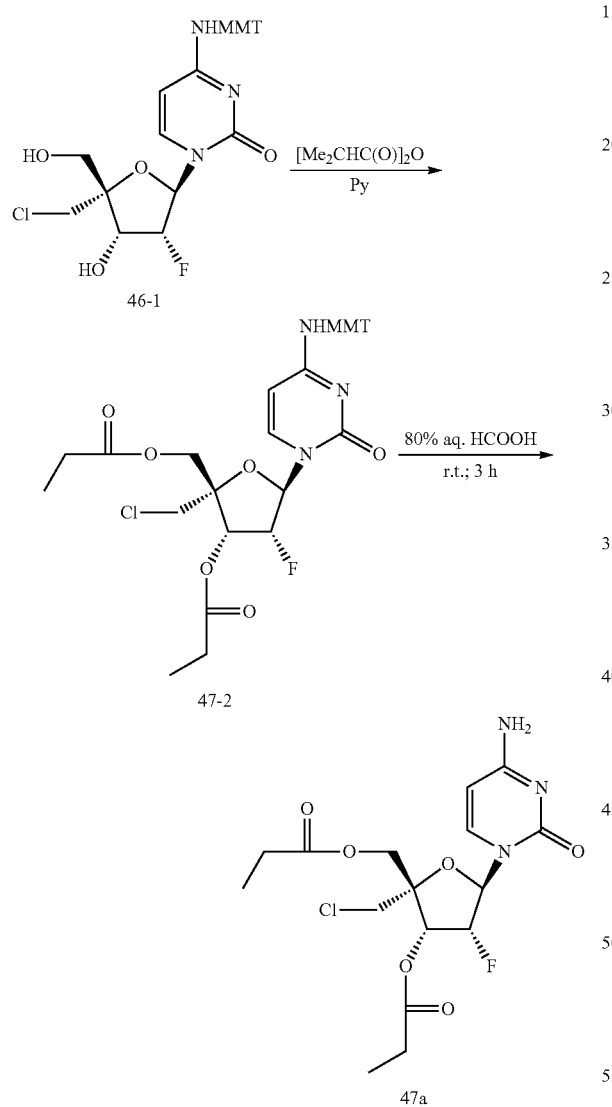

Preparation of (47-2):

47-2 was prepared from 46-1 (274 mg, 0.46 mmol) and propyonic anhydride (0.12 mL, 2 equiv.) in pyridine (5 mL) in the same manner as described for 46-2 (260 mg, 80%).

Preparation of (47a):

47-2 (120 mg, 0.2 mmol) was treated with 80% aq. HCOOH at R.T. for 3 hours. The mixture was evaporated, coevaporated with toluene and purified on silica (10 g column) with a CH$_2$Cl$_2$/MeOH solvent system (4-10% gradient) to yield 47a (62 mg, 75%). MS: m/z=404 (M−1).

Example 47

Preparation of Compound (48a)

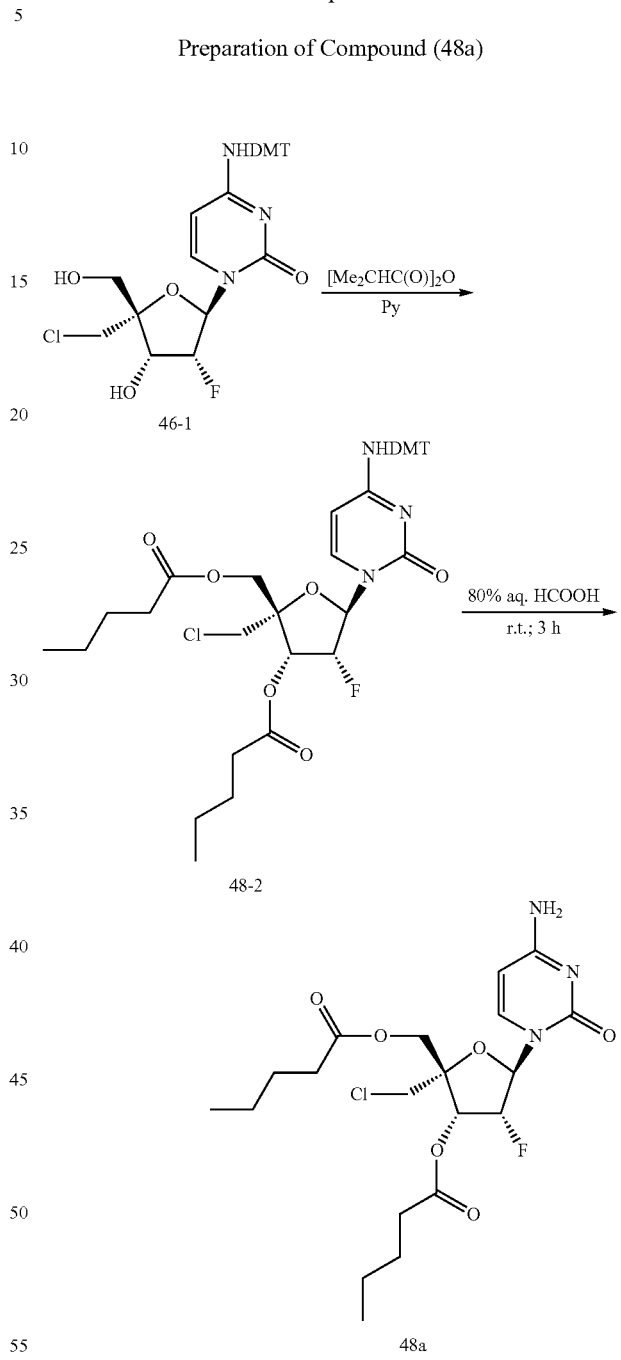

Preparation of (48-2):

48-2 was prepared from 46-1 (150 mg, 0.27 mmol) and valeric anhydride (0.11 mL, 2 equiv.) in pyridine (3 mL) in the same manner as described for 46-2 (150 mg, 73%).

Preparation of (48a):

48-2 (140 mg, 0.18 mmol) was treated with 80% aq. HCOOH at R.T. for 3 hours. The mixture was evaporated and purified on silica (10 g column) with a CH$_2$Cl$_2$/MeOH solvent system (4-10% gradient) to yield 48a (70 mg, 84%). MS: m/z=462 (M+1).

Example 48

Preparation of Compounds (49a), (50a) and (51a)

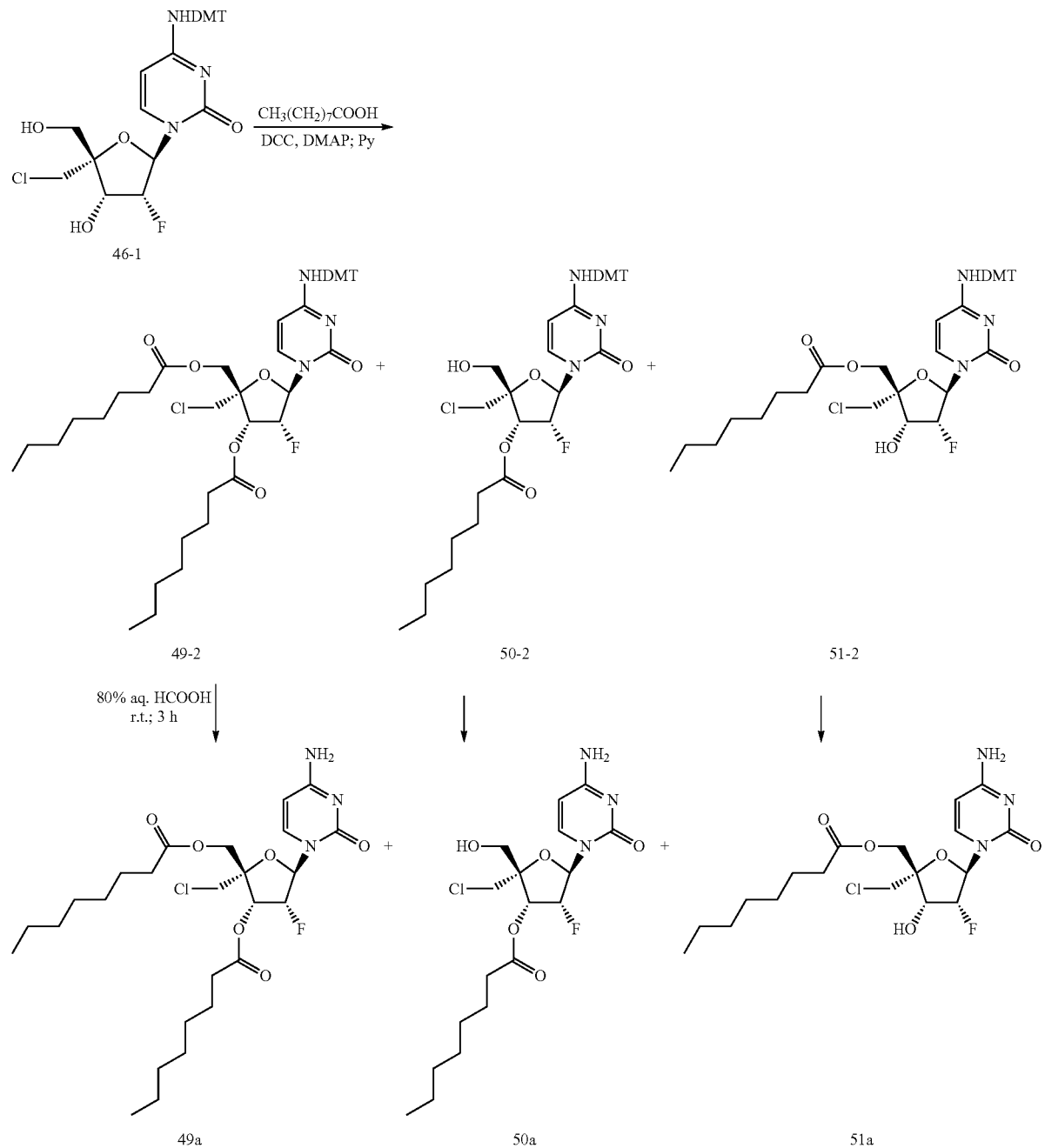

Preparation of (49-2), (50-2) and (51-2):

To a solution of 46-1 (1.26 g, 2.12 mmol) in pyridine (15 mL) were added n-octanoic acid (0.34 mL, 1.0 equiv.), DCC (60% in xylene; 0.81 mL, 1 equiv.) and DMAP (52 mg; 0.2 equiv.). The resulting mixture was stirred for 6 hours at R.T. The mixture was evaporated, and the residue partitioned between $CH_2Cl_2$ (100 mL) and saturated aq. $NaHCO_3$ (25 mL). The organic layer was washed with water, brine and dried ($Na_2SO_4$). The residue was treated with toluene. The solid material was filtered off, and the filtrate was purified on silica (25 g column) with a hexanes/EtOAc solvent system (30-100% gradient) to yield 49-2 (0.57 g, 32%), 50-2 (0.18 g, 12%), and 51-2 (0.2 g, 13%).

Preparation of (49a):

A mixture of 49-2 (114 mg, 0.13 mmol) and 80% aq. formic acid was stirred for 3 hours at R.T. The mixture was evaporated and coevaporated with toluene and purified on silica (10 g column) with a $CH_2Cl_2$/MeOH solvent system (2-8% gradient) to yield 49a (53 mg, 75%). MS: m/z=544 (M−1).

Preparation of (50a):

50a (44 mg, 75% yield) was prepared from 50-2 (104 mg, 0.14 mmol) in the same manner as described for 49a by using a 4-10% gradient of MeOH in CH$_2$Cl$_2$ for purification. MS: m/z=418 (M−1).

Preparation of (51a):

51a (60 mg, 71% yield) was prepared from 50-2 (140 mg, 0.2 mmol) in the same manner as described for 49a by using a 4-10% gradient of MeOH in CH$_2$Cl$_2$ for purification. MS: m/z=418 (M−1).

Example 49

Preparation of Compound (52a)

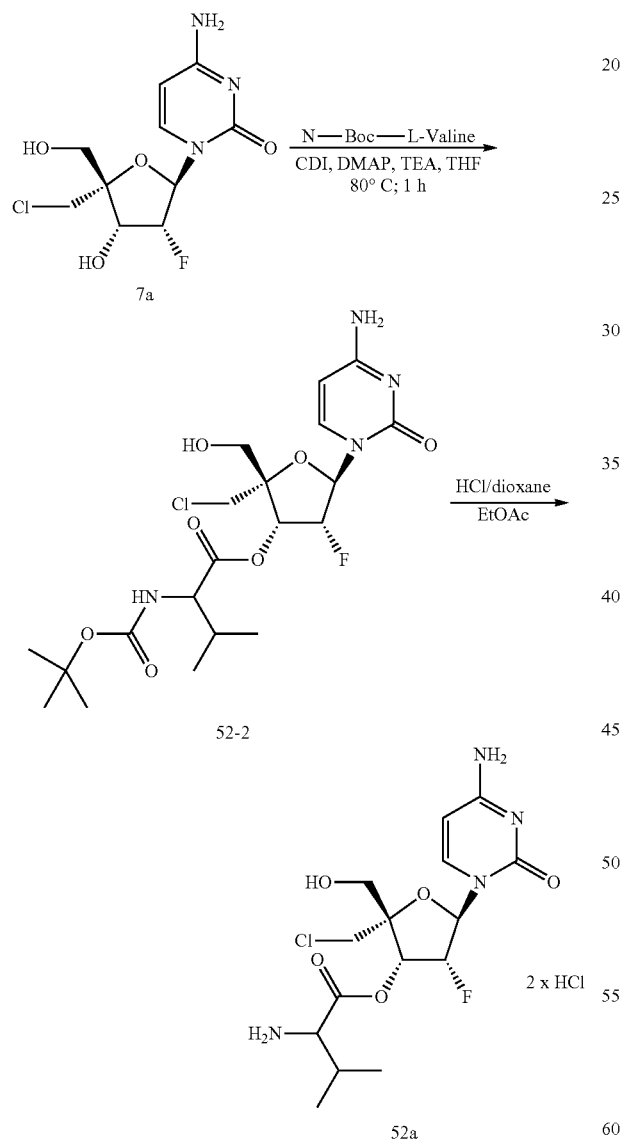

Preparation of (52-2):

A solution of N-(tert-butoxycarbonyl)-L-valine (0.41 g, 1.9 mmol) and carbonyldiimidazole (0.31 g, 1.9 mmol) in THF (9 mL) was stirred at R.T. for 1.5 hours. The mixture was then stirred at 40° C. for 20 mins. The mixture was added to a solution of 7a (0.42 g, 1.43 mmol) and DMAP (25 mg, 0.2 mmol) in DMF (8 mL) and TEA (4 mL) at 80° C. The reaction mixture was stirred at 80° C. for 1 h, then cooled and concentrated. The residue was partitioned between tert-butyl methyl ether (100 mL) and water. The organic layer was washed with water, brine and dried (Na$_2$SO$_4$). The residue was purified on silica (25 g column) with a CH$_2$Cl$_2$/MeOH solvent system (2-10% gradient) to yield 52-2 (0.32 g, 90% in the mixture with 5'-isomer), which was repurified by RP-HPLC (10-100% B; A: water, B: MeOH). Yield: 0.25 g (35%).

Preparation of (52a):

A solution of 52-2 (0.12 g; 0.24 mmol) in EtOAc (0.6 mL) was treated with HCl/dioxane (4 M; 0.6 mL) for 20 mins. with vigorous shaking. The white precipitate was filtered, washed with diethyl ether and dried to yield 52a as the dihydrochloride salt (95 mg; 85%). MS: m/z=391 (M−1).

Example 50

Preparation of Compound (53a)

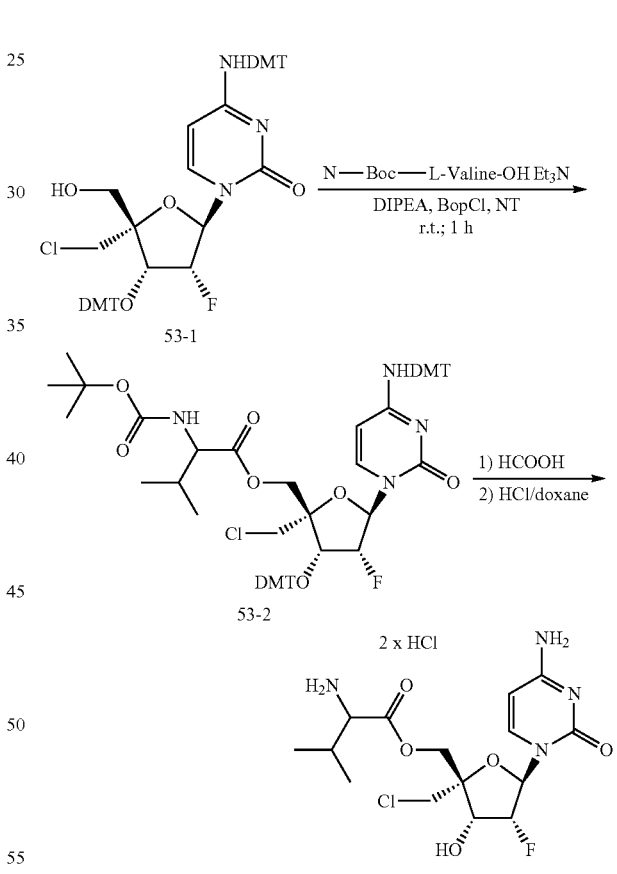

Preparation of (53-2):

To a solution of N-Boc-Val-OH (0.16 g, 0.74 mmol) and Et$_3$N (0.14 mL, 1.0 mmol) in THF was added 53-1. The resulting mixture was evaporated, coevaporated with pyridine and toluene and dissolved in THF (4 mL). DIPEA (0.38 mL, 2.2 mmol) was added, followed by BOP-Cl (0.28 g, 1.1 mmol) and 3-nitro-1,2,4-triazole (0.13 g, 1.1 mmol). The reaction mixture was stirred at R.T. for 1 h. The mixture was diluted with CH$_2$Cl$_2$ (40 mL) and washed with saturated aq.

NaHCO$_3$ and brine. The combined aqueous layers were back extracted with CH$_2$Cl$_2$. The combined organic extract was dried (Na$_2$SO$_4$), evaporated, and the residue was purified on silica (10 g column) with a hexanes/0.5% Et$_3$N/EtOAc solvent system (20-100% gradient) to yield 53-2 (0.39 g, 81%).

Preparation of (53a):

A mixture of 14-2 (0.37 g, 0.33 mmol) and 80% aq. HCOOH (10 mL) was stirred at R.T. for 3 hours. The mixture was evaporated, and the residue was partitioned between water and CH$_2$Cl$_2$. The aqueous layer was washed with CH$_2$Cl$_2$ and evaporated. The solid residue was suspended in EtOAc (1.5 mL) and treated with 4N HCl in dioxane (1.5 mL) with vigorous shaking. The solid was filtered, washed with diethyl ether and purified by RP-HPLC (A: 0.5N HCOOH in water, B: 0.5N HCOOH in acetonitrile). The resulting formic acid salt of 5'-O-valyn ester was converted into 53a dihydrochloride salt (63 mg, 40%) by suspending in EtOAc (2 mL) and treatment with 4N HCl/dioxane (2 mL). MS: m/z=391 (M−1).

Example 51

Preparation of Compound (39a)

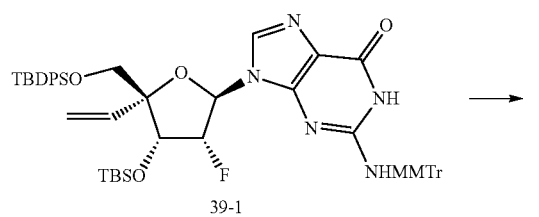

39-1

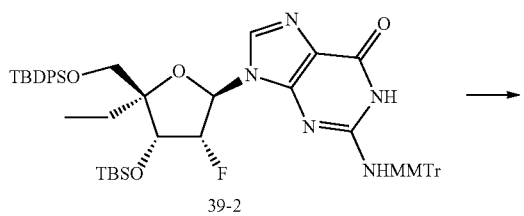

39-2

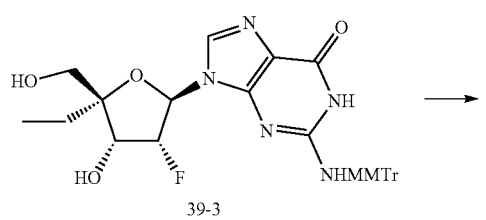

39-3

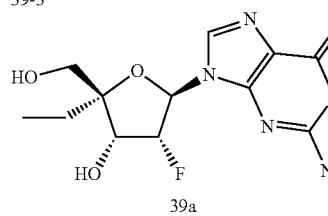

39a

Preparation of (39-2):

A solution of 39-1 (1.3 g, 1.4 mmol) in anhydrous MeOH (20 mL) was charged with Pd/C (1.3 g) and stirred at 25° C. under hydrogen (1 atm) atmosphere for 1 hour. The solution was filtered, evaporated to dryness, and purified on a silica gel column (DCM:MeOH=100:1 to 50:1) to give 39-2 (1.2 g, 92.3%) as a white solid.

Preparation of (39-3):

To a solution of 39-2 (1.2 g, 1.3 mmol) in MeOH (40 mL) was added NH$_4$F (370 mg, 10 mmol) at 25° C. and stirred at 60° C. for 6 hours. The solution was filtered, evaporated to dryness, and purified on a silica gel column (DCM:MeOH=200:1 to 20:1) to give 39-3 as a white solid (249 mg, 30.7%). $^1$H NMR (MeOD, 400 MHz) δ 7.92 (s, 1H), 7.19-7.33 (m, 12H), 6.83-6.85 (m, 2H), 5.50 (dd, J$_1$=4.0 Hz, J$_2$=14.8 Hz, 1H), 4.19-4.88 (m, 1H), 4.22 (dd, J$_1$=5.2 Hz, J$_2$=16.0 Hz, 1H), 3.76 (s, 3H), 3.41 (dd, J$_1$=12.0 Hz, J$_2$=36.8 Hz, 2H), 1.52-1.74 (m, 2H), 0.87 (t, J=7.6 Hz, 3H); ESI-LCMS: m/z 586.1 [M+H]$^+$.

Preparation of (39a):

A solution of 39-3 of 80% formic acid/20% water (3 mL) stood at RT for 2 hours, and then was concentrated to dryness. The residue was co-evaporated with MeOH/toluene (3 times) and then ethyl acetate added. The suspension in ethyl acetate was heated at 70° C. for 5 mins. The solvent was removed using a pipet. This washing was repeated 3 times. The resulting product (44 mg) was further purified on reverse-phase HPLC using acetonitrile/water as mobile phase to give 39a (20 mg) as an off-white solid. $^1$H NMR (DMSO, 400 MHz) δ 7.92 (s, 1H), 10.82 br, 1H), 7.96 (s, 1H), 6.56 (s, 2H), 5.99 (dd, J=6.0, 12.8 Hz, 1H), 5.65 (d, J=4.8 Hz, 1H), 5.58, 5.45 (2t, J=5.2 Hz, 0.5H, 0.5H), 5.25 (br, 1H), 4.19-4.88 (m, 1H), 4.22 (dd, J$_1$=5.2 Hz, J$_2$=16.0 Hz, 1H), 3.76 (s, 3H), 3.41 (dd, J$_1$=12.0 Hz, J$_2$=36.8 Hz, 2H), 1.52-1.74 (m, 2H), 0.87 (t, J=7.6 Hz, 3H); ESI-LCMS: m/z 443.6 [M+6-methyl-2-heptylamine)]$^+$.

Example 52

Preparation of Compounds (55a) and (56a)

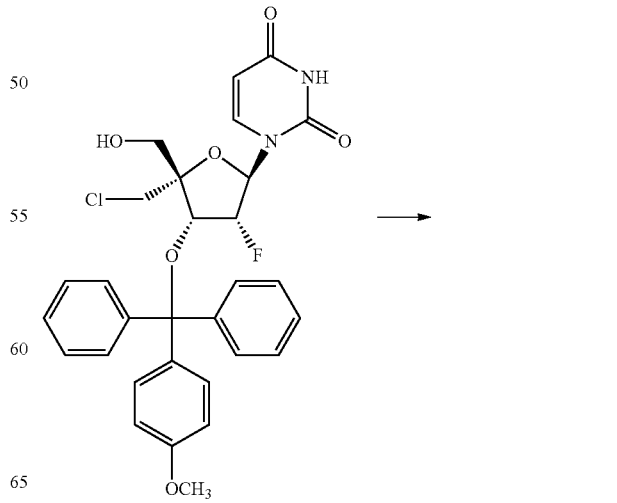

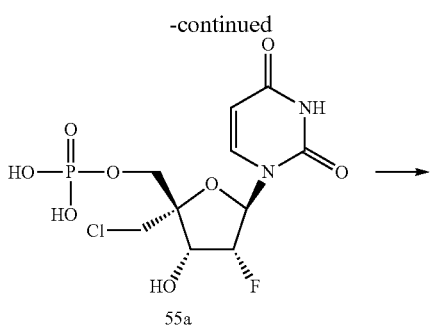

55a

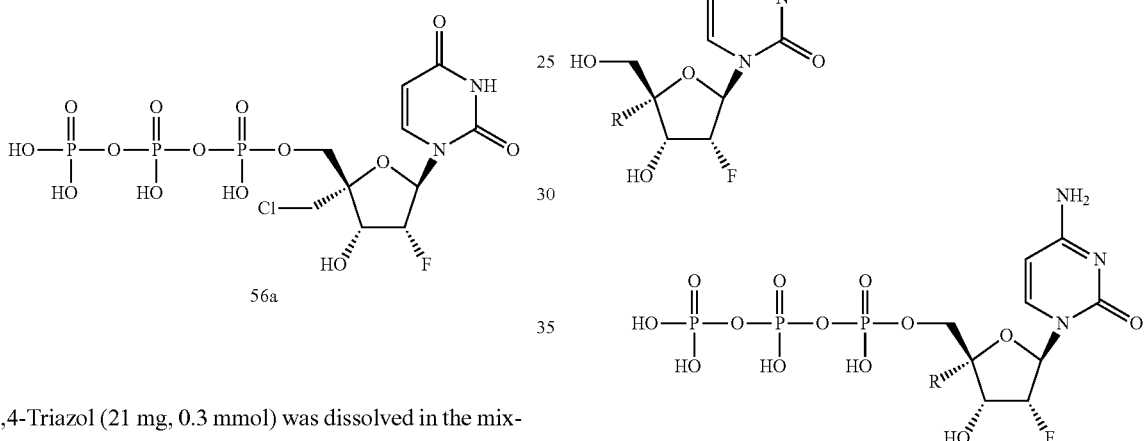

1,2,4-Triazol (21 mg, 0.3 mmol) was dissolved in the mixture of CH$_3$CN (0.7 mL) and Et$_3$N (44 µL, 0.31 mmol). POCl$_3$ (9 ul, 0.1 mmol) was added, and the mixture was kept at R.T. for 20 mins. The white precipitate was filtered, and the filtrate added to the dry nucleoside (28 mg, 0.05 mmol). The reaction was controlled by TLC and monitored by the disappearance of the starting nucleoside. After completion of the reaction, tetrabutylammonium salt of pyrophosphate (150 mg) was added, followed by DMF (0.5 mL) to get a homogeneous solution. After 1.5 hours at ambient temperature, the reaction was diluted with water (4 mL) and extracted with DCM (2×5 mL). The combined organic extracts were evaporated, dissolved in 5 mL of 80% HCOOH and left for 2 hours at R.T. The reaction mixture was concentrated and distributed between water (5 mL) and DCM (5 mL). The aqueous fraction was loaded on the column HiLoad 16/10 with Q Sepharose High Performance. Separation was done in a linear gradient of NaCl from 0 to 1N in 50 mM TRIS-buffer (pH7.5). Two fractions were obtained. The first fraction, containing the monophosphate (55a) was eluted at 70-75% B. and triphosphate (56a) was eluted at 75-80% B. Both fractions were desalted by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer.

Example 53

Preparation of Compounds (56b-e)

1,2,4-Triazol (21 mg, 0.3 mmol) was dissolved in the mixture of CH$_3$CN (0.7 mL) and Et$_3$N (44 µL, 0.31 mmol). POCl$_3$ (9 ul, 0.1 mmol) was added, and the mixture was kept at R.T. for 20 mins. The white precipitate was filtered, and the filtrate added to the dry nucleoside (28 mg, 0.05 mmol). The reaction was controlled by TLC and monitored by the disappearance of the starting nucleoside. After completion of the reaction, tetrabutylammonium salt of pyrophosphate (150 mg) was added followed by DMF (0.5 mL) to get a homogeneous solution. After 1.5 hours at ambient temperature, the reaction was diluted with water (4 mL) and extracted with DCM (2×5 mL). The combined organic extracts were evaporated, dissolved in 5 mL of 80% HCOOH and left for 4 hours at 38° C. The reaction mixture was concentrated and distributed between water (5 mL) and DCM (5 mL). The aqueous fraction was loaded on the column HiLoad 16/10 with Q Sepharose High Performance. Separation was done in a linear gradient of NaCl from 0 to 1N in 50 mM TRIS-buffer (pH7.5). Two fractions were obtained. The triphosphate (56b-e) was eluted at 75-80% B. Desaltin was performed by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer.

TABLE 3
Triphosphates obtained from Example 53
| Structure | MS (M − 1) | P(α) | P(β) | P(γ) |
|---|---|---|---|---|
| 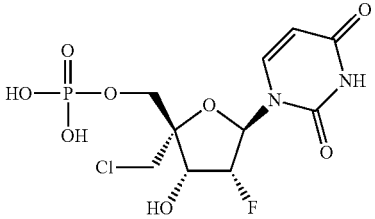 55a | 373.00 | +3.64 (s) | NA | NA |
| 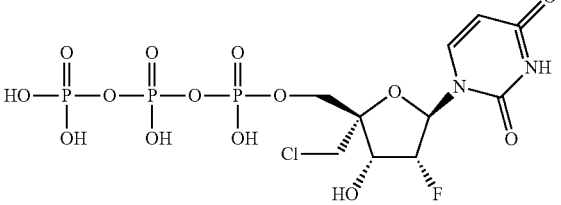 56a | 532.95 | −6.67<br>−6.74<br>(d) | −21.87 (t) | −11.51<br>−11.63<br>(d) |
| 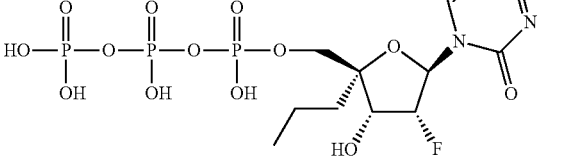 56b | 526.05 | −6.33<br>−6.74<br>(d) | −22.48 (t) | −11.53<br>−11.64<br>(d) |
| 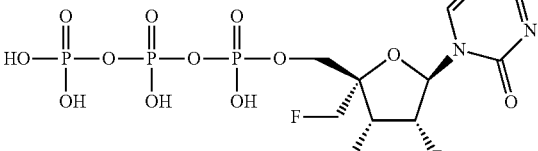 56c | 516.00 | −63.2 (bs) | −22.45 (t) | −11.64 (d) |
| 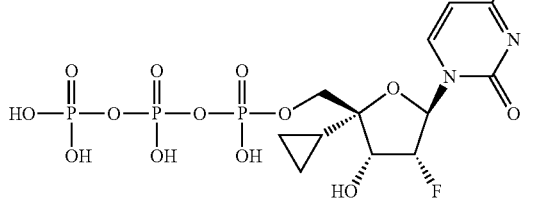 56d | 524.4 | −10.57<br>−10.67<br>(d) | −23.31 (t) | −11.31<br>−11.94<br>(d) |

TABLE 3-continued

Triphosphates obtained from Example 53

| Structure | MS (M − 1) | P(α) | P(β) | P(γ) |
|---|---|---|---|---|
| 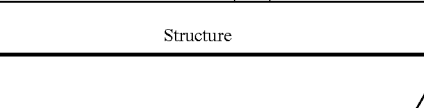　56e | 529.8 | −6.17 (bs) | −21.96 (bs) | −11.42 (bs) |

Example 54

Preparation of Compound (57a)

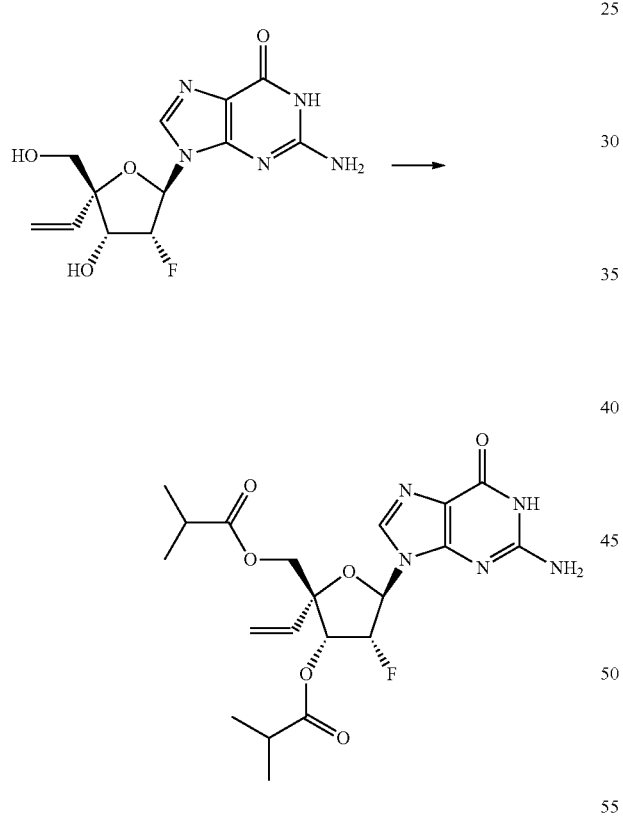

2'-Deoxy-2'-fluoro-4'-C-(ethenyl)guanosine (25a, 31 mg, 0.1 mmol) was dissolved in dry pyridine (3 mL). Isobutyric anhydrate (50 μL, 0.3 mmol) was added. The reaction mixture was kept at ambient temperature. After 40 hours, isobutyric anhydrate (100 μL, 0.6 mmol) was added, and the reaction mixture was left overnight. The pyridine was evaporated. The residue was purified by silica gel chromatography using a gradient of methanol in DCM from 3% to 10% to yield 57a (20 mg, 50%). $^1$H NMR (DMSO-d6) δ: 10.72 (s, 1H), 7.88 (s, 1H), 6.47 (s, 2H), 6.18-6.13 (dd, 1H), 5.90-5.83 (dd, 1H), 5.79-5.62 (m, 2H), 5.49-5.44 (d, 1H), 5.35-5.32 (d, 1H), 4.28-4.25 (d, 1H), 4.12-4.10 (d, 1H), 2.60-2.45 (m, 2H), 1.12-1.09 (m, 6H), 1.02-0.96 (m, 6H); m/z 452 (M+1).

Example 55

Preparation of Compound (58a)

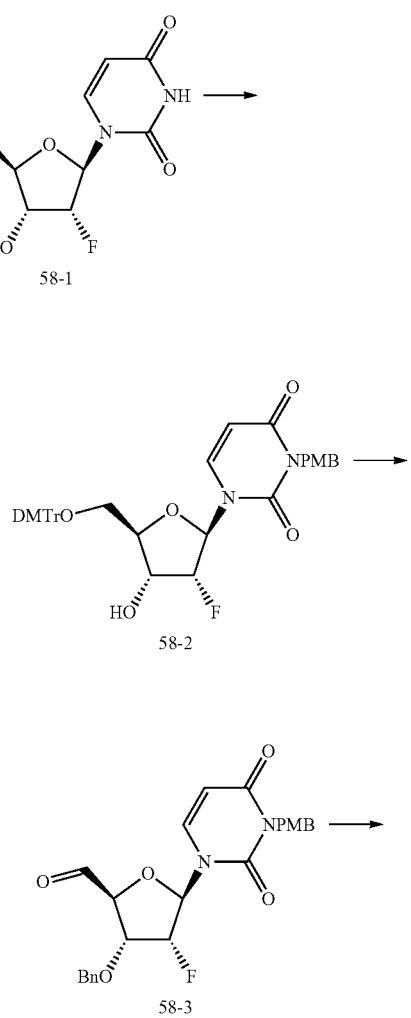

-continued

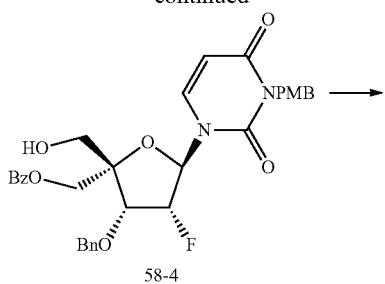
58-4

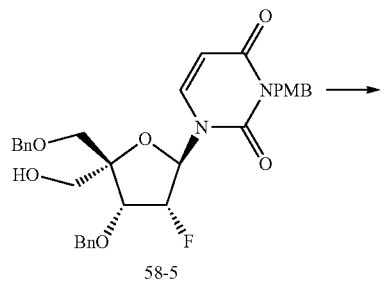
58-5

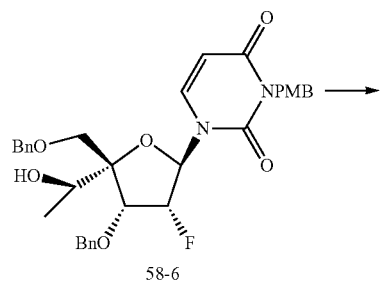
58-6

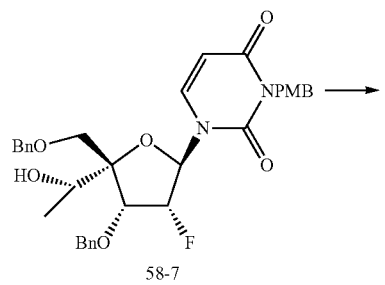
58-7

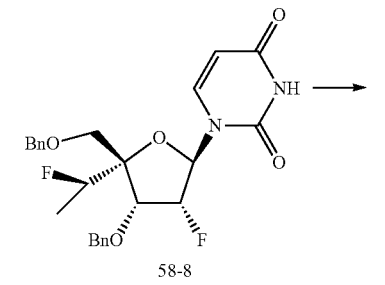
58-8

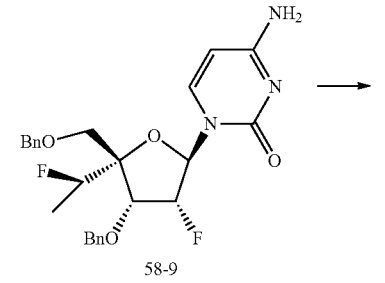
58-9

-continued

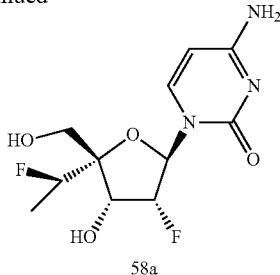
58a

Preparation of (58-2):

To a solution of 58-1 (50.0 g, 205 mmol) in pyridine (250 mL) was added DMTrCl (75.0 g, 225.0 mmol). The solution was stirred at R.T. for 15 hours. MeOH (120 mL) was added, and the mixture was concentrated to dryness under reduced pressure. The residue was dissolved in EA and washed with water. The organic layer was dried over Na$_2$SO$_4$ and concentrated to give the crude DMTr protected derivative (80.5 g, 89%) as a light yellow solid. Dried K$_2$CO$_3$ (80.52 g, 583.2 mmol) and then PMBCl (31.7 g, 109.2 mmol) were added to a stirred solution of the DMTr protected derivative (80 g, 146 mmol) in anhydrous DMF (300 mL). The stirring was continued at ambient temperature for overnight. The reaction was monitored by TLC. The mixture was diluted with EA and washed with water. The organic layer was dried over Na$_2$SO$_4$ and concentrated to give 58-2 (98.8 g, 90%) as light yellow solid.

Preparation of (58-3):

NaH (10.4 g, 260.5 mmol) and BnBr (73.8 g, 434.2 mmol) were added to a stirred solution of 58-2 (98.8 g, 147.9 mmol) in anhydrous DMF (300 mL), and the stiffing was continued at 25° C. overnight. The reaction was monitored by TLC. The reaction was quenched with water, extracted with EA and washed with brine. The solvent was removed, and the residue was purified on silica gel (PE:EA=10:1 to 3:1) to give the Bn protected derivative (101.1 g, 90%) as a light yellow solid. The Bn protected derivative (101.1 g, 133.4 mmol) was dissolved in 80% HOAc (900 mL) at 25° C. The mixture was stirred at 25° C. overnight. The reaction was quenched with MeOH, and the solvent was removed to give the alcohol (42.1 g, 70%) as a white foam. To a solution of the alcohol (42.1 g, 92.6 mmol) in anhydrous CH$_3$CN (300 mL) was added IBX (28.5 g, 121.7 mmol) at 25° C. The reaction mixture was refluxed for 1 hour and then cooled to 0° C. The precipitate was filtered-off, and the filtrate was concentrated to give 58-3 (39.2 g, 93%) as a yellow solid.

Preparation of (58-4):

To a solution of 58-3 (39.2 g, 86.39 mmol) in 1,4-dioxane (250 mL) was added 37% CH$_2$O (28.1 mL, 345.6 mmol) and 2N NaOH aqueous solution (86.4 mL, 172.8 mmol). The mixture was stirred at 25° C. for 2 h and then neutralized with AcOH to pH=7. To the reaction were added EtOH (200 mL) and NaBH$_4$ (19.7 g, 518.6 mmol). The mixture was stirred at 25° C. for 30 mins. The reaction was quenched with saturated aqueous NH$_4$Cl. The mixture was extracted with EA, and the organic layer was dried over Na$_2$SO$_4$ and concentrated. The residue was purified by silica gel column chromatography (PE:EA=4:1 to 2:1) to give the diol derivative (25.5 g, 55%) as a white solid. To a stirred solution of the diol derivative (25.5 g, 52.5 mmol) in anhydrous pyridine (150 mL) and anhydrous CH$_3$CN (150 mL) was added BzCl (6.6 g, 52.47 mmol) dropwise at 0° C. The mixture was then stirred at 25° C. for 14 h. The reaction was quenched with H$_2$O, and the solution was concentrated. The residue was dissolved in EA and washed with NaHCO$_3$. The organic layer was dried over Na$_2$SO$_4$ and concentrated. The residue was purified on a silica gel column (PE/EA=5:4) to give 58-4 (18.1 g, 60%) as a white foam.

Preparation of (58-5):

Cs$_2$CO$_3$ (30.0 g, 92.0 mmol) and BnBr (10.4 g, 61.3 mmol) were added to a stirred solution of compound 58-4 (18.1 g, 30.6 mmol) in anhydrous DMF (300 mL), and stirring was continued at 25° C. overnight. The reaction was quenched with NH$_4$Cl, extracted with EA and washed with brine. The solvent was removed to give the Bz protected derivative (19.3 g, 95%) as a light yellow solid. To a stirred solution of the Bz protected derivative (19.3 g, 28.4 mmol) in anhydrous MeOH (230 mL) was added NaOMe (24.9 g, 460 mmol) at 25° C. for 1 h. The reaction was quenched with AcOH (10 mL) and concentrated. The residue was purified on a silica gel column (PE/EA=1/2) to afford 58-5 (11.2 g, 54%) as a white solid.

Preparation of (58-6):

To a stirred solution of 58-5 (200 mg, 0.347 mmol) in anhydrous DCM (5 mL) was added DMP (168 mg, 0.674 mmol) at 25° C. The mixture was stirred at 25° C. for 2 h. The solvent was removed, and the residue was purified on a silica gel column (PE:EA=5:1 to 1:1) to give the aldehyde derivative (161 mg, 81%). To a stirred solution of the aldehyde derivative (200 mg, 0.348 mmol) in anhydrous THF (5 mL) was added MeMgBr (1.0 mL, 1.01 mmol) at −78° C. The mixture was stirred at −78° C. for 1 h. The reaction was quenched with NH$_4$Cl and extracted with EA. The concentrated organic phase was purified by column chromatography (PE:EA=5:1 to 1:1) to give 58-6 (135 mg, 65%).

Preparation of (58-7):

To a solution of 58-6 (900 mg, 1.5 mmol) in DCM was added DMP (2.5 g, 6.0 mmol) at 0° C. After stirring at 0° C. for 1 h, the mixture was quenched with Na$_2$S$_2$O$_3$. The solvent was removed, and the residue was purified on a silica gel column (PE:EA=5:1 to 1:1) to give the ketone derivative (700 mg, 78%). To a solution of the ketone derivative (700 mg, 1.52 mmol) in MeOH was added NaBH$_4$ in portions. After stiffing at the same temperature for 1 h, the mixture was quenched with water. The solvent was removed, and the residue was purified on a silica gel column (PE:EA=5:1 to 1:1) to give 58-7 (500 mg, 71%).

Preparation of (58-8):

To a stirred solution of DAST (1.39 g, 8.68 mmol) in anhydrous toluene (15 mL) was added dropwise a solution of 58-6 (1.0 g, 1.73 mmol) at −78° C. The mixture was stirred at −78° C. for 30 min. The solution was warmed to 25° C. slowly and stirring continued overnight. The mixture was poured into a saturated Na$_2$CO$_3$ solution. The concentrated organic phase was purified on a silica gel column (PE:EA=10:1 to 4:1) to give the fluoride derivative (449 mg, 45%). A mixture of the fluoride derivative (1.20 g, 2.07 mmol) and CAN (3.41 g, 6.23 mmol) in a 3:1 solution of MeCN and water (10 mL) was stirred at 25° C. overnight. Brine (10 mL) was added, and the mixture extracted with EA. The combined organic extracts were dried and evaporated under reduced pressure. Purification by chromatography on silica with PE:EA=10:1 to 2:1 gave 58-8 as a yellow solid (475 mg, 50%).

Preparation of (58-9):

To a stirred solution of 58-8 (550 mg, 210 mmol) in anhydrous MeCN (10 mL) were added TPSCl (725 mg, 2.40 mmol), DMAP (293 mg, 2.40 mmol) and TEA (242 mg, 2.40 mmol) at 25° C. The mixture was stirred at 25° C. overnight. NH$_4$OH (25 mL) was added and stirred for 2 h. The solvent was removed, and the residue was purified on a silica gel column (DCM:MeOH=10:1) to give 58-9 (300 mg). $^1$H NMR (CD$_3$OD, 400 MHz) δ 7.70 (d, J=8.4 Hz, 1H), 7.25-7.36 (m, 10H), 6.13 (dd, J=2.8, 16.8 Hz, 1H), 5.40 (d, J=7.6 Hz, 1H), 5.15 (m, 1H), 4.81 (d, J=11.6 Hz, 1H), 4.40-4.52 (m, 4H), 3.82 (d, J=8.8 Hz, 7H), 3.62 (d, J=9.6 Hz, 7H), 1.35 (dd, J=2.8, 14.4 Hz, 3H). ESI-MS: m/z 472.1 [M+H]$^+$.

Preparation of (58a):

A 1 M boron trichloride solution in CH$_2$Cl$_2$ (3.2 mL; 3.2 mmol) was added dropwise to a solution of 58-9 (200 mg, 0.42 mmol) in anhydrous CH$_2$Cl$_2$ (10 mL) at −78° C. The mixture was slowly (in 4 h) warmed to −30° C. and stirred at −30 to −20° C. for 3 h. Ammonium acetate (1 g) and MeOH (5 mL) were added, and the resulting mixture allowed to warm to ambient temperature. The solvent was removed, and residue purified by RP-HPLC (0-60% B; A: 50 mM aqueous TEAA, B: 50 mM TEAA in MeOH) to yield 58a (75 mg). $^1$H NMR (CD$_3$OD) δ 7.97 (d, 1H), 6.20 (dd, 1H), 5.92 (d, 1H), 5.22 (dt, 1H), 4.98 (dq, 1H), 4.58 (dd, 1H), 3.73 (m, 2H), 1.40 (dd, 3H). $^{19}$F NMR (CD$_3$OD) δ −205.80 (m, 1F), −188.54 (m, 1F). ESI-MS: m/z 290.4 [M−H]$^−$.

Example 56

Preparation of Compound (59a)

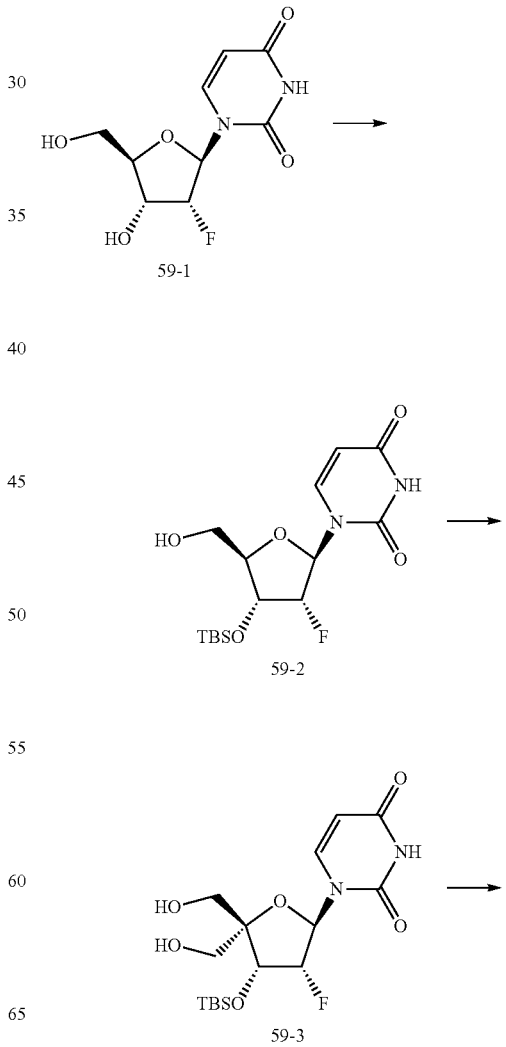

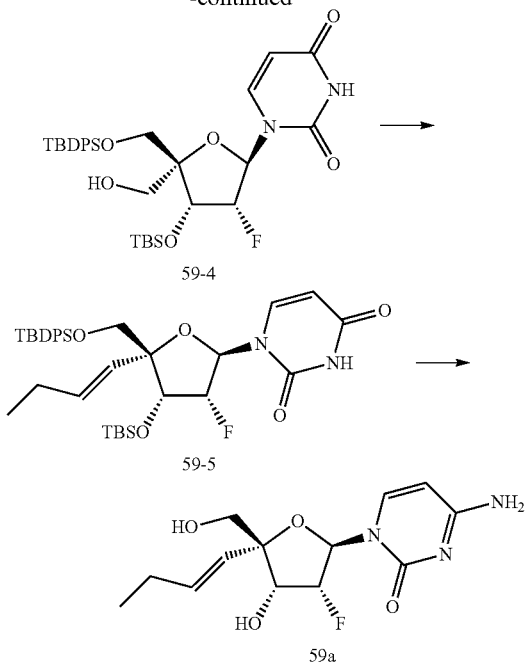

Preparation of (59-2):

To a solution of 59-1 (100.0 g, 406.5 mmol) in pyridine (750 mL) was added DMTrCl (164.9 g, 487.8 mmol). The solution was stirred at R.T. for 15 h. MeOH (300 mL) was added, and the mixture was concentrated to dryness under reduced pressure. The residue was dissolved in EtOAc and washed with water. The organic layer was dried over $Na_2SO_4$ and concentrated. The residue was dissolved in DCM (500 mL). To this solution were added imidazole (44.3 g, 650.4 mmol) and TBSCl (91.9 g, 609.8 mmol). The resulting reaction mixture was stirred at R.T. for 14 h. The reaction solution was washed with $NaHCO_3$ and brine. The organic layer was dried over $Na_2SO_4$, and concentrated to give the crude product as a light yellow solid. The crude product (236.4 g, 356.6 mmol) was dissolved in 80% HOAc aqueous solution (500 mL). The mixture was stirred at R.T. for 15 h. The mixture was diluted with EtOAc, washed with $NaHCO_3$ solution and brine. The organic layer was dried over $Na_2SO_4$ and purified on a silica gel column chromatography (1-2% MeOH in DCM) to give 59-2 (131.2 g, 89.6%) as a light yellow solid. $^1$H NMR (DMSO-d6, 400 MHz) δ 11.39 (s, 1H), 7.88 (d, J=7.2 Hz, 1H), 5.89 (dd, J=18.0 Hz, J=2.0 Hz, 1H), 5.64 (d, J=8.0 Hz, 1H), 5.21 (dd, $J_1$=$J_2$=7.2 Hz, 1H), 5.18-5.03 (m, 1H), 4.37-4.29 (m, 1H), 3.86 (dd, J=3.2 Hz, J=3.2 Hz, 3H), 3.78-3.73 (m, 1H), 3.51-3.56 (m, 1H), 3.31 (s, 1H), 0.89 (s, 9H), 0.11 (s, 6H); ESI-MS: m/z 802 [M+H]$^+$.

Preparation of (59-3):

To a solution of 59-2 (131.2 g, 364.0 mmol) in anhydrous $CH_3CN$ (1200 mL) was added IBX (121.2 g, 432.8 mmol) at R.T. The reaction mixture was refluxed for 3 h and then cooled to 0° C. The precipitate was filtered-off, and the filtrate was concentrated to give the crude aldehyde (121.3 g) as a yellow solid. The aldehyde was dissolved in 1,4-dioxane (1000 mL). 37% $CH_2O$ (81.1 mL, 1.3536 mol) and 2M NaOH aqueous solution (253.8 mL, 507.6 mmol) were added. The mixture was stirred at R.T. for 2 h and then neutralized with AcOH to pH=7. To the solution were added EtOH (400 mL) and $NaBH_4$ (51.2 g, 1.354 mol). The mixture was stirred at R.T. for 30 mins and quenched with sat. aqueous $NH_4Cl$. The mixture was extracted with EA. The organic layer was dried over $Na_2SO_4$ and concentrated. The residue was purified by silica gel column chromatography (1-3% MeOH in DCM) to give 59-3 (51.4 g, 38.9%) as a white solid.

Preparation of (59-4):

To a solution of 59-3 (51.4 g, 131.6 mmol) in anhydrous DCM (400 mL) were added pyridine (80 mL) and DMTrCl (49.1 g, 144.7 mmol) at 0° C. The reaction was stirred at R.T. for 14 h, and then treated with MeOH (30 mL). The solvent was removed, and the residue was purified by silica gel column chromatography (1-3% MeOH in DCM) to give the mono-DMTr protected intermediate as a yellow foam (57.4 g, 62.9%). To the mono-DMTr protected intermediate (57.4 g, 82.8 mmol) in $CH_2Cl_2$ (400 mL) was added imidazole (8.4 g, 124.2 mmol) and TBDPSCl (34.1 g, 124.2 mmol). The mixture was stirred at R.T. for 14 h. The precipitated was filtered off, and the filtrate was washed with brine and dried over $Na_2SO_4$. The solvent was removed to give the residue (72.45 g) as a white solid, which was dissolved in 80% HOAc aqueous solution (400 mL). The mixture was stirred at R.T. for 15 h. The mixture was diluted with EtOAc, washed with $NaHCO_3$ solution and brine. The organic layer was dried over $Na_2SO_4$ and purified by silica gel column chromatography (1-2% MeOH in DCM) to give 59-4 (37.6 g, 84.2%) as a white solid. $^1$H NMR ($CD_3OD$, 400 MHz) δ 7.76 (d, J=4.0 Hz, 1H), 7.70 (dd, J=1.6 Hz, J=8.0 Hz, 2H), 7.66-7.64 (m, 2H), 7.48-7.37 (m, 6H), 6.12 (dd, J=2.8 Hz, J=16.8 Hz, 1H), 5.22 (d, J=8.0 Hz, 1H). 5.20-5.05 (m, 1H), 4.74 (dd, J=5.6 Hz, J=17.6 Hz, 1H), 4.16 (d, J=12.0 Hz, 1H), 3.87-3.80 (m, 2H), 3.56 (d, J=12.0 Hz, 1H), 1.16 (s, 9H), 0.92 (s, 9H), 0.14 (s, 6H).

Preparation of (59-5):

To a solution of 59-4 (3.0 g, 4.78 mmol) in anhydrous DCM (100 mL) was added Dess-Martin periodinane (10.4 g, 23.9 mmol) at 0° C. under nitrogen. The reaction mixture was stirred at R.T. for 5 h. The mixture was poured into $NaHCO_3$ and $Na_2S_2O_3$ (1:1) aqueous solution. The organic layer was dried over anhydrous $Na_2SO_4$ and concentrated to give a residue. The residue was purified on a silica gel column (20% EtOAc in PE) to give the intermediate (2.5 g, 83.1%) as a white solid.

To a mixture of bromotriphenyl(propyl)phosphorane (6.45 g, 16.8 mmol) in anhydrous THF (3 mL) was added t-BuOK (16.8 mL, 16.8 mmol) at 0° C. under nitrogen. The reaction mixture was stirred at 0° C. for 50 mins. A solution of the above intermediate (1.5 g, 2.4 mmol) in anhydrous THF (3 mL) was added dropwise at 0° C. under nitrogen. The reaction mixture was stirred at R.T. for 3 h. The reaction was quenched by $NH_4Cl$ aqueous solution and extracted with EtOAc. The organic layer was dried over anhydrous $Na_2SO_4$ and concentrated to give a residue. The residue was purified on a silica gel column (20% EtOAc in PE) to give 59-5 (1.3 g, 83%) as a white solid.

Preparation of (59a):

To a solution of 59-5 (300 mg, 0.45 mmol) in anhydrous $CH_3CN$ (2 mL) were added TPSCl (341 mg, 1.13 mmol), DMAP (138 mg, 1.13 mmol) and $NEt_3$ (571 mg, 5.65 mmol) at R.T. The reaction mixture was stirred at R.T. for 2 h. $NH_4OH$ (1 mL) was added, and the reaction mixture was stirred for 1 h. The mixture was diluted with EA and washed with water. The organic layer was dried and concentrated to give a residue. The residue was purified on a silica gel column (2% MeOH in DCM) to give the cytidine derivative (285 mg, 95.0%) as a white solid.

To a solution of the cytidine derivative (280 mg, 0.43 mmol) in MeOH (10 mL) was added $NH_4F$ (1.0 g) at R.T. The reaction mixture was refluxed for 12 h. The mixture was filtered, and the filtrate was concentrated. The residue was purified on a silica gel column (10% MeOH in DCM) to give 59a (81 mg, 61%) as a white solid. $^1$H NMR (CD$_3$OD, 400 MHz) δ 8.11 (d, J=8.0 Hz, 1H), 5.91 (dd, J=1.2 Hz, J=17.6 Hz, 1H), 5.90 (d, J=7.6 Hz, 1H), 5.57-5.59 (m, 2H), 4.82-4.96 (m, 1H), 4.42 (dd, J=4.8 Hz, J=24.4 Hz, 1H), 3.72 (d, J=12.4 Hz, 1H) 3.58 (d, J=12.4 Hz, 1H), 2.31-2.41 (m, 2H), 0.99 (t, J=7.6 Hz, 3H). ESI-TOF-MS: m/z 300.1 [M+H]$^+$.

Example 57

Preparation of Compound (60a)

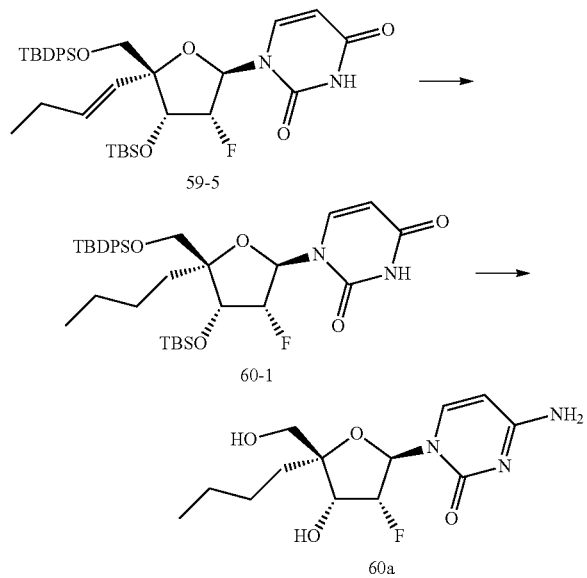

Preparation of (60-1):

To a solution of 59-5 (450 mg, 0.69 mmol) in MeOH (10 mL) was added Pd/C (200 mg) at R.T. The reaction mixture was stirred R.T. for 1 h under H$_2$ (balloon). The mixture was filtered, and the filtrate was concentrated to give crude 60-1 (440 mg, 97.1%) as a white solid.

Preparation of (60a):

To a solution of 60-1 (440 mg, 0.67 mmol) in anhydrous CH$_3$CN (2 mL) were added TPSCl (510 mg, 1.68 mmol), DMAP (205 mg, 1.68 mmol) and NEt$_3$ (338 mg, 3.35 mmol) at R.T. The reaction mixture was stirred at R.T. for 2 h. NH$_4$OH (1 mL) was added, and the reaction was stirred for 1 h. The mixture was diluted with EA and washed with water. The solvent was removed. The crude product was purified on a silica gel column (2% MeOH in DCM) to give the cytidine derivative (205 mg, 46.5%) as a white solid.

To a solution of the cytidine derivative (205 mg, 0.31 mmol) in MeOH (6 mL) was added NH$_4$F (0.6 g) at R.T. The reaction mixture was refluxed overnight. After cooling to R.T., the mixture was filtered. The filtrate was concentrated, and the residue was purified on a silica gel column (10% MeOH in DCM) to give 60a (59 mg, 62.8%) as a white solid. $^1$H NMR (CD$_3$OD, 400 MHz) δ 8.09 (d, J=7.6 Hz, 1H), 6.01 (dd, J=3.2 Hz, J=15.6 Hz, 1H), 5.89 (d, J=7.2 Hz, 1H), 4.95-5.12 (m, 1H), 4.41 (dd, J=5.2 Hz, J=17.2 Hz, 1H), 3.75 (d, J=12.0 Hz, 1H) 3.56 (d, J=11.6 Hz, 1H), 1.73-1.80 (m, 1H), 1.55-1.63 (m, 1H), 1.40-1.46 (m, 4H), 0.92 (t, J=7.6 Hz, 3H). ESI-MS: m/z 301.8 [M+H]$^+$.

Example 58

Preparation of Compound (61a)

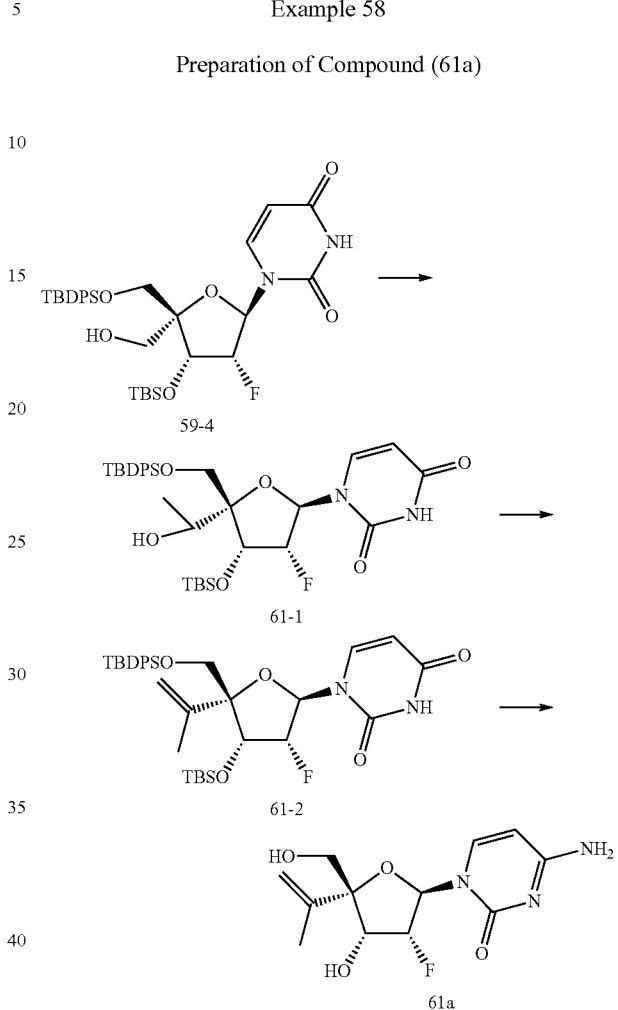

Preparation of (61-1):

To a solution of 59-4 (1.5 g, 2.39 mmol) in anhydrous DCM (100 mL) was added Dess-Martin periodinane (5.2 g, 11.95 mmol) at 0° C. under nitrogen. The reaction mixture was stirred at R.T. for 5 h. The mixture was poured into NaHCO$_3$ and Na$_2$S$_2$O$_3$ solution and washed with brine. The organic layer was dried with anhydrous Na$_2$SO$_4$, and concentrated to give the crude intermediate (1.5 g) as a white solid.

To a solution of the crude intermediate (1.5 g, 2.39 mmol) in THF (12 mL) was added methylmagnesium bromide (2.4 mL, 7.2 mmol) dropwise at 0° C. The resulting mixture was stirred at 0° C. for 2 h. After the starting material was consumed, the reaction was quenched with saturated NH$_4$Cl. The reaction mixture was extracted with DCM. The organic layer was washed with brine, dried and concentrated to give crude 61-1 (1.5 g).

Preparation of (61-2):

To a solution of 61-1 (1.5 g, 2.39 mmol) in anhydrous DCM (50 mL) was added Dess-Martin periodinane (4.5 g, 10.6 mmol). The reaction mixture was stirred at R.T. overnight. The mixture was poured into NaHCO$_3$ and Na$_2$S$_2$O$_3$ aqueous solution. The organic layer was separated, washed with brine, dried and concentrated to give a residue. The residue was purified on a silica gel column (10% EtOAc in PE) to give the intermediate (907 mg, 58.6%) as a white solid.

To a mixture of bromo(methyl)triphenylphosphorane (5.0 g, 14 mmol) in anhydrous THF (8 mL) was added t-BuOK (12.6 mL, 12.6 mmol) at 0° C. under nitrogen. The mixture was stirred at R.T. for 50 mins. A solution of the above intermediate (900 mg, 1.4 mmol) in anhydrous THF (4 mL) was added dropwise at 0° C. under nitrogen. The reaction mixture was stirred at R.T. for 3 h. The reaction mixture was quenched with NH$_4$Cl aqueous solution and extracted with DCM. The organic layer was separated, washed with brine, dried and concentrated to give a residue. The residue was purified on a silica gel column (5% EtOAc in PE) to give 61-2 (700 mg, 78.0%) as a white solid.

Preparation of (61a):

To a solution of 61-2 (298 mg, 0.46 mmol) in anhydrous CH$_3$CN (5.5 mL) were added TPSCl (346.5 mg, 1.14 mmol), DMAP (139.6 mg, 1.14 mmol) and NEt$_3$ (115.6 mg, 1.14 mmol) at R.T. The reaction mixture was stirred at R.T. for 2 h. NH$_4$OH (1 mL) was added, and the mixture was stirred for another 1 h. The mixture was diluted with DCM and washed with water. The organic layer was separated, washed with brine, dried and concentrated to give a residue. The residue was purified on a silica gel column (2% MeOH in DCM) to give the cytidine derivative (250 mg, 85.0%) as a white solid.

To a solution of the cytidine derivative (250 mg, 0.39 mmol) in MeOH (10 mL) was added NH$_4$F (1.0 g) at R.T. The reaction was refluxed for 12 h. The mixture was filtered, and the filtrate was concentrated. The residue was purified on a silica gel column (10% MeOH in DCM) to give 61a (55 mg, 49%) as a white solid. $^1$H NMR (CD$_3$OD, 400 MHz) δ 8.11 (d, J=7.6 Hz, 1H), 6.21 (dd, J=4.2 Hz, J=14.0 Hz, 1H), 5.91 (d, J=7.6 Hz, 1H), 5.10 (dt, J=4.8 Hz, J=53.6 Hz, 1H), 5.13 (brs, 1H), 5.00 (brs, 1H), 4.46 (dd, J=4.8 Hz, J=11.6 Hz, 1H), 3.83 (d, J=11.6 Hz, 1H), 3.54 (d, J=11.6 Hz, 1H), 1.84 (s, 3H). ESI-MS: m/z 285.9 [M+H]±.

Example 59

Preparation of Compound (62a)

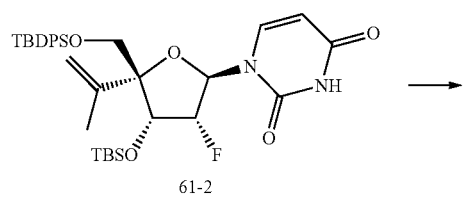
61-2

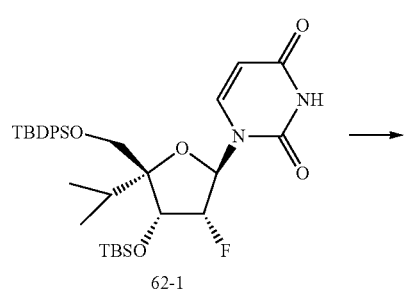
62-1

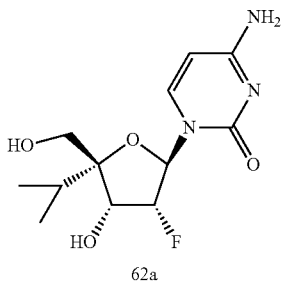
62a

Preparation of (62-1):

To a solution of 61-2 (400 mg, 0.63 mmol) in MeOH (10 mL) was added Pd/C (400 mg) at R.T. The reaction was stirred at R.T. for 5 h under H$_2$ (balloon). The mixture was filtered, and the filtrate was concentrated to give crude 62-2 (350 mg, 87%) as a white solid.

Preparation of (62a):

To a solution of 62-1 (350 mg, 0.55 mmol) in anhydrous CH$_3$CN (6 mL) were added TPSCl (414 mg, 1.4 mmol), DMAP (166.8 mg, 1.4 mmol) and NEt$_3$ (138.1 mg, 1.4 mmol) at R.T. The reaction mixture was stirred at R.T. for 2 h. NH$_4$OH (1 mL) was added, and the reaction was stirred for another 1 h. The mixture was diluted with EA and washed with water. The organic layer was separated, dried and concentrated to give a residue. The residue was purified on a silica gel column (2% MeOH in DCM) to give the cytidine derivative (300 mg, 85%) as a white solid.

To a solution of the cytidine derivative (300 mg, 0.47 mmol) in MeOH (10 mL) was added NH$_4$F (1.5 g) at R.T. The reaction mixture was refluxed overnight. After cooling to R.T., the mixture was filtered. The filtrate was concentrated. The crude product was purified on a silica gel column (10% MeOH in DCM) to give 62a (83 mg, 61%) as a white solid. $^1$H NMR (CD$_3$OD, 400 MHz) δ 8.12 (d, J=7.6 Hz, 1H), 6.22 (dd, J=6.4 Hz, J=12.4 Hz, 1H), 5.94 (d, J=7.6 Hz, 1H), 5.25 (dt, J=5.6 Hz, J=54.0 Hz, 1H), 4.38 (t, J=4.8 Hz, 1H), 3.72 (d, J=11.6 Hz, 1H), 3.67 (d, J=11.6 Hz, 1H), 2.31-2.42 (m, 1H), 0.99 (2d, J=7.2 Hz, 6H). ESI-MS: m/z 287.8 [M+H]$^+$.

Example 60

Preparation of Compound (63a)

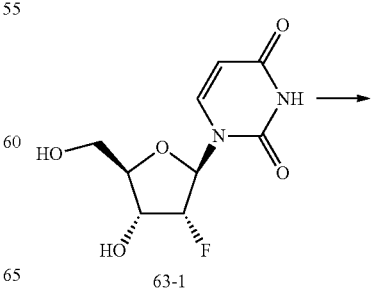
63-1

-continued

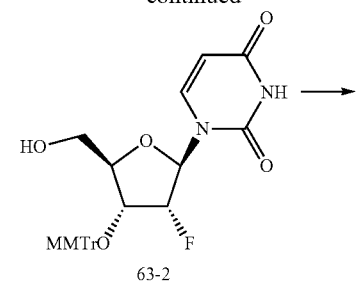
63-2

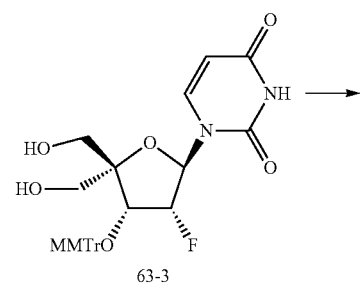
63-3

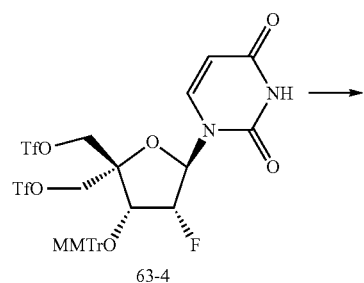
63-4

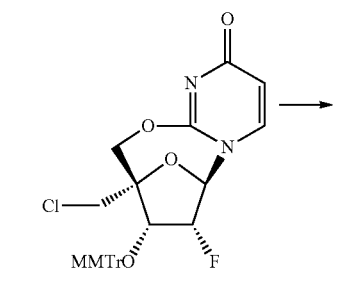
63-5

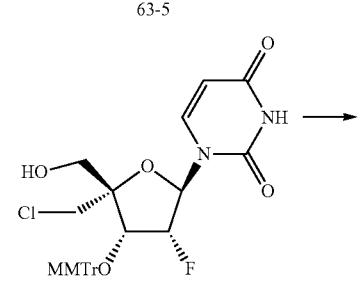
63-6

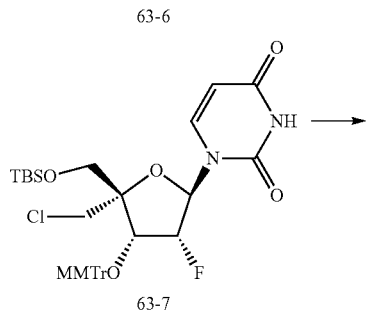
63-7

-continued

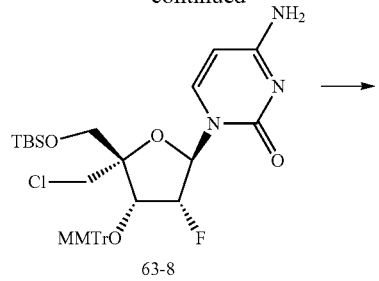
63-8

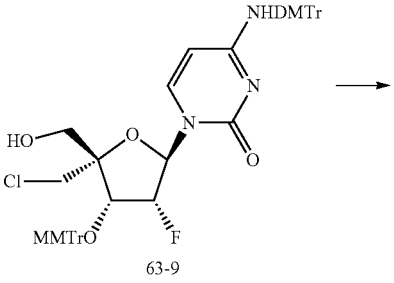
63-9

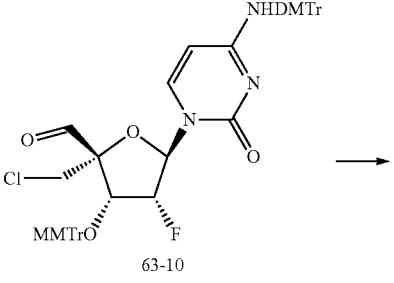
63-10

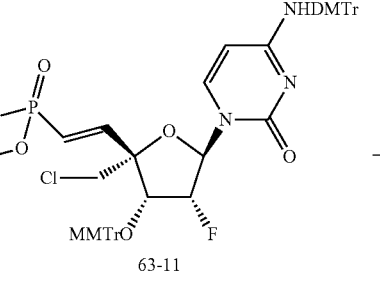
63-11

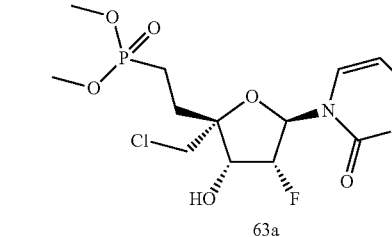
63a

Preparation of (63-2):

To a solution of 63-1 (50 g, 203 mmol) in anhydrous pyridine (200 mL) was added TBDPS-Cl (83.7 g, 304 mmol). The reaction was allowed to proceed overnight at R.T. The solution was concentrated under reduced pressure to give a residue. The residue was partitioned between ethyl acetate and water. The organic layer was separated, washed with brine, dried over magnesium sulfate and concentrated under reduced pressure to give 5'-OTBDPS ether as a white foam (94 g).

To a solution of the 5'-OTBDPS ether (94.0 g, 194.2 mmol) in anhydrous DCM (300 mL) were added silver nitrate (66.03 g, 388.4 mmol) and collidine (235 mL, 1.94 mol). The mixture was stirred at R.T. After most of silver nitrate was dissolved (~15 min), the mixture was cooled to 0° C. Monomethoxytrityl chloride (239.3 g, 776.8 mmol) was added as a single portion, and the mixture was stirred overnight at R.T. The mixture was filtered through Celite, and the filtrate was diluted with MTBE. The solution was washed successively with 1M citric acid, diluted brine and 5% sodium bicarbonate. The organic solution was dried over sodium sulfate and concentrated under vacuum to give the fully protected intermediate as a yellow foam.

The fully protected intermediate was dissolved in toluene (100 mL), and the solution was concentrated under reduced pressure. The residue was dissolved in anhydrous THF (250 mL) and treated with TBAF (60 g, 233 mmol). The mixture was stirred for 2 hours at R.T., and the solvent was removed under reduced pressure. The residue was taken into ethyl acetate, and the solution was washed with saturated sodium bicarbonate and brine. After drying over magnesium sulfate, the solvent was removed in vacuum. The residue was purified by column chromatography (PE:EA=5:1, 1:1) to give 63-2 (91 g, 86.4%) as a white foam.

Preparation of (63-3):

To a solution of 63-2 (13.5 g, 26 mmol) in DCM (100 mL) was added pyridine (6.17 mL, 78 mmol). The solution was cooled to 0° C. and Dess-Martin periodinane (33.8 g, 78 mmol) was added as a single portion. The reaction mixture was stirred for 4 h at R.T. The reaction was quenched with $Na_2S_2O_3$ solution (4%) and sodium bicarbonate aqueous solution (4%) (the solution was adjusted to pH 6, ~150 mL). The mixture was stirred for 15 min. The organic layer was separated, washed with diluted brine and concentrated under reduced pressure. The residue was dissolved in dioxane (100 mL), and the solution was treated with 37% aqueous formaldehyde (21.2 g, 10 eq) and 2N aqueous sodium hydroxide (10 eq). The reaction mixture was stirred at R.T. overnight. After stiffing for 0.5 h at R.T., the excess of aqueous sodium hydroxide was neutralized with saturated with $NH_4Cl$ (~150 mL). The mixture was concentrated under reduced pressure. The residue was partitioned between ethyl acetate and 5% sodium bicarbonate. The organic phase was separated, washed with brine, dried over magnesium sulfate and concentrated. The residue was purified by column chromatography (MeOH: DCM=100:1-50:1) to give 63-3 (9.2 g, 83.6%) as a white foam.

Preparation of (63-4):

63-3 (23 g, 42.0 mmol) was co-evaporated with toluene twice. The residue was dissolved in anhydrous DCM (250 mL) and pyridine (20 mL). The solution was cooled to −35° C. Triflic anhydride (24.9 g, 88.1 mmol) was added dropwise over 10 mins. The reaction was stirring for 40 min at −35° C. When TLC (PE:EA=2:1 and DCM:MeOH=15:1) showed that the reaction was complete, the reaction was quenched with water (50 mL) at 0° C. The mixture was stirred 30 mins, extracted with EA. The organic phase was dried over $Na_2SO_4$ and filtered through a silica gel pad. The filtrate was concentrated under reduced pressure. The residue was purified by column chromatography (PE:EA=100:1-1:1) to give 63-4 (30.0 g, 88.3%) as a brown foam.

Preparation of (63-5):

63-4 (30 g, 36.9 mmol) was co-evaporated twice with toluene. The resulting bis-triflate was dissolved in anhydrous DMF (150 mL), cooled to 0° C. and treated with sodium hydride (60% in mineral oil; 1.5 g, 40.6 mmol, 1.1 eq). The reaction mixture was stirred at R.T. for 1 h until TLC (DCM: MeOH=15:1) showed the disappearance of the bis-triflate and formation of the 2,5'-anhydro intermediate. Lithium chloride (4.6 g, 110.7 mmol, 3 eq) was added, and the stirring was continued for 2 h. The mixture was taken into 100 mL of half saturated ammonium chloride and ethyl acetate. The organic phase was separated, washed with diluted brine and concentrated under reduced pressure to give 63-5.

Preparation of (63-6):

63-5 was dissolved in THF (150 mL), and the solution was treated with 1N aqueous sodium hydroxide (~41 mL, 40.1 mmol, 1.1 eq). The mixture was stirred at R.T. for 1 h. The reaction was monitored by LCMS. The reaction was diluted with half saturated sodium bicarbonate (~60 mL) and extracted with ethyl acetate. The organic phase was dried (magnesium sulfate) and concentrated under reduced pressure. Purification of the residue by column chromatography (DCM:MeOH=300:1-60:1) gave 63-6 (18.3 g, 87.6%) as a yellow foam.

Preparation of (63-7):

To a solution of 63-6 (18.3 g, 32.33 mmol) in anhydrous DCM (150 mL) was added TBS-Cl (17.7 g, 64.6 mmol) and imidazole (6.6 g, 97 mmol). The reaction was allowed to proceed overnight at R.T. The reaction was diluted with water and extracted with DCM. The organic layer was separated, washed with brine, dried over $Na_2SO_4$ and concentrated. Purification of the residue by column chromatography (DCM:MeOH=300:1~80:1) gave 63-7 (18.4 g, 83.7%) as a white foam.

Preparation of (63-8):

A solution of 63-7 (18.4 g, 27.1 mmol), DMAP (6.6 g, 54.0 mmol) and TEA (5.4 g, 54.0 mmol) in MeCN (450 mL) was treated with 2,4,6-triisopropylbenzenesulfonyl chloride (TPSCl, 16.3 g, 54.0 mmol). The mixture was stirred at R.T. for 3 h. $NH_3H_2O$ (70 mL) was added, and the mixture was stirred for 2 h. The solution was evaporated under reduced pressure, and the residue was purified on a silica gel column (DCM: MeOH=100:1 to 15:1) to give 63-8 (18.0 g) as a light yellow solid.

Preparation of (63-9):

To a solution of 63-8 (18.0 g, 26.5 mmol) in anhydrous DCM (150 mL) was added collidine (8.1 g, 66.3 mmol, 2.5 eq), silver nitrate (4.5 g, 26.5 mmol, 1.0 eq) and DMTrCl (13.4 g, 39.7 mmol, 1.5 eq). The reaction was allowed to proceed overnight at R.T. The mixture was filtered. The filtrate was washed with brine and extracted with DCM. The organic layer was separated, dried over $Na_2SO_4$ and concentrated. The residue was purified by column chromatography (PE:EA=60:1~3:1) as a yellow foam. The foam was dissolved in THF (150 mL), and TBAF (10.4 g, 39.7 mmol, 1.5 eq) was added. The reaction was allowed to proceed overnight at R.T. The mixture was concentrated, washed with brine and extracted with EA. The organic layer was separated, dried over $Na_2SO_4$ and concentrated. Purification of the residue by column chromatography (PE:EA=60:1~EA) gave 63-9 (21.3 g, 92.4%) as a yellow foam.

Preparation of (63-10):

To a solution of 63-9 (2.0 g, 2.3 mmol) in anhydrous DCM (20 mL) was added Dess-Martin periodinane (1.95 g, 4.6 mmol) at 0° C. under nitrogen. The reaction was stirred at R.T. for 5 h. The mixture was diluted with EtOAc (100 mL) and washed with a mixture of saturated aqueous $Na_2S_2O_3$ and saturated aqueous $NaHCO_3$. The crude product was purified by column chromatography on silica gel (PE:EtOAc=2:1) to give 63-10 (1.8 g, 90%) as a yellow solid.

Preparation of (63-11):

To a solution of tetramethyl methylenediphosphonate (390 mg, 1.68 mmol) in anhydrous THF (10 mL) was added NaH (84 mg, 2.1 mmol) at 0° C. under nitrogen. The reaction was stirred at 0° C. for 30 min. A solution of 63-10 (1.2 g, 1.4 mmol) in anhydrous THF (10 mL) was added dropwise at 0°

C. The reaction mixture was stirred at R.T. for 1 h. The reaction was quenched by saturated aqueous NH$_4$Cl, and the crude product was purified by column chromatography on silica gel (DCM:MeOH=150:1) to give 63-11 (1.2 g, 88.2%) as a yellow solid. $^1$H NMR (DMSO-d6, 400 MHz) δ 8.51 (s, 1H), 7.46-7.09 (m, 22H), 6.88-6.82 (m, 6H), 6.62 (q, J$_1$=17.2 Hz, J$_2$=22.4 Hz, 1H), 6.12 (d, J=7.2 Hz, 1H), 5.86-5.75 (m, 2H), 5.43 (d, J=25.2 Hz, 1H), 4.63 (dd, J=4.8 Hz, J=21.2 Hz, 1H), 4.45 (d, J=12.0 Hz, 1H), 3.94 (d, J=12.0 Hz, 1H), 3.72 (s, 9H), 3.53 (q, J=11.2 Hz, J=16.0 Hz, 6H). ESI-MS: m/z 971.59 [M+H]$^+$.

Preparation of (63a):

A solution of 63-11 (1.0 g, 1.03 mmol) in 80% HOAc (46 mL) was stirred at 80-90° C. for 2 h. The solvent was removed, and the crude product was purified by column chromatography on silica gel (DCM:MeOH=20:1) to give an intermediate (337 mg, 82.3%) as a white solid. The intermediate was dissolved in MeOH and wet Pd/C (300 mg) was added. The reaction mixture was stirred under H$_2$ (1 atm) for 1 h and then filtered. The solvent was removed, and the residue was purified on a silica gel column (DCM:MeOH=20:1) to give 63a (192 mg, 63.9%) as a white solid. $^1$H NMR (CD$_3$OD, 400 MHz) δ 7.60 (d, J=7.6 Hz, 1H), 5.87 (d, J=7.2 Hz, 1H), 5.70 (dd, J=2.0 Hz, J=21.6 Hz, 1H), 5.31 (m, 1H), 4.67 (dd, J=5.6 Hz, J=19.6 Hz, 1H), 3.80 (m, 2H), 3.75 (2d, J=2.4 Hz, 6H), 1.92-2.20 (m, 4H). $^{31}$P NMR (CD$_3$OD, 162 MHz) δ 35.77. ESI-MS: m/z 400.0 [M+H]$^+$.

Example 61

Preparation of Compound (64a)

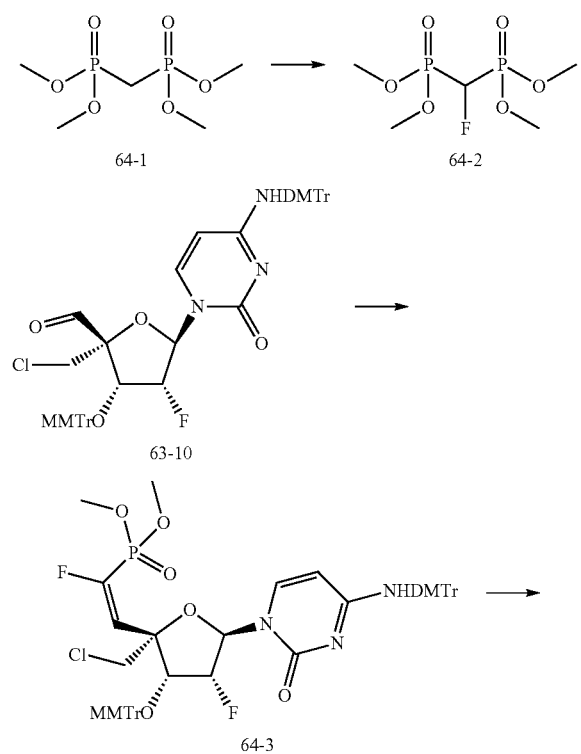

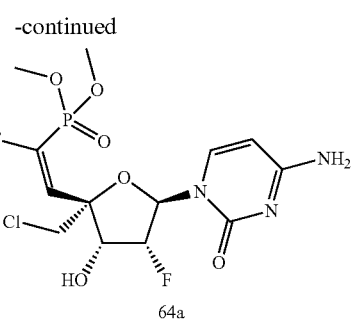

Preparation of (64-2):

To a solution of 64-1 (1.0 g, 4.3 mmol) in THF (20 mL) was added NaH (120 mg, 3.0 mmol), and the reaction mixture was stirred at 0° C. for 1 h. Selectfluor (1.2 g, 3.4 mmol) was added into the reaction mixture. The crude product was purified on a silica gel column and eluted with EA to give 64-2 (500 mg, 57%) as a white solid. $^1$H NMR (CD$_3$OD, 400 MHz) δ 5.65 (dt, J=14.0 Hz, J=44.8 Hz, 1H), 3.90 (d, J=9.6 Hz, 12H).

Preparation of (64-3):

To a solution of compound 64-2 (390 mg, 1.68 mmol) in anhydrous THF (10 mL) was added NaH (84 mg, 2.1 mmol) at 0° C. under nitrogen. The reaction mixture was stirred at 0° C. for 30 mins. A solution of 63-10 (1.2 g, 1.4 mmol) in anhydrous THF (10 mL) was added dropwise at 0° C. The reaction mixture was stirred at R.T. for 1 h. The reaction was quenched with saturated aqueous NH$_4$Cl and concentrated to give a residue. The residue was purified on a silica gel column (DCM:MeOH=150:1) to give crude 64-3 (1.2 g, 88.2%) as a yellow solid.

Preparation of (64a):

A solution of crude 64-3 (230 mg, 0.23 mmol) in 80% HOAc (3 mL) was stirred at 80-90° C. for 2 h. The crude product was purified on a silica gel column (eluted with DCM:MeOH=20:1) to give 64a (54 mg, 53.7%) as a white solid. $^1$H NMR (DMSO, 400 MHz) δ 7.69 (d, J=7.2 Hz, 1H), 7.37 (d, J=1.6 Hz, 2H), 6.62-6.78 (m, 1H), 6.40 (d, J=5.6 Hz, 1H), 6.03-6.07 (m, 1H), 5.77 (d, J=7.6 Hz, 1H), 5.61-5.64 (m, 1H), 5.48-5.51 (m, 1H), 4.60-4.64 (m, 1H), 4.38 (d, J=11.6 Hz, 1H), 3.98 (d, J=11.6 Hz, 1H), 3.75 (2d, J=11.6 Hz, 6H). ESI-MS: m/z 416.3 [M+H]$^+$.

Example 62

Preparation of Compound (65a)

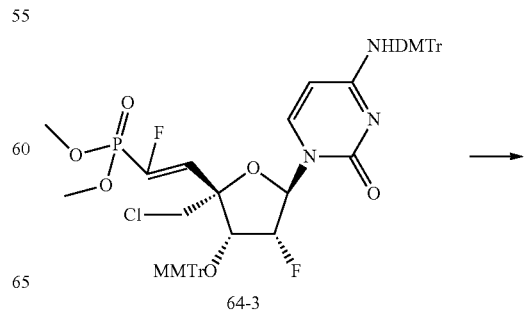

-continued

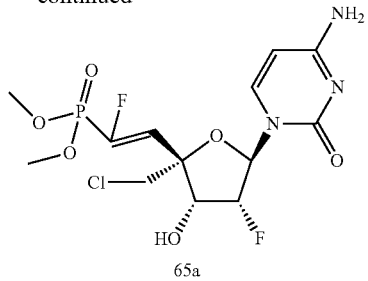

65a

A solution of crude 64-3 (230 mg, 0.23 mmol) in 80% HOAc (3 mL) was stirred at 80-90° C. for 2 h. The crude product was purified on a silica gel column (eluted with DCM:MeO=20:1) to give 64a (52 mg, 33.7%) as a white solid. $^1$H NMR (DMSO, 400 MHz) δ 7.59 (d, J=7.2 Hz, 1H), 7.32 (s, 2H), 6.25-6.28 (m, 1H), 5.86-6.02 (m, 2H), 5.73 (s, 1H), 5.31 (d, J=14.0 Hz, 1H), 4.72 (d, J=16.4 Hz, 1H), 3.90 (d, J=10.0 Hz, 1H), 3.73 (2d, J=11.6 Hz, 6H).

Example 63

Preparation of Compound (66a)

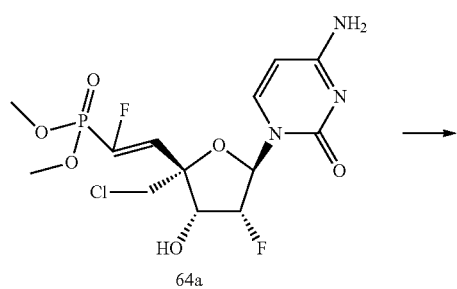

64a

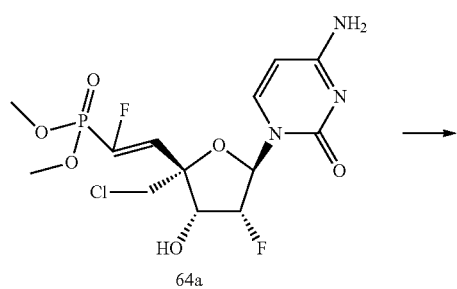

66a

A solution of 64a (130 mg, 0.3 mmol) in EA:MeOH (5:1, 20 mL) was stirred under H$_2$ (15 Psi) at R.T. for 2 h. The reaction mixture was filtered and concentrated to give a residue. The residue was purified on a silica gel column (DCM: MeOH, 20:1) to give 66a (70 mg, 54%) as a white solid. $^1$H NMR (DMSO, 400 MHz) δ 7.61 (d, J=7.2 Hz, 1H), 5.87 (d, J=7.2 Hz, 1H), 5.58-5.80 (m, 1H), 5.26-5.47 (m, 2H), 4.97-5.03 (m, 1H), 5.58-5.80 (m, 1H), 3.73-3.94 (m, 6H), 2.33-2.59 (m, 2H). ESI-MS: m/z 418.3 [M+H]$^+$.

Example 64

Preparation of Compound (67a)

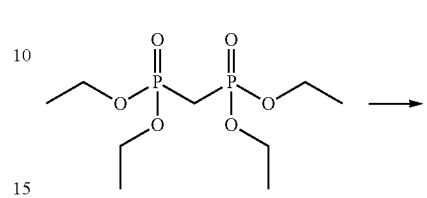

67-1

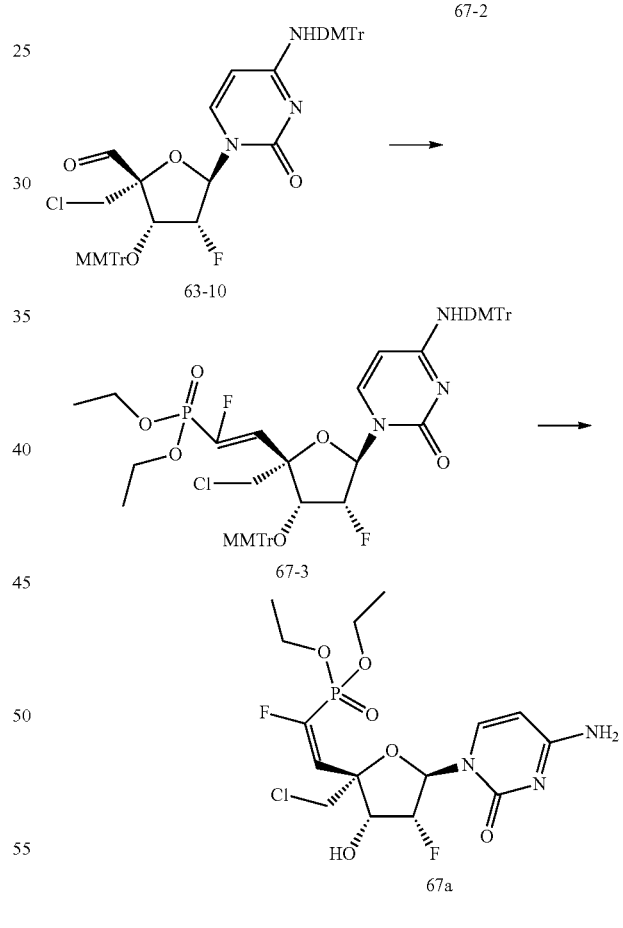

Preparation of (67-2):

To a solution of 67-1 (2.0 g, 6.9 mmol) in THF (20 mL) was added NaH (110 mg, 2.8 mmol), and the reaction mixture was stirred at 0° C. for 1 h. Selectfluor (5.0 g, 13.6 mmol) was added into the reaction mixture. The reaction was quenched with saturated NH$_4$Cl and extracted with EA. The organic layer was separated, dried and concentrated to give the crude product. The crude product was purified on a silica gel column (eluted with EA) to give 67-2 (600 mg, 28.3%) as a white solid. $^1$H NMR (CD$_3$OD, 400 MHz) δ 5.65 (dt, J=14.0 Hz, J=44.8 Hz, 1H), 4.24-4.46 (m, 8H), 1.35-1.39 (m, 12H).

Preparation of (67-3):

To a solution of 67-2 (2.14 g, 7.0 mmol) in anhydrous THF (10 mL) was added NaH (84 mg, 2.1 mmol) at 0° C. under nitrogen. The reaction mixture was stirred at 0° C. for 30 mins. A solution of 63-10 (3.0 g, 3.5 mmol) in anhydrous THF (10 mL) was added in dropwise at 0° C. The reaction mixture was stirred at R.T. for 1 h. The reaction was quenched with saturated aqueous NH$_4$Cl and concentrated to give a residue. The residue was purified on a silica gel column (DCM: MeOH=150:1) to give crude 67-3 (2.9 g, 79.5%) as a yellow solid.

Preparation of (67a):

A solution of crude 67-3 (1.0 g, 0.98 mmol) in 80% HOAc (25 mL) was stirred at 80-90° C. for 2 h. The crude product was purified on a silica gel column (eluted with DCM: MeO=20:1) to give 67a (133 mg, 32.5%) as a white solid. $^1$H NMR (DMSO, 400 MHz) δ 7.67 (d, J=7.2 Hz, 1H), 7.34 (d, J=12.8 Hz, 2H), 6.33-6.69 (m, 1H), 6.05 (d, J=6.8 Hz, 1H), 6.00-6.05 (m, 1H), 5.76 (d, J=7.6 Hz, 1H), 5.45-5.61 (m, 1H), 4.60-4.63 (m, 1H), 4.08-4.14 (m, 5H), 1.23-1.29 (m, 6H). $^{31}$P NMR (DMSO, 162 MHz) δ 1.93, 1.30. ESI-MS: m/z 466.1 [M+Na]$^+$.

Example 65

Preparation of Compound (68a)

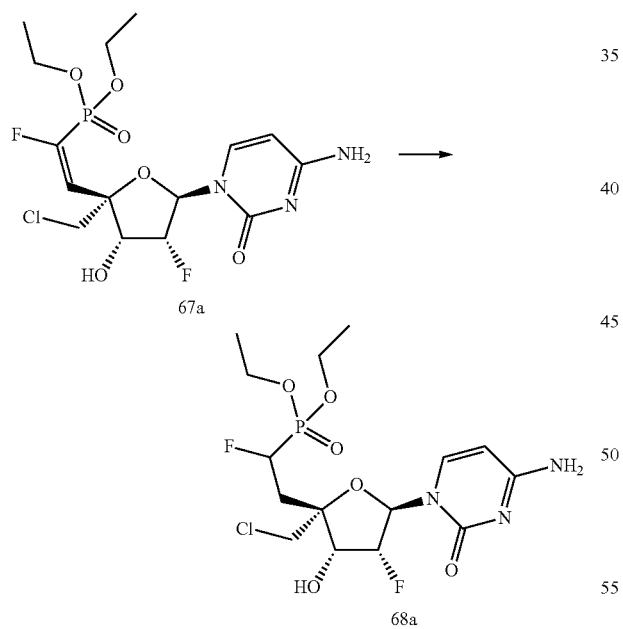

To a solution of 67a (130 mg, 0.29 mmol) in MeOH (20 mL) was stirred under H$_2$ (15 Psi) at R.T. for 2 h. The reaction mixture was filtered and concentrated to give a residue. The residue was purified on a silica gel column (eluted with DCM: MeO=20:1) to give a mixture of diastereomers of 68a (90 mg, 69.2%) as a white solid. $^1$H NMR (DMSO, 400 MHz) δ 7.61-7.68 (m, 1H), 7.28-7.38 (m, 2H), 5.89-5.95 (m, 1H), 5.58-5.79 (m, 2H), 5.18-5.39 (m, 1H), 4.53-4.85 (m, 1H), 4.04-4.39 (m, 4H), 3.71-3.83 (m, 2H), 2.21-2.35 (m, 2H), 1.21-1.27 (m, 6H). $^{31}$P NMR (DMSO, 162 MHz) δ 18.2, 18.02, 17.73, 17.56. ESI-MS: m/z 446.1 [M+H]$^+$ Example 66

Preparation of Compound (69a)

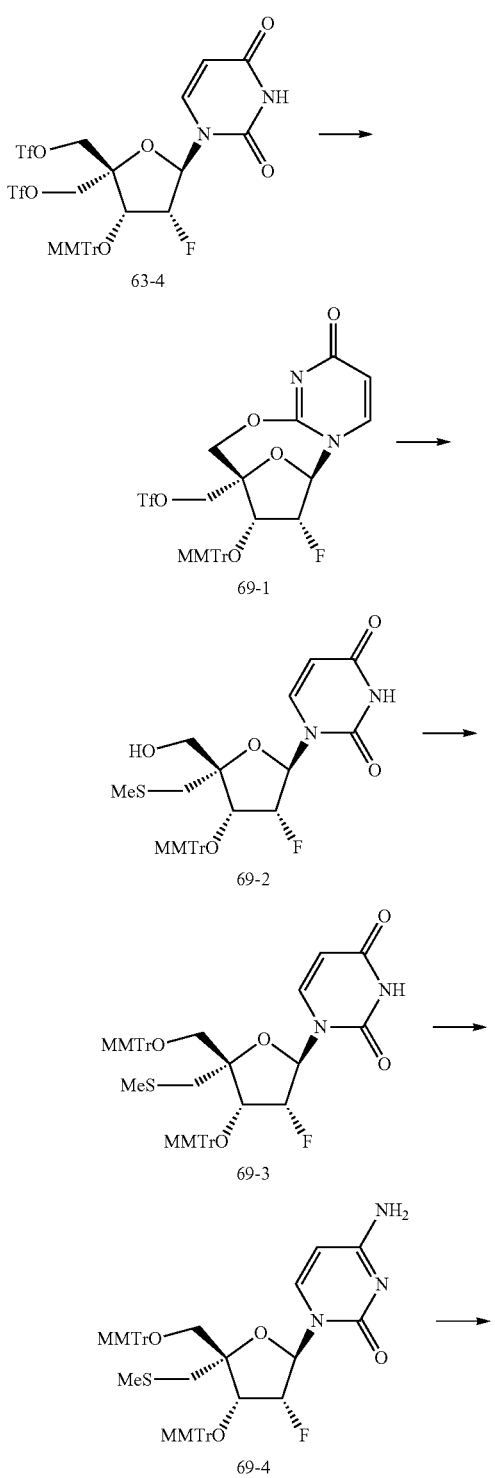

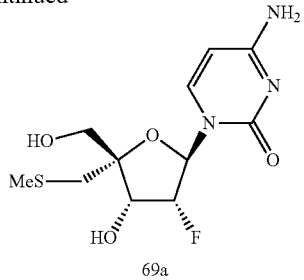

69a

Preparation of (69-1):

63-4 (3.0 g, 3.69 mmol) was co-evaporated twice with toluene. The resulting bis-triflate was dissolved in anhydrous DMF (20 mL). The solution was cooled to 0° C. and treated with sodium hydride (60% in mineral oil; 177 mg, 0.43 mmol). The reaction was stirred at R.T. for 1 h (TLC (PE: EA=2:1) showed complete disappearance of the bis-triflate and clean formation of the 2',5'-anhydro intermediate). The reaction mixture was used for the next step without any further workup Preparation of (69-2):

To the above stirred reaction mixture was added NaSMe (9.0 g, 0.13 mmol) and 15-Crown-5 (4.87 g, 22.14 mmol) at 0° C. under nitrogen. The solution was stirred at R.T. for 2 h (TLC (PE:EA=1:1) showed the reaction was complete). The reaction was quenched with water. The mixture was extracted by EtOAc, washed with brine, and dried over MgSO$_4$. The mixture was filtered and concentrated to give a residue. The residue was purified on a silica gel column (PE:EA=5:2) to give 69-2 (1.23 g, 59.0%) as a white foam.

Preparation of (69-3):

To a stirred solution of 69-2 (1.34 g, 2.32 mmol) in anhydrous DCM (10 mL) was added MMTrCl (1.32 g, 4.64 mmol), AgNO3 (1.17 g, 6.96 mmol) and Collidine (1.41 g, 11.6 mmol) at R.T. under nitrogen. The reaction mixture was stirred at R.T. for 1 h (TLC (PE:EA=1:1) showed the reaction was complete). The mixture was filtered and concentrated. The residue was purified on a silica gel column (PE:EA=8:1) to give 69-3 (1.31 g, 66.5%) as a white foam.

Preparation of (69-4):

To a solution of 69-3 (900 mg, 1.06 mmol) in anhydrous MeCN (9 mL) was added DMAP (259 mg, 2.12 mmol), TEA (214 mg, 2.12 mmol) and TPSCl (640 mg, 2.12 mmol) at R.T. under nitrogen. The reaction mixture was stirred at R.T. for 2 h (TLC (DCM:MeOH=10:1) showed the reaction was complete). NH$_4$OH (10 mL) was added, and the reaction mixture was stirred for another 1 h (LCMS showed the reaction was complete). The solution was diluted with water, extracted with EtOAc. The organic layer was washed with 1M HCl, saturated NaHCO$_3$ and brine, and dried over MgSO$_4$. The mixture was filtered and concentrated to give a residue. The residue was purified on a silica gel column (DCM:MeOH=70:1) to give 69-4 (870 mg, 68.5%) as a white solid.

Preparation of (69a):

69-4 (800 mg, 0.95 mmol) was dissolved in 80% HOAc aq. (50 mL). The reaction mixture was heated to 75° C. overnight (LCMS showed the reaction was complete). The reaction mixture was concentrated and purified on a silica gel column (DCM:MeOH=15:1) to give 69a (180 mg, 62.5%) as a white solid. $^1$H NMR (CD$_3$OD, 400 MHz) δ 8.05 (d, J=7.2 Hz, 1H), 6.11 (dd, J=3.2 Hz J=15.6 Hz, 1H), 5.87 (d, J=7.6 Hz, 1H), 5.05 (dt, J=4.8 Hz, J=53.6 Hz, 1H), 4.47 (dd, J=5.2 Hz J=17.6 Hz, 1H), 3.83 (d, J=12.0 Hz, 2H), 2.84 (d, J=14.4 Hz, 2H), 2.15 (s, 3H). ESI-MS: m/z 305.8 [M+H]$^+$ Example 67

Preparation of Compound (70a)

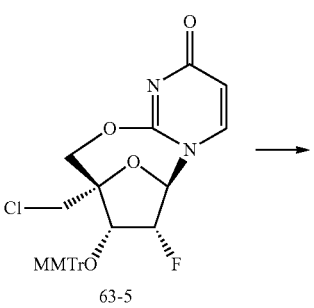

63-5

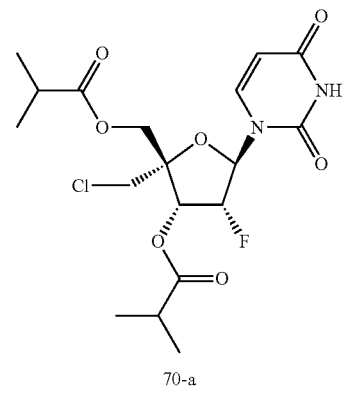

70-a

To a solution of 63-5 (100 g, 182.5 mmol) in MeCN (2 L) was added 6N HCl aq. (15 g). The mixture was stirred at 40° C. for 7 h, and then neutralized to pH=5~6 with a 25% ammonia solution (~8 g). The mixture was filtered to give a solid, which was further washed by PE to give an intermediate (32.2 g, 60%) as a white solid. To a mixture of the intermediate (32.2 g, 109.5 mmol), TEA (22.1 g, 219 mmol) and DMAP (1.34 g, 11 mmol) in MeCN (1 L) was added with isobutyric anhydrous (69.2 g, 438 mmol). The mixture was stirred at R.T. for 3 h. The reaction was quenched by the addition of water (200 mL) and extracted with 2-Me-THF (800 mL). The organic layer was washed with saturated NaHCO$_3$ and brine. The organic layer was dried and concentrated to give a residue, which was purified by a silica gel column (10% toluene in heptane) to give 70a (42.3 g, 89%) as a white solid. $^1$H NMR (CD$_3$OD, 400 MHz) δ 7.65 (d, J=8.0

Hz, 1H), 5.95 (dd, J=2.8, 20.4 Hz, 1H), 5.55-5.74 (m, 3H), 4.33-4.41 (m, 2H), 3.88 (s, 2H), 2.57-2.72 (m, 2H), 1.14-1.22 (m, 12H).

Example 68

Preparation of Compound (71a)

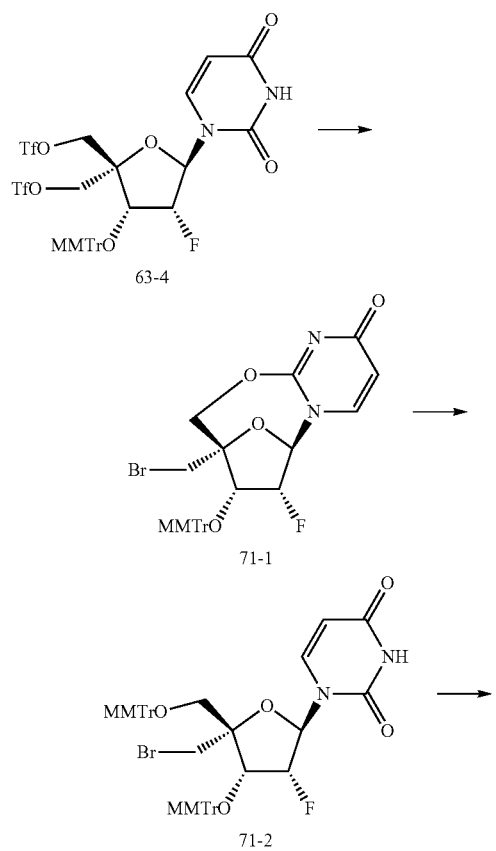

Preparation of (71-1):

To a solution of 63-4 (4.2 g, 5.17 mmol) in DMF (50 mL) at 0° C. was added NaH (227 mg of 60% dispersion, 5.7 mmol). The mixture was stirred at 0° C. for 2 h, and then LiBr (1.34 g, 15.5 mmol) was added. The mixture was stirred overnight at R.T., diluted with EA (150 mL) and washed successively with water and brine. The organic layer was dried over Na$_2$SO$_4$ and concentrated. The residue was purified on a silica gel column eluted with 10% EA in PE to give 71-1 as a yellow solid (2 g, 66%)

Preparation of (71-2):

To a solution of 71-1 (1.74 g, 2.9 mmol) in THF (20 mL) at 0° C. was added 1N NaOH (3.2 mL, 3.2 mmol), and the mixture was stirred at 0° C. for 2 h. The mixture was partitioned between EA (100 mL) and water (20 mL), and the organic layer was dried over Na$_2$SO$_4$ and evaporated to dryness. The residue was purified on a silica gel column eluted with 20% EA in PE to give the 5'-OH derivative as a yellow solid (1.6 g, 90%).

To a solution of 5'-OH derivative (2.3 g, 3.76 mmol) in anhydrous DCM (20 mL) were added collidine (0.8 g, 6.7 mol) and MMTrCl (2.7 g, 8.7 mmol). The reaction mixture was stirred at R.T. overnight. The mixture was filtered and washed successively with saturated aqueous NaHCO$_3$ and brine, dried over Na$_2$SO$_4$ and concentrated. The residue was purified on a silica gel column eluted with 10% EA in PE to give 71-2 as a yellow solid (2.4 g, 73%).

Preparation of (71a):

To a solution of 71-2 (2.4 g, 2.72 mmol) in anhydrous CH$_3$CN (30 mL) were added TPSCl (1.65 g, 5.44 mmol), DMAP (0.663 g, 5.44 mmol) and NEt$_3$ (1.5 mL) at R.T. The mixture was stirred at R.T. for 3 h, and 28% aqueous ammonia (30 mL) was added. The mixture was stirred for 1 h. The mixture was diluted with EA (150 mL) and washed successively with water, saturated aqueous NaHCO$_3$ and brine. The solvent was removed, and the residue was purified on a silica gel column eluted with 2% MeOH in DCM to give a cytidine derivative as a yellow solid (1.5 g, 62%).

The cytidine derivative (1.35 g, 1.5 mmol) was dissolved in 80% AcOH (40 mL), and the mixture was stirred at 60° C. for 2 h. The mixture was concentrated, and the residue was purified on a silica gel column using 5% MeOH in DCM as elute to give 71a as a white solid (180 mg, 35%). $^1$H NMR (MeOD, 400 MHz) δ 8.00 (d, J=7.2 Hz, 1H), 6.12 (dd, J=3.6 Hz, J=15.6 Hz, 1H), 5.88 (d, J=7.6 Hz, 1H), 5.10 (dd, J=4.8 Hz, J=53.2 Hz, 1H), 4.59 (dd, J=5.2 Hz, J=16.4 Hz, 1H), 3.95 (d, J=11.6 Hz, 1H), 3.76 (d, J=11.6 Hz, 1H), 3.70 (d, J=11.6 Hz, 1H), 3.63 (d, J=11.2 Hz, 1H); ESI-TOF-MS: m/z 337.9 [M+H]$^+$.

Example 69

Preparation of Compound (72a)

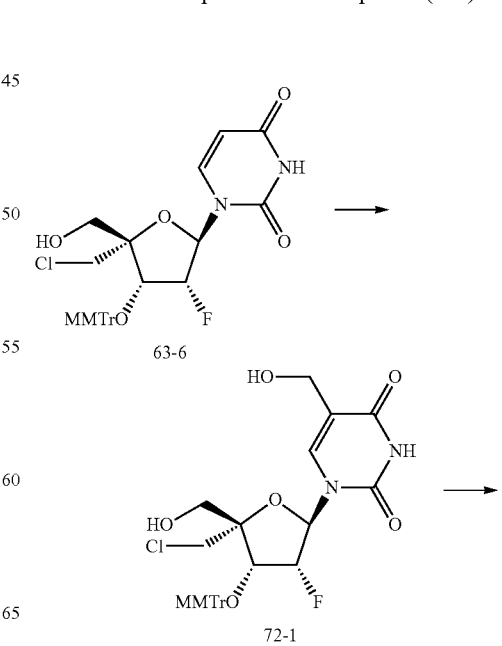

-continued

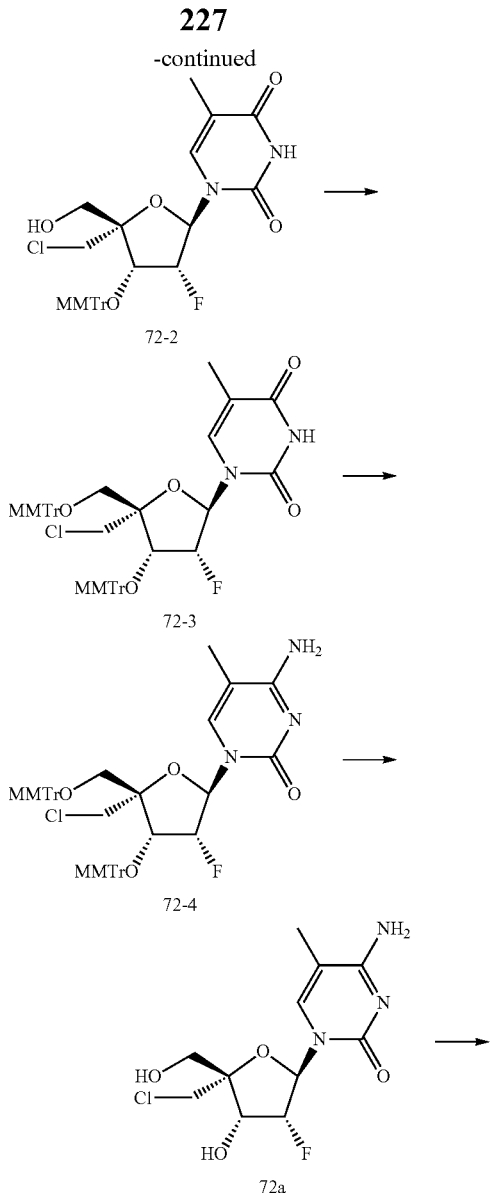

Preparation of (72-1):

To a solution of 63-6 (1.0 g, 1.8 mmol) in 1,4-dioxane (2 mL) was added TEA (3 mL) and 37% HCHO (3 mL). The reaction mixture was stirred for 10 h at 60° C. The reaction was concentrated to dryness under vacuum, and the residue was purified by column on a silica gel column (DCM:MeOH=100:1-30:1) to give 72-1 (470 mg, 45%) as a white foam. $^1$H NMR (DMSO-d6, 400 MHz) δ 11.4 (s, 1H), 7.27-7.49 (m, 13H), 6.89 (d, J=8.8 Hz, 2H), 4.90-4.95 (m, 1H), 4.58 (dd, J=5.2 Hz, J=23.6 Hz, 1H), 3.96-4.07 (m, 4H), 3.73 (s, 3H), 3.50-3.62 (m, 1H), 3.37-3.39 (m, 1H), ESI-TOF-MS: m/z 596.9 [M+H]$^+$.

Preparation of (72-2):

To a solution of 72-1 (430 mg, 0.72 mmol) in dioxane (2 mL) was added 30% CH$_3$COOH (0.7 mL) and PtO$_2$ (290 mg). The reaction mixture was stirred under H$_2$ (1 atm) at R.T. for 2 h. The mixture was filtered, and the filtrate was concentrated to dryness. The residue was purified on a silica gel column (DCM:MeOH=100:1-30:1) to give 72-2 (268 mg, 64%) as a white foam. $^1$H NMR (DMSO-d6, 400 MHz) 811.3 (s, 1H), 7.27-7.46 (m, 13H), 6.88 (d, J=8.8 Hz, 2H), 5.78 (d, J=20.8 Hz, 1H), 5.06-5.08 (t, J=20.8 Hz, 1H), 4.49 (dd, J=4.2 Hz, J=24.4 Hz, 1H), 3.94-4.04 (m, 2H), 3.70 (s, 3H), 3.59-3.63 (m, 1H), 3.52-3.53 (m, 1H), 3.34-3.40 (m, 1H), 1.66 (s, 3H). ESI-TOF-MS: m/z 580.9 [M+H]$^+$.

Preparation of (72-3):

To a solution of 72-2 (260 mg, 0.45 mmol) in anhydrous DCM (3 mL) was added AgNO$_3$ (228 mg, 1.35 mmol), collidine (223 mg, 1.8 mmol) and MMTrCl (456 mg, 1.35 mmol). The mixture was stirred at R.T. for 10 h. The reaction mixture was filtered, and the filtrate was concentrated to dryness. The residue was purified on a silica gel column (PE:EA=50:1-3:1) to give 72-3 (303 mg, 80%) as a white foam.

Preparation of (72-4):

To a solution of 72-3 (300 mg, 0.35 mmol) in anhydrous CH$_3$CN (3 mL) was added DMAP (107 mg, 0.88 mmol), TEA (141 mg, 1.4 mmol) and TPSCl (106 mg, 0.35 mmol) at R.T. The reaction mixture was stirred at R.T. for 4 h. NH$_4$OH (1 mL) was added, and the mixture was stirred at R.T. for another 1 h. The solvent was removed, and the residue was partitioned by EA and water. The organic layer was washed by brine twice, dried and concentrated to give a residue. The residue was purified on a silica gel column (PE:EA=50:1-3:1) to give 72-4 (270 mg, 90%) as a white foam.

Preparation of (72a):

72-4 (260 mg, 0.31 mmol) in 10 mL of 60% HCOOH was stirred at R.T. for 2 h. The solvent was removed, and the residue was washed with EA to give 72a (31 mg, 32%) as a white powder. $^1$H NMR (MeOD, 400 MHz) δ 7.85 (d, J=0.8 Hz, 1H), 6.12 (dd, J=4.0 Hz, J=15.2 Hz, 1H), 5.08-5.22 (m, 1H), 4.58 (dd, J=4.8 Hz, J=14.8 Hz, 1H), 3.92 (d, J=15.6 Hz, 1H), 3.74-3.84 (m, 3H), 1.94 (d, J=0.8 Hz, 1H). ESI-TOF-MS: m/z 307.9 [M+H]$^+$.

Example 70

Preparation of Compound (73a)

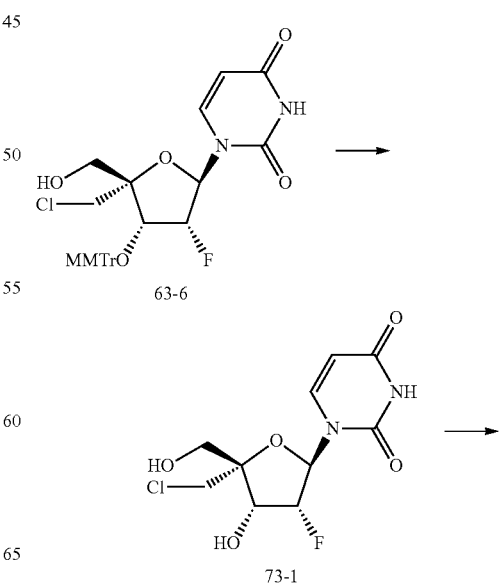

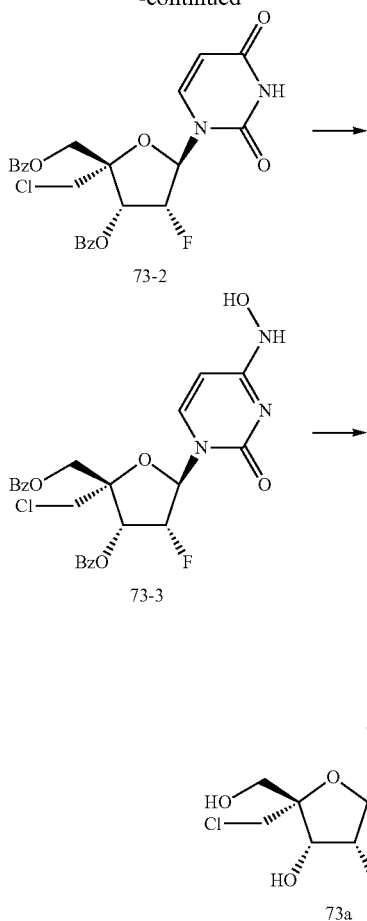

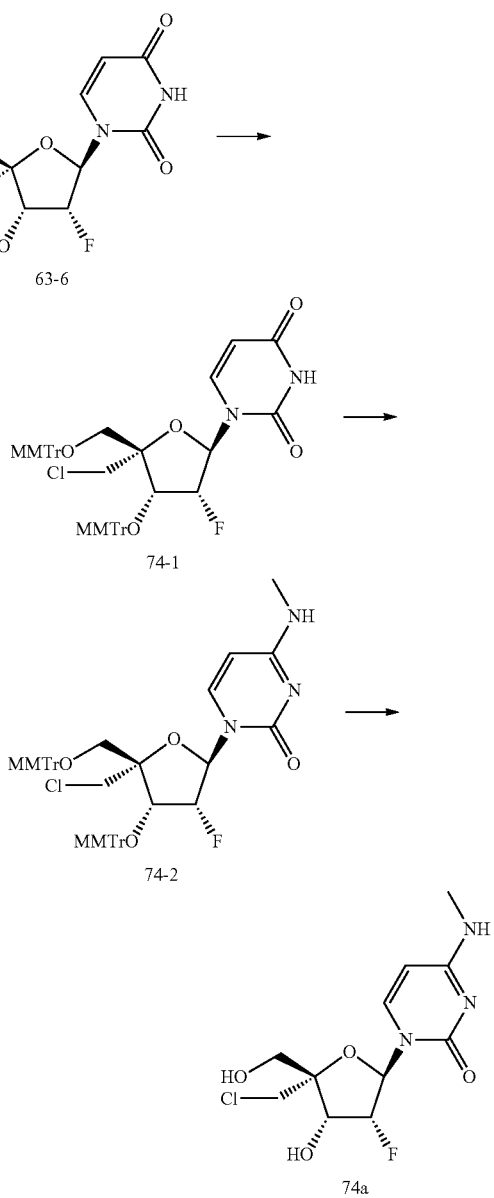

Preparation of (73-1):

63-6 (600 mg, 1.06 mmol) in formic acid (5 mL, 80% in water) was stirred at R.T. overnight. Completion of the reaction was determined by TLC (DCM:MeOH=10:1). The solvent was removed to give crude 73-1 (290 mg, 93.2%).

Preparation of (73-2):

To a solution of 73-1 (290 mg, 0.98 mmol) in pyridine (5 mL) and acetonitrile (5 mL) was added BzCl (371 mg, 2.65 mmol). The reaction mixture was stirred at 0° C. for 0.5 h. The reaction was warmed to R.T. and stirred for 2 h. Completion of the reaction was determined by LCMS. The reaction was quenched with water and extracted with EA. The organic layer was washed with brine, dried over MgSO$_4$, filtered and concentrated. The residue was purified on a silica gel column (DCM:MeOH=200:1) to give 73-2 (245 mg, 49.8%) as a white solid.

Preparation of (73-3):

To a solution of 73-2 (245 mg, 0.49 mmol) in anhydrous acetonitrile (2.5 mL) was added TPSCl (394 mg, 0.98 mmol), DMAP (119.5 mg, 0.98 mmol) and TEA (98 mg, 0.98 mmol). The mixture was stirred at R.T. for 3 h. NH$_2$OH.HCl (68 mg, 0.98 mmol) and DBU (368 mg, 1.47 mmol) were added, and the reaction mixture was stirred at R.T. for 2 h. The reaction mixture was diluted with water and extracted with EtOAc. The combined organic layer was washed with 1M HCl, saturated NaHCO$_3$ and brine, dried and concentrated. The residue was purified on a silica gel column (DCM:MeOH=20:1) to give 73-3 (49 mg, 32.9%) as a white solid.

Preparation of (73a):

73-3 (49 mg, 0.1 mmol) in NH$_3$/MeOH (30 mL) was stirred at R.T. for 2 days. The solvent was removed. The residue was purified on a silica gel column (DCM:MeOH=30:1) to give 73a (12.9 mg, 44.0%) as a white solid. $^1$H NMR (DMSO-d$_6$, 400 MHz) δ 10.07 (brs, 1H), 9.68 (brs, 1H), 7.02 (d, J=8.0 Hz, 1H), 6.06 (dd, J=6.4 Hz, J=13.6 Hz, 1H), 5.94 (d, J=5.6 Hz, 1H), 5.60 (d, J=8.4 Hz, 1H), 5.36 (t, J=5.2 Hz, 1H), 5.16 (dt, J=5.2 Hz, J=53.6 Hz, 1H), 4.31-4.35 (m, 1H), 3.58-3.76 (m, 2H), 3.57-3.58 (m, 2H). ESI-TOF-MS: m/z 308.1 [M−H]$^+$.

Example 71

Preparation of Compound (74a)

Preparation of (74-1):

To a solution of 63-6 (1.2 g, 2.12 mmol) in anhydrous DCM (20 mL) were added collidine (750 mg, 6.51 mol) and MMTrCl (2.6 g, 8.5 mmol). The reaction mixture was stirred at R.T. overnight. The reaction was filtered and washed successively with saturated aqueous NaHCO$_3$ and brine, dried over Na$_2$SO$_4$ and concentrated. The residue was purified on a silica gel column eluted with 10% EA in PE to give 74-1 as a yellow solid (1.4 g, 72%).

Preparation of (74-2):

To a stirred solution of 74-1 (600 mg, 0.715 mmol) in anhydrous acetonitrile (6 mL) were added TPSCl (432 mg, 1.43 mmol), DMAP (174 mg, 1.43 mmol) and TEA (144 mg, 1.43 mmol). The mixture was stirred at R.T. for 2 h. Completion of the reaction was determined by TLC (DCM:MeOH=10:1). CH$_3$NH$_2$ (310 mg, 10 mmol) was added dropwise at 0° C. The reaction mixture was stirred at R.T. for 2 h. The mixture was diluted with water and extracted with EtOAc. The combined organic layer was washed with 1M HCl, saturated NaHCO$_3$ and brine. The solvent was removed, and the residue was purified by prep-TLC (DCM:MeOH=10:1) to give 74-2 (307 mg, 50.45%) as a white solid.

Preparation of (74a):

74-2 (300 mg, 0.352 mmol) in formic acid (10 mL, 80% in water) was stirred at R.T. overnight. Completion of the reaction was determined by TLC (DCM:MeOH=10:1). The solvent was removed to dryness. The residue was dissolved in 20 mL of methanol. Ammonia (0.5 mL) was added, and the mixture was stirred at R.T. for 5 mins. The solvent was removed, and the residue was washed with PE (5×) to give 74a (103 mg, 95.3%) as a white solid. $^1$H NMR (DMSO-d$_6$, 400 MHz) δ 7.79 (d, J=4.8 Hz, 1H), 7.72 (d, J=5.2 Hz, 1H), 6.10 (dd, J=4.4 Hz, J=14.8 Hz, 1H), 5.97 (brs, 1H), 5.73 (d, J=7.6 Hz, 1H), 5.39 (brs, 1H), 5.08 (dt, J=4.2 Hz, J=53.2 Hz, 1H), 4.37-4.40 (m, 1H), 3.73 (s, 2H), 3.54-3.70 (m, 2H), 2.73 (d, J=4.4 Hz, 3H). ESI-TOF-MS: m/z 308.1 [M+H]$^+$.

Example 72

Preparation of Compound (75a)

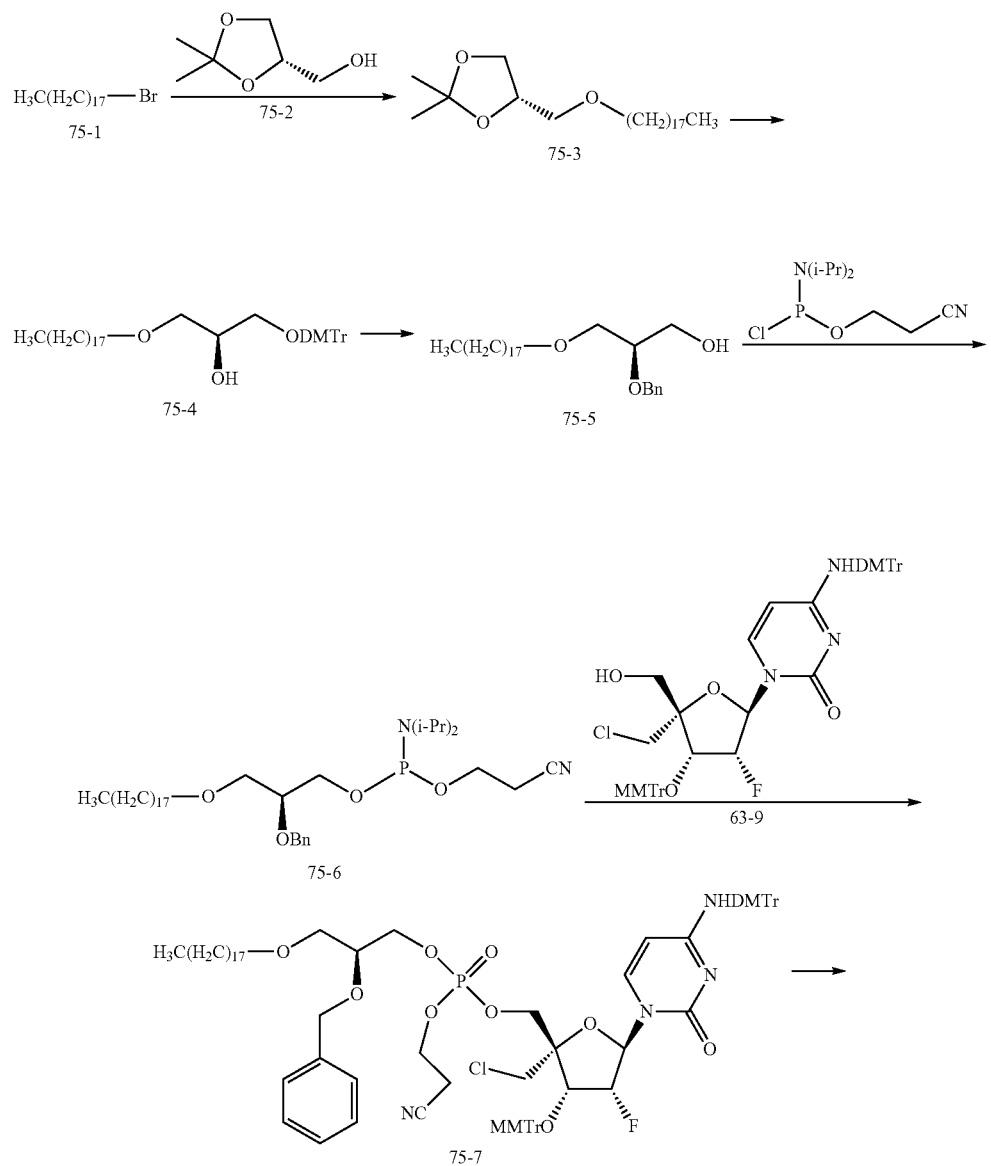

-continued

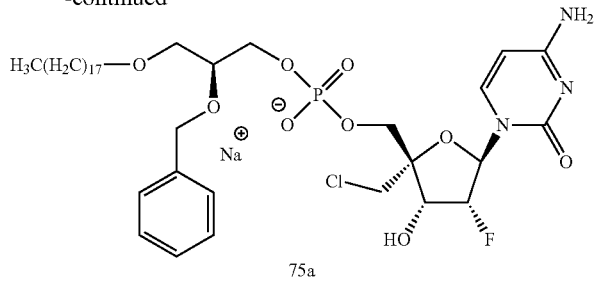

75a

Preparation of (75-3):

To a stirred solution of 75-1 (20.0 g, 151 mmol) in anhydrous THF (200 mL) was added NaH (7.8 g, 196 mmol) in portions at 0° C. The mixture was stirred for 1 h, and 75-2 (65.0 g, 196 mmol) was added dropwise at 0° C. The mixture was stirred at R.T. for 10 h. The reaction was quenched with water and extracted with EA. The reaction was washed with brine, and the organic layer was concentrated to obtain crude 75-3 (72 g).

Preparation of (75-4):

Crude 75-3 (72 g, 151 mmol) was dissolved with 80% $CH_3COOH$ (300 mL) and stirred for 10 h. The solvent was removed under reduced pressure. The residue was dissolved in EA and washed with saturated $NaHCO_3$ and brine successively. The organic layer was dried over $Na_2SO_4$ and concentrated to dryness. The residue was purified on a silica gel column to give the crude intermediate, which was dissolved in anhydrous pyridine (80 mL) and DCM (400 mL). A solution of DMTrCl (56.0 g, 166 mmol) in DCM (150 mL) was added dropwise at 0° C. The mixture was stirred at R.T. for 10 h. The reaction mixture was concentrated to dryness, and the residue was purified by column on silica gel (PE:EA=2:1) to give 75-4 (58.5 g, 61%).

Preparation of (75-5):

To a stirred solution of 75-4 (10.0 g, 15.5 mmol) in anhydrous DMF (80 mL) was added NaH (0.8 g, 20 mmol) at 0° C. The mixture was stirred at R.T. for 1 h, and BnBr (33.8 g, 20 mmol) was added. The reaction mixture was stirred at R.T. for 10 h. The reaction was quenched with water and extracted with EA. The reaction was washed with brine, and the organic layer was concentrated to give the crude intermediate (10.5 g, 92%) as a white foam. The crude intermediate (10.2 g, 13.8 mmol) in 80% $CH_3COOH$ (100 mL) was stirred at R.T. for 12 h. The solvent was removed. The residue was dissolved in EA, washed with saturated $NaHCO_3$ and brine successively, dried and concentrated to give a residue. The residue was purified on a silica gel column twice (PE:EA=3:1) to give 75-5 (4.2 g, 70%) as a white foam.

Preparation of (75-6):

To a solution of 75-5 (4.0 g, 9.2 mmol) in anhydrous $CH_3CN$ (30 mL) was added DIPEA (6.1 g, 47.6 mmol) and 2-cyanoethyl N,N-diisopropylchlorophosphoramidite (2.8 g, 11.9 mmol). The mixture was stirred at R.T. for 2 h. The solvent was removed, and residue was partitioned by EA and saturated $NaHCO_3$. The organic layer was dried over $MgSO_4$ and concentrated to give a residue. The residue was purified on a silica gel column (PE:EA=3:1) to give 75-6 (5.1 g, 88%) as a white solid.

Preparation of (75-7):

To a solution of 75-6 (1.0 g, 1.6 mmol) and 63-9 (925 mg, 1.1 mmol) in anhydrous MeCN (1 mL) was added tetrazole (12 mL, 0.45M in MeCN, 5.5 mmol) dropwise at R.T. After stirred for 3 h, TBDPH (0.96 mL, 5M 4.8 mmol) was added.

The reaction mixture was stirred at R.T. for 1 h. The mixture was diluted with EA and washed with saturated $Na_2SO_3$ and brine, dried over anhydrous $Na_2SO_4$ and concentrated. The residue was purified by silica gel chromatography (PE/EA=50:1 to 1:1) to give 75-7 (1.1 g, 73.3%) as a white solid.

Preparation of (75a):

75-7 (1.0 g, 0.7 mmol) in 60% HCOOH (3 mL) was stirred at R.T. for 12 h. The solvent was removed. The residue was dissolved in EA and washed with saturated $NaHCO_3$ and brine successively, dried and concentrated to give a residue. The residue was purified twice on a silica gel column (DCM:MeOH=30:1) to give crude 75a (510 mg, 86%) as a white foam. To a solution of crude 75a (275 mg, 0.33 mmol) in $C_2H_5OH$ was added a few drops 1N NaOH until pH~7.0. The mixture was stirred for 0.5 h. The mixture was concentrated to give a residue. The residue was purified by HPLC (MeCN and water, neutral system) to give 75a (sodium salt, 170 mg, 64%) as a white solid. $^1H$ NMR ($CD_3OD$, 400 MHz) δ 8.01 (d, J=7.6 Hz, 1H), 7.23-7.37 (m, 5H), 6.22 (dd, J=3.6 Hz, J=14.4 Hz, 1H), 6.01 (d, J=7.6 Hz, 1H), 5.01-5.16 (m, 1H), 4.63-4.72 (m, 2H), 4.52-4.11 (m, 1H), 4.23-4.29 (m, 1H), 3.91-4.09 (m, 3H), 3.69-3.81 (m, 3H), 3.51-3.60 (m, 2H), 3.41-3.45 (m, 2H), 1.48-1.55 (m, 2H), 1.21-1.35 (m, 32H), 0.87-0.91 (m, 3H). $^{31}P$ NMR ($CD_3OD$, 162 MHz) δ −0.223. ESI-TOF-MS: m/z 788.3 $[M-H]^+$.

Example 73

Preparation of Compound (76a)

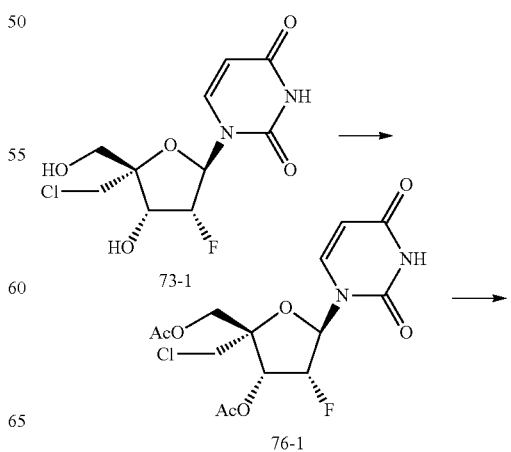

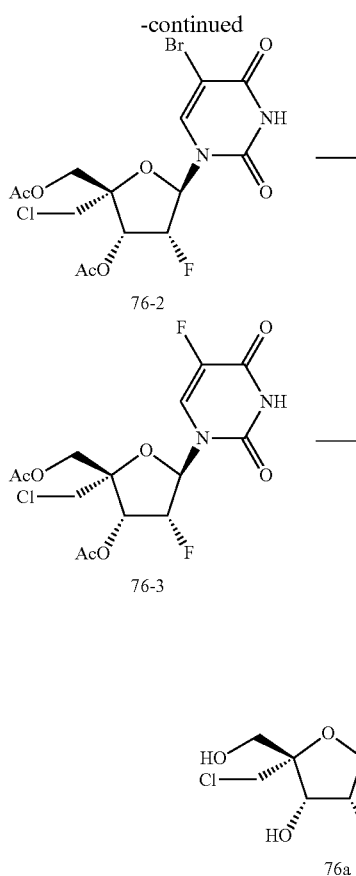

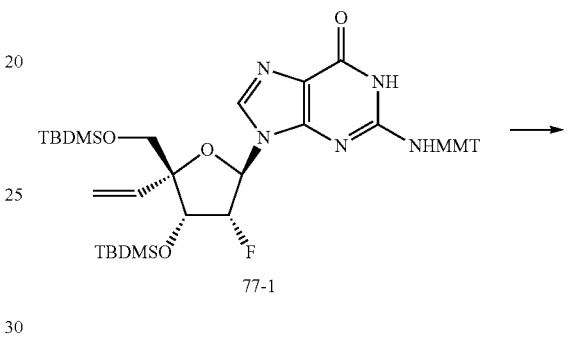

77-1

The organic layer was dried and concentrated. The residue was purified on a silica gel column (PE:EA=1:1) to give an intermediate (60 mg, 60.1%). The intermediate (50 mg, 0.13 mmol) in NH₃/MeOH (5 mL) was stirred at R.T. for 3 h. The mixture was concentrated, and the residue was purified on a silica gel column (MeOH: DCM=1:10) to give 76a (30 mg, 76.2%). ¹H NMR (CD$_3$OD, 400 MHz) δ 8.25 (d, J=6.8 Hz, 1H), 6.09 (d, J=16.0 Hz, 1H), 5.00 (dt, J=4.0 Hz, J=53.2 Hz, 1H), 4.48-4.54 (m, 1H), 3.73-3.95 (m, 4H). ESI-TOF-MS: m/z 312.1 [M+H]⁺.

Example 74

Preparation of Compound (77a)

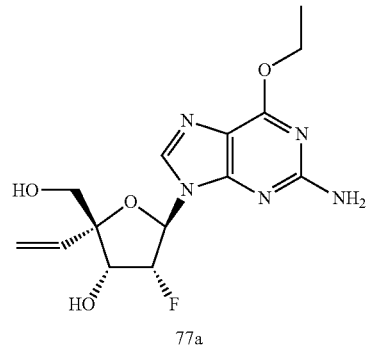

77a

Preparation of (76-1):

To a solution of 73-1 (4.1 g, 13.95 mmol) in pyridine (40 mL) was added Ac₂O (3.13 g, 30.68 mmol) at R.T., and the mixture was stirred overnight. The mixture was concentrated, and the residue was purified on a silica gel column (PE:EA=3:1) to give 76-1 (4.0 g, 75.9%).

Preparation of (76-2):

To a solution of 76-1 (1.3 g, 3.44 mmol) in pyridine (20 mL) was added NBS (1.22 g, 6.88 mmol) at R.T., and the mixture was stirred overnight. The mixture was concentrated, and the residue was purified on a silica gel column (PE:EA=4:1) to give 76-2 (1.43 g, 72.2%).

Preparation of (76-3):

To a solution of 76-2 (770 mg, 1.68 mmol) in dioxane (10 mL) was added Me₆Sn₂ (1.1 g, 3.36 mmol) and (PPh₃)₂PdCl₂ (100 mg) under N₂ atmosphere. The mixture was heated at 80° C. for 4 h. The mixture was concentrated, and the residue was purified on a silica gel column to give an intermediate (400 mg, 43.96%). To a solution of the intermediate (330 mg, 0.61 mmol) in anhydrous MeCN (3 mL) was added Selectfluor® (462 mg, 1.34 mmol) at R.T. The mixture was stirred at R.T. for 2 days. The mixture was concentrated, and the residue was purified on a silica gel column (PE:EA=4:1) to give 76-3 (100 mg, 41.5%).

Preparation of (76a):

To a solution of 76-3 (100 mg, 0.25 mmol) in MeCN (2 mL) was added DMAP (62 mg, 0.51 mmol), TEA (51 mg, 0.51 mmol) and TPSCl (153 mg, 0.51 mmol). The mixture was stirred at R.T. for 0.5 h. NH₃.H₂O (0.75 mL) was added. The mixture was stirred at R.T. for 0.5 h. The mixture was extracted with EtOAc and washed with 1N HCl and brine.

77-1 (680 mg, 0.8 mmol) and triphenylphosphine (312 mg, 1.2 mmol) were dissolved in the mixture of 5 mL of dioxine and 0.25 mL of dry ethanol. A solution of diisopropyl azadicarboxylate (40% w solution in toluene, 1.28 mmol) in 3 mL of dioxane was added, and the mixture was stirred at R.T. for 2 h. The mixture was evaporated to dryness. The residue was dissolved in 10 mL of THF, cooled down to 4° C. and 2 equivalents of TBAF in THF were added. The mixture was warmed up to R.T. and the solvent was evaporated. The resulting nucleoside was treated with 80% HCOOH at R.T. for 3 h, and then the acid was evaporated. Isolated by isocratic silica gel chromatography using mixture of DCM (950 mL), MeOH (50 mL), and NH₄OH (2.5 mL) for elution gave 77a (80 mg, 30%). ¹H-NMR (DMSO-D₆) δ: 8.06 (s, 1H), 6.41 (s, 2H), 6.11-6.06 (dd, 1H), 5.98-5.89 (dd, 1H), 5.65-5.64 (d, 1H), 5.34-5.26 (m, 2H), 5.18-5.11 (m, 1H), 4.58-4.50 (dt, 1H), 4.42-4.36 (q, 2H), 3.50-3.28 (m, 2H), 1.30 (t, 3H). MS: 384 (M−1+HCOOH).

Example 75

Preparation of Compound (78a)

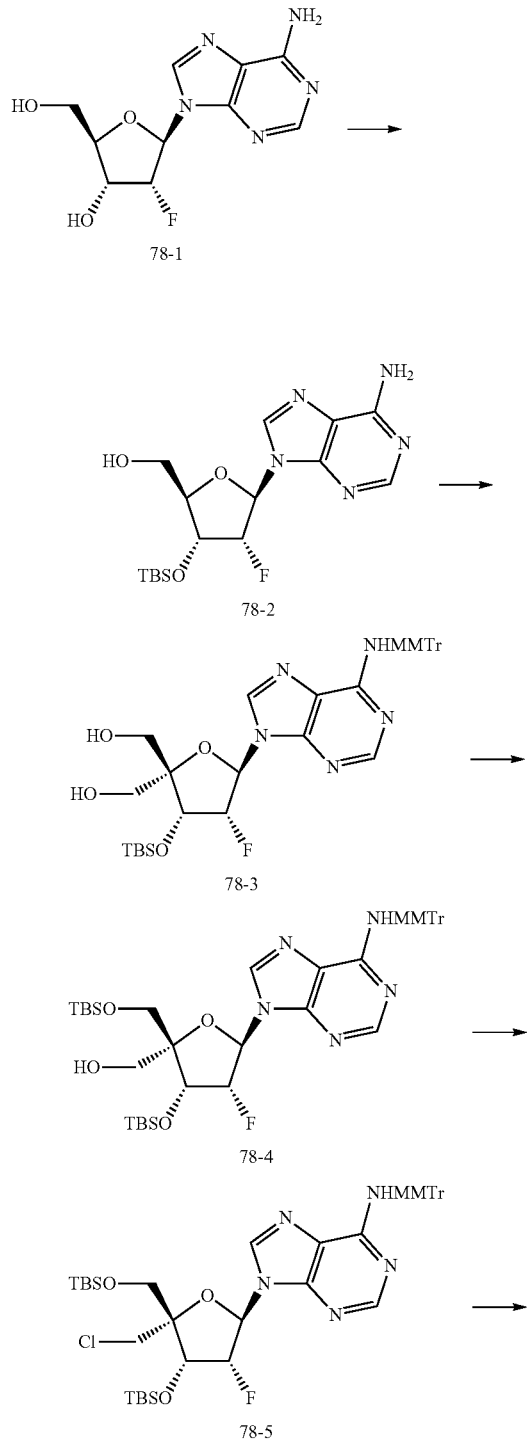

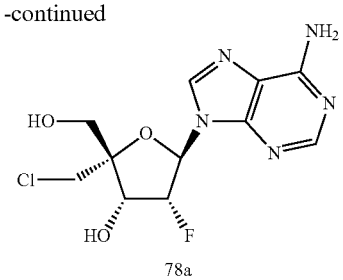

Preparation of (78-2):

To a solution of 78-1 (10.0 g, 37.17 mmol) in anhydrous pyridine (100 mL) was added imidazole (9.54 g, 140.4 mmol) and TBSCl (21.1 g, 140.4 mmol) at 25° C. The solution was stirred at 25° C. for 15 h. The solution was concentrated to dryness under reduced pressure. The residue was dissolved in EtOAc (200 mL) and washed with water and brine. The organic layer was separated, dried over anhydrous Na$_2$SO$_4$ and filtered. The filtrate was concentrated in vacuo to give a residue. The residue was purified by a silica gel column (PE/EA=10:1 to 2:1) to give an intermediate (11.8 g, 64%). To an ice-cold solution of the intermediate (11.8 g, 23.7 mmol) in CH$_2$Cl$_2$ (150 mL) was added a solution of p-toluenesulfonic acid monohydrate (8.2 g, 47.5 mmol) in small portion under N$_2$. The mixture was stirred at 25° C. for 30 min, and then washed with saturated aq. NaHCO$_3$. The organic layer was separated, dried over anhydrous Na$_2$SO$_4$ and filtered. The filtrate was concentrated in vacuum to give a residue, which was purified by silica gel (PE/EA=10:1 to 1:1) to give 78-2 (6.7 g, 74%) as a solid.

Preparation of (78-3):

To a solution of 78-2 (6.7 g, 17.5 mmol) in anhydrous pyridine (50 mL) was added TMSCl (2.8 g, 26.2 mmol) in small portions at 0° C. under N$_2$. The reaction mixture was stirred at 25° C. overnight. AgNO$_3$ (77.8 g, 510 mmol) and MMTrCl (156.8 g, 510 mmol) in anhydrous pyridine (50 mL) was added in small portions under N$_2$. The reaction mixture was stirred at 25° C. overnight. Ammonia (30 mL) was added, and the reaction mixture was stirred for 30 min. The mixture was filtered through a Buchner funnel, and the filtrate was washed with saturated NaHCO$_3$ solution and brine. The organic layer was separated, dried over anhydrous Na$_2$SO$_4$, filtered and concentrated. Chromatography on silica gel (PE:EA=10:1 to 2:1) gave an amine protected derivative (6.1 g, 53%). To a solution of pyridine (142 mg, 1.8 mmol) in anhydrous DMSO (2 mL) at 0° C. was added TFA (1.3 mg, 0.9 mmol) dropwise. The mixture was stirred at 25° C. until a clear solution formed. The solution was then added into a solution of the amine protected derivative (1.0 g, 1.5 mmol) and DCC (0.95 g, 4.6 mmol) in anhydrous DMSO at 0° C. dropwise. Stirring was continued at 25° C. for 10 h. Water (10 mL) was added, and the mixture was stirred at 25° C. for 1 h. The precipitate was removed by filtration, and the filtrate was extracted with EtOAc (20 mL). The organic layer was washed with brine (20 mL) and then dried over Na$_2$SO$_4$. The solvent was removed, and the residue was purified on a silica gel column (EA:PE=10:1 to 2:1) to give the aldehyde derivative (850 mg, 85%). To a solution of the aldehyde derivative (2.6 g, 4.0 mmol) in 1,4-dioxane (30 mL) was added 37% CH$_2$O (1.3 g, 16.0 mmol) and 2N NaOH aqueous solution (3.0 mL, 6.0 mmol). The mixture was stirred at 25° C. for 2 h and then neutralized with AcOH to pH=7. To the reaction were added EtOH (10 mL) and NaBH$_4$ (912 mg, 24.0 mmol). The reaction was stirred for 30 mins, and then quenched with saturated aqueous NH₄Cl. The mixture was extracted with EA, and the organic layer was dried over Na₂SO₄. Purification by silica gel column chromatography (EA:PE=10:1 to 2:1) gave 78-3 (1.1 g, 40%) as a yellow solid.

Preparation of (78-4):

A stirred solution of 78-3 (685 mg, 1.0 mmol) in anhydrous CH₃CN (5 mL) and anhydrous pyridine (5 mL) was cooled to 0° C. BzCl (126 mg, 0.9 mmol) was added, and the reaction mixture was stirred at 25° C. After 1.5 h, water (5 mL) was added. The resulting mixture was extracted with DCM (2×30 mL). The combined extracts were washed with a saturated aqueous solution of NaHCO₃ (20 mL), dried over MgSO₄, and evaporated under reduced pressure. The residue was purified by silica gel column chromatography (DCM:MeOH=200:1 to 50:1) to give the Bz-protected derivative (679 mg, 86%). To a stirred solution of Bz-protected derivative (432 mg, 0.55 mmol) in anhydrous DMF (5 mL) was added imidazole (258 mg, 3.85 mmol) and TBSCl (240.0 mg, 1.65 mmol). The mixture was stirred for 15 h. Water (10 mL) was added, and the mixture was extracted with EA. The combined extracts were washed with aqueous solution of NaHCO₃ (60 mL) and brine (60 mL), dried over MgSO₄, and evaporated under reduced pressure to give the two-TBS protected derivative (680 mg, 137%). The two-TBS protected derivative (680 mg, 0.75 mmol) was dissolved in anhydrous CH₃OH (5 mL), and NaOCH₃ (162 mg, 3.0 mmol) was added. The reaction mixture was stirred at 35° C. for 2 h. The reaction was quenched with 80% AcOH (3 mL) and extracted with DCM (2×50 mL). The combined extracts were washed with aqueous solution of NaHCO₃ (20 mL), dried over MgSO₄, and evaporated under reduced pressure. The residue was purified by silica gel column chromatography (EA:PE=20:1 to 3:1) to give 78-4 (239 mg, 40%) as a white foam.

Preparation of (78-5):

78-4 (239 mg, 0.30 mmol) was co-evaporated with toluene three times to remove H₂O. To a solution of 78-4 in DCM (5 mL) was added DMAP (182 mg, 1.50 mmol) and TfCl (69 mg, 0.45 mmol) at 0° C. under N₂. The mixture was stirred 0° C. for 40 mins. Completion of the reaction was determined by LCMS. The mixture was concentrated to give the crude Tf-derivative (353 mg). To a solution of the Tf-derivative in DMF (5 mL) was added LiCl (31 mg, 0.76 mmol) at 0° C. under N₂. The mixture was stirred at 25° C. for 40 mins. The mixture was washed with NaHCO₃ and extracted with EA. The combined organic layer was dried over Na₂SO₄ and concentrated to give crude 78-5 (268 mg) as a light yellow oil.

Preparation of (78a):

To a solution of 78-5 (268 mg, 0.328 mmol) in MeOH (5 mL) was added NH₄F (37 mg, 0.984 mmol) at 25° C. for 4 h. The solution was filtered and evaporated to dryness. The residue was dissolved in HCOOH (20 mL) and H₂O (4 mL) at 25° C. The mixture was stirred at 25° C. for 1 h and concentrated. The residue was dissolved in MeCN and purified by prep-HPLC to give 78a (32 mg) as a white solid. ¹H NMR (MeOD, 400 MHz) δ 8.33 (s, 1H), 8.20 (s, 1H), 6.32 (dd, J=5.6, 12.4 Hz, 1H), 5.77 (m, 1H), 4.69 (m, 1H), 3.85 (m, 1H). ESI-MS: m/z 317.9 [M+H]⁺.

Example 76

Preparation of Compound (79a)

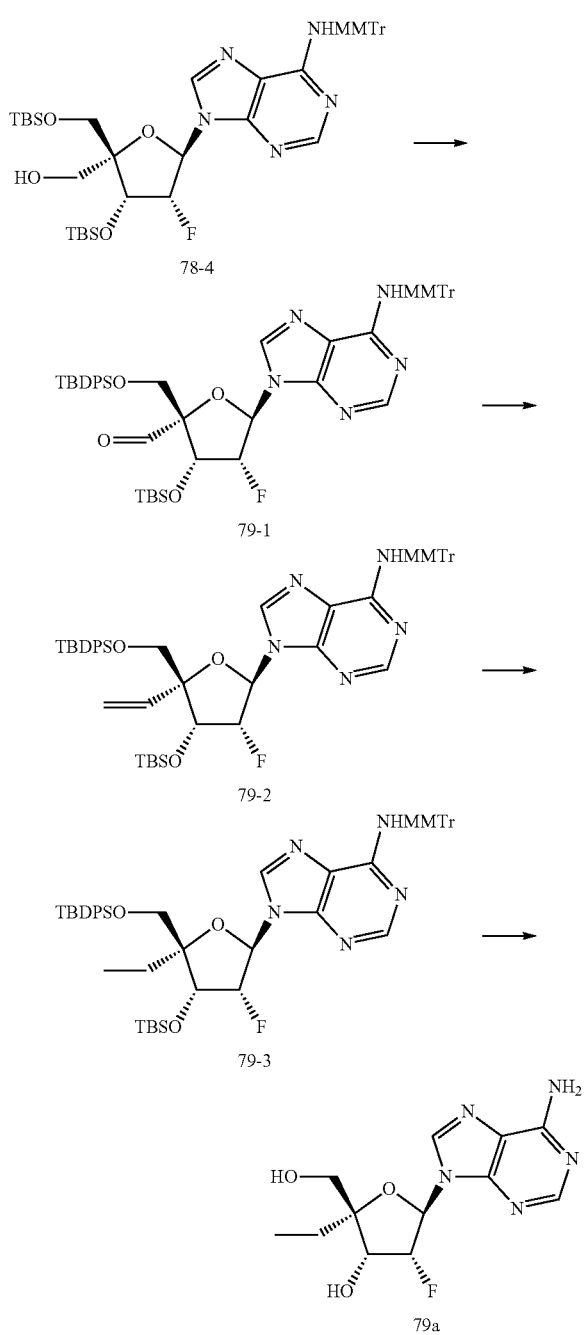

Preparation of (79-1):

To a solution of 78-4 (1.1 g, 1.33 mmol) in anhydrous DCM (6.6 mL) at 0° C. under nitrogen was added Dess-Martin periodinane (1.45 g, 3.33 mol). The mixture was stirred at 25° C. for 4 h. The solvent was removed in vacuum, and the residue triturated with methyl-t-butyl ether (30 mL). The mixture was filtered through a pad of MgSO₄, and the organic solvent was stirred with an equal volume of Na₂S₂O₃ in 30 mL of saturated NaHCO₃ until the organic layer became clear (approx. 10 min). The organic layer was separated, washed with brine, and dried over MgSO₄. Prior to removing the solvent in vacuum, the residue was purified on a silica gel column (PE:EA=7:1) to give 79-1 (750 mg, 75%) as a white solid.

Preparation of (79-2):

To a stirred solution of methyl-triphenyl-phosphonium bromide (1.74 g, 4.89 mmol) in anhydrous THF (8 mL) was added n-BuLi (1.91 mL, 4.89 mmol, 2.5 M in THF) at −78° C. dropwise. The mixture was stirred at 0° C. for 1 h. 79-1 (750 mg, 0.81 mmol) was added, and the mixture stirred at 25° C. overnight. The reaction was quenched with saturated NH₄Cl (30 mL), and extracted with EtOAc (2×30 mL). The combined organic phase was washed with brine, dried with MgSO₄, filtered and evaporated to dryness to give a light white solid. The solid was purified by column chromatography (PE:EA=5:1) to give 79-2 (440 mg, 60%).

Preparation of (79-3):

To a solution of 79-2 (440 mg, 0.48 mmol) in MeOH (8 mL) was added Pd/C (500 mg, 10%) at R.T. under hydrogen atmosphere. The mixture was stirred at R.T. for 1.5 h. The mixture was filtered, and the filtrate was concentrated to dryness. Crude 79-3 (365 mg, 83%) was used for the next step without further purification.

Preparation of (79a):

79-3 (365 mg, 0.40 mmol) in MeOH (50 mL) was added NH₄F (5.6 g, 0.15 mmol), and the solution was heated to refluxed overnight. Completion of the reaction was determined by LCMS. The mixture was filtered, and the filtrate was concentrated to dryness. The residue was purified on a silica gel column (PE:EA=3:1) to give the amine protected derivative (173 mg, 77%) as a white solid. The amine protected derivative (100 mg, 0.18 mmol) in formic acid (4.4 mL) was stirred at 25° C. overnight. The solution was concentration to dryness, and the residue was purified on a silica gel column (PE:EA=1:3) to give 79a (40 mg, 90%) as a white solid. ¹H NMR (400 MHz, CD₃OD) δ 8.25 (s, 1H), 8.09 (s, 1H), 6.14 (dd, J=6.0, 12.8 Hz, 1H), 5.58 (m, 1H), 4.45-4.48 (m, 1H), 3.60 (q, 2H), 1.66-1.74 (m, 2H), 0.88 (t, 3H); ESI-MS: m/z 297.9 [M+H]⁺.

Example 77

Preparation of Compound (80a)

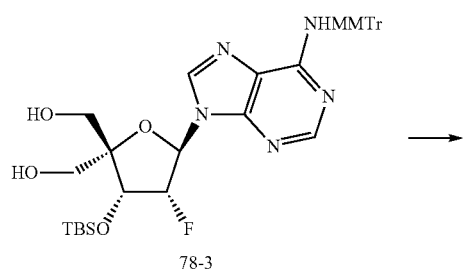

78-3

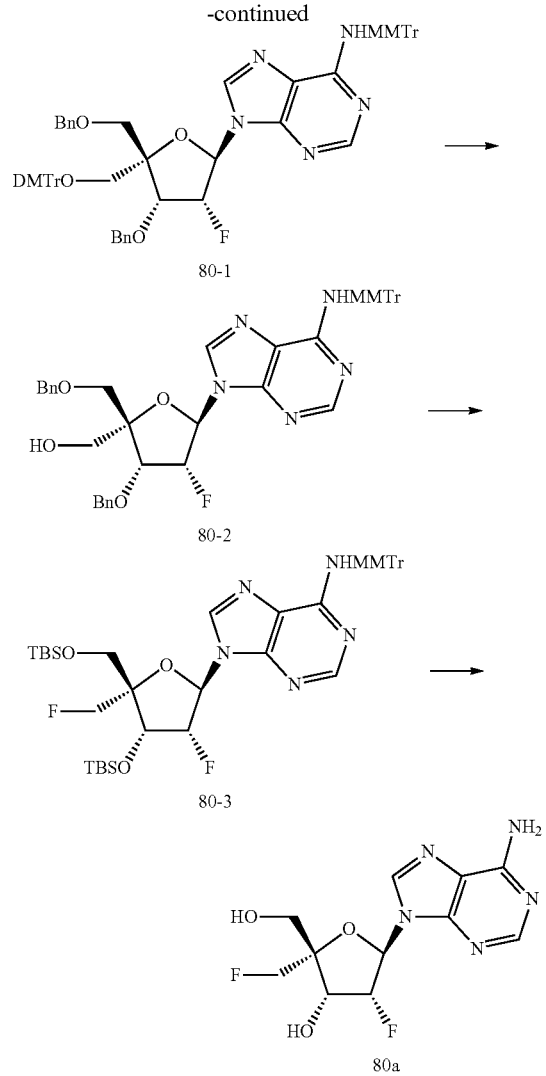

Preparation of (80-1):

To a solution of 78-3 (4.4 g, 6.4 mmol) in anhydrous pyridine (5 mL) and DCM (25 mL). A solution of DMTrCl (2.37 g, 7.04 mmol) in DCM (5 mL) was added dropwise at 0° C. under N₂. After 2 h, the reaction was quenched with CH₃OH and concentrated to dryness. The residue was purified on a column of silica gel (PE:EA=100:1 to 2:1) to obtain the DMTr protected derivative (4.3 g, 68%). The DMTr protected derivative (2.2 g, 2.5 mmol) in 1M TBAF (2.5 mL) of THF (2.5 mL) solution was stirred at 25° C. for 3 h. The solvent was removed in vacuum, and the residue was purified by column chromatography (PE/EA=50:1 to 1:2) to give the diol derivative (1.86 g, 96%). To a solution of the diol derivative (1.3 g, 1.5 mmol) in anhydrous THF (5 mL) was added NaH (132 mg, 3.3 mmol) at 0° C. The mixture was stirred for 1 h, and TBI (276 mg, 0.75 mmol), and BnBr (558 mg, 3.3 mmol) was added. The mixture was stirred for 10 h at 25° C. The reaction was quenched with water, and the solvent was evaporated. The mixture was extracted with EA and brine. The organic layer was dried over Na₂SO₄, and evaporated to afford the crude product. The product was purified by silica gel (PE/EA=100:1 to 3:1) to afford 80-1 (1.4 g, 90%) as a white foam.

243

Preparation of (80-2):

To a solution of 80-1 (1.3 g, 1.23 mmol) in anhydrous DCM (17 mL) was added Cl$_2$CHCOOH (1.57 g, 12.3 mmol) at −78° C. The mixture was stirred at −20-10° C. for 40 mins. The reaction was quenched with saturated NaHCO$_3$, and diluted with DCM (50 mL). The mixture was washed with brine, and the organic solution was dried over Na$_2$SO$_4$ and concentrated in vacuum. The residue was purified on a silica gel column (PE/EA=100:1 to 1:1) to give 80-2 (652 mg, 70%) as a white foam.

Preparation of (80-3):

To a solution of 80-2 (630 mg, 0.84 mmol) in anhydrous DCM (5 mL) was added DAST (1.35 g, 8.4 mmol) at −78° C. The mixture was gradually warmed to 0° C. The reaction was quenched with saturated NaHCO$_3$. The mixture was diluted with DCM (50 mL) and washed with brine. The organic solution was dried over Na$_2$SO$_4$ and concentrated in vacuum. The residue was purified on a silica gel column (PE/EA=100:1 to 2:1) to give 80-3 as a white solid (302 mg, 48%).

Preparation of (80a):

A mixture of 80-3 (210 mg, 0.28 mmol) and Pd(OH)$_2$ (200 mg) in methanol (3 mL) was stirred at 0° C. at 40 psi H$_2$ for 20 h. Pd(OH)$_2$ was filtered off, and the filtrate was concentrated to dryness. The residue was purified by column (DCM/MeOH=10:1) to give 80a (12 mg). $^1$H NMR (400 MHz, CD$_3$OD) δ 8.33 (s, 1H), 8.20 (s, 1H), 6.33 (dd, J=6.0, 13.2 Hz, 1H), 5.79 (t, J=5.6 Hz, 1H), 5.66 (t, J=5.2 Hz, 1H), 4.52-4.80 (m, 3H), 3.80-3.82 (m, 2H). ESI-MS: m/z 302.0 [M+H]$^+$.

Example 78

Preparation of Compound (81a)

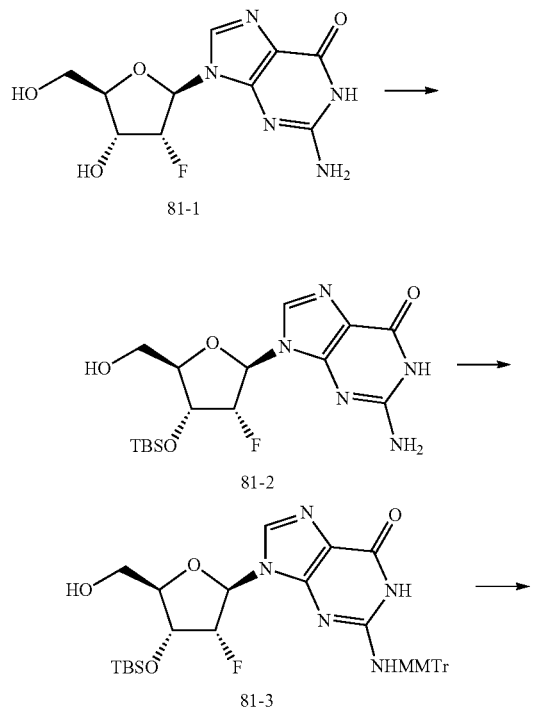

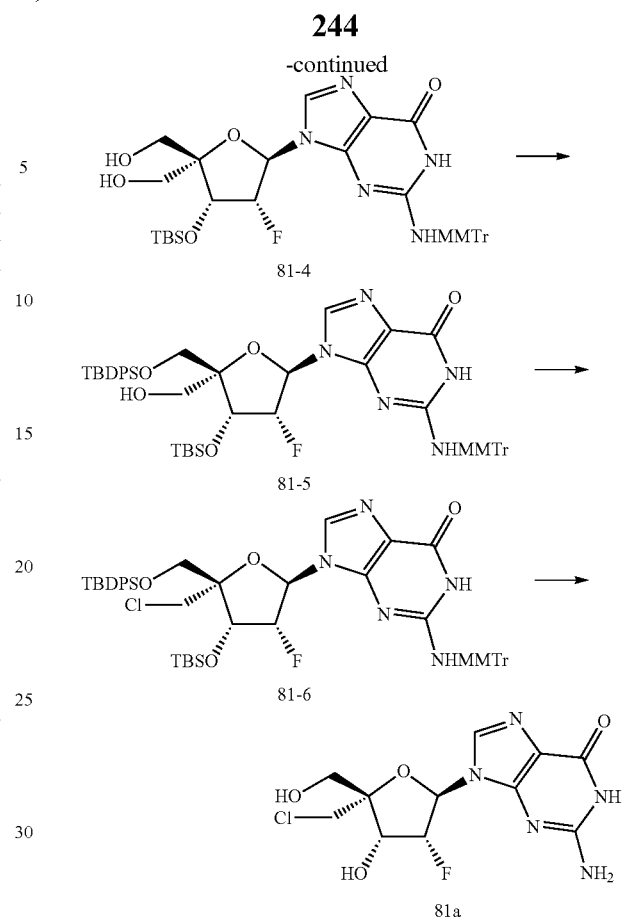

Preparation of (81-2):

To a solution of 81-1 (20.0 g, 70.2 mmol) in anhydrous pyridine (200 mL) was added imidazole (19.1 g, 280 mmol) and TBSCl (42.1 g, 281 mmol) at 25° C. The solution was stirred at 25° C. for 15 h, and then concentrated to dryness under reduced pressure. The residue was dissolved in EtOAc and then filtered. The filtrate was concentrated to dryness to give the TBS protected derivative (36.4 g, 99%). The TBS protected derivative (36.5 g, 71.1 mmol) was dissolved in THF (150 mL). H$_2$O (100 mL), and then AcOH (300 mL) were added. The solution was stirred at 80° C. for 13 h. The reaction was cooled to R.T., and then concentrated to dryness under reduced pressure to give 81-2 (31.2 g, 61%) as a white solid.

Preparation of (81-3):

To a solution of 81-2 (31.2 g, 78.2 mmol) in anhydrous pyridine (300 mL) was added Ac$_2$O (11.9 g, 117.3 mmol). The mixture was stirred at 25° C. for 18 h. MMTrCl (72.3 g, 234.6 mmol) and AgNO$_3$ (39.9 g, 234.6 mmol) were added, and the solution was stirred at 25° C. for 15 h. H$_2$O was added to quench the reaction and the solution was concentrated to dryness under reduced pressure. The residue was dissolved in EtOAc and washed with water. The organic layer was dried over Na$_2$SO$_4$ and filtered. The filtrate was concentrated in vacuum to give a residue, which was purified by silica gel (DCM:MeOH=200:1 to 50:1) to give the MMTr protected amine derivative (35.2 g, 63%). The MMTr protected amine derivative (35.2 g, 49.3 mmol) was dissolved in NH$_3$/MeOH (300 mL). The mixture was stirred at 25° C. for 20 h. The solution was evaporated to dryness, and purified by a silica gel column (DCM:MeOH=100:1 to 50:1) to give 81-3 as a yellow solid (28.6 g, 87%).

Preparation of (81-4):

To a solution of 81-3 (12.0 g, 17.9 mmol) in anhydrous DCM (200 mL) was added Dess-Martin periodinane (11.3 g, 26.8 mmol) at 0° C. The mixture was stirred at 0° C. for 2 h, and then at R.T. for 2 h. The mixture was quenched with a saturated NaHCO$_3$ and Na$_2$S$_2$O$_3$ solution. The organic layer was washed with brine (2×) and dried over anhydrous Na$_2$SO$_4$. The solvent was evaporated to give the aldehyde (12.6 g), which was used directly in the next step. To a solution of the aldehyde (12.6 g, 18.0 mmol) in 1,4-dioxane (120 mL) was added 37% HCHO (11.6 g, 144 mmol) and 2N NaOH aqueous solution (13.5 mL, 27 mmol). The mixture was stirred at 25° C. overnight. EtOH (60 mL) and NaBH$_4$ (10.9 g, 288 mmol) were added, and the reaction was stirred for 30 mins. The mixture was quenched with saturated aqueous NH$_4$Cl, and then extracted with EA. The organic layer was dried over Na$_2$SO$_4$, and purified by silica gel column chromatography (DCM:MeOH=200:1 to 50:1) to give 81-4 (7.5 g, 59%) as a yellow solid.

Preparation of (81-5):

To a solution of 81-4 (3.8 g, 5.4 mmol) in DCM (40 mL) was added pyridine (10 mL) and DMTrCl (1.8 g, 5.4 mmol) at 0° C. The solution was stirred at 25° C. for 1 h. MeOH (15 mL) was added, and the solution was concentrated. The residue was purified by silica gel column chromatography (DCM:MeOH=200:1 to 50:1) to give the MMTr protected derivative (3.6 g, 66%) as a yellow solid. To a solution of the MMTr protected derivative (3.6 g, 3.6 mmol) in anhydrous pyridine (30 mL) was added TBDPSCl (2.96 g, 10.8 mmol) and AgNO$_3$ (1.84 g, 10.8 mmol). The mixture was stirred at 25° C. for 15 h. The mixture was filtered and concentrated. The mixture was dissolved in EtOAc and washed with brine. The organic layer was dried over Na$_2$SO$_4$., and then purified by silica gel column chromatography (DCM:MeOH=200:1 to 50:1) to give the TBDPS protected derivative (3.8 g, 85.1%) as a solid. To a solution of the TBDPS protected derivative (3.6 g, 2.9 mmol) in anhydrous DCM (50 mL) was added Cl$_2$CHCOOH (1.8 mL) in anhydrous DCM (18 mL). The mixture was stirred at −78° C. for 1 h. Cl$_2$CHCOOH (3.6 mL) was added at −78° C. The mixture was stirred at −10° C. for 30 mins. The mixture was quenched with saturated aqueous NaHCO$_3$ and extracted with DCM. The organic layer was dried over Na$_2$SO$_4$, and then purified by silica gel column chromatography (DCM:MeOH=200:1 to 50:1) to give 81-5 (2.2 g, 80%).

Preparation of (81-6):

To an ice cooled solution of 81-5 (800 mg, 0.85 mmol) in anhydrous DCM (20 mL) was added pyridine (336 mg, 4.25 mmol) and Tf$_2$O (360 mg, 1.28 mmol) dropwise. The reaction mixture was stirred at 0° C. for 15 mins. The reaction was quenched by ice water and stirred for 30 mins. The mixture was extracted with EtOAc, washed with brine (50 mL) and dried over MgSO$_4$. The solvent was evaporated to give the crude bis(triflate) derivative. To the bis(triflate) derivative (790 mg, 0.73 mmol) in anhydrous DMF (35 mL) was added LiCl (302 mg, 7.19 mmol). The mixture was heated to 40° C. and stirred overnight. Completion of the reaction was determined by LCMS. The solution was washed with brine and extracted with EtOAc. The combined organic layers were dried over MgSO$_4$, and the residue was purified on a silica gel column (DCM/MeOH=100:1) to give 81-6 (430 mg, 61%).

Preparation of (81a):

To 81-6 (470 mg, 0.49 mmol) in MeOH (85 mL) was added NH$_4$F (8.1 g, 5.92 mmol), and the solution was heated to reflux overnight. The mixture was filtered, and the filtrate was concentrated to dryness. The residue was purified on a silica gel column (DCM/MeOH=20:1) to give the diol (250 mg, 84%) as a white solid. The diol (130 mg, 0.21 mmol) in formic acid (5 mL) was stirred at 25° C. overnight. The solution was concentration to dryness, and the residue in MeOH (30 mL) was stirred at 70° C. overnight. Completion of the reaction was determined by LCMS and HPLC. The solvent was removed, and the crude product was washed with EtOAc to give 81a (58 mg, 81%) as a white solid. $^1$H NMR (DMSO-d$_6$, 400 MHz) δ 10.73 (br, 1H), 7.98 (s, 1H), 6.58 (br, 2H), 6.08 (q, J=4.8, 9.2 Hz, 2H), 5.64 (dt, J=5.6, 52.8 Hz, 1H), 5.40 (m, 1H), 4.52 (m, 1H), 3.80-3.82 (m, 2H), 3.64 (q, 2H). ESI-MS: m/z 333.8 [M+H]$^+$, 666.6 [2M+H]$^+$ Example 79

Preparation of Compound (82a)

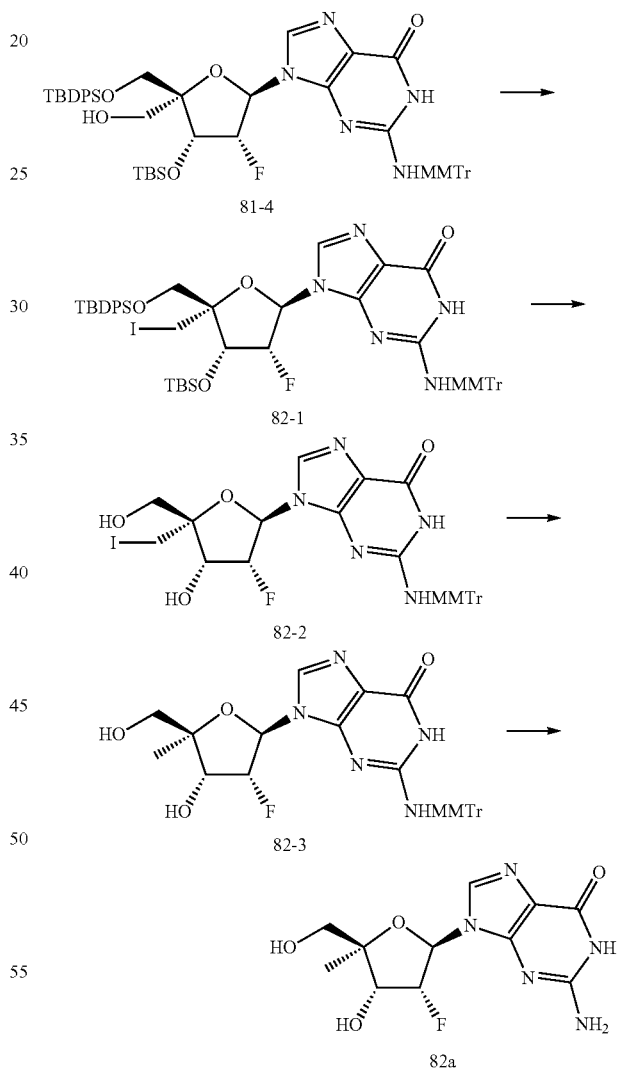

Preparation of (82-1):

To a solution of 81-4 (310 mg, 0.33 mmol) in anhydrous DCM (10 mL) was added pyridine (130 mg, 1.65 mmol) and Tf$_2$O (139 mg, 0.49 mmol) diluted by DCM dropwise at 0° C. The mixture was stirred at 0° C. for 15 mins. The reaction was quenched with ice cold water. The organic layer was separated and washed with brine. The organic layer was dried over Na₂SO₄ and evaporated to give to give the triflate derivative (420 mg crude), which was used directly in the next step. To a solution of the triflate derivative (420 mg crude) in anhydrous pentan-2-one was added NaI (396 mg, 2.64 mmol). The mixture was stirred at 40° C. for 3 h, and then dissolved with EtOAc. The organic layer were washed with Na₂S₂O₃ twice and washed with brine. The organic layer was dried over Na₂SO₄ and evaporated to give a residue. The residue was purified by a column (DCM:MeOH=300:1 to 100:1) to give 82-1 (195 mg, 56% for two steps).

Preparation of (82-2):

To a solution of 82-1 (650 mg, 0.62 mmol) in MeOH (10 mL) was added NH₄F (45.8 g, 12.4 mmol). The mixture was refluxed overnight. The mixture was filtered and evaporated to dryness. The residue was purified on a silica gel column (DCM/MeOH=200:1 to 20:1) to give 82-2 (250 mg, 58%).

Preparation of (82-3):

To a stirred solution of 82-2 (300 mg, 0.43 mmol), Et₃N (217 mg, 2.15 mmol) in anhydrous MeOH (10 mL) was added 10% Pd/C (50 mg). The mixture was stirred in a hydrogenation apparatus (30 psi hydrogen) at R.T. overnight. The catalyst was filtrated off, and the filtrate was evaporated to give a residue. The residue was purified on a silica gel column (DCM/MeOH=200:1 to 20:1) to afford 82-3 as a white solid (180 mg, 73%).

Preparation of (82a):

82-3 (110 mg, 0.19 mmol) was dissolved in HCOOH (18 g) and H₂O (6 g) at 25° C., and stirred for 1 h. The solution was evaporated to dryness, dissolved in MeOH (30 mL). The mixture was stirred at 60° C. for 12 h. The solution was evaporated to dryness, and dissolved in EtOAc (50 mL). The mixture was stirred at 60° C. for 1 h. The mixture was filtered and washed with EtOAc to give 82a as a white solid (45.3 mg, 80%). ¹H NMR (400 MHz, MeOD) 88.00 (s, 1H), 6.11-6.15 (m, 1H), 5.35-5.50 (m, 1H), 4.53-4.59 (m, 1H), 3.54-3.64 (m, 2H), 1.26 (s, 3H). ESI-MS: m/z 299.76 [M+1]⁺, 598.66 [2M+1]⁺.

Example 80

Preparation of Compound (83a)

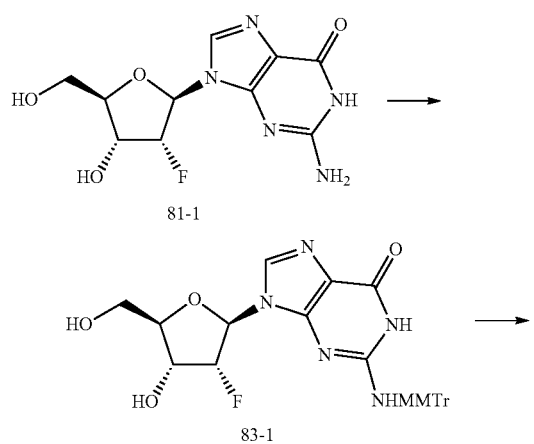

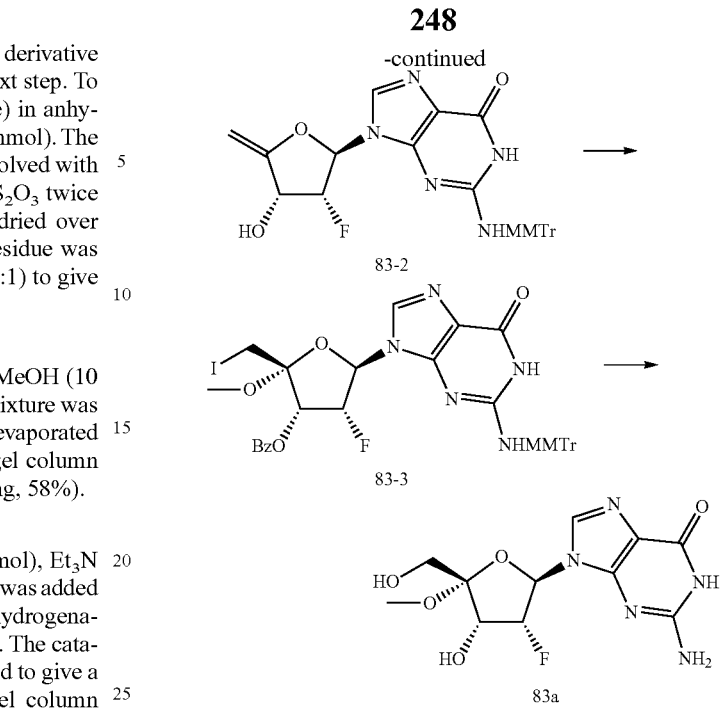

Preparation of (83-1):

81-1 (5.7 g. 20 mmol) was co-evaporated with pyridine three times, and then dissolved in pyridine (20 mL). The mixture was cooled to 0° C. and Ac₂O (5.8 mL, 60 mmol) was added dropwise. The mixture was stirred at 25° C. for 10 h, and then cooled to 0° C. AgNO₃ (8.5 g, 50 mmol), and then MMTrCl (15.5 g, 50 mmol) were added in portions. The mixture was stirred at 25° C. for 10 h. The reaction was quenched with saturated NaHCO₃ and extracted with EA. The organic layer was dried over Na₂SO₄ and concentrated. The residue was purified by silica gel column chromatography (DCM/MeOH=100:1 to 50:1) to afford the Ac protected derivative (12.1 g, 93%) as a light yellow solid. The Ac protected derivative (12.1 g) was dissolved in methanolic NH₃ (saturated). The mixture was stirred at 25° C. for 14 h. The solvent was removed, and the residue was purified on a silica gel column (DCM/MeOH=80:1 to 30:1) to give 83-1 (9.2 g, 87%).

Preparation of (83-2):

To a stirred solution of 83-1 (9.2 g, 16.5 mmol) in dry THF (300 mL) was added imidazole (9.0 g, 132 mmol) and PPh₃ (34.8 g, 132 mmol). A solution of I₂ (26.0 g, 103 mmol) in THF (100 mL) was added dropwise under N₂ at 0° C. The mixture was stirred at 25° C. for 18 h and then quenched with a Na₂S₂O₃ solution. The mixture was extracted with EtOAc. The organic layer was dried over Na₂SO₄ and concentrated. The residue was purified on a silica gel column (DCM/MeOH=80:1 to 30:1) to give the iodide derivative (10.3 g, 93%) as a light yellow solid. To a stirred solution of the iodide derivative (10.2 g, 15.3 mmol) in dry THF (300 mL) was added DBU (4.7 g, 30.1 mmol). The mixture was stirred at 60° C. for 8 h. The solution was diluted with a NaHCO₃ solution and extracted with EtOAc. The organic layer was dried over Na₂SO₄ and concentrated. The residue was purified on a silica gel column (PE/EtOAc=3:1 to 1:3) to afford 83-2 (6.2 g, yield 76%).

Preparation of (83-3):

To a stirred solution of 83-2 (5.42 g, 10 mmol) in anhydrous CH₃OH (100 mL) was added PbCO₃ (13.7 g, 53.1 mmol). A solution of I₂ (12.3 g, 48.9 mmol) in CH₃OH (300 mL) was added dropwise at 0° C. The mixture was stirred at 25° C. for 10 h. The solution was quenched with a Na$_2$S$_2$O$_3$ solution and extracted with DCM. The organic layer was washed with a NaHCO$_3$ solution, dried over Na$_2$SO$_4$ and concentrated to give a residue. The residue was purified by HPLC (0.1% HCOOH in water and MeCN) to give the desired methoxyl derivative (2.4 g, 34%). To a stirred solution of the methoxyl derivative (2.4 g, 3.4 mmol) in dry pyridine (20 mL) was added BzCl (723 mg, 5.2 mmol) dropwise at 0° C. The mixture was stirred at 0° C. for 1 h. The solution was quenched with a NaHCO$_3$ solution and extracted with EtOAc. The organic layer was dried over Na$_2$SO$_4$ and concentrated. Purified by a silica gel column (PE/EtOAc=5:1 to 1:1) afforded 83-3 (2.1 g, 77%) as a white solid.

Preparation of (83a):

83-3 (2.0 g, 2.5 mmol), BzONa (3.6 g, 25 mmol) and 15-crown-5 (5.5 g, 25 mmol) were suspended in DMF (50 mL). The mixture was stirred at 110-125° C. for 5 days. The precipitate was removed by filtration, and the filtrate was diluted with EA. The solution was washed with brine and dried over Na$_2$SO$_4$. The solvent was removed, and the residue was purified on a silica gel column (PE/EA=10/1 to 2/1) to afford the crude Bz protected derivative (1.6 g, 80%). The Bz protected derivative (1.6 g, 2.0 mmol) was dissolved in methanolic ammonia (100 mL), and the mixture was stirred at 25° C. for 20 h. The solvent was removed, and the residue was purified by a silica gel column (DCM/MeOH=100:1 to 20:1) to the diol derivative as a white solid (410 mg, 35%). The diol derivative (200 mg, 0.34 mmol) was dissolved in HCOOH (24 g) and H$_2$O (6 g) at 25° C., and the mixture was stirred at 25° C. for 1 h. The solution was evaporated to dryness, and dissolved in MeOH (30 mL). The mixture was stirred at 60° C. for 12 h. The solution was evaporated to dryness and dissolved in EtOAc (50 mL). The mixture was stirred at 60° C. for 1 h. The mixture was then filtered and washed with EtOAc to give 83a as a white solid (46.1 mg, 43%). $^1$H NMR (CD$_3$OD, 400 MHz) δ 7.92 (s, 1H), 6.22 (dd, J=1.6, 18.8 Hz, 1H), 5.17-5.32 (m, 1H), 4.89-4.91 (m, 1H), 3.77 (m, 2H), 3.44 (s, 3H). ESI-MS: m/z 316.1 [M+H]$^+$.

Example 81

Preparation of Compound (84a)

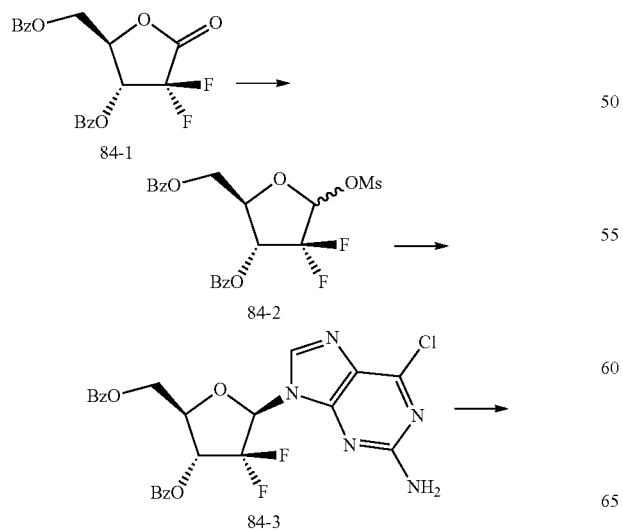
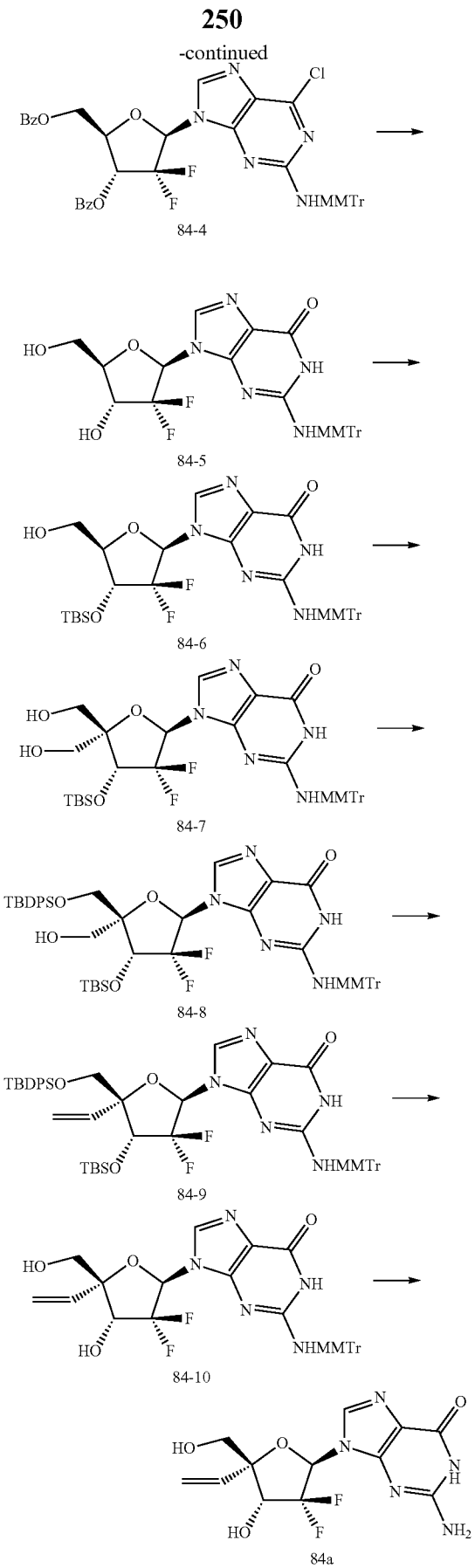

Preparation of (84-2):

To a stirred solution of 84-1 (100.0 g, 265.9 mmol) in dry THF (1000 mL) was added Li(O-t-Bu)$_3$AlH (318.9 mL, 318.9 mmol) at −78° C. under N$_2$. The mixture was stirred at −78° C. for 1 h and then at R.T for 1 h. The reaction mixture was cooled to −50° C. and quenched with ice and a saturated NH$_4$Cl solution. The mixture was extracted with EtOAc. The organic layer was dried over Na$_2$SO$_4$ and concentrated to afford the 1'-OH derivative (100.5 g) as a white solid. To a stirred solution of the 1'-OH derivative (100.5 g, 265.9 mmol) in dry DCM (600 mL), NEt$_3$ (110 mL) and MsCl (45.5 g, 298.0 mmol) were added dropwise at 0° C. The mixture was stirred at R.T. for 2 h. The mixture was quenched with ice water at 0° C. and extracted with DCM. The organic layer was dried over Na$_2$SO$_4$, concentrated and purified on a silica gel column (PE:EA=50:1 to 5:1) to afford 84-2 (113.4 g, yield: 93.9%) as a white solid.

Preparation of (84-3):

To a suspension of compound 6-chloro-9H-purin-2-amine (70.1 g, 414.7 mmol), HMDS (480 mL) and (NH$_4$)$_2$SO$_4$ (0.8 g) was added dry DCE (400 mL). The mixture was refluxed under N$_2$ for 18 h and then cooled to R.T. To the silylated 2-amino-6-chloropurine solution was added 84-2 (78.0 g, 171.1 mmol) and TMSOTf (60 mL, 331.9 mmol). The mixture was refluxed overnight, concentrated and neutralized with a NaHCO$_3$ solution. The resulting precipitate was filtered, and the filtrate was extracted with EtOAc. The organic layer was dried over Na$_2$SO$_4$ and concentrated. Chromatography on a silica gel column (PE:EA=5:1 to 2:1) gave 84-3 (10.8 g, yield: 11.9%) as a light yellow solid.

Preparation of (84-4):

To a suspension of 84-3 (30.0 g, 56.6 mmol) in DCM (300 mL) were added MMTrCl (34.9 g, 113.2 mmol) and AgNO$_3$ (19.3 g, 113.2 mmol). The reaction mixture was cooled to 0° C., and collidine (18.0 g, 150 mmol) was added. The resulting suspension was stirred at R.T. for 12 h. The suspension was filtered. The filtrate was extracted with DCM and washed with a NaHCO$_3$ solution. The organic layer was dried over Na$_2$SO$_4$ and concentrated. Purification by a silica gel column (PE:EA=20:1 to 3:1) to give 84-4 (35.0 g, yield: 77.9%) as a light yellow solid. $^1$H NMR (CDCl$_3$, 400 MHz) δ 7.94-7.96 (m, 4H), 7.05-7.58 (m, 18H), 6.62-6.67 (m, 2H), 6.55 (dd, J=6.0 Hz, J=9.6 Hz, 1H), 5.60-5.66 (m, 1H), 4.69-4.76 (m, 2H), 4.55-4.58 (m, 1H), 3.64 (s, 1H). ESI-MS: m/z 802 [M+H]$^+$.

Preparation of (84-5):

To a stirred solution of 84-4 (35.0 g, 43.6 mmol) in dry MeOH (400 mL) was added NaOMe (23.5 g, 436 mmol) and 2-mercapto-ethanol (30.6 g, 392.4 mmol). The mixture was refluxed overnight. The pH was adjusted to 9-10 with CO$_2$. The precipitate was filtered, and the filtrate was concentrated. Purification on a silica gel column (PE:EA=10:1 to 1:1) gave pure 84-5 (24.0 g, yield 95.7%) as a light yellow solid.

Preparation of (84-6):

To a solution of 84-5 (24.0 g, 41.7 mmol) in pyridine (250 mL) was added DMTrCl (28.2 g, 83.5 mmol) at 0° C. The solution was stirred at R.T. for 15 h. MeOH (50 mL) was added, and the mixture was concentrated to dryness under reduced pressure. The residue was dissolved in EtOAc and washed with water. The organic layer was dried over Na$_2$SO$_4$, filtered, concentrated and purified by a silica gel column (DCM:MeOH=200:1 to 50:1) to give a first intermediate (27.6 g) as a yellow solid. To a solution of the first intermediate (27.6 g, 31.5 mmol) in DCM (200 mL) was added imidazole (4.3 g, 63 mmol) and TBSCl (9.5 g, 63 mmol). The mixture was stirred at R.T. for 12 h. The solution was washed with NaHCO$_3$ and brine. The organic layer was dried over Na$_2$SO$_4$, filtered, concentrated and purified by a silica gel column (DCM:MeOH=200:1 to 100:1) to give a second intermediate (30.2 g) as a yellow solid. To a solution of the second intermediate (30.2 g, 30.4 mmol) in anhydrous DCM (50 mL) was added Cl$_2$CHCOOH (20 ml) in anhydrous DCM (500 mL). The mixture was stirred at −78° C. for 1 h. Cl$_2$CHCOOH (30 mL) was added at −78° C. The mixture was stirred at −20° C. for 2 h. The mixture was quenched with saturated aqueous NaHCO$_3$ and extracted with DCM. The organic layer was dried over Na$_2$SO$_4$, and then purified by a silica gel column (DCM:MeOH=200:1 to 30:1) to give 84-6 (18.0 g, 62.5%) as a white solid. $^1$H NMR (400 MHz, MeOD) δ 8.27 (s, 1H), 7.16-7.38 (m, 12H), 6.79-6.83 (m, 2H), 6.42 (dd, J=4.4 Hz, J=10.0 Hz, 1H), 4.54-4.62 (m, 1H), 3.92 (d, J=8.8 Hz, 2H), 3.74 (s, 3H), 3.70-3.72 (m, 1H), 0.92 (s, 9H), 0.11-0.13 (m, 6H). ESI-LCMS: m/z 690.0 [M+H]$^+$.

Preparation of (84-7):

84-6 (7.0 g, 10.0 mmol) was added to a suspension of DMP (10.6 g, 25 mmol) in anhydrous CH$_2$Cl$_2$ (100 mL) at 0° C. The mixture was stirred at 25° C. for 2 h. The solvent was removed in vacuo, and the residue triturated with diethyl ether (100 mL). The mixture was filtered through a pad of MgSO$_4$. The organic solvent was stirred with an equal volume of Na$_2$S$_2$O$_3$.5H$_2$O in 100 mL of saturated NaHCO$_3$ until the organic layer became clear (10 min). The organic layer was separated, washed with brine, and dried over MgSO$_4$. The solvent was removed in vacuo to give a third intermediate as a red solid (6.5 g, 95%). To a solution of the third intermediate (6.5 g, 9.5 mmol) in 1,4-dioxane (80 mL) was added 37% CH$_2$O (6.0 mL, 60 mmol) and 2N NaOH aqueous solution (9.5 mL, 19 mmol). The mixture was stirred at 25° C. for 2 h and then neutralized with AcOH to pH 7. EtOH (30 mL) and NaBH$_4$ (3.8 g, 100 mmol) were added, and the mixture was stirred for 30 mins. The mixture was quenched with saturated aqueous NH$_4$Cl, and then extracted with EA. The organic layer was dried over Na$_2$SO$_4$. Purification by a silica gel column (DCM:MeOH=200:1 to 30:1) gave 84-7 (4.2 g, 58.3%) as a yellow solid.

Preparation of (84-8):

To a solution of 84-7 (4.2 g, 5.8 mmol) in DCM (50 mL) was added pyridine (5 mL) and DMTrCl (1.9 g, 5.8 mmol) at −20° C. The solution was stirred at 0° C. for 2 h. The reaction mixture was treated with MeOH (15 mL), and then concentrated. The residue was purified by a silica gel column (DCM:MeOH=200:1 to 50:1) to give the fourth intermediate (1.3 g) as a yellow solid. To a solution of the fourth intermediate (1.3 g, 1.3 mmol) in anhydrous pyridine (15 mL) was added TBDPSCl (1.1 g, 3.9 mmol) and AgNO$_3$ (0.68 g, 4.0 mmol). The mixture was stirred at 25° C. for 15 h. The mixture was filtered, concentrated, dissolved in EtOAc and washed with brine. The organic layer was dried over Na$_2$SO$_4$. Purification by a silica gel column (DCM:MeOH=200:1 to 100:1) gave a fifth intermediate (1.4 g) as a solid. To a solution of the fifth intermediate (1.4 g, 1.1 mmol) in anhydrous DCM (50 mL) was added Cl$_2$CHCOOH (0.7 ml) in anhydrous DCM (18 mL). The mixture was stirred at −78° C. for 1 h. Cl$_2$CHCOOH (1.5 ml) was added at −78° C., and the mixture was stirred at −20° C. for 1.5 h. The mixture was quenched with saturated aqueous NaHCO$_3$ and extracted with DCM. The organic layer was dried over Na$_2$SO$_4$. Purification by a silica gel column (DCM:MeOH=200:1 to 50:1) gave 84-8 (650 mg, 11.6%) as a white solid.

Preparation of (84-9):

To a solution of pyridine (521 mg, 6.59 mmol) in anhydrous DMSO (5 mL) was added TFA (636 mg, 5.58 mmol) dropwise at 10° C. under N$_2$. The mixture was stirred until a clear solution formed. To this solution (0.8 mL) was added a mixture of 84-8 (650 mg, 0.68 mmol) and DCC (410 mg, 2.0 mmol) in anhydrous DMSO (5 mL) at R.T. under $N_2$. The mixture was stirred at 20° C. overnight. Water (30 mL) was added. The mixture was diluted with DCM (30 mL) and filtered. The filtrate was extracted with DCM. The organic layers were washed with saturated aqueous $NaHCO_3$, dried over $Na_2SO_4$ and concentrated in vacuo. The crude product was purified on a silica gel column (PE:EA=10:1 to 1:1) to give the sixth intermediate (600 mg) as a yellow solid. To a stirred solution of Methyl-triphenyl-phosphonium bromide (714 mg, 2.0 mmol) in anhydrous THF (5 mL) was added n-BuLi (0.8 mL, 2.0 mmol, 2.5 M in THF) at −78° C. dropwise over 1 min. Stirring was continued at 0° C. for 1 h. The sixth intermediate (600 mg, 0.63 mmol) was added to the mixture, and the mixture was stirred at 25° C. for 15 h. The reaction was quenched with saturated $NH_4Cl$ (20 mL) and extracted with EtOAc. The combined organic phase was dried with $Na_2SO_4$, filtered and evaporated to dryness to give a light yellow oil. The oil was purified by column chromatography (DCM:MeOH=200:1 to 50:1) to give 84-9 (250 mg, 38.5%) as a yellow solid.

Preparation of (84-10):

84-9 (250 mg, 0.26 mmol) was dissolved in THF (5.0 mL). TBAF (131 mg, 0.5 mmol) was added at 20° C., and stiffing was continued for 2 h. The solution was evaporated to dryness. The residue was dissolved in EA (50 mL) and washed with water (2×). The solution was evaporated to dryness, and purified by a silica gel column (PE:EA=10:1 to 1:2) to give 84-10 (57.6 mg, 36.9%) as a white solid. $^1$H NMR (400 MHz, MeOD) δ 8.34 (s, 1H), 7.15-7.38 (m, 12H), 6.79-6.82 (m, 2H), 6.44 (dd, J=2.0 Hz, J=10.0 Hz, 1H), 6.01 (dd, J=11.2 Hz, J=17.6 Hz, 1H), 5.51 (dd, J=1.6 Hz, J=17.2 Hz, 1H), 5.35 (dd, J=1.6 Hz, J=17.2 Hz, 1H), 4.68-4.76 (m, 1H), 3.74 (s, 3H), 3.63 (dd, J=2.0 Hz, J=12.8 Hz, 1H) 3.52 (dd, J=2.0 Hz, J=12.8 Hz, 1H). ESI-LCMS: m/z 602.0 $[M+H]^+$.

Preparation of (84a):

A solution of 84-10 (27 mg) in 1.5 mL of 80% formic acid stood at R.T. for 4.5 h and then concentrated to dryness. The residue was mixed with water and lyophilized. MeOH (1.5 mL) and TEA (0.1 mL) were added, and the mixture was concentrated. The precipitate from MeOH and EtOAc was filtered and washed with EtOAc to give 84 (9.3 mg) as a slightly-amber solid. $^1$H NMR ($CD_3OD$, 400 MHz) δ 8.44 (s, 1H), 6.57 (d, J=10.8 Hz, 1H), 6.05 (dd, J=17.6 Hz, 10.8 Hz, 1H), 5.45 (dd, J=17.6 Hz, J=1.6 Hz, 1H), 5.37 (dd, J=10.8 Hz, 1.6 Hz, 1H), 4.78 (dd, J=18.4 Hz, 17.2 Hz, 1H), 3.67 (d, J=12.4 Hz, 1H), 3.56 (dd, J=12.4 Hz, 2.0 Hz, 1H); ESI-MS: m/z 328.4 $[M–H]^-$.

Example 82

Preparation of Compound (85a)

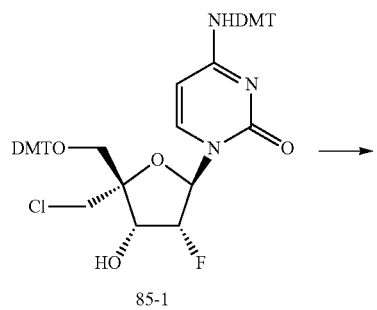

85-1

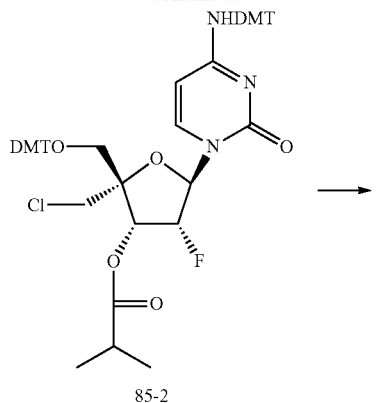

85-2

Preparation of (85-2):

A mixture of 85-1 (200 mg; 0.22 mmol) in pyridine (2.5 mL) and isobutyric anhydride (44 µL; 1.2 equiv) was stirred R.T. overnight. The mixture was concentrated, and the residue partitioned between EtOAc (50 mL) and water. The organic layer was washed with 1N citric acid, water, saturated aqueous $NaHCO_3$ and brine. The mixture was dried with $Na_2SO_4$. The solvent was evaporated and the residue was purified on a silica column (10 g column) using hexanes/EtOAc (30 to 100% gradient) to give 85-2 (0.16 g, 75%).

Preparation of (85a):

A solution of 85-2 (0.16 g; 0.16 mmol) in 80% aq. HCOOH (5 mL) was stirred at R.T. for 3 h. The solvent was evaporated and then co-evaporated with toluene. Purification on a silica column (10 g column) with $CH_2Cl_2$/MeOH (4-10% gradient) gave 85a (43 mg, 74%). $^1$H-NMR (DMSO-$d_6$): δ 7.75 (d, 1H), 7.33 (d, 2H), 6.07 (dd, 1H), 5.75 (d, 1H), 5.55 (dd, 1H), 5.43

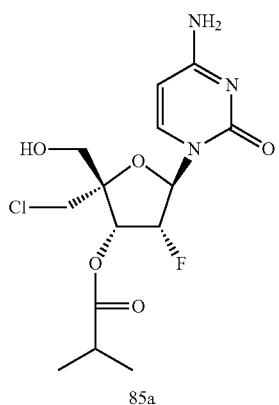

85a (dt, 1H), 5.43 (t, 1H), 3.79 (dd, 2H), 3.63 (ddd, 2H), 2.64 (sept, 1H), 1.12 (d, 6H). MS: m/z=362. [M+1]

Example 83

Preparation of Compound (86a)

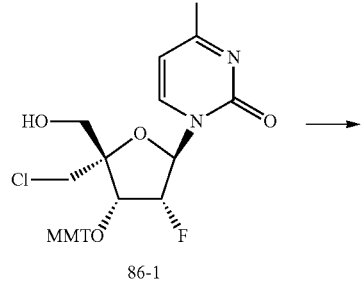
86-1

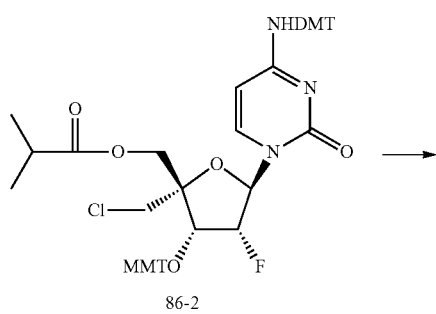
86-2

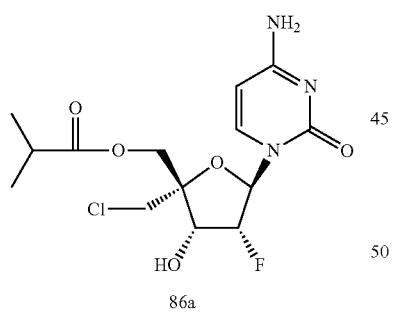
86a

Preparation of (86-2):

86-2 was prepared using a similar procedure for preparing 85-2 with the following:

86-1 (220 mg; 0.22 mmol), (2.5 mL), isobutyric anhydride (0.13 mL; 3.6 equiv), EtOAc (30 mL), and hexanes/EtOAc (30 to 100% gradient) to give 86-2 (175 mg, 85%).

Preparation of (86a):

86a was prepared using a similar procedure for preparing 85a with the following: 86-2 (117 mg; 0.13 mmol), 80% aq. HCOOH (4 mL) and CH$_2$Cl$_2$/MeOH (4-10% gradient) to give 86a (36 mg, 77%). $^1$H-NMR (DMSO-d$_6$): δ 7.58 (d, 1H), 7.29 (d, 2H), 6.00 (s, 1H), 5.73 (d, 1H), 5.24 (ddd, 1H), 4.55 (dd, 1H), 4.22 (dd, 2H), 3.80 (dd, 2H), 2.58 (sept, 1H), 1.08, 1.07 (2d, 6H). MS: m/z=364 [M+1].

Example 84

Preparation of Compounds (87a)

87-1

87-2

87a

Preparation of (87-2):

87-2 was prepared using a similar procedure for preparing 46-2 with the following: 87-1 (178 mg, 0.3 mmol), hexanoic anhydride (0.14 mL, 2 equiv.), pyridine (3 mL) to give 87-2. (120 mg, 50%).

Preparation of (87a):

87a was prepared using a similar procedure for preparing 85a with the following: 87-2 (120 mg, 0.15 mmol), 80% aq. HCOOH and CH$_2$Cl$_2$/MeOH (4-10% gradient) to give 87a (62 mg, 85%). ¹H-NMR (CDCl₃): δ 8.2 (br, 1H), 7.42 (d, 1H), 6.8 (br, 1H), 6.03 (d, 1H), 5.77 (dd, 1H), 5.64 (dd, 1H), 5.51 (ddd, 1H), 4.43 (dd, 2H), 3.82 (dd, 2H), 2.41 (m, 2H), 2.33 (m, 2H), 1.64 (m, 4H), 1.31 (m, 8H), 0.82 (m, 6H). MS: m/z=488 [M−1].

Example 85

Preparation of Compound (88a)

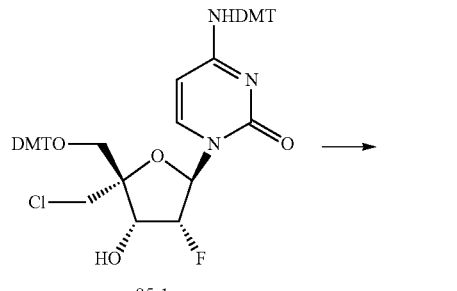

85-1

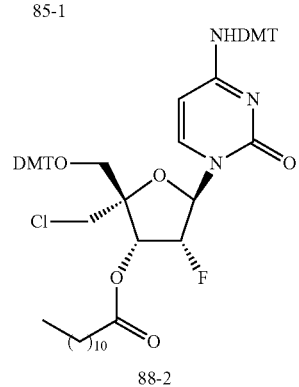

88-2

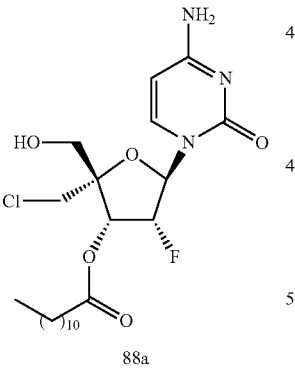

88a

Preparation of (88-2):

88-2 was prepared using a similar procedure for preparing 85-2 with the following: 85-1 (220 mg; 0.24 mmol), pyridine (3 mL), dodecanoycanhydride (0.12 g; 1.3 equiv), EtOAc (50 mL) and hexanes/EtOAc (25 to 80% gradient) to give 88-2 (0.22 g, 85%).

Preparation of (88a):

88a was prepared using a similar procedure for preparing 85a with the following: 88-2 (0.19 g; 0.17 mmol), 80% aq. HCOOH (5 mL) and CH₂Cl₂/MeOH (4-10% gradient) to give 88a (66 mg, 82%). ¹H-NMR (DMSO-d₆): δ 7.77 (d, 1H), 7.35 (d, 2H), 6.07 (dd, 1H), 5.77 (d, 1H), 5.60 (dd, 1H), 5.55 (ddd, 1H), 5.43 (t, 1H), 3.78 (dd, 2H), 3.65 (ddd, 2H), 2.41 (m, 2H), 1.56 (m, 2H), 1.24 (m, 16H), 0.85 (m, 3H). MS: m/z=474 [M−1].

Example 86

Preparation of Compounds (89a) and (90a)

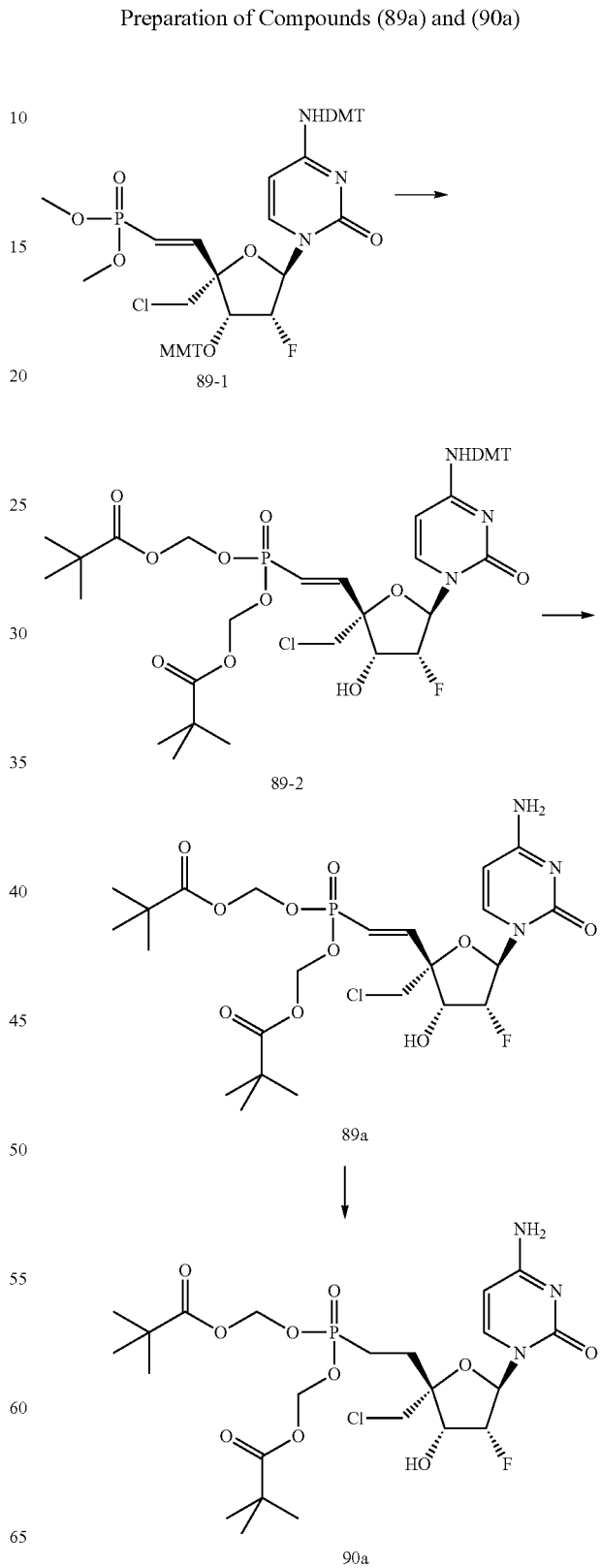

259

Preparation of (89-2):

To a solution of 89-1 (175 mg; 0.18 mmol) in MeCN (2.5 mL) at 0° C. was added TMSBr (0.28 mL; 10 equiv.). The mixture was stirred at R.T. for 1 h, evaporated and treated with water. The obtained white solid was filtered, dried and washed with $CH_2Cl_2$. The white solid was then dissolved in NMP (2 mL) and treated with DIPEA (94 µL; 3 equiv.) and pivaloyloxymethyliodide (84 µL; 3 equiv.). The mixture was stirred at R.T. for 1 day, and then partitioned between water (20 mL) and tert-butyl methyl ether (TBME; 60 mL). The organic layer was washed with saturated aqueous $NaHCO_3$, water and brine. The combined aqueous washings were back extracted with TBME (2×20 mL). The combined organic extract was dried and purified on a silica column (10 g column) with $CH_2Cl_2$/i-PrOH (2-10% gradient) to give 89-2 (42 mg, 26%).

Preparation of (89a):

A solution of 89-2 in 80% aq. HCOOH was stirred at R.T. for 3 h. The solvent was evaporated and then co-evaporated with toluene. Purification on a silica column (10 g column) with $CH_2Cl_2$/MeOH (4-15% gradient) gave 89a (17 mg, 74%). $^1$H-NMR ($CD_3OD$): δ 7.47 (d, 1H), 6.28 (dd, 1H), 6.04 (dd, 1H), 5.77-5.71 (m, 2H), 5.53 (m, 4H), 5.18 (ddd, 1H), 5.60 (dd, 1H), 3.77 (dd, 2H), 1.08 (m, 18H). $^{31}$P-NMR ($CD_3OD$): δ 17.64. MS: m/z=598 [M+1].

Preparation of (90a):

A mixture of 89a (12 mg; 0.02 mmol) in EtOH (1 mL) and Pd/C (10%; 2.5 mg) was stirred overnight under an atmospheric pressure of hydrogen. The mixture was filtered through a Celite pad. The solvent was evaporated and the product was purified on a silica column (10 g column) with $CH_2Cl_2$/MeOH (4-17% gradient) to give 90a (6 mg, 50%). $^1$H-NMR ($CD_3OD$): δ 7.51 (d, 1H), 5.79 (d, 1H), 5.65-5.54 (m, 5H), 5.20 (ddd, 1H), 5.60 (dd, 1H), 3.70 (dd, 2H), 2.17-2.06 (m, 1H), 2.02-1.87 (m, 3H), 1.13 (m, 18H). $^{31}$P-NMR ($CD_3OD$): δ 33.16. MS: m/z=600 [M+1].

Example 87

Preparation of Compound (91a)

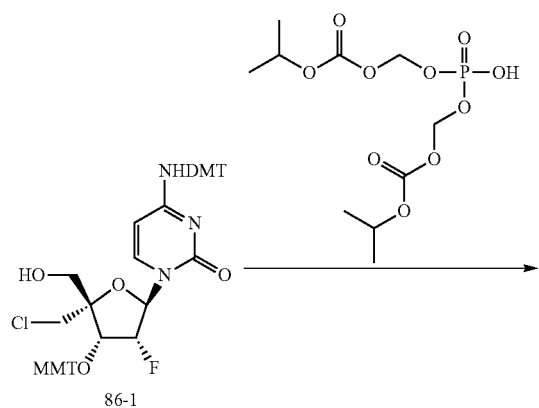

86-1

260

-continued

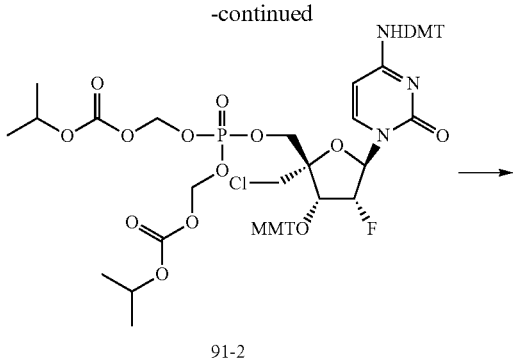

91-2

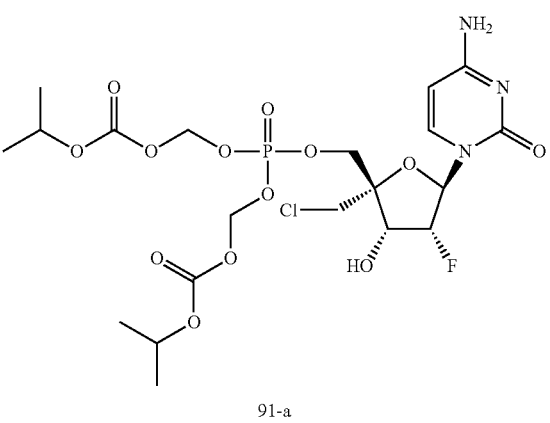

91-a

Preparation of (91-2):

To a solution of triethylammonium bis(isopropyloxycarbonyloxymethyl)phosphate (0.33 mmol, prepared from 110 mg of bis(POC)phosphate and 0.1 mL of $Et_3N$) in THF (2 mL) was added 86-1 (100 mg; 0.11 mmol), followed by diisopropylethyl amine (0.19 mL; 10 equiv), BOP-Cl (140 mg; 5 equiv) and 3-nitro-1,2,4-triazole (63 mg; 5 equiv). The mixture was stirred at R.T. for 90 mins., and then diluted with $CH_2Cl_2$ (30 mL). The mixture was washed with saturated aqueous $NaHCO_3$ and brine. The mixture was dried with $Na_2SO_4$. The solvent was evaporated, and the residue was purified on a silica column (10 g column) with hexanes/EtOAc (40-100% gradient) to give 91-2 (117 mg, 90%).

Preparation of (91a):

91a was prepared using a similar procedure for preparing 85a with the following: 91-2 (87 mg; 0.07 mmol), 80% aq. HCOOH (5 mL) and $CH_2Cl_2$/MeOH (4-15% gradient) to give 91a (36 mg, 85%). $^1$H-NMR ($CD_3CN$): δ 7.67 (dd, 1H), 6.35 (dd, 1H), 6.1 (br, 2H), 5.82 (d, 1H), 5.62 (m, 4H), 5.22 (dm, 1H), 4.98 (br, 1H), 4.89 (m, 2H), 4.49 (d, 1H), 4.34 (m, 2H), 3.88 (dd, 2H), 1.29 (d, 6H), 1.28 (d, 6H); $^{31}$P-NMR ($CD_3CN$): δ −4.49. MS: m/z=606 [M+1].

Example 88

Preparation of Compound (92a)

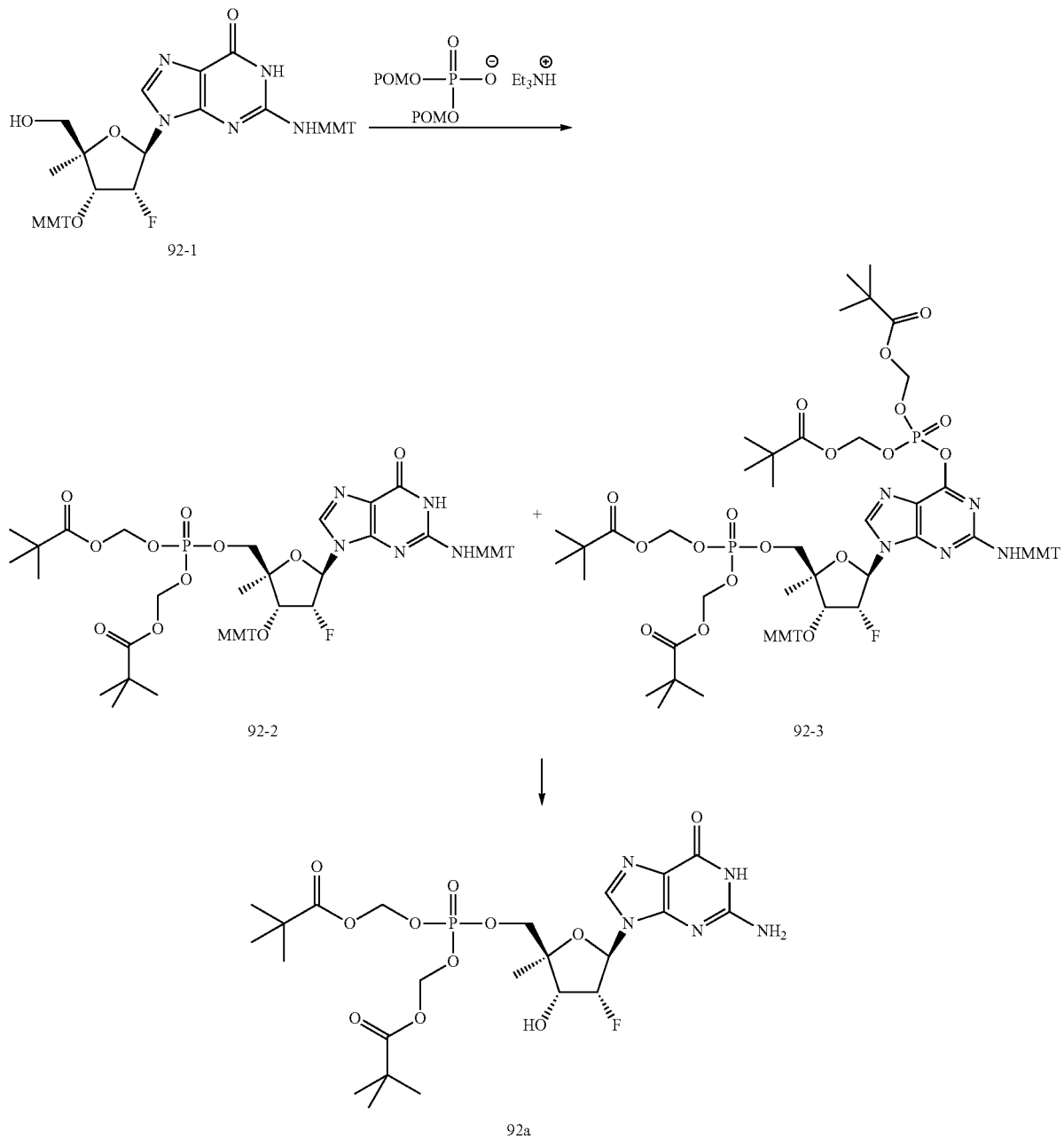

Preparation of (92-2) and (92-3):

To a solution of triethylammonium bis(POM)phosphate (0.48 mmol, prepared from 176 mg of bis(POM)phosphate and 0.15 mL of $Et_3N$) in THF (2 mL) was added 92-1 (150 mg; 0.18 mmol) followed by diisopropylethyl amine (0.31 mL; 10 equiv), BOP-Cl (229 mg; 5 equiv), and 3-nitro-1,2,4-triazole (103 mg; 5 equiv). The mixture was stirred at R.T. for 90 mins., and then diluted with $CH_2Cl_2$ (30 mL). The mixture was washed with saturated aqueous $NaHCO_3$ and brine. The mixture was dried with $Na_2SO_4$. The solvent was evaporated, and the residue was purified on a silica column (10 g column) with $CH_2Cl_2$/i-PrOH (2-10% gradient) to obtain 92-2 (44 mg, 21%) and 92-3 (73 mg, 28%).

Preparation of (92a):

A mixture of 92-2 and 92-3 (73 mg and 44 mg) and 80% aq. HCOOH (3 mL) was heated for 30 mins., at 35° C. The solvent was evaporated and then coevaporated with toluene. The solvent was evaporated, and the residue was purified on a silica column (10 g column) with $CH_2Cl_2$/MeOH (4-10% gradient) to obtain 92a (40 mg, 75%). $^1$H-NMR (DMSO-$D_6$): δ 10.6 (br, 1H), 7.76 (s, 1H), 6.44 (br, 2H), 5.99 (dd, 1H), 5.83

(d, 1H), 5.53-5.27 (2 m, 6H), 4.39 (dt, 1H), 4.04 (m, 2H), 1.17 (s, 3H), 1.06, 1.08 (2 s, 18H). $^{31}$P-NMR (DMSO-d$_6$): δ −4.09. MS: m/z=608 [M+1].
Example 89
Preparation of Compound (93a)
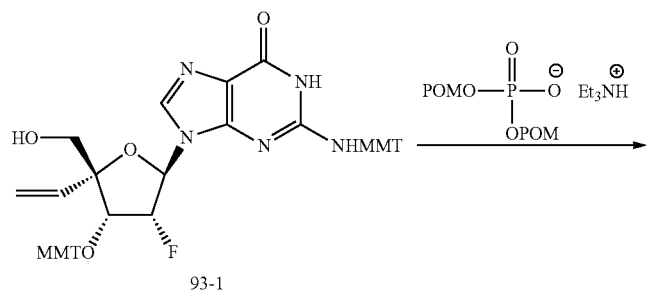
93-1
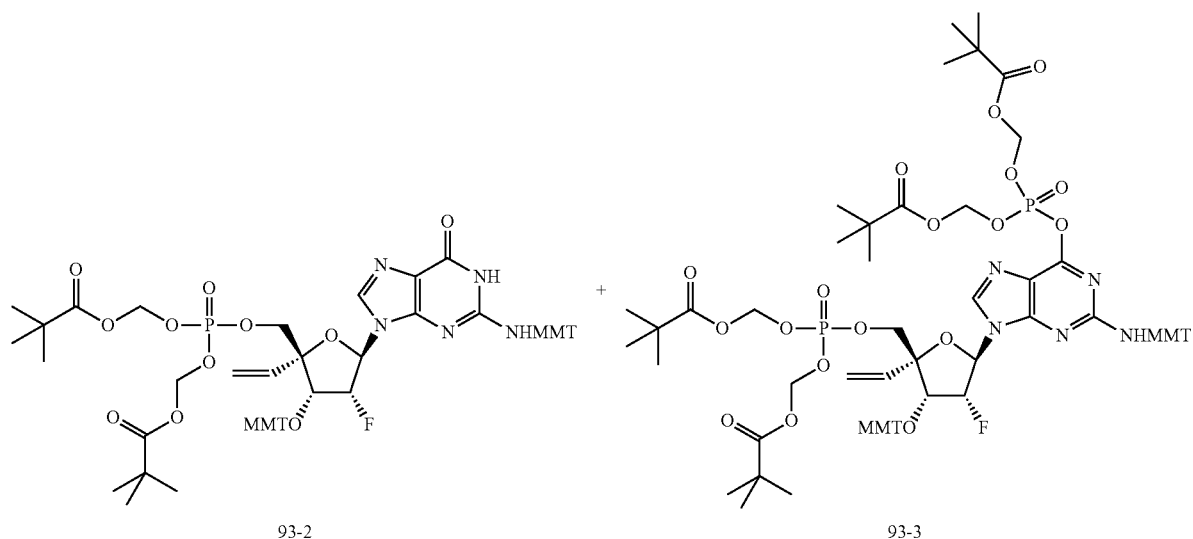
93-2 + 93-3
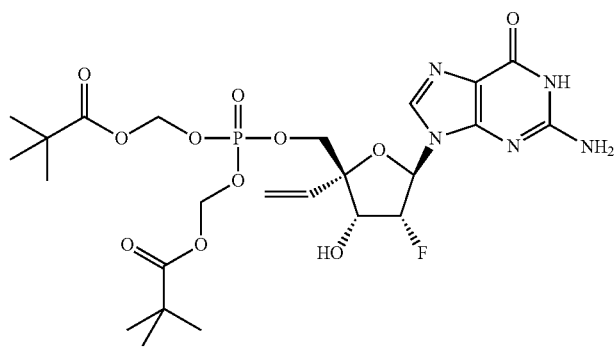
93a Preparation of (93-2) and (93-3):

93-2 and 93-3 (68 mg and 80 mg, respectively) were prepared in the same manner from 93-1 (200 mg; 0.23 mmol) and bis(POM) phosphate (230 mg) with DIPEA (0.4 mL), BopCl (290 mg), and 3-nitro-1,2,4-triazole (130 mg) in THF (3 mL) as 92-2 and 92-3 from 92-1.

Preparation of (93a):

93-2 and 93-3 (68 mg and 80 mg, respectively) were converted into 93 (42 mg) with formic acid in the same manner as 92 from 92-2 and 92-3. $^1$H-NMR (DMSO-D$_6$): δ 7.73 (s, 1H), 6.46 (br, 2H), 6.04 (dd, 1H), 5.91 (dd, 1H), 5.87 (d, 1H), 5.48 (d, 4H), 5.33 (m, 1H), 5.24 (ddd, 1H), 4.60 (dt, 1H), 4.07 (m, 2H), 1.07, 1.06, 1.05 (4 s, 18H). $^{31}$P-NMR (DMSO-d$_6$): δ −4.37. MS: m/z=620 [M+1].

Example 90

Preparation of Compound (94a)

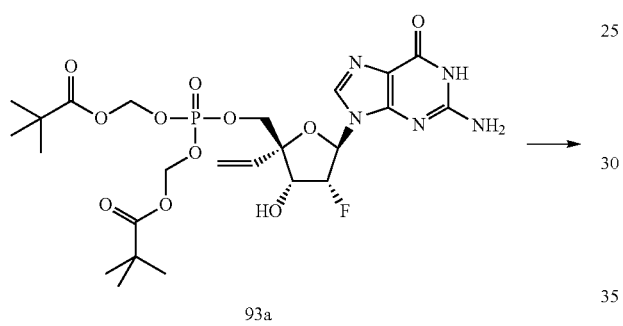

93a

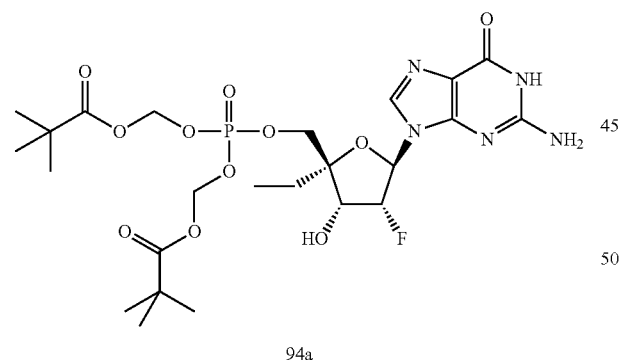

94a

To a solution of 93a (53 mg; 0.09 mmol) in EtOH (2 mL) was added 10% Pd/C (10 mg). The mixture stirred under hydrogen at atmospheric pressure for 1 h. The mixture was filtered through a Celite pad, and the filtrate evaporated. Purification on a silica column (10 g column) with CH$_2$Cl$_2$/MeOH (4-11% gradient) yielded 94a (45 mg, 81%). $^1$H-NMR (DMSO-D$_6$): δ 10.6 (br, 1H), 7.81 (s, 1H), 6.4 (br, 2H), 5.97 (dd, 1H), 5.85 (d, 1H), 5.60-5.44 (m, 5H), 4.37 (m, 1H), 4.11 (ddd, 2H), 1.66 (m, 2H), 1.09, 1.06 (2 s, 18H), 0.81 (7, 3 H); $^{31}$P-NMR (DMSO-d$_6$): δ −4.10. MS: m/z=622 [M+1].

Example 91

Preparation of Compounds (95a) and (96a)

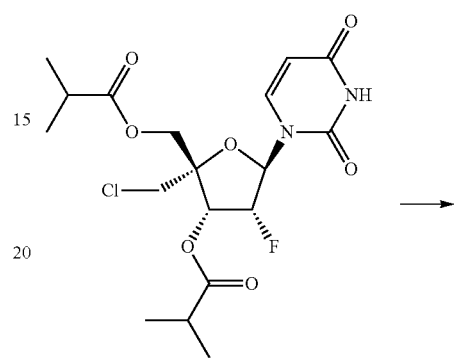

70a

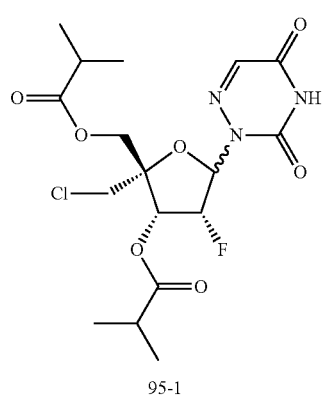

95-1

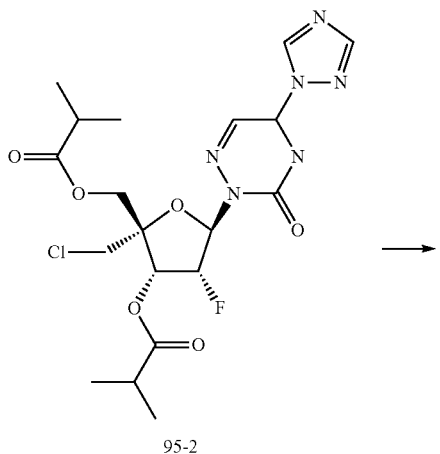

95-2

5.45-5.47 (m, 1H), 4.70 (dd, J=4.8 Hz, J=16.2 Hz, 1H), 3.83 (s, 2H), 3.71 (d, J=1.6 Hz, 2H). ESI-TOF-MS: m/z 295.1 [M+H]$^+$.

Example 92

Preparation of Compounds (97a-g)

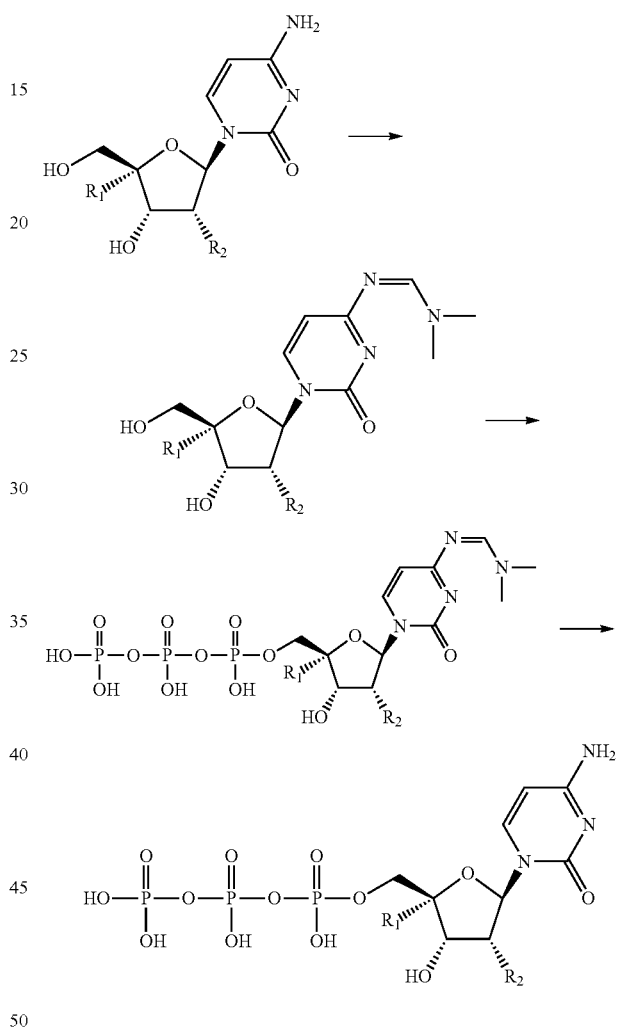

Preparation of (95-1):

To a solution of 5-Amino-2H-[1,2,4]triazin-3-one (180 mg, 1.5 mmol) in HMDS was added a catalytic amount of $(NH_4)_4SO_4$. The mixture was heated to reflux for 5 h. HMDS was evaporated to give a crude product. To a solution of the crude product in anhydrous $CH_3CN$ was added 70a (220 mg, 0.5 mmol) and TMSOTf (0.45 mL, 2.5 mmol). The mixture was heated to reflux for 24 h in a sealed tube. The reaction was quenched with $NaHCO_3$ and diluted with EA. The organic solvent was removed, and the residue was purified by prep-TLC first, and the by RP-HPLC (0.5% HCOOH in water and MeCN) to give the pure 95-1 (100 mg, 46%).

Preparation of (95-2):

To a solution of 95-1 (80 mg, 0.18 mmol) in anhydrous $CH_3CN$ was added 1,2,4-triazole (911 mg, 11.7 mmol) and TEA (1.45 g, 14.4 mmol). The mixture was cooled to 0° C. and $POCl_3$ was added. The reaction mixture was stirred at 25° C. for 24 h. The solvent was evaporated and partitioned with EA and water. The organic layer was concentrated to give the crude 95-2 (80 mg, 90%).

Preparation of (95a):

95-2 (90 mg, 0.18 mmol) was dissolved in 20 mL of saturated THF ammonia. The resulting solution was stirred at 25° C. for 2 h. The solvent was removed, and the residue was purified on a silica gel column (EA:PE=6:1) to give 95a as a white solid (70 mg, 70%).

Preparation of (96a):

95a (70 mg, 0.16 mmol) was dissolved in 20 mL of saturated MeOH ammonia. The resulting solution was stirred at 25° C. for 2 h. The solvent was removed, and the residue was purified by RP-HPLC (0.5% HCOOH in water and MeCN) to give 96a (5 mg, 11%) as a white solid. $^1$H NMR (CD$_3$OD, 400 MHz) δ 7.57 (s, 1H), 6.35 (dd, J=3.6 Hz, J=15.6 Hz, 1H), Dry nucleoside (0.05 mmol) was dissolved in a mixture of DMF (3 mL) and DMA-DMF (0.04 mL, 0.1 mmol). The reaction was kept at ambient temperature for 4 h and then evaporated to dryness. The residue was dissolved in a mixture of PO(OMe)$_3$ (0.7 mL) and pyridine (0.3 mL). The mixture was evaporated in vacuum for 15 min. at 42° C., than cooled down to R.T. N-Methylimidazole (0.009 mL, 0.11 mmol) was added followed by POCl$_3$ (9 µl, 0.11 mmol). The mixture was kept at R.T. for 20-40 mins. The reaction was controlled by LCMS and monitored by the appearance of the corresponding nucleoside 5'-monophosphate. After completion of the reaction, tetrabutylammonium salt of pyrophosphate (150 mg) was added, followed by DMF (0.5 mL) to get a homogeneous solution. After 1.5 h at ambient temperature, the reaction was diluted with water (10 mL). The mixture was loaded on the column HiLoad 16/10 with Q Sepharose High Performance, and separation was done in a linear gradient of NaCl from 0 to 1N in 50 mM TRIS-buffer (pH7.5). The triphosphate (97a-f) was eluted at 75-80% B. The corresponding fractions were concentrated. The residue was dissolved in 5% ammonium hydroxide, kept for 15 min. at R.T. and concentrated. Desalting was achieved by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer.

TABLE 4

Triphosphates obtained from Example 92

| Structure | MS (M − 1) | P(α) | P(β) | P(γ) |
|---|---|---|---|---|
| 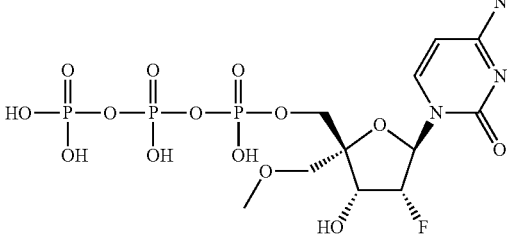 97a | 528.0 | −6.71<br>−6.82<br>(d) | −21.43<br>(t) | −11.35<br>−11.47<br>(d) |
| 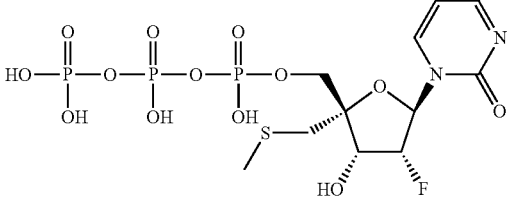 97b | 544.0 | −6.25<br>(bs) | −21.45<br>(bs) | −11.44<br>−11.56<br>(d) |
| 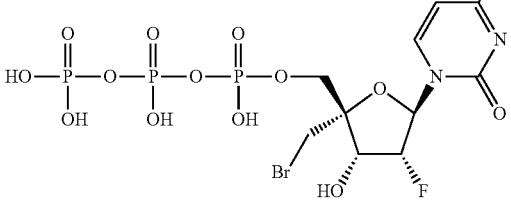 97c | 575.7 | −8.86<br>−9.00<br>(d) | −22.95<br>(t) | −11.81<br>−11.94<br>(d) |
| 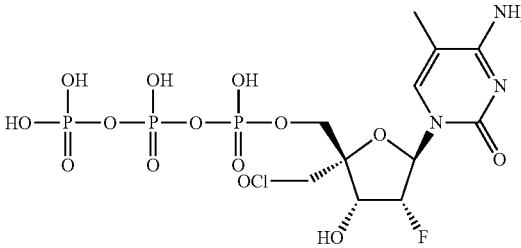 97d | 545.9 | −9.41<br>−9.44<br>(d) | −23.04<br>(t) | −12.00<br>−12.13<br>(d) |

TABLE 4-continued

Triphosphates obtained from Example 92

| Structure | MS (M − 1) | P(α) | P(β) | P(γ) |
|---|---|---|---|---|
| 97e | 552.1 | −10.32<br>−10.44<br>(d) | −23.26<br>(t) | −11.84<br>−11.96<br>(d) |
| 97f | 508.4 | −8.30<br>(bs) | −22.72<br>(bs) | −11.51<br>−11.63<br>(d) |
| 97g | 550.1 | −9.17<br>−9.29<br>(d) | −23.04<br>(t) | −11.97<br>−12.09<br>(d) |

Example 93

Preparation of Compounds (98a-e) and (99a)

Dry nucleoside (0.05 mmol) was dissolved in a mixture of PO(OMe)$_3$ (0.7 mL) and pyridine (0.3 mL). The mixture was evaporated in vacuum for 15 mins. at 42° C., than cooled down to R.T. N-Methylimidazole (0.009 mL, 0.11 mmol) was added followed by POCl$_3$ (94 μl, 0.11 mmol). The mixture was kept at R.T. for 20-40 mins. The reaction was controlled by LCMS and monitored by the appearance of the corresponding nucleoside 5′-monophosphate. After completion of the reaction, tetrabutylammonium salt of pyrophosphate (150 mg) was added, followed by DMF (0.5 mL) to get a homogeneous solution. After 1.5 h at ambient temperature, the reaction was diluted with water (10 mL) and loaded on the column HiLoad 16/10 with Q Sepharose High Performance. Separation was done in a linear gradient of NaCl from 0 to 1N in 50 mM TRIS-buffer (pH7.5). The triphosphate (98a-e) was eluted at 75-80% B. The corresponding fractions were concentrated. Desalting was achieved by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer.

TABLE 5

Compounds obtained from Example 93

| Structure | MS (M − 1) | P(α) | P(β) | P(γ) |
|---|---|---|---|---|
| 98a | 538.0 | −5.21<br>−5.33<br>(d) | −20.56<br>(t) | −11.09<br>−11.20<br>(t) |
| 98b | 556.2 | −10.85<br>(bs) | −23.11<br>(bs) | −11.76<br>−11.88<br>(d) |
| 98c | 540.4 | −8.86<br>(bs) | −23.84<br>(t) | −11.68<br>−11.80<br>(d) |
| 98d | 536.0 | −9.35<br>−9.47<br>(d) | −23.05<br>(t) | −11.60<br>−11.72<br>(d) |
| 98e | 545.9 | −10.54<br>−10.66 | −23.26 | −11.80<br>−11.93<br>(d) |

TABLE 5-continued

Compounds obtained from Example 93

| Structure | MS (M − 1) | P(α) | P(β) | P(γ) |
|---|---|---|---|---|
| 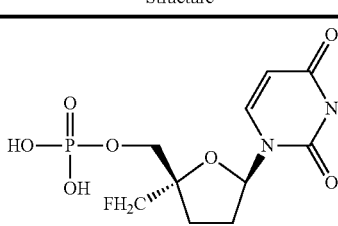 99a | 357.2 | 1.42 (s) | NA | NA |

Example 94

Preparation of Compound (100a)

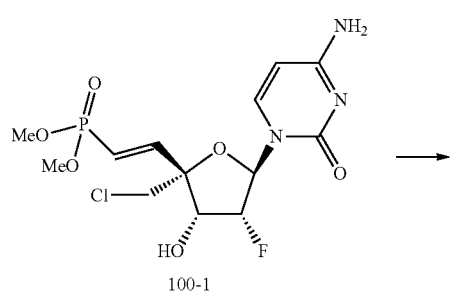

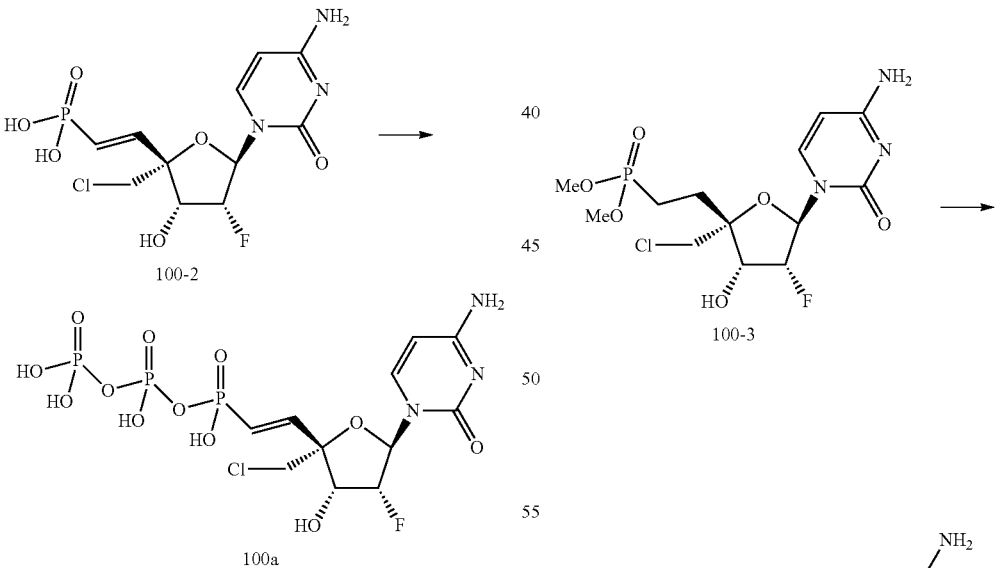

Preparation of (100-2):

To an ice-cold solution of 100-1 (22 mg; 0.055 mmol) in acetonitrile (0.5 mL) was added TMSBr (80 μL; 10 equiv.). The resulting mixture was stirred at R.T. for 1 h. The mixture was concentrated, and the residue was partitioned between water and diethyl ether. The aqueous layer was washed with Et₂O, neutralized with triethylammonium bicarbonate buffer and lyophilized to yield the triethylammonium salt of 100-2.

Preparation of (100a):

100-2 was rendered anhydrous by coevaporating with pyridine and toluene. Anhydrous 100-2 was dissolved in HMPA (1 mL) and 1,1-carbonyldiimidazole (32 mg; 0.2 mmol) was added. The mixture was stirred at R.T. for 6 h. A solution of tetrabutylammonium pyrophosphate (0.22 g; ~0.2 mmol) in DMF (2 mL) was added. The mixture was stirred overnight at R.T. The mixture was diluted with triethylammonium acetate buffer and purified by RP-HPLC with a gradient 0-60% B (A: 50 mM aqueous TEAA, B: 50 mM TEAA in MeOH) and repurified by RP-HPLC with a gradient 0-30% B to give 100a.
$^{31}$P-NMR (D$_2$O): δ 3.22 (d, 1P), −8.21 (br, 1P), −22.91 (br, 1P). MS: m/z=528 (M−1).

Example 95

Preparation of Compound (100b)

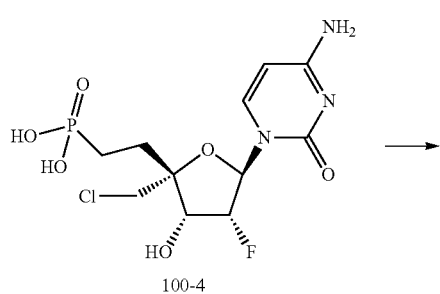

-continued

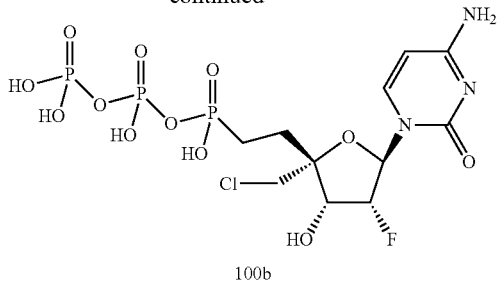

100b

Preparation of (100-4):

100-4 was prepared from 100-3 (54 mg; 0.13 mmol) in acetonitrile (1.3 mL) with TMSBr (0.18 mL) using a similar procedure as described for the preparation of 100-2.

Preparation of (100b):

100b was prepared from 100-4 in HMPA (2 mL) with CDI (84 mg) and tetrabutylammonium pyrophosphate (0.5 g) in DMF (2 mL) using a similar procedure as described for the preparation of 100a. $^{31}$P-NMR (D$_2$O): δ 17.90 (d, 1P), −9.00 (d, 1P), −22.91 (t, 1P). MS: m/z=530 (M−1).

Example 96

Preparation of Compound (100c)

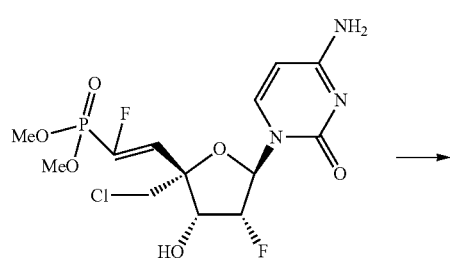

100-5

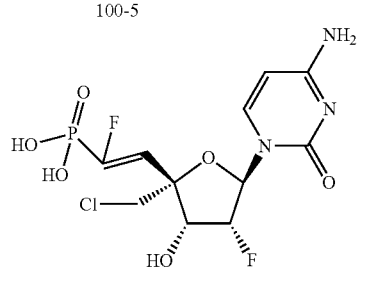

100-6

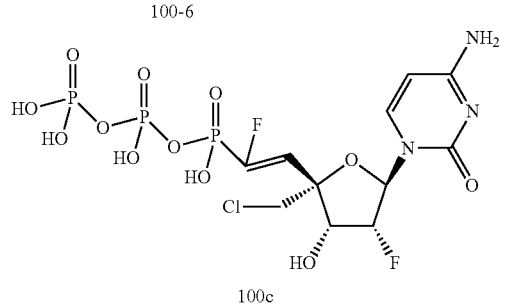

100c

Preparation of (100-6):

100-6 was prepared from 100-5 (40 mg; 0.09 mmol) in acetonitrile (1 mL) with TMSBr (0.1 mL) using a similar procedure as described for the preparation of 100-2.

Preparation of (100c):

100c was prepared from 100-6 in HMPA (1.5 mL) with CDI (50 mg) and tetrabutylammonium pyrophosphate (0.3 g) using a similar procedure as described for the preparation of 100a. $^{31}$P-NMR (D$_2$O): δ −7.13 (br, 1P), −10.14 (d, 1P), −22.84 (br, 1P). $^{19}$F-NMR (D$_2$O): δ −117.53 (dd, 1F), −197.8 (m, 1F). MS: m/z=545.5 (M−1).

Example 97

Preparation of Compounds (100d) and (100e)

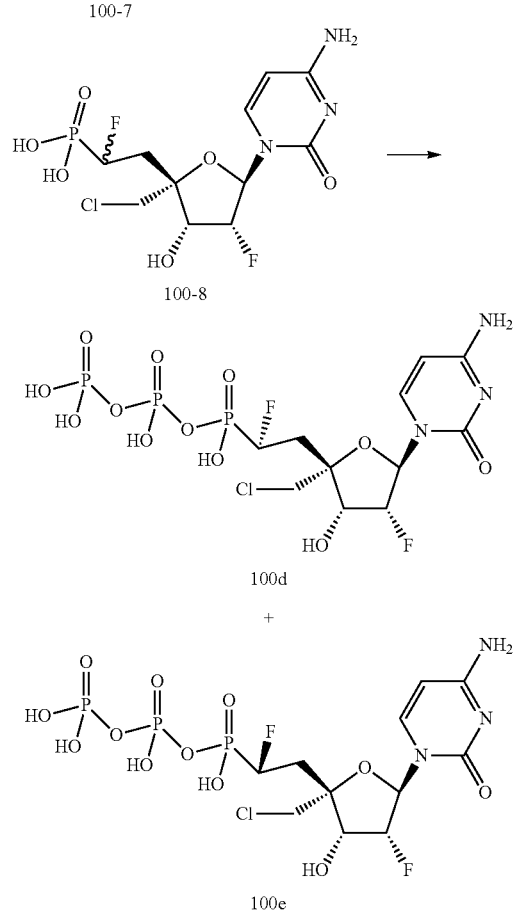

Preparation of (100-8):

To an ice-cold solution of diastereomers 100-7 (35 mg; 0.08 mmol) in acetonitrile (1 mL) was added TMSBr (0.1 mL; 10 equiv.). The resulting mixture was stirred overnight at R.T. and then concentrated. The residue was partitioned between water and CH$_2$Cl$_2$. The aqueous layer was washed with CH$_2$Cl$_2$, neutralized with triethylammonium bicarbonate buffer and lyophilized to yield the triethylammonium salt of 100-8.

Preparation of (100d) and (100e):

100-8 was rendered anhydrous by coevaporating with pyridine and toluene. Anhydrous 100-8 was dissolved in DMF (1.5 mL) and CDI (54 mg; 0.3 mmol) was added. The mixture was stirred at R.T. for 7 h. A solution of tetrabutylammonium pyrophosphate (0.3 g; ~0.3 mmol) in DMF (4 mL) was added. The mixture was stirred at R.T for 3 days. The mixture was diluted with triethylammonium acetate buffer. Two consecutive RP-HPLC purifications with a gradient 0-60% B (A: 50 mM aqueous TEAA, B: 50 mM TEAA in MeOH) and 0-40% B gave 100d and 100e as single diastereomers. 100d: $^{31}$P-NMR (D$_2$O): δ 4.28 (dd, 1P), −6.37 (d, 1P), −22.36 (t, 1P). MS: m/z=548.1 (M−1). 100e: $^{31}$P-NMR (D$_2$O): δ 4.13 (dd, 1P), −6.38 (d, 1P), −22.46 (t, 1P). MS: m/z=548.1 (M−1).

Example 98

Preparation of Compound (101a)

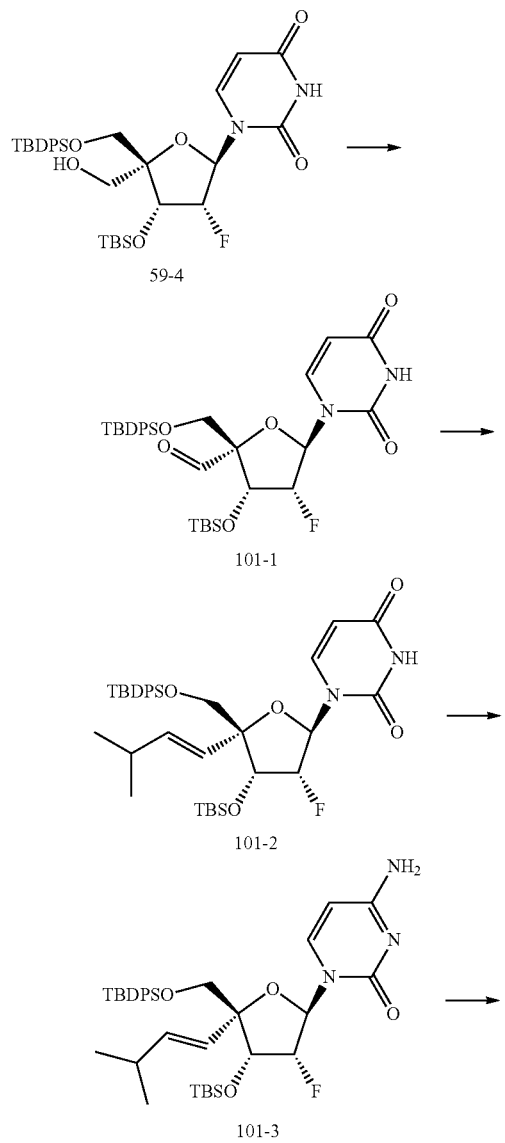

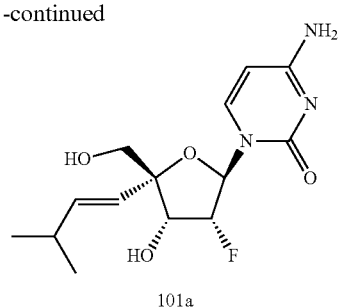

Preparation of (101-1):

To a solution of 59-4 (1.5 g, 2.39 mmol) in anhydrous DCM (100 mL) was added Dess-Martin periodinane (5.2 g, 11.95 mmol) at 0° C. under nitrogen. The mixture was stirred at R.T. for 5 h. The mixture was poured into NaHCO$_3$ and Na$_2$S$_2$O$_3$ aq. Solution. The organic layer was washed with brine, dried over with anhydrous Na$_2$SO$_4$, and concentrated to dryness to give the crude 101-1 (1.5 g) as a white solid, which was used for the next step without further purification.

Preparation of (101-2):

To a mixture of bromo(isobutyl)triphenylphosphorane (4.8 g, 12.03 mmol) in anhydrous THF (8 mL) was added t-BuOK (11.2 mL, 11.2 mmol) at 0° C. under nitrogen. The mixture was stirred at R.T. for 1 h. A solution of 101-1 (1.0 g, 1.6 mmol) in anhydrous THF (4 mL) was added dropwise at 0° C. The mixture was stirred at R.T. for 3 h. The reaction was quenched with a NH$_4$Cl aq. solution and extracted with DCM. The organic layer was dried and concentrated to give a residue, which was purified by silica gel column chromatography (5% EtOAc in PE) to give 101-2 (793 mg, 74.4%) as a white solid.

Preparation of (101-3):

To a solution of 101-2 (364 mg, 0.547 mmol) in anhydrous CH$_3$CN (6 mL) were added TPSCl (414 mg, 1.37 mmol), DMAP (167 mg, 1.37 mmol) and NEt$_3$ (138 mg, 1.37 mmol) at R.T. The mixture was stirred at R.T. for 2 h. NH$_4$OH (6 mL) was added, and the mixture was stirred for another 1 h. The mixture was diluted with DCM and washed with a NaHCO$_3$ aq. solution. The organic layer was separated and concentrated to give a residue, which was purified by silica gel column chromatography (2% MeOH in DCM) to give 101-3 (347 mg, 95.0%) as white solid.

Preparation of (101a):

To a solution of 27-3 (347 mg, 0.52 mmol) in MeOH (10 mL) was added NH$_4$F (1.5 g) at R.T. The reaction mixture was refluxed for 12 h, and then filtered. The filtrate was concentrated in vacuo, and the residue was purified by silica gel column chromatography (10% MeOH in DCM) to give 101a (87 mg, 53%) as a white solid. $^1$H NMR (CD$_3$OD, 400 MHz) δ 8.11 (d, J=7.6 Hz, 1H), 6.03 (dd, J=1.2, 17.6 Hz, 1H), 5.88 (d, J=7.2 Hz, 1H), 6.03 (dd, J=1.6, 11.6 Hz, 1H), 5.39 (d, J=10.8 Hz, 1H), 4.88 (dd, J=3.2, 60.0 Hz, 1H), 4.41 (dd, J=4.8, 24.4 Hz, 1H), 3.70 (d, J=12.4 Hz, 1H), 3.57 (d, J=12.0 Hz, 1H), 3.08-3.14 (m, 1H), 0.94-0.98 (m, 6H). ESI-MS: m/z 626.9 [2M+H]$^+$.

Example 99

Preparation of Compound (102a)

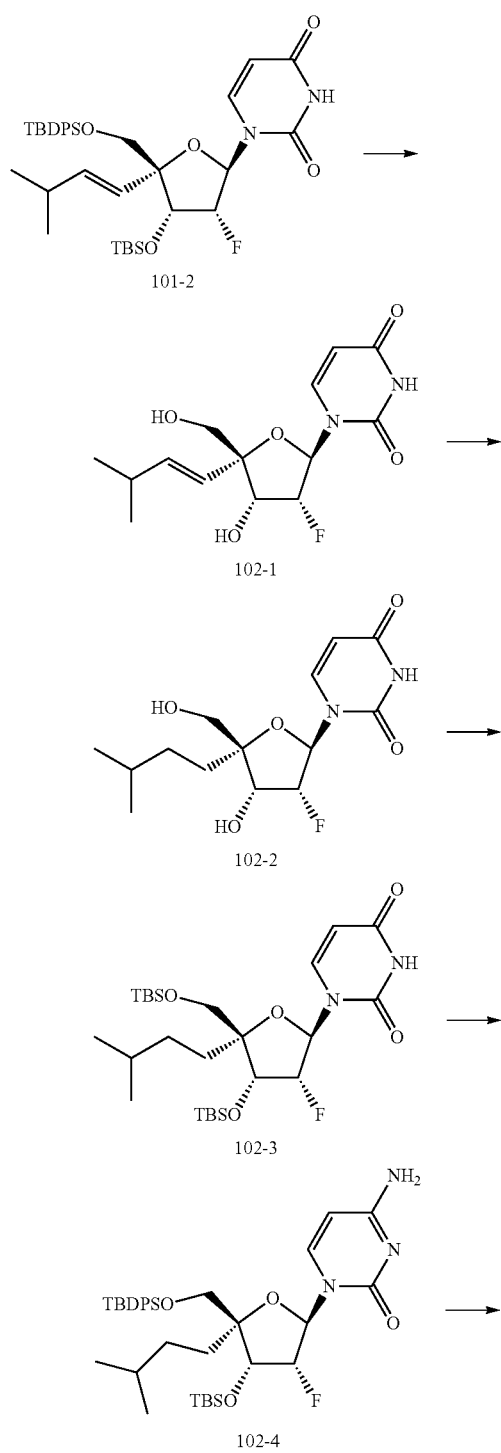

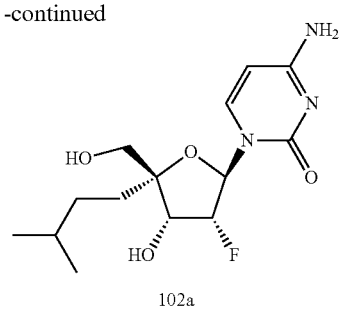

Preparation of (102-1):

To a solution of 101-2 (1.0 g, 1.5 mmol) in MeOH (20 mL) was added NH$_4$F (6 g) at R.T., and the mixture was refluxed overnight. After cooling to R.T., the mixture was filtered, and the filtrate was concentrated. The residue was purified by silica gel column chromatography (8% MeOH in DCM) to give 102-1 (400 mg, 85%) as a white solid.

Preparation of (102-2):

To a solution of 102-1 (400 mg, 1.27 mmol) in MeOH (10 mL) was added Pd/C (400 mg) at R.T. The mixture was stirred at R.T. under a balloon of H$_2$ for 1.5 h. The mixture was filtered, and the filtrate was concentrated in vacuo to give 102-2 (400 mg, 99%) as a white solid.

Preparation of (102-3):

To a solution of 102-2 (400 mg, 1.26 mmol) in anhydrous DMF (5 mL) were added imidazole (968 mg, 14.2 mmol), and TBSCl (1.5 g, 10.0 mmol) at R.T. The mixture was stirred at 50° C. overnight. The mixture was diluted with DCM and washed with a NaHCO$_3$ aq. solution. The organic layer was dried and concentrated. The residue was purified by silica gel column chromatography (10% EA in PE) to give 102-3 (676 mg, 98%) as a white solid.

Preparation of (102-4):

To a solution of 102-3 (676 mg, 1.24 mmol) in anhydrous CH$_3$CN (6 mL) were added TPSCl (941 mg, 13.11 mmol), DMAP (379 mg, 3.11 mmol) and NEt$_3$ (314 mg, 3.11 mmol) at R.T. The reaction was stirred at R.T. for 3 h. NH$_4$OH (1 mL) was added, and the reaction was stirred for 4 h. The mixture was diluted with DCM and washed with a NaHCO$_3$ solution. The organic layer was dried and concentrated. The residue was purified by silica gel column chromatography (2% MeOH in DCM) to give 102-4 (450 mg, 67%) as a white solid.

Preparation of (102a):

To a solution of 102-4 (450 mg, 0.83 mmol) in MeOH (10 mL) was added NH$_4$F (2 g) at R.T. The reaction mixture was refluxed overnight. After cooling to R.T., the mixture was filtered, and the filtrate was concentrated. The residue was purified by silica gel column chromatography (8% MeOH in DCM) to give 102a (166.6 mg, 64%) as a white solid. $^1$H NMR (CD$_3$OD, 400 MHz) δ 8.09 (d, J=7.6 Hz, 1H), 6.07 (d, J=3.6 Hz, 1H), 6.05 (d, J=2.8 Hz, 1H), 5.89 (d, J=7.6 Hz, 1H), 5.03 (dd, J=5.2, 57.2 Hz, 1H), 4.41 (dd, J=4.2, 17.2 Hz, 1H), 3.74 (d, J=12.0 Hz, 1H), 3.54 (d, J=12.0 Hz, 1H), 1.23-1.78 (m, 5H), 0.90 (d, J=6.4 Hz, 6H). ESI-MS: m/z 631.1 [2M+H]+.

Example 100

Preparation of Compound (103a)

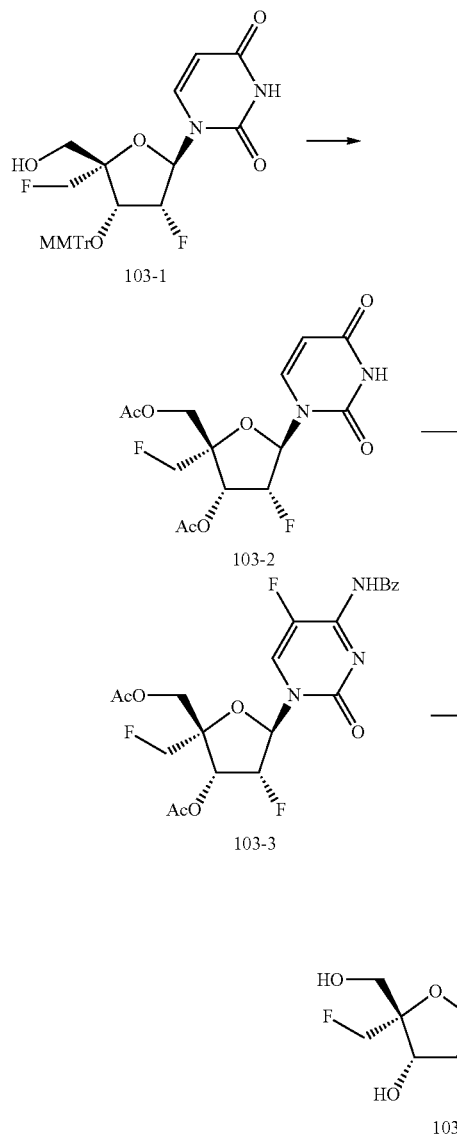

Preparation of (103-2):

103-1 (3.8 g, 6.9 mmol) in 80% AcOH aq. was stirred at 50° C. for 4 h. The mixture was concentrated to give a residue, which was purified by silica gel column chromatography (5% MeOH in DCM) to give the uridine derivative (1.5 g, 78.2%) as a white solid. To a solution of the uridine derivative (1.5 g, 5.4 mmol) in Py (10 mL) was added Ac₂O (1.38 g, 13.5 mmol) at R.T. The mixture was stirred at R.T. for 12 h. The mixture was concentrated to give a residue, which was purified by silica gel column chromatography (20% EA in PE) to give 103-2 (1.3 g, 68%) as a white solid.

Preparation of (103-3):

To a solution of N-(5-fluoro-2-hydroxy-1,2-dihydropyrimidin-4-yl)benzamide (0.5 g, 2.1 mmol) in anhydrous PhCl (5 mL) was added ammonium sulfate (6 mg, 0.043 mmol), followed by HMDS (0.7 g, 4.3 mmol). The mixture was heated to 130° C. for 8 h. The mixture was concentrated under vacuum to 2 mL, and then cooled to 0° C. TMSOTf (310 mg, 1.4 mmol) was then added. After stiffing for 10 min at 0° C., 103-2 (150 mg, 0.4 mmol) in PhCl (5 mL) was added. The mixture was stirred at 130° C. for 10 h. The mixture was concentrated, and the residue was re-dissolved in DCM (10 mL), washed with water (5 mL) and saturated NaHCO₃. The organic layer was dried over Na₂SO₄, evaporated to dryness and the crude product was purified by silica gel column chromatography (60% PE in EA) to give 103-3 (30 mg, 16%) as a white solid.

Preparation of (103a):

A solution of 103-3 (150 mg, 0.34 mmol) in NH₃/MeOH (10 mL) was stirred at R.T. for 3 h. The mixture was concentrated, and the residue was purified by HPLC separation (0.1% HCOOH in water and MeCN) to give 103a (60 mg, 60%) as a white solid. ¹H NMR (CD₃OD, 400 MHz) δ 8.28 (d, J=6.8 Hz, 1H), 6.10 (dd, J=2.0, 15.2 Hz, 1H), 4.99-5.15 (m, 1H), 4.62-4.65 (m, 1H), 4.49-4.55 (m, 2H), 3.89 (dd, J=1.6, 12.0 Hz, 1H), 3.75 (dd, J=1.2, 12.0 Hz, 1H). ESI-MS: m/z 613.1 [2M+Na]+.

Example 101

Preparation of Compound (104a)

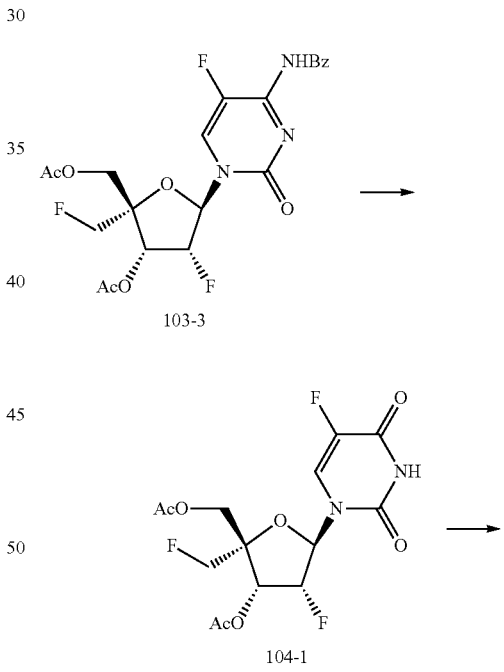

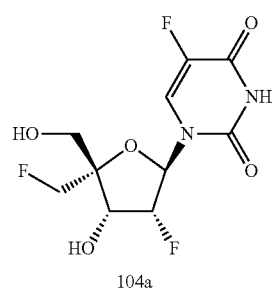

Preparation of (104-1):

103-3 (150 mg, 0.31 mmol) was dissolved in 80% aqueous acetic acid (3 mL). The solution was heated to reflux for 2 h. The mixture was cooled to ambient temperature and diluted with water (5 mL), neutralized to pH>7 with saturated NaHCO$_3$ and extracted with EA. The organic layer was dried and evaporated to dryness. The residue was purified by silica gel column chromatography (50% EA in PE) to give 104-1 (80 mg, 70%) as a white solid.

Preparation of (104a):

104-1 (80 mg, 0.22 mmol) in saturated NH$_3$/MeOH (10 mL) was stirred at R.T. for 3 h. The mixture was concentrated, and the residue was purified by silica gel column chromatography (5% MeOH in DCM) to give 104a (40 mg, 60%) as a white solid. $^1$H NMR (CD$_3$OD, 400 MHz) δ 8.30 (d, J=6.8 Hz, 1H), 6.18 (dd, J=4.0, 14.0 Hz, 1H), 5.13-5.65 (m, 1H), 4.52-4.56 (m, 1H), 3.980-3.95 (m, 2H), 3.76 (s, 3H). ESI-MS: m/z 319.1 [M+Na]$^+$.

Example 102

Preparation of Compound (105a)

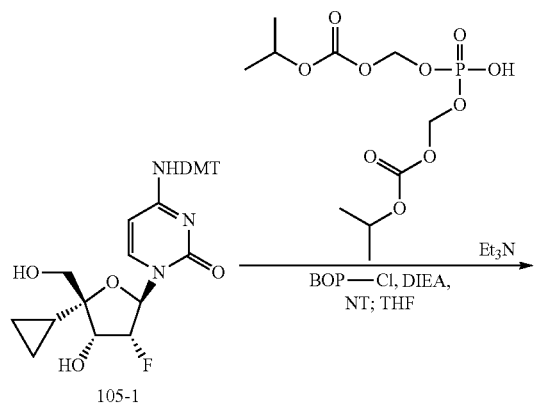

Preparation of (105-2):

To a solution of triethylammonium bis(isopropyloxycarbonyloxymethyl)phosphate (0.065 mmol, prepared from 22 mg of bis(POC)phosphate and Et$_3$N) in THF was added 105-1 (31 mg; 0.05 mmol). The resulting mixture evaporated, and the residue was rendered anhydrous by coevaporation with pyridine, followed by toluene. The anhydrous evaporated residue was dissolved THF (1 mL) and cooled in an ice-bath. To the solution was added diisopropylethyl amine (35 μL; 4 equiv), followed by BOP-Cl (25 mg; 2 equiv) and 3-nitro-1,2,4-triazole (11 mg; 2 equiv). The mixture was stirred at 0° C. for 90 min. The mixture was diluted with CH$_2$Cl$_2$, washed with saturated aq. NaHCO$_3$ and brine, and dried with Na$_2$SO$_4$. The evaporated residue was purified on silica (10 g column) with a CH$_2$Cl$_2$/i-PrOH solvent system (3-10% gradient) to give 105-2 (13 mg, 28%).

Preparation of (105a):

A solution of 105-2 (13 mg; 0.014 mmol) in 80% aq. HCOOH (2 mL) was stirred at R. T. for 3 h. The mixture was evaporated and then coevaporated with toluene. The product was purified on silica (10 g column) with a CH$_2$Cl$_2$/MeOH solvent system (4-15% gradient) to give 105a (7 mg, 78%). $^1$H-NMR (DMSO-d$_6$): δ 7.52 (d, 1H), 7.28, 7.24 (2 br s, 2H) 5.92 (dd, 1H), 5.74 (d, 1H), 5.69 (d, 1H), 5.62 (d, 4H), 4.97 (ddd, 1H), 4.82 (m, 2H), 4.38 (dt, 1H), 4.07 (m, 2H), 1.23 (m, 12H), 1.04 (m, 1H), 0.37 (m, 4H). $^{31}$P-NMR (DMSO-d$_6$): δ −4.51. $^{19}$F-NMR (DMSO-d$_6$): δ −199.23 (dt). MS: m/z=598.4 (M+1).

Example 103

Preparation of Compound (106a)

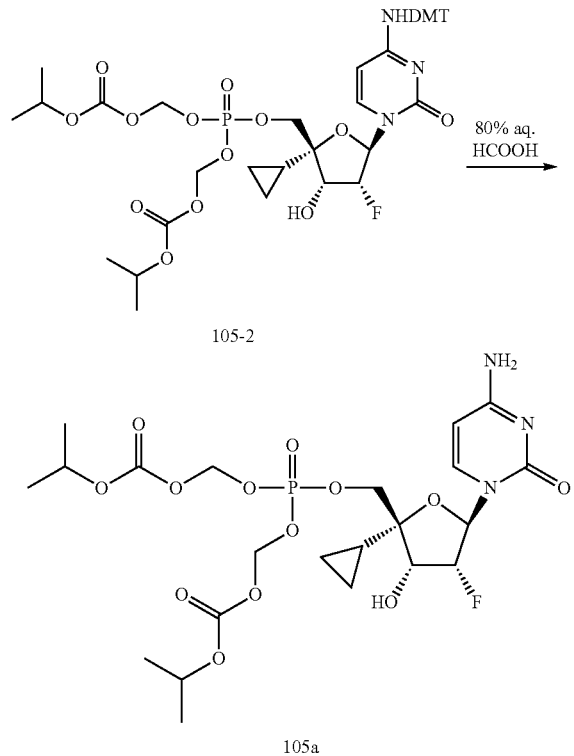

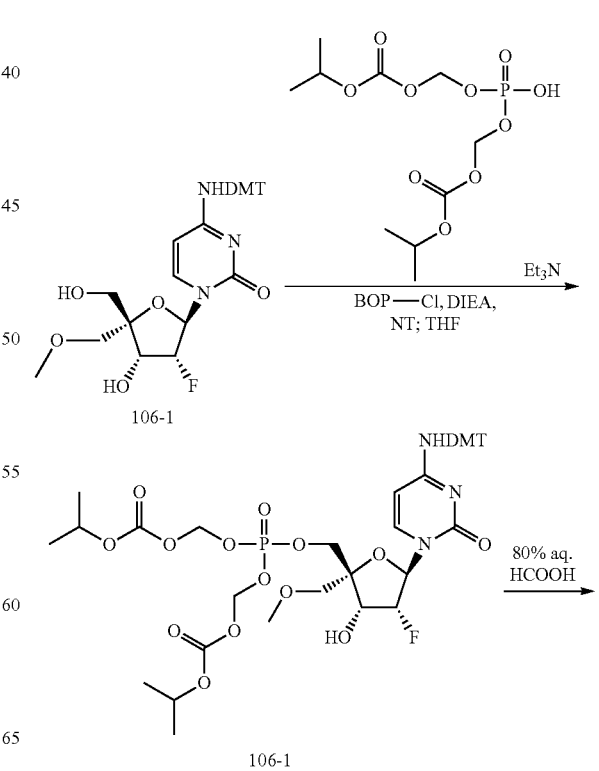

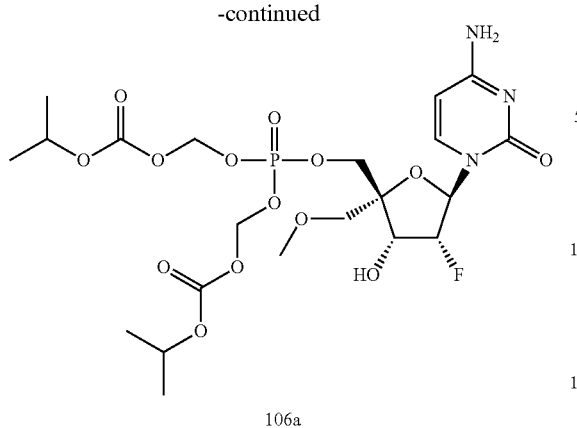

106a

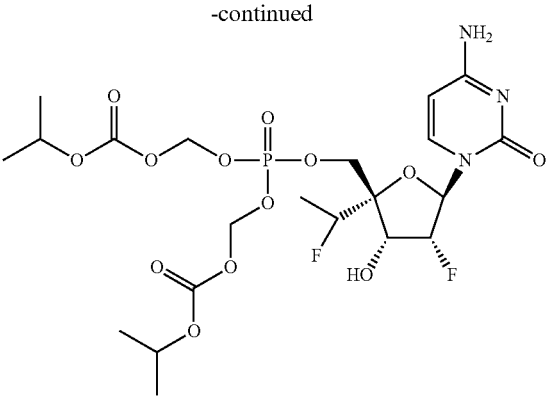

107a

Preparation of (106-1):

106-1 (15 mg; 30% yield) was prepared in the same manner from 43-5 (32 mg; 0.057 mmol) and bis(POC)phosphate (24 mg) with DIPEA (40 μL), BopCl (29 mg) and 3-nitro-1,2,4-triazole (13 mg) as 105-2 from 105-1.

Preparation of (106a):

106-1 (15 mg) was converted in formic acid to 106a (8 mg; 78% yield) in the same manner as 105-2 to 105a. $^1$H-NMR (DMSO-d$_6$): δ 7.55 (d, 1H), 7.32, 7.27 (2 br s, 2H) 6.06 (dd, 1H), 5.84 (d, 1H), 5.73 (d, 1H), 5.61 (d, 4H), 5.08 (ddd, 1H), 4.83 (m, 2H), 4.36 (m, 1H), 4.21 (dd, H), 4.16 (dd, 1H), 3.56 (d, 1H), 3.49 (d, 1H), 3.28 (s, 3H), 1.25, 1.24 (2 d, 12H). $^{31}$P-NMR (DMSO-d$_6$): δ −4.45. MS: m/z=602.4 (M+1).

Example 104

Preparation of Compound (107a)

Preparation of (107-1):

107-1 (30 mg; 30% yield) was prepared in the same manner from 40-10 (65 mg; 0.115 mmol) and bis(POC)phosphate (49 mg) with DIPEA (80 μL), BopCl (58 mg) and 3-nitro-1,2,4-triazole (26 mg) as 105-2 from 105-1.

Preparation of (106a):

107-1 (30 mg) was converted in formic acid to 107a (15 mg; 73% yield) in the same manner as 105-2 to 105a. $^1$H-NMR (DMSO-d$_6$): δ 7.60 (d, 1H), 7.36, 7.32 (2 br s, 2H) 6.02 (m, 2H), 5.74 (d, 1H), 5.62 (m, 4H), 5.17 (ddd, 1H), 4.99 (dq, 1H), 4.83 (m, 2H), 4.61 (m, 1H), 4.19 (m, 2H), 1.40 (dd, 3H), 1.24, 1.23 (2 d, 12H). $^{31}$P-NMR (DMSO-d$_6$): δ −4.52. $^{19}$F-NMR (DMSO-d$_6$): δ −185.92 (m, 1F), −200.48 (d, 1F). MS: m/z=604.3 (M+1).

Example 105

Preparation of Compound (108a)

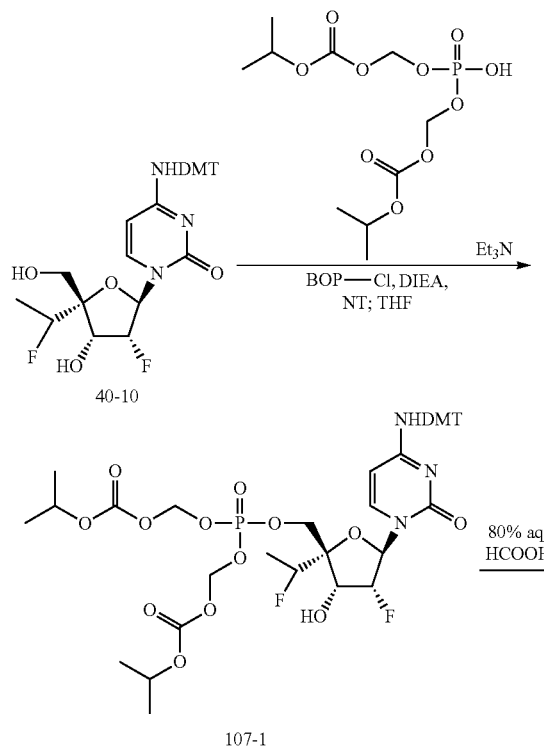

107-1

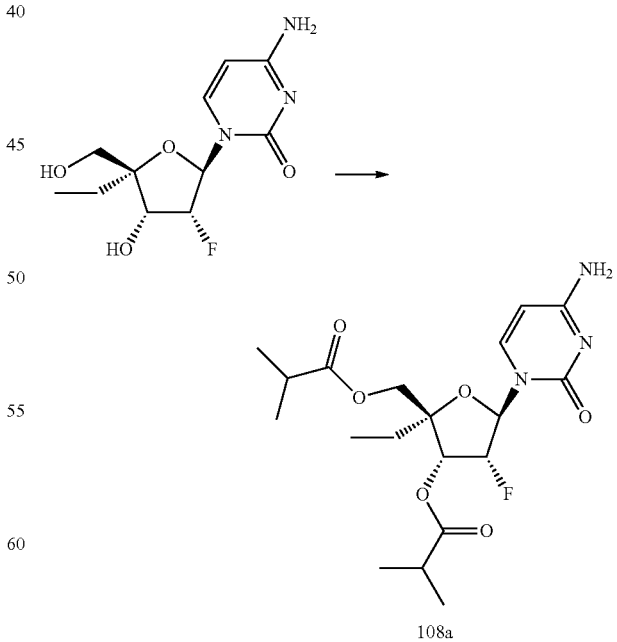

108a

To a solution of 4'-ethyl-2'-fluorocytidine (50 mg, 0.183 mmol) in DMF (1 mL) were added DCC (113 mg, 0.55 mmol), isobutyric acid (48.54 μl, 0.55 mmol) and DMAP (22 mg, 0.183 mmol). The mixture was stirred at R.T. overnight. The mixture was filtered, and the filtrate was concentrated with a rotary evaporator until half of its original volume was achieved. EA was added to the mixture. The mixture was washed with water, followed by brine. The mixture was dried over anhydrous $Na_2SO_4$ and concentrated in vacuo to give a residue, which was purified by silica gel with DCM/MeOH=95:5 to give 108a (40.8 mg, 54%) as a white solid. $^1H$ NMR (DMSO-d6, 400 MHz) δ 7.67 (d, J=7.2 Hz, 1H), 7.34 (br s, 2H), 5.85, 5.8 (2d, J=21.2, 22 Hz, 1H), 5.72 (d, J=7.6 Hz, 1H), 5.55-5.41 (m, 2H), 4.1 (q, 2H), 2.68-2.52 (m, 2H), 1.77-1.64 (m, 2H), 1.13, 1.14 (2s, 2×3H), 1.09-1.07 (m, 6H), 0.96 (t, J=7.6 Hz, 3H); MS m/z 414 (M−H$^+$), 829 (2M+H$^+$).

Example 106
Preparation of Compound (109a)

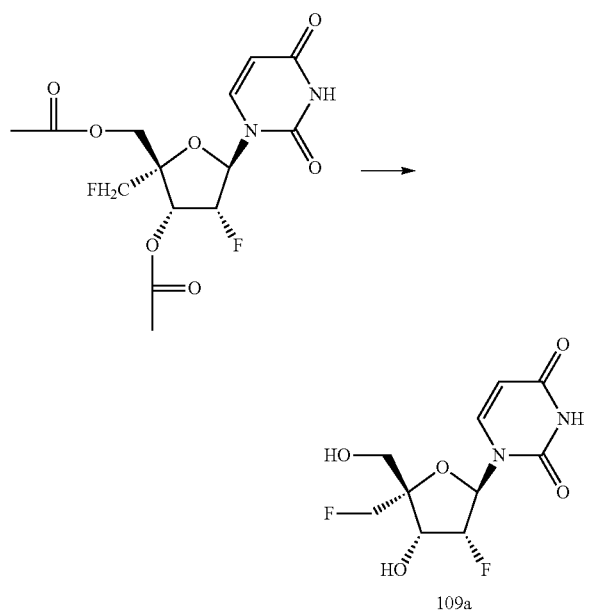

3',5'-diacetylnucleoside (36 mg, 1 mmol) was dissolved in methanol saturated with $NH_4OH$ and kept overnight at R.T. The solvent was evaporated, and the product isolated by column chromatography in gradient of methanol in DCM from 0 to 15% on a 10 g Biotage cartridge. The product was 109a obtained (20 mg, 73%). $^1$H-NMR (DMSO-d$_6$): δ 11.4 (s, 1H), 11.84-11.82 (d, 1H); 6.10-6.05 (m, 1H), 5.95-5.83 (d, 1H), 5.71 (s, 1H), 5.65-5.63 (d, 1H), 5.37-3.36 (t, 1H), 5.26-5.20 (t, 1H), 5.11-5.07 (t, 1H), 4.56-4.55 (m, 1H), 4.46-4.33 (m, 2H), 3.58-3.56 (m, 2H). MS 277.2 (M−H).

Example 107
Preparation of Compound (110a)

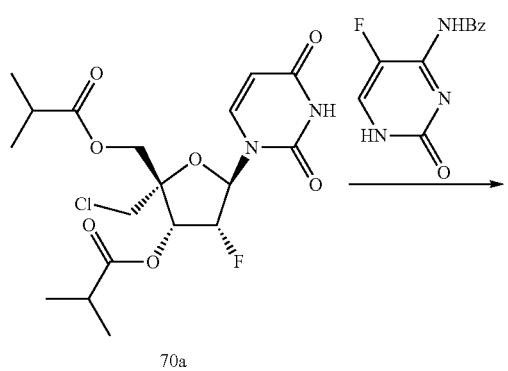

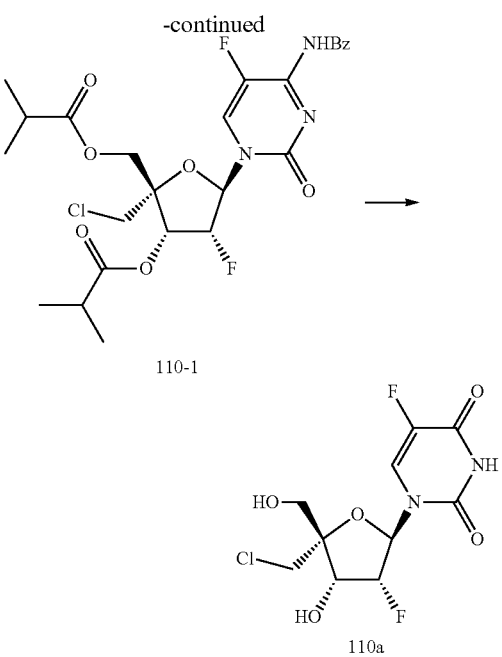

Preparation of (110-1):

To a solution of 70a (6.55 g, 2.1 mmol) and the benzoyl protected base moiety (2.3 g, 5.3 mmol) in PhCl (50 mL) was added TMSOTf (3.6 g, 16.1 mmol). After addition, the mixture was heated to 140° C. for 8 h. The mixture was cooled to R.T., and evaporated to give a residue. The residue was re-dissolved in DCM and washed with saturated $NaHCO_3$ and brine. The organic layer was dried and concentrated to give a residue, which was purified by silica gel column (40% EA in PE) to give 110-1 (300 mg, 10%) as a white solid.

Preparation of (110a):

110-1 (300 mg, 0.55 mmol) in 80% aqueous acetic acid (5 mL) was heated to reflux for 2 h. The mixture was cooled to ambient temperature and diluted with water (5 mL), and then extracted with EA. The organic layer was washed with saturated $NaHCO_3$ and brine. The mixture was dried and concentrated to give a residue, which was purified by silica gel column (10% EA in PE) to give the protected uridine derivative (180 mg, 70%) as a white solid. The protected uridine derivative (180 mg, 0.4 mmol) in saturated $NH_3$/MeOH (10 mL) was stirred at R.T. for 3 h. The mixture was concentrated to give a residue, which was purified by preparative HPLC (0.1% HCOOH in water and MeCN) to give 110a (80 mg, 60%) as a white solid. $^1$H NMR (CD$_3$OD, 400 MHz) 88.31 (d, J=6.8 Hz, 1H), 6.17 (dd, J=4.0, 14.0 Hz, 1H), 5.13-5.27 (m, 1H), 4.52-4.56 (m, 1H), 3.92 (dd, J=12.0, 58.8 Hz, 2H). ESI-TOF-MS: m/z 334.7 [M+Na]$^+$.

Example 108

RSV Antiviral Assays

CPE reduction assays are performed as described by Sidwell and Huffman et al., *Appl Microbiol.* (1971) 22(5):797-801 with slight modifications. HEp-2 cells (ATCC) at a concentration of 6000 cell/well are infected with RSV Long strain (ATCC) at a multiplicity of infection (m.o.i.) of 0.01, and each of the test compounds are provided to duplicate wells at final concentrations starting from 100 μM using ⅓ stepwise dilutions. For each compound, two wells are set aside as uninfected, untreated cell controls (CC), and two wells per test compound receive virus only as a control for virus replication (VC). The assay is stopped after 6 days, before all of the cells in the virus-infected untreated control wells exhibited signs of virus cytopathology (giant cell formation, syncytia). At the end of the incubation, 20 µl of cell counting kit-8 reagent (CCK-8, Dojindo Molecular Technologies, Inc.) are added to each well. After 4 hour incubation, the absorbance is measured in each well according to manufacturer's instruction, and the 50% effective concentration ($EC_{50}$) is calculated by using regression analysis, based on the mean O.D. at each concentration of compound.

RT-PCR based assays were performed in HEp-2 cells (ATCC: CCL-23) at a concentration of 20000 cell/well were plated in 96 well plates and incubated overnight. Each of the test compounds were 1/3 serially diluted and dosed to HEp-2 cells in duplicates. The highest final concentration for each compound was 100 uM. After 24 hour compound pre-incubation, RSV A2 (ATCC: VR-1540) at MOI of 0.1 was added. Two wells per compound were set aside as uninfected, untreated cell controls (CC), and four wells per test compound received virus only as a control for virus replication (VC). The assay was stopped 4 days after virus infection and conditioned media was removed for viral RNA isolation. The quantities of the RSV virus were measured by real-time PCR using a set of RSV specific primers and probe. The data was analyzed with Prism software with EC50 defined as drug concentration that reduced the viral load 50% from the viral control (VC).

Standard RSV polymerase assays were conducted in the presence of 3 µL extract of RSV-infected cells in a reaction buffer containing 50 mM tris-acetate pH 8, 120 mM K-acetate, 4.5 mM $MgCl_2$, 5% glycerol, 2 mM EDTA, 50 ug/mL BSA, and 3 mM DTT. Varying concentration of test compounds were used to initiate RNA synthesis for 120 mins at 30° C., and radioactive 33P GTP (15 uCi) was used as tracer. The reaction was stopped by adding 50 mM EDTA, and RNA samples were purified through G-50 size exclusion spin columns and phenol-chloroform extraction. The radio-labeled RNA products were resolved by electrophoresis on a 6% polyacrylamide TBE gel, and visualized and quantitated after being exposed on a phosphorImager screen. Polymerase inhibition experiments ($IC_{50}$) were conducted the same way in the presence of increasing concentration of test compounds.

Compounds of Formula (I), Formula (II) and Formula (III) are active in the assay as noted in Tables 6 and 7. In Table 6, 'A' indicates an $EC_{50}$<2 µM, 'B' indicates an $EC_{50}$ of ≥2 µM and <10 µM and 'C' indicates an $EC_{50}$≥10 µM and <50 µM. In Table 7, 'A' indicates an $EC_{50}$<1 µM, 'B' indicates an $EC_{50}$ of ≥1 µM and <10 µM and 'C' indicates an $EC_{50}$≥10 µM and <100 µM.

TABLE 6

Activity of compounds as determined by RSV polymerase assay

| No. | $EC_{50}$ |
| --- | --- |
| 35a | A |
| 36a | A |
| 36c | A |
| 36e | A |
| 36i | B |
| 36j | B |
| 56a | B |
| 56a | B |
| 56c | A |
| 56da | A |
| 56e | A |

TABLE 6-continued

Activity of compounds as determined by RSV polymerase assay

| No. | $EC_{50}$ |
| --- | --- |
| 97a | A |
| 97b | A |
| 97c | A |
| 97d | A |
| 97g | A |
| 98b | A |
| 98c | A |

TABLE 7

Activity of compounds as determined by RT-PCR assay

| No. | $EC_{50}$ |
| --- | --- |
| 1a | C |
| 2a | C |
| 3a | A |
| 4a | C |
| 7a | A |
| 9a | C |
| 11a | B |
| 13a | C |
| 14a | A |
| 20a | B |
| 21a | A |
| 22a | C |
| 23a | A |
| 25a | C |
| 26a | B |
| 27a | B |
| 28a | B |
| 30a | A |
| 31a | B |
| 33a | A |
| 39a | B |
| 41a | B |
| 46a | B |
| 45a | C |
| 48a | B |
| 50a | A |
| 52a | A |
| 58a | C |
| 69a | A |
| 71a | A |
| 73a | C |
| 76a | A |
| 81a | B |
| 82a | A |
| 83a | B |
| 85a | A |
| 86a | A |
| 87a | A |
| 92a | C |
| 105a | C |
| 106a | C |
| 108a | B |
| — | — |
| — | — |
| — | — |
| — | — |
| — | — |

Example 109

Influenza Antiviral Assay

Human lung carcinoma A549 cells (ATCC, Manassas, Va.) were plated at a density of $5\times10^4$ cells/mL ($5\times10^3$ cells/well) in assay media (Ham's F12 media supplemented with 0.3% FBS, 1% penicillin/streptomycin (all Mediatech, Manassas, Va.) and 1% DMSO (Sigma-Aldrich, St Louis, Mo.)) in black 96-well plates. After 24 hours, serially diluted test compounds were added to cells and incubated for an additional 24 hours. Cells were infected with 250 IU/well of Influenza strain A/WSN/33 (H1N1) (Virapur, San Diego Calif.) and incubated for 20 hours at 37° C., 5% $CO_2$. The cell culture supernatant was aspirated off and 50 μL of 25 μM 2'-(4-Methylumbelliferyl)-α-D-N-acetylneuraminic acid (Sigma-Aldrich) dissolved in 33 mM MES, pH 6.5 (Emerald Biosystems, Bainbridge Island, Wash.) was added to the cells. After incubation for 45 mins at 30° C., reactions were stopped by addition of 150 μL stop solution (100 mM glycine, pH 10.5, 25% ethanol, all Sigma-Aldrich). Fluorescence was measured with excitation and emission filters of 355 and 460 nm, respectively, on a Victor X3 multi-label plate reader (Perkin Elmer, Waltham, Mass.). Cytotoxicity of uninfected parallel cultures was determined by addition of 100 μL of CellTiter-Glo® reagent (Promega, Madison, Wis.), and incubation for 10 mins at R.T. Luminescence was measured on a Victor X3 multi-label plate reader.

Compounds of Formula (I), Formula (II) and Formula (III) are active in the assay as noted in Table 8, where 'A' indicates an $EC_{50}$<20 μM, 'B' indicates an $EC_{50}$ of ≥20 μM and <100 μM and 'C' indicates an $EC_{50}$≥100 μM and <250 μM.

TABLE 8

Activity of compounds

| No. | % Inhibition |
|---|---|
| 1a | C |
| 2a | C |
| 3a | C |
| 4a | C |
| 6a | C |
| 7a | C |
| 9a | C |
| 12a | C |
| 16a | C |
| 17a | C |
| 18a | C |
| 20a | C |
| 21a | C |
| 22a | C |
| 23a | C |
| 25a | A |
| 26a | C |
| 27a | B |
| 28a | C |
| 30a | C |
| 31a | C |
| 39a | B |

Example 110

Influenza Pol Assay

Recombinant influenza polymerase trimer is obtained as described (Aggarwal S. et al., PLoS ONE 2010). Standard RNA polymerization assays are conducted in the presence of 0.15 uM enzyme, 1.5 uM 50-mer oligonucleotide template, 400 uM AG primer and varying concentration of the test compounds are incubated together for 40 minutes at 30° C. Radioactive 33P GTP are used as the tracer and the radiolabeled RNA products are resolved by electrophoresis on a 15% polyacrylamide TBE gel, and is visualized and quantitated after being exposed on a phosphorImager screen. Polymerase inhibition experiments ($IC_{50}$) are conducted the same way in the presence of increasing concentration of test compounds.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound selected from Formula (I), or a pharmaceutically acceptable salt thereof:

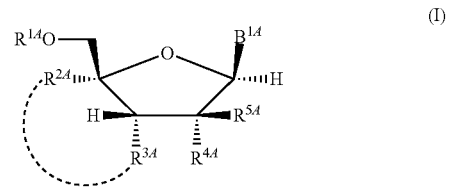

(I)

wherein:

$B^{1A}$ is an optionally substituted heterocyclic base or an optionally substituted heterocyclic base with a protected amino group;

$R^{1A}$ is selected from the group consisting of hydrogen, an optionally substituted acyl, an optionally substituted O-linked amino acid,

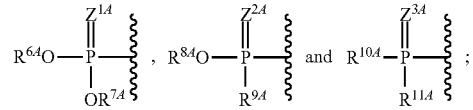

the dashed line (------) is absent;

$R^{2A}$ is selected from the group consisting of an unsubstituted $C_{1-6}$ alkyl, a halogen substituted $C_{1-6}$ alkyl, a hydroxy substituted $C_{1-6}$ alkyl, an alkoxy substituted $C_{1-6}$ alkyl, a sulfenyl substituted $C_{1-6}$ alkyl, an optionally substituted $C_{2-6}$ alkenyl, an optionally substituted $C_{2-6}$ alkynyl, an optionally substituted $C_{3-6}$ cycloalkyl, an optionally substituted —O—$C_{1-6}$ alkyl, an optionally substituted —O—$C_{3-6}$ alkenyl, an optionally substituted —O—$C_{3-6}$ alkynyl and cyano;

$R^{3A}$ is selected from the group consisting of OH, —OC(=O)$R^{nA}$ and an optionally substituted O-linked amino acid;

$R^{4A}$ is fluoro or chloro;

$R^{5A}$ is hydrogen or halogen;

$R^{6A}$, $R^{7A}$ and $R^{8A}$ are independently selected from the group consisting of absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl, an optionally substituted aryl($C_{1-6}$ alkyl), an optionally substituted *—(CR$^{15A}$R$^{16A}$)$_p$—O—C$_{1-24}$ alkyl, an optionally substituted *—(CR$^{17A}$R$^{18A}$)$_q$—O—C$_{1-24}$ alkenyl,

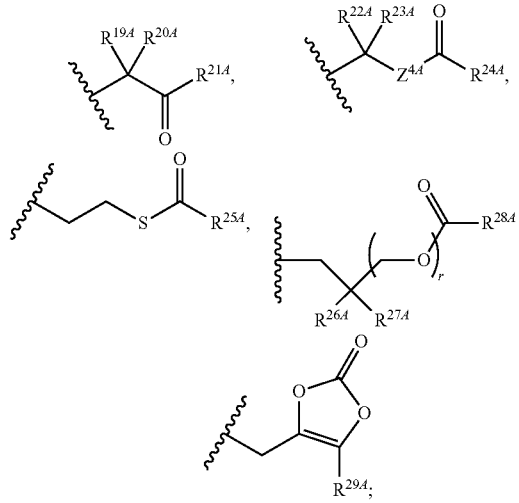

or $R^{6A}$ is

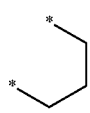 [SMILES: *CCC*]

and $R^{7A}$ is absent or hydrogen; or $R^{6A}$ and $R^{7A}$ are taken together to form a moiety selected from the group consisting of an optionally substituted

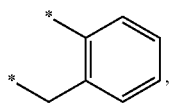

and an optionally substituted

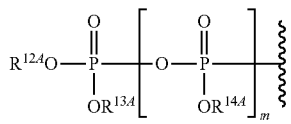

wherein the oxygens connected to $R^{6A}$ and $R^{7A}$, the phosphorus and the moiety form a six-membered to ten-membered ring system;

$R^{9A}$ is independently selected from the group consisting of an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, $NR^{30A}R^{31A}$, an optionally substituted N-linked amino acid and an optionally substituted N-linked amino acid ester derivative;

$R^{10A}$ and $R^{11A}$ are independently an optionally substituted N-linked amino acid or an optionally substituted N-linked amino acid ester derivative;

$R^{12A}$, $R^{13A}$ and $R^{14A}$ are independently absent or hydrogen;

each $R^{15A}$, each $R^{16A}$, each $R^{17A}$ and each $R^{18A}$ are independently hydrogen, an optionally substituted $C_{1-24}$ alkyl or alkoxy;

$R^{19A}$, $R^{20A}$, $R^{22A}$ and $R^{23A}$ are independently selected from the group consisting of hydrogen, an optionally substituted $C_{1-24}$ alkyl and an optionally substituted aryl;

$R^{21A}$ and $R^{24A}$ are independently selected from the group consisting of hydrogen, an optionally substituted $C_{1-24}$ alkyl, an optionally substituted aryl, an optionally substituted —O—$C_{1-24}$ alkyl and an optionally substituted —O-aryl;

$R^{25A}$ and $R^{29A}$ are independently selected from the group consisting of hydrogen, an optionally substituted $C_{1-24}$ alkyl and an optionally substituted aryl;

$R^{26A}$ and $R^{27A}$ are independently —C≡N or an optionally substituted substituent selected from the group consisting of $C_{2-8}$ organylcarbonyl, $C_{2-8}$ alkoxycarbonyl and $C_{2-8}$ organylaminocarbonyl;

$R^{28A}$ is selected from the group consisting of hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

$R^{30A}$ and $R^{31A}$ are independently selected from the group consisting of hydrogen, an optionally substituted $C_{1-24}$-alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl;

$R^{nA}$ is an optionally substituted $C_{1-24}$-alkyl;

m is 0 or 1;

p and q are independently selected from the group consisting of 1, 2 and 3;

r is 1 or 2;

$Z^{1A}$, $Z^{2A}$, $Z^{3A}$ and $Z^{4A}$ are independently O or S; and provided that when $R^{1A}$ is

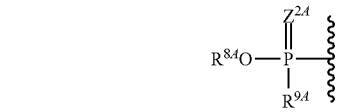

wherein $R^{8A}$ is an unsubstituted $C_{1-4}$ alkyl or phenyl optionally para-substituted with a halogen or methyl and $R^{9A}$ is methyl ester, ethyl ester, isopropyl ester, n-butyl ester, benzyl ester or phenyl ester of an amino acid selected from the group consisting of glycine, alanine, valine, leucine, phenylalanine, tryptophan, methionine and proline; $R^{3A}$ is OH; $R^{4A}$ is fluoro; $R^{5A}$ is fluoro or hydrogen; and $B^{1A}$ is an unsubstituted uracil; then $R^{2A}$ cannot be —OCH$_3$;

provided that when $R^{1A}$ is H; $R^{3A}$ is OH; $R^{4A}$ is fluoro; $R^{5A}$ is fluoro; and $B^{1A}$ is an unsubstituted cytosine; then $R^{2A}$ cannot be allenyl; and provided that when $R^{1A}$ is H; $R^{3A}$ is OH; $R^{4A}$ is fluoro; $R^{5A}$ is fluoro; and $B^{1A}$ is an unsubstituted cytosine; then $R^{2A}$ cannot be ethynyl.

2. The compound of claim 1, wherein $R^{1A}$ is

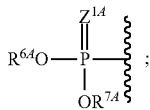

is

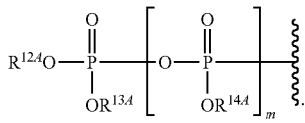

; and $R^{7A}$ is absent or hydrogen.

3. The compound of claim 1, wherein $R^{1A}$ is an optionally substituted acyl.

4. The compound of claim 1, wherein $R^{1A}$ is H.

5. The compound of claim 1, wherein $R^{1A}$ is an optionally substituted O-linked amino acid.

6. The compound of claim 1, wherein $R^{1A}$ is

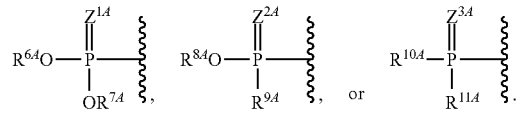

7. The compound of claim 6, wherein both $R^{6A}$ and $R^{7A}$ are independently selected from the group consisting of an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl, an optionally substituted aryl, an optionally substituted heteroaryl and an optionally substituted aryl($C_{1-6}$ alkyl).

8. The compound of claim 6, wherein both $R^{6A}$ and $R^{7A}$ are independently selected from the group consisting of

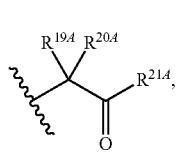 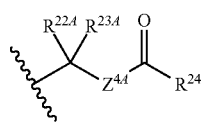 and

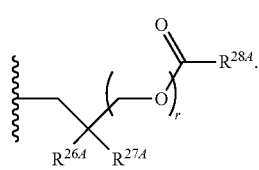

9. The compound of claim 6, wherein $R^{6A}$ and $R^{7A}$ are both

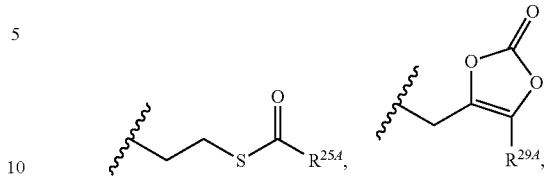

$*-(CR^{15A}R^{16A})_p-O-C_{1-24}$ alkyl or $*-(CR^{17A}R^{18A})_q-O-C_{2-24}$ alkenyl; or wherein $R^{6A}$ and $R^{7A}$ can be taken together to form a moiety selected from the group consisting of an optionally substituted

and an optionally substituted

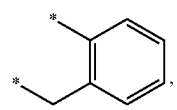

wherein the oxygens connected to $R^{6A}$ and $R^{7A}$, the phosphorus and the moiety form a six-membered to ten-membered ring system.

10. The compound of claim 6, wherein $R^{8A}$ is selected from the group consisting of absent, hydrogen, an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl and an optionally substituted $C_{3-6}$ cycloalkenyl; and $R^{9A}$ is independently selected from the group consisting of an optionally substituted $C_{1-24}$ alkyl, an optionally substituted $C_{2-24}$ alkenyl, an optionally substituted $C_{2-24}$ alkynyl, an optionally substituted $C_{3-6}$ cycloalkyl, an optionally substituted $C_{3-6}$ cycloalkenyl and $NR^{30A}R^{31A}$.

11. The compound of claim 6, wherein $R^{8A}$ is an optionally substituted aryl; and $R^{9A}$ is an optionally substituted N-linked amino acid or an optionally substituted N-linked amino acid ester derivative.

12. The compound of claim 6, wherein $R^{1A}$ is

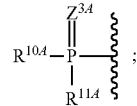

and, $R^{10A}$ and $R^{11A}$ are both independently an optionally substituted N-linked amino acid or an optionally substituted N-linked amino acid ester derivative.

13. The compound of claim 1, wherein $B^{1A}$ is selected from the group consisting of:

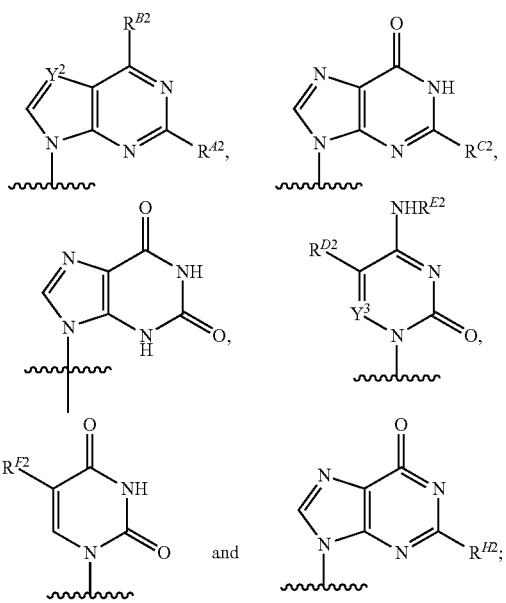

wherein:
- $R^{A2}$ is selected from the group consisting of hydrogen, halogen and $NHR^{J2}$, wherein $R^{J2}$ is selected from the group consisting of hydrogen, —C(=O)$R^{K2}$ and —C(=O)O$R^{L2}$;
- $R^{B2}$ is halogen or $NHR^{W2}$, wherein $R^{W2}$ is selected from the group consisting of hydrogen, an optionally substituted $C_{1-6}$ alkyl, an optionally substituted $C_{2-6}$ alkenyl, an optionally substituted $C_{3-8}$ cycloalkyl, —C(=O)$R^{M2}$ and —C(=O)O$R^{N2}$;
- $R^{C2}$ is hydrogen or $NHR^{O2}$, wherein $R^{O2}$ is selected from the group consisting of hydrogen, —C(=O)$R^{P2}$ and —C(=O)O$R^{Q2}$;
- $R^{D2}$ is selected from the group consisting of hydrogen, halogen, an optionally substituted $C_{1-6}$ alkyl, an optionally substituted $C_{2-6}$ alkenyl and an optionally substituted $C_{2-6}$ alkynyl;
- $R^{E2}$ is selected from the group consisting of hydrogen, hydroxy, an optionally substituted $C_{1-6}$ alkyl, an optionally substituted $C_{3-8}$ cycloalkyl, —C(=O)$R^{R2}$ and —C(=O)O$R^{S2}$;
- $R^{F2}$ is selected from the group consisting of hydrogen, halogen, an optionally substituted $C_{1-6}$alkyl, an optionally substituted $C_{2-6}$ alkenyl and an optionally substituted $C_{2-6}$ alkynyl;
- $Y^2$ and $Y^3$ are independently N or $CR^{12}$, wherein $R^{12}$ is selected from the group consisting of hydrogen, halogen, an optionally substituted $C_{1-6}$-alkyl, an optionally substituted $C_{2-6}$-alkenyl and an optionally substituted $C_{1-6}$-alkynyl;
- $R^{G2}$ is an optionally substituted $C_{1-6}$ alkyl;
- $R^{H2}$ is hydrogen or $NHR^{T2}$, wherein $R^{T2}$ is independently selected from the group consisting of hydrogen, —C(=O)$R^{U2}$ and —C(=O)O$R^{V2}$; and
- $R^{K2}$, $R^{L2}$, $R^{M2}$, $R^{N2}$, $R^{P2}$, $R^{Q2}$, $R^{R2}$, $R^{S2}$, $R^{U2}$ and $R^{V2}$ are independently selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl).

14. The compound of claim 1, wherein $R^{2A}$ is a halogen substituted $C_{1-6}$ alkyl or a sulfenyl substituted $C_{1-6}$ alkyl, and $R^{3A}$ is OH or —OC(=O)$R^{nA}$.

15. The compound of claim 1, wherein the compound of Formula (I) is selected from the group consisting of:

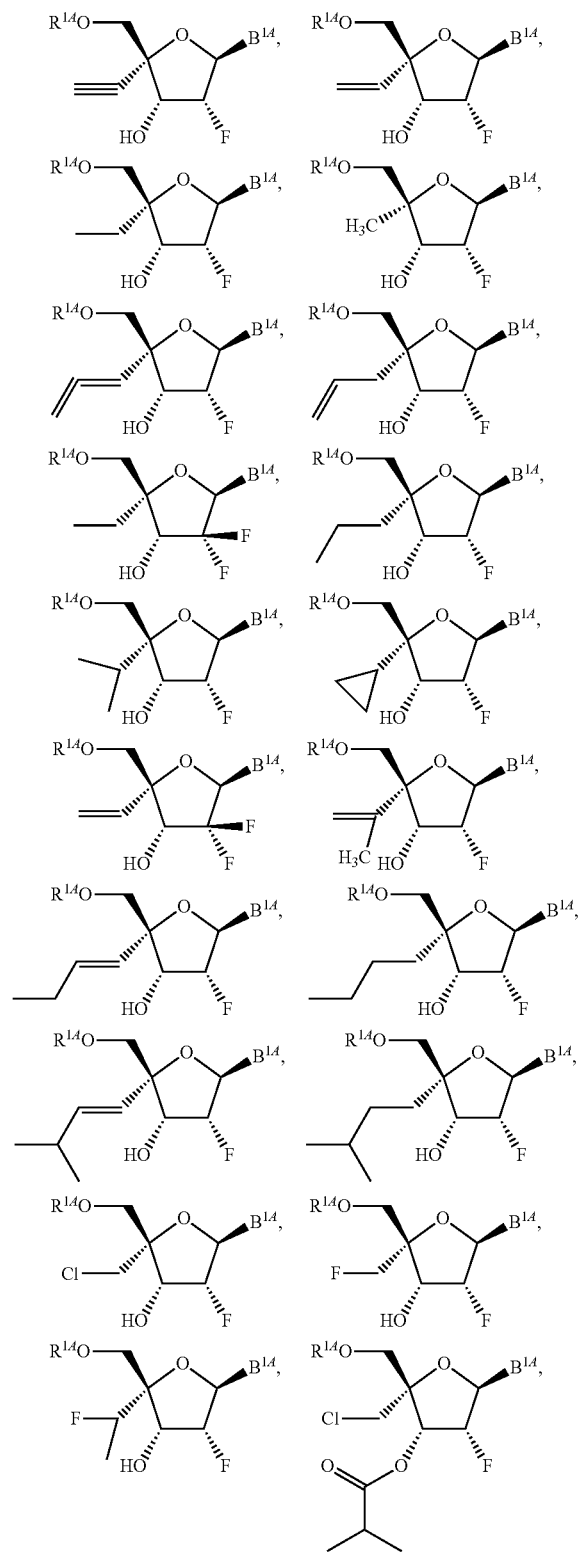

-continued
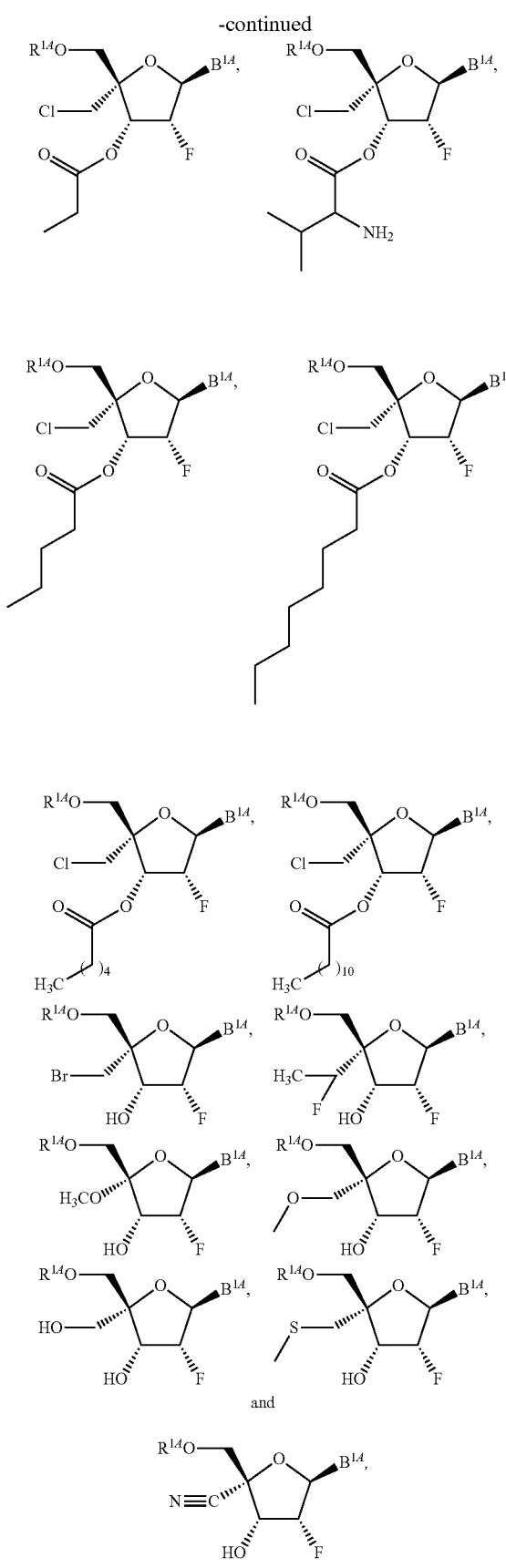
or a pharmaceutically acceptable salt thereof.
16. The compound of claim 1, wherein the compound of Formula (I) is selected from the group consisting of:
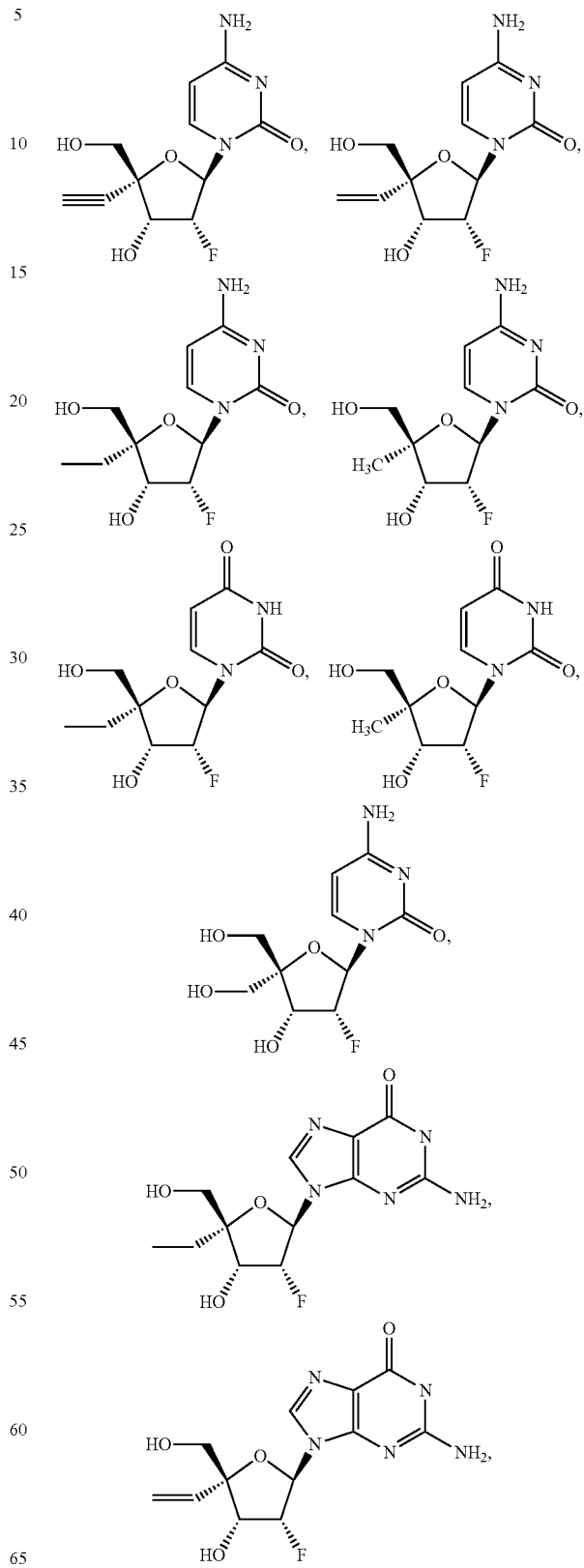

-continued
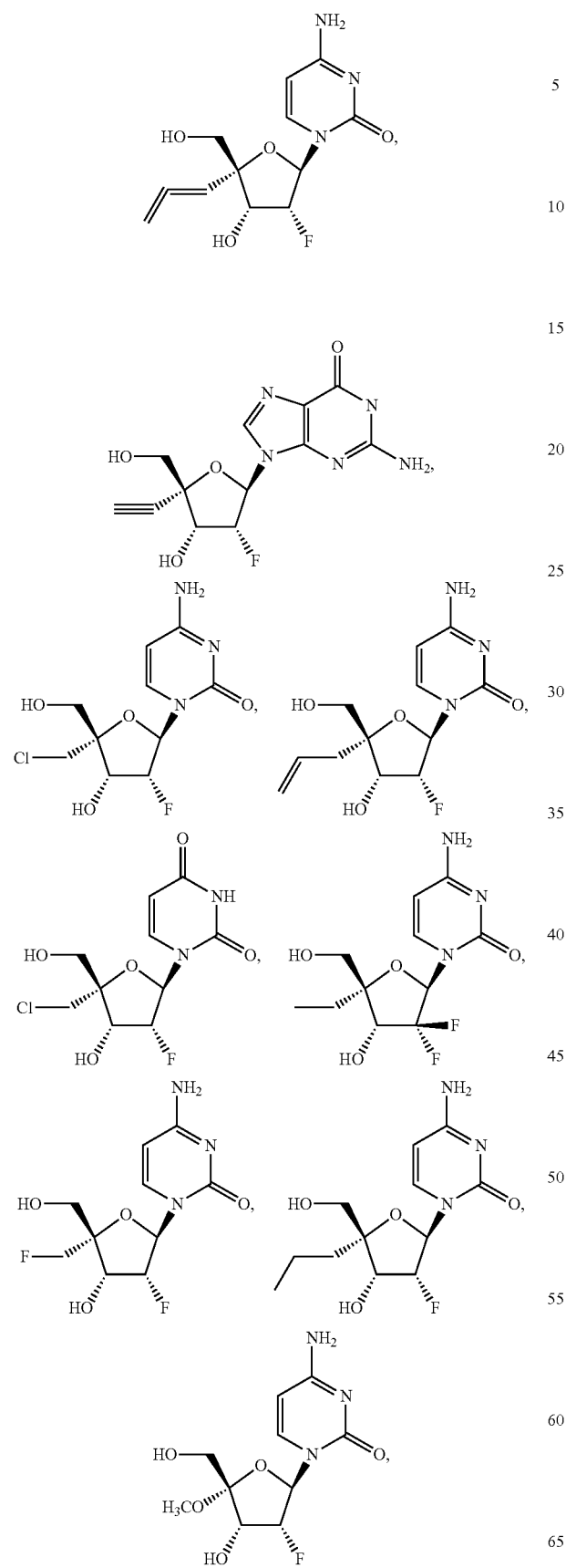
-continued
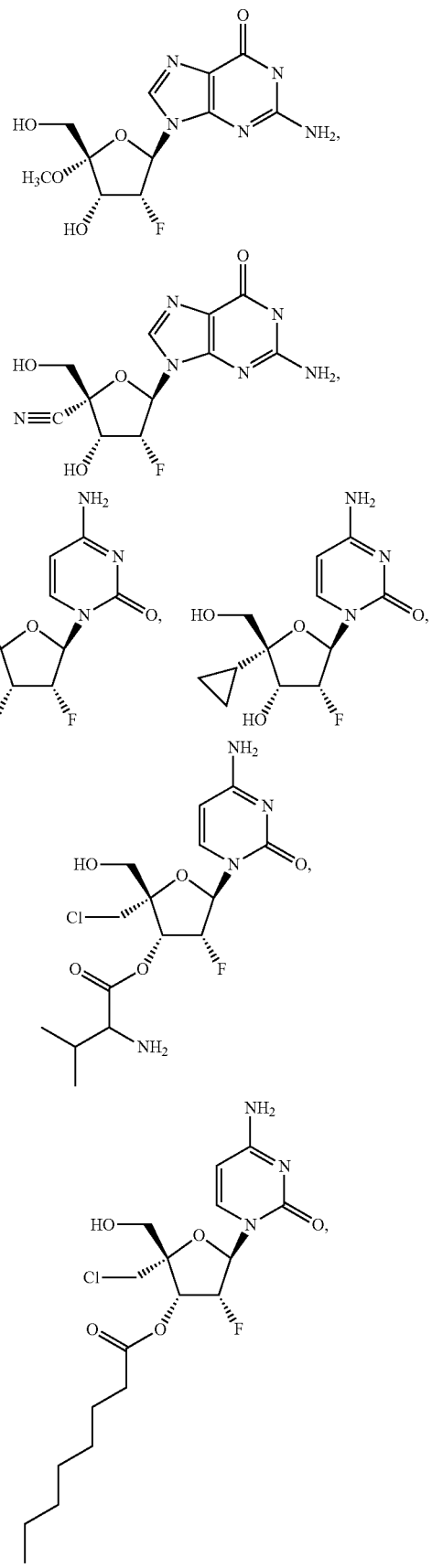

305
-continued
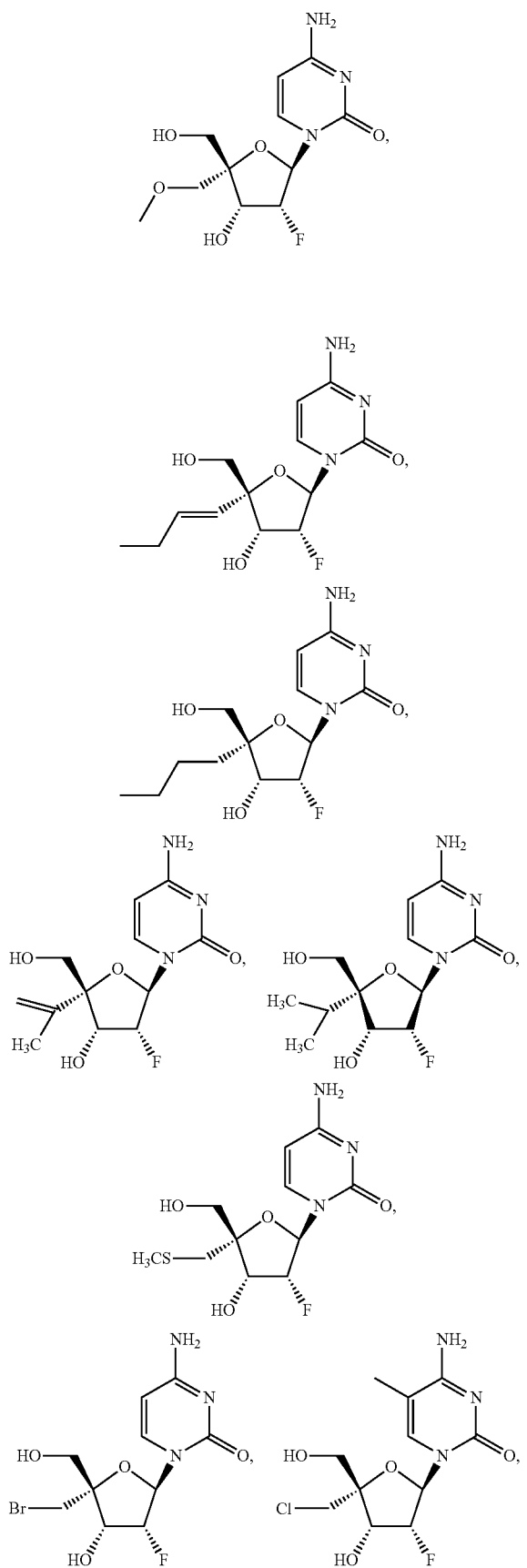
306
-continued
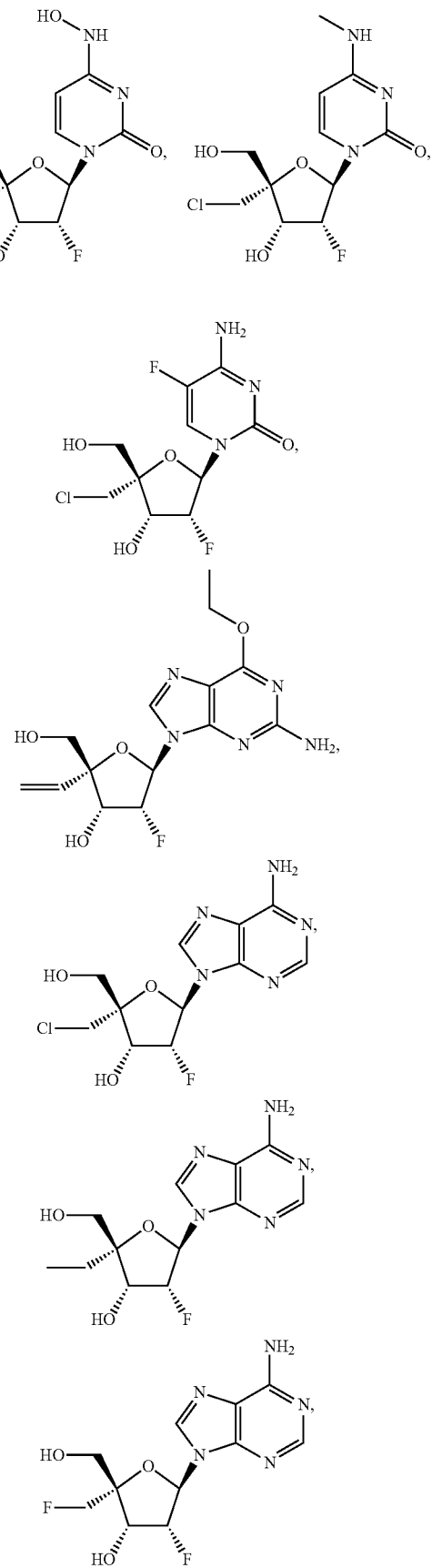

307
-continued
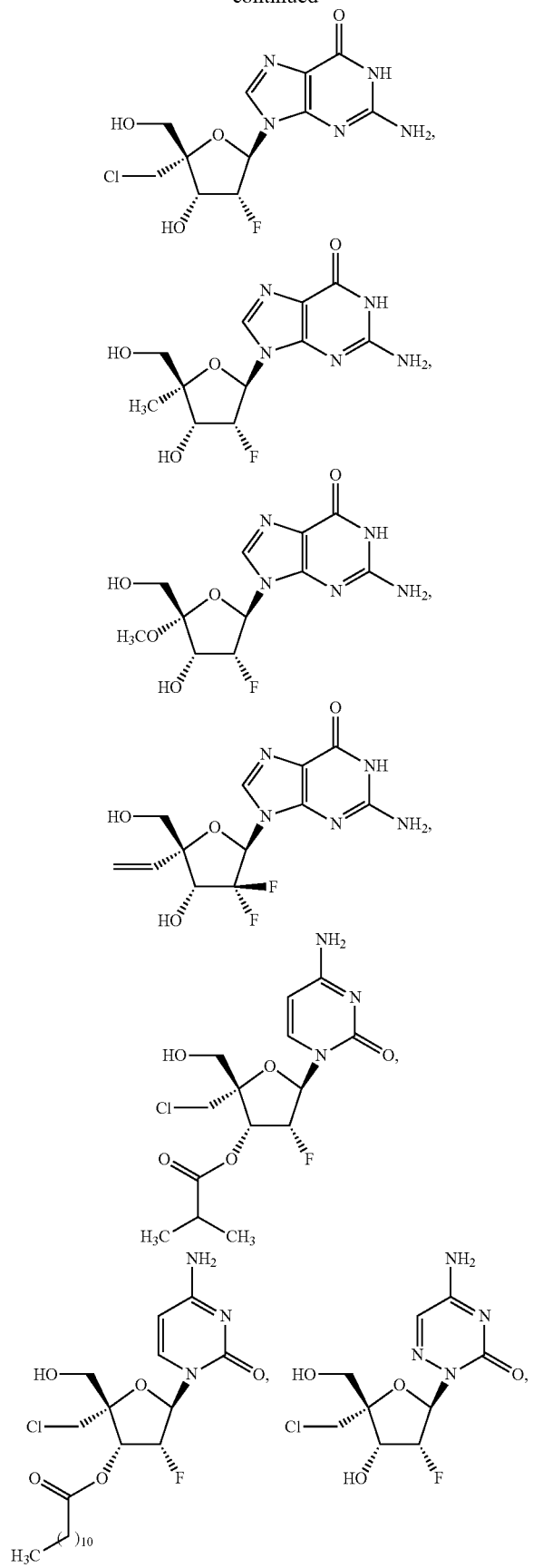
308
-continued
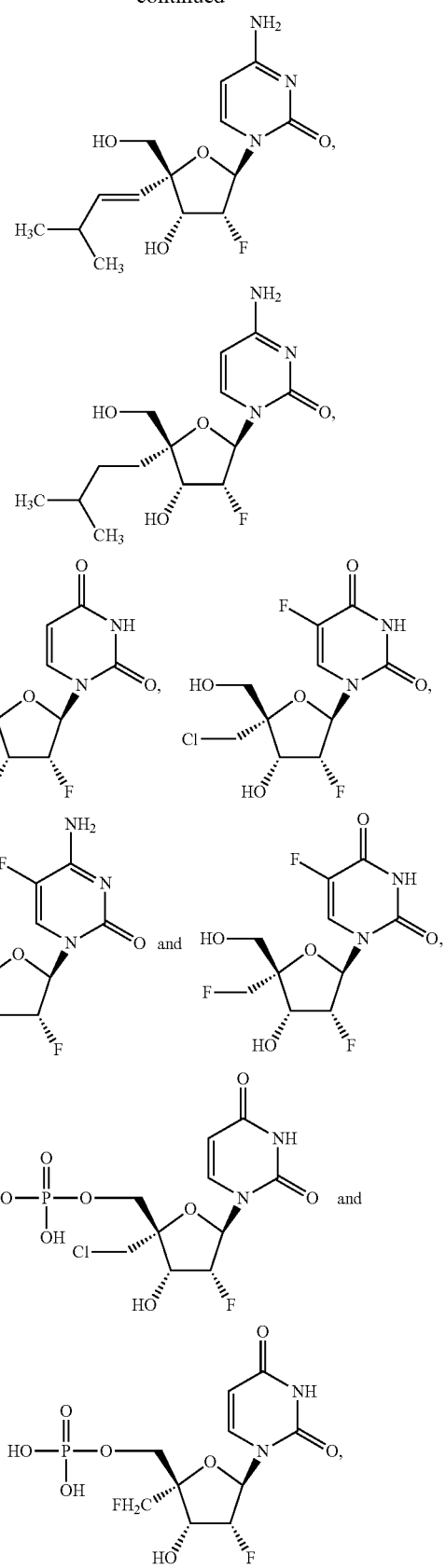
or a pharmaceutically acceptable salt of the foregoing.

17. The compound of claim 1, wherein the compound of Formula (I) is selected from the group consisting of:
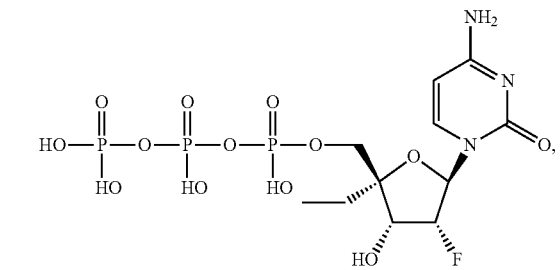
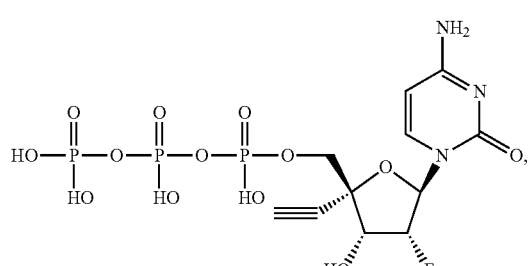
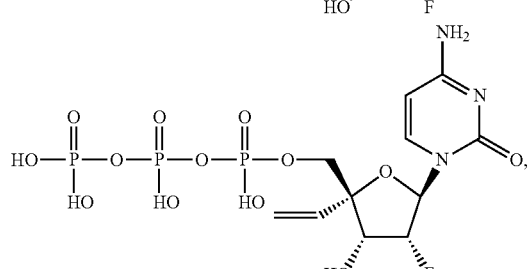
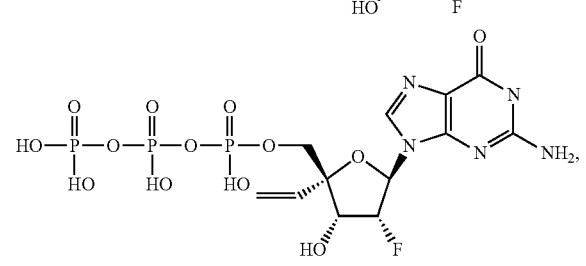
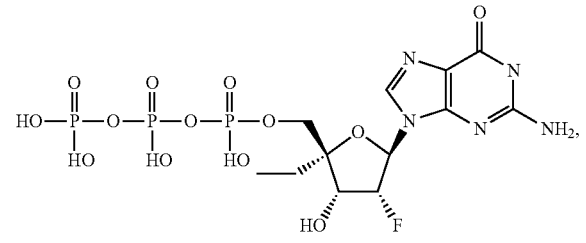
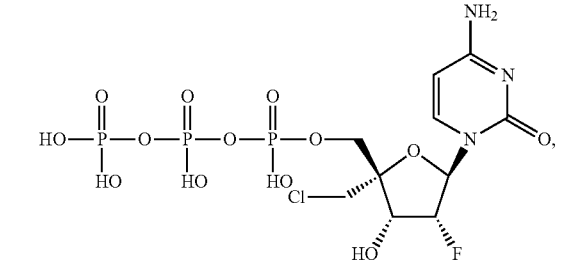
-continued
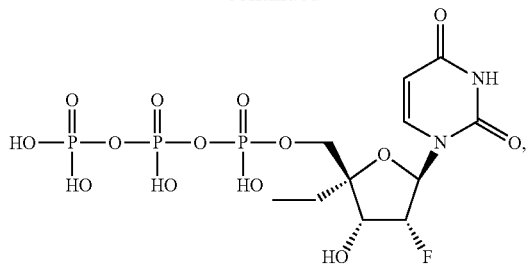
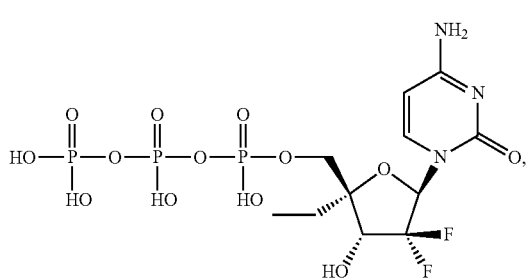
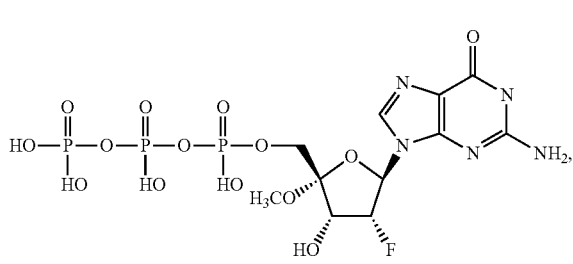
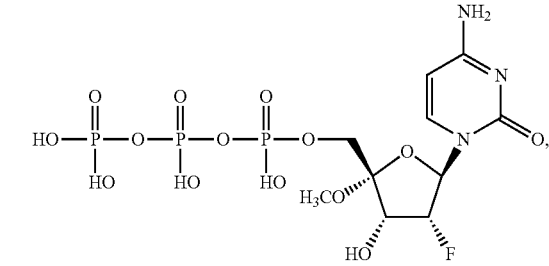
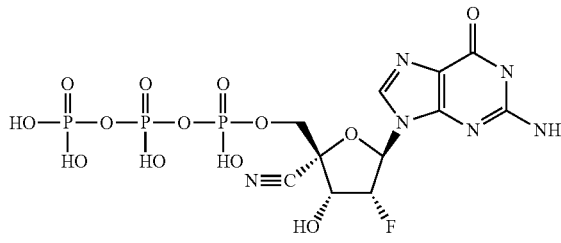
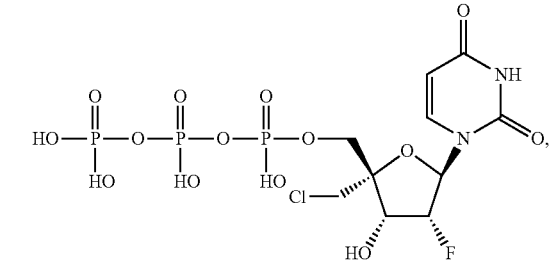

311
-continued
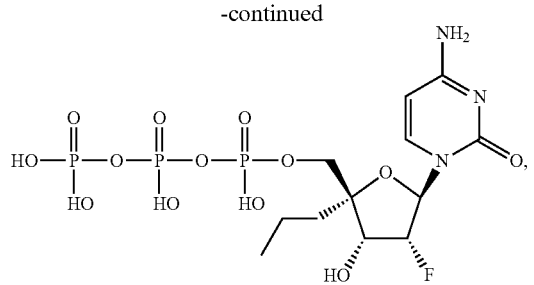
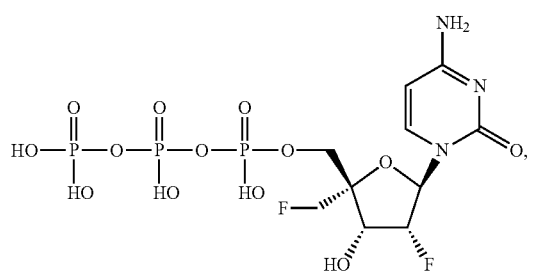
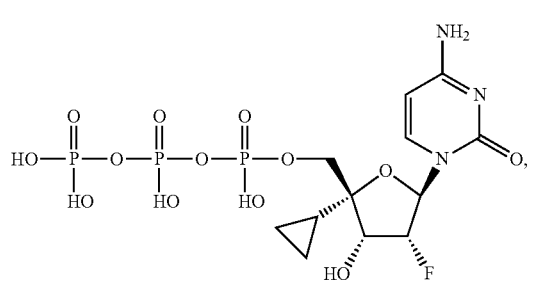
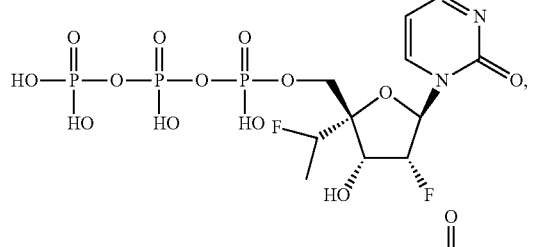
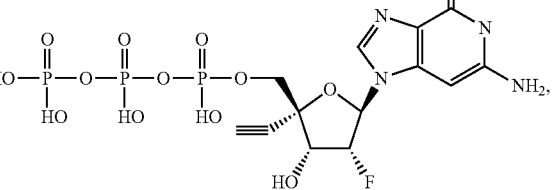
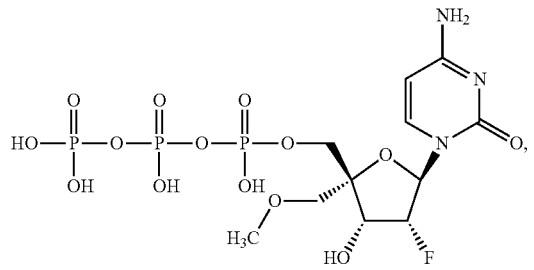
312
-continued
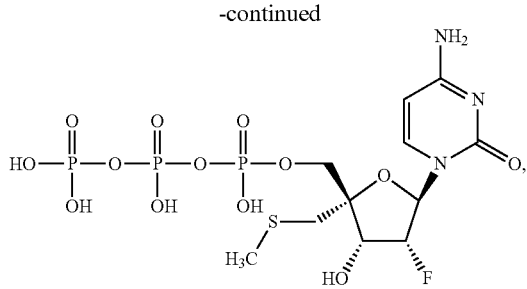
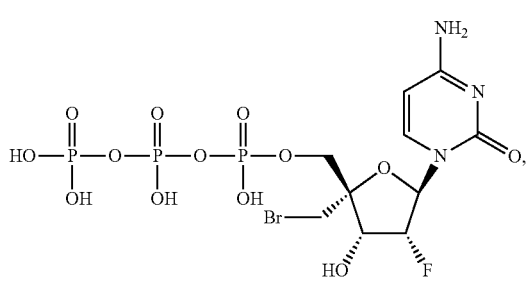
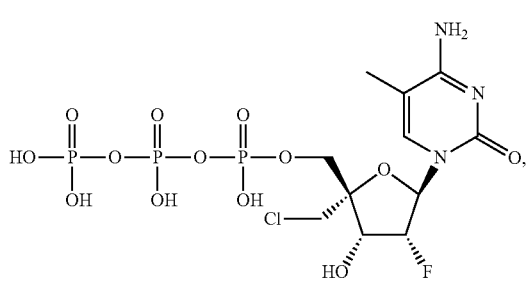
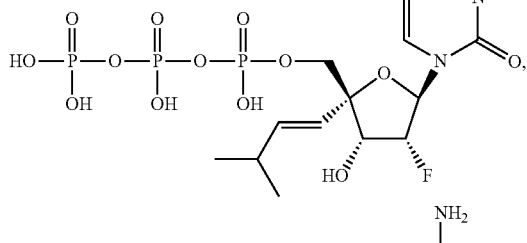
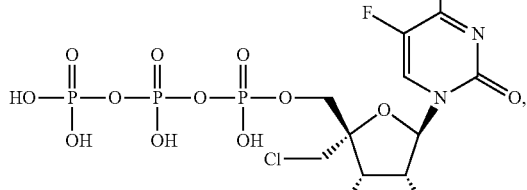
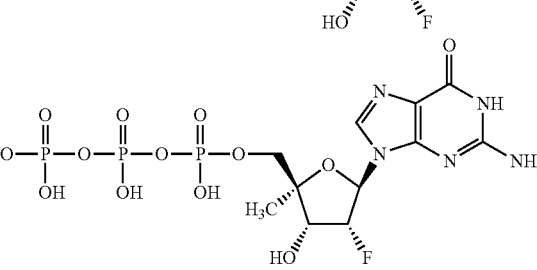

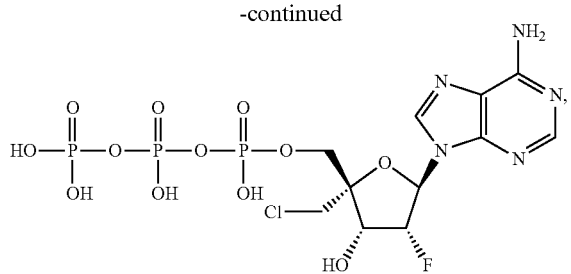
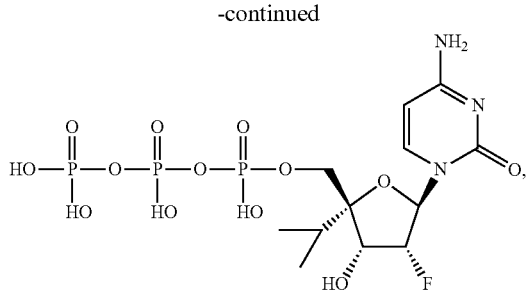
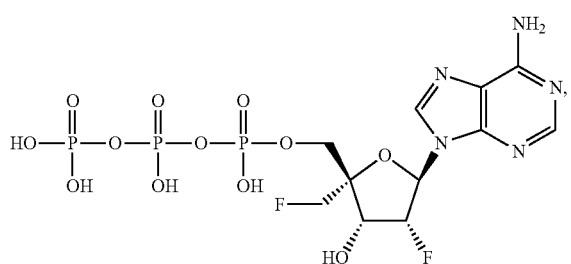
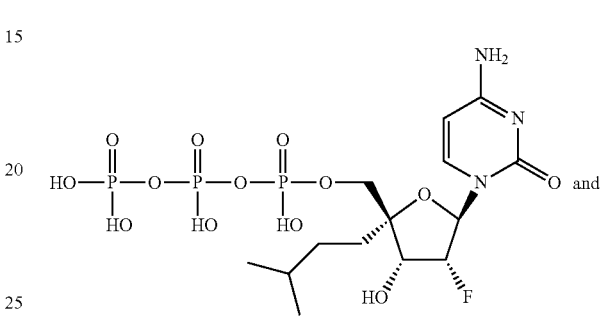
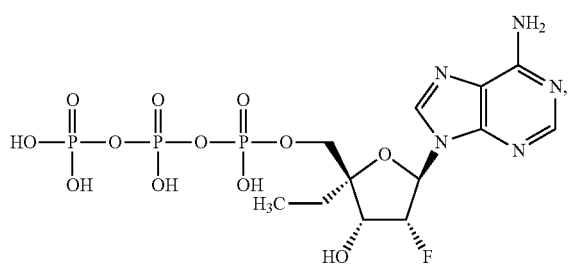
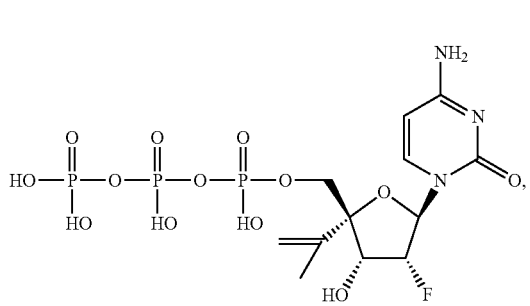 [SMILES: C=C(C)[C@]1(COP(=O)(O)OP(=O)(O)OP(=O)(O)O)O[C@@H](n2ccc(N)nc2=O)[C@H](F)[C@@H]1O]
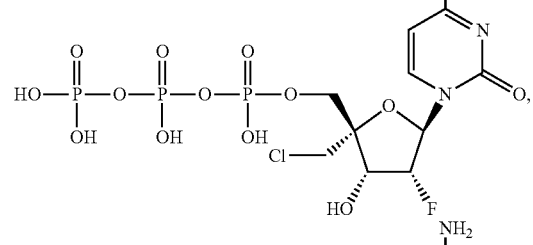
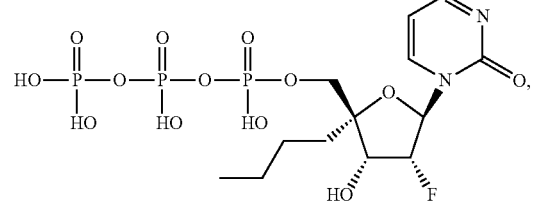
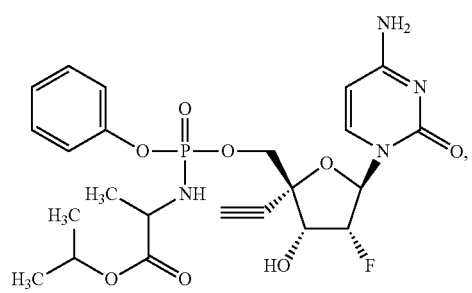
or a pharmaceutically acceptable salt of the foregoing.
18. The compound of claim 1, wherein the compound of Formula (I) is selected from the group consisting of:
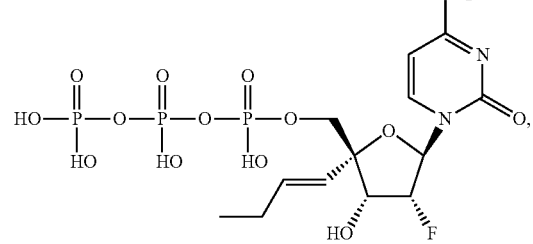
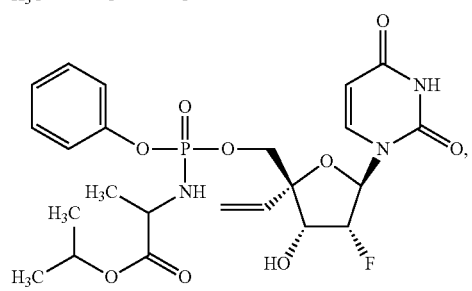

315
-continued
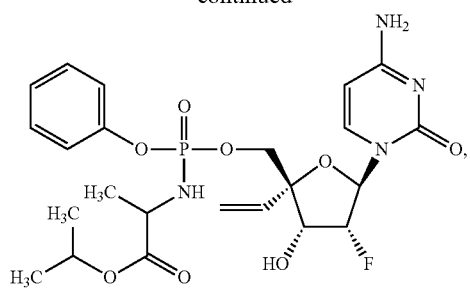
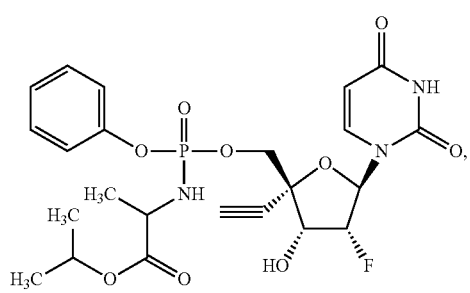
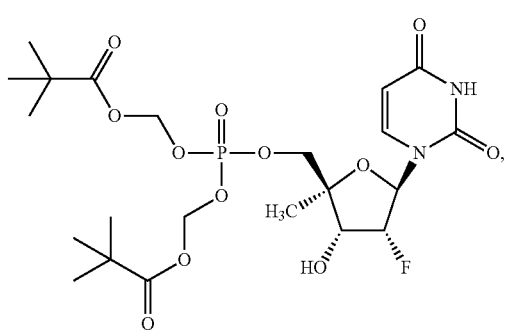
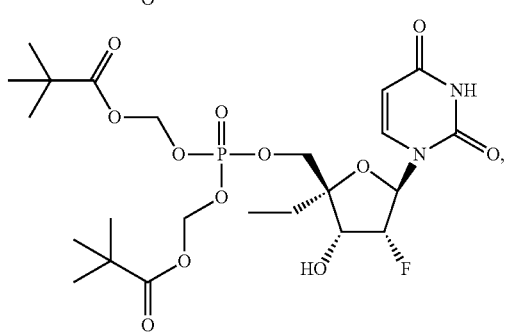
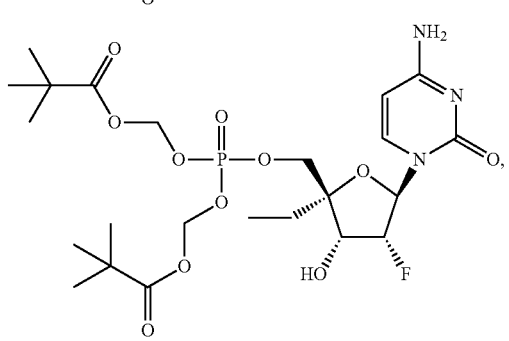
316
-continued
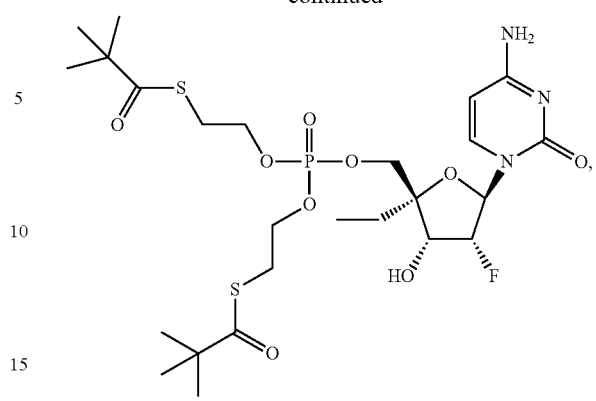
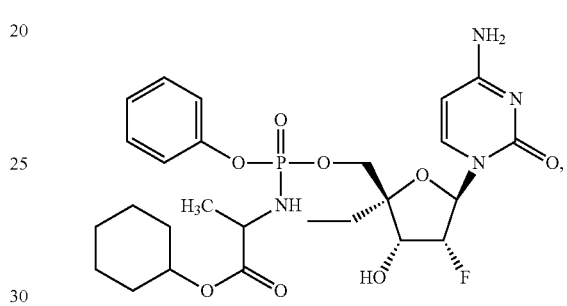
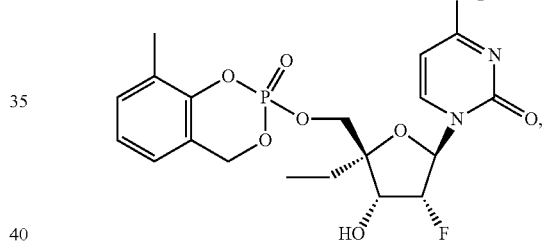
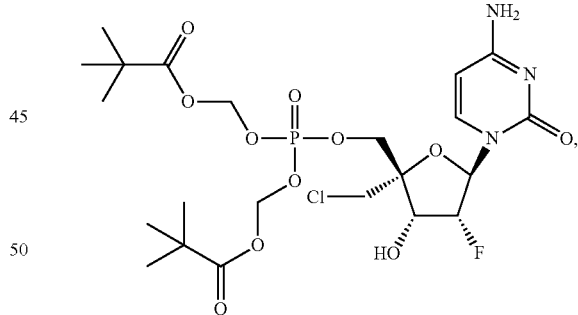
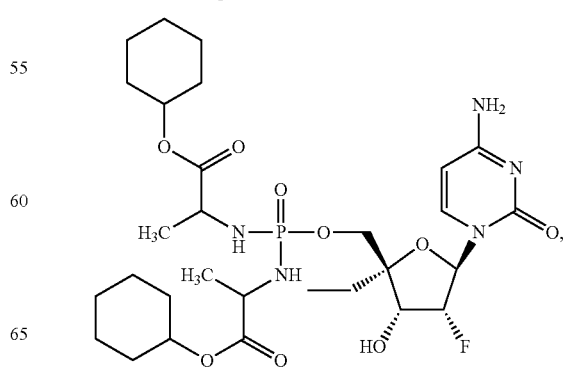

317
-continued
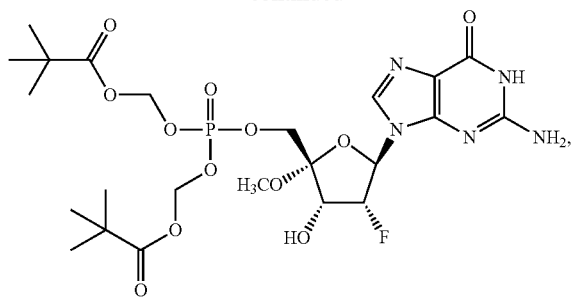
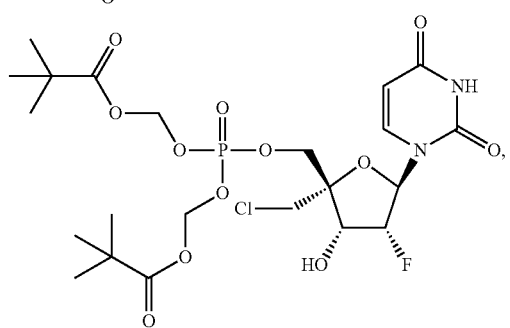
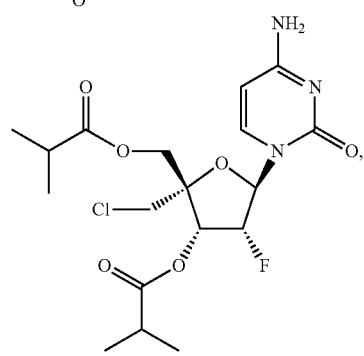
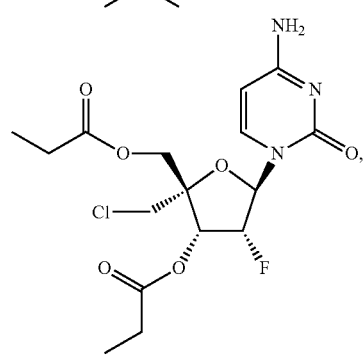
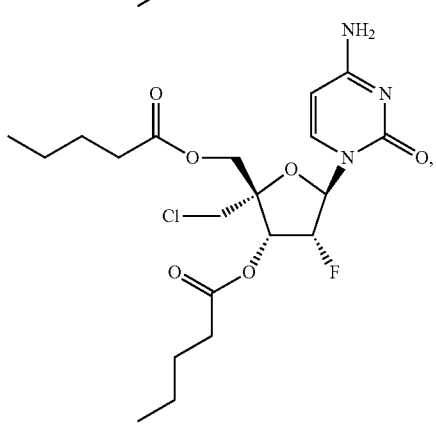
318
-continued
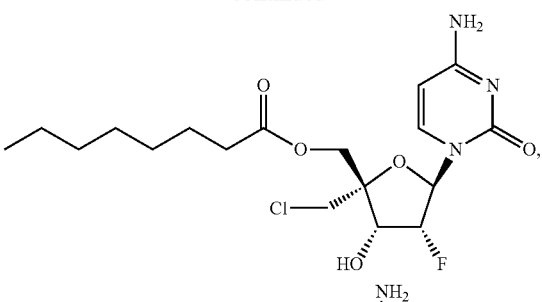
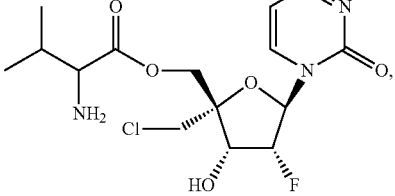
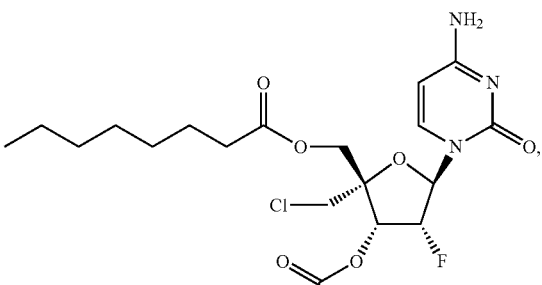
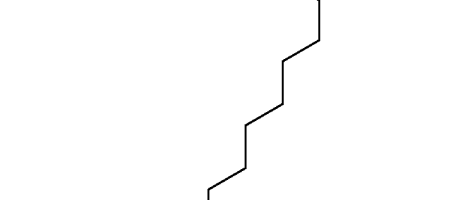
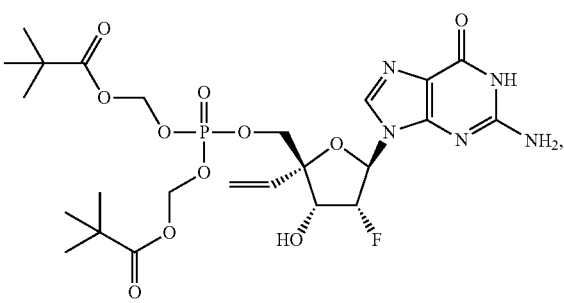
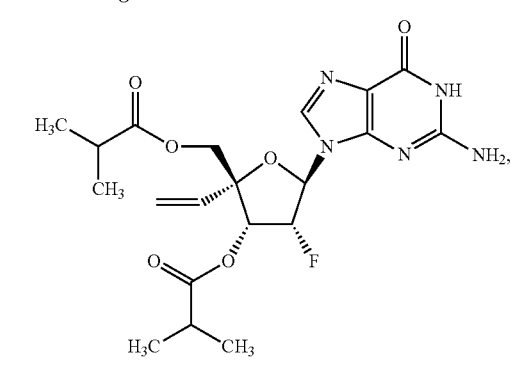

319
-continued
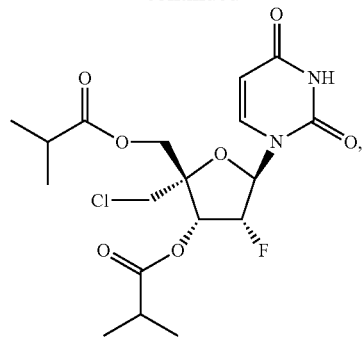
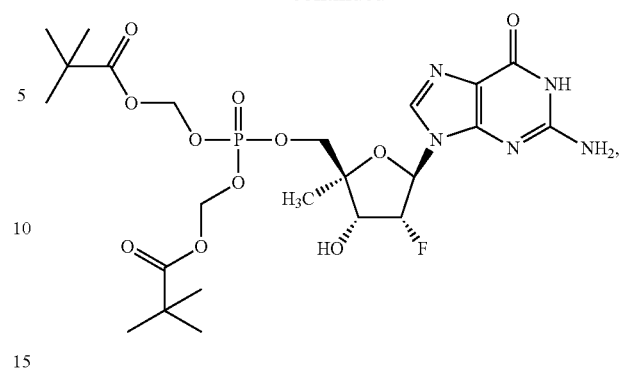
320
-continued
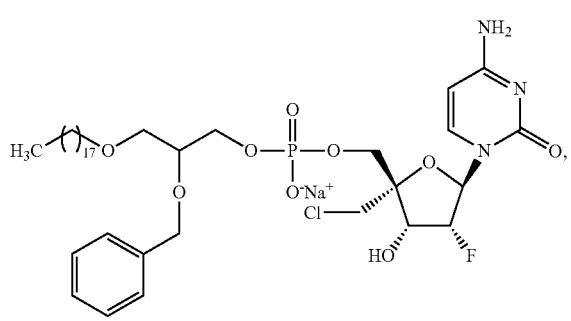
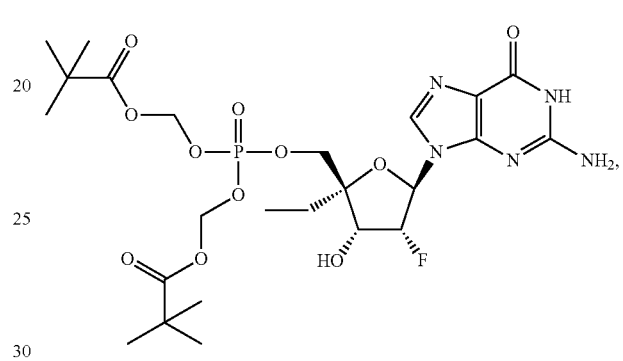
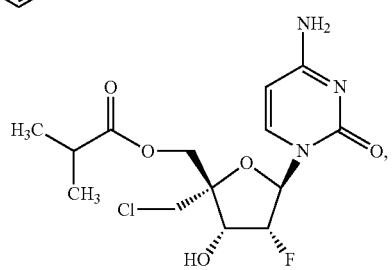
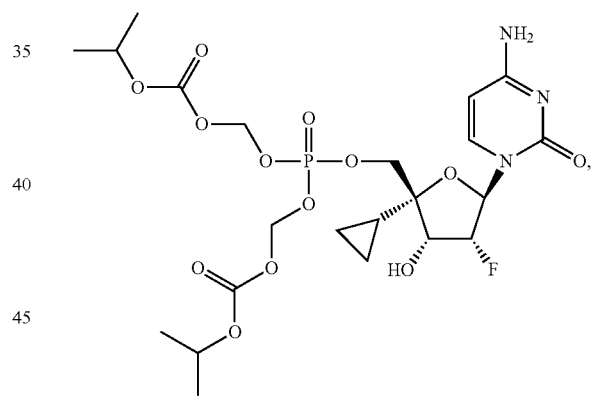
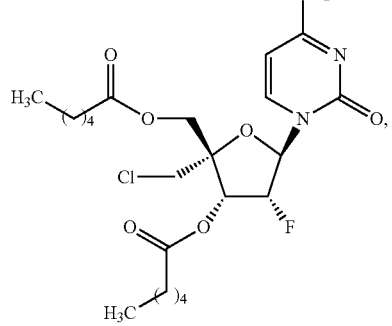
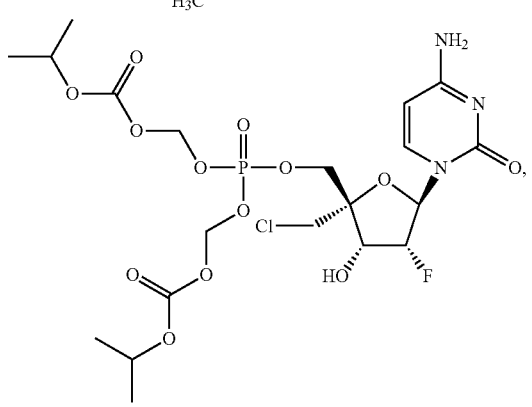
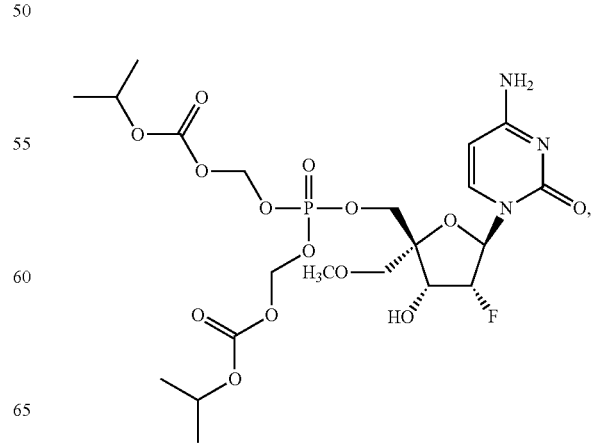

-continued

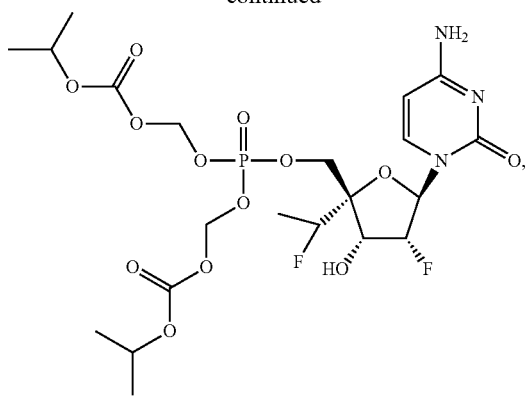

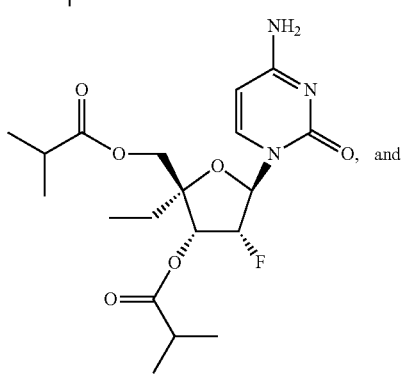

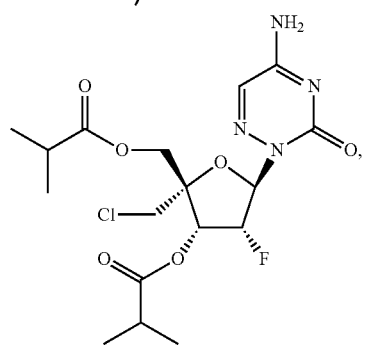

or a pharmaceutically acceptance salt of the foregoing.

19. A pharmaceutical composition comprising an effective amount of a compound of claim 1, or a pharmaceutically acceptable salt thereof, and a pharmaceutically acceptable carrier, diluent, excipient, or combination thereof.

20. A method for ameliorating or treating a viral infection comprising contacting a cell infected with the virus in a subject identified as suffering from the viral infection with an effective amount of a compound of claim 1, or a pharmaceutically acceptable salt thereof; and wherein the viral infection is selected from a paramyxovirus viral infection and an orthomyxovirus viral infection.

21. A method for ameliorating or treating a viral infection in combination with one or more agents comprising administering to or contacting a cell in a subject identified as suffering from the viral infection with an effective amount of a compound of claim 1, or a pharmaceutically acceptable salt thereof; and wherein the viral infection is selected from a paramyxovirus viral infection and an orthomyxovirus viral infection.

22. The compound of claim 1, wherein the compound of Formula (I) is

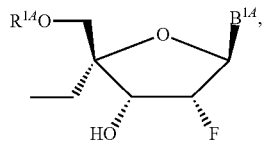

or a pharmaceutically acceptable salt thereof.

23. The compound of claim 1, wherein the compound of Formula (I) is

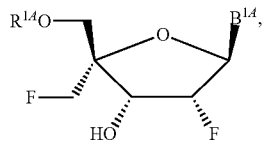

or a pharmaceutically acceptable salt thereof.

24. The compound of claim 1, wherein the compound of Formula (I) is

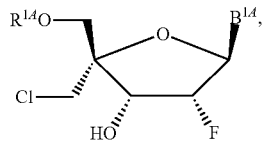

or a pharmaceutically acceptable salt thereof.

25. The compound of claim 1, wherein the compound of Formula (I) is

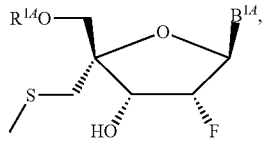

or a pharmaceutically acceptable salt thereof.

26. The compound of claim 1, wherein the compound of Formula (I) is

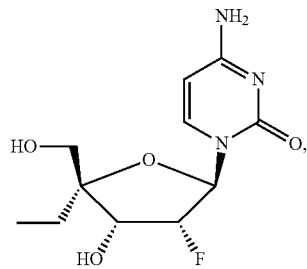 [SMILES: CC[C@]1(CO)O[C@@H](n2ccc(N)nc2=O)[C@H](F)[C@@H]1O]

or a pharmaceutically acceptable salt thereof.

27. The compound of claim 1, wherein the compound of Formula (I) is

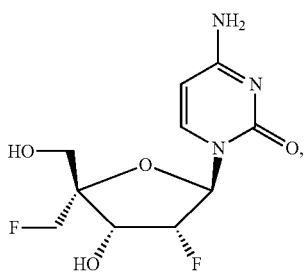 [SMILES: Nc1ccn([C@@H]2O[C@@](CO)(CF)[C@@H](O)[C@H]2F)c(=O)n1]

or a pharmaceutically acceptable salt thereof.

28. The compound of claim 1, wherein the compound of Formula (I) is

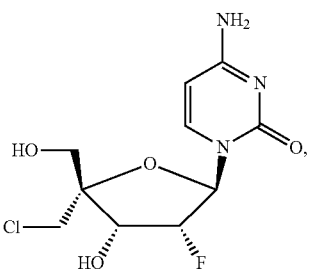 [SMILES: Nc1ccn([C@@H]2O[C@@](CO)(CCl)[C@@H](O)[C@H]2F)c(=O)n1]

or a pharmaceutically acceptable salt thereof.

29. The compound of claim 1, wherein the compound of Formula (I) is

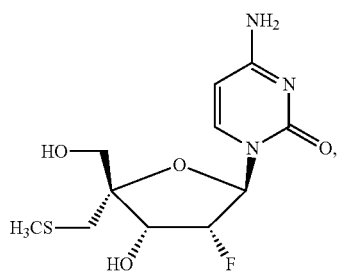

or a pharmaceutically acceptable salt thereof.

30. The compound of claim 1, wherein the compound of Formula (I) is

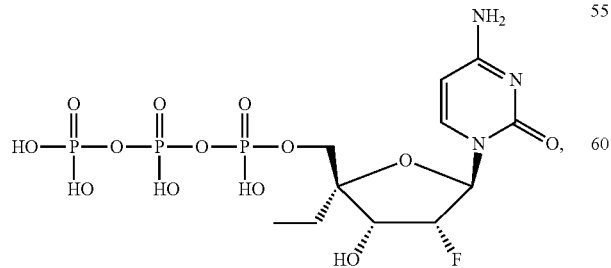

or a pharmaceutically acceptable salt thereof.

31. The compound of claim 1, wherein the compound of Formula (I) is

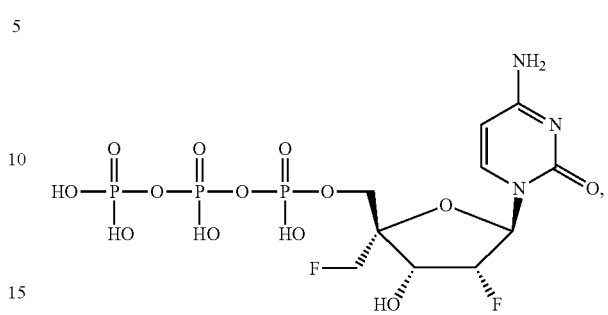

or a pharmaceutically acceptable salt thereof.

32. The compound of claim 1, wherein the compound of Formula (I) is

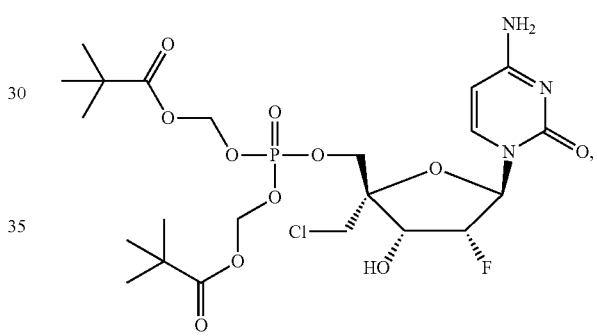

or a pharmaceutically acceptable salt thereof.

33. The compound of claim 1, wherein the compound of Formula (I) is

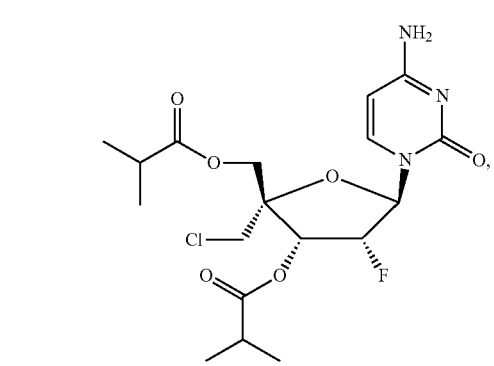 [SMILES: CC(C)C(=O)OC[C@@]1(CCl)O[C@@H](n2ccc(N)nc2=O)[C@H](F)[C@@H]1OC(=O)C(C)C]

or a pharmaceutically acceptable salt thereof.

34. The compound of claim 1, wherein the compound of Formula (I) is

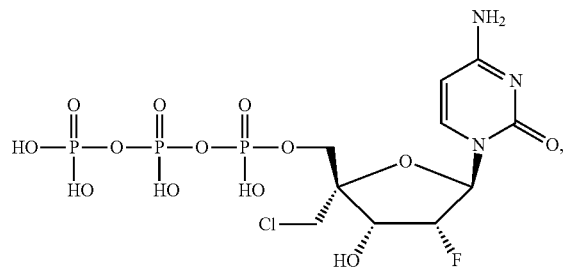 [SMILES: Nc1ccn([C@@H]2O[C@](CCl)(COP(=O)(O)OP(=O)(O)OP(=O)(O)O)[C@@H](O)[C@H]2F)c(=O)n1]

or a pharmaceutically acceptable salt thereof.

35. The compound of claim 1, wherein the compound of Formula (I) is

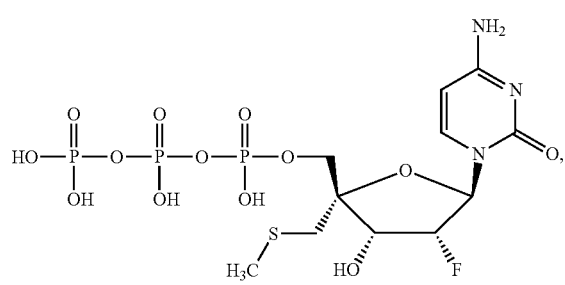 [SMILES: CSC[C@]1(COP(=O)(O)OP(=O)(O)OP(=O)(O)O)O[C@@H](n2ccc(N)nc2=O)[C@H](F)[C@@H]1O]

or a pharmaceutically acceptable salt thereof.

36. The compound of claim 1, wherein the compound of Formula (I) is

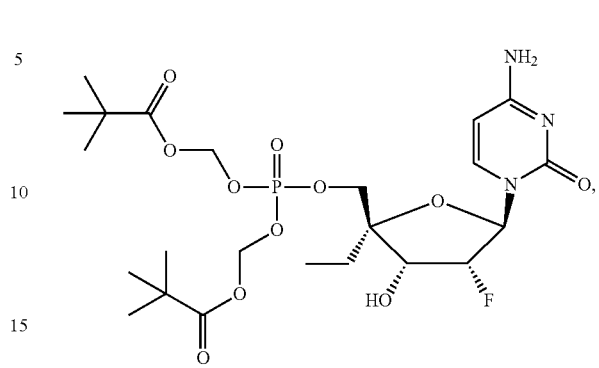

or a pharmaceutically acceptable salt thereof.

37. The method of claim 20, wherein the viral infection is a paramyxovirus viral infection.

38. The method of claim 37, wherein the paramyxovirus viral infection is human respiratory syncytial virus infection.

39. The method of claim 21, wherein the viral infection is a paramyxovirus viral infection.

40. The method of claim 39, wherein the paramyxovirus viral infection is human respiratory syncytial virus infection.

* * * * *